(12) United States Patent
Tani et al.

(10) Patent No.: US 8,026,273 B2
(45) Date of Patent: *Sep. 27, 2011

(54) 8-AZAPROSTAGLANDIN DERIVATIVE COMPOUND AND AGENT COMPRISING THE COMPOUND AS ACTIVE INGREDIENT

(75) Inventors: Kousuke Tani, Mishima-gun (JP); Kaoru Kobayashi, Mishima-gun (JP); Toru Maruyama, Mishima-gun (JP); Tohru Kambe, Mishima-gun (JP); Mikio Ogawa, Mishima-gun (JP); Tsutomu Shiroya, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/683,609

(22) Filed: Jan. 7, 2010

(65) Prior Publication Data

US 2010/0113388 A1  May 6, 2010

Related U.S. Application Data

(60) Continuation of application No. 12/139,260, filed on Jun. 13, 2008, now Pat. No. 7,683,094, which is a division of application No. 10/506,536, filed as application No. PCT/JP03/02478 on Mar. 4, 2003, now Pat. No. 7,402,605.

(30) Foreign Application Priority Data

Mar. 5, 2002 (JP) ................ 2002-058487
Jul. 25, 2002 (JP) ................ 2002-216567
Jan. 22, 2003 (JP) ................ 2003-013447

(51) Int. Cl.
*A61K 31/40* (2006.01)
*A61K 31/405* (2006.01)
*C07D 207/00* (2006.01)
*C07D 209/00* (2006.01)

(52) U.S. Cl. .............................. 514/424; 548/551

(58) Field of Classification Search .............. 514/424; 548/551
See application file for complete search history.

(56) References Cited

U.S. PATENT DOCUMENTS

| | | | |
|---|---|---|---|
| 5,310,499 A | 5/1994 | Scherowsky et al. | |
| 6,552,067 B2 | 4/2003 | Cameron et al. | |
| 7,858,650 B2 * | 12/2010 | Yamamoto et al. | 514/369 |
| 2008/0114043 A1 * | 5/2008 | Yamamoto et al. | 514/369 |

FOREIGN PATENT DOCUMENTS

| | | |
|---|---|---|
| EP | 471201 | 2/1992 |
| EP | 1110949 | 6/2001 |
| EP | 1132086 | 6/2001 |
| EP | 1121939 | 8/2001 |
| JP | 2001-181210 | 7/2001 |
| JP | 2001-220357 | 8/2001 |
| JP | 2001-233792 | 8/2001 |
| WO | 02/24647 | 3/2002 |
| WO | 02/42268 | 5/2002 |
| WO | 03/007941 | 1/2003 |
| WO | 03/008377 | 1/2003 |
| WO | 03/009872 | 2/2003 |

OTHER PUBLICATIONS

Patani et al., Bioisoterism: A Rational Approach in Drug Design, Chem. Rev. 1996, 96, 3147-3176, especially p. 3156.

* cited by examiner

*Primary Examiner* — Susannah Chung

(74) *Attorney, Agent, or Firm* — Sughrue Mion, PLLC

(57) ABSTRACT

An 8-azaprostaglandin represented by formula (I)

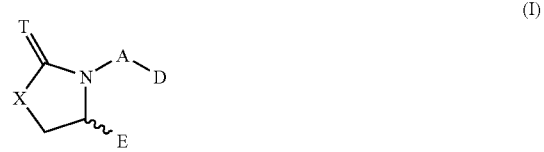

(wherein all symbols have the same meanings as described in the specification), a pharmaceutically acceptable salt thereof or a cyclodextrin clathrate thereof. Since the compound represented by formula (I) binds to EP2 subtype among PGE receptor strongly, it is useful for preventive and/or treatment for immune diseases, allergic diseases, neuronal cell death, dysmenorrhea, premature birth, abortion, baldness, retinal neuropathy such as glaucoma, erectile dysfunction, arthritis, pulmonary injury, pulmonary fibrosis, pulmonary emphysema, bronchitis, chronic obstructive pulmonary disease, hepatic injury, acute hepatitis, liver cirrhosis, shock, nephritis, renal failure, circulatory diseases, systemic inflammatory response syndrome, sepsis, hemophagocytosis syndrome, macrophage activation syndrome, still disease, Kawasaki Disease, burn, systemic granuloma, ulcerative colitis, Crohn disease, hypercytokinemia at dialysis, multiple organ failure, or bone diseases etc.

8 Claims, No Drawings

8-AZAPROSTAGLANDIN DERIVATIVE COMPOUND AND AGENT COMPRISING THE COMPOUND AS ACTIVE INGREDIENT

CROSS-REFERENCE

This application is a continuation of U.S. application Ser. No. 12/139,260 filed Jun. 13, 2008, which is a divisional of U.S. application Ser. No. 10/506,536 filed Sep. 3, 2004 (now U.S. Pat. No. 7,402,605), which is a U.S. National Stage Application of PCT/JP03/02478 filed Mar. 4, 2003; which claims benefit of Japanese Application Nos. 2002-58487, filed Mar. 5, 2002, 2002-216567, filed Jul. 25, 2002, and 2003-13447, filed Jan. 22, 2003, the disclosure of each of which is incorporated herein by reference in its entirety.

TECHNICAL FIELD

The present invention relates to 8-azaprostaglandins.
More specifically, the present invention relates to:
(1) an 8-azaprostaglandin derivative compound represented by formula (I):

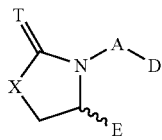

(wherein all symbols have the same meanings as described below), a pharmaceutically acceptable salt thereof or a cyclodextrin clathrate thereof,
(2) a process for the preparation thereof, and
(3) a pharmaceutical composition comprising thereof as an active ingredient.

BACKGROUND ART

Prostaglandin $E_2$ (abbreviated as $PGE_2$) has been known as a metabolite in the arachidonate cascade. It has been known that $PGE_2$ possesses cyto-protective activity, uterine contractive activity, a pain-inducing effect, a promoting effect on digestive peristalsis, an awakening effect, a suppressive effect on gastric acid secretion, hypotensive activity and diuretic activity and so on.

A recent study has proved existence of various PGE subtype receptors possessing a different physical role from each other. At present, four receptor subtypes are known and they are called $EP_1$, $EP_2$, $EP_3$, and $EP_4$ (Negishi M., et al., *J. Lipid Mediators Cell Signaling*, 12, 379-391 (1995)).

It is thought that $EP_2$ subtype receptor relates to inhibition of producing TNF-α and acceleration of producing IL-10. Therefore, the compounds which can bind on $EP_2$ subtype receptor are expected to be useful for the prevention and/or treatment of immune diseases (e.g., autoimmune diseases such as amyotrophic lateral sclerosis (ALS), multiple sclerosis, Sjogren's syndrome, rheumatoid arthritis and systemic lupus erythematosus etc., and rejection after organ transplantation), allergic diseases (e.g., asthma, allergic rhinitis, allergic conjunctivitis, atopic dermatitis, food allergy), neuronal cell death, dysmenorrhea, premature birth, abortion, baldness, retinal neuropathy such as glaucoma, erectile dysfunction, arthritis, pulmonary injury, pulmonary fibrosis, pulmonary emphysema, bronchitis, chronic obstructive pulmonary disease, hepatic injury, acute hepatitis, liver cirrhosis, shock, nephritis (acute nephritis, chronic nephritis), renal failure, circulatory diseases (e.g., hypertension, myocardial ischemia, chronic arterial obstruction, vibration disease), systemic inflammatory response syndrome, sepsis, hemophagocytosis syndrome, macrophage activation syndrome, still disease, Kawasaki Disease, burn, systemic granuloma, ulcerative colitis, Crohn disease, hypercytokinemia at dialysis, multiple organ failure, and bone diseases (e.g., fracture, refracture, intractable fracture, nonunion, pseudarthrosis, osteomalacia, Paget's disease of bone, ankylosing spondylitis, bone metastasis, osteroarthritis and destruction of bone/cartilage due to these analogous diseases) etc. It is also considered that the compounds are useful as an agent for accelerating the osteogenesis/cure after bone surgery (e.g., fracture, bone graft, artificial arthrogenesis, spinal fusion, surgery for multiple myeloma, lung cancer, breast cancer, etc., other bone repair) or substitute treatment for bone grafting. It is further considered that the compounds are useful agents for accelerating the regeneration of peridontium in periodontal disease etc.

As an 8-azaprostaglandin derivative, for example, compounds represented by formula (A):

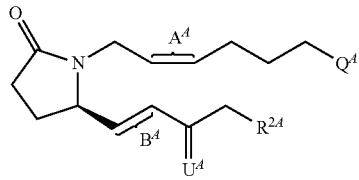

(wherein $Q^A$ is selected from the group consisting of —$COOR^{3A}$, tetrazol-5-yl and —$CONHR^{4A}$;
$A^A$ is a single or cis double bond;
$B^A$ is a single or trans double bond;
$U^A$ is

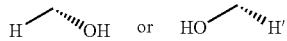

$R^{2A}$ is selected from the group consisting of α-thienyl, phenyl, phenoxy, monosubstituted phenyl and monosubstituted phenoxy, said substituents being selected from the group consisting of chloro, fluoro, phenyl, methoxy, trifluoromethyl and alkyl having from one to three carbon atoms;
$R^{3A}$ is selected from the group consisting of hydrogen, alkyl having from one to five carbon atoms, phenyl and p-biphenyl;
$R^{4A}$ is selected from the group consisting of —$COR^{5A}$ and —$SO_2R^{5A}$; said $R^{5A}$ being selected from the group consisting of phenyl and alkyl having from one to five carbon atoms.), a C5 epimer thereof, or an alkali, alkaline earth or ammonium salt of the compound having a carboxylate or tetrazol-5-yl group is described (ref. Japanese published unexamined application No. 53-21159 (U.S. Pat. No. 4,177,346)).

Furthermore, in the specification, a compound represented by formula (A'):

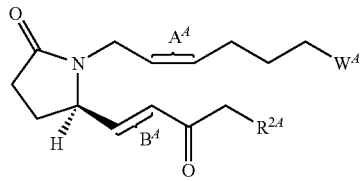

(wherein, $W^A$ is selected from the group consisting of —$COOR^{3A}$, tetrazol-5-yl, N-(acyloxymethyl)tetrazol-5-yl (having from two to five carbon atoms in the acyloxy group), N-(phthalidyl)tetrazol-5-yl and N-(tetrahydropyran-2-yl)-tetrazol-5-y, and the other symbol have the same meanings as described above.), a C5 epimer thereof, or an alkali, alkaline earth or ammonium salt of the compound having a carboxylate or tetrazol-5-yl group is described.

Moreover, a pyrrolidone represented by formula (B):

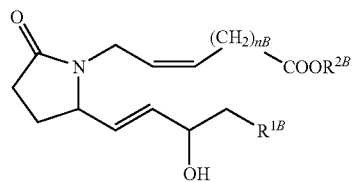

(B)

(wherein $R^{1B}$ represents a straight or branched chain, saturated or unsaturated, aliphatic hydrocarbon radical having up to 10 carbon atoms, or a cycloaliphatic hydro-carbon radical having 3 to 7 carbon atoms, which radicals may be unsubstituted or substituted by one or more of the following:
a) a straight or branched chain alkoxy-, alkylthio-, alkenyloxy- or alkenylthio group of up to 5 carbon atoms,
b) a phenoxy group which may carry one or two substituents selected from optionally halogenated alkyl groups of 1 to 3 carbon atom(s), halogen atoms, optionally halogenated phenoxy groups, and alkoxy groups of 1 to 4 carbon atoms,
c) a furyloxy, thienyloxy or benzyloxy group which may carry, on the nucleus, one or two substituents selected from optionally halogenated alkyl groups of 1 to 3 carbon atom(s), halogen atoms and alkoxy groups of 1 to 4 carbon atoms,
d) a trifluoromethyl or pentafluoroethyl group,
e) a cycloalkyl group of 3 to 7 carbon atoms,
f) a phenyl, thienyl or furyl group which may carry one or two substituents selected from optionally halogenated alkyl groups of 1 to 3 carbon atom(s), halogen atoms, and alkoxy groups of 1 to 4 carbon atoms, $R^{2B}$ represents a straight or branched chain, saturated or unsaturated, aliphatic or cycloaliphatic hydrocarbon radical having up to 6 carbon atoms, or an araliphatic hydrocarbon radical having 7 or 8 carbon atoms, and $n^B$ represents the integer two, three or four), corresponding free acids thereof, or a physiologically tolerable metal or amine salt thereof is described (ref. Japanese published unexamined application No. 52-5764 (DT 2,528,664)).

In the other specification, a pyrrolidone of the same kind is described (ref. Japanese published unexamined application No. 52-73865 (BE 849,346) and Japanese published unexamined application No. 52-133975 (BE 854,268)).

Moreover, a compound represented by formula (c):

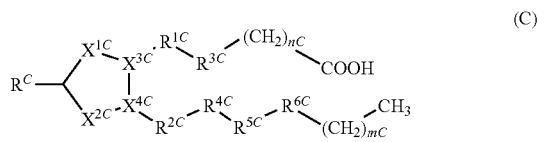

(C)

(wherein $X^{1C}$ and $X^{2C}$ are, independently, $CH_2$ or CO, $X^{3C}$ is a nitrogen atom or CH, $R^C$ is a hydrogen atom or hydroxyl, $R^{1C}$ and $R^{2C}$ are, independently, $CH_2$ or CO, $R^{3C}$ is $CH_2$, NH or oxygen atom, $R^{4C}$ is NH, $CH_2$ or CO, $R^{5C}$ is $CH_2$ or NH, $R^{6C}$ is $CH_2$ or CO, $m^C$ is between 0 and 4, $n^C$ is between 0 and 5.) and a pharmaceutically tolerable salt thereof is described (ref. EP 572,365).

Moreover, a compound represented by formula (D):

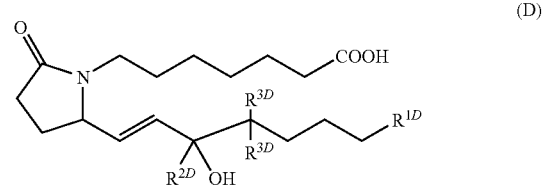

(D)

(when $R^{1D}$ is a hydrogen atom or ethyl, $R^{2D}$ is a hydrogen atom or methyl, and $R^{3D}$ is hydrogen. When $R^{1D}$ is methyl, $R^{2D}$ is a hydrogen atom and $R^{3D}$ is methyl.) or a pharmaceutically tolerable salt thereof is described. In the other specification, an 8-azaprostanoic acid of the same kind is described (ref. Japanese published unexamined application No. 51-127068, Japanese published unexamined application No. 51-128961 and Japanese published unexamined application No. 52-100467 (GB 1,523,178)).

Moreover, compounds represented by formulae (E), (E') and (E''):

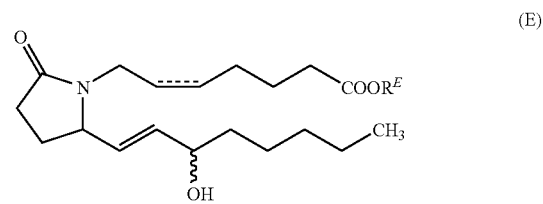

(E)

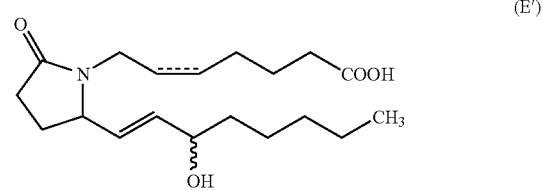

(E')

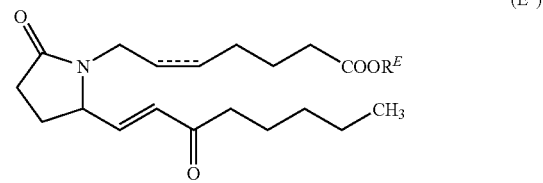

(E'')

(wherein $R^E$ is ester residue, dotted line is double bond or not, and wavy line is α-configuration or β-configuration.) are described (ref. Japanese published unexamined application No. 51-1461).

Moreover, a prostaglandin derivate represented by formula (F):

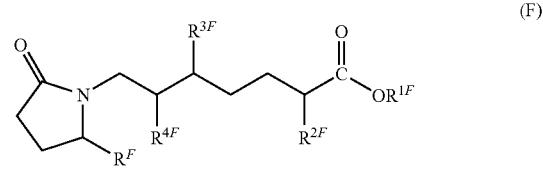

(F)

(wherein $R^{1F}$ represents hydrogen, methyl or ethyl, $R^{2F}$, $R^{3F}$ and $R^{4F}$, which are the same or different, each represents hydrogen or methyl and RF is selected from the groups consisting of:

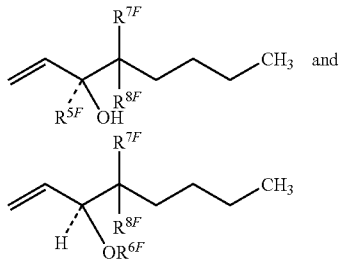

(wherein $R^{5F}$ represents hydrogen, methyl or ethyl, $R^{6F}$ represents methyl, ethyl or acetyl and $R^{7F}$ and $R^{3F}$ each represents hydrogen or a straight-chain alkyl group having from 1 to 3 carbon atom(s).). With the provisos that, when $R^{7F}$ and $R^{3F}$ represent hydrogen, $R^{5F}$ is methyl or ethyl, or when $R^{5F}$ represents methyl and $R^{2F}$, $R^{3F}$, $R^{4F}$, $R^{7F}$ and $R^{3F}$ all represent hydrogen, $R^{1F}$ represents ethyl.) is disclosed (ref. Japanese published unexamined application No. 52-142060 (BE 852,941)). Furthermore, a prostaglandin derivative of the same kind is described (ref. Japanese published unexamined application No. 51-138671 (BE 839,761)).

Moreover, a racemic compound selected from the group represented by formulae (G) and (G'):

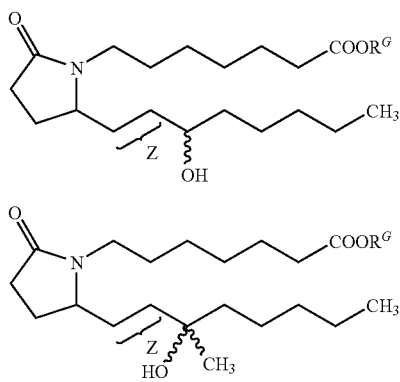

(wherein $R^G$ is a hydrogen atom, lower alkyl group having from 1 to 4 carbon atoms, when $R^G$ is a hydrogen atom, the compounds may form pharmaceutically acceptable nontoxic salts; Z is trans-double bond or saturated bond; waved line is α-configuration, β-configuration or a mixture thereof.) is disclosed (ref. Japanese published unexamined application No. 51-143663 (BE 841,165)).

DISCLOSURE OF THE INVENTION

The present inventors have studied to find out the compounds which can bind on $EP_2$ subtype receptor specifically, and which have strong agonistic activity. Finally, the compound of formula (I) was found out to meet this purpose, and this invention was accomplished. Furthermore, the present inventors also found out the compound which binds on both $EP_2$ and $EP_4$ subtype receptor. The compound which binds on both $EP_4$ and $EP_2$ subtype receptor is expected additive or multiplier effect when treatment of the disease associated with both subtype receptor.

The present invention relates to (1) an 8-azaprostaglandin derivative compound represented by formula (I):

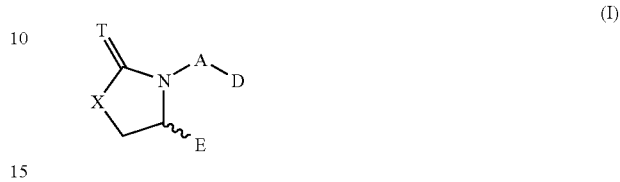

wherein T is (1) an oxygen atom or (2) a sulfur atom;
X is (1) —$CH_2$—, (2) —O— or (3) —S—;
A is $A^1$ or $A^2$;
$A^1$ is (1) C2-8 straight-chain alkylene optionally substituted by 1 to 2 C1-4 alkyl(s), (2) C2-8 straight-chain alkenylene optionally substituted by 1 to 2 C1-4 alkyl(s) or (3) C2-8 straight-chain alkynylene optionally substituted by 1 to 2 C1-4 alkyl(s);
$A^2$ is -$G^1$-$G^2$-$G^3$-;
$G^1$ is (1) C1-4 straight-chain alkylene optionally substituted by 1 to 2 C1-4 alkyl(s), (2) C2-4 straight-chain alkenylene optionally substituted by 1 to 2 C1-4 alkyl(s) or (3) C2-4 straight-chain alkynylene optionally substituted by 1 to 2 C1-4 alkyl(s);
$G^2$ is (1) —Y—, (2)-ring1-, (3) —Y-ring1-, (4)-ring1-Y— or (5) —Y—C1-4 alkylene-ring1-;
Y is (1) —S—, (2) —SO—, (3) —$SO_2$—, (4) —O— or (5) —$NR^1$—;
$R^1$ is (1) a hydrogen atom, (2) C1-10 alkyl or (3) C2-10 acyl;
$G^3$ is (1) a bond, (2) C1-4 straight-chain alkylene optionally substituted by 1 to 2 C1-4 alkyl(s), (3) C2-4 straight-chain alkenylene optionally substituted by 1 to 2 C1-4 alkyl(s) or (4) C2-4 straight-chain alkynylene optionally substituted by 1 to 2 C1-4 alkyl(s);
D is $D^1$ or $D^2$
$D^1$ is (1) —COOH, (2) —$COOR^2$, (3) tetrazol-5-yl or (4) —$CONR^3SO_2R^4$;
$R^2$ is (1) C1-10 alkyl, (2) phenyl, (3) C1-10 alkyl substituted by phenyl or (4) biphenyl;
$R^3$ is (1) a hydrogen atom or (2) C1-10 alkyl;
$R^4$ is (1) C1-10 alkyl or (2) phenyl;
$D^2$ is (1) —$CH_2OH$, (2) —$CH_2OR^5$, (3) hydroxy, (4) —$OR^5$, (5) formyl, (6) —$CONR^6R^7$, (7) —$CONR^6SO_2R^8$, (8) —CO—(NH-amino acid residue-CO)$_m$—OH, (9) —O—(CO-amino acid residue-NH)$_m$—H, (10) —$COOR^9$, (11) —OCO—$R^{10}$, (12) —COO—$Z^1$—$Z^2$—$Z^3$, or

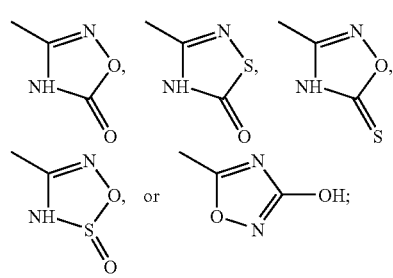

R$^5$ is C1-10 alkyl;

R$^6$ and R$^7$ are, each independently, (1) a hydrogen atom or (2) C1-10 alkyl;

R$^8$ is C1-10 alkyl substituted by phenyl;

R$^9$ is (1) C1-10 alkyl substituted by biphenyl optionally substituted by 1 to 3 substituent(s) selected from C1-10 alkyl, C1-10 alkoxy and halogen or (2) biphenyl substituted by 1 to 3 substituent(s) selected from C1-10 alkyl, C1-10 alkoxy and halogen atom;

R$^{10}$ is (1) phenyl or (2) C1-10 alkyl;

m is 1 or 2;

Z$^1$ is (1) C1-15 alkylene, (2) C2-15 alkenylene or (3) C2-15 alkynylene;

Z$^2$ is (1) —CO—, (2) —OCO—, (3) —COO—, (4) —CONR$^{Z1}$—, (5) —NR$^{Z2}$CO—, (6) —O—, (7) —S—, (8) —SO$_2$—, (9) —SO$_2$—NR$^{Z2}$—, (10) —NR$^{Z2}$SO$_2$—, (11) —NR$^{Z3}$-, (12) —NR$^{Z4}$CONR$^{Z5}$-, (13) —NR$^{Z6}$COO—, (14) —OCONR$^{Z7}$— or (15) —OCOO—;

Z$^3$ is (1) a hydrogen atom, (2) C1-15 alkyl, (3) C2-15 alkenyl, (4) C2-15 alkynyl, (5) ringZ or (6) C1-10 alkyl substituted by C1-10 alkoxy, C1-10 alkylthio, C1-10 alkyl-NR$^{Z8}$- or ringZ;

ringZ is (1) C3-15 mono-, bi- or tri-carbocyclic aryl which may be partially or fully saturated or (2) 3- to 15-membered mono-, bi- or tri-heterocyclic aryl which may be partially or fully saturated and contains 1 to 4 hetero atom(s) selected from oxygen, nitrogen and sulfur atom(s);

R$^{Z1}$, R$^{Z2}$, R$^{Z3}$, R$^{Z4}$, R$^{Z5}$, R$^{Z6}$, R$^{Z7}$ and R$^{Z8}$ are, each independently, a hydrogen atom or C1-15 alkyl;

R$^{Z1}$ and Z$^3$ may be taken together with the nitrogen atom to which they are attached to form a 5- to 7-membered saturated mono-heterocyclic ring, and the heterocyclic ring may contain other one hetero atom selected from oxygen, nitrogen and sulfur atoms;

ringZ and the saturated mono-heterocyclic ring formed by R$^{Z1}$, Z$^3$ and the nitrogen atom to which they are attached may be substituted by 1-3 groups selected from following (1) to (4):

(1) C1-15 alkyl, (2) C2-15 alkenyl, (3) C2-15 alkynyl, (4) C1-10 alkyl substituted by C1-10 alkoxy, C1-10 alkylthio or C1-10 alkyl-NR$^{Z9}$—;

R$^{Z9}$ is a hydrogen atom or C1-10 alkyl;

E is E$^1$ or E$^2$;

E$^1$ is

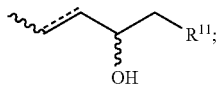

R$^{11}$ is (1) C1-10 alkyl, (2) C1-10 alkylthio, (3) C1-10 alkyl substituted by C3-8 cycloalkyl, (4) C1-10 alkyl substituted by ring2 or (5) C1-10 alkyl substituted by —W$^1$—W$^2$-ring2;

W$^1$ is (1) —O—, (2) —S—, (3) —SO—, (4) —SO$_2$—, (5) —NR$^{11-1}$-, (6) carbonyl, (7) —NR$^{11-1}$SO$_2$—, (8) carbonylamino or (9) aminocarbonyl;

R$^{11-1}$ is (1) a hydrogen atom, (2) C1-10 alkyl or (3) C2-10 acyl;

W$^2$ is (1) a bond or (2) C1-8 alkyl optionally substituted by C1-4 alkyl, halogen or hydroxy;

E$^2$ is (1) U$^1$—U$^2$—U$^3$ or (2) ring4;

U$^1$ is (1) C1-4 alkylene, (2) C2-4 alkenylene, (3) C2-4 alkynylene, (4)-ring3-, (5) C1-4 alkylene-ring3-, (6) C2-4 alkenylene-ring3- or (7) C2-4 alkynylene-ring3-;

U$^2$ is (1) a bond, (2) —CH$_2$—, (3) —CHOH—, (4) —O—, (5) —S—, (6) —SO—, (7) —SO$_2$—, (8) —NR$^{12}$—, (9) carbonyl, (10) —NR$^{12}$SO$_2$—, (11) carbonylamino or (12) aminocarbonyl;

R$^{12}$ is (1) a hydrogen atom, (2) C1-10 alkyl or (3) C2-10 acyl;

U$^3$ is (1) C1-8 alkyl optionally substituted by 1 to 3 substituent(s) selected from C1-10 alkyl, halogen, hydroxy, alkoxy, alkylthio and NR$^{13}$R$^{14}$, (2) C2-8 alkenyl optionally substituted by 1 to 3 substituent(s) selected from C1-10 alkyl, halogen, hydroxyl, alkoxy, alkylthio and —NR$^{13}$R$^{14}$, (3) C2-8 alkynyl optionally substituted by 1 to 3 substituent(s) selected from C1-10 alkyl, halogen, hydroxy, alkoxy, alkylthio and —NR$^{13}$R$^{14}$, (4) C1-8 alkyl substituted by ring4 or (5) ring4;

R$^{13}$ and R$^{14}$ are, each independently, (1) a hydrogen atom or (2) C1-10 alkyl;

ring1, ring2, ring3 or ring4 may be substituted by 1 to 5R;

R is (1) C1-10 alkyl, (2) C2-10 alkenyl, (3) C2-10 alkynyl, (4) C1-10 alkoxy, (5) C1-10 alkylthio, (6) halogen, (7) hydroxy, (8) nitro, (9) —NR$^{15}$R$^{16}$, (10) C1-1 alkyl substituted by C1-10 alkoxy, (11) C1-10 alkyl substituted by 1 to 3 halogen atom(s), (12) C1-10 alkyl substituted by C1-10 alkoxy substituted by 1 to 3 halogen atom(s), (13) C1-10 alkyl substituted by —NR$^{15}$R$^{16}$, (14) ring5, (15) —O-rings, (16) C1-10 alkyl substituted by ring5, (17) C2-10 alkenyl substituted by ring5, (18) C2-10 alkynyl substituted by ring5, (19) C1-10 alkoxy substituted by ring5, (20) C1-10 alkyl substituted by —O-ring5, (21) COOR$^{17}$, (22) C1-10 alkoxy substituted by 1 to 4 halogen atom(s), (23) formyl, (24) C1-10 alkyl substituted by hydroxy or (25) C2-10 acyl;

R$^{15}$, R$^{16}$ and R$^{17}$ are, each independently, (1) a hydrogen atom or (2) C1-10 alkyl;

ring5 may be substituted by 1 to 3 substituent(s) selected from following (1)-(9):

(1) C1-10 alkyl, (2) C2-10 alkenyl, (3) C2-10 alkynyl, (4) C1-10 alkoxy, (5) C1-10 alkyl substituted by C1-10 alkoxy, (6) halogen atom, (7) hydroxy, (8) C1-10 alkyl substituted by 1 to 3 halogen atom(s), (9) C1-10 alkyl substituted by C1-10 alkoxy substituted by 1 to 3 halogen atom(s);

ring1, ring2, ring3, ring4 and ring5 are, each independently, (1) C3-15 mono-, bi- or tri-carbocyclic aryl which may be partially or fully saturated or (2) 3- to 15-membered mono-, bi- or tri-heterocyclic aryl which may be partially or fully saturated and contains a hetero atom(s) selected from 1 to 4 nitrogen, 1 to 2 oxygen and/or 1 to 2 sulfur atom(s); and wherein 1) when E is E$^2$, E$^2$ is U$^1$—U$^2$—U$^3$, and U$^1$ is C2 alkylene or C2 alkenylene, U$^2$ is not —CHOH—, 2) when U$^3$ is C1-8 alkyl substituted by at least one hydroxy, U$^1$—U$^2$ is not C2 alkylene or C2 alkenylene, 3) when A is A$^1$ and D is D$^1$, then E is not E$^1$, 4) when T is oxygen atom, X is —CH$_2$—, D is D$^1$, D$^1$ is COOH, A is A$^1$, A$^1$ is C2-8 straight-chain alkylene, E is E$^2$, E$^2$ is U$^1$—U$^2$—U$^3$, U$^1$ is C1-4 alkylene and U$^3$ is C1-8 alkyl, then U$^2$ is not a bond, —CH$_2$—, —NR$^{12}$— or carbonyl, 5) when T is an oxygen atom, X is —CH$_2$—, D is D$^1$, D$^1$ is COOH, A is A$^2$, G$^1$ is C1-4 alkylene, G$^2$ is —O— or —NR$^1$—, G$^3$ is a bond or C1-4 alkylene, E is E$^2$, E$^2$ is U$^1$—U$^2$—U$^3$, U$^1$ is C1-4 alkylene and U$^3$ is C1-8 alkyl, the U$^2$ is not a bond, —CH$_2$—, —NR$^{12}$— or carbonyl, 6) when T is an oxygen atom, X is —CH$_2$—, D is D$^1$, E is E$^2$, E$^2$ is U$^1$—U$^2$—U$^3$, U$^1$ is C2 alkylene or C2 alkenylene and U$^2$ is —CO—, then A is not A$^1$, 7) 4-[(2-{(2R)-2-[(1E,3S)-3-hydroxy-oct-1-enyl]-5-oxo-pyrrolidin-1-yl}ethyl)thio]butanoic acid and 4-{2-[(R)-2-((E)-3-hydroxy-oct-1-enyl)-5-oxo-pyrrolidin-1-yl]-ethyl}-benzoic acid are excluded, a pharmaceutically acceptable salt thereof or a cyclodextrin clathrate thereof,
(2) a process for the preparation thereof, and
(3) a pharmaceutical composition comprising thereof as an active ingredient.

In the present invention, C1-4 alkyl includes methyl, ethyl, propyl, butyl and isomers thereof.

In the present invention, C1-8 alkyl includes methyl, ethyl, propyl, butyl, pentyl, hexyl, heptyl, octyl and isomers thereof.

In the present invention, C1-10 alkyl includes methyl, ethyl, propyl, butyl, pentyl, hexyl, heptyl, octyl, nonyl, decyl and isomers thereof.

In the present invention, C1-15 alkyl includes methyl, ethyl, propyl, butyl, pentyl, hexyl, heptyl, octyl, nonyl, decyl, undecyl, dodecyl, tridecyl, tetradecyl, pentadecyl and isomers thereof.

In the present invention, C2-8 alkenyl includes ethenyl, propenyl, butenyl, pentenyl, hexenyl, heptenyl, octenyl and isomers thereof.

In the present invention, C2-10 alkenyl includes ethenyl, propenyl, butenyl, pentenyl, hexenyl, heptenyl, octenyl, nonenyl, decenyl and isomers thereof.

In the present invention, C2-15 alkenyl includes ethenyl, propenyl, butenyl, pentenyl, hexenyl, heptenyl, octenyl, nonenyl, decenyl, undecenyl, dodecenyl, tridecenyl, tetradecenyl, pentadecenyl and isomers thereof.

In the present invention, C2-8 alkynyl includes ethynyl, propynyl, butynyl, pentynyl, hexynyl, heptynyl, octynyl and isomers thereof.

In the present invention, C2-10 alkynyl includes ethynyl, propynyl, butynyl, pentynyl, hexynyl, heptynyl, octynyl, nonynyl, decynyl and isomers thereof.

In the present invention, C2-15 alkynyl includes ethynyl, propynyl, butynyl, pentynyl, hexynyl, heptynyl, octynyl, nonynyl, decynyl, undecynyl, dodecynyl, tridecynyl, tetradecynyl, pentadecynyl and isomers thereof.

In the present invention, C1-4 straight-chain alkylene includes methylene, ethylene, trimethylene and tetramethylene.

In the present invention, C2-8 straight-chain alkylene includes ethylene, trimethylene, tetramethylene, pentamethylene, hexamethylene, heptamethylene and octamethylene.

In the present invention, C1-4 alkylene includes methylene, ethylene, trimethylene, tetramethylene and isomers thereof.

In the present invention, C1-15 alkylene includes methylene, ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene and isomers thereof.

In the present invention, C2-4 straight-chain alkenylene includes ethenylene, propenylene, butenylene and isomers thereof.

In the present invention, C2-8 straight-chain alkenylene means C2-8 alkenylene which has 1 to 2 double bond(s). It includes ethenylene, propenylene, butenylene, butadienylene, pentenylene, pentadienylene, hexenylene, hexadienylene, heptenylene, heptadienylene, octenylene and octadienylene.

In the present invention, C2-4 alkenylene includes ethenylene, propenylene, butenylene and isomers thereof.

In the present invention, C2-15 alkenylene includes ethenylene, propenylene, butenylene, pentenylene, hexenylene, heptenylene, octenylene, nonenylene, decenylene, undecenylene, dodecenylene, tridecenylene, tetradecenylene, pentadecenylene and isomers thereof.

In the present invention, C2-4 straight-chain alkynylene includes ethynylene, propynylene and butynylene.

In the present invention, C2-8 straight-chain alkynylene means C2-8 alkenylene which has 1 to 2 triple bond(s). It includes ethynylene, propynylene, butynylene, butadiynylene, pentynylene, pentadiynylene, hexynylene, hexadiynylene, heptynylene, heptadiynylene, octynylene and octadiynylene.

In the present invention, C2-4 alkynylene includes ethynylene, propynylene, butynylene and isomers thereof.

In the present invention, C2-15 alkynylene includes ethynylene, propynylene, butynylene, pentynylene, hexynylene, heptynylene, octynylene, nonynylene, decynylene, undecynylene, dodecynylene, tridecynylene, tetradecynylene, pentadecynylene and isomers thereof.

In the present invention, C1-10 alkoxy includes methoxy, ethoxy, propoxy, butoxy, pentyloxy, hexyloxy, heptyloxy, octyloxy, nonyloxy, decyloxy and isomers thereof.

In the present invention, C1-10 alkylthio includes methylthio, ethylthio, propylthio, butylthio, pentylthio, hexylthio, heptylthio, octylthio, nonylthio, decylthio and isomers thereof.

In the present invention, C3-8 cycloalkyl includes cyclopropyl, cyclobutyl, cyclopentyl, cyclohexyl, cycloheptyl and cyclooctyl.

In the present invention, C2-10 acyl includes ethanoyl, propanoyl, butanoyl, pentanoyl, hexanoyl, heptanoyl, octanoyl, nonanoyl, decanoyl and isomers thereof.

In the present invention, biphenyl includes 2-phenylphenyl, 3-phenylphenyl or 4-phenylphenyl.

In the present invention, halogen atom includes fluoride, chloride, bromide and iodide atom.

In the present invention, amino acid residue in —CO—(NH-amino acid residue-CO)$_m$—OH and —O—(CO-amino acid residue-NH)$_m$—H includes the amino acid residue of natural amino acid or abnormal amino acid. Natural amino acids or abnormal amino acid include, for example, glycine, alanine, valine, leucine, isoleucine, serine, threonine, cystein, methionine, proline, asparagine, glutamine, phenylalanine, tyrosine, tryptophan, aspartic acid, glutamic acid, lysine, arginine, histidine, β-alanine, cystathionine, cystine, homoserine, isoleucine, lanthionine, norleucine, norvaline, ornithine, sarcosine, thyronine etc.

In amino acid residue in —CO—(NH— amino acid residue-CO)$_m$—OH and —O—(CO-amino acid residue-NH)$_m$—H, an amino acid with protecting group is included.

In the present invention, C3-15 mono-, bi- or tri-carbocyclic aryl which may be partially or fully saturated represented by ring1, ring2, ring3, ring4, ring5 or ringZ includes, for example, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[2.2.1]heptane, bicyclo

[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane, noradamantane etc.

In the present invention, among the 3- to 15-membered mono-, bi- or tri-heterocyclic aryl which may be partially or fully saturated and contains a hetero atom(s) selected from 1 to 4 nitrogen, 1 to 2 oxygen, and/or 1 to 2 sulfur atom(s) represented by ring1, ring2, ring3, ring4, ring5 or ringZ, 3- to 15-membered mono-, bi- or tri-heterocyclic aryl containing a hetero atom(s) selected from 1 to 4 nitrogen, 1 to 2 oxygen, and/or 1 to 2 sulfur atom(s) includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine ring etc.

The 3- to 15-membered mono-, bi- or tri-heterocyclic aryl which is partially or fully saturated and contains a hetero atom(s) selected from 1 to 4 nitrogen, 1 to 2 oxygen and/or 1 to 2 sulfur atom(s) includes aziridine, azetidine, azocane, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane, benzodithiane ring etc.

In the present invention, C3-10 mono- or bi-carbocyclic aryl which may be partially or fully saturated includes, for example, cyclopropane, cyclobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, spiro[4.4]nonane, spiro[4.5]decane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane, noradamantane etc.

In the present invention, among the 3- to 10-membered mono- or bi-heterocyclic aryl which may be partially or fully saturated and contains a hetero atom(s) selected from 1 to 4 nitrogen, 1 to 2 oxygen, and/or 1 to 2 sulfur atom(s), 3- to 10-membered mono- or bi-heterocyclic aryl containing a hetero atom(s) selected from 1 to 4 nitrogen, 1 to 2 oxygen, and/or 1 to 2 sulfur atom(s) includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole ring etc.

The 3- to 10-membered mono- or bi-heterocyclic aryl which is partially or fully saturated and contains a hetero atom(s) selected from 1 to 4 nitrogen, 1 to 2 oxygen and/or 1 to 2 sulfur atom(s) includes aziridine, azetidine, azocane, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxー epine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, dioxane, dithiolane, dithiane, dioxaindan, benzodioxane, chroman, benzodithiolane, benzodithiane ring etc.

In the present invention, C3-7 mono-carbocyclic aryl which may be partially or fully saturated includes, for example, cyclopropane, cyclobutane, cyclopentane, cyclohexane, cycloheptane, cyclopentene, cyclohexene, cycloheptene, cyclopentadiene, cyclohexadiene, cycloheptadiene, benzene etc.

In the present invention, among the 3- to 7-membered mono-heterocyclic aryl which may be partially or fully saturated and contains a hetero atom(s) selected from 1 to 4 nitrogen, 1 to 2 oxygen, and/or 1 to 2 sulfur atom(s), 3- to 7-membered mono-heterocyclic aryl containing a hetero atom(s) selected from 1 to 4 nitrogen, 1 to 2 oxygen, and/or 1 to 2 sulfur atom(s) includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine ring etc.

The 3- to 7-membered mono-heterocyclic aryl which is partially or fully saturated and contains a hetero atom(s) selected from 1 to 4 nitrogen, 1 to 2 oxygen and/or 1 to 2 sulfur atom(s) includes aziridine, azetidine, azocane, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane ring etc.

In the present invention, C5 or 6 mono-carbocyclic aryl which may be partially or fully saturated includes, for example, cyclopropane, cyclobutane, cyclopentane, cyclohexane, cycloheptane, cyclopentene, cyclohexene, cycloheptene, cyclopentadiene, cyclohexadiene, cycloheptadiene, benzene etc.

In the present invention, among the 5- or 6-membered mono-heterocyclic aryl which may be partially or fully saturated and contains a hetero atom(s) selected from 1 to 4 nitrogen, 1 to 2 oxygen, and/or 1 to 2 sulfur atom(s), 5- or 6-membered mono-heterocyclic aryl containing a hetero atom(s) selected from 1 to 4 nitrogen, 1 to 2 oxygen, and/or 1 to 2 sulfur atom(s) includes, for example, pyrrole, imidazole, triazole, tetrazole, pyrazole, pyridine, pyrazine, pyrimidine, pyridazine, furan, pyran, thiophene, oxazole, isoxazole, thiazole, isothiazole, furazan, oxadiazole, oxazine, oxadiazine, thiadiazole, thiazine, thiadiazine ring etc.

The 5- or 6-membered mono-heterocyclic aryl which is partially or fully saturated and contains a hetero atom(s) selected from 1 to 4 nitrogen, 1 to 2 oxygen and/or 1 to 2 sulfur atom(s) includes pyrroline, pyrrolidine, imidazoline, imidazolidine, triazoline, triazolidine, tetrazoline, tetrazolidine, pyrazoline, pyrazolidine, piperidine, piperazine, morpholine, thiomorpholine, oxathiane, dioxolane, dioxane, dithiolane, dithiane ring etc.

In the present invention, among the 3- to 15-membered mono-, bi- or tri-heterocyclic aryl which may be partially or fully saturated and contains at least one nitrogen atom and optionally 1 to 2 oxygen, and/or 1 to 2 sulfur atom(s), 3- to 15-membered mono-, bi- or tri-heterocyclic aryl containing at least one nitrogen atom and optionally 1 to 2 oxygen, and/or 1 to 2 sulfur atom(s) includes, for example, pyrrole, imidazole, triazole, tetrazole, pyrazole, indazole, purine, benzimidazole, benzazepine, benzotriazole, carbazole, β-carboline, phenothiazine, phenoxazine, perimidine etc.

The 3- to 15-membered mono-, bi- or tri-heterocyclic aryl which is partially or fully saturated and contains at least one nitrogen atom and optionally 1 to 2 oxygen, and/or 1 to 2 sulfur atom(s) includes aziridine, azetidine, azocane, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, dihydrobenzoxazepine, tetrahydrobenzoxazepine, dihydrocarbazole, tetrahydrocarbazole, perhydrocarbazole, dihydroacridine, tetrahydroacridine, perhydroacridine etc.

In the present invention, among the 5- to 7-membered mono-heterocyclic aryl which may be partially or fully saturated and contains at least one nitrogen atom and optionally 1 to 2 oxygen, and/or 1 to 2 sulfur atom(s), 5- to 7-membered mono-heterocyclic aryl containing at least one nitrogen atom and optionally 1 to 2 oxygen, and/or 1 to 2 sulfur atom(s) includes, for example, pyrrole, imidazole, triazole, tetrazole, pyrazole etc.

The 5- to 7-membered mono-heterocyclic aryl which is partially or fully saturated and contains at least one nitrogen atom and optionally 1 to 2 oxygen, and/or 1 to 2 sulfur atom(s) includes pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine etc.

Unless otherwise specified, all isomers are included in the present invention. For example, alkyl, alkenyl, alkynyl, alkoxy, alkylthio, alkylene, alkenylene, alkynylene group includes straight or branched ones. In addition, isomers on double bond, ring, fused ring (E-, Z-, cis-, trans-isomer), isomers generated from asymmetric carbon atom(s) (R—, S—, α-, β-isomer, enantiomer, diastereomer), optically active isomers (D-, L-, d-, l-isomer), polar compounds generated by chromatographic separation (more polar compound, less polar compound), equilibrium compounds, rotamer, mixtures thereof at voluntary ratios and racemic mixtures are also included in the present invention.

According to the present invention, unless otherwise indicated and as is apparent for those skilled in the art, symbol  indicates that it is bound to the opposite side of the sheet (namely α-configuration), symbol  indicates that it is bound to the front side of the sheet (namely α-configuration), symbol  indicates that it is α-configuration, β-configuration or a mixture thereof, and symbol  indicates that it is a mixture of α-configuration and β-configuration.

The compound represented by formula (I) can be converted into a pharmaceutically acceptable salt by known methods.

A pharmaceutically acceptable salt includes salt of alkali metal, salt of alkaline earth metal, ammonium salt, amine salt or acid addition salt etc.

The salt is preferably water-soluble. The suitable salt means, for example, salt of alkali metal (potassium, sodium, lithium, etc.), salt of alkaline earth metal (calcium, magnesium, etc.), ammonium salt, pharmaceutically acceptable salt of organic amine (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine, etc.).

The acid addition salt is preferably water-soluble. The suitable acid addition salt means, for example, inorganic acid salt (hydrochloride, hydrobromate, hydroiodate, sulfate, phosphate, nitrate, etc.), or organic acid salt (acetate, lactate, tartrate, benzoate, citrate, methane sulfonate, ethane sulfonate, benzene sulfonate, toluene sulfonate, isethionate, glucuronate, gluconate, etc.), etc.

The compound represented by formula (I) and the salt thereof may be converted solvate.

The solvate is preferably non toxic and water-soluble. The suitable solvate is, for example, solvate of water or alcohol (e.g., ethanol).

The compounds of the present invention represented by formula (I) may be converted into the corresponding cyclodextrin clathrates by the method described in the specification of JP-B-50-3362 corresponding to U.S. Pat. No. 3,816,393, and in the specification of JP-B-52-31404 or 61-52146, the disclosure of each of which is incorporated by reference, using α-, β- or γ-cyclodextrin or a mixture thereof. Converting into the corresponding cyclodextrin clathrates serves to increase the stability and solubility in water of the compounds, and therefore it is useful in the use for pharmaceuticals.

Among the compounds of formula (I), A is preferably $A^1$ or $A^2$, and particularly preferably $A^2$.

Ring1 is preferably C3-10 mono- or bi-carbocyclic aryl which may be partially or fully saturated, or 3- to 10-membered mono- or bi-heterocyclic aryl which may be partially or fully saturated and contains a hetero atom(s) selected from 1 to 4 nitrogen, 1 to 2 oxygen and/or 1 to 2 sulfur atom(s), and particularly preferably C3-7 mono-carbocyclic aryl which may be partially or fully saturated, or 3- to 7-membered mono-heterocyclic aryl which may be partially or fully saturated and contains a hetero atom(s) selected from 1 to 4 nitrogen, 1 to 2 oxygen and/or 1 to 2 sulfur atom(s).

Most preferably, ring1 is C5 or 6 mono-carbocyclic aryl which may be partially or fully saturated, or 5- or 6-membered mono-heterocyclic aryl which may be partially or fully saturated and contains a hetero atom(s) selected from 1 to 4 nitrogen, 1 to 2 oxygen and/or 1 to 2 sulfur atom(s), and furan, thiophene, oxazole or benzene is most preferable of all them.

Among the compounds of formula (I), D is preferably $D^1$ or $D^2$ and particularly preferably $D^1$.

$D^1$ is preferably —COOH or —COOR$^2$.

$D^2$ is preferably —COO—$Z^1$—$Z^2$—$Z^3$.

$Z^1$ is preferably C1-15 alkylene, more preferably C1-8 alkylene and particularly preferably C1-4 alkylene.

$Z^2$ is preferably —CO—, —OCO—, —COO—, —CONR$^{Z1}$, —OCONR$^{Z7}$ or —OCOO—, and particularly preferably —OCO—, —OCONR$^{Z7}$ or —OCOO—.

$Z^3$ is preferably C1-15 alkyl or C1-10 alkyl substituted by C1-10 alkoxy, C1-10 alkylthio, C1-10 alkyl-NR$^8$- or ringZ, and particularly preferably C4-12 alkyl.

Among the compounds of formula (I), T is preferably oxygen atom or sulfur atom, and particularly preferably oxygen atom.

Among the compounds of formula (I), X is preferably —CH$_2$—, —O— or —S—, and particularly preferably —CH$_2$—.

Among the compounds of formula (I), E is preferably $E_2$.

Among the compounds of formula (I), preferably compound is a compound represented by formula (I-A):

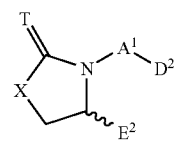
(I-A)

(wherein all symbols have the same meanings as described above.), formula (I-B):

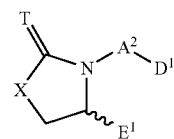
(I-B)

(wherein all symbols have the same meanings as described above.), formula (IC):

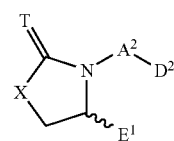
(I-C)

(wherein all symbols have the same meanings as described above.), formula (I-D):

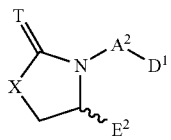
(I-D)

(wherein all symbols have the same meanings as described above.), formula (I-E):

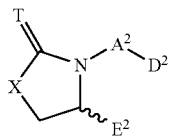
(I-E)

(wherein all symbols have the same meanings as described above.) or formula (I-F):

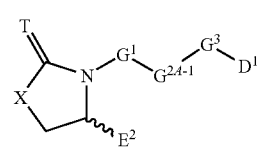
(I-F)

(wherein all symbols have the same meanings as described above.).

Among the compounds of formula (I-A), preferably compound is a compound represented by formula (I-A1):

(I-A1)

(wherein $G^{2A-1}$ is —$Y^a$-ring1-, $Y^a$ is —S—, —SO$_2$—, —O— or —NR$_1$—, and other symbols have the same meanings as described above.).

Among the compounds of formula (I-A), particularly preferably compound is a compound represented by formula (I-A1-a)

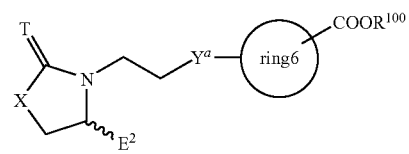
(I-A1-a)

(wherein ring6 is C5 or 6 mono-carbocyclic aryl, or 5- or 6-membered mono-heterocyclic aryl which may be partially or fully saturated and contains a hetero atom(s) selected from 1 to 4 nitrogen, 1 to 2 oxygen, and/or 1 to 2 sulfur atom(s), $R^{100}$ is a hydrogen atom or C1-4 alkyl, and other symbols have the same meanings as described above.).

Ring6 is particularly preferably furan, thiophene, oxazole, thiazole or benzene, and concretely,

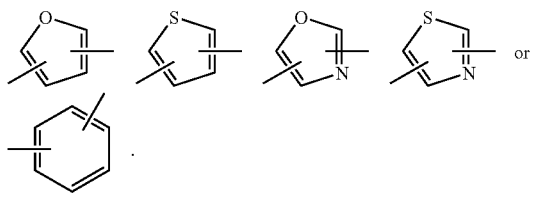

The bonds may bind to any position, if the bonds do not bind to the same carbon atom.

Among the compounds of formula (I-A), most preferably compound is a compound represented by formula (I-A1-a1):

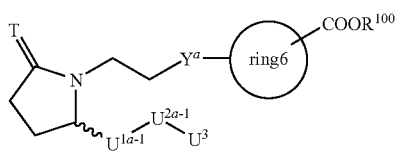

(I-A1-a1)

(wherein, $U^{1a-1}$ is C1-4 alkylene, C2-4 alkenylene or C2-4 alkynylene, $U^{2a-1}$ is —O—, —S—, —SO—, —SO$_2$— or —NR$^{12}$—, and other symbols have the same meanings as described above.). A compound represented by formula (I-a1-1):

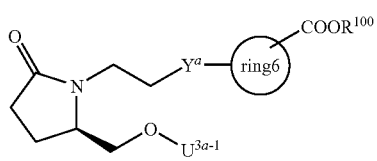

(I-a1-1)

(wherein $U^{3a-1}$ is C1-8 alkylene or ring4, and other symbols have the same meanings as described above.) or a compound represented by formula (I-a1-2):

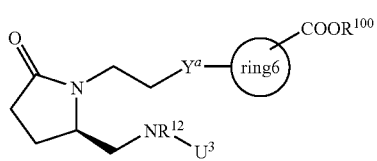

(I-a1-2)

(wherein all symbols have the same meanings as described above.) is most preferable of all them.

Moreover, a compound represented by formula (I-A1-a2):

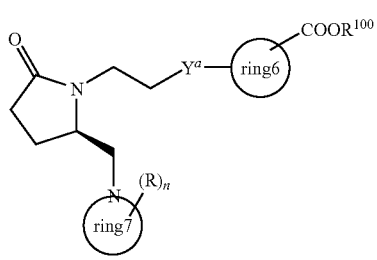

(I-A1-a2)

(wherein ring7 is 3- to 15-membered mono-, bi- or tri-heterocyclic aryl which may be partially or fully saturated and contains at least one nitrogen atom and optionally 1 to 2 oxygen, and/or 1 to 2 sulfur atom(s), n is an integer from 1 to 3. Other symbols have the same meanings as described above.), a compound represented by formula (I-A1-a3):

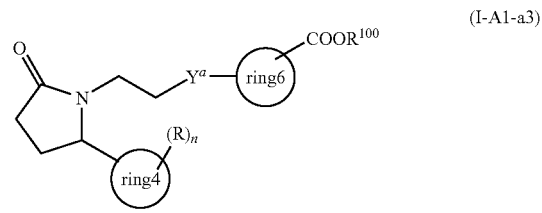

(I-A1-a3)

(wherein all symbols have the same meanings as described above.), or a compound represented by formula (I-A1-a4):

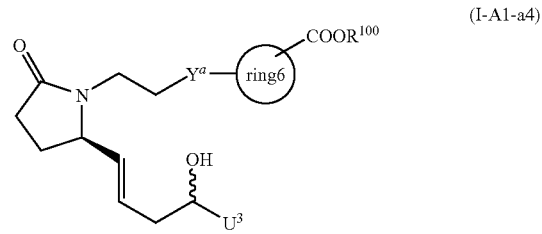

(I-A1-a4)

(wherein all symbols have the same meanings as described above.) is preferable.

Among compounds represented by formula (I-A1-a4), a compound represented by

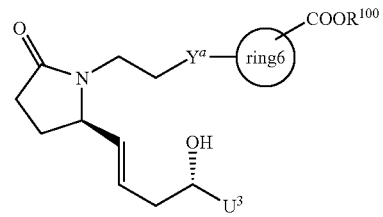

(wherein all symbols have the same meanings as described above.) is particularly preferable.

Particularly preferably, ring7 is 5- to 7-membered mono-heterocyclic aryl which may be partially or fully saturated and contains at least one nitrogen atom and optionally 1 to 2 oxygen, and/or 1 to 2 sulfur atom(s).

Among compounds represented by formula (I-E), a compound represented by formula (I-E1):

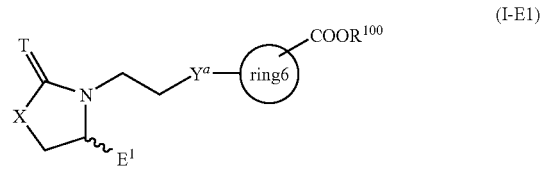

(I-E1)

(wherein all symbols have the same meanings as described above.), or a compound represented by formula (I-E2):

(I-E2)

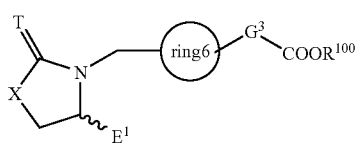

(wherein all symbols have the same meanings as described above.) is preferable.

Moreover, a compound represented by formula (I-F):

(I-F)

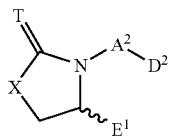

(wherein all symbols have the same meanings as described above.), a compound represented by formula (I-G):

(I-G)

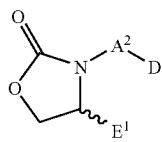

(wherein all symbols have the same meanings as described above.), or a compound represented by formula (I-H):

(I-H)

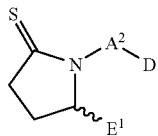

(wherein all symbols have the same meanings as described above.) is preferable.

Among compounds represented by formula (I), compounds represented by formula (Ia-1):

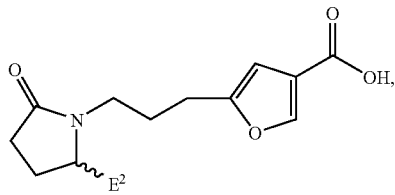

formula (Ia-2):

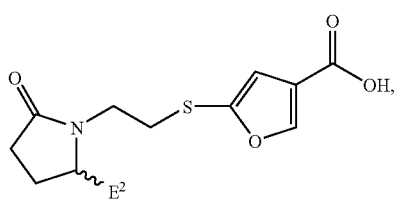

formula (Ia-3):

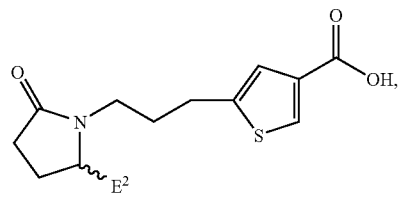

formula (Ia-4):

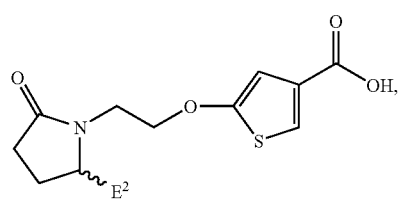

formula (Ia-5):

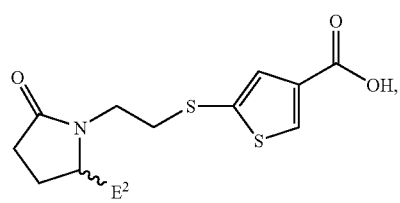

formula (Ia-6):

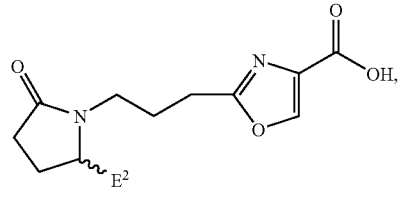

formula (Ia-7):

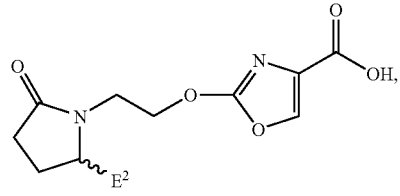

formula (Ia-8):

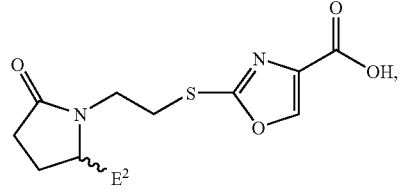

formula (Ia-9):

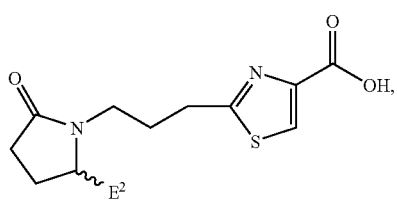

formula (Ia-10):

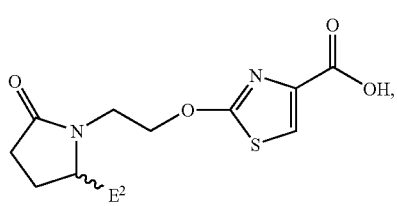

formula (Ia-11):

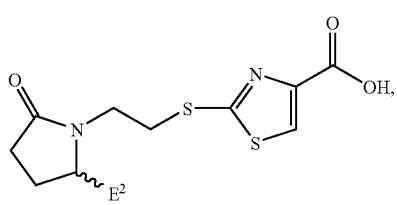

formula (Ia-12):

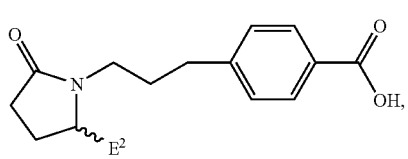

formula (Ia-13):

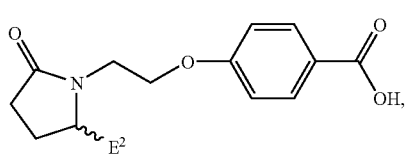

formula (Ia-14):

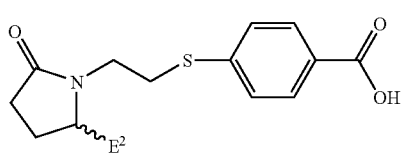

(wherein all symbols have the same meanings as described above.) is particularly preferable.

A compound represented by formula (Ia-15):

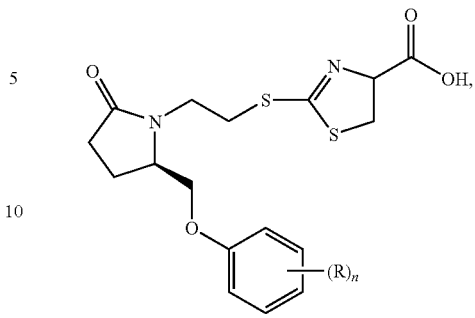

formula (Ia-16):

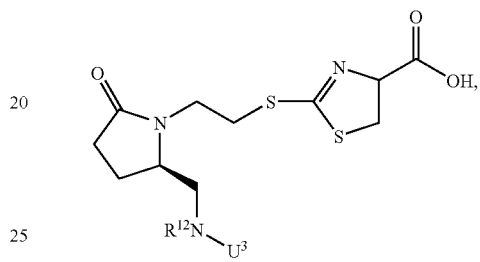

formula (Ia-17):

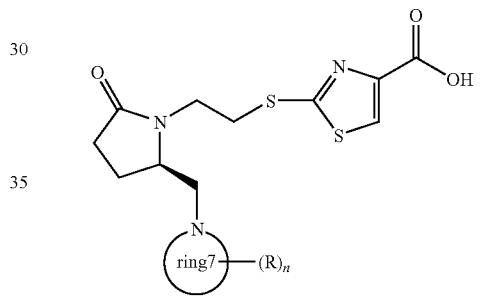

formula (Ia-18):

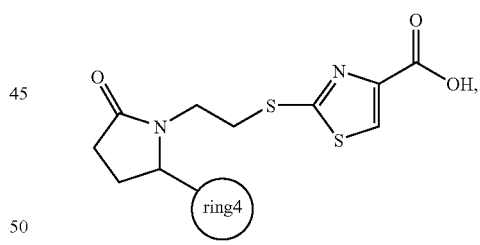

formula (Ia-19):

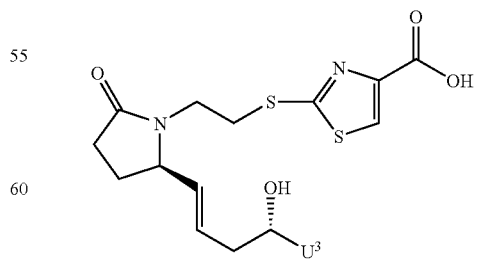

(wherein all symbols have the same meanings as described above.) is most preferable.

As concrete compounds in present invention, compounds in following table to 68, compounds described in Example, and pharmaceutically acceptable salts thereof and cyclodextrin clathrates thereof are given.

TABLE 1

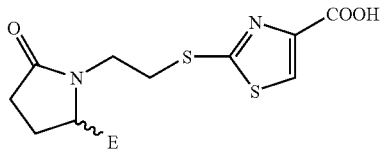

(I-A-1)

| No. | E |
|---|---|
| 1 | —CH=CH—CH₂—CH₂—CH₂—CH₃ |
| 2 | —CH=CH—(CH₂)₄—CH₃ |
| 3 | —CH=CH—(CH₂)₅—CH₃ |
| 4 | —CH=CH—(CH₂)₆—CH₃ |
| 5 | —CH=CH—CH₂—CH₂—C(CH₃)₃ |
| 6 | —CH=CH—CH₂—CH₂—C(CH₃)₂—CH₂—CH₃ |
| 7 | —CH=CH—(CH₂)₄—CH₃ (saturated variant) |
| 8 | —CH=CH—CH₂—CH(OH)—CH₂—CH₃ |
| 9 | —CH=CH—CH₂—C(cyclopropyl)(CH₃) |
| 10 | —CH=CH—CH₂—C(cyclobutyl)(CH₃) |
| 11 | —CH=CH—CH₂—CH₂—C(cyclobutyl)(CH₃) |
| 12 | —CH=CH—CH₂—CH₂—C*(OH)(cyclobutyl)(CH₂CH₃) |

TABLE 1-continued

| No. | E |
|---|---|
| 13 | —CH=CH—CH₂—C*(OH)(cyclobutyl)(CH₂CH₃) |
| 14 | —CH=CH—CH₂—C(=O)—C(cyclobutyl)(CH₂CH₃) |
| 15 | —CH=CH—CH₂—O—C(cyclobutyl)(CH₂CH₃) |
| 16 | —CH=CH—CH₂—O—C(CH₃)₂—CH₃ |
| 17 | —CH=CH—CH₂—O—phenyl |
| 18 | —(o-tolyl) |
| 19 | —(p-tolyl)—CH₂—CH₃ |
| 20 | —(p-tolyl)—CH₂—CH₂—CH₃ |
| 21 | —(p-tolyl)—CH₂—CH₂—CH₂—CH₃ |

TABLE 1-continued
(I-A-1)
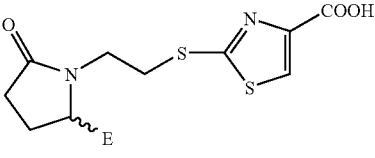
| No. | E |
|-----|---|
| 22 | 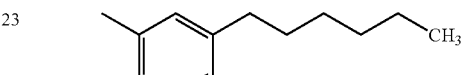 |
| 23 | 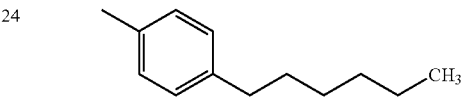 |
| 24 | 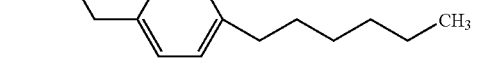 |
| 25 | 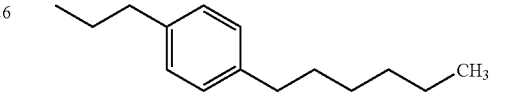 |
| 26 | 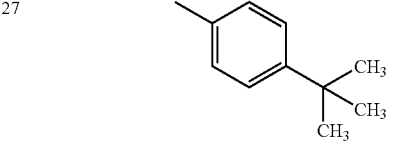 |
| 27 | 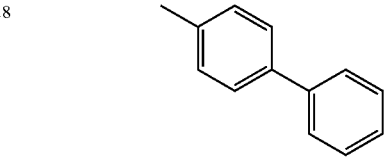 |
| 28 | 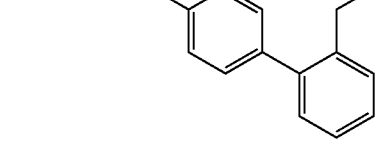 |
| 29 | 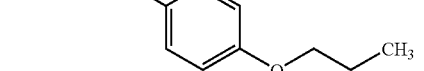 |
| 30 | 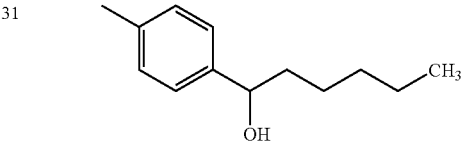 |
| 31 | 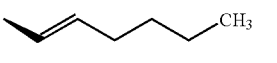 |
TABLE 2
(I-A-2)
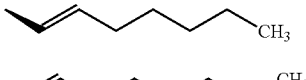
| No. | E |
|-----|---|
| 1 | 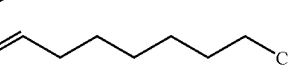 |
| 2 | 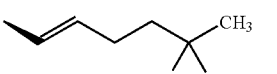 |
| 3 | 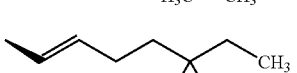 |
| 4 | 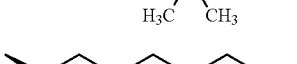 |
| 5 | 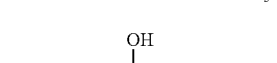 |
| 6 | 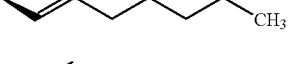 |
| 7 | 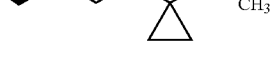 |
| 8 | 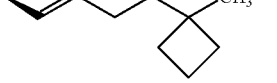 |
| 9 | 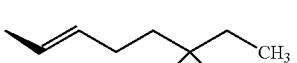 |
| 10 | 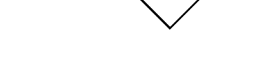 |
| 11 | 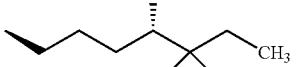 |
| 12 | 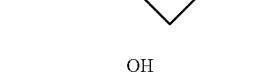 |
| 13 |  |
| 14 |  |

TABLE 2-continued (I-A-2)

| No. | E |
|---|---|
| 15 | allyl-O-C(ethyl)(cyclobutyl) |
| 16 | allyl-O-C(CH3)3 |
| 17 | allyl-O-phenyl |
| 18 | phenyl |
| 19 | 4-ethylphenyl (with methyl) |
| 20 | 4-propylphenyl (with methyl) |
| 21 | 4-butylphenyl (with methyl) |
| 22 | 4-pentylphenyl (with methyl) |
| 23 | 3-hexylphenyl (with methyl) |
| 24 | 4-hexylphenyl (with methyl) |
| 25 | 4-hexyl-2-ethylphenyl |
| 26 | 4-hexyl-2-propylphenyl |
| 27 | 4-tert-butylphenyl (with methyl) |
| 28 | 4'-methylbiphenyl |
| 29 | 2'-(hydroxymethyl)-4'-methylbiphenyl |
| 30 | 4-propoxyphenyl (with methyl) |
| 31 | 4-(1-hydroxypentyl)phenyl (with methyl) |

TABLE 3

(I-A-3)

| No. | E |
|---|---|
| 1 | pentenyl chain |
| 2 | hexenyl chain |
| 3 | heptenyl chain |
| 4 | octenyl chain |

TABLE 3-continued
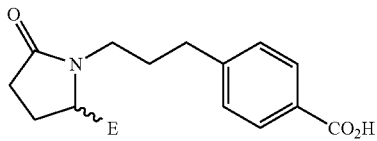
(I-A-3)
| No. | E |
|---|---|
| 5 | 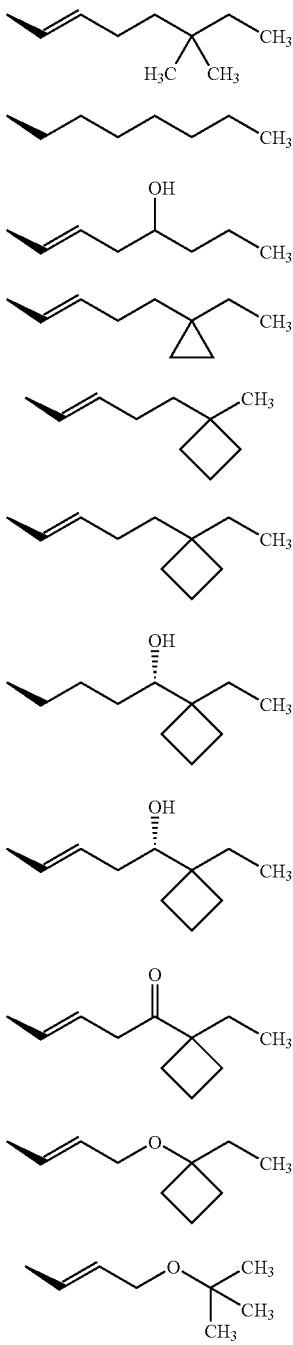 |
| 6 | 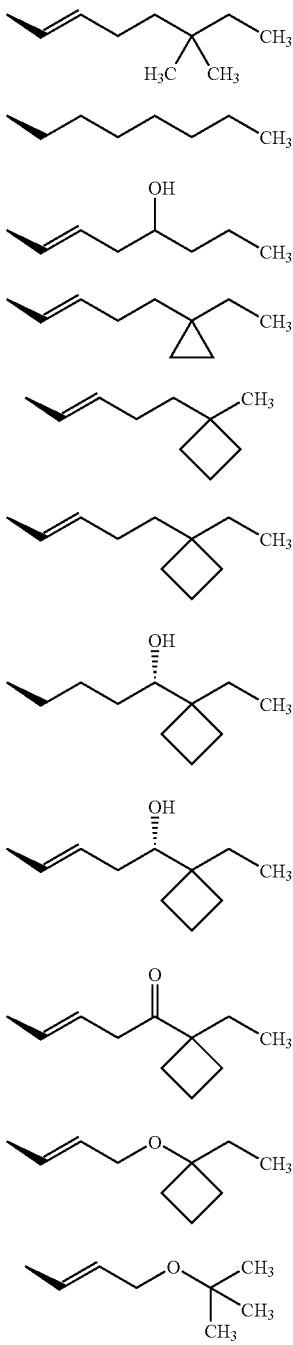 |
| 7 | 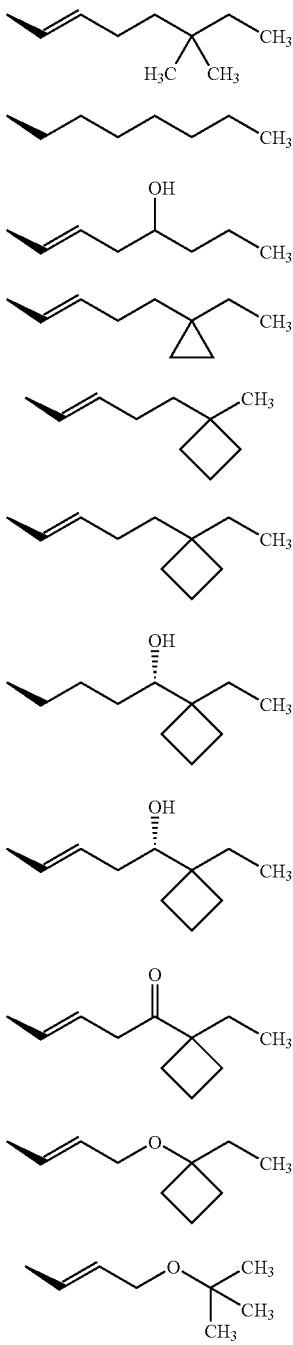 |
| 8 | 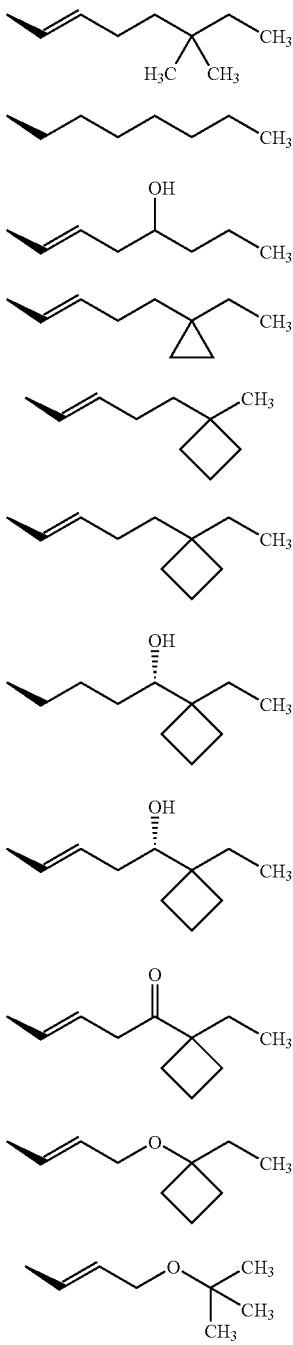 |
| 9 | 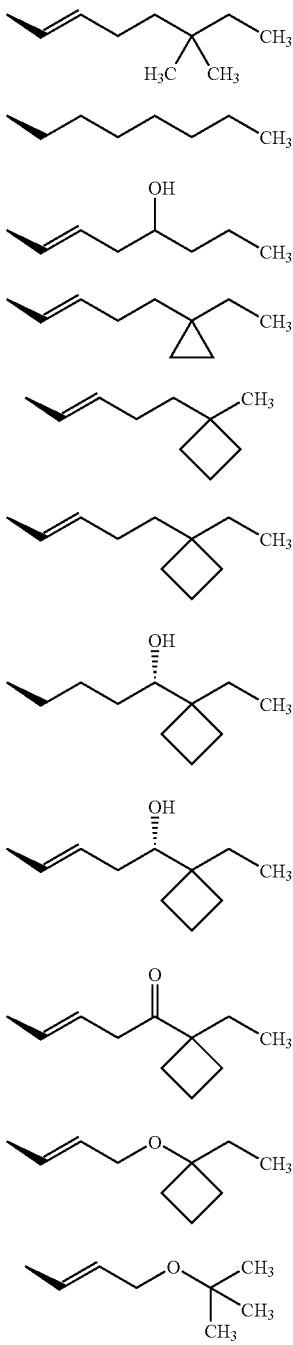 |
| 10 | 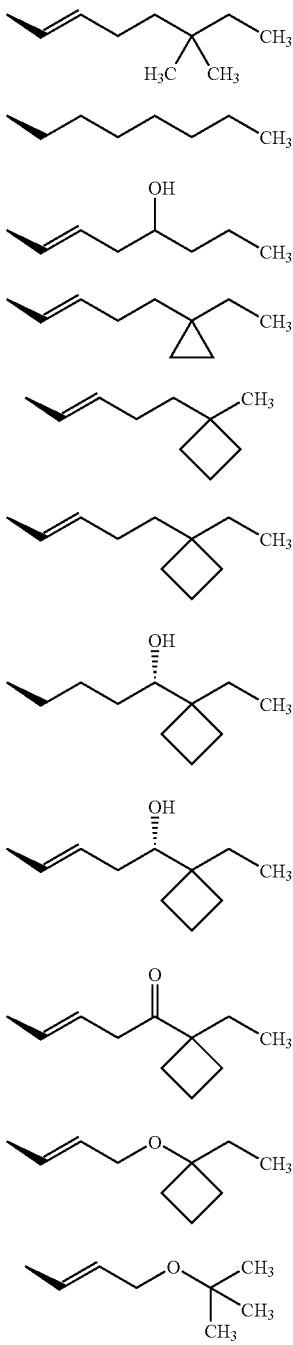 |
| 11 | 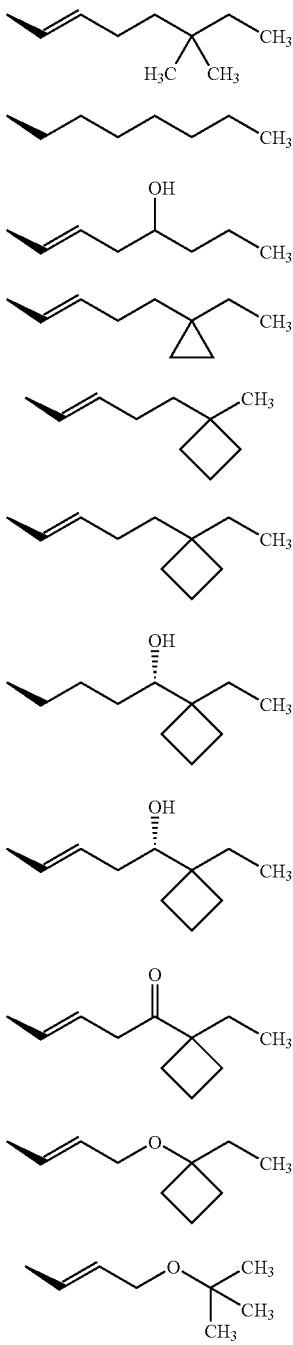 |
| 12 | 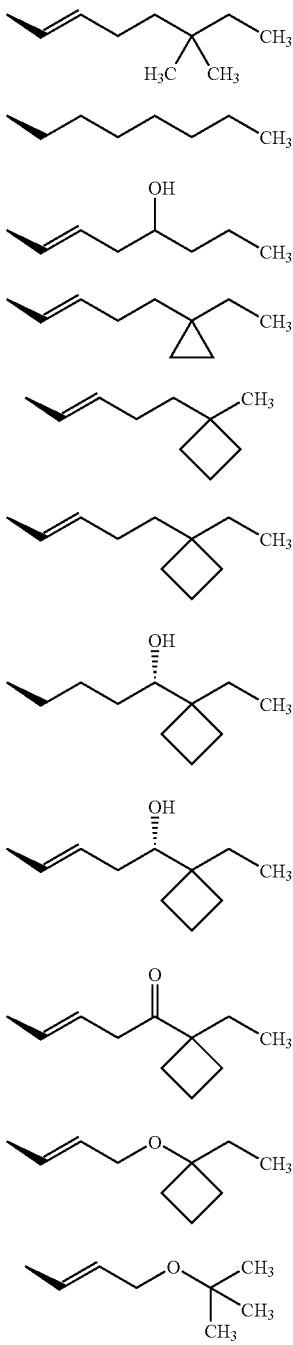 |
| 13 | 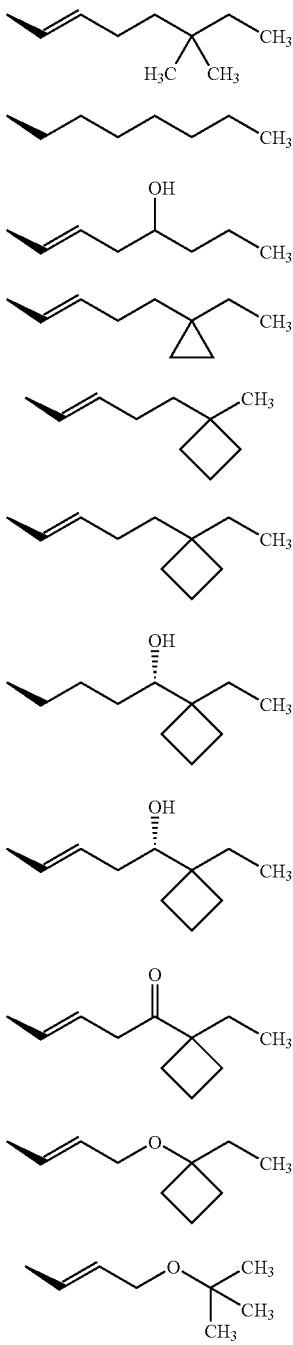 |
| 14 | 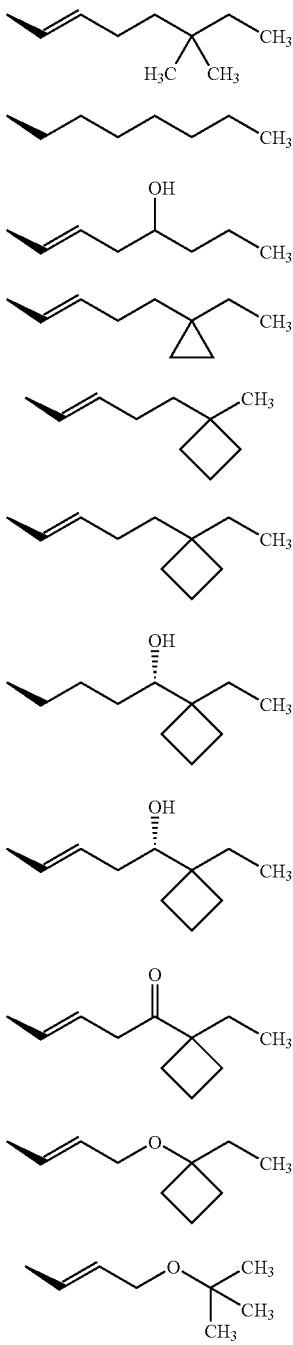 |
| 15 | 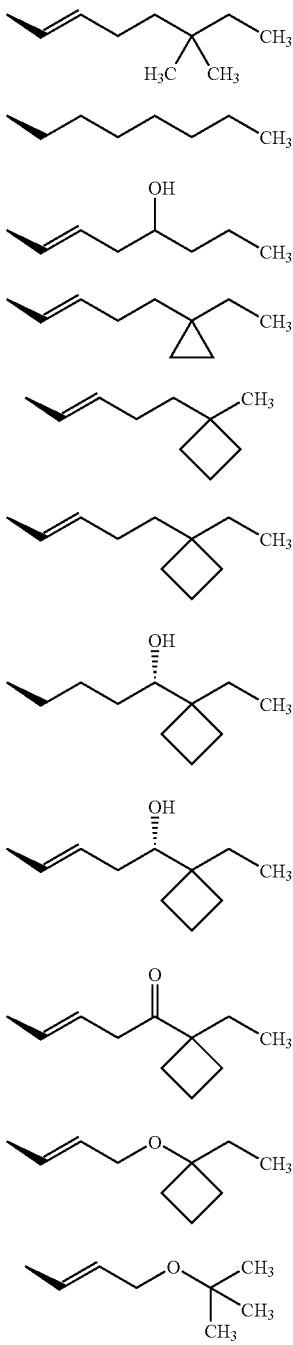 |
| 16 | 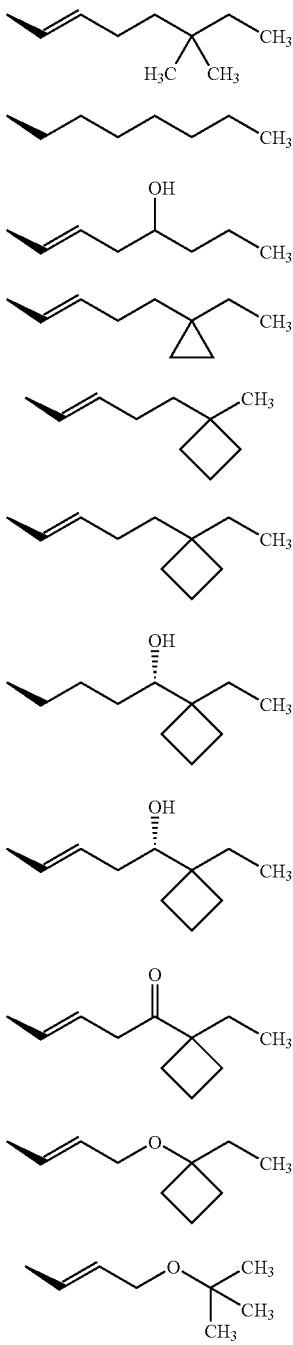 |
TABLE 3-continued
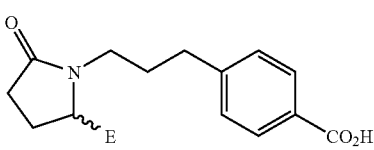
(I-A-3)
| No. | E |
|---|---|
| 17 | 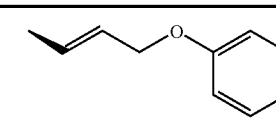 |
| 18 | 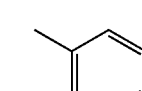 |
| 19 | 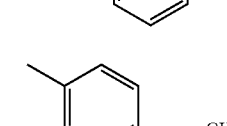 |
| 20 | 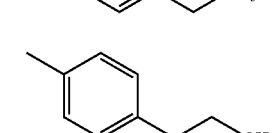 |
| 21 | 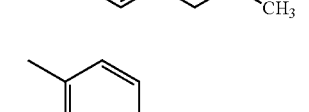 |
| 22 | 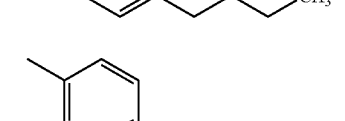 |
| 23 | 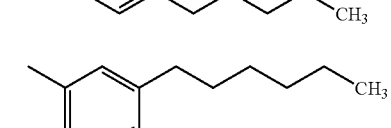 |
| 24 |  |
| 25 | 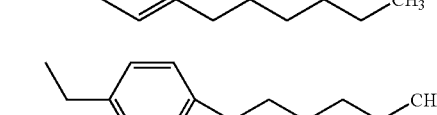 |
| 26 | 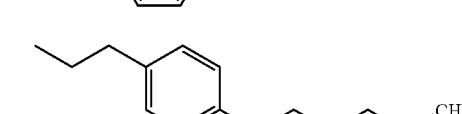 |
| 27 | 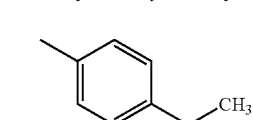 |

TABLE 3-continued
(I-A-3)
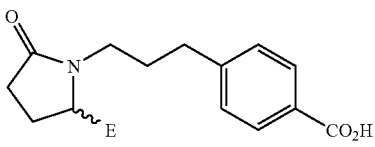
| No. | E |
|---|---|
| 28 | 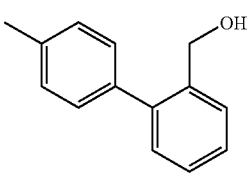 |
| 29 | 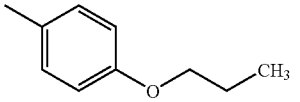 |
| 30 | 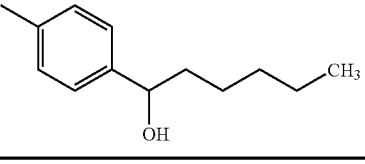 |
| 31 | 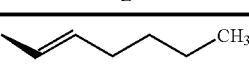 |
TABLE 4
(I-A-4)
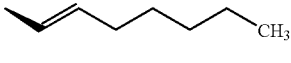
| No. | E |
|---|---|
| 1 | 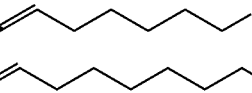 |
| 2 | 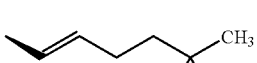 |
| 3 | 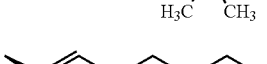 |
| 4 | 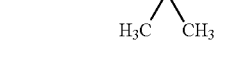 |
| 5 |  |
| 6 | 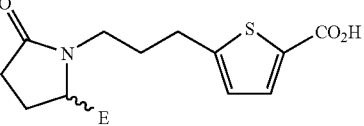 |
| 7 | 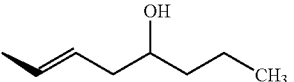 |
TABLE 4-continued
(I-A-4)
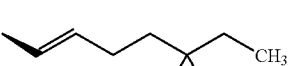
| No. | E |
|---|---|
| 8 | 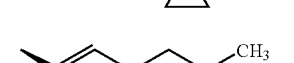 |
| 9 |  |
| 10 | 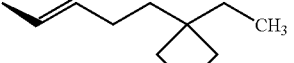 |
| 11 | 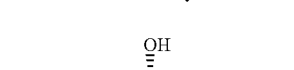 |
| 12 | 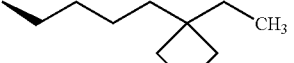 |
| 13 | 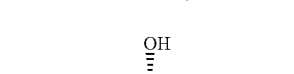 |
| 14 | 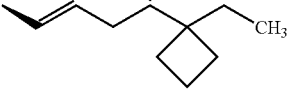 |
| 15 | 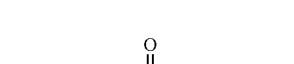 |
| 16 | 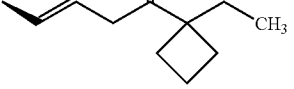 |
| 17 | |
| 18 | |

TABLE 4-continued (I-A-4)

| No. | E |
|---|---|
| 19 | 4-ethylphenyl |
| 20 | 4-propylphenyl |
| 21 | 4-butylphenyl |
| 22 | 4-pentylphenyl |
| 23 | 3-hexylphenyl |
| 24 | 4-hexylphenyl |
| 25 | 4-ethyl, 4'-hexylphenyl |
| 26 | 4-propyl, 4'-hexylphenyl |
| 27 | 4-tert-butylphenyl |
| 28 | 4-biphenyl |
| 29 | 2-(hydroxymethyl)biphenyl-4-yl |
| 30 | 4-(propoxy)phenyl |
| 31 | 4-(1-hydroxyhexyl)phenyl |

TABLE 5

(I-A-5)

| No. | E |
|---|---|
| 1 | hex-1-enyl |
| 2 | hept-1-enyl |
| 3 | oct-1-enyl |
| 4 | non-1-enyl |
| 5 | 5,5-dimethylhex-1-enyl |
| 6 | 5-ethyl-5-methylhept-1-enyl |
| 7 | oct-1-enyl (branched) |
| 8 | 4-hydroxyhept-1-enyl |
| 9 | 4-(1-ethylcyclopropyl)but-1-enyl |
| 10 | 4-(1-methylcyclobutyl)but-1-enyl |

TABLE 5-continued
(I-A-5)
| No. | E |
|---|---|
| 11 | 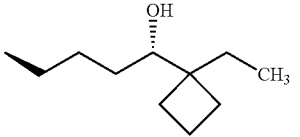 |
| 12 | 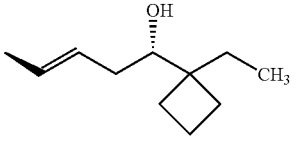 |
| 13 | 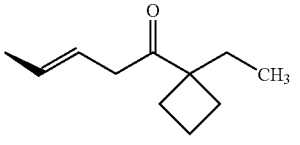 |
| 14 | 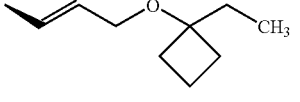 |
| 15 | 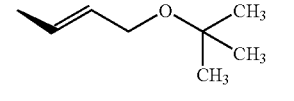 |
| 16 | 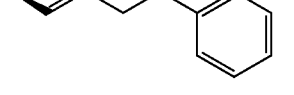 |
| 17 | 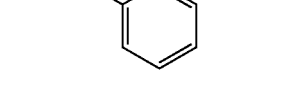 |
| 18 | 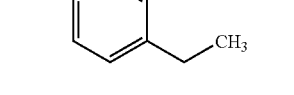 |
| 19 | 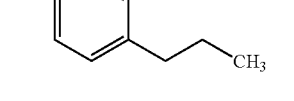 |
| 20 | 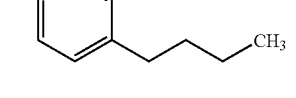 |
| 21 | 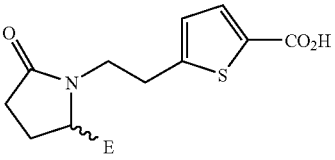 |
TABLE 5-continued
(I-A-5)
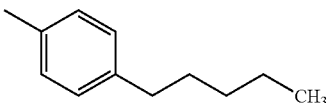
| No. | E |
|---|---|
| 22 | 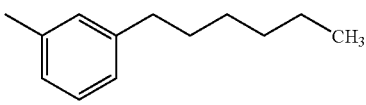 |
| 23 | 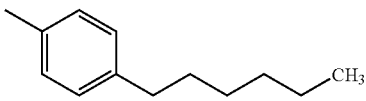 |
| 24 | 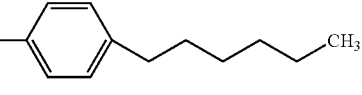 |
| 25 | 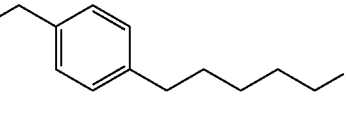 |
| 26 | 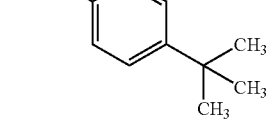 |
| 27 | 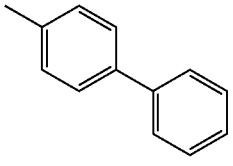 |
| 28 | 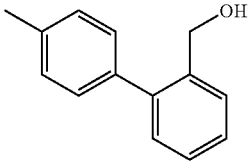 |
| 29 | 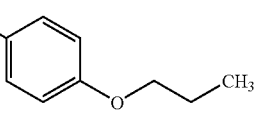 |
| 30 | 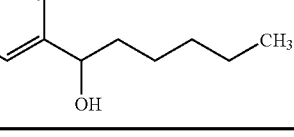 |
| 31 |  |

TABLE 6

(I-A-6)

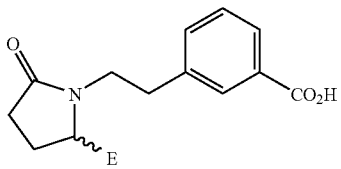

| No. | E |
|---|---|
| 1 | CH=CH-CH2CH2CH2CH3 |
| 2 | CH=CH-(CH2)4CH3 |
| 3 | CH=CH-(CH2)5CH3 |
| 4 | CH=CH-(CH2)6CH3 |
| 5 | CH=CH-CH2CH2C(CH3)3 |
| 6 | CH=CH-CH2CH2C(CH3)2C2H5 |
| 7 | CH=CH-(CH2)4CH3 |
| 8 | CH=CH-CH2CH(OH)CH2CH3 |
| 9 | CH=CH-CH2-C(cyclopropyl)(C2H5) |
| 10 | CH=CH-CH2-C(cyclobutyl)(CH3) |
| 11 | CH=CH-CH2-C(cyclobutyl)(C2H5) |
| 12 | CH2-CH2CH2-C(OH)(cyclobutyl)(C2H5) |
| 13 | CH=CH-CH2-C(OH)(cyclobutyl)(C2H5) |
| 14 | CH=CH-CH2-C(=O)-C(cyclobutyl)(CH3) |

TABLE 6-continued (I-A-6)

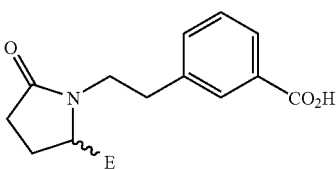

| No. | E |
|---|---|
| 15 | CH=CH-CH2-O-C(cyclobutyl)(C2H5) |
| 16 | CH=CH-CH2-O-C(CH3)3 |
| 17 | CH=CH-CH2-O-phenyl |
| 18 | phenyl |
| 19 | 4-methylphenyl-CH3 |
| 20 | 4-methylphenyl-C2H5 (propyl) |
| 21 | 4-methylphenyl-(CH2)3CH3 |
| 22 | 4-methylphenyl-(CH2)4CH3 |
| 23 | 3-methylphenyl-(CH2)5CH3 |
| 24 | 4-methylphenyl-(CH2)5CH3 |
| 25 | 4-ethylphenyl-(CH2)5CH3 |
| 26 | 4-propylphenyl-(CH2)5CH3 |

TABLE 6-continued (I-A-6)

| No. | E |
|---|---|
| 27 | 4-tert-butylphenyl |
| 28 | 4-phenylphenyl (biphenyl) |
| 29 | 2'-(hydroxymethyl)biphenyl-4-yl |
| 30 | 4-propoxyphenyl |
| 31 | 4-(1-hydroxyhexyl)phenyl |

TABLE 7

(I-A-7)

| No. | E |
|---|---|
| 1 | (E)-hex-1-en-1-yl |
| 2 | (E)-hept-1-en-1-yl |
| 3 | (E)-oct-1-en-1-yl |
| 4 | (E)-non-1-en-1-yl |
| 5 | (E)-5,5-dimethylhex-1-en-1-yl |
| 6 | (E)-5-ethyl-5-methylhept-1-en-1-yl |
| 7 | (E)-oct-1-en-1-yl |
| 8 | (E)-5-hydroxyhept-1-en-1-yl |
| 9 | (E)-3-(1-ethylcyclopropyl)prop-1-en-1-yl |
| 10 | (E)-3-(1-methylcyclobutyl)prop-1-en-1-yl |
| 11 | (E)-3-(1-ethylcyclobutyl)prop-1-en-1-yl |
| 12 | (R)-1-(1-ethylcyclobutyl)pentyl (OH) |
| 13 | (E,R)-4-(1-ethylcyclobutyl)-4-hydroxybut-2-en-1-yl |
| 14 | (E)-4-(1-ethylcyclobutyl)-4-oxobut-2-en-1-yl |
| 15 | (E)-3-((1-ethylcyclobutyl)oxy)prop-1-en-1-yl |
| 16 | (E)-3-tert-butoxyprop-1-en-1-yl |

TABLE 7-continued (I-A-7)

| No. | E |
|---|---|
| 17 | (cinnamyl phenyl ether group) |
| 18 | 4-methylphenyl |
| 19 | 4-ethylphenyl (with CH₃ para) |
| 20 | 4-propylphenyl |
| 21 | 4-butylphenyl |
| 22 | 4-pentylphenyl |
| 23 | 3-hexylphenyl |
| 24 | 4-hexylphenyl |
| 25 | 4-ethyl, hexyl phenyl |
| 26 | 4-propyl, hexyl phenyl |
| 27 | 4-tert-butylphenyl |

TABLE 7-continued (I-A-7)

| No. | E |
|---|---|
| 28 | 4-methylbiphenyl |
| 29 | 4'-methyl-2-(hydroxymethyl)biphenyl |
| 30 | 4-methylphenyl propyl ether |
| 31 | 1-(4-methylphenyl)-1-hydroxyhexyl |

TABLE 8

(I-A-8)

| No. | E |
|---|---|
| 1 | hexenyl |
| 2 | heptenyl |
| 3 | octenyl |
| 4 | nonenyl |
| 5 | (neopentyl)pentenyl |
| 6 | (neopentyl)hexenyl |

TABLE 8-continued (I-A-8)

[Structure: 2-oxopyrrolidine N-substituted with ethylene linker to thiazole-5-carboxylic acid; 5-position of pyrrolidinone bears substituent E]

| No. | E |
|---|---|
| 7 | –CH=CH–CH2CH2CH2CH2CH3 (hept-1-enyl) |
| 8 | –CH=CH–CH2–CH(OH)–CH2CH3 |
| 9 | –CH=CH–CH2–C(cyclopropyl)(CH3)– (1-methylcyclopropyl substituted) |
| 10 | –CH=CH–CH2–C(cyclobutyl)(CH3) |
| 11 | –CH=CH–CH2–C(cyclobutyl)(CH2CH3) |
| 12 | –CH2CH2CH2–C(OH)(cyclobutyl)(CH2CH3) (with stereochemistry) |
| 13 | –CH=CH–CH2–C(OH)(cyclobutyl)(CH2CH3) (with stereochemistry) |
| 14 | –CH=CH–CH2–C(=O)–C(cyclobutyl)(CH2CH3) |
| 15 | –CH=CH–CH2–O–C(cyclobutyl)(CH2CH3) |
| 16 | –CH=CH–CH2–O–C(CH3)2–CH3 |
| 17 | –CH=CH–CH2–O–phenyl |
| 18 | phenyl |
| 19 | 4-methylphenyl-CH2– (4-methylbenzyl) |
| 20 | 4-methylphenyl-CH2CH3 |
| 21 | 4-methylphenyl-(CH2)3CH3 |
| 22 | 4-methylphenyl-(CH2)4CH3 |
| 23 | 3-methylphenyl-(CH2)5CH3 |
| 24 | 4-methylphenyl-(CH2)5CH3 |
| 25 | 4-ethylphenyl-(CH2)5CH3 |
| 26 | 4-propylphenyl-(CH2)5CH3 |
| 27 | 5-methyl-2-thienyl-C(CH3)3 (tert-butyl on thiophene) |
| 28 | 4-methylbiphenyl |
| 29 | 4-methyl-2'-(hydroxymethyl)biphenyl |

TABLE 8-continued (I-A-8)

| No. | E |
|---|---|
| 30 | 4-propoxyphenyl-methyl |
| 31 | 4-(1-hydroxypentyl)phenyl-methyl |

TABLE 9

(I-A-9)

| No. | E |
|---|---|
| 1 | pent-1-enyl-pentyl chain |
| 2 | hex-1-enyl chain |
| 3 | hept-1-enyl chain |
| 4 | oct-1-enyl chain |
| 5 | 5,5-dimethylhex-1-enyl |
| 6 | 4,4-dimethylhex-1-enyl |
| 7 | hept-1-enyl |
| 8 | 4-hydroxyhept-1-enyl |
| 9 | 3-(1-ethylcyclopropyl)prop-1-enyl |
| 10 | 3-(1-methylcyclobutyl)prop-1-enyl |

TABLE 9-continued (I-A-9)

| No. | E |
|---|---|
| 11 | 3-(1-ethylcyclobutyl)prop-1-enyl |
| 12 | (S)-3-(1-ethylcyclobutyl)-3-hydroxyprop...  |
| 13 | (S)-hydroxy-(1-ethylcyclobutyl)prop-1-enyl |
| 14 | 3-(1-ethylcyclobutyl)-3-oxoprop-1-enyl |
| 15 | 3-(1-ethylcyclobutoxy)prop-1-enyl |
| 16 | 3-tert-butoxyprop-1-enyl |
| 17 | 3-phenoxyprop-1-enyl |
| 18 | benzyl |
| 19 | 4-methylphenyl-ethyl |
| 20 | 4-methylphenyl-propyl |
| 21 | 4-methylphenyl-butyl |

TABLE 9-continued (I-A-9)

Structure: pyrrolidinone-N-CH2CH2CH2-oxazole-COOH with E substituent on pyrrolidinone ring

| No. | E |
|-----|---|
| 22 | 4-pentylphenyl |
| 23 | 3-hexylphenyl |
| 24 | 4-hexylphenyl |
| 25 | 4-hexyl-(ethyl)phenyl |
| 26 | 4-hexyl-(propyl)phenyl |
| 27 | 4-tert-butylphenyl |
| 28 | biphenyl-4-yl |
| 29 | 2'-(hydroxymethyl)biphenyl-4-yl |
| 30 | 4-propoxyphenyl |
| 31 | 4-(1-hydroxypentyl)phenyl |

TABLE 10

(I-A-10)

Structure: pyrrolidinone-N-CH2CH2-thiazole-CO2H with E substituent on pyrrolidinone ring

| No. | E |
|-----|---|
| 1 | (E)-pent-1-enyl |
| 2 | (E)-hex-1-enyl |
| 3 | (E)-hept-1-enyl |
| 4 | (E)-oct-1-enyl |
| 5 | (E)-4,4-dimethylpent-1-enyl |
| 6 | (E)-4-ethyl-4-methylhex-1-enyl |
| 7 | hexyl |
| 8 | (E)-4-hydroxyhex-1-enyl |
| 9 | (E)-3-(1-ethylcyclopropyl)prop-1-enyl |
| 10 | (E)-3-(1-methylcyclobutyl)prop-1-enyl |
| 11 | (E)-3-(1-ethylcyclobutyl)prop-1-enyl |
| 12 | (R)-1-(1-ethylcyclobutyl)-1-hydroxybutyl |
| 13 | (E,R)-4-(1-ethylcyclobutyl)-4-hydroxybut-1-enyl |
| 14 | (E)-4-(1-ethylcyclobutyl)-4-oxobut-1-enyl |

TABLE 10-continued
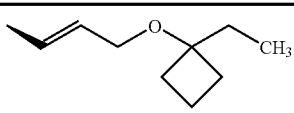
(I-A-10)
| No. | E |
|---|---|
| 15 | 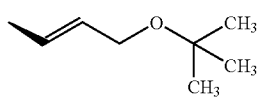 |
| 16 | 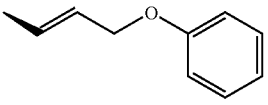 |
| 17 | 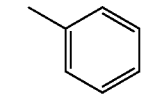 |
| 18 | 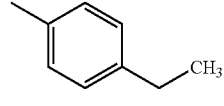 |
| 19 | 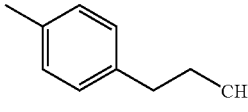 |
| 20 | 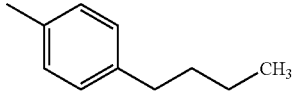 |
| 21 | 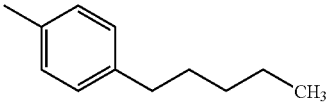 |
| 22 | 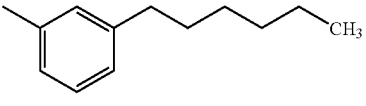 |
| 23 | 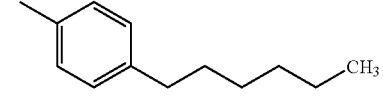 |
| 24 | 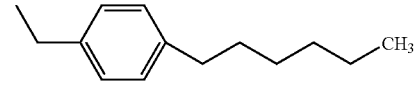 |
| 25 | 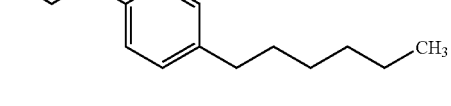 |
| 26 | 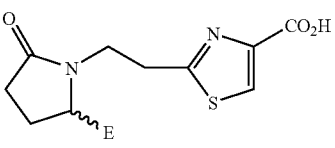 |
TABLE 10-continued
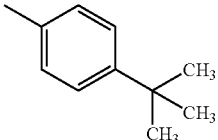
(I-A-10)
| No. | E |
|---|---|
| 27 | 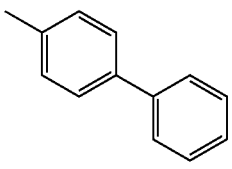 |
| 28 | 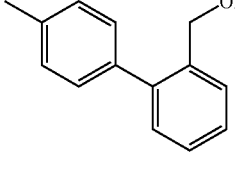 |
| 29 | 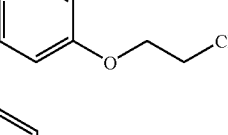 |
| 30 | 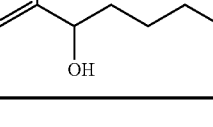 |
| 31 | 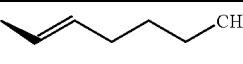 |
TABLE 11
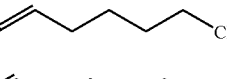
(I-A-11)
| No. | E |
|---|---|
| 1 | 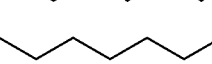 |
| 2 |  |
| 3 | |
| 4 | |

TABLE 11-continued
(I-A-11)
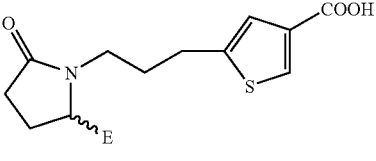
| No. | E |
|---|---|
| 5 | 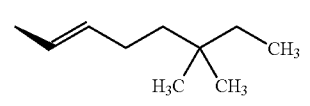 |
| 6 | 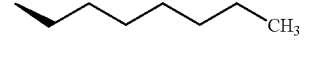 |
| 7 | 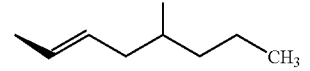 |
| 8 | 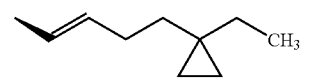 |
| 9 | 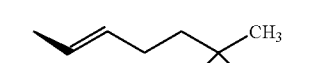 |
| 10 |  |
| 11 | 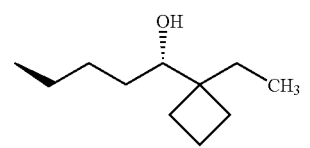 |
| 12 | 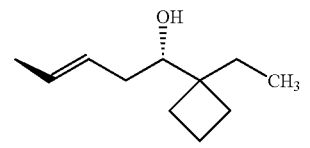 |
| 13 | 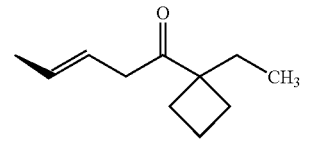 |
| 14 | 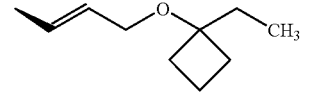 |
| 15 | 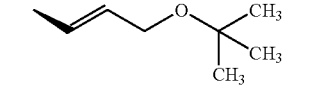 |
| 16 | 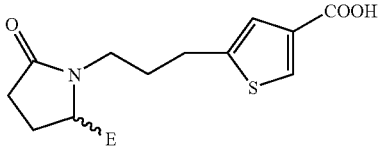 |
TABLE 11-continued
(I-A-11)
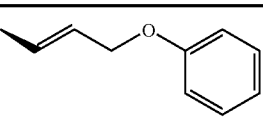
| No. | E |
|---|---|
| 17 | 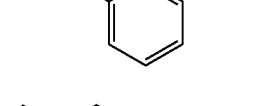 |
| 18 | 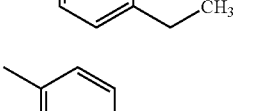 |
| 19 | 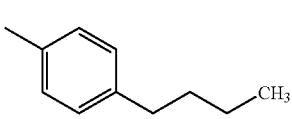 |
| 20 | 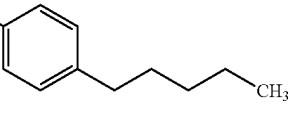 |
| 21 |  |
| 22 | 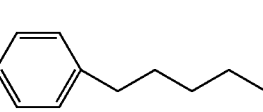 |
| 23 | 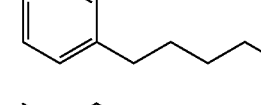 |
| 24 | 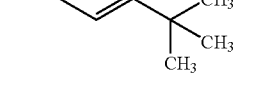 |
| 25 |  |
| 26 |  |
| 27 |  |

TABLE 11-continued
(I-A-11)
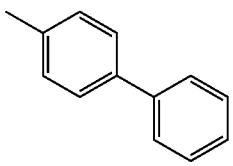
| No. | E |
|---|---|
| 28 | 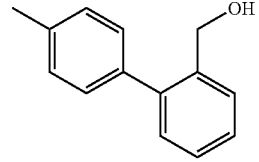 |
| 29 | 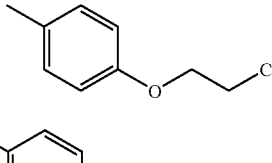 |
| 30 | 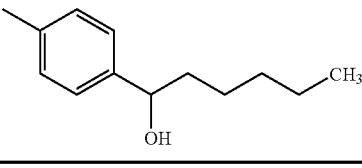 |
| 31 | 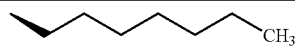 |
TABLE 12
(I-A-12)
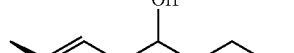
| No. | E |
|---|---|
| 1 | 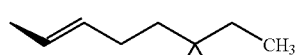 |
| 2 | 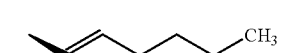 |
| 3 |  |
| 4 | 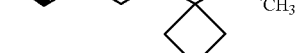 |
| 5 | 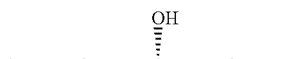 |
| 6 |  |
TABLE 12-continued
(I-A-12)
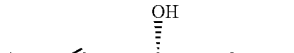
| No. | E |
|---|---|
| 7 | 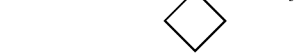 |
| 8 | 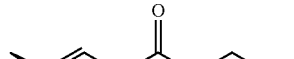 |
| 9 | 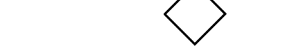 |
| 10 |  |
| 11 | 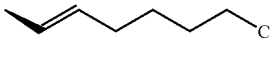 |
| 12 | 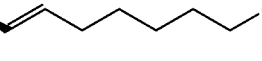 |
| 13 | 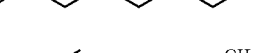 |
| 14 | 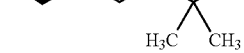 |
| 15 | 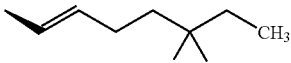 |
| 16 | |
| 17 | |
| 18 | |

TABLE 12-continued (I-A-12)

| No. | E |
|---|---|
| 19 | 4-ethylphenyl (4-methyl attachment, ethyl substituent) |
| 20 | 4-propylphenyl |
| 21 | 4-butylphenyl |
| 22 | 4-pentylphenyl |
| 23 | 3-hexylphenyl |
| 24 | 4-hexylphenyl |
| 25 | 4-ethyl, 4-hexyl phenyl (2-ethyl-hexyl substituted) |
| 26 | propyl-phenyl-hexyl |
| 27 | 4-tert-butylphenyl |
| 28 | 4-phenylphenyl (biphenyl) |
| 29 | biphenyl-2-methanol |
| 30 | 4-methylphenoxy-propyl |
| 31 | 1-(4-methylphenyl)-1-hydroxy-pentyl |

TABLE 13

(I-A-13)

| No. | E |
|---|---|
| 1 | CH=CH-CH2-CH2-CH3 |
| 2 | CH=CH-CH2-CH2-CH2-CH3 |
| 3 | CH=CH-(CH2)4-CH3 |
| 4 | CH=CH-(CH2)5-CH3 |
| 5 | CH=CH-CH2-C(CH3)3 |
| 6 | CH=CH-CH2-C(CH3)2-CH2CH3 |
| 7 | CH2-(CH2)4-CH3 |
| 8 | CH=CH-CH(OH)-CH2-CH2-CH3 |
| 9 | CH=CH-CH2-C(ethyl)(cyclopropyl) |
| 10 | CH=CH-CH2-C(CH3)(cyclobutyl) |

TABLE 13-continued
(I-A-13)
| No. | E |
|-----|---|
| 11 | 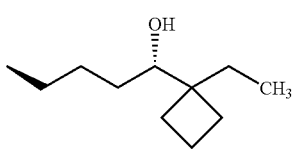 |
| 12 | 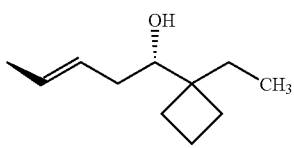 |
| 13 | 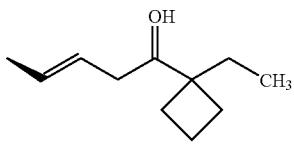 |
| 14 | 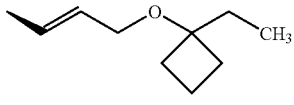 |
| 15 | 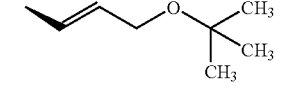 |
| 16 | 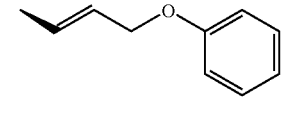 |
| 17 | 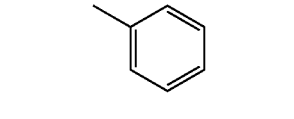 |
| 18 | 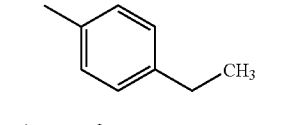 |
| 19 | 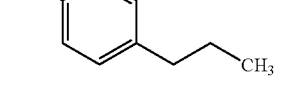 |
| 20 | 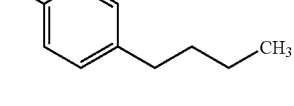 |
| 21 | 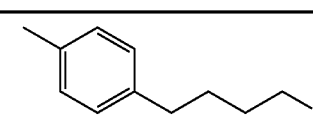 |
TABLE 13-continued
(I-A-13)
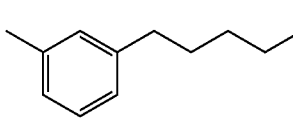
| No. | E |
|-----|---|
| 22 | 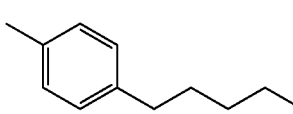 |
| 23 | 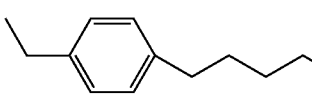 |
| 24 | 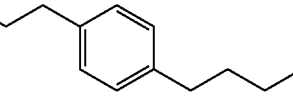 |
| 25 | 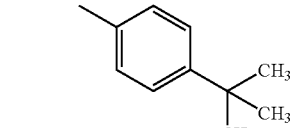 |
| 26 | 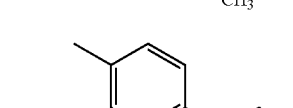 |
| 27 |  |
| 28 | 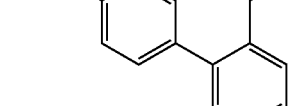 |
| 29 | 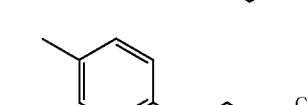 |
| 30 |  |
| 31 |  |

TABLE 14

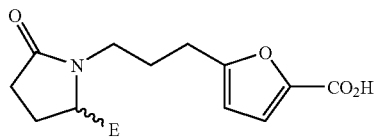

(I-A-14)

| No. | E |
|---|---|
| 1 | (2-hexenyl) |
| 2 | (2-heptenyl) |
| 3 | (2-octenyl) |
| 4 | (2-nonenyl) |
| 5 | (5,5-dimethyl-2-hexenyl) |
| 6 | (5-ethyl-5-methyl-2-heptenyl) |
| 7 | (2-octenyl variant) |
| 8 | (hydroxyheptenyl) |
| 9 | (1-ethylcyclopropyl allyl) |
| 10 | (1-methylcyclobutyl allyl) |
| 11 | (1-ethylcyclobutyl allyl) |
| 12 | (hydroxy-1-ethylcyclobutyl pentyl) |
| 13 | (hydroxy-1-ethylcyclobutyl pentenyl) |
| 14 | (hydroxy-1-ethylcyclobutyl butenyl) |

TABLE 14-continued

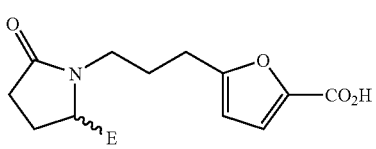

(I-A-14)

| No. | E |
|---|---|
| 15 | (1-ethylcyclobutyl methoxy allyl) |
| 16 | (tert-butoxy allyl) |
| 17 | (phenoxy allyl) |
| 18 | phenyl |
| 19 | (4-ethylphenyl) |
| 20 | (4-propylphenyl) |
| 21 | (4-butylphenyl) |
| 22 | (4-pentylphenyl) |
| 23 | (3-hexylphenyl) |
| 24 | (4-hexylphenyl) |
| 25 | (4-ethyl, hexyl phenyl) |
| 26 | (4-propyl, pentyl phenyl) |

TABLE 14-continued (I-A-14)

| No. | E |
|---|---|
| 27 | 4-tert-butylphenyl |
| 28 | biphenyl-4-yl |
| 29 | 4'-(hydroxymethyl)biphenyl-4-yl |
| 30 | 4-propoxyphenyl |
| 31 | 4-(1-hydroxyhexyl)phenyl |

TABLE 15

(I-A-15)

| No. | E |
|---|---|
| 1 | (E)-hept-1-en-1-yl |
| 2 | (E)-oct-1-en-1-yl |
| 3 | (E)-non-1-en-1-yl |
| 4 | (E)-dec-1-en-1-yl |
| 5 | (E)-5,5-dimethylhex-1-en-1-yl |
| 6 | (E)-5-ethyl-5-methylhept-1-en-1-yl |
| 7 | (E)-hept-1-en-1-yl |
| 8 | (E)-7-hydroxynon-1-en-1-yl (with OH) |
| 9 | (E)-4-(1-ethylcyclopropyl)but-1-en-1-yl |
| 10 | (E)-4-(1-methylcyclobutyl)but-1-en-1-yl |
| 11 | (E)-4-(1-ethylcyclobutyl)but-1-en-1-yl |
| 12 | (E)-(S)-5-(1-ethylcyclobutyl)-5-hydroxypent-1-en-1-yl |
| 13 | (E)-(S)-5-(1-ethylcyclobutyl)-5-hydroxypent-1-en-1-yl |
| 14 | (E)-5-(1-ethylcyclobutyl)-5-hydroxypent-1-en-1-yl |
| 15 | (E)-3-((1-ethylcyclobutyl)oxy)prop-1-en-1-yl |
| 16 | (E)-3-(tert-butoxy)prop-1-en-1-yl |
| 17 | (E)-3-phenoxyprop-1-en-1-yl |

TABLE 15-continued (I-A-15)

| No. | E |
|---|---|
| 18 | phenyl |
| 19 | 4-ethylphenyl |
| 20 | 4-propylphenyl |
| 21 | 4-butylphenyl |
| 22 | 4-pentylphenyl |
| 23 | 3-hexylphenyl |
| 24 | 4-hexylphenyl |
| 25 | 4-hexyl-2-ethylphenyl |
| 26 | 4-hexyl-2-propylphenyl |
| 27 | 4-tert-butylphenyl |
| 28 | 4-phenylphenyl |
| 29 | 2-(hydroxymethyl)-4-biphenyl |
| 30 | 4-propoxyphenyl |
| 31 | 4-(1-hydroxyhexyl)phenyl |

TABLE 16

(I-A-16)

| No. | E |
|---|---|
| 1 | CH=CH-CH2-CH2-CH3 |
| 2 | CH=CH-(CH2)3-CH3 |
| 3 | CH=CH-(CH2)4-CH3 |
| 4 | CH=CH-(CH2)5-CH3 |
| 5 | CH=CH-CH2-C(CH3)3 |
| 6 | CH=CH-CH2-C(CH3)2-C2H5 |
| 7 | CH=CH-(CH2)4-CH3 |
| 8 | CH=CH-CH2-CH(OH)-CH2-CH2-CH3 |

TABLE 16-continued
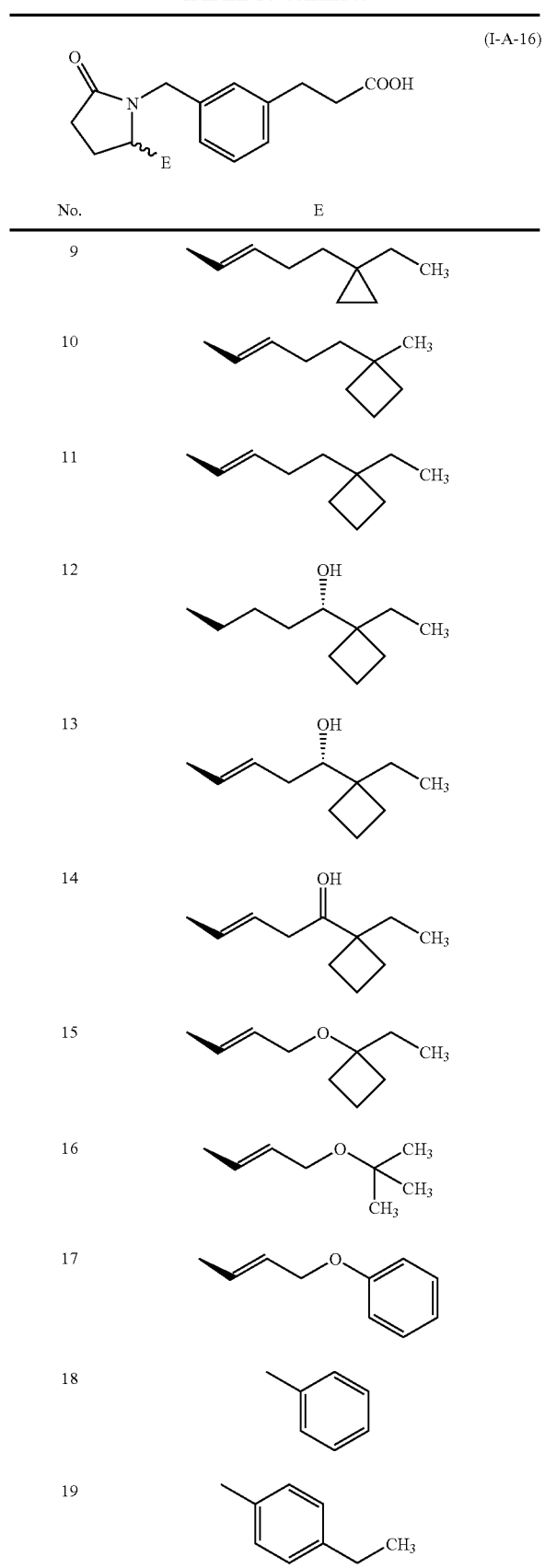
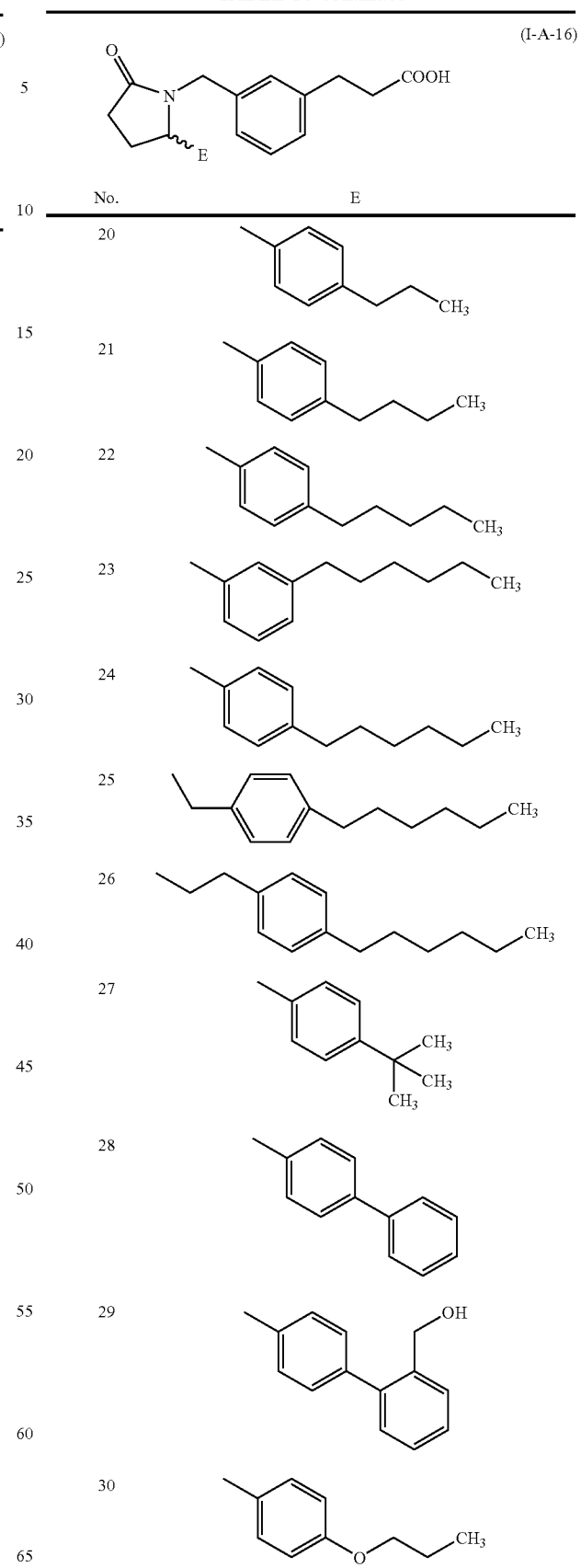

TABLE 16-continued (I-A-16)

| No. | E |
|---|---|
| 31 | 4-methylphenyl-CH(OH)-butyl |

TABLE 17

(I-A-17)

| No. | E |
|---|---|
| 1 | pentenyl-CH3 |
| 2 | hexenyl-CH3 |
| 3 | heptenyl-CH3 |
| 4 | octenyl-CH3 |
| 5 | -CH=CH-CH2-C(CH3)3 |
| 6 | -CH=CH-CH2-C(CH3)2-CH2CH3 |
| 7 | heptyl |
| 8 | -CH=CH-CH2-CH(OH)-CH2-CH2-CH3 |
| 9 | -CH=CH-CH2-C(CH3)(cyclopropyl) |
| 10 | -CH=CH-CH2-C(CH3)(cyclobutyl) |
| 11 | -CH=CH-CH2-C(CH2CH3)(cyclobutyl) |

TABLE 17-continued (I-A-17)

| No. | E |
|---|---|
| 12 | propyl-C(OH)(CH2CH3)(cyclobutyl) |
| 13 | -CH=CH-C(OH)(CH2CH3)(cyclobutyl) |
| 14 | -CH=CH-C(O)-C(CH2CH3)(cyclobutyl) |
| 15 | -CH=CH-CH2-O-C(CH2CH3)(cyclobutyl) |
| 16 | -CH=CH-CH2-O-C(CH3)3 |
| 17 | -CH=CH-CH2-O-phenyl |
| 18 | phenyl |
| 19 | 4-methylphenyl-CH3 |
| 20 | 4-methylphenyl-CH2CH3 |
| 21 | 4-methylphenyl-CH2CH2CH3 |
| 22 | 4-methylphenyl-CH2CH2CH2CH3 |

TABLE 17-continued
(I-A-17)
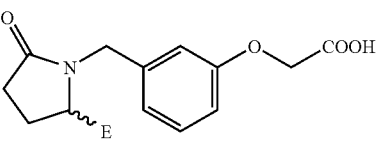
| No. | E |
|---|---|
| 23 | 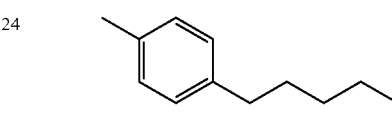 |
| 24 | 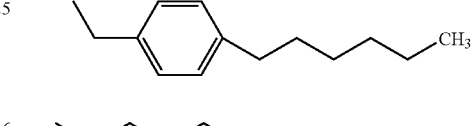 |
| 25 | 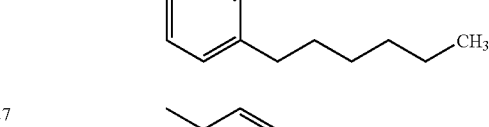 |
| 26 | 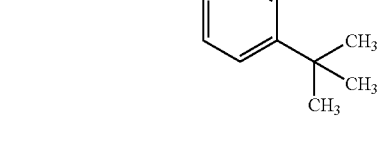 |
| 27 | 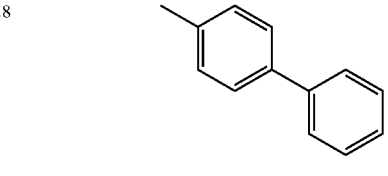 |
| 28 | 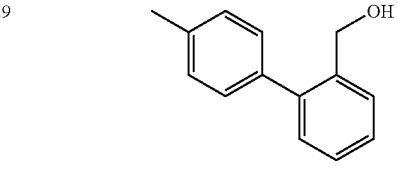 |
| 29 | 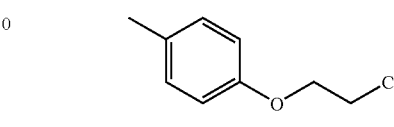 |
| 30 | 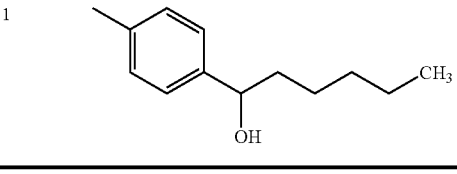 |
| 31 | 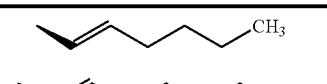 |
TABLE 18
(I-A-18)
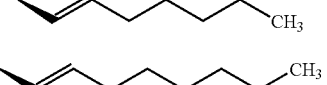
| No. | E |
|---|---|
| 1 | 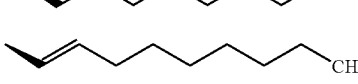 |
| 2 | 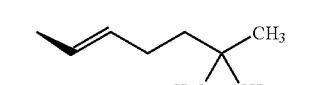 |
| 3 | 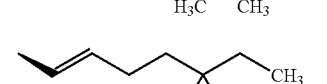 |
| 4 | 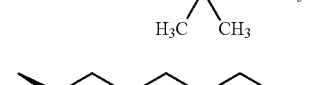 |
| 5 | 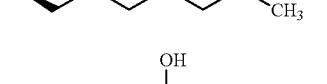 |
| 6 | 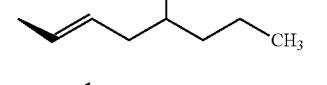 |
| 7 | 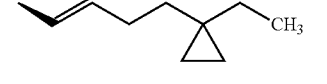 |
| 8 | 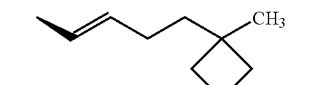 |
| 9 | 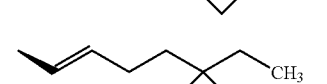 |
| 10 |  |
| 11 | 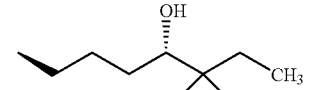 |
| 12 | 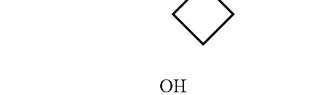 |
| 13 |  |
| 14 |  |

TABLE 18-continued (I-A-18)

| No. | E |
|---|---|
| 15 | CH₂=CH-CH₂-O-C(cyclobutyl)(CH₂CH₃) |
| 16 | CH₃-CH=CH-CH₂-O-C(CH₃)₃ |
| 17 | CH₃-CH=CH-CH₂-O-phenyl |
| 18 | phenyl |
| 19 | 4-ethylphenyl |
| 20 | 4-propylphenyl |
| 21 | 4-butylphenyl |
| 22 | 4-pentylphenyl |
| 23 | 3-hexylphenyl |
| 24 | 4-hexylphenyl |
| 25 | 4-ethyl-(4-hexyl)phenyl |
| 26 | 4-propyl-(4-pentyl)phenyl |
| 27 | 4-tert-butylphenyl |
| 28 | 4-phenylphenyl (biphenyl) |
| 29 | 4'-(hydroxymethyl)biphenyl |
| 30 | 4-propoxyphenyl |
| 31 | 4-(1-hydroxyhexyl)phenyl |

TABLE 19

(I-A-19)

| No. | E |
|---|---|
| 1 | CH=CH-(CH₂)₃-CH₃ |
| 2 | CH=CH-(CH₂)₄-CH₃ |
| 3 | CH=CH-(CH₂)₅-CH₃ |
| 4 | CH=CH-(CH₂)₆-CH₃ |
| 5 | CH=CH-(CH₂)₃-C(CH₃)₃ |

TABLE 19-continued (I-A-19)

[Structure: pyrrolidinone-N-CH₂CH₂-O-C₆H₄-COOH with E substituent on pyrrolidinone ring]

| No. | E |
|---|---|
| 6 | CH₃CH=CH-CH₂-C(CH₃)(CH₃)-CH₂CH₃ (alkene chain with gem-dimethyl and ethyl) |
| 7 | CH₃CH=CH-(CH₂)₄-CH₃ |
| 8 | CH₃CH=CH-CH₂-CH(OH)-CH₂CH₃ |
| 9 | CH=CH-CH₂-[1-ethylcyclopropyl] |
| 10 | CH=CH-CH₂-[1-methylcyclobutyl] |
| 11 | CH=CH-CH₂-[1-ethylcyclobutyl] |
| 12 | CH₃-CH₂-CH₂-CH(OH)-[1-ethylcyclobutyl] (with stereochemistry) |
| 13 | CH=CH-CH₂-CH(OH)-[1-ethylcyclobutyl] (with stereochemistry) |
| 14 | CH=CH-CH₂-C(=O)-[1-ethylcyclobutyl] |
| 15 | CH=CH-CH₂-O-[1-ethylcyclobutyl] |
| 16 | CH=CH-CH₂-O-C(CH₃)₃ |
| 17 | CH=CH-CH₂-O-C₆H₅ |
| 18 | phenyl |
| 19 | 4-ethylphenyl |
| 20 | 4-propylphenyl |
| 21 | 4-butylphenyl |
| 22 | 4-pentylphenyl |
| 23 | 3-hexylphenyl |
| 24 | 4-hexylphenyl |
| 25 | 4-ethyl-...-hexylphenyl |
| 26 | 4-propyl-...-hexylphenyl |
| 27 | 4-tert-butylphenyl |
| 28 | 4-biphenyl |

TABLE 19-continued (I-A-19)

| No. | E |
|---|---|
| 29 | 4'-(hydroxymethyl)biphenyl-4-yl |
| 30 | 4-propoxyphenyl-methyl |
| 31 | 4-(1-hydroxyhexyl)phenyl-methyl |

TABLE 20

(I-A-20)

| No. | E |
|---|---|
| 1 | (E)-hex-1-enyl |
| 2 | (E)-hept-1-enyl |
| 3 | (E)-oct-1-enyl |
| 4 | (E)-non-1-enyl |
| 5 | (E)-6,6-dimethylhept-1-enyl |
| 6 | (E)-6-ethyl-6-methyloct-1-enyl |
| 7 | oct-1-yl |
| 8 | (E)-4-hydroxyhept-1-enyl |
| 9 | (E)-4-(1-ethylcyclopropyl)but-1-enyl |
| 10 | (E)-4-(1-methylcyclobutyl)but-1-enyl |
| 11 | (E)-4-(1-ethylcyclobutyl)but-1-enyl |
| 12 | (R)-4-(1-ethylcyclobutyl)-4-hydroxybut-1-yl |
| 13 | (E,R)-4-(1-ethylcyclobutyl)-4-hydroxybut-1-enyl |
| 14 | (E)-4-(1-ethylcyclobutyl)-4-oxobut-1-enyl |
| 15 | (E)-3-(1-ethylcyclobutoxy)prop-1-enyl |
| 16 | (E)-3-tert-butoxyprop-1-enyl |
| 17 | (E)-3-phenoxyprop-1-enyl |
| 18 | phenyl-methyl |
| 19 | 4-ethylphenyl-methyl |

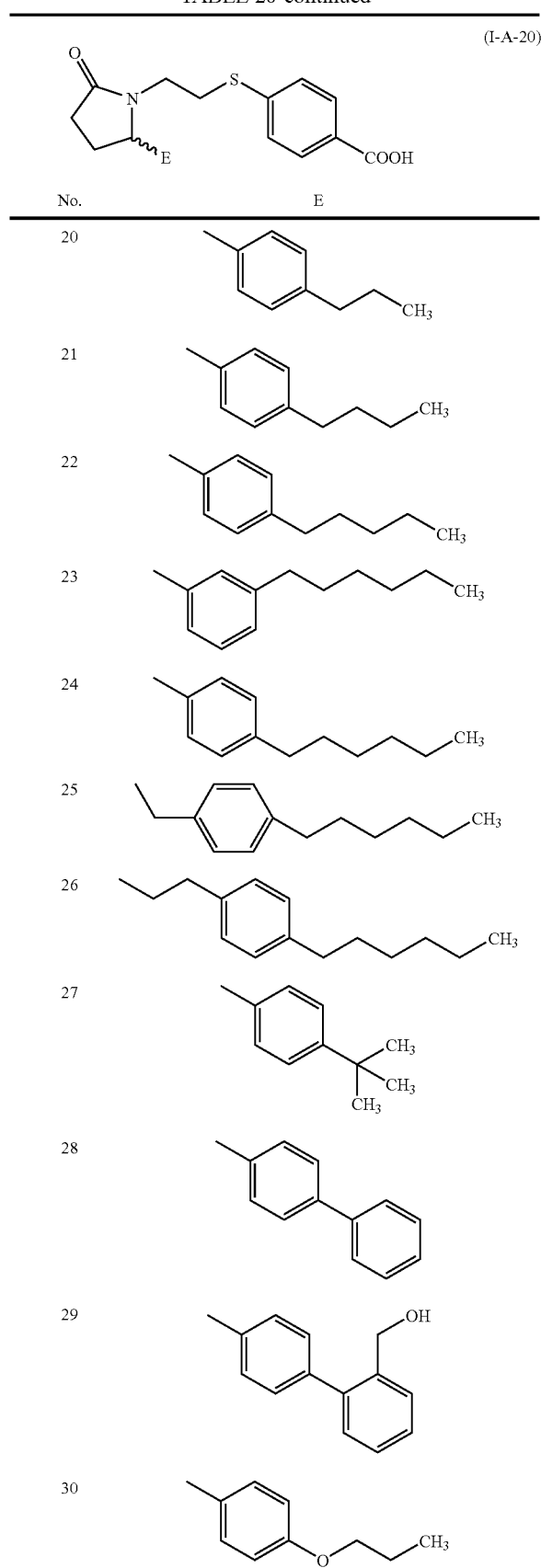
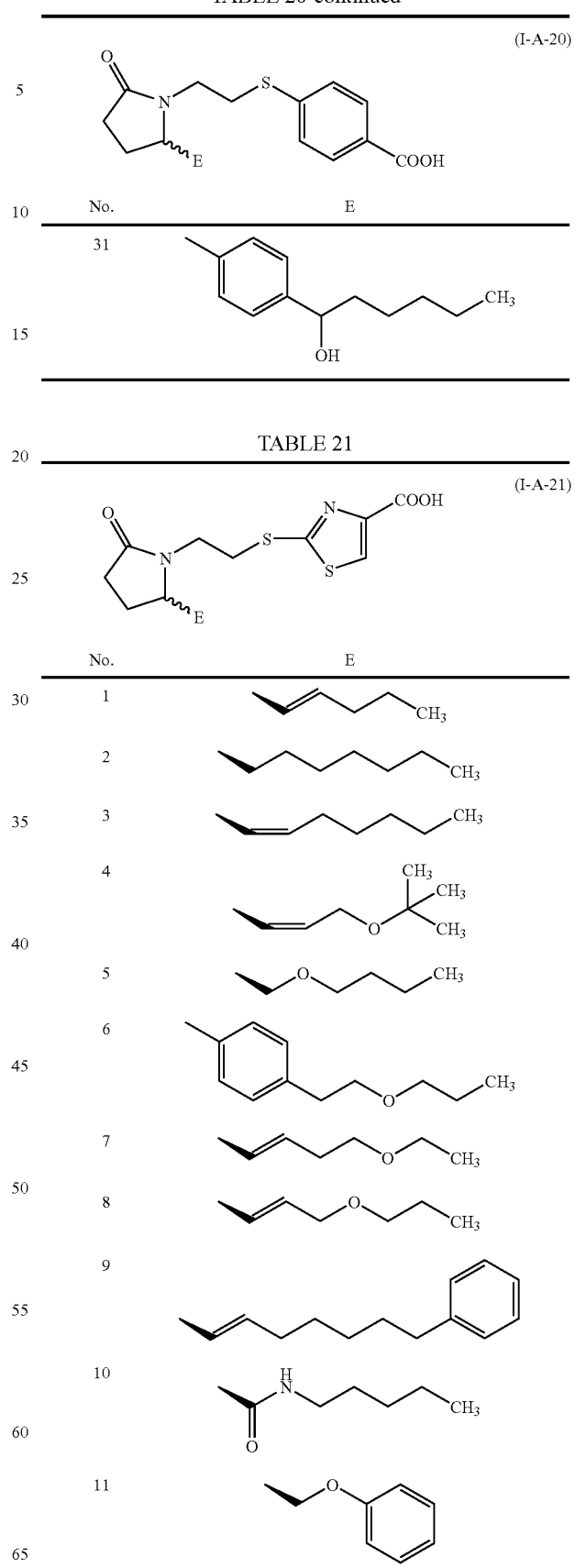

TABLE 21-continued (I-A-21)

| No. | E |
|---|---|
| 12 | 3-pyridyl ethoxy |
| 13 | 3,5-dichlorophenyl ethoxy |
| 14 | 2,5-dichlorophenyl ethoxy |
| 15 | 2,4,5-trichlorophenyl ethoxy |
| 16 | 3,4-dichlorophenyl ethoxy |
| 17 | pentafluorophenyl ethoxy |
| 18 | 3,4-difluorophenyl ethoxy |
| 19 | 2-nitro-3-methylphenyl ethoxy |
| 20 | 2-chloro-4-formylphenyl ethoxy (CHO) |
| 21 | 2-methyl-4-nitrophenyl ethoxy |
| 22 | 2-methyl-3-nitrophenyl ethoxy |
| 23 | 2-methyl-4-chlorophenyl ethoxy |
| 24 | 3-nitro-4-methylphenyl ethoxy |
| 25 | 3-bromophenyl ethoxy |
| 26 | 2,3-dimethylphenyl ethoxy |
| 27 | 2,6-dimethyl-4-chlorophenyl ethoxy |
| 28 | 2-naphthyl ethoxy |
| 29 | 2-fluoro-3-(trifluoromethyl)phenyl ethoxy |
| 30 | 3,5-dimethylphenyl ethoxy |

TABLE 21-continued (I-A-21)

| No. | E |
|---|---|
| 31 | 3,4,5-trimethylphenyl ethoxy |
| 32 | 5,6,7,8-tetrahydronaphthalen-1-yl ethoxy |
| 33 | 4-acetyl-3-methylphenyl ethoxy |
| 34 | naphthalen-1-yl ethoxy |
| 35 | 2-chloro-3-(trifluoromethyl)phenyl ethoxy |

TABLE 22

(I-A-22)

| No. | E |
|---|---|
| 1 | (E)-pent-2-enyl |
| 2 | oct-2-enyl |
| 3 | (Z)-oct-2-enyl |
| 4 | 3-(tert-butoxy)prop-1-enyl |
| 5 | 4-ethoxybutyl (chain) |
| 6 | 2-(4-methylphenyl)ethoxy propyl |
| 7 | (E)-4-ethoxybut-2-enyl |
| 8 | (E)-4-propoxybut-2-enyl |
| 9 | (E)-7-phenylhept-2-enyl |
| 10 | N-pentylacetamide |
| 11 | 2-phenoxyethyl |
| 12 | 2-(pyridin-3-yloxy)ethyl |
| 13 | 2-(3,5-dichlorophenoxy)ethyl |
| 14 | 2-(2,5-dichlorophenoxy)ethyl |
| 15 | 2-(2,4,5-trichlorophenoxy)ethyl |
| 16 | 2-(3,4-dichlorophenoxy)ethyl |

TABLE 22-continued
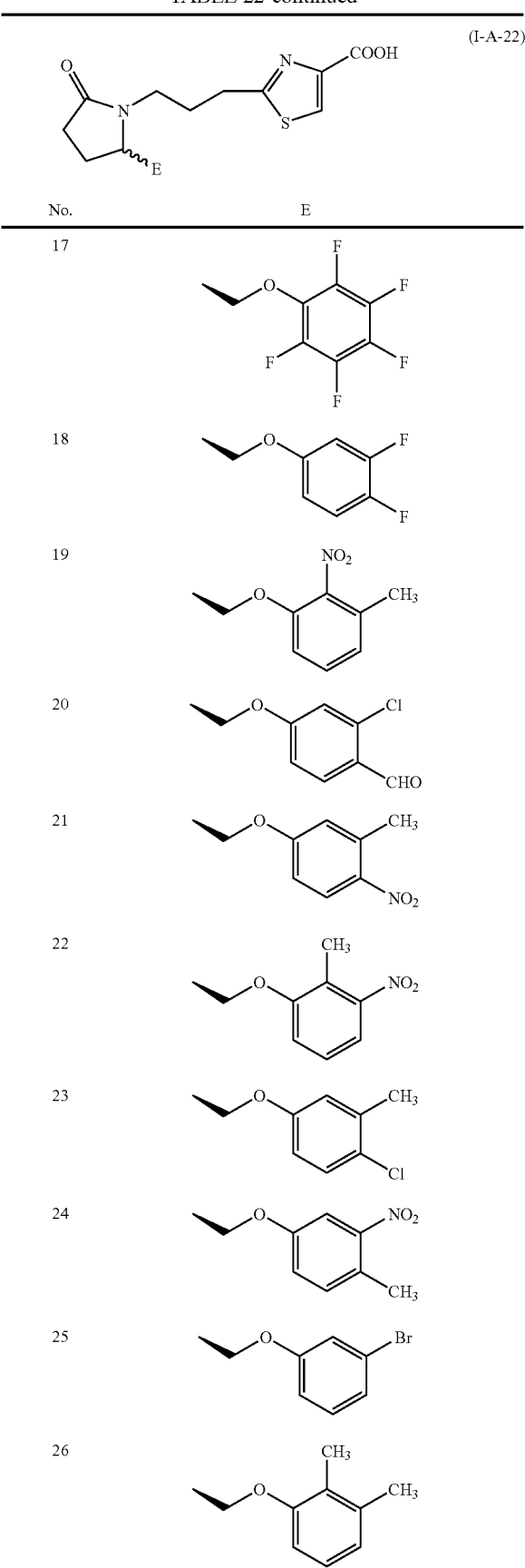
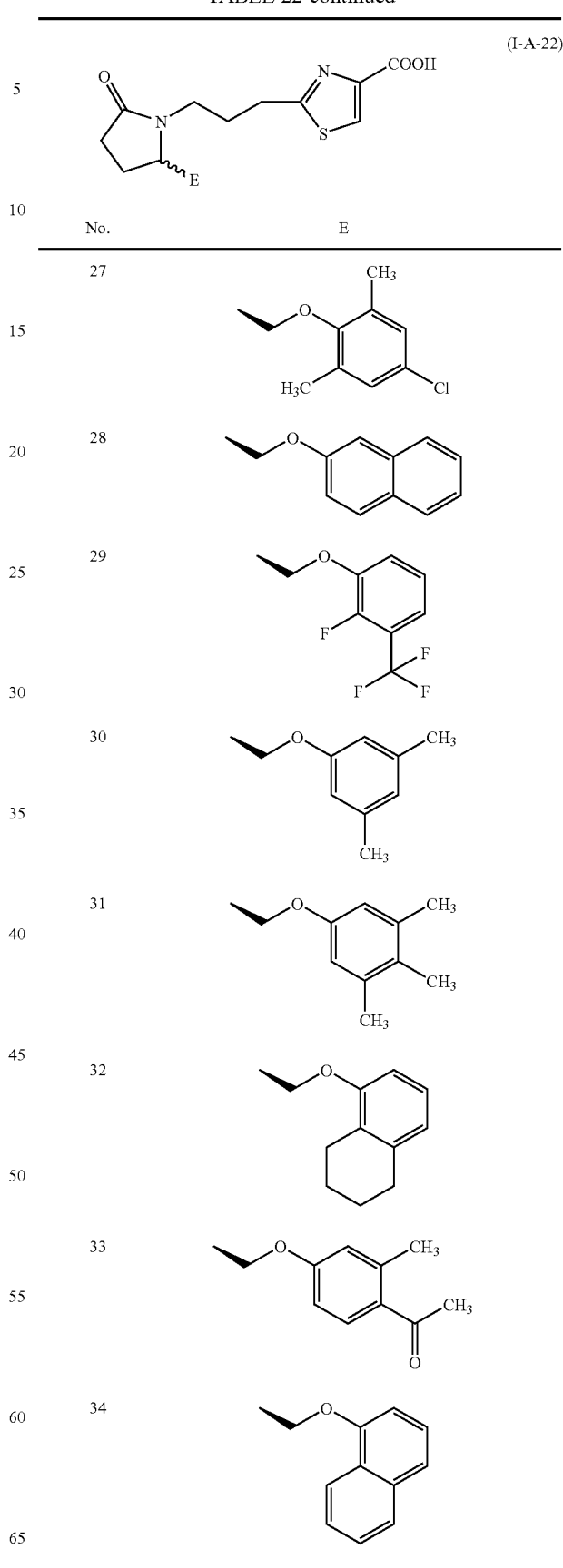

TABLE 22-continued (I-A-22)

| No. | E |
|---|---|
| 35 | 2-chloro-3-ethoxy-trifluoromethylphenyl group |

TABLE 23

(I-A-23)

| No. | E |
|---|---|
| 1 | -CH=CH-CH₂-CH₂-CH₃ |
| 2 | -CH₂-CH₂-CH₂-CH₂-CH₂-CH₃ |
| 3 | -CH₂-CH=CH-CH₂-CH₂-CH₂-CH₃ (cis) |
| 4 | -CH=CH-CH₂-O-C(CH₃)₃ |
| 5 | -CH₂-O-CH₂-CH₂-CH₃ |
| 6 | 4-methylphenyl-CH₂-O-CH₂-CH₂-CH₃ |
| 7 | -CH=CH-CH₂-O-CH₂-CH₃ |
| 8 | -CH=CH-CH₂-O-CH₂-CH₂-CH₃ |
| 9 | -CH=CH-CH₂-CH₂-CH₂-CH₂-phenyl |
| 10 | -C(O)-NH-CH₂-CH₂-CH₂-CH₂-CH₃ |
| 11 | -CH₂-O-phenyl |

TABLE 23-continued (I-A-23)

| No. | E |
|---|---|
| 12 | 3-ethoxypyridinyl |
| 13 | 3,5-dichloro-ethoxyphenyl |
| 14 | 2,5-dichloro-ethoxyphenyl |
| 15 | 2,4,5-trichloro-ethoxyphenyl |
| 16 | 3,4-dichloro-ethoxyphenyl |
| 17 | pentafluoro-ethoxyphenyl |
| 18 | 3,4-difluoro-ethoxyphenyl |
| 19 | 2-nitro-3-methyl-ethoxyphenyl |
| 20 | 2-chloro-4-ethoxy-benzaldehyde |
| 21 | 2-methyl-4-nitro-ethoxyphenyl |

TABLE 23-continued (I-A-23)

| No. | E |
|---|---|
| 22 | 3-ethoxy-2-methyl-1-nitrophenyl |
| 23 | 4-chloro-3-ethoxy-2-methylphenyl |

(Structures shown for entries 22–35 and TABLE 24 entries 1–4)

TABLE 24

(I-A-24)

TABLE 24-continued
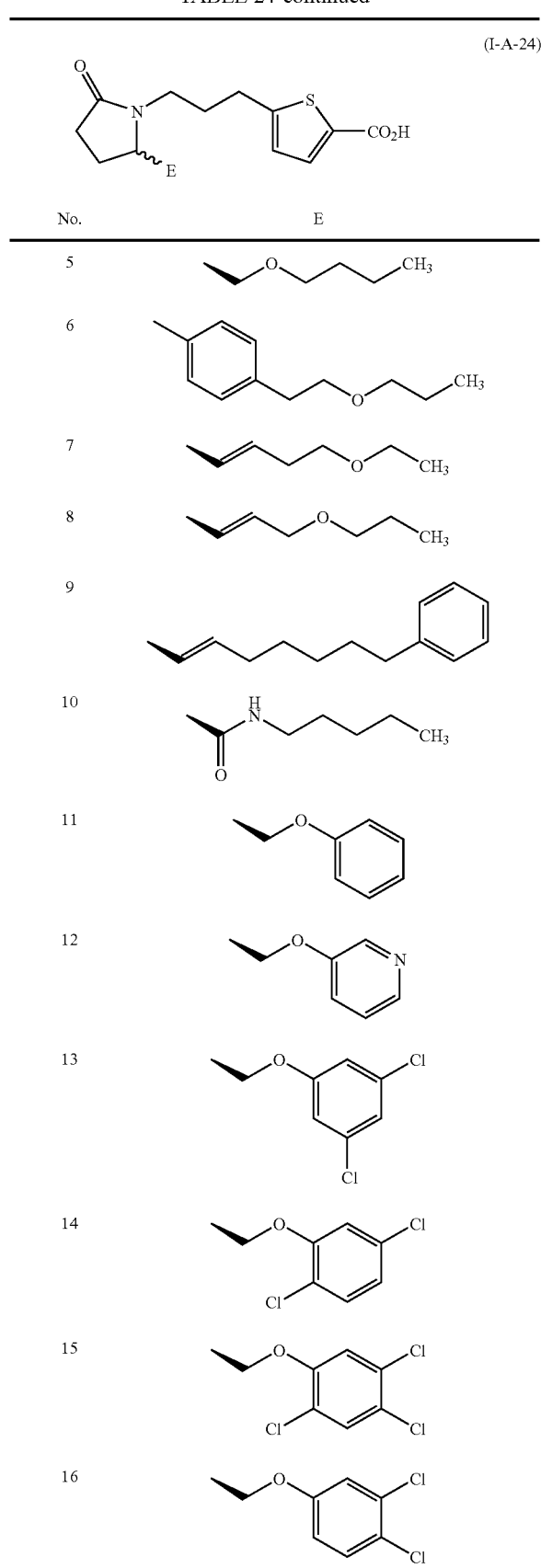
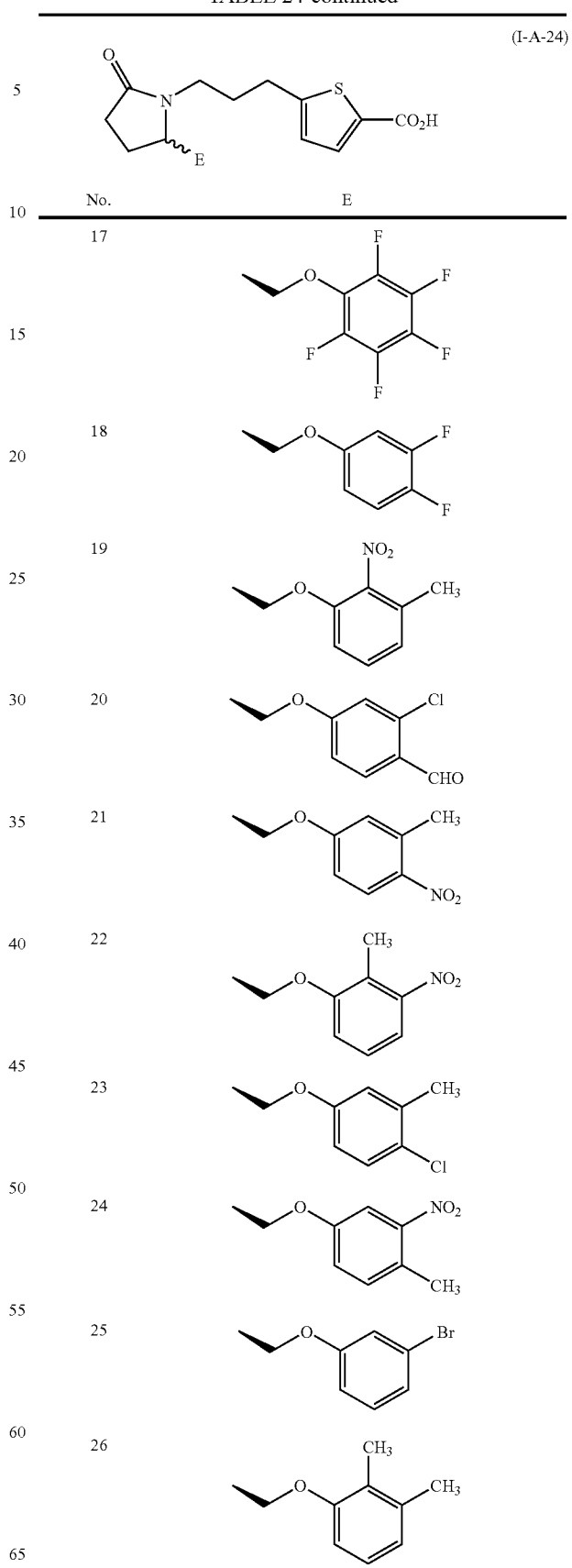

TABLE 24-continued (I-A-24)

| No. | E |
|---|---|
| 27 | 4-chloro-2-ethoxy-3,5-dimethylphenyl (ethoxy group with 2,6-dimethyl and 4-Cl) |
| 28 | 2-ethoxynaphthalen-6-yl |
| 29 | 3-ethoxy-2-fluoro-1-(trifluoromethyl)phenyl |
| 30 | 3-ethoxy-3,5-dimethylphenyl |
| 31 | 3-ethoxy-3,4,5-trimethylphenyl |
| 32 | 8-ethoxy-5,6,7,8-tetrahydronaphthalenyl |
| 33 | 1-(4-ethoxy-2-methylphenyl)ethanone |
| 34 | 1-ethoxynaphthalenyl |

TABLE 24-continued (I-A-24)

| No. | E |
|---|---|
| 35 | 2-chloro-3-ethoxy-1-(trifluoromethyl)phenyl |

TABLE 25

(I-A-25)

| No. | E |
|---|---|
| 1 | –CH=CH–CH$_2$–CH$_2$–CH$_3$ |
| 2 | –CH=CH–CH$_2$–CH$_2$–CH$_2$–CH$_2$–CH$_3$ |
| 3 | –CH=CH–CH$_2$–CH$_2$–CH$_2$–CH$_3$ (cis) |
| 4 | –CH=CH–CH$_2$–O–C(CH$_3$)$_3$ |
| 5 | –CH$_2$–O–CH$_2$–CH$_2$–CH$_2$–CH$_3$ |
| 6 | –CH$_2$–(4-methylphenyl)–CH$_2$–CH$_2$–O–CH$_2$–CH$_2$–CH$_3$ |
| 7 | –CH=CH–CH$_2$–CH$_2$–O–CH$_2$–CH$_3$ |
| 8 | –CH=CH–CH$_2$–CH$_2$–O–CH$_2$–CH$_3$ |
| 9 | –CH=CH–CH$_2$–CH$_2$–CH$_2$–CH$_2$–(phenyl) |
| 10 | –NH–C(=O)–CH$_2$–CH$_2$–CH$_2$–CH$_2$–CH$_2$–CH$_3$ (acetamide) |
| 11 | –CH$_2$–O–(phenyl) |

TABLE 25-continued
(I-A-25)
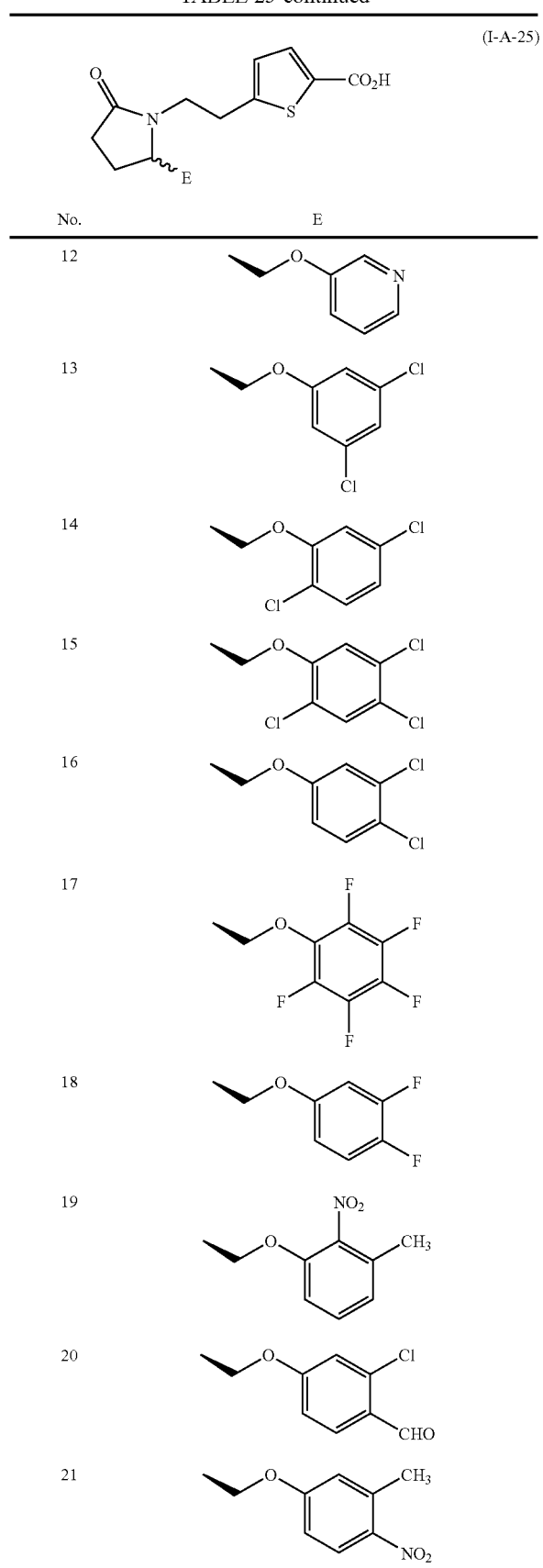
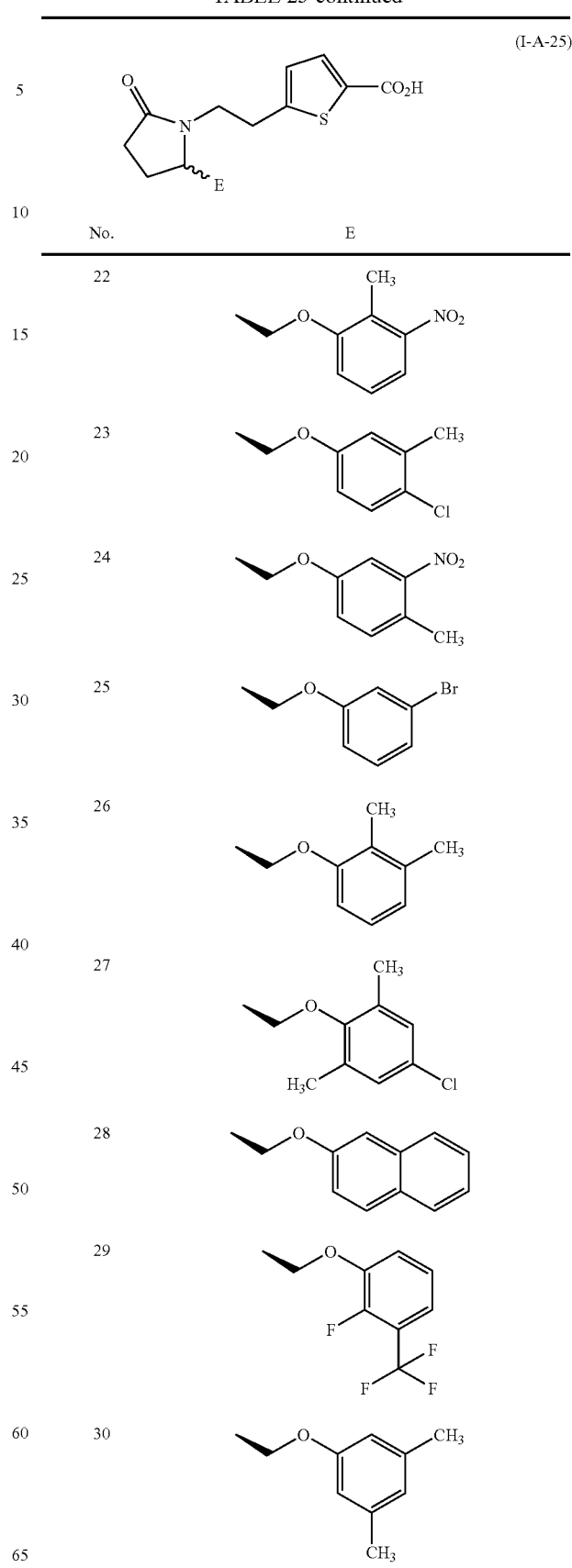

TABLE 25-continued
(I-A-25)
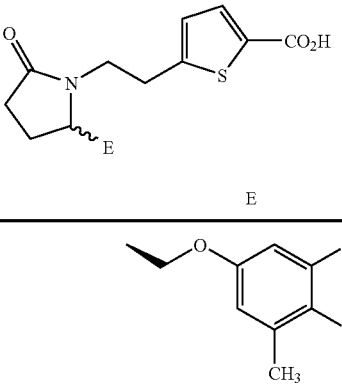
| No. | E |
|---|---|
| 31 | 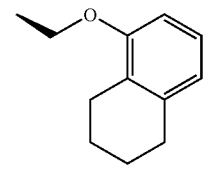 |
| 32 | 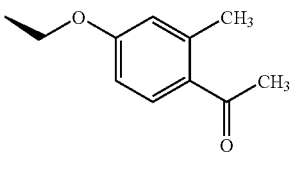 |
| 33 | 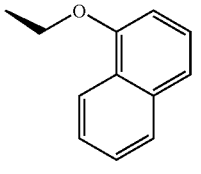 |
| 34 | 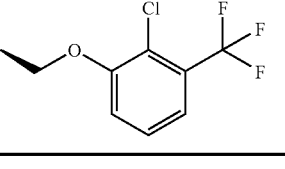 |
| 35 | 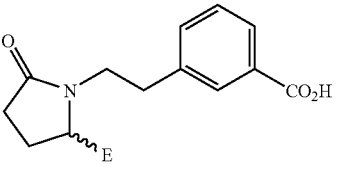 |
TABLE 26
(I-A-26)
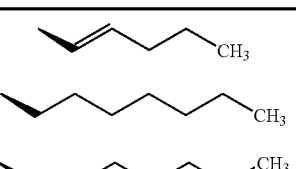
| No. | E |
|---|---|
| 1 |  |
| 2 | 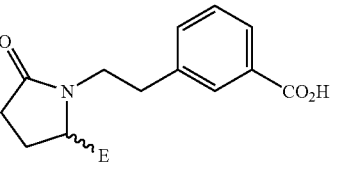 |
| 3 | 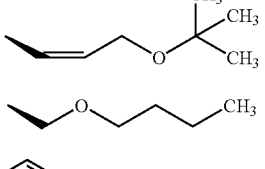 |
TABLE 26-continued
(I-A-26)
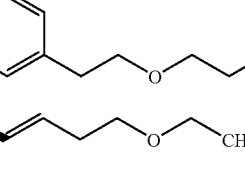
| No. | E |
|---|---|
| 4 | 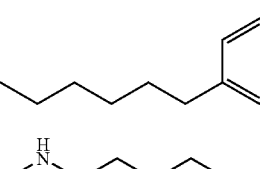 |
| 5 | 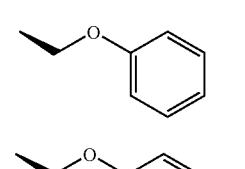 |
| 6 | 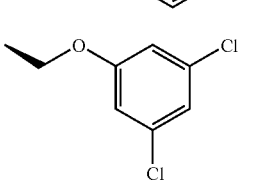 |
| 7 | 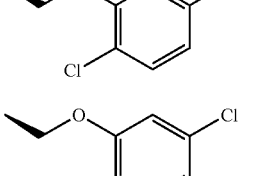 |
| 8 | 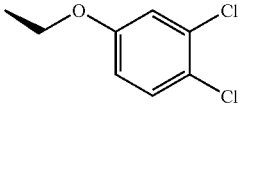 |
| 9 |  |
| 10 | |
| 11 | |
| 12 | |
| 13 | |
| 14 | |
| 15 | |
| 16 | |

TABLE 26-continued (I-A-26)

| No. | E |
|---|---|
| 17 | 3-ethoxy-2,4,5,6-tetrafluorophenyl |
| 18 | 3-ethoxy-5,6-difluorophenyl |
| 19 | 2-ethoxy-6-methyl-3-nitrophenyl (ethoxy, NO₂, CH₃ substituted phenyl) |
| 20 | 4-ethoxy-2-chloro-benzaldehyde substituted phenyl |
| 21 | 4-ethoxy-2-methyl-1-nitro substituted phenyl |
| 22 | 2-ethoxy-3-methyl-nitro substituted phenyl |
| 23 | 4-ethoxy-2-methyl-1-chloro substituted phenyl |
| 24 | 4-ethoxy-2-nitro-1-methyl substituted phenyl |
| 25 | 3-ethoxy-bromo substituted phenyl |
| 26 | 2-ethoxy-3,4-dimethyl substituted phenyl |
| 27 | 2-ethoxy-3,5-dimethyl-4-chloro substituted phenyl |
| 28 | 2-ethoxy-naphthyl |
| 29 | 3-ethoxy-2-fluoro-trifluoromethyl substituted phenyl |
| 30 | 3-ethoxy-5-methyl-3-methyl substituted phenyl |
| 31 | 3-ethoxy-5,6,7-trimethyl substituted phenyl |
| 32 | 8-ethoxy-tetrahydronaphthyl |
| 33 | 4-ethoxy-2-methyl-acetyl substituted phenyl |
| 34 | ethoxy-naphthyl |

TABLE 26-continued (I-A-26)

[Structure: pyrrolidinone-N-CH2CH2-phenyl-CO2H with E substituent]

| No. | E |
|---|---|
| 35 | [3-ethoxy-2-chloro-(trifluoromethyl)phenyl group] |

TABLE 27

(I-A-27)

[Structure: pyrrolidinone-N-CH2CH2-O-thiazole-COOH with E substituent]

| No. | E |
|---|---|
| 1 | [CH=CH-CH2-CH2-CH3] |
| 2 | [CH2-(CH2)5-CH3] |
| 3 | [cis-CH=CH-CH2-CH2-CH2-CH3] |
| 4 | [CH=CH-CH2-O-C(CH3)3] |
| 5 | [CH2-O-CH2-CH2-CH2-CH3] |
| 6 | [CH2-(4-methylphenyl)-O-CH2-CH2-CH3 – 4-methylbenzyl propyl ether group] |
| 7 | [CH=CH-CH2-CH2-O-CH2-CH3] |
| 8 | [CH=CH-CH2-O-CH2-CH2-CH3] |
| 9 | [CH=CH-(CH2)5-phenyl] |
| 10 | [CH2-NH-C(=O)-CH2-CH2-CH2-CH2-CH3] |
| 11 | [CH2-O-phenyl] |

TABLE 27-continued (I-A-27)

[Structure: pyrrolidinone-N-CH2CH2-O-thiazole-COOH with E substituent]

| No. | E |
|---|---|
| 12 | [ethoxy-pyridin-3-yl] |
| 13 | [3,5-dichlorophenyl ethoxy] |
| 14 | [2,5-dichlorophenyl ethoxy] |
| 15 | [2,4,5-trichlorophenyl ethoxy] |
| 16 | [3,4-dichlorophenyl ethoxy] |
| 17 | [pentafluorophenyl ethoxy] |
| 18 | [3,4-difluorophenyl ethoxy] |
| 19 | [2-nitro-3-methylphenyl ethoxy] |
| 20 | [2-chloro-4-formylphenyl ethoxy] |
| 21 | [2-methyl-4-nitrophenyl ethoxy] |

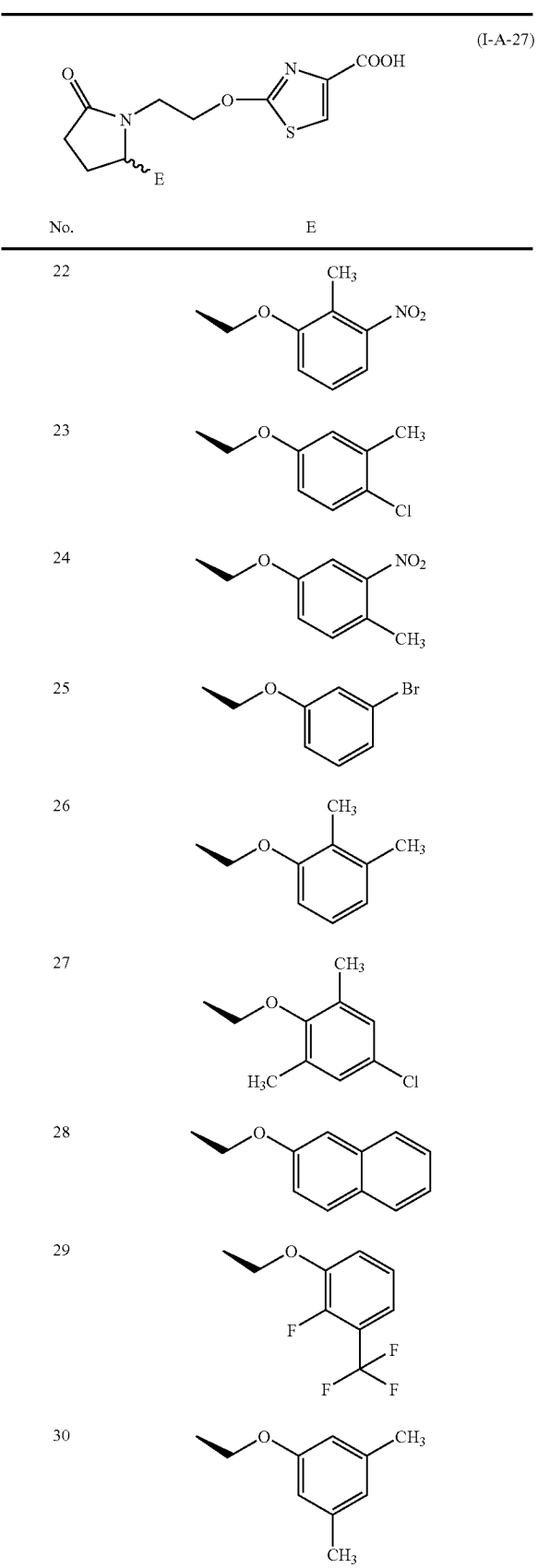
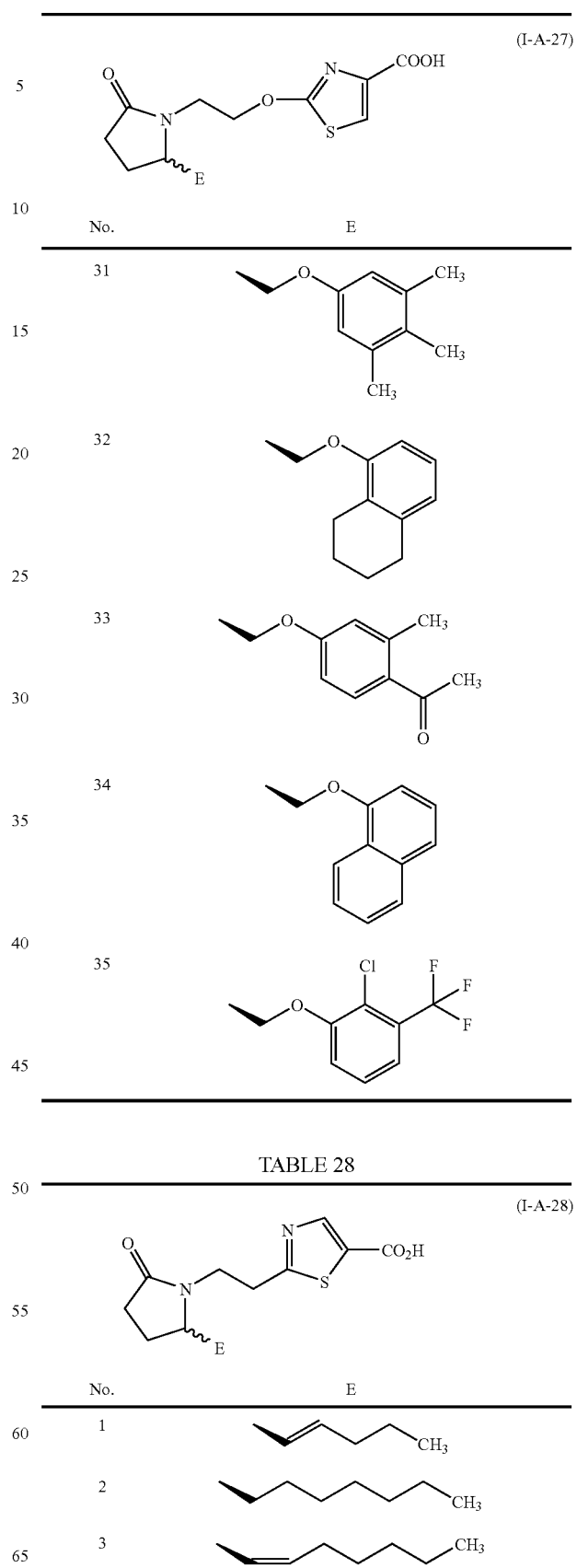

TABLE 28-continued
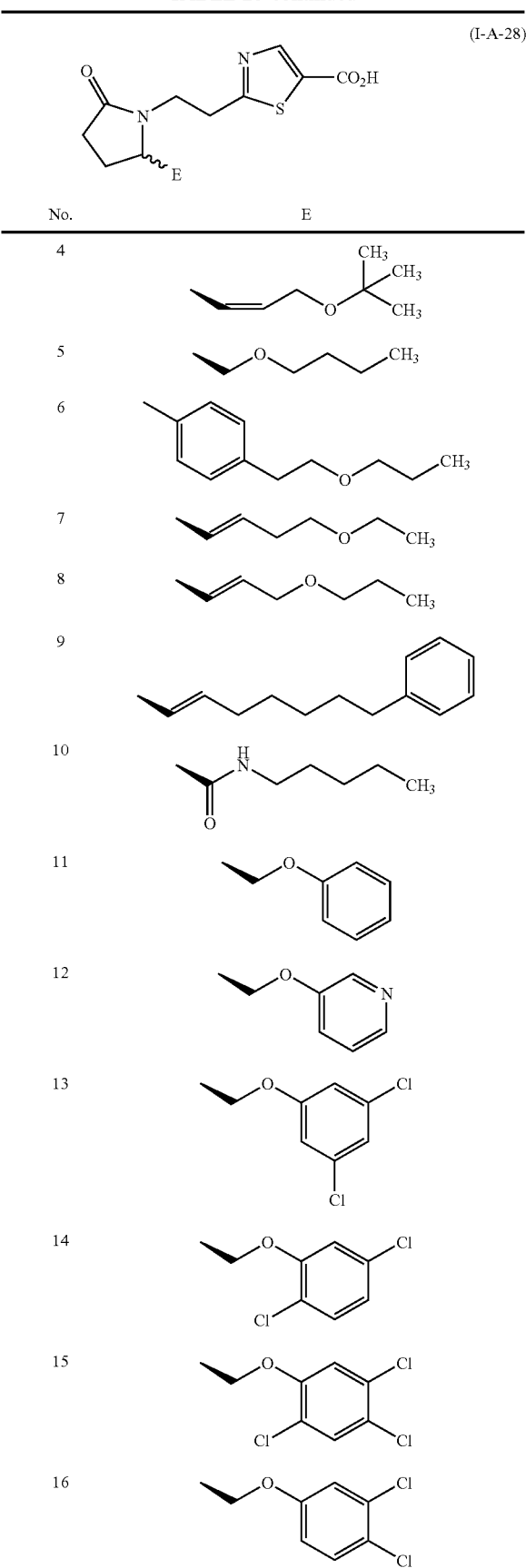
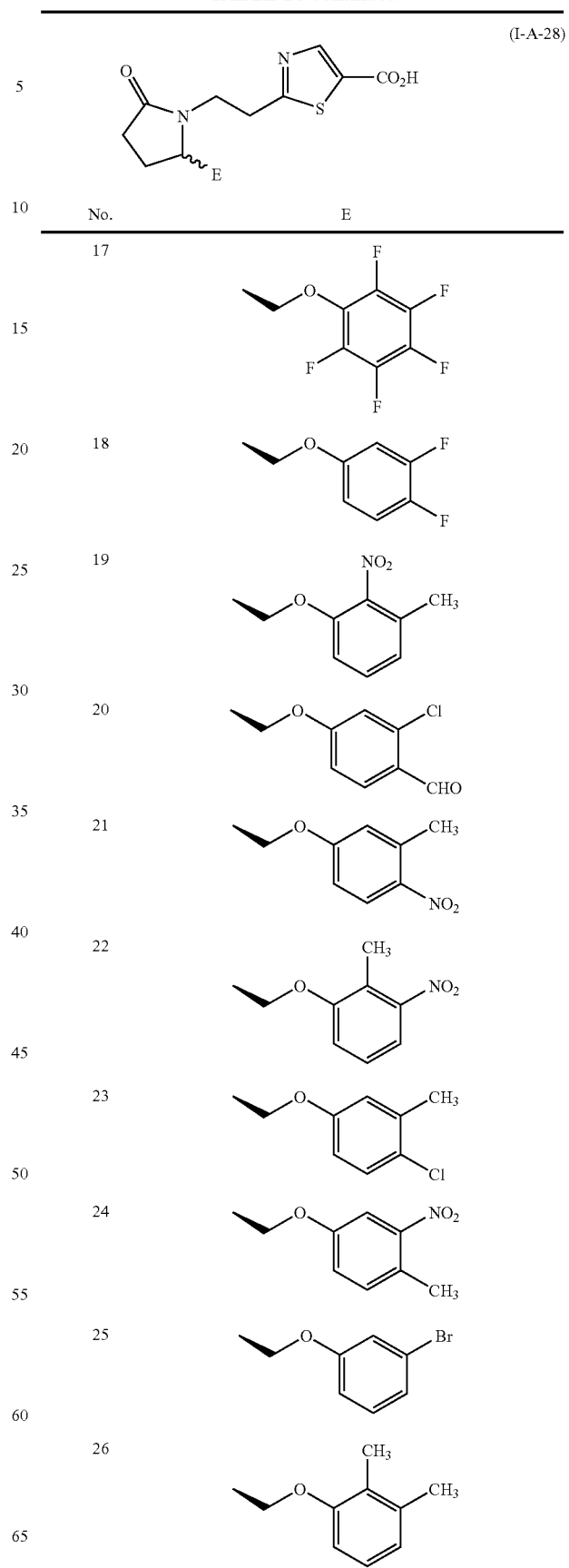

TABLE 28-continued (I-A-28)

| No. | E |
|---|---|
| 27 | 4-chloro-2-ethoxy-3,5-dimethylphenyl |
| 28 | 2-ethoxynaphthalen-3-yl |
| 29 | 3-ethoxy-2-fluoro-6-(trifluoromethyl)phenyl |
| 30 | 3-ethoxy-5-methylphenyl (3,5-dimethyl) |
| 31 | 3-ethoxy-4,5-dimethylphenyl (trimethyl) |
| 32 | 8-ethoxy-5,6,7,8-tetrahydronaphthalen-1-yl |
| 33 | 1-(4-ethoxy-2-methylphenyl)ethanone |
| 34 | 1-ethoxynaphthalen-2-yl |

TABLE 28-continued (I-A-28)

| No. | E |
|---|---|
| 35 | 2-chloro-3-ethoxy-1-(trifluoromethyl)phenyl |

TABLE 29

(I-A-29)

| No. | E |
|---|---|
| 1 | pent-2-enyl |
| 2 | oct-2-enyl |
| 3 | oct-2-enyl (Z) |
| 4 | 3-(tert-butoxy)prop-1-enyl |
| 5 | 4-butoxybut-2-enyl (ether chain) |
| 6 | 2-(4-methylphenyl)ethyl propyl ether |
| 7 | 4-ethoxybut-2-enyl |
| 8 | 4-propoxybut-2-enyl |
| 9 | 8-phenyloct-2-enyl |
| 10 | N-pentylacetamide |
| 11 | phenoxymethyl |

TABLE 29-continued

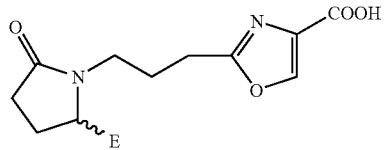

(I-A-29)

| No. | E |
|---|---|
| 12 | 3-ethoxypyridine |
| 13 | 3,5-dichloro ethoxybenzene |
| 14 | 2,5-dichloro ethoxybenzene |
| 15 | 2,4,5-trichloro ethoxybenzene |
| 16 | 3,4-dichloro ethoxybenzene |
| 17 | pentafluoro ethoxybenzene |
| 18 | 3,4-difluoro ethoxybenzene |
| 19 | 2-nitro-3-methyl ethoxybenzene |
| 20 | 2-chloro-4-CHO ethoxybenzene |
| 21 | 2-methyl-4-nitro ethoxybenzene |

TABLE 29-continued

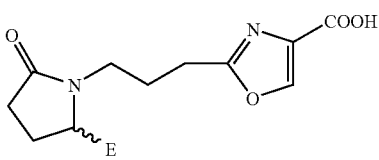

(I-A-29)

| No. | E |
|---|---|
| 22 | 2-methyl-3-nitro ethoxybenzene |
| 23 | 2-methyl-4-chloro ethoxybenzene |
| 24 | 3-nitro-4-methyl ethoxybenzene |
| 25 | 3-bromo ethoxybenzene |
| 26 | 2,3-dimethyl ethoxybenzene |
| 27 | 2,6-dimethyl-4-chloro ethoxybenzene |
| 28 | 2-ethoxynaphthalene |
| 29 | 2-fluoro-3-trifluoromethyl ethoxybenzene |
| 30 | 3,5-dimethyl ethoxybenzene |

TABLE 29-continued (I-A-29)

| No. | E |
|---|---|
| 31 | 3,4,5-trimethylphenoxyethyl |
| 32 | 5,6,7,8-tetrahydronaphthalen-1-yloxyethyl |
| 33 | 4-acetyl-3-methylphenoxyethyl |
| 34 | naphthalen-1-yloxyethyl |
| 35 | 2-chloro-3-(trifluoromethyl)phenoxyethyl |

TABLE 30

(I-A-30)

| No. | E |
|---|---|
| 1 | (E)-hex-2-enyl |
| 2 | octyl |
| 3 | (Z)-hept-2-enyl |
| 4 | (Z)-3-(tert-butoxy)prop-1-enyl |
| 5 | 2-butoxyethyl |
| 6 | 2-(4-methylphenyl)-2-propoxyethyl (propoxyethyl with p-tolyl) |
| 7 | (E)-4-ethoxybut-2-enyl |
| 8 | (E)-4-propoxybut-2-enyl |
| 9 | (E)-7-phenylhept-2-enyl |
| 10 | N-pentylacetamido |
| 11 | 2-phenoxyethyl |
| 12 | 2-(pyridin-3-yloxy)ethyl |
| 13 | 2-(3,5-dichlorophenoxy)ethyl |
| 14 | 2-(2,5-dichlorophenoxy)ethyl |
| 15 | 2-(2,4,5-trichlorophenoxy)ethyl |
| 16 | 2-(3,4-dichlorophenoxy)ethyl |

TABLE 30-continued (I-A-30)

[Structure: pyrrolidinone-N-CH2CH2-thiazole-CO2H with E substituent on pyrrolidinone]

| No. | E |
|-----|---|
| 17 | 2-ethoxy-3,4,5,6-tetrafluorophenyl |
| 18 | 2-ethoxy-5,6-difluorophenyl (ethoxy-difluorophenyl) |
| 19 | 2-ethoxy-6-methyl-3-nitrophenyl |
| 20 | 4-ethoxy-2-chloro-benzaldehyde (ethoxy-chloro-CHO phenyl) |
| 21 | 4-ethoxy-3-methyl-6-nitrophenyl |
| 22 | 2-ethoxy-3-methyl-6-nitrophenyl (wait: methyl/NO2) |
| 23 | 3-ethoxy-5-methyl-4-chlorophenyl |
| 24 | 4-ethoxy-2-nitro-5-methylphenyl |
| 25 | 3-ethoxy-5-bromophenyl |
| 26 | 2-ethoxy-3,6-dimethylphenyl |
| 27 | 2-ethoxy-3,5-dimethyl-5-chlorophenyl |
| 28 | 6-ethoxy-naphthalen-2-yl |
| 29 | 3-ethoxy-2-fluoro-6-(trifluoromethyl)phenyl |
| 30 | 3-ethoxy-4,6-dimethylphenyl |
| 31 | 3-ethoxy-4,5,6-trimethylphenyl |
| 32 | 8-ethoxy-5,6,7,8-tetrahydronaphthalen-1-yl |
| 33 | 4-ethoxy-2-methyl-1-acetylphenyl |
| 34 | 1-ethoxy-naphthalen-2-yl |

TABLE 30-continued (I-A-30)

[Structure: pyrrolidinone-N-CH2CH2-thiazole-CO2H with E substituent on pyrrolidinone ring]

| No. | E |
|-----|---|
| 35 | 2-chloro-3-(trifluoromethyl)phenyl ethoxy group |

TABLE 31

(I-A-31)

[Structure: pyrrolidinone-N-(CH2)3-thiophene-COOH with E substituent on pyrrolidinone ring]

| No. | E |
|-----|---|
| 1 | -CH=CH-CH2-CH2-CH3 (trans) |
| 2 | -CH2-CH2-CH2-CH2-CH2-CH3 |
| 3 | -CH=CH-CH2-CH2-CH2-CH3 (cis) |
| 4 | -CH=CH-CH2-O-C(CH3)3 |
| 5 | -CH2-O-CH2-CH2-CH2-CH3 |
| 6 | -CH2-(4-methylphenyl)... -O-CH2-CH2-CH3 |
| 7 | -CH=CH-CH2-O-CH2-CH3 |
| 8 | -CH=CH-CH2-O-CH2-CH2-CH3 |
| 9 | -CH=CH-CH2-CH2-CH2-CH2-CH2-phenyl |
| 10 | -C(=O)-NH-CH2-CH2-CH2-CH2-CH3 |
| 11 | -CH2-O-phenyl |

TABLE 31-continued (I-A-31)

[Structure: pyrrolidinone-N-(CH2)3-thiophene-COOH with E substituent on pyrrolidinone ring]

| No. | E |
|-----|---|
| 12 | ethoxy-pyridin-3-yl |
| 13 | 3,5-dichlorophenyl ethoxy |
| 14 | 2,5-dichlorophenyl ethoxy |
| 15 | 2,4,5-trichlorophenyl ethoxy |
| 16 | 3,4-dichlorophenyl ethoxy |
| 17 | pentafluorophenyl ethoxy |
| 18 | 3,4-difluorophenyl ethoxy |
| 19 | 2-nitro-3-methylphenyl ethoxy |
| 20 | 2-chloro-4-formylphenyl ethoxy |
| 21 | 2-methyl-4-nitrophenyl ethoxy |

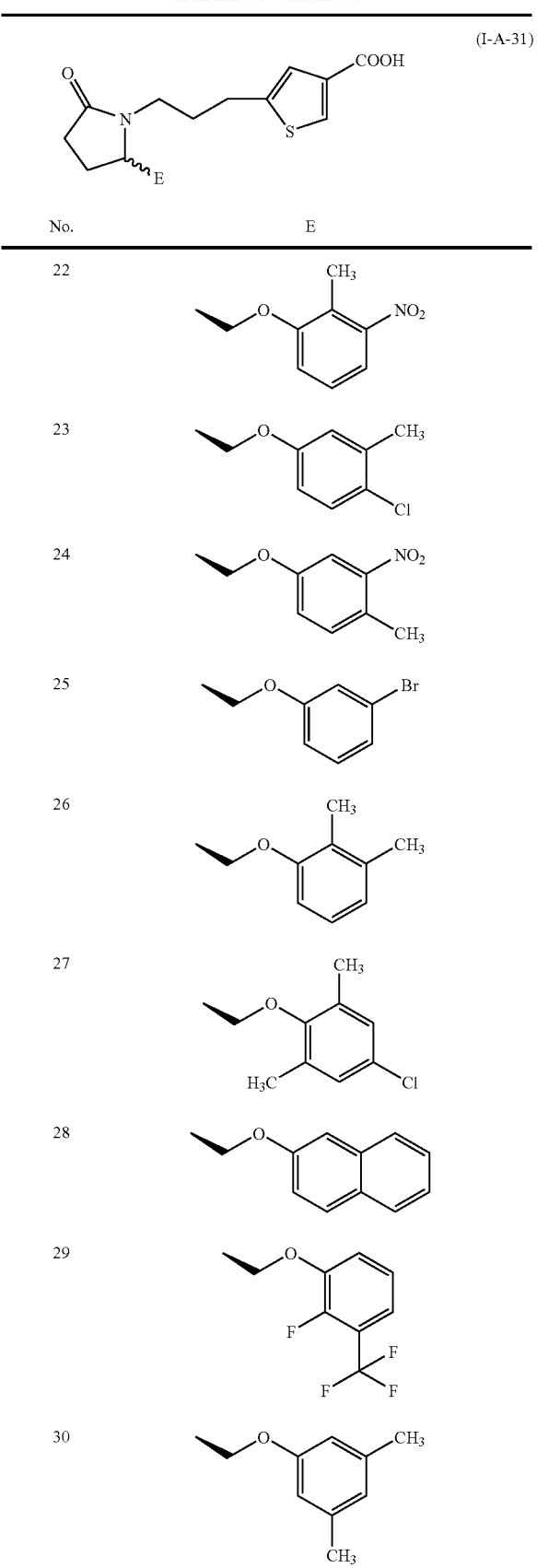
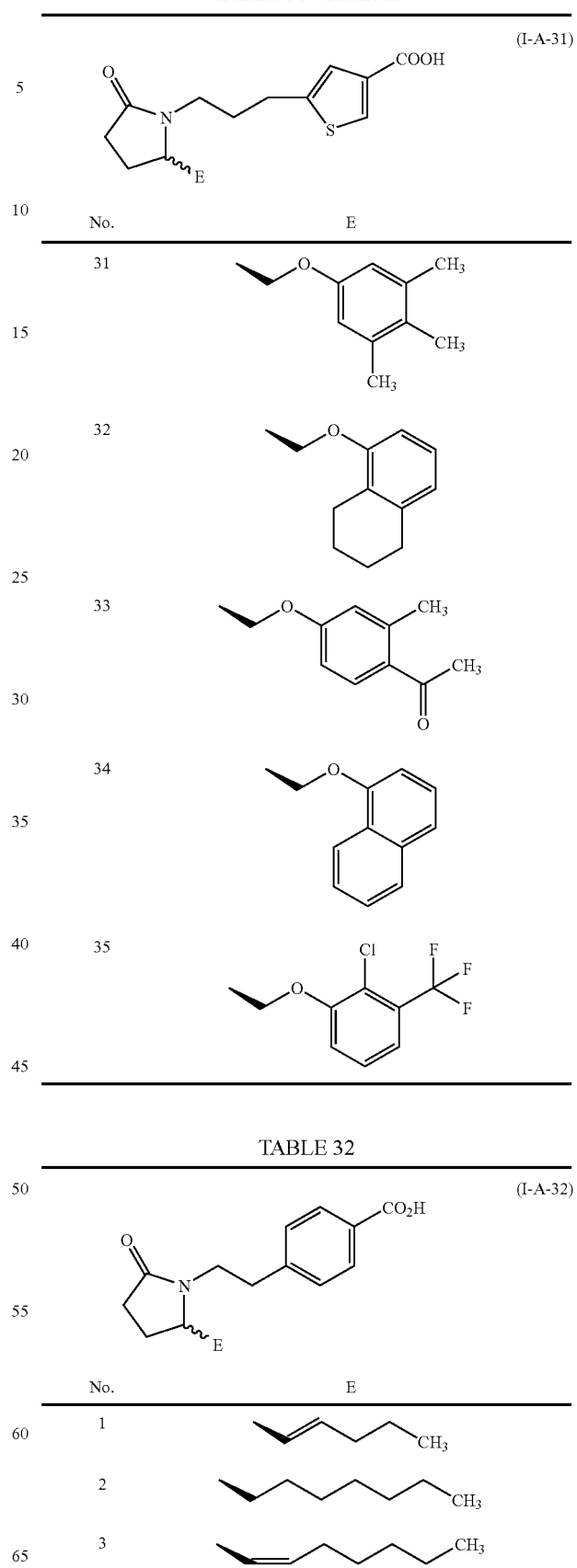

TABLE 32-continued (I-A-32)

Structure: pyrrolidinone with N-CH2CH2-C6H4-CO2H at N, and E substituent at position 5 of pyrrolidinone ring.

| No. | E |
|---|---|
| 4 | -CH2-CH=CH-CH2-O-C(CH3)3 (cis) |
| 5 | -CH2-CH2-O-CH2-CH2-CH2-CH3 |
| 6 | -CH2-(4-methylphenyl)-CH2-CH2-O-CH2-CH2-CH3 |
| 7 | -CH=CH-CH2-CH2-O-CH2-CH3 |
| 8 | -CH=CH-CH2-O-CH2-CH2-CH3 |
| 9 | -CH=CH-(CH2)4-C6H5 |
| 10 | -CH2-NH-C(=O)-CH2-CH2-CH2-CH2-CH3 |
| 11 | -CH2-O-C6H5 |
| 12 | -CH2-O-(pyridin-3-yl) |
| 13 | -CH2-O-(3,5-dichlorophenyl) |
| 14 | -CH2-O-(2,5-dichlorophenyl) |
| 15 | -CH2-O-(2,4,5-trichlorophenyl) |
| 16 | -CH2-O-(3,4-dichlorophenyl) |
| 17 | -CH2-O-(pentafluorophenyl) |
| 18 | -CH2-O-(3,4-difluorophenyl) |
| 19 | -CH2-O-(2-nitro-3-methylphenyl) |
| 20 | -CH2-O-(3-chloro-4-formylphenyl) |
| 21 | -CH2-O-(3-methyl-4-nitrophenyl) |
| 22 | -CH2-O-(2-methyl-3-nitrophenyl) |
| 23 | -CH2-O-(3-methyl-4-chlorophenyl) |
| 24 | -CH2-O-(3-nitro-4-methylphenyl) |
| 25 | -CH2-O-(3-bromophenyl) |

TABLE 32-continued (I-A-32)

| No. | E |
|---|---|
| 26 | 2-ethoxy-2,3-dimethylphenyl |
| 27 | 2-ethoxy-3,5-dimethyl-5-chlorophenyl (ethoxy with two CH3 and Cl) |
| 28 | 2-ethoxynaphthalenyl |
| 29 | 3-ethoxy-2-fluoro-4-(trifluoromethyl)phenyl |
| 30 | 3-ethoxy-3,5-dimethylphenyl |
| 31 | 5-ethoxy-2,3,4-trimethylphenyl |
| 32 | 8-ethoxy-1,2,3,4-tetrahydronaphthalenyl |
| 33 | 4-ethoxy-2-methyl-1-acetylphenyl |

TABLE 32-continued (I-A-32)

| No. | E |
|---|---|
| 34 | 1-ethoxynaphthalenyl |
| 35 | 3-ethoxy-2-chloro-1-(trifluoromethyl)phenyl |

TABLE 33

(I-A-33)

| No. | E |
|---|---|
| 1 | pentenyl chain with CH3 |
| 2 | heptyl chain with CH3 |
| 3 | heptenyl (cis) with CH3 |
| 4 | CH2-O-C(CH3)3 alkenyl |
| 5 | -CH=CH-O-CH2CH2CH3 |
| 6 | 4-methylphenyl-CH2CH2-O-CH2CH2CH3 |
| 7 | -CH=CH-CH2-O-CH2CH3 |
| 8 | -CH=CH-CH2-O-CH2CH2CH3 |
| 9 | -CH=CH-(CH2)4-phenyl |

TABLE 33-continued (I-A-33)

| No. | E |
|---|---|
| 10 | N-pentyl acetamide (CH₃(CH₂)₄NHC(O)–) |
| 11 | phenoxy (via ethoxy linker) |
| 12 | 3-pyridyloxy (via ethoxy linker) |
| 13 | 3,5-dichlorophenoxy (via ethoxy linker) |
| 14 | 2,5-dichlorophenoxy (via ethoxy linker) |
| 15 | 2,4,5-trichlorophenoxy (via ethoxy linker) |
| 16 | 3,4-dichlorophenoxy (via ethoxy linker) |
| 17 | pentafluorophenoxy (via ethoxy linker) |
| 18 | 3,4-difluorophenoxy (via ethoxy linker) |
| 19 | 2-nitro-3-methylphenoxy (via ethoxy linker) |
| 20 | 2-chloro-4-ethoxybenzaldehyde moiety |
| 21 | 4-ethoxy-2-methyl-3-nitrophenyl |
| 22 | 3-ethoxy-2-methyl-nitrophenyl |
| 23 | 4-chloro-3-methyl-ethoxyphenyl |
| 24 | 5-nitro-4-methyl-ethoxyphenyl |
| 25 | 3-bromo-ethoxyphenyl |
| 26 | 2,3-dimethyl-ethoxyphenyl |
| 27 | 4-chloro-2,6-dimethyl-ethoxyphenyl |
| 28 | 2-naphthyloxy (via ethoxy linker) |
| 29 | 2-fluoro-3-(trifluoromethyl)-ethoxyphenyl |

125
TABLE 33-continued
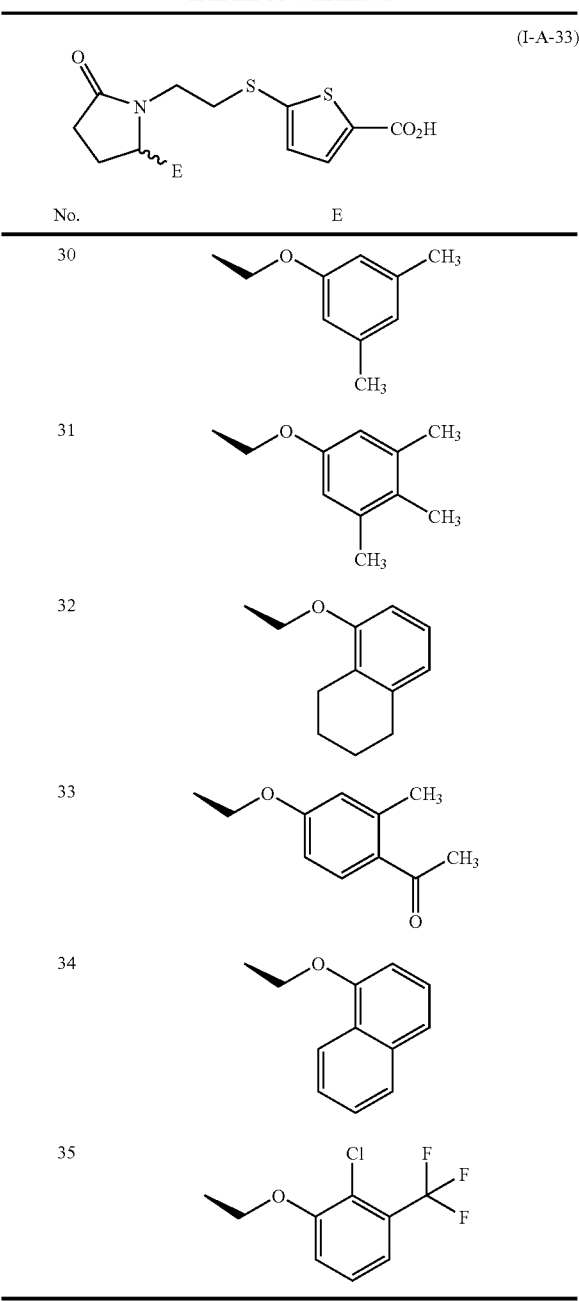
126
TABLE 34-continued
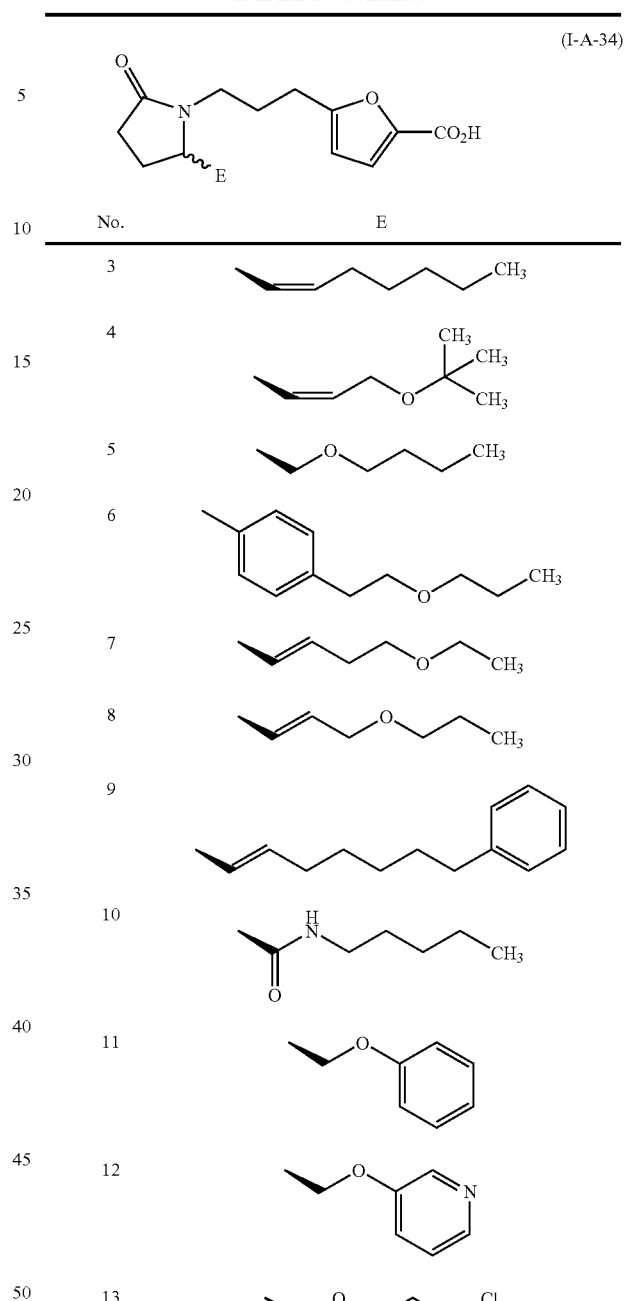
TABLE 34
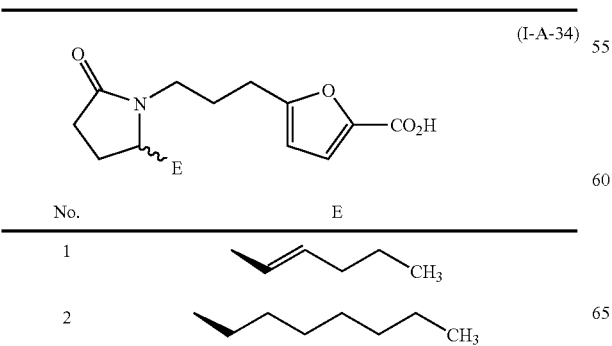
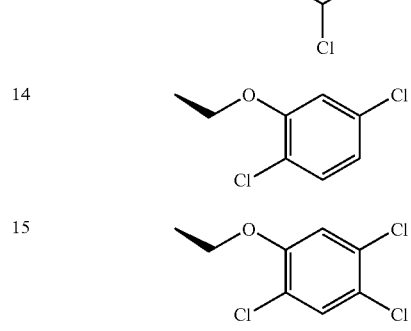

TABLE 34-continued
(I-A-34)
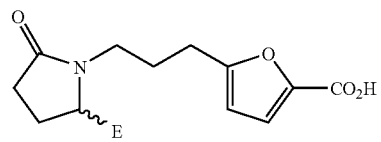
| No. | E |
|---|---|
| 16 | 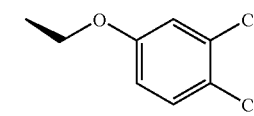 |
| 17 | 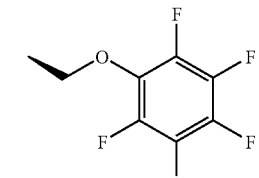 |
| 18 | 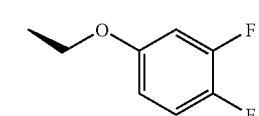 |
| 19 | 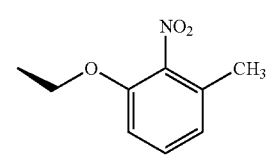 |
| 20 | 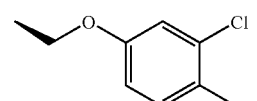 |
| 21 | 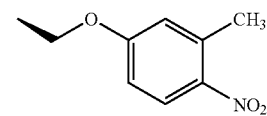 |
| 22 | 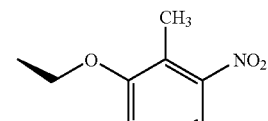 |
| 23 | 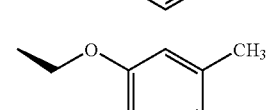 |
| 24 | 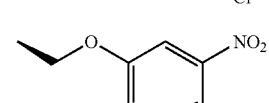 |
| 25 | 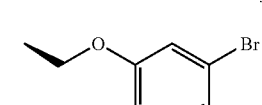 |
TABLE 34-continued
(I-A-34)
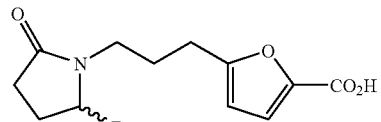
| No. | E |
|---|---|
| 26 | 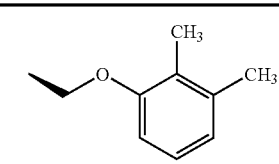 |
| 27 | 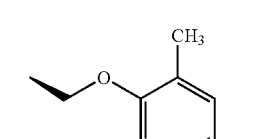 |
| 28 | 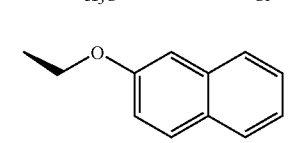 |
| 29 | 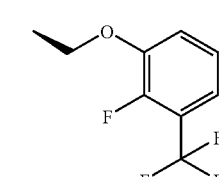 |
| 30 | 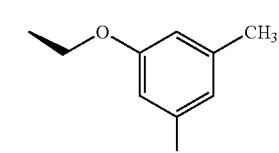 |
| 31 | 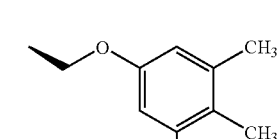 |
| 32 | 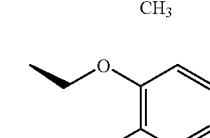 |
| 33 | 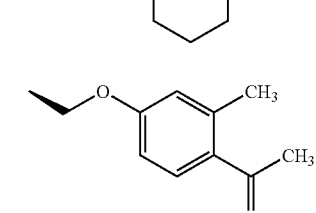 |

TABLE 34-continued (I-A-34)

[Structure: pyrrolidinone-N-CH2CH2CH2-furan-CO2H with E substituent]

| No. | E |
|---|---|
| 34 | 1-ethoxynaphthalene |
| 35 | 2-chloro-3-(trifluoromethyl)phenyl ethoxy |

TABLE 35

(I-A-35)

[Structure: pyrrolidinone-N-CH2-(3-substituted phenyl)-CH2COOH with E substituent]

| No. | E |
|---|---|
| 1 | –CH=CH–CH2–CH2–CH3 |
| 2 | –CH=CH–(CH2)4–CH3 |
| 3 | –CH=CH–(CH2)4–CH3 (cis) |
| 4 | –CH=CH–CH2–O–C(CH3)3 |
| 5 | –CH(–O–CH2CH2CH2CH3)– |
| 6 | –(4-methylphenyl)–CH2–CH2–O–CH2CH2CH3 |
| 7 | –CH=CH–CH2–CH2–O–CH2CH3 |
| 8 | –CH=CH–CH2–CH2–O–CH2CH2CH3 |
| 9 | –CH=CH–(CH2)4–CH2–phenyl |

TABLE 35-continued (I-A-35)

[Structure: pyrrolidinone-N-CH2-(3-substituted phenyl)-CH2COOH with E substituent]

| No. | E |
|---|---|
| 10 | –C(=O)–NH–(CH2)4–CH3 |
| 11 | phenoxy ethyl |
| 12 | 3-pyridyloxy ethyl |
| 13 | 3,5-dichlorophenoxy ethyl |
| 14 | 2,5-dichlorophenoxy ethyl |
| 15 | 2,4,5-trichlorophenoxy ethyl |
| 16 | 3,4-dichlorophenoxy ethyl |
| 17 | pentafluorophenoxy ethyl |
| 18 | 3,4-difluorophenoxy ethyl |
| 19 | 2-nitro-3-methylphenoxy ethyl |

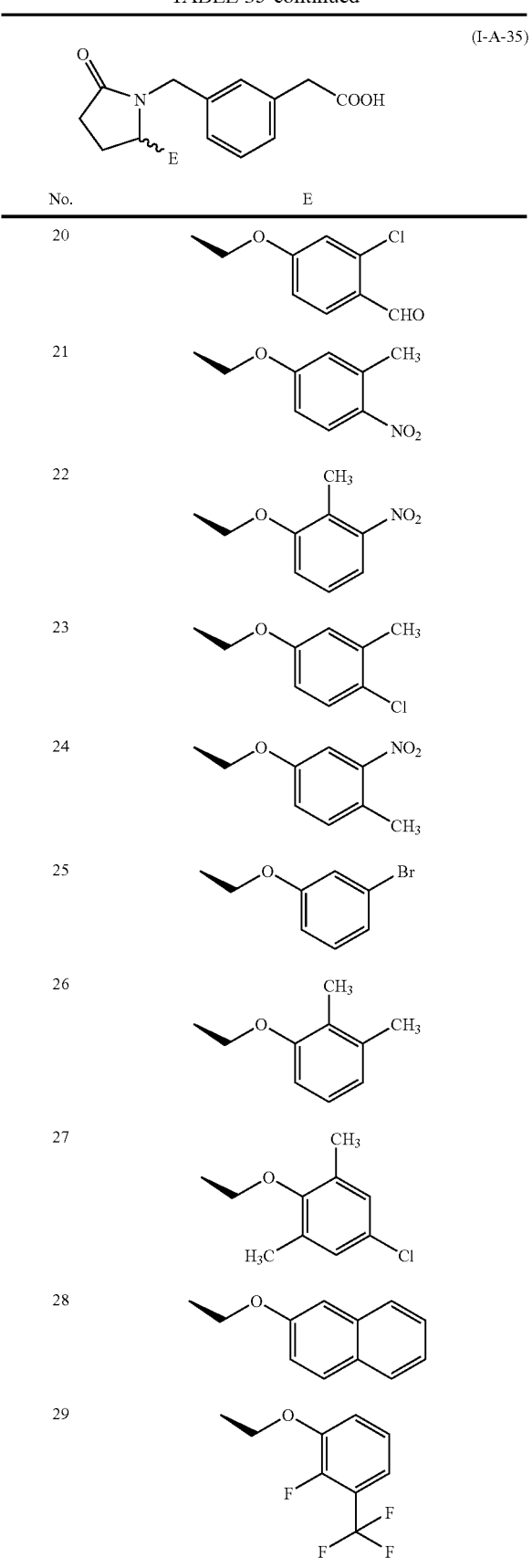
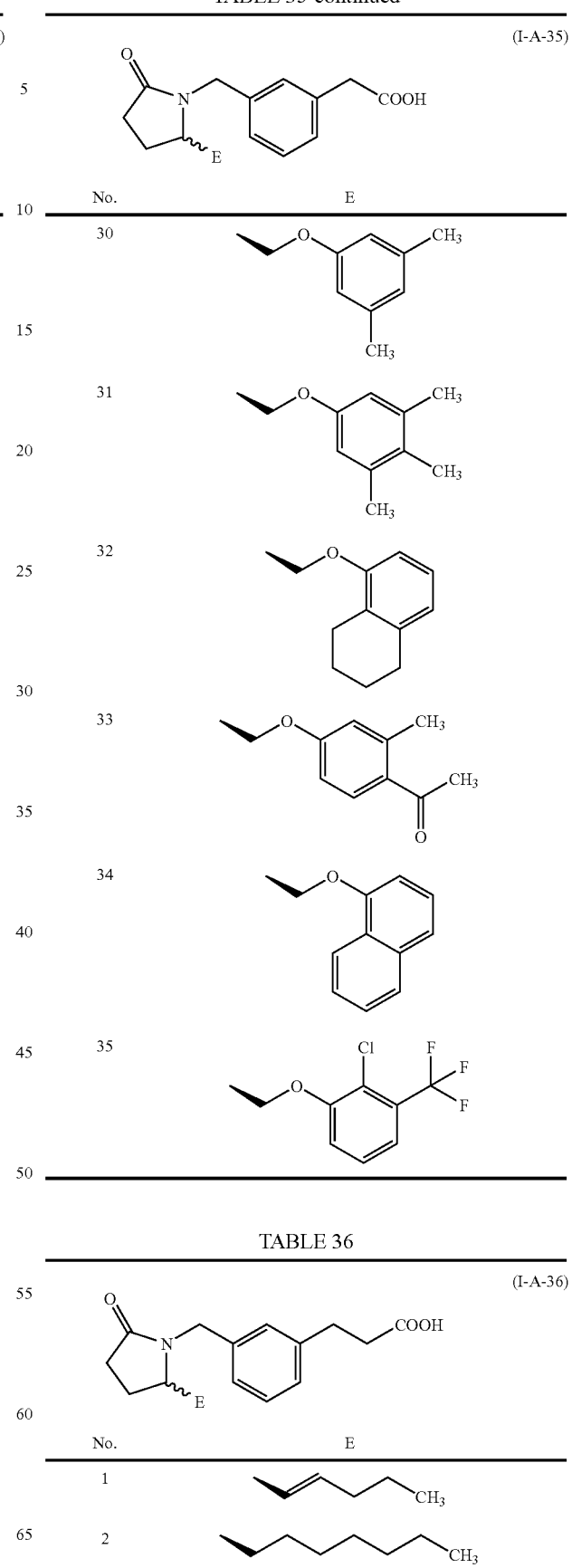

TABLE 36-continued (I-A-36)

| No. | E |
|---|---|
| 3 | CH=CH-CH2-CH2-CH2-CH3 (cis) |
| 4 | CH2-O-C(CH3)3 allyl |
| 5 | CH2-O-CH2-CH2-CH2-CH3 |
| 6 | CH2-CH2-O-CH2-C6H4-CH3 (p-tolyl) |
| 7 | CH=CH-CH2-O-CH2-CH3 |
| 8 | CH=CH-CH2-O-CH2-CH2-CH3 |
| 9 | CH=CH-(CH2)4-C6H5 |
| 10 | CH2-NH-C(=O)-CH2-CH2-CH2-CH2-CH3 |
| 11 | CH2-O-C6H5 |
| 12 | CH2-O-(3-pyridyl) |
| 13 | CH2-O-(3,5-dichlorophenyl) |
| 14 | CH2-O-(2,5-dichlorophenyl) |
| 15 | CH2-O-(2,4,5-trichlorophenyl) |

TABLE 36-continued (I-A-36)

| No. | E |
|---|---|
| 16 | CH2-O-(3,4-dichlorophenyl) |
| 17 | CH2-O-(pentafluorophenyl) |
| 18 | CH2-O-(3,4-difluorophenyl) |
| 19 | CH2-O-(2-nitro-3-methylphenyl) |
| 20 | CH2-O-(2-chloro-4-formylphenyl) |
| 21 | CH2-O-(3-methyl-4-nitrophenyl) |
| 22 | CH2-O-(2-methyl-3-nitrophenyl) |
| 23 | CH2-O-(3-methyl-4-chlorophenyl) |
| 24 | CH2-O-(3-nitro-4-methylphenyl) |
| 25 | CH2-O-(3-bromophenyl) |

TABLE 36-continued
(I-A-36)
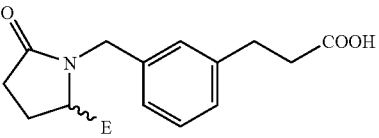
| No. | E |
|---|---|
| 26 | 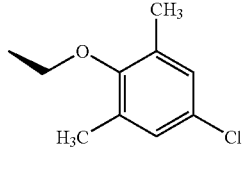 |
| 27 | 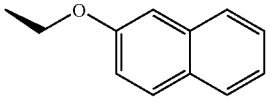 |
| 28 | 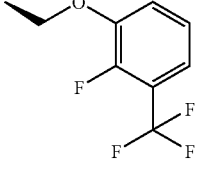 |
| 29 | 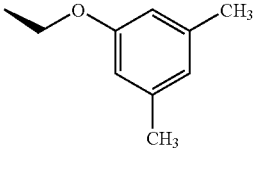 |
| 30 | 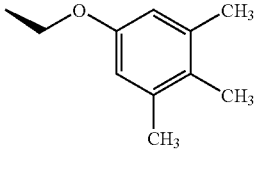 |
| 31 | 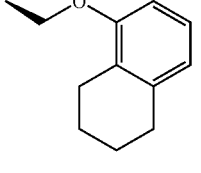 |
| 32 | 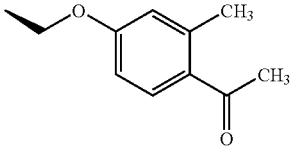 |
| 33 | 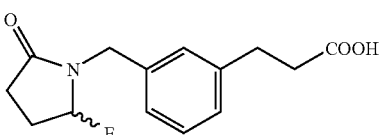 |
TABLE 36-continued
(I-A-36)
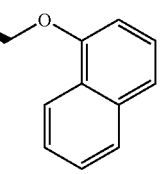
| No. | E |
|---|---|
| 34 | 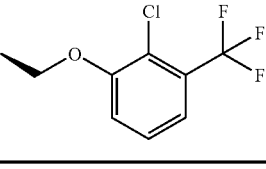 |
| 35 | 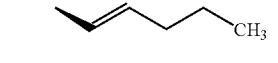 |
TABLE 37
(I-A-37)
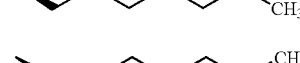
| No. | E |
|---|---|
| 1 |  |
| 2 | 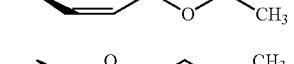 |
| 3 |  |
| 4 | 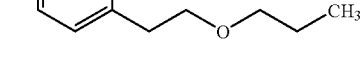 |
| 5 | 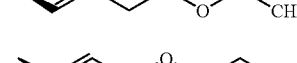 |
| 6 |  |
| 7 | |
| 8 | |
| 9 | 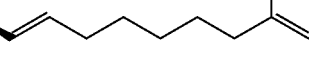 |

TABLE 37-continued (I-A-37)

| No. | E |
|---|---|
| 10 | acetamido-pentyl (CH₃CH₂CH₂CH₂CH₂NHC(O)-) |
| 11 | 2-ethoxyphenyl |
| 12 | 3-ethoxypyridin-? |
| 13 | 3,5-dichloro-1-ethoxyphenyl |
| 14 | 2,5-dichloro-1-ethoxyphenyl |
| 15 | 2,4,5-trichloro-1-ethoxyphenyl |
| 16 | 3,4-dichloro-1-ethoxyphenyl |
| 17 | 2,3,4,5,6-pentafluoro-1-ethoxyphenyl |
| 18 | 3,4-difluoro-1-ethoxyphenyl |
| 19 | 2-nitro-3-methyl-1-ethoxyphenyl |
| 20 | 2-chloro-4-ethoxybenzaldehyde-substituted |
| 21 | 4-ethoxy-3-methyl-1-nitrophenyl |
| 22 | 2-methyl-3-nitro-1-ethoxyphenyl |
| 23 | 4-chloro-3-methyl-1-ethoxyphenyl |
| 24 | 3-nitro-4-methyl-1-ethoxyphenyl |
| 25 | 3-bromo-1-ethoxyphenyl |
| 26 | 2,3-dimethyl-1-ethoxyphenyl |
| 27 | 2,6-dimethyl-4-chloro-1-ethoxyphenyl |
| 28 | 2-naphthyl ethoxy |
| 29 | 2-fluoro-3-trifluoromethyl-1-ethoxyphenyl |

TABLE 37-continued
(I-A-37)
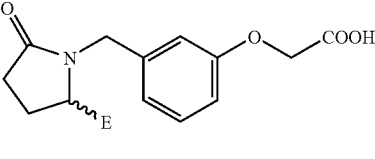
| No. | E |
|---|---|
| 30 | 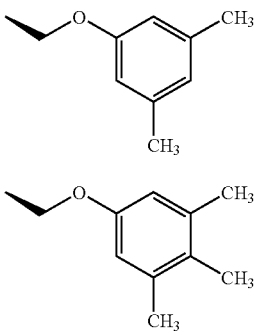 |
| 31 | 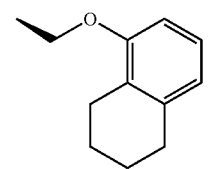 |
| 32 | 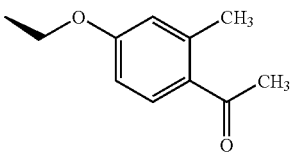 |
| 33 | 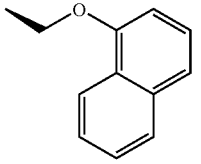 |
| 34 | 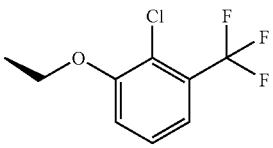 |
| 35 | 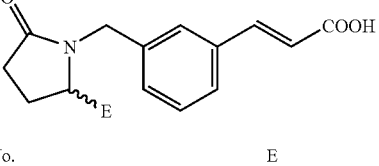 |
TABLE 38
(I-A-38)
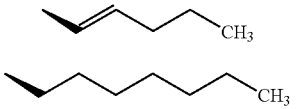
| No. | E |
|---|---|
| 1 | 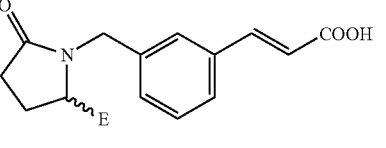 |
| 2 | 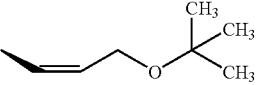 |
TABLE 38-continued
(I-A-38)
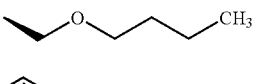
| No. | E |
|---|---|
| 3 | 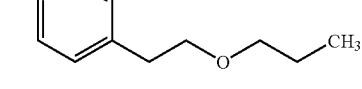 |
| 4 | 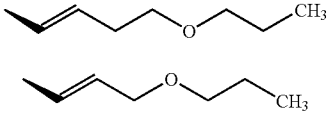 |
| 5 |  |
| 6 | 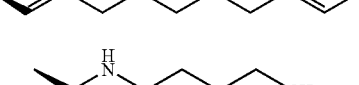 |
| 7 |  |
| 8 | 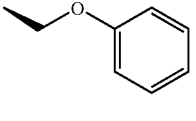 |
| 9 | 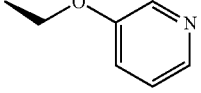 |
| 10 | 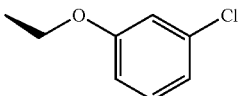 |
| 11 | 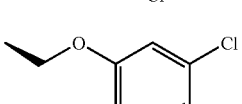 |
| 12 | 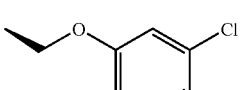 |
| 13 | |
| 14 | |
| 15 | |

TABLE 38-continued (I-A-38)

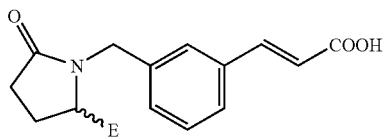

| No. | E |
|---|---|
| 16 | 3,4-dichloro-phenoxyethyl |
| 17 | pentafluorophenoxyethyl |
| 18 | 3,4-difluorophenoxyethyl |
| 19 | 2-nitro-3-methyl-phenoxyethyl |
| 20 | 2-chloro-4-CHO-phenoxyethyl |
| 21 | 2-methyl-4-nitro-phenoxyethyl |
| 22 | 2-methyl-3-nitro-phenoxyethyl |
| 23 | 2-methyl-4-chloro-phenoxyethyl |
| 24 | 2-nitro-4-methyl-phenoxyethyl |
| 25 | 3-bromophenoxyethyl |

TABLE 38-continued (I-A-38)

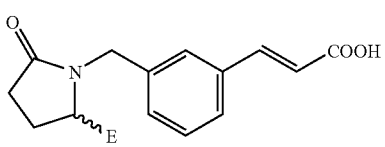

| No. | E |
|---|---|
| 26 | 2,3-dimethylphenoxyethyl |
| 27 | 2,6-dimethyl-4-chloro-phenoxyethyl |
| 28 | naphthalen-2-yloxyethyl |
| 29 | 2-fluoro-3-trifluoromethyl-phenoxyethyl |
| 30 | 3,5-dimethylphenoxyethyl |
| 31 | 3,4,5-trimethylphenoxyethyl |
| 32 | 5,6,7,8-tetrahydronaphthalen-1-yloxyethyl |
| 33 | 4-acetyl-3-methyl-phenoxyethyl |

TABLE 38-continued (I-A-38)

| No. | E |
|-----|---|
| 34 | (1-ethoxynaphthalene) |
| 35 | (2-chloro-3-ethoxy-1-trifluoromethylbenzene) |

TABLE 39

(I-A-39)

| No. | E |
|-----|---|
| 1 | -CH=CH-CH2-CH2-CH3 |
| 2 | -CH=CH-CH2-CH2-CH2-CH2-CH3 |
| 3 | -CH=CH-CH2-CH2-CH2-CH2-CH2-CH3 |
| 4 | -CH=CH-CH2-O-C(CH3)3 |
| 5 | -CH(O-CH2-CH2-CH2-CH3) |
| 6 | 4-methylphenyl-CH2-CH2-O-CH2-CH2-CH3 |
| 7 | -CH=CH-CH2-O-CH2-CH3 |
| 8 | -CH=CH-CH2-O-CH2-CH2-CH3 |
| 9 | -CH=CH-(CH2)4-phenyl |

TABLE 39-continued (I-A-39)

| No. | E |
|-----|---|
| 10 | -NH-C(=O)-CH2-CH2-CH2-CH2-CH3 |
| 11 | -O-phenyl |
| 12 | -O-(3-pyridyl) |
| 13 | 3,5-dichlorophenoxy |
| 14 | 2,5-dichlorophenoxy |
| 15 | 2,4,5-trichlorophenoxy |
| 16 | 3,4-dichlorophenoxy |
| 17 | pentafluorophenoxy |
| 18 | 3,4-difluorophenoxy |
| 19 | 2-nitro-3-methylphenoxy |

TABLE 39-continued
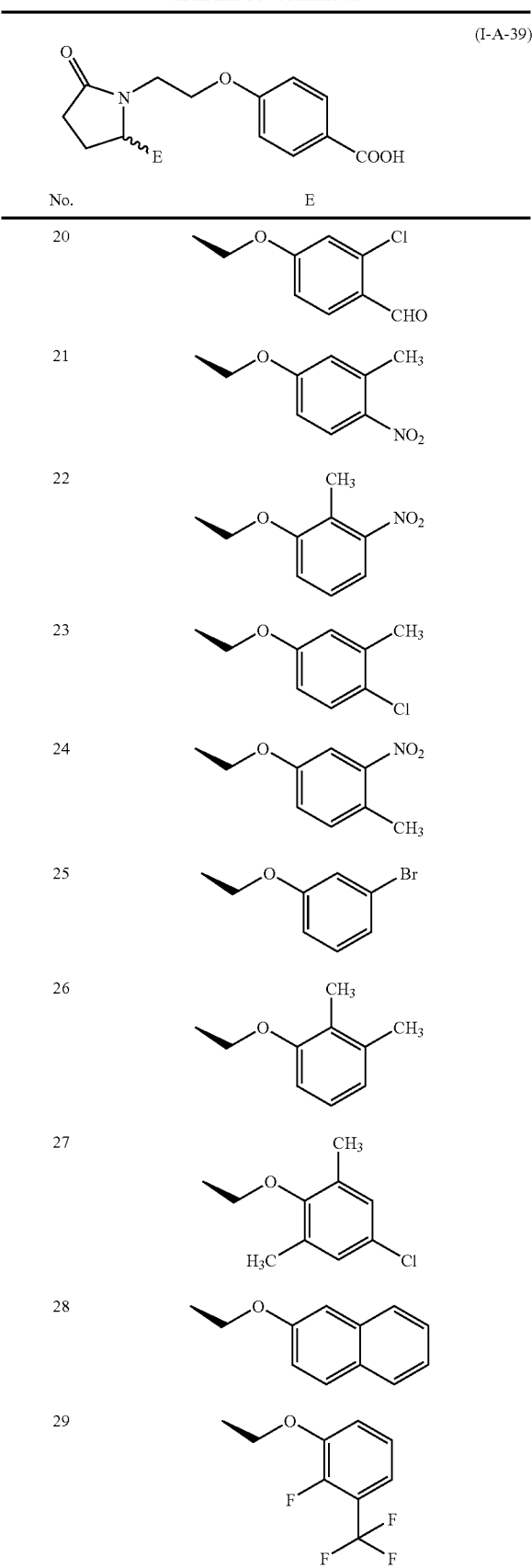
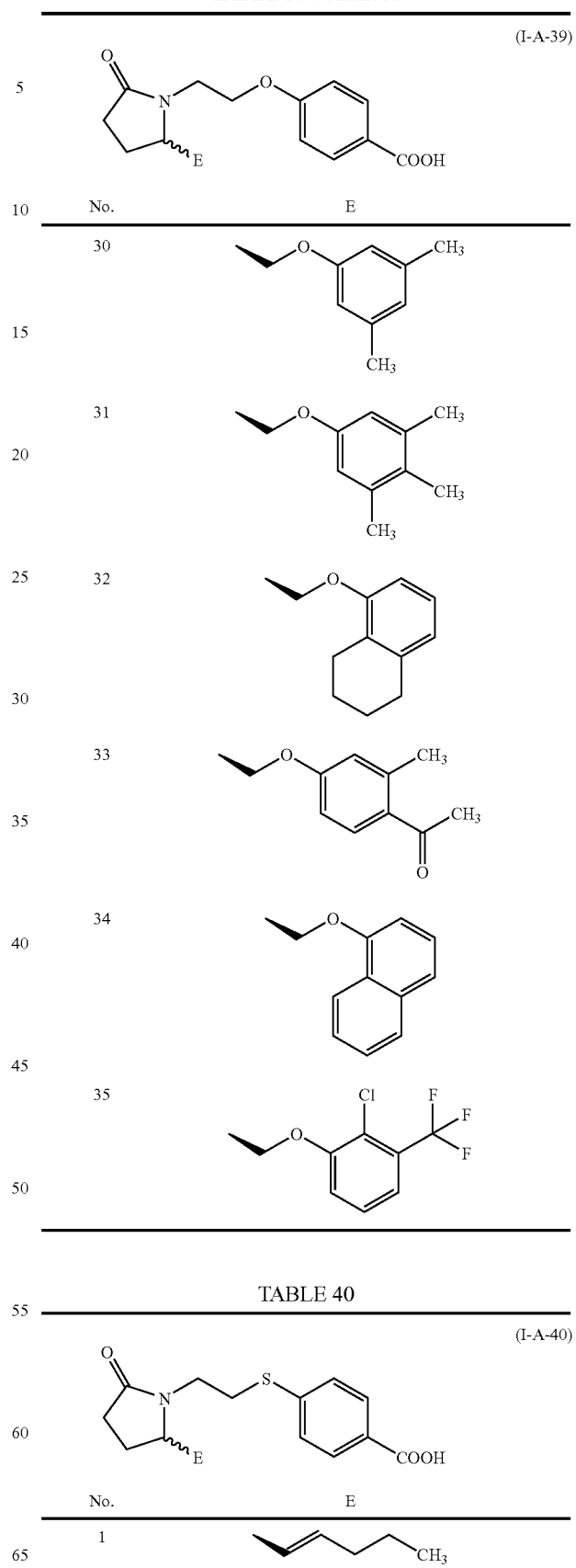

TABLE 40-continued (I-A-40)

| No. | E |
|---|---|
| 2 | *hept-2-enyl (CH3 terminus)* |
| 3 | *hept-2-enyl (Z)* |
| 4 | CH2-O-C(CH3)3 (allyl tert-butyl ether) |
| 5 | CH2-O-CH2CH2CH2CH3 |
| 6 | CH2CH2-O-CH2CH2CH3 with p-tolyl |
| 7 | CH2-O-CH2CH3 (allyl ethyl ether) |
| 8 | CH2-O-CH2CH2CH3 (allyl propyl ether) |
| 9 | CH2-(CH2)4-C6H5 (phenylhexenyl) |
| 10 | CH2-NH-C(=O)-(CH2)4CH3 |
| 11 | CH2-O-C6H5 |
| 12 | CH2-O-(3-pyridyl) |
| 13 | CH2-O-(3,5-dichlorophenyl) |
| 14 | CH2-O-(2,5-dichlorophenyl) |
| 15 | CH2-O-(2,4,5-trichlorophenyl) |

TABLE 40-continued (I-A-40)

| No. | E |
|---|---|
| 16 | CH2-O-(3,4-dichlorophenyl) |
| 17 | CH2-O-(pentafluorophenyl) |
| 18 | CH2-O-(3,4-difluorophenyl) |
| 19 | CH2-O-(2-methyl-3-nitrophenyl) |
| 20 | CH2-O-(2-chloro-4-formylphenyl) |
| 21 | CH2-O-(3-methyl-4-nitrophenyl) |
| 22 | CH2-O-(2-methyl-3-nitrophenyl) |
| 23 | CH2-O-(3-methyl-4-chlorophenyl) |
| 24 | CH2-O-(3-nitro-4-methylphenyl) |
| 25 | CH2-O-(3-bromophenyl) |

TABLE 40-continued
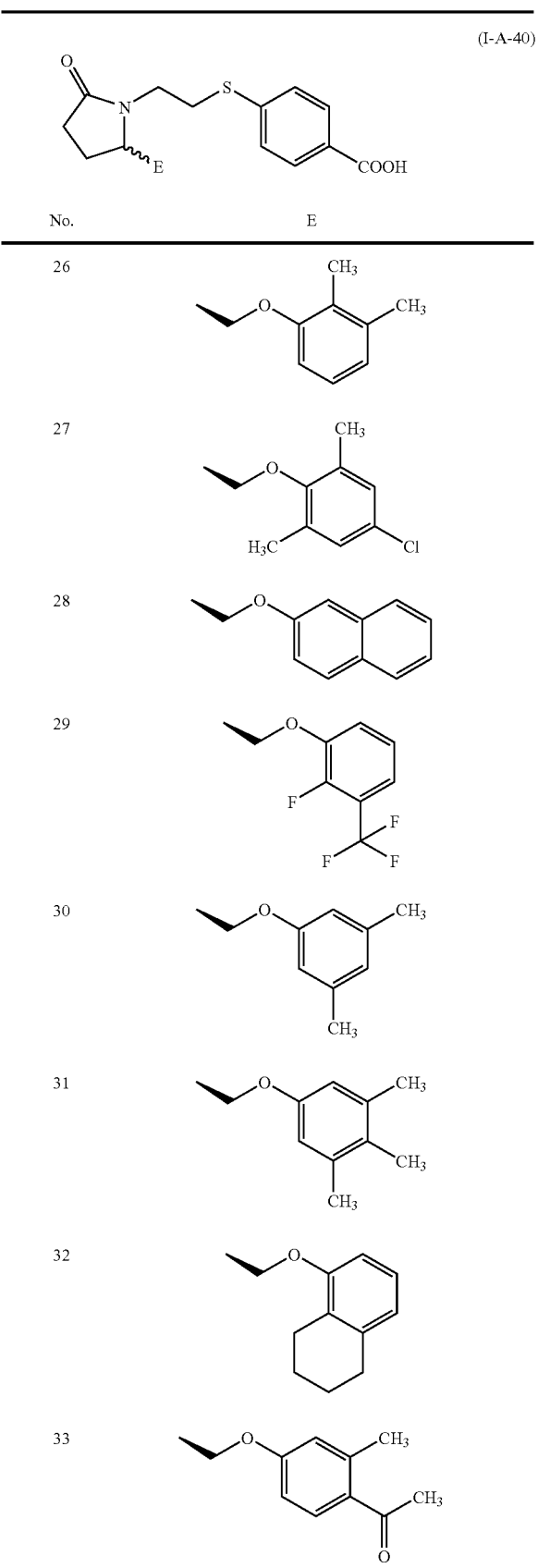
TABLE 40-continued
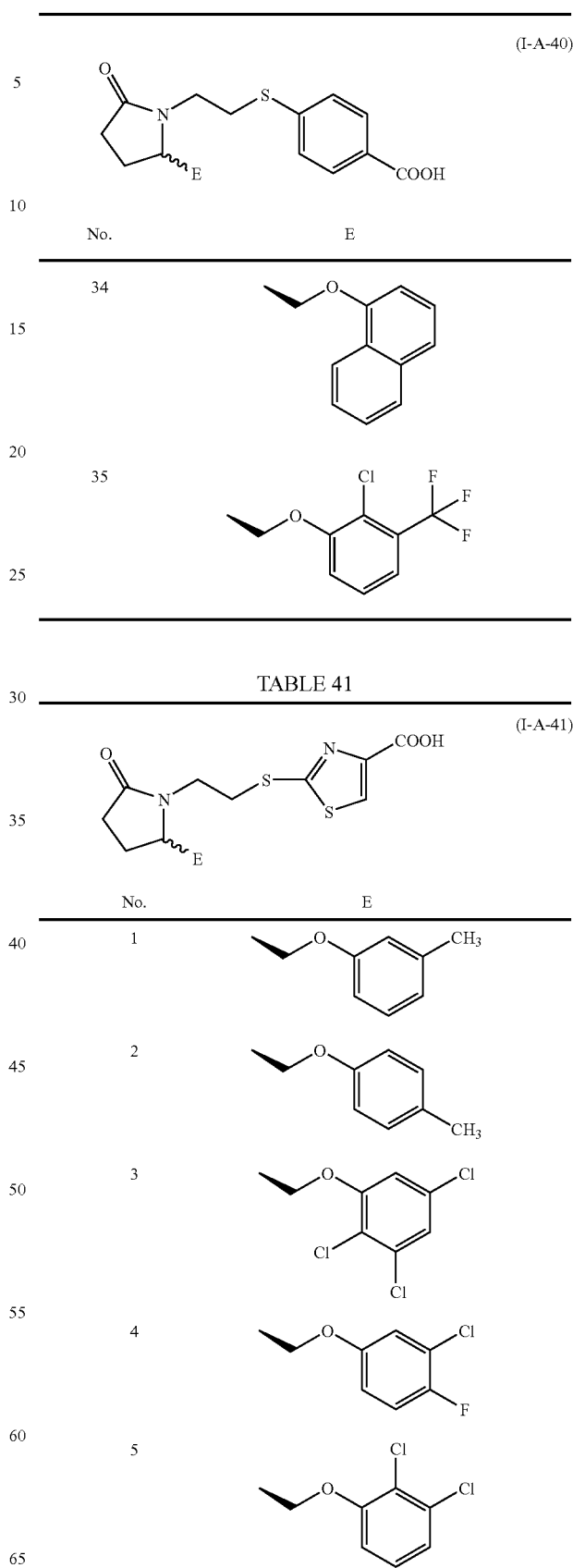

TABLE 41-continued
(I-A-41)
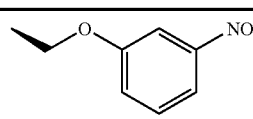
| No. | E |
|---|---|
| 6 | 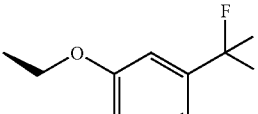 |
| 7 | 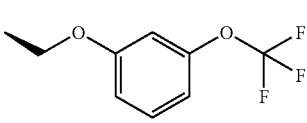 |
| 8 | 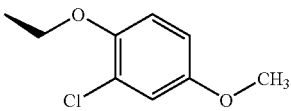 |
| 9 | 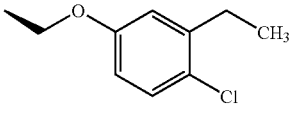 |
| 10 | 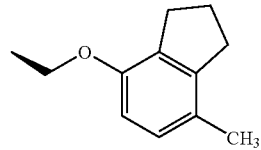 |
| 11 | 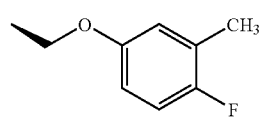 |
| 12 | 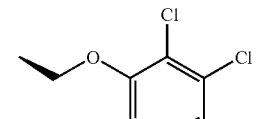 |
| 13 | 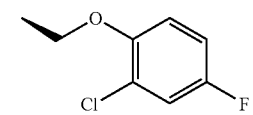 |
| 14 | 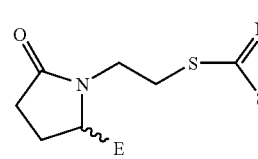 |
| 15 | 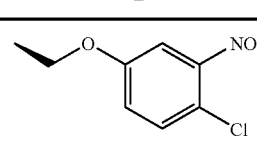 |
| 16 | 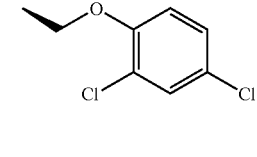 |
| 17 | 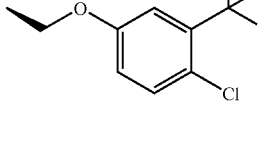 |
| 18 | 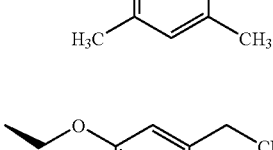 |
| 19 | 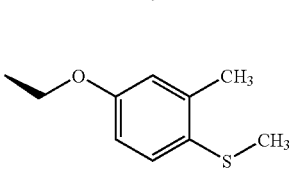 |
| 20 | 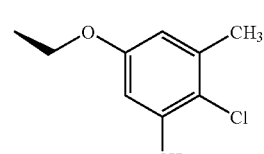 |
| 21 | 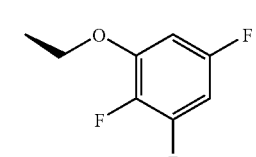 |
| 22 |  |

TABLE 41-continued (I-A-41)

| No. | E |
|---|---|
| 23 | 5-ethoxy-2-fluoro-4-(trifluoromethyl)phenyl (ethoxy linker to phenyl with CF3 and F substituents) |
| 24 | 4-chloro-3-fluoro-phenyl ethoxy |
| 25 | 3,5-dichlorophenyl propyl |
| 26 | 3,5-dichloro-N-ethylaniline |
| 27 | 3,5-dichlorophenyl ethylthio |
| 28 | 3,5-dimethylphenyl propyl |
| 29 | 3,5-dimethyl-N-ethylaniline |
| 30 | 3,5-dimethylphenyl ethylthio |

TABLE 41-continued (I-A-41)

| No. | E |
|---|---|
| 31 | 3,5-dichlorophenyl methoxyethyl |

TABLE 42

(I-A-42)

| No. | E |
|---|---|
| 1 | 3-methylphenyl ethoxy |
| 2 | 4-methylphenyl ethoxy |
| 3 | 2,3,5-trichlorophenyl ethoxy |
| 4 | 3-chloro-4-fluorophenyl ethoxy |
| 5 | 2,3-dichlorophenyl ethoxy |
| 6 | 3-nitrophenyl ethoxy |

TABLE 42-continued
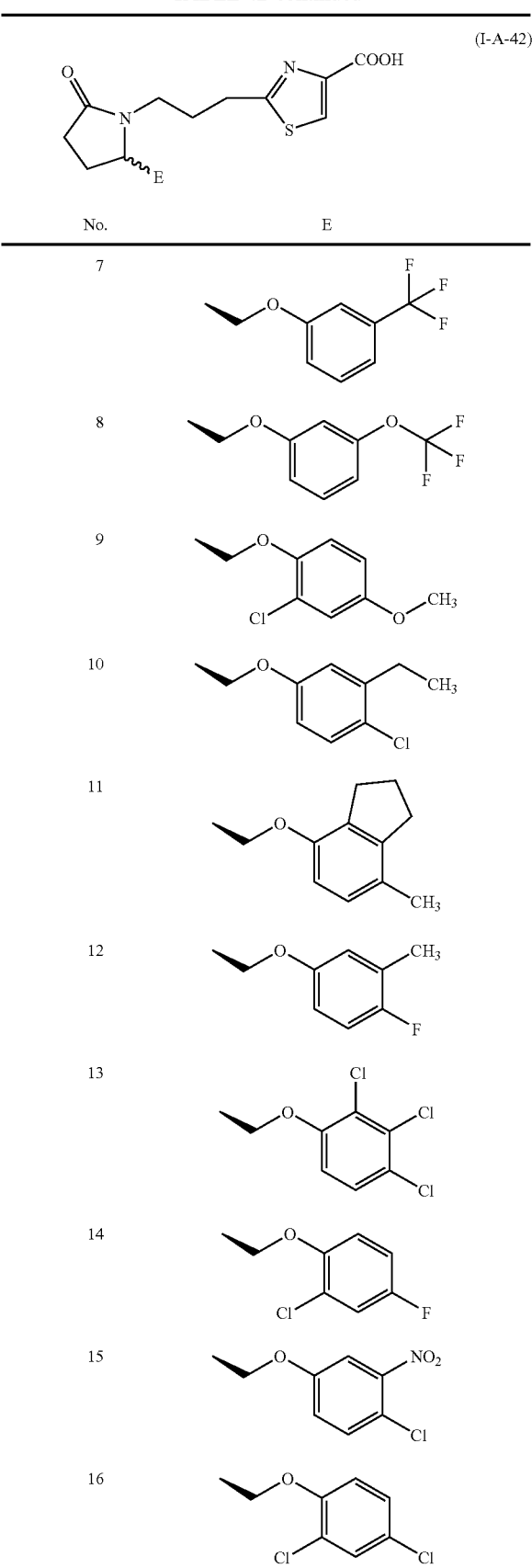
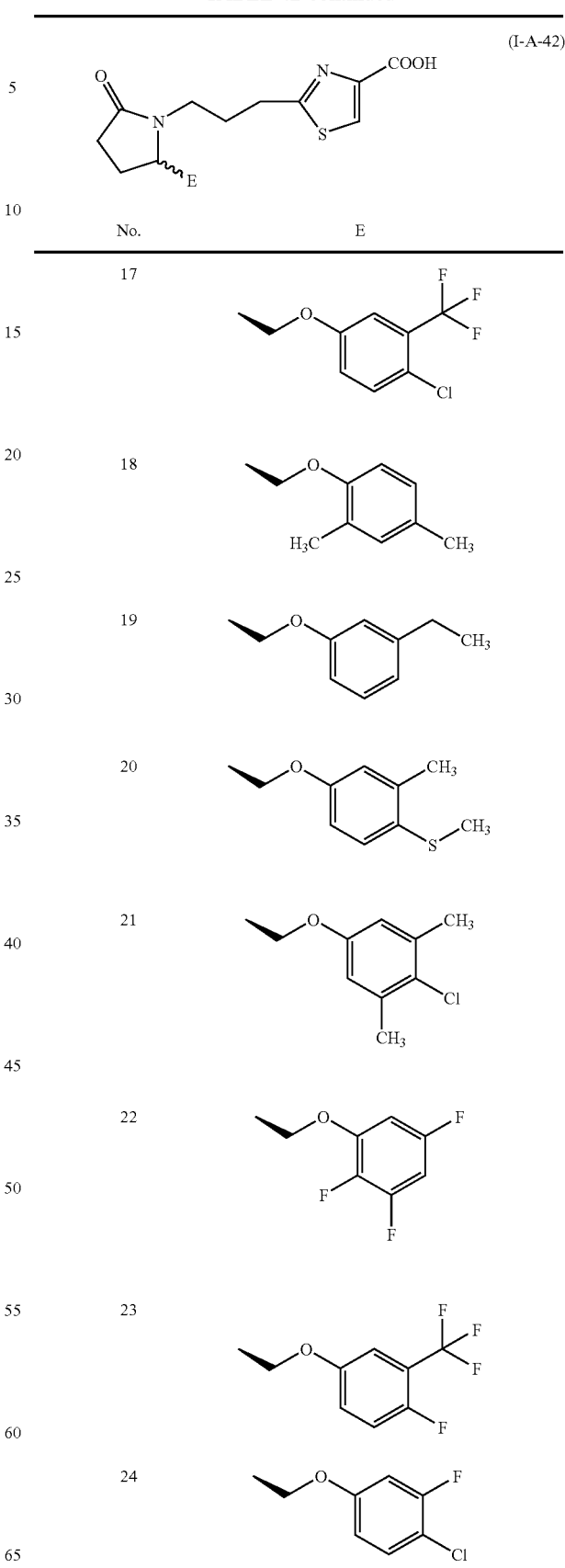

TABLE 42-continued (I-A-42)

| No. | E |
|---|---|
| 25 | 3,5-dichlorophenylpropyl |
| 26 | (3,5-dichlorophenylamino)ethyl |
| 27 | (3,5-dichlorophenylthio)ethyl |
| 28 | 3,5-dimethylphenylpropyl |
| 29 | (3,5-dimethylphenylamino)ethyl |
| 30 | (3,5-dimethylphenylthio)ethyl |
| 31 | (3,5-dichlorobenzyloxy)ethyl |

TABLE 43

(I-A-43)

| No. | E |
|---|---|
| 1 | (3-methylphenoxy)ethyl |
| 2 | (4-methylphenoxy)ethyl |
| 3 | (2,3,5-trichlorophenoxy)ethyl |
| 4 | (3-chloro-4-fluorophenoxy)ethyl |
| 5 | (2,3-dichlorophenoxy)ethyl |
| 6 | (3-nitrophenoxy)ethyl |
| 7 | (3-trifluoromethylphenoxy)ethyl |
| 8 | (3-trifluoromethoxyphenoxy)ethyl |
| 9 | (2-chloro-4-methoxyphenoxy)ethyl |
| 10 | (2-ethyl-4-chlorophenoxy)ethyl |

TABLE 43-continued (I-A-43)

| No. | E |
|---|---|
| 11 | 4-ethoxy-7-methyl-indane |
| 12 | 5-ethoxy-2-fluoro-3-methyl-phenyl |
| 13 | 2,3,4-trichloro-phenyl ethoxy |
| 14 | 2-chloro-4-fluoro-phenyl ethoxy |
| 15 | 4-chloro-3-nitro-phenyl ethoxy |
| 16 | 2,4-dichloro-phenyl ethoxy |
| 17 | 4-chloro-3-trifluoromethyl-phenyl ethoxy |
| 18 | 2,4-dimethyl-phenyl ethoxy |
| 19 | 3-ethyl-phenyl ethoxy |
| 20 | 2-methyl-4-methylthio-phenyl ethoxy |
| 21 | 4-chloro-3,5-dimethyl-phenyl ethoxy |
| 22 | 2,3,5-trifluoro-phenyl ethoxy |
| 23 | 4-fluoro-3-trifluoromethyl-phenyl ethoxy |
| 24 | 4-chloro-3-fluoro-phenyl ethoxy |
| 25 | 3,5-dichloro-phenyl ethyl |
| 26 | 3,5-dichloro-phenyl ethylamino |
| 27 | 3,5-dichloro-phenyl ethylthio |
| 28 | 3,5-dimethyl-phenyl ethyl |

TABLE 43-continued (I-A-43)

| No. | E |
|---|---|
| 29 | 3,5-dimethylphenyl-NH-CH2CH2- |
| 30 | 3,5-dimethylphenyl-S-CH2CH2- |
| 31 | 3,5-dichlorophenyl-CH2-O-CH2CH2- |

TABLE 44

(I-A-44)

| No. | E |
|---|---|
| 1 | 3-methylphenyl-O-CH2CH2- |
| 2 | 4-methylphenyl-O-CH2CH2- |
| 3 | 2,3,5-trichlorophenyl-O-CH2CH2- |
| 4 | 3-chloro-4-fluorophenyl-O-CH2CH2- |

TABLE 44-continued (I-A-44)

| No. | E |
|---|---|
| 5 | 2,3-dichlorophenyl-O-CH2CH2- |
| 6 | 3-nitrophenyl-O-CH2CH2- |
| 7 | 3-trifluoromethylphenyl-O-CH2CH2- |
| 8 | 3-trifluoromethoxyphenyl-O-CH2CH2- |
| 9 | 2-chloro-4-methoxyphenyl-O-CH2CH2- |
| 10 | 3-ethyl-4-chlorophenyl-O-CH2CH2- |
| 11 | 7-methyl-indanyl-O-CH2CH2- |
| 12 | 2-methyl-3-fluorophenyl-O-CH2CH2- |
| 13 | 2,3,4-trichlorophenyl-O-CH2CH2- |
| 14 | 2-chloro-4-fluorophenyl-O-CH2CH2- |

TABLE 44-continued
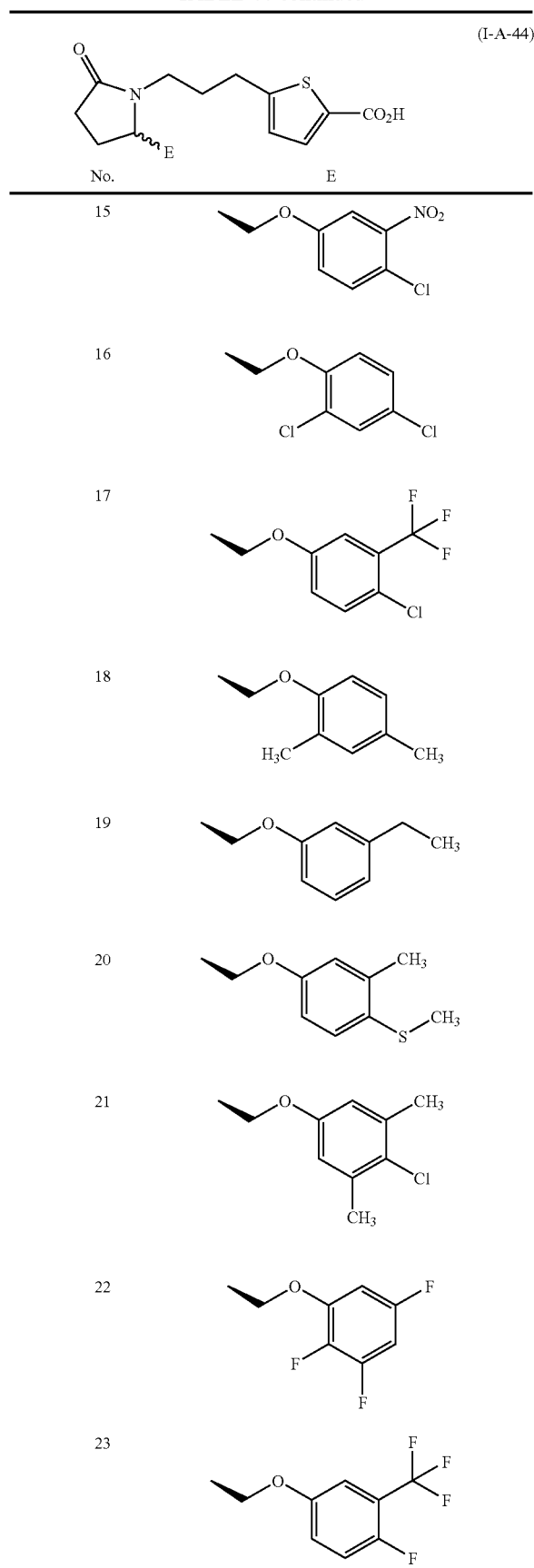
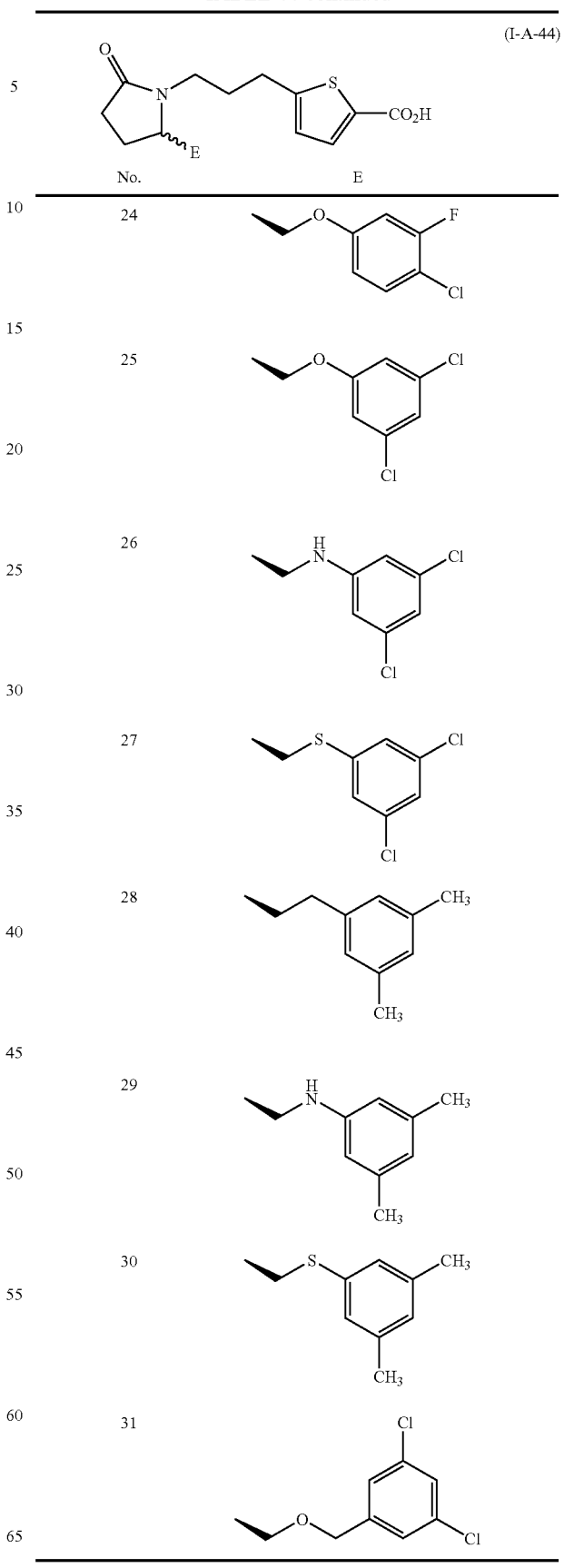

TABLE 45

(I-A-45)

Structure: Pyrrolidinone-N-CH₂CH₂-thiophene-CO₂H with substituent E on pyrrolidinone ring (wavy bond)

| No. | E |
|-----|---|
| 1 | -O-(3-methylphenyl) (ethoxy linkage) |
| 2 | -O-(4-methylphenyl) |
| 3 | -O-(2,3,5-trichlorophenyl) |
| 4 | -O-(3-chloro-4-fluorophenyl) |
| 5 | -O-(2,3-dichlorophenyl) |
| 6 | -O-(3-nitrophenyl) |
| 7 | -O-(3-trifluoromethylphenyl) |
| 8 | -O-(3-trifluoromethoxyphenyl) |
| 9 | -O-(2-chloro-4-methoxyphenyl) |
| 10 | -O-(3-ethyl-4-chlorophenyl) |
| 11 | -O-(4-methylindanyl) |
| 12 | -O-(3-methyl-4-fluorophenyl) |
| 13 | -O-(2,3,4-trichlorophenyl) |
| 14 | -O-(2-chloro-4-fluorophenyl) |
| 15 | -O-(3-nitro-4-chlorophenyl) |
| 16 | -O-(3,4-dichlorophenyl) |
| 17 | -O-(3-trifluoromethyl-4-chlorophenyl) |
| 18 | -O-(2,4-dimethylphenyl) |
| 19 | -O-(3-ethylphenyl) |
| 20 | -O-(3-methyl-4-methylthiophenyl) |

TABLE 45-continued (I-A-45)

| No. | E |
|---|---|
| 21 | 4-chloro-3,5-dimethylphenyl ethoxy |
| 22 | 2,3,5-trifluorophenyl ethoxy |
| 23 | 4-fluoro-2-(trifluoromethyl)phenyl ethoxy |
| 24 | 4-chloro-2-fluorophenyl ethoxy |
| 25 | 3,5-dichlorophenyl propyl |
| 26 | 3,5-dichlorophenyl ethylamino |
| 27 | 3,5-dichlorophenyl ethylthio |
| 28 | 3,5-dimethylphenyl propyl |
| 29 | 3,5-dimethylphenyl ethylamino |
| 30 | 3,5-dimethylphenyl ethylthio |
| 31 | 3,5-dichlorophenyl ethoxymethyl |

TABLE 46

(I-A-46)

| No. | E |
|---|---|
| 1 | 3-methylphenyl ethoxy |
| 2 | 4-methylphenyl ethoxy |
| 3 | 2,3,5-trichlorophenyl ethoxy |
| 4 | 3-chloro-4-fluorophenyl ethoxy |

TABLE 46-continued
(I-A-46)
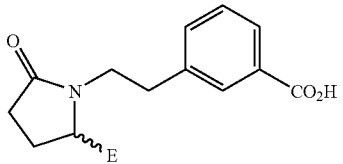
| No. | E |
|---|---|
| 5 | 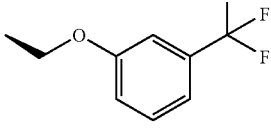 |
| 6 | 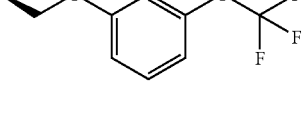 |
| 7 | 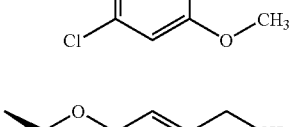 |
| 8 | 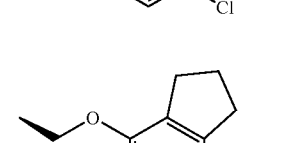 |
| 9 | 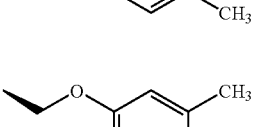 |
| 10 | 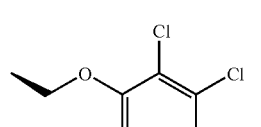 |
| 11 | 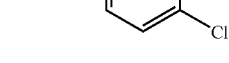 |
| 12 | 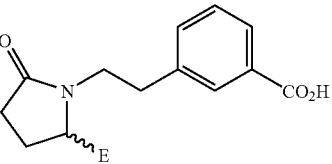 |
| 13 | 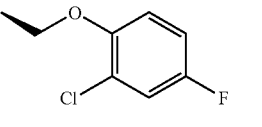 |
TABLE 46-continued
(I-A-46)
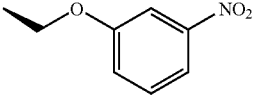
| No. | E |
|---|---|
| 14 | 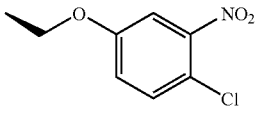 |
| 15 | 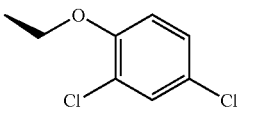 |
| 16 | 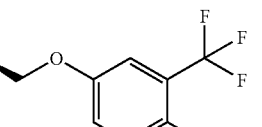 |
| 17 | 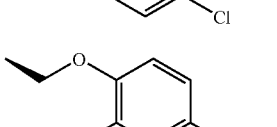 |
| 18 | 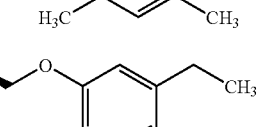 |
| 19 | 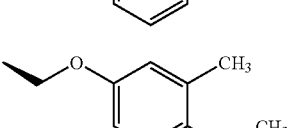 |
| 20 | 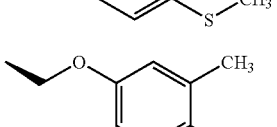 |
| 21 | 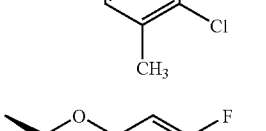 |
| 22 | 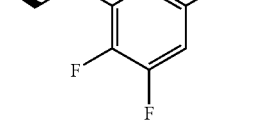 |
| 23 | 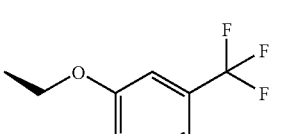 |

TABLE 46-continued (I-A-46)

[Structure: pyrrolidinone with N-CH2CH2-(3-carboxyphenyl) group and E substituent at 5-position]

| No. | E |
|---|---|
| 24 | 4-chloro-3-fluoro-phenoxyethyl (–CH2–O–C6H3(F)(Cl)) |
| 25 | 3,5-dichlorophenyl-propyl |
| 26 | N-ethyl-3,5-dichloroaniline |
| 27 | 3,5-dichlorophenylthioethyl |
| 28 | 3,5-dimethylphenyl-propyl |
| 29 | N-ethyl-3,5-dimethylaniline |
| 30 | 3,5-dimethylphenylthioethyl |
| 31 | 3,5-dichlorobenzyloxyethyl |

TABLE 47

(I-A-47)

[Structure: pyrrolidinone with N-CH2CH2-O-(thiazole-4-carboxylic acid) group and E substituent at 5-position]

| No. | E |
|---|---|
| 1 | 3-methylphenoxyethyl |
| 2 | 4-methylphenoxyethyl |
| 3 | 2,3,5-trichlorophenoxyethyl |
| 4 | 3-chloro-4-fluorophenoxyethyl |
| 5 | 2,3-dichlorophenoxyethyl |
| 6 | 3-nitrophenoxyethyl |
| 7 | 3-trifluoromethylphenoxyethyl |
| 8 | 3-trifluoromethoxyphenoxyethyl |
| 9 | 2-chloro-4-methoxyphenoxyethyl |
| 10 | 2-ethyl-4-chlorophenoxyethyl |

TABLE 47-continued (I-A-47)

| No. | E |
|---|---|
| 11 | 4-methyl-7-ethoxy-indane |
| 12 | 5-ethoxy-2-fluoro-3-methylphenyl |
| 13 | 2,3,4-trichloro-6-ethoxyphenyl |
| 14 | 2-chloro-4-fluoro-6-ethoxyphenyl |
| 15 | 4-chloro-3-nitro-6-ethoxyphenyl |
| 16 | 2,4-dichloro-6-ethoxyphenyl |
| 17 | 4-chloro-3-trifluoromethyl-6-ethoxyphenyl |
| 18 | 3,5-dimethyl-6-ethoxyphenyl |
| 19 | 3-ethyl-6-ethoxyphenyl |
| 20 | 3-methyl-4-methylthio-6-ethoxyphenyl |
| 21 | 3,5-dimethyl-4-chloro-6-ethoxyphenyl |
| 22 | 2,3,5-trifluoro-6-ethoxyphenyl |
| 23 | 4-fluoro-3-trifluoromethyl-6-ethoxyphenyl |
| 24 | 4-chloro-3-fluoro-6-ethoxyphenyl |
| 25 | 3,5-dichlorophenyl-ethyl |
| 26 | 3,5-dichloro-N-ethylaniline |
| 27 | 3,5-dichlorophenyl-ethylthio |
| 28 | 3,5-dimethylphenyl-ethyl |

TABLE 47-continued (I-A-47)

| No. | E |
|---|---|
| 29 | ethyl-NH-(3,5-dimethylphenyl) |
| 30 | ethyl-S-(3,5-dimethylphenyl) |
| 31 | ethyl-O-CH2-(3,5-dichlorophenyl) |

TABLE 48

(I-A-48)

| No. | E |
|---|---|
| 1 | ethoxy-(3-methylphenyl) |
| 2 | ethoxy-(4-methylphenyl) |
| 3 | ethoxy-(2,3,5-trichlorophenyl) |
| 4 | ethoxy-(3-chloro-4-fluorophenyl) |

TABLE 48-continued (I-A-48)

| No. | E |
|---|---|
| 5 | ethoxy-(2,3-dichlorophenyl) |
| 6 | ethoxy-(3-nitrophenyl) |
| 7 | ethoxy-(3-trifluoromethylphenyl) |
| 8 | ethoxy-(3-trifluoromethoxyphenyl) |
| 9 | ethoxy-(2-chloro-4-methoxyphenyl) |
| 10 | ethoxy-(3-ethyl-4-chlorophenyl) |
| 11 | ethoxy-(7-methylindanyl) |
| 12 | ethoxy-(3-methyl-4-fluorophenyl) |
| 13 | ethoxy-(2,3,4-trichlorophenyl) |
| 14 | ethoxy-(3-chloro-4-fluorophenyl) |

TABLE 48-continued (I-A-48)

[Structure: pyrrolidinone-N-CH2CH2-O-thiazole-COOH with E substituent]

| No. | E |
|-----|---|
| 15 | 2-chloro-5-ethoxy-nitrobenzene (ethoxy, NO2, Cl substituents) |
| 16 | 2,4-dichloro-ethoxybenzene |
| 17 | 4-chloro-2-trifluoromethyl-ethoxybenzene |
| 18 | 2,4-dimethyl-ethoxybenzene |
| 19 | 3-ethyl-ethoxybenzene |
| 20 | 2-methyl-4-methylthio-ethoxybenzene |
| 21 | 4-chloro-3,5-dimethyl-ethoxybenzene |
| 22 | 3,4,5-trifluoro-ethoxybenzene |
| 23 | 4-fluoro-2-trifluoromethyl-ethoxybenzene |

TABLE 48-continued (I-A-48)

[Structure: pyrrolidinone-N-CH2CH2-O-thiazole-COOH with E substituent]

| No. | E |
|-----|---|
| 24 | 4-chloro-3-fluoro-ethoxybenzene |
| 25 | 3,5-dichloro-ethylbenzene |
| 26 | 3,5-dichloro-N-ethylaniline |
| 27 | 3,5-dichloro-ethylthiobenzene |
| 28 | 3,5-dimethyl-ethylbenzene |
| 29 | 3,5-dimethyl-N-ethylaniline |
| 30 | 3,5-dimethyl-ethylthiobenzene |
| 31 | 3,5-dichloro-benzyloxyethyl |

TABLE 49

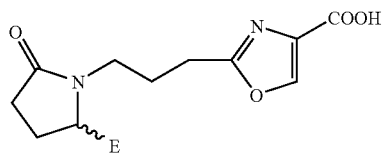

(I-A-49)

| No. | E |
|---|---|
| 1 | 3-ethoxy-methylbenzene |
| 2 | 4-ethoxy-methylbenzene |
| 3 | ethoxy-trichlorobenzene |
| 4 | ethoxy-chloro-fluorobenzene |
| 5 | ethoxy-dichlorobenzene |
| 6 | ethoxy-nitrobenzene |
| 7 | ethoxy-trifluoromethylbenzene |
| 8 | ethoxy-trifluoromethoxybenzene |
| 9 | ethoxy-chloro-methoxybenzene |
| 10 | ethoxy-ethyl-chlorobenzene |

TABLE 49-continued

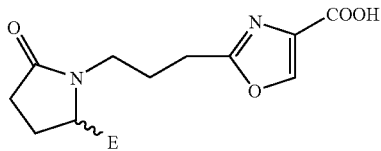

(I-A-49)

| No. | E |
|---|---|
| 11 | ethoxy-methyl-indane |
| 12 | ethoxy-methyl-fluorobenzene |
| 13 | ethoxy-trichlorobenzene |
| 14 | ethoxy-chloro-fluorobenzene |
| 15 | ethoxy-nitro-chlorobenzene |
| 16 | ethoxy-dichlorobenzene |
| 17 | ethoxy-trifluoromethyl-chlorobenzene |
| 18 | ethoxy-dimethylbenzene |
| 19 | ethoxy-ethylbenzene |
| 20 | ethoxy-methyl-methylthiobenzene |

TABLE 49-continued (I-A-49)

| No. | E |
|-----|---|
| 21 | 3-chloro-4,5-dimethyl-phenoxyethyl |
| 22 | 2,3,5-trifluoro-phenoxyethyl |
| 23 | 4-fluoro-3-trifluoromethyl-phenoxyethyl |
| 24 | 4-chloro-3-fluoro-phenoxyethyl |
| 25 | 3,5-dichloro-phenylethyl |
| 26 | 3,5-dichloro-phenyl-ethylamino |
| 27 | 3,5-dichloro-phenylthioethyl |
| 28 | 3,5-dimethyl-phenylethyl |
| 29 | 3,5-dimethyl-phenyl-ethylamino |
| 30 | 3,5-dimethyl-phenylthioethyl |
| 31 | 3,5-dichloro-benzyloxyethyl |

TABLE 50

(I-A-50)

| No. | E |
|-----|---|
| 1 | 3-methyl-phenoxyethyl |
| 2 | 4-methyl-phenoxyethyl |
| 3 | 2,3,5-trichloro-phenoxyethyl |
| 4 | 3-chloro-4-fluoro-phenoxyethyl |

TABLE 50-continued
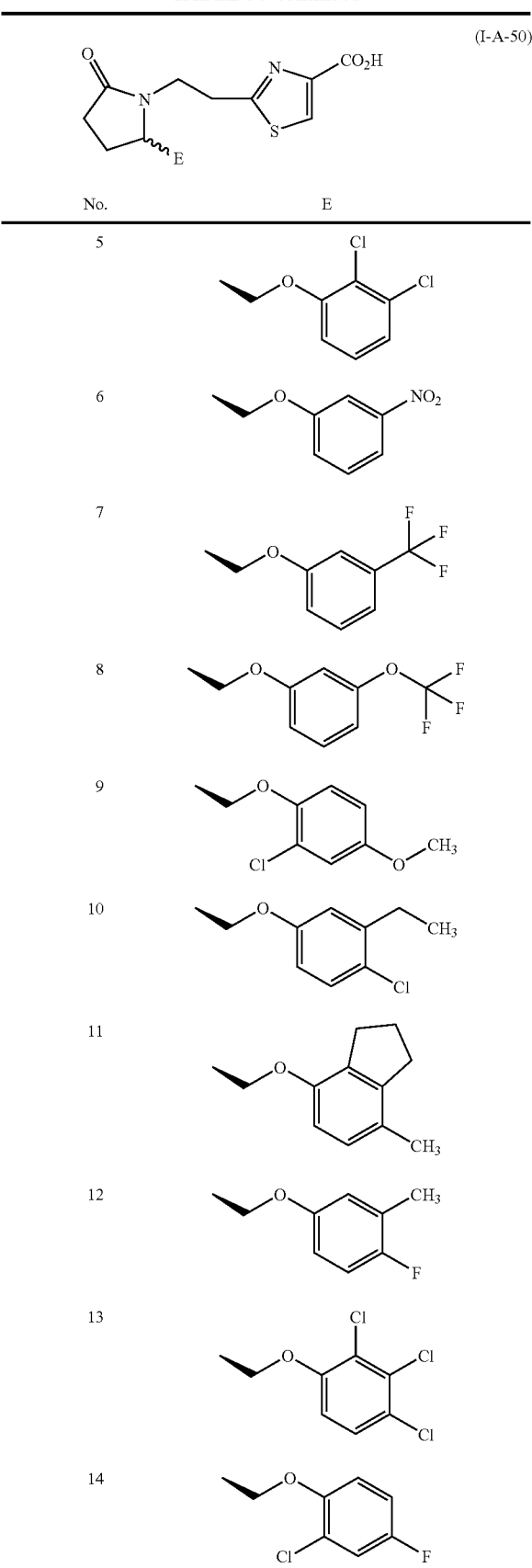
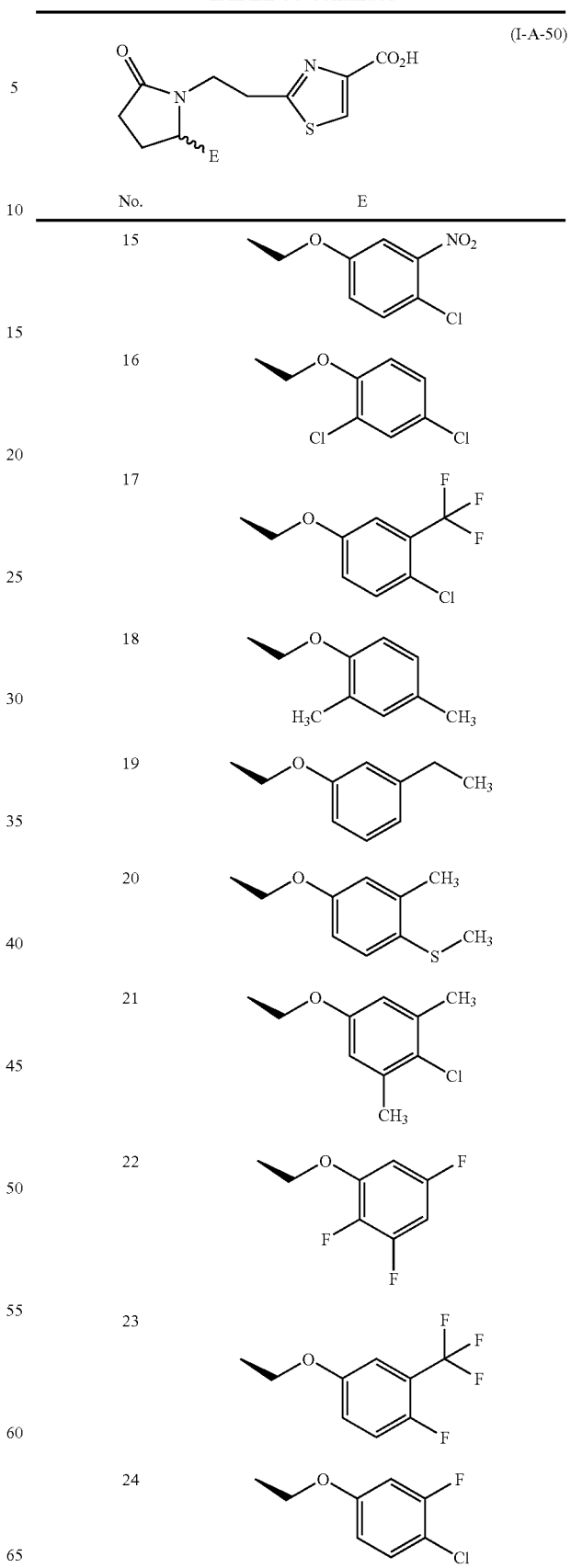

TABLE 50-continued
(I-A-50)
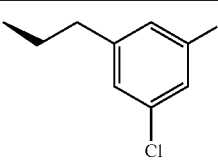
| No. | E |
|---|---|
| 25 | 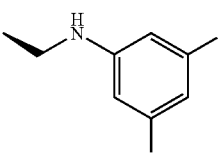 |
| 26 | 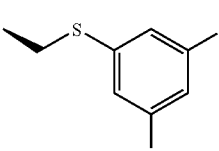 |
| 27 | 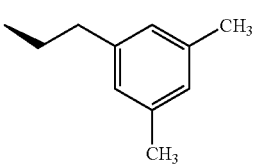 |
| 28 | 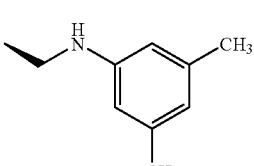 |
| 29 | 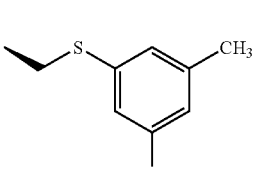 |
| 30 | 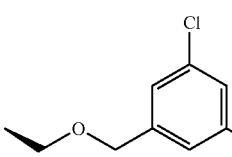 |
| 31 | 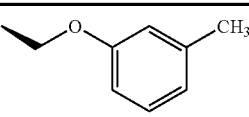 |
TABLE 51
(I-A-51)
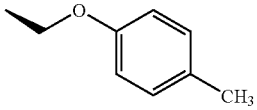
| No. | E |
|---|---|
| 1 | 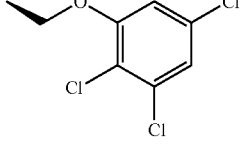 |
| 2 | 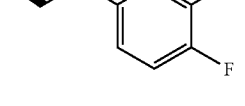 |
| 3 | 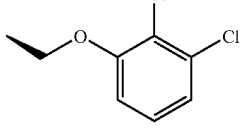 |
| 4 | 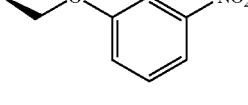 |
| 5 | 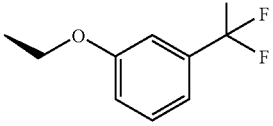 |
| 6 | 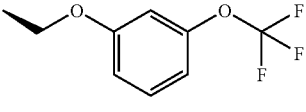 |
| 7 | 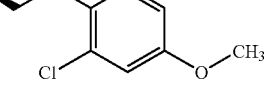 |
| 8 | 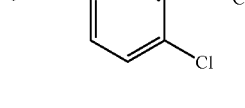 |
| 9 | |
| 10 | |

TABLE 51-continued (I-A-51)

| No. | E |
|---|---|
| 11 | 4-ethoxy-7-methyl-2,3-dihydro-1H-indene |
| 12 | ethoxy-(3-methyl-4-fluoro)phenyl |
| 13 | ethoxy-(2,3,4-trichloro)phenyl |
| 14 | ethoxy-(2-chloro-4-fluoro)phenyl |
| 15 | ethoxy-(3-nitro-4-chloro)phenyl |
| 16 | ethoxy-(3,4-dichloro)phenyl |
| 17 | ethoxy-(3-trifluoromethyl-4-chloro)phenyl |
| 18 | ethoxy-(3,5-dimethyl)phenyl (H3C positions 3,4) |
| 19 | ethoxy-(3-ethyl)phenyl |
| 20 | ethoxy-(3-methyl-4-methylthio)phenyl |
| 21 | ethoxy-(3,5-dimethyl-4-chloro)phenyl |
| 22 | ethoxy-(2,3,5-trifluoro)phenyl |
| 23 | ethoxy-(3-trifluoromethyl-4-fluoro)phenyl |
| 24 | ethoxy-(3-fluoro-4-chloro)phenyl |
| 25 | ethyl-(3,5-dichloro)phenyl |
| 26 | ethylamino-(3,5-dichloro)phenyl |
| 27 | ethylthio-(3,5-dichloro)phenyl |
| 28 | ethyl-(3,5-dimethyl)phenyl |

TABLE 51-continued
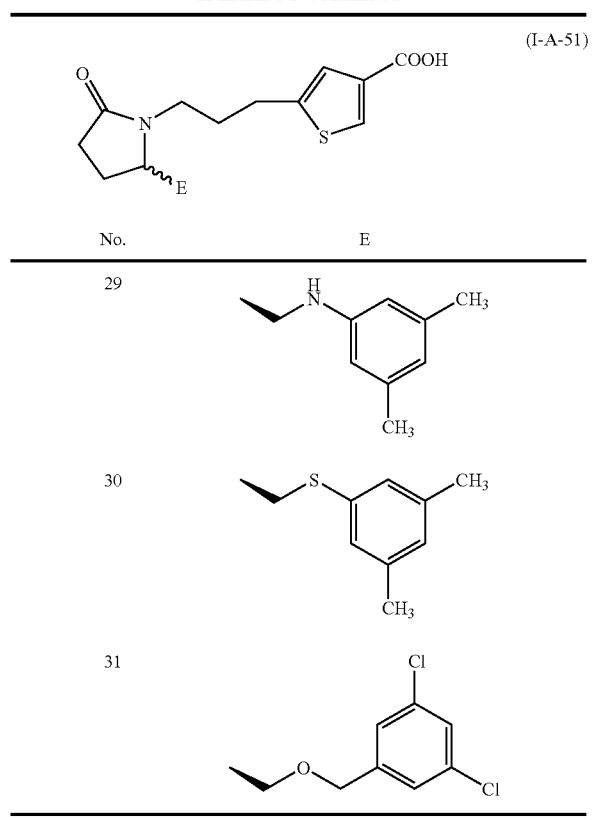
TABLE 52
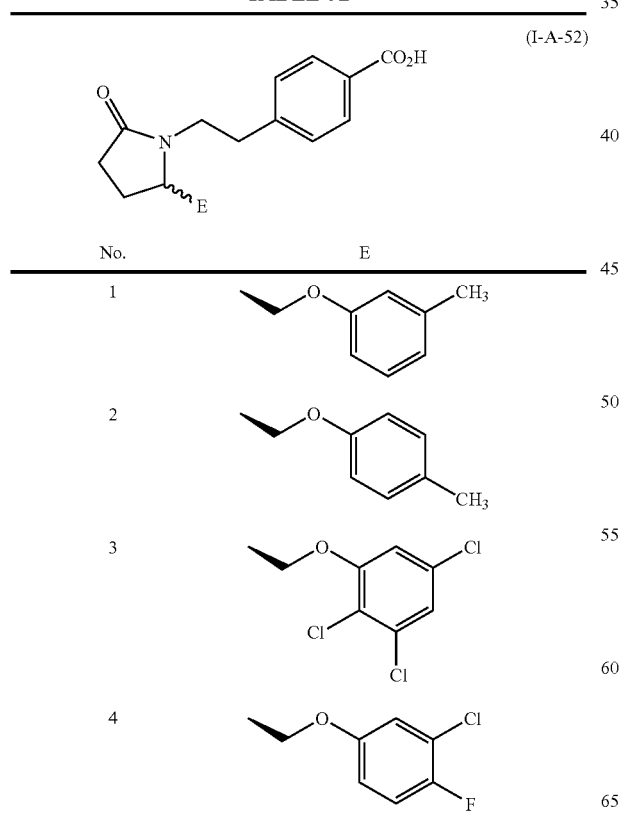
TABLE 52-continued
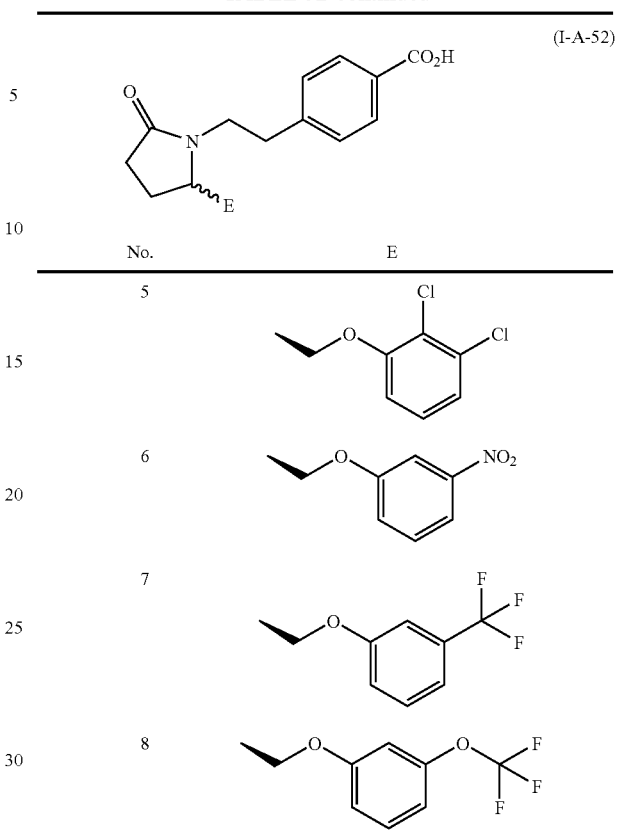

TABLE 52-continued
(I-A-52)
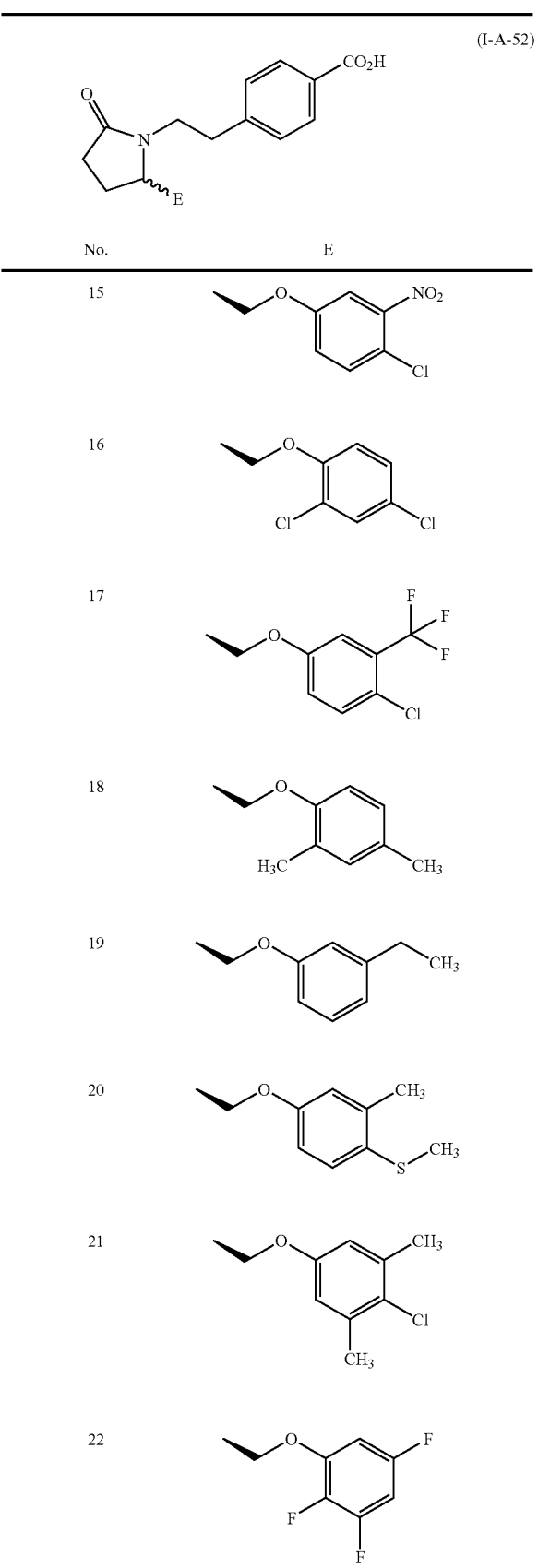
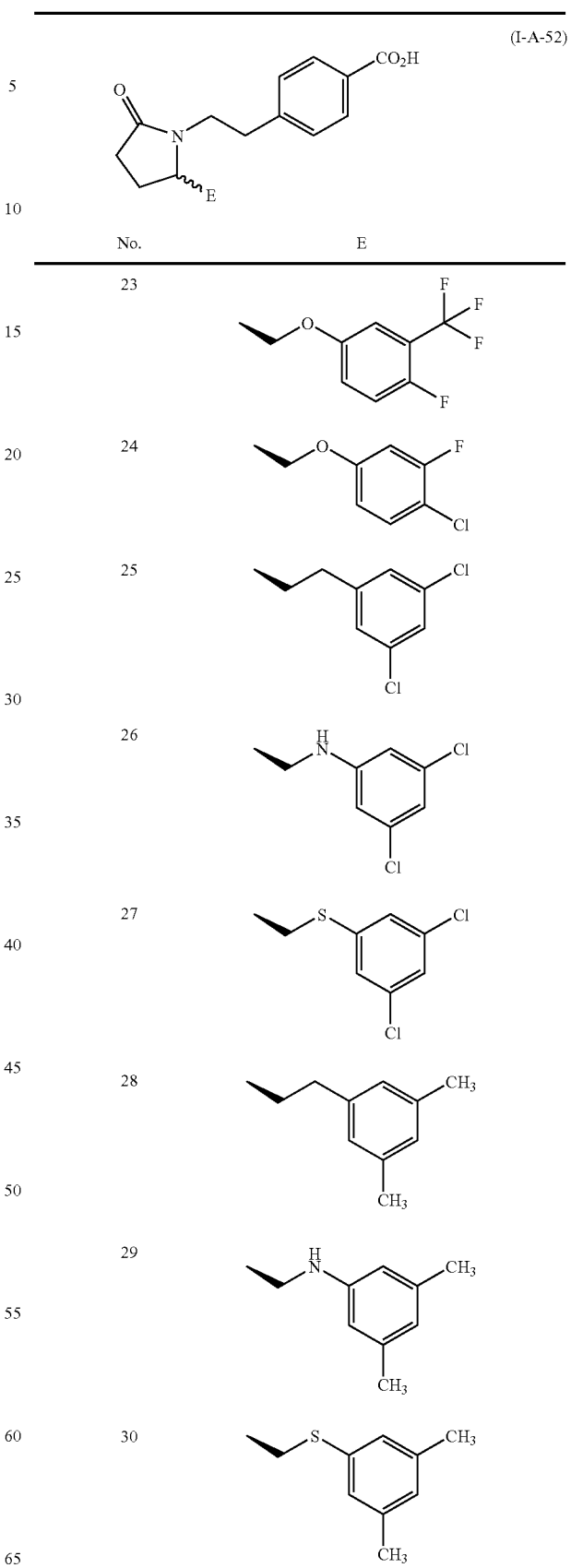

TABLE 52-continued (I-A-52)

[Structure: pyrrolidinone-N-CH2CH2-phenyl-CO2H with E substituent]

| No. | E |
|-----|---|
| 31 | 3,5-dichlorobenzyl ethoxy |

TABLE 53

(I-A-53)

[Structure: pyrrolidinone-N-CH2CH2-S-thiophene-CO2H with E substituent]

| No. | E |
|-----|---|
| 1 | 3-methylphenyl ethoxy |
| 2 | 4-methylphenyl ethoxy |
| 3 | 2,3,5-trichlorophenyl ethoxy |
| 4 | 3-chloro-4-fluorophenyl ethoxy |
| 5 | 2,3-dichlorophenyl ethoxy |
| 6 | 3-nitrophenyl ethoxy |

TABLE 53-continued (I-A-53)

[Structure: pyrrolidinone-N-CH2CH2-S-thiophene-CO2H with E substituent]

| No. | E |
|-----|---|
| 7 | 3-(trifluoromethyl)phenyl ethoxy |
| 8 | 3-(trifluoromethoxy)phenyl ethoxy |
| 9 | 2-chloro-4-methoxyphenyl ethoxy |
| 10 | 4-chloro-2-ethylphenyl ethoxy |
| 11 | 7-methyl-indanyl ethoxy |
| 12 | 4-fluoro-3-methylphenyl ethoxy |
| 13 | 2,3-dichlorophenyl ethoxy |
| 14 | 2-chloro-4-fluorophenyl ethoxy |
| 15 | 4-chloro-3-nitrophenyl ethoxy |
| 16 | 2,4-dichlorophenyl ethoxy |

TABLE 53-continued (I-A-53)

| No. | E |
|---|---|
| 17 | 4-chloro-2-(trifluoromethyl)phenoxyethyl |
| 18 | 2,4-dimethylphenoxyethyl |
| 19 | 3-ethylphenoxyethyl |
| 20 | 2-methyl-4-(methylthio)phenoxyethyl (with CH₃ and SCH₃) |
| 21 | 4-chloro-3,5-dimethylphenoxyethyl |
| 22 | 2,3,5-trifluorophenoxyethyl |
| 23 | 4-fluoro-3-(trifluoromethyl)phenoxyethyl |
| 24 | 4-chloro-3-fluorophenoxyethyl |
| 25 | 3,5-dichlorophenoxyethyl |

TABLE 53-continued (I-A-53)

| No. | E |
|---|---|
| 26 | 3,5-dichlorophenyl(ethyl)amino |
| 27 | 3,5-dichlorophenyl ethylsulfanyl |
| 28 | 3,5-dimethylphenylpropyl |
| 29 | 3,5-dimethylphenyl(ethyl)amino |
| 30 | 3,5-dimethylphenyl ethylsulfanyl |
| 31 | 3,5-dichlorobenzyloxyethyl |

TABLE 54

(I-A-54)

| No. | E |
|---|---|
| 1 | 3-methylphenoxyethyl |

TABLE 54-continued
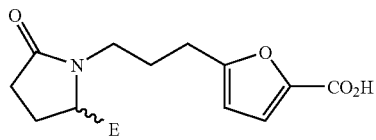
(I-A-54)
| No. | E |
|---|---|
| 2 | 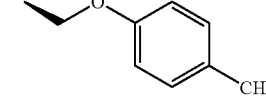 |
| 3 | 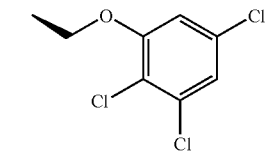 |
| 4 | 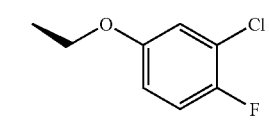 |
| 5 | 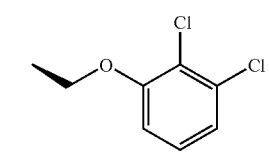 |
| 6 | 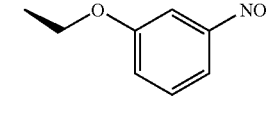 |
| 7 | 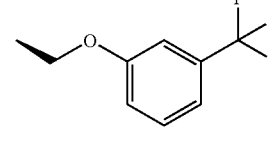 |
| 8 | 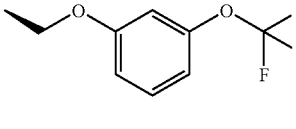 |
| 9 | 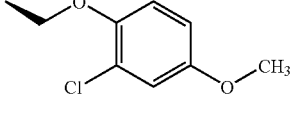 |
| 10 | 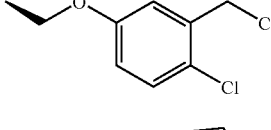 |
| 11 | 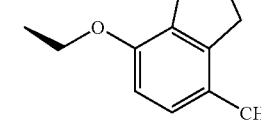 |
TABLE 54-continued
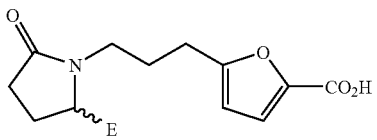
(I-A-54)
| No. | E |
|---|---|
| 12 |  |
| 13 |  |
| 14 |  |
| 15 |  |
| 16 |  |
| 17 |  |
| 18 |  |
| 19 |  |
| 20 |  |
| 21 |  |

TABLE 54-continued (I-A-54)

| No. | E |
|---|---|
| 22 | 2,3,5-trifluorophenyl ethoxy |
| 23 | 4-fluoro-3-(trifluoromethyl)phenyl ethoxy |
| 24 | 4-chloro-3-fluorophenyl ethoxy |
| 25 | 3,5-dichlorophenyl ethyl |
| 26 | 3,5-dichlorophenyl ethylamino |
| 27 | 3,5-dichlorophenyl ethylthio |
| 28 | 3,5-dimethylphenyl ethyl |
| 29 | 3,5-dimethylphenyl ethylamino |
| 30 | 3,5-dimethylphenyl ethylthio |
| 31 | 3,5-dichlorophenyl ethoxymethyl |

TABLE 55

(I-A-55)

| No. | E |
|---|---|
| 1 | 3-methylphenyl ethoxy |
| 2 | 4-methylphenyl ethoxy |
| 3 | 2,3,5-trichlorophenyl ethoxy |
| 4 | 3-chloro-4-fluorophenyl ethoxy |
| 5 | 2,3-dichlorophenyl ethoxy |
| 6 | 3-nitrophenyl ethoxy |

TABLE 55-continued
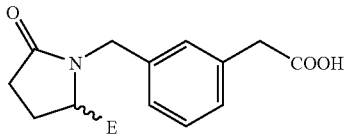
(I-A-55)
| No. | E |
|---|---|
| 7 | 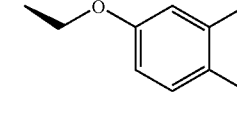 |
| 8 | 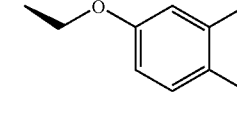 |
| 9 | 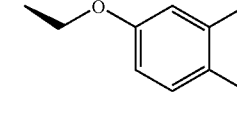 |
| 10 | 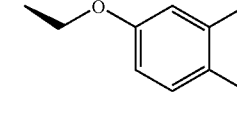 |
| 11 | 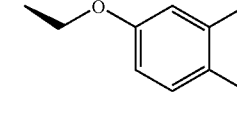 |
| 12 | 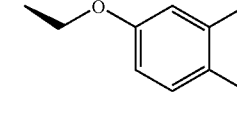 |
| 13 | 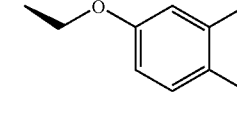 |
| 14 | 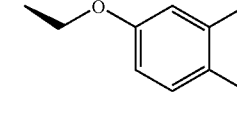 |
| 15 | 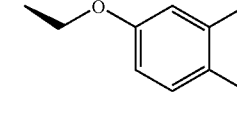 |
| 16 | 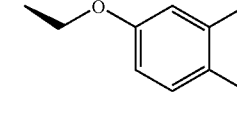 |
TABLE 55-continued
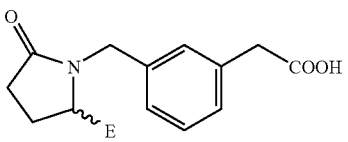
(I-A-55)
| No. | E |
|---|---|
| 17 | 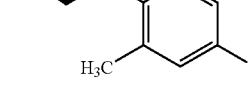 |
| 18 | 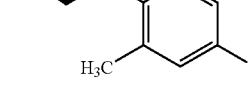 |
| 19 | 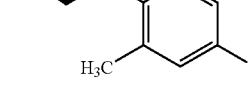 |
| 20 | 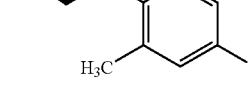 |
| 21 | 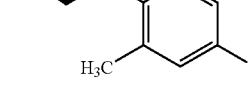 |
| 22 | 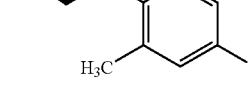 |
| 23 | 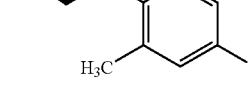 |
| 24 | 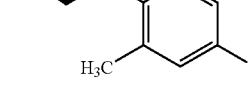 |
| 25 | 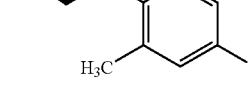 |

TABLE 55-continued (I-A-55)

| No. | E |
|---|---|
| 26 | 3,5-dichloro-N-ethylaniline group |
| 27 | (3,5-dichlorophenyl)thioethyl group |
| 28 | 3,5-dimethylphenylpropyl group |
| 29 | N-ethyl-3,5-dimethylaniline group |
| 30 | (3,5-dimethylphenyl)thioethyl group |
| 31 | 3,5-dichlorophenylmethoxyethyl group |

TABLE 56

(I-A-56)

| No. | E |
|---|---|
| 1 | 3-methylphenoxyethyl group |
| 2 | 4-methylphenoxyethyl group |
| 3 | 2,3,5-trichlorophenoxyethyl group |
| 4 | 3-chloro-4-fluorophenoxyethyl group |
| 5 | 2,3-dichlorophenoxyethyl group |
| 6 | 3-nitrophenoxyethyl group |
| 7 | 3-trifluoromethylphenoxyethyl group |
| 8 | 3-trifluoromethoxyphenoxyethyl group |
| 9 | 2-chloro-4-methoxyphenoxyethyl group |
| 10 | 3-ethyl-4-chlorophenoxyethyl group |
| 11 | 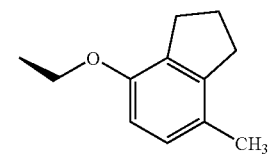 |

TABLE 56-continued (I-A-56)

| No. | E |
|---|---|
| 12 | 4-fluoro-3-methyl-phenyl ethoxy |
| 13 | 2,3,4-trichloro-phenyl ethoxy |
| 14 | 2-chloro-4-fluoro-phenyl ethoxy |
| 15 | 4-chloro-2-nitro-phenyl ethoxy |
| 16 | 3,4-dichloro-phenyl ethoxy |
| 17 | 4-chloro-2-(trifluoromethyl)phenyl ethoxy |
| 18 | 2,4-dimethyl-phenyl ethoxy |
| 19 | 3-ethyl-phenyl ethoxy |
| 20 | 2-methyl-4-(methylthio)phenyl ethoxy |
| 21 | 3-chloro-2,4-dimethyl-phenyl ethoxy |
| 22 | 2,3,5-trifluoro-phenyl ethoxy |
| 23 | 4-fluoro-2-(trifluoromethyl)phenyl ethoxy |
| 24 | 4-chloro-2-fluoro-phenyl ethoxy |
| 25 | 3,5-dichloro-phenyl ethyl |
| 26 | 3,5-dichloro-phenyl ethylamino |
| 27 | 3,5-dichloro-phenyl ethylthio |
| 28 | 3,5-dimethyl-phenyl ethyl |
| 29 | 3,5-dimethyl-phenyl ethylamino |

TABLE 56-continued (I-A-56)

| No. | E |
|-----|---|
| 30 | (ethylthio-3,5-dimethylphenyl) |
| 31 | (ethoxymethyl-3,5-dichlorophenyl) |

TABLE 57

(I-A-57)

| No. | E |
|-----|---|
| 1 | (ethoxy-3-methylphenyl) |
| 2 | (ethoxy-4-methylphenyl) |
| 3 | (ethoxy-2,3,5-trichlorophenyl) |
| 4 | (ethoxy-3-chloro-4-fluorophenyl) |
| 5 | (ethoxy-2,3-dichlorophenyl) |
| 6 | (ethoxy-3-nitrophenyl) |

TABLE 57-continued (I-A-57)

| No. | E |
|-----|---|
| 7 | (ethoxy-3-trifluoromethylphenyl) |
| 8 | (ethoxy-3-trifluoromethoxyphenyl) |
| 9 | (ethoxy-2-chloro-4-methoxyphenyl) |
| 10 | (ethoxy-2-ethyl-4-chlorophenyl) |
| 11 | (ethoxy-methylindanyl) |
| 12 | (ethoxy-3-methyl-4-fluorophenyl) |
| 13 | (ethoxy-2,3-dichlorophenyl) |
| 14 | (ethoxy-2-chloro-4-fluorophenyl) |
| 15 | (ethoxy-3-nitro-4-chlorophenyl) |
| 16 | (ethoxy-2,4-dichlorophenyl) |

TABLE 57-continued
(I-A-57)
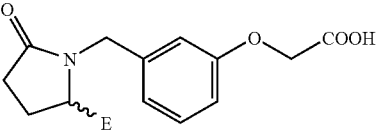
| No. | E |
|---|---|
| 17 | 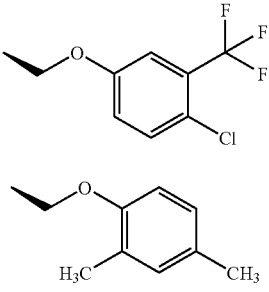 |
| 18 | 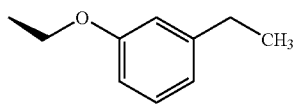 |
| 19 | 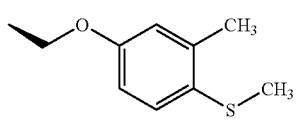 |
| 20 | 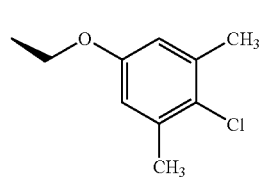 |
| 21 | 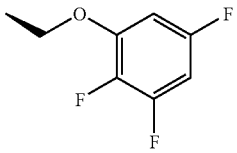 |
| 22 | 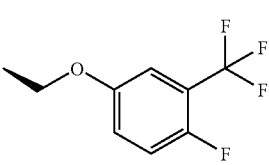 |
| 23 | 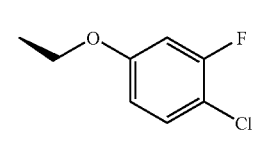 |
| 24 | 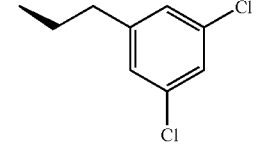 |
| 25 | 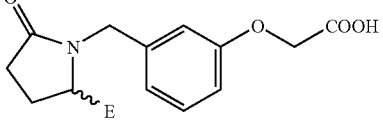 |
| 26 | 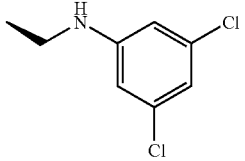 |
| 27 | 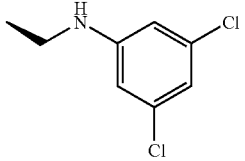 |
| 28 | 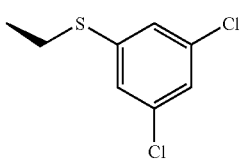 |
| 29 | 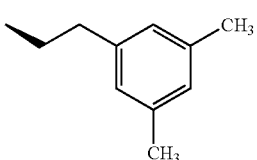 |
| 30 | 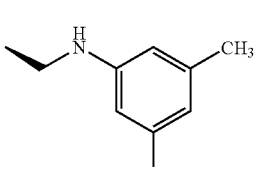 |
| 31 | 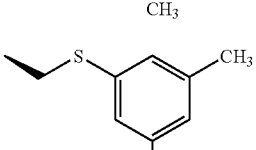 |
TABLE 58
(I-A-58)
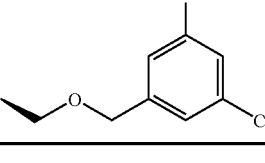
| No. | E |
|---|---|
| 1 | 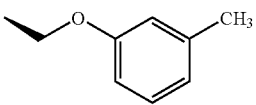 |

TABLE 58-continued (I-A-58)

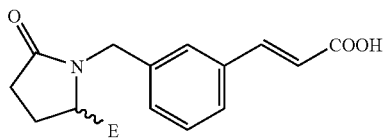

| No. | E |
|---|---|
| 2 | 4-methyl-phenyl ethoxy |
| 3 | 2,3,5-trichloro-phenyl ethoxy |
| 4 | 3-chloro-4-fluoro-phenyl ethoxy |
| 5 | 2,3-dichloro-phenyl ethoxy |
| 6 | 3-nitro-phenyl ethoxy |
| 7 | 3-trifluoromethyl-phenyl ethoxy |
| 8 | 3-trifluoromethoxy-phenyl ethoxy |
| 9 | 2-chloro-4-methoxy-phenyl ethoxy |
| 10 | 2-ethyl-4-chloro-phenyl ethoxy |
| 11 | 4-methyl-indan-7-yl ethoxy |

TABLE 58-continued (I-A-58)

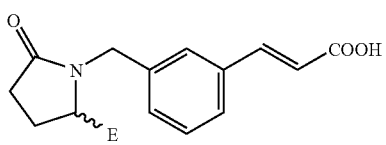

| No. | E |
|---|---|
| 12 | 3-methyl-4-fluoro-phenyl ethoxy |
| 13 | 2,3,4-trichloro-phenyl ethoxy |
| 14 | 2-chloro-4-fluoro-phenyl ethoxy |
| 15 | 3-nitro-4-chloro-phenyl ethoxy |
| 16 | 2,4-dichloro-phenyl ethoxy |
| 17 | 2-trifluoromethyl-4-chloro-phenyl ethoxy |
| 18 | 2,4-dimethyl-phenyl ethoxy |
| 19 | 3-ethyl-phenyl ethoxy |
| 20 | 2-methyl-4-methylthio-phenyl ethoxy |
| 21 | 2,5-dimethyl-4-chloro-phenyl ethoxy |

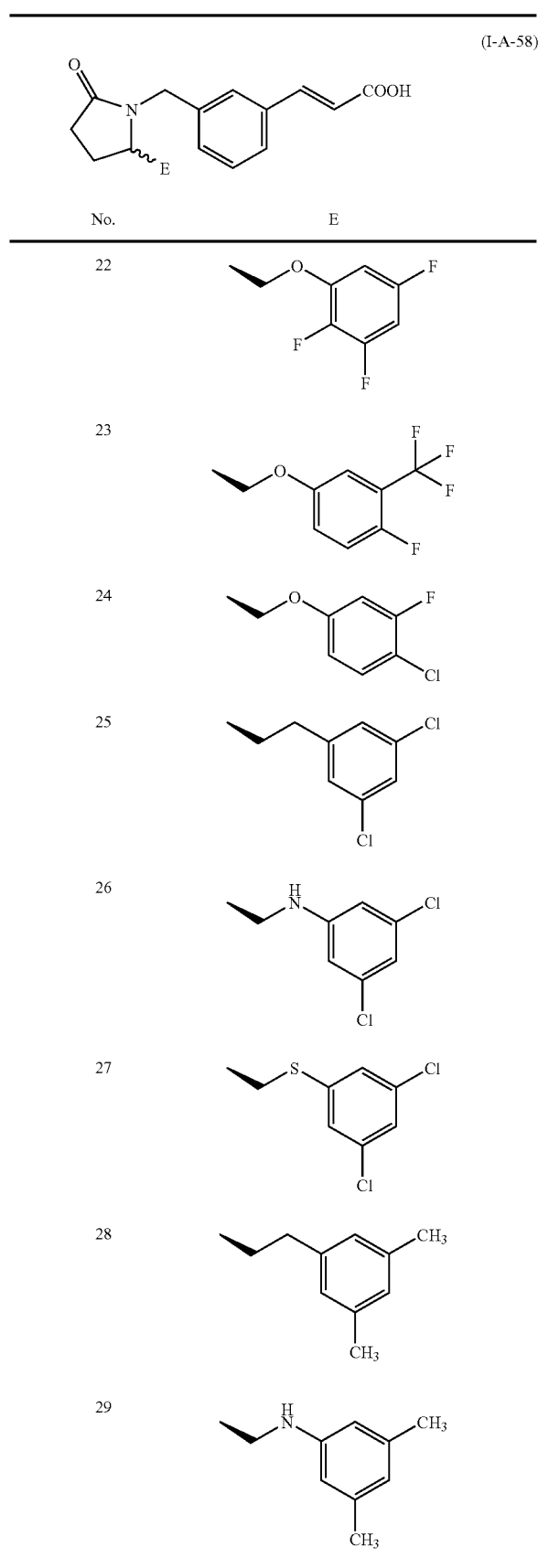
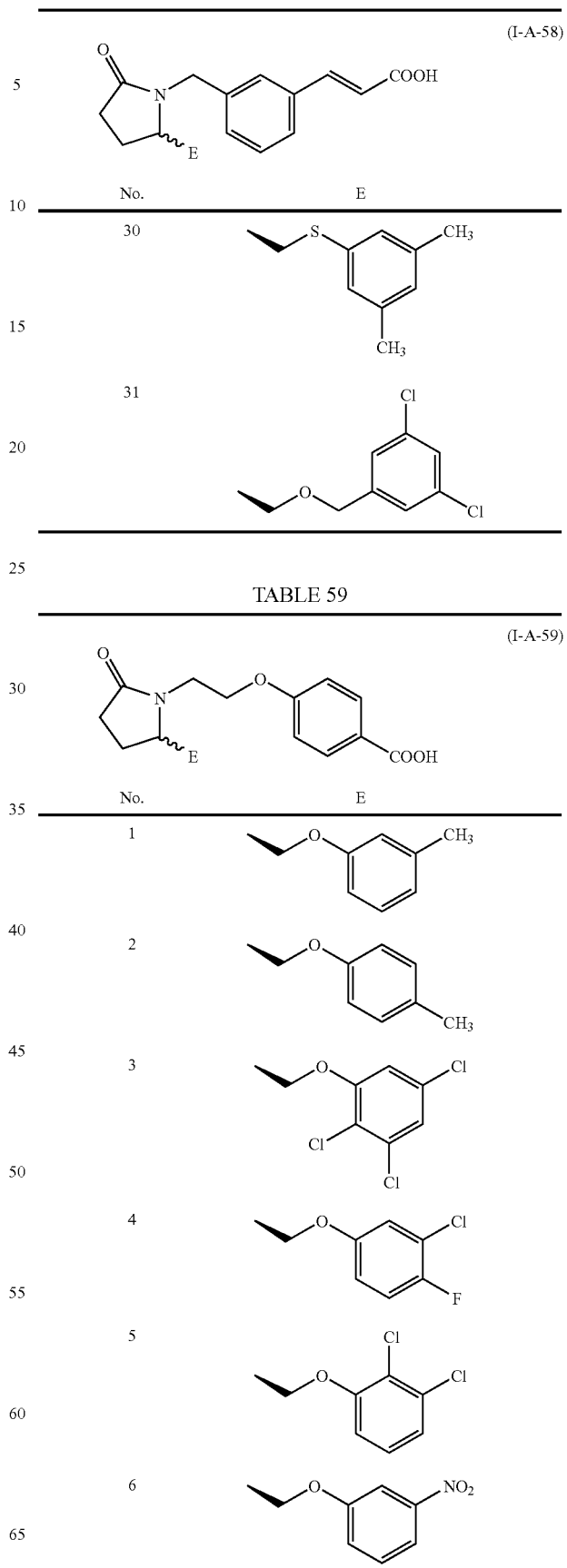

TABLE 59-continued (I-A-59)

| No. | E |
|---|---|
| 7 | 3-(trifluoromethyl)phenyl ethoxy |
| 8 | 3-(trifluoromethoxy)phenyl ethoxy |
| 9 | 2-chloro-4-methoxyphenyl ethoxy |
| 10 | 2-ethyl-4-chlorophenyl ethoxy |
| 11 | 7-methyl-indan-4-yl ethoxy |
| 12 | 3-methyl-4-fluorophenyl ethoxy |
| 13 | 2,3,4-trichlorophenyl ethoxy |
| 14 | 2-chloro-4-fluorophenyl ethoxy |
| 15 | 2-nitro-4-chlorophenyl ethoxy |
| 16 | 2,4-dichlorophenyl ethoxy |

TABLE 59-continued (I-A-59)

| No. | E |
|---|---|
| 17 | 2-chloro-5-(trifluoromethyl)phenyl ethoxy |
| 18 | 2,4-dimethylphenyl ethoxy |
| 19 | 3-ethylphenyl ethoxy |
| 20 | 2-methyl-4-(methylthio)phenyl ethoxy |
| 21 | 3,5-dimethyl-4-chlorophenyl ethoxy |
| 22 | 2,3,5-trifluorophenyl ethoxy |
| 23 | 3-(trifluoromethyl)-4-fluorophenyl ethoxy |
| 24 | 3-fluoro-4-chlorophenyl ethoxy |
| 25 | 3,5-dichlorophenyl propyl |

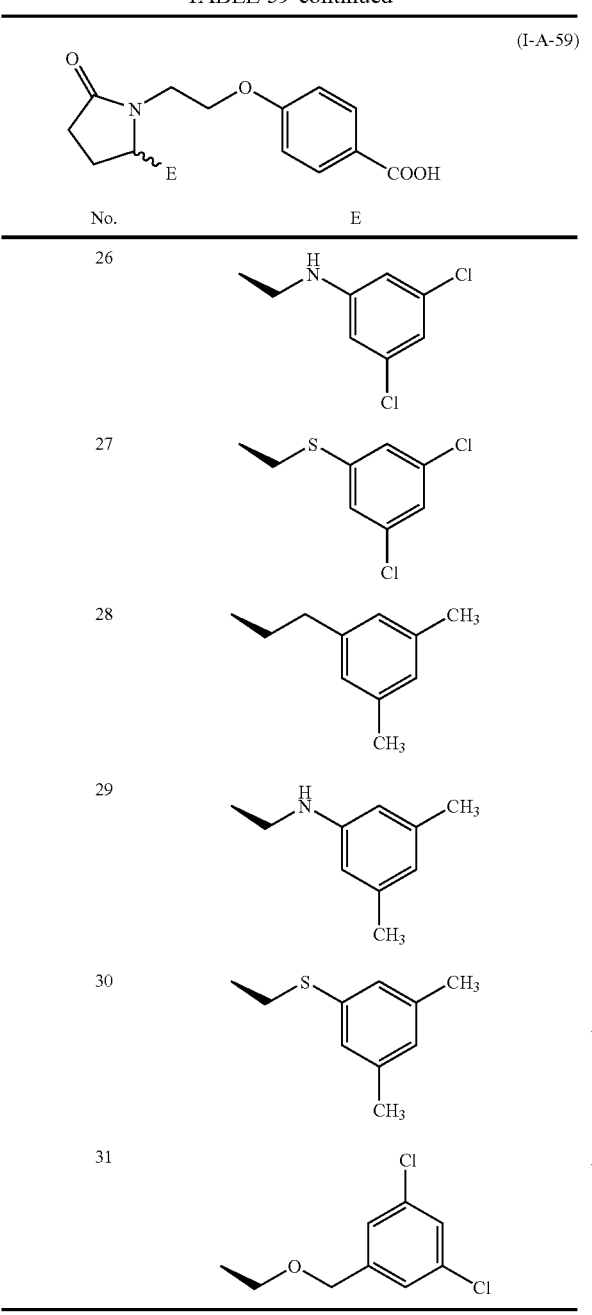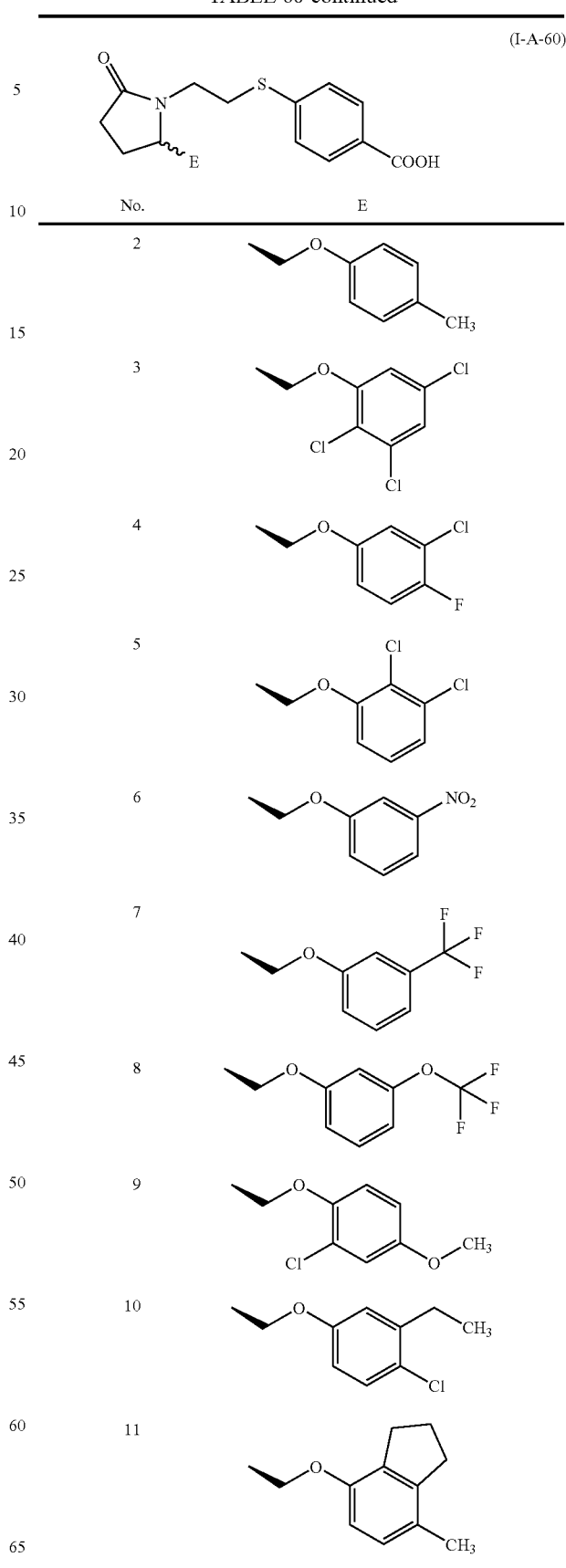

TABLE 60-continued (I-A-60)

[Structure: pyrrolidinone-N-CH2CH2-S-C6H4-COOH with substituent E]

| No. | E |
|-----|---|
| 12 | 4-fluoro-5-ethoxy-2-methylphenyl (ethoxy, CH3, F) |
| 13 | 2,3,4-trichloro-5-ethoxyphenyl |
| 14 | 2-chloro-4-fluoro-5-ethoxyphenyl (ethoxy, Cl, F) |
| 15 | 4-chloro-3-nitro-5-ethoxyphenyl (ethoxy, NO2, Cl) |
| 16 | 3,4-dichloro-5-ethoxyphenyl |
| 17 | 4-chloro-2-trifluoromethyl-5-ethoxyphenyl |
| 18 | 2,4-dimethyl-5-ethoxyphenyl |
| 19 | 3-ethyl-5-ethoxyphenyl |
| 20 | 4-methylthio-3-methyl-5-ethoxyphenyl |
| 21 | 4-chloro-3,5-dimethyl-2-ethoxyphenyl |
| 22 | 2,3,5-trifluoro-6-ethoxyphenyl |
| 23 | 4-fluoro-2-trifluoromethyl-5-ethoxyphenyl |
| 24 | 4-chloro-3-fluoro-5-ethoxyphenyl |
| 25 | 3,5-dichlorophenyl-ethyl |
| 26 | N-ethyl-3,5-dichloroaniline |
| 27 | ethylthio-3,5-dichlorophenyl |
| 28 | 3,5-dimethylphenyl-ethyl |
| 29 | N-ethyl-3,5-dimethylaniline |

TABLE 60-continued
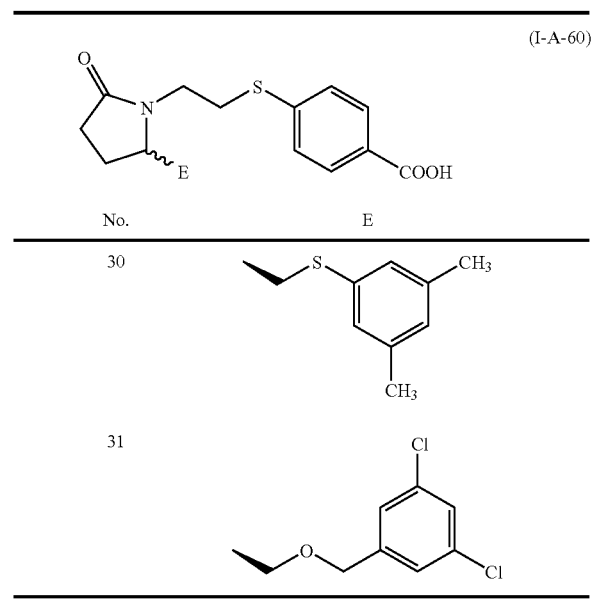
TABLE 61
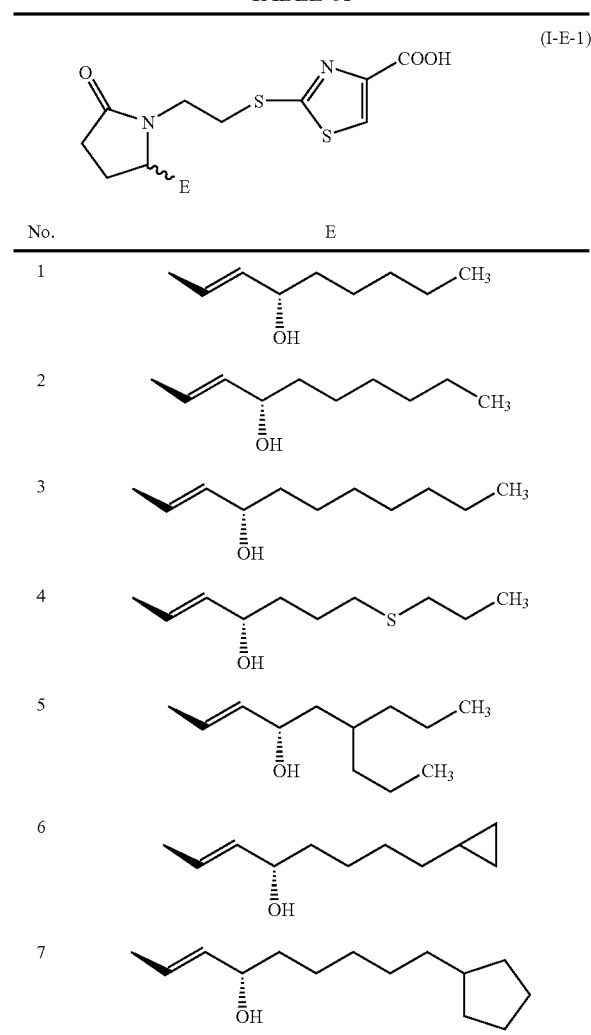
TABLE 61-continued
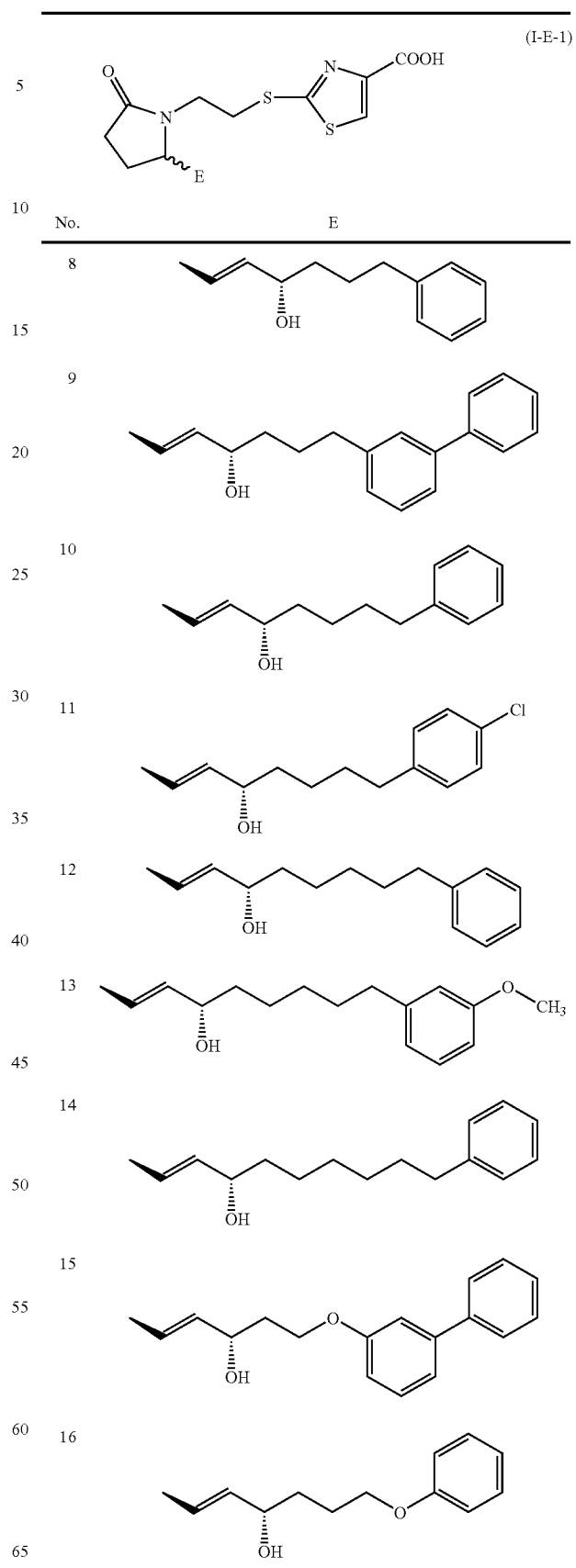

TABLE 61-continued
(I-E-1)
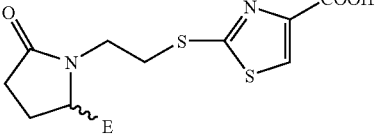
| No. | E |
|---|---|
| 17 | 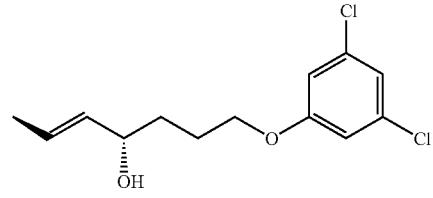 |
| 18 | 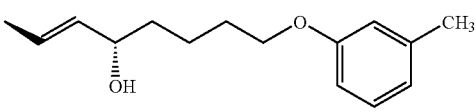 |
| 19 | 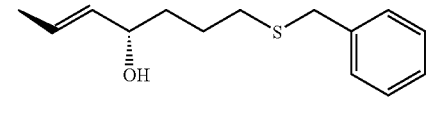 |
| 20 | 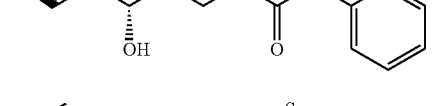 |
| 21 |  |
| 22 | 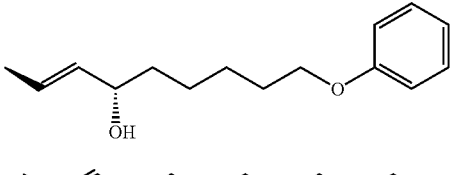 |
| 23 |  |
| 24 |  |
| 25 | 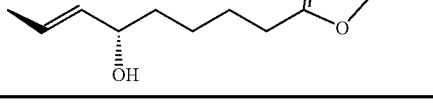 |
| 26 | 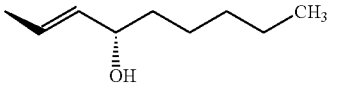 |
TABLE 62
(I-E-2)
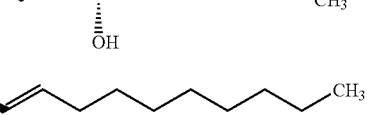
| No. | E |
|---|---|
| 1 | 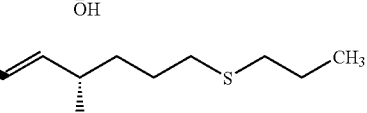 |
| 2 | 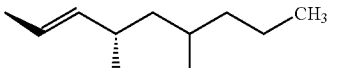 |
| 3 | 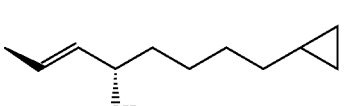 |
| 4 | 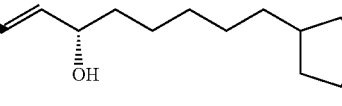 |
| 5 |  |
| 6 | 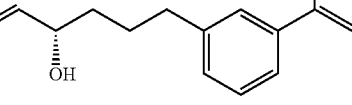 |
| 7 | 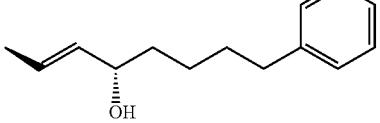 |
| 8 | 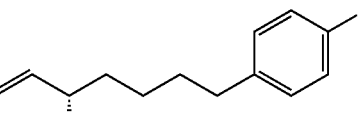 |
| 9 |  |
| 10 | |
| 11 | |

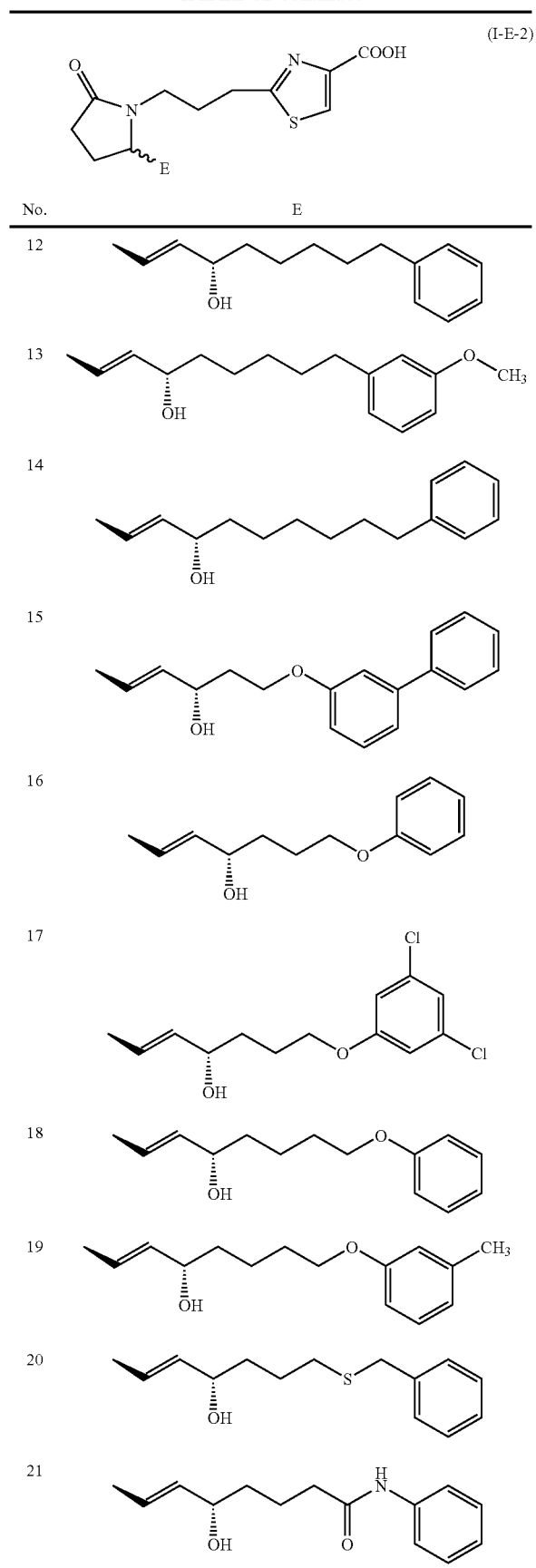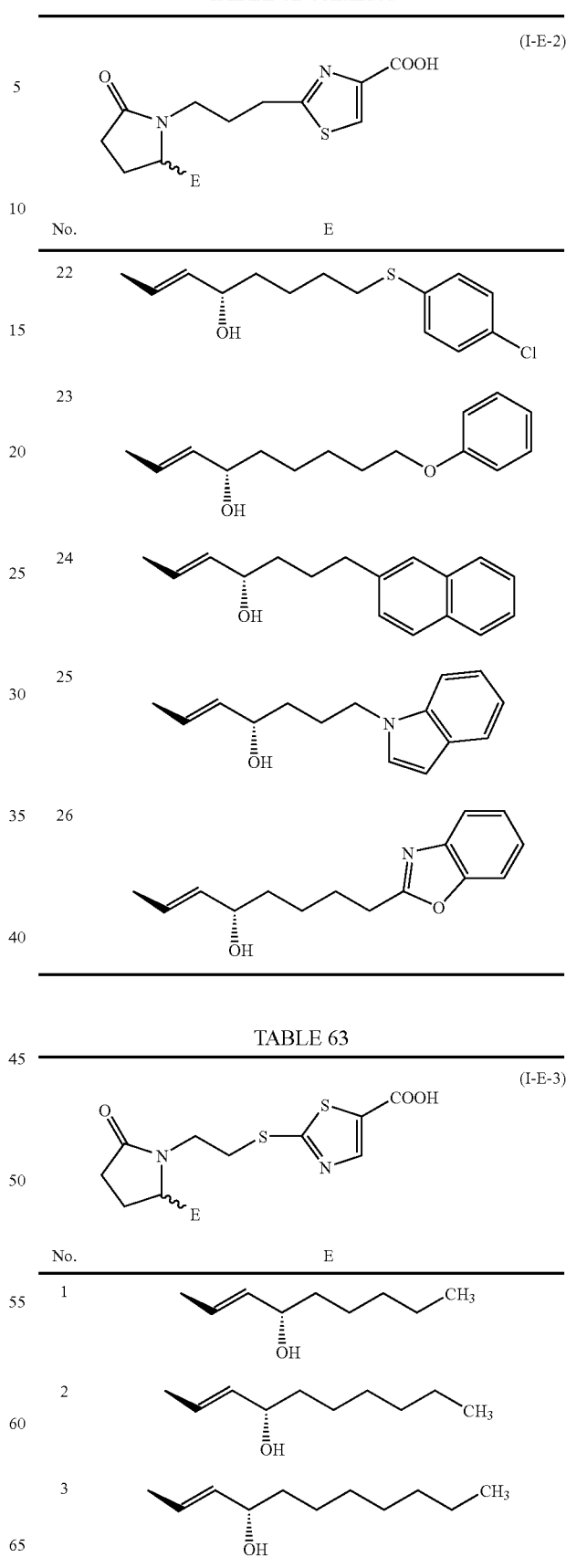

227
TABLE 63-continued
(I-E-3)
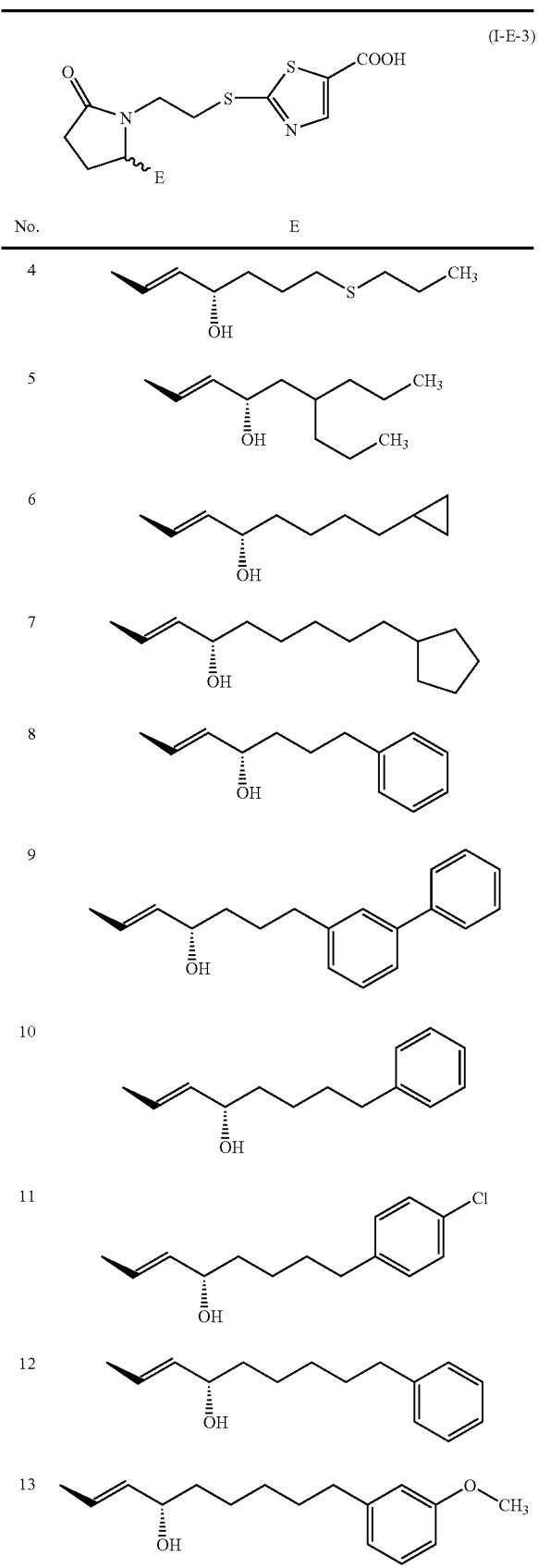
228
TABLE 63-continued
(I-E-3)
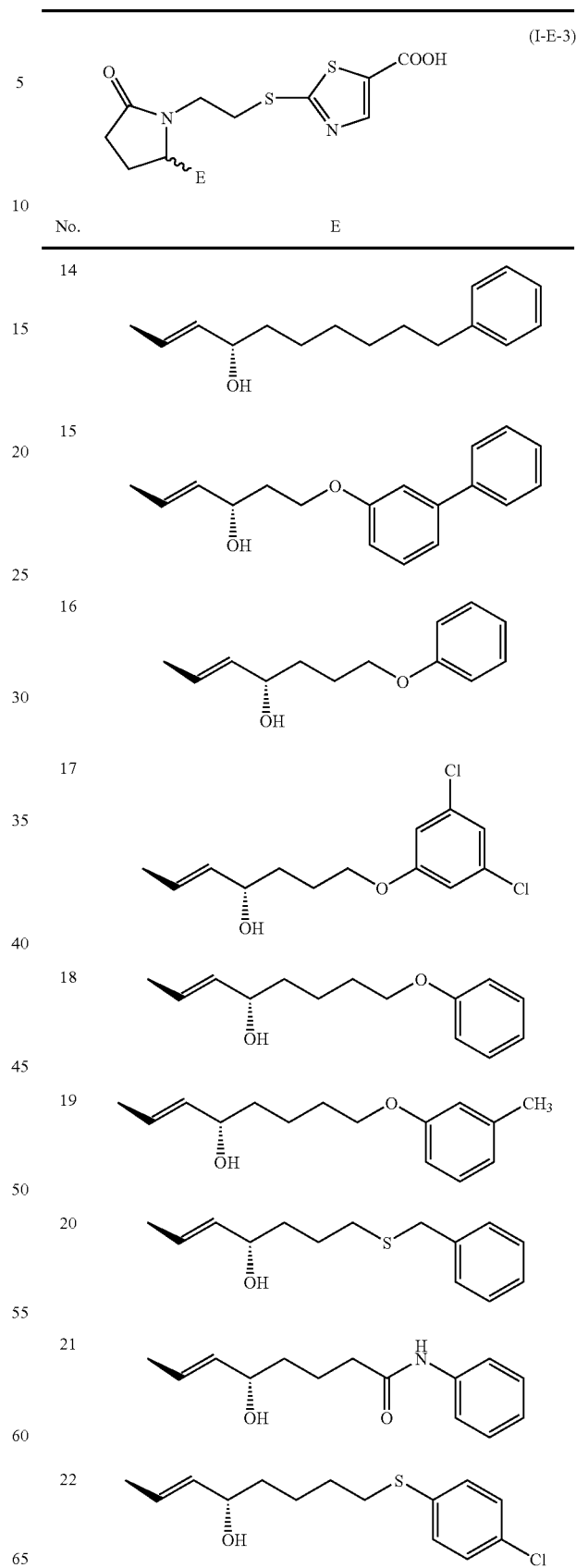

TABLE 63-continued (I-E-3)

| No. | E |
|---|---|
| 23 | (CH=CH–CH(OH)–(CH2)4–O–phenyl) |
| 24 | (CH=CH–CH(OH)–(CH2)3–2-naphthyl) |
| 25 | (CH=CH–CH(OH)–(CH2)3–N-indolyl) |
| 26 | (CH=CH–CH(OH)–(CH2)4–benzoxazol-2-yl) |

TABLE 64

(I-E-4)

| No. | E |
|---|---|
| 1 | (CH=CH–CH(OH)–(CH2)4–CH3) |
| 2 | (CH=CH–CH(OH)–(CH2)5–CH3) |
| 3 | (CH=CH–CH(OH)–(CH2)6–CH3) |
| 4 | (CH=CH–CH(OH)–(CH2)3–S–CH2CH3) |
| 5 | (CH=CH–CH(OH)–CH2–CH(CH2CH2CH3)2) |
| 6 | (CH=CH–CH(OH)–(CH2)4–cyclopropyl) |
| 7 | (CH=CH–CH(OH)–(CH2)4–cyclopentyl) |
| 8 | (CH=CH–CH(OH)–(CH2)3–phenyl) |
| 9 | (CH=CH–CH(OH)–(CH2)3–3-biphenyl) |
| 10 | (CH=CH–CH(OH)–(CH2)4–phenyl) |
| 11 | (CH=CH–CH(OH)–(CH2)3–(4-Cl-phenyl)) |
| 12 | (CH=CH–CH(OH)–(CH2)4–phenyl) |
| 13 | (CH=CH–CH(OH)–(CH2)4–(3-OCH3-phenyl)) |
| 14 | (CH=CH–CH(OH)–(CH2)5–phenyl) |

TABLE 64-continued (I-E-4)

| No. | E |
|---|---|
| 15 | 3-biphenylyloxy substituent |
| 16 | phenoxy substituent |
| 17 | 3,5-dichlorophenoxy substituent |
| 18 | phenoxy (longer chain) |
| 19 | 3-methylphenoxy |
| 20 | benzylthio |
| 21 | N-phenyl amide |
| 22 | 4-chlorophenylthio |
| 23 | phenoxy |
| 24 | 2-naphthyl |
| 25 | 1-indolyl |
| 26 | benzoxazol-2-yl |

TABLE 65

(I-E-5)

| No. | E |
|---|---|
| 1 | n-pentyl |
| 2 | n-hexyl |
| 3 | n-heptyl |
| 4 | ethylthio |
| 5 | 3-ethyl substituent with ethyl |
| 6 | cyclopropyl |
| 7 | cyclopentyl |

TABLE 65-continued (I-E-5)

Structure: pyrrolidinone-N-(CH₂)₃-thiophene-COOH with substituent E at the 5-position of pyrrolidinone

| No. | E |
|-----|---|
| 8 | (E)-CH=CH-CH(OH)-CH₂CH₂-phenyl |
| 9 | (E)-CH=CH-CH(OH)-(CH₂)₃-(3-biphenyl) |
| 10 | (E)-CH=CH-CH(OH)-(CH₂)₃-phenyl |
| 11 | (E)-CH=CH-CH(OH)-(CH₂)₃-(4-Cl-phenyl) |
| 12 | (E)-CH=CH-CH(OH)-(CH₂)₄-phenyl |
| 13 | (E)-CH=CH-CH(OH)-(CH₂)₄-(3-OCH₃-phenyl) |
| 14 | (E)-CH=CH-CH(OH)-(CH₂)₅-phenyl |
| 15 | (E)-CH=CH-CH(OH)-CH₂-O-(3-biphenyl) |
| 16 | (E)-CH=CH-CH(OH)-CH₂CH₂-O-phenyl |
| 17 | (E)-CH=CH-CH(OH)-(CH₂)₃-O-(3,5-diCl-phenyl) |
| 18 | (E)-CH=CH-CH(OH)-(CH₂)₃-O-phenyl |
| 19 | (E)-CH=CH-CH(OH)-(CH₂)₃-O-(3-CH₃-phenyl) |
| 20 | (E)-CH=CH-CH(OH)-CH₂CH₂-S-CH₂-phenyl |
| 21 | (E)-CH=CH-CH(OH)-CH₂-C(=O)-NH-phenyl |
| 22 | (E)-CH=CH-CH(OH)-(CH₂)₃-S-(4-Cl-phenyl) |
| 23 | (E)-CH=CH-CH(OH)-(CH₂)₄-O-phenyl |
| 24 | (E)-CH=CH-CH(OH)-(CH₂)₃-(2-naphthyl) |
| 25 | (E)-CH=CH-CH(OH)-CH₂CH₂-(1-indolyl) |
| 26 | (E)-CH=CH-CH(OH)-(CH₂)₃-(2-benzoxazolyl) |

TABLE 66

(I-E-6)

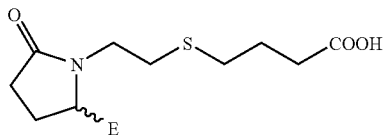

| No. | E |
|---|---|
| 1 | (E)-CH=CH-CH(OH)-(CH2)4-CH3 |
| 2 | (E)-CH=CH-CH(OH)-(CH2)5-CH3 |
| 3 | (E)-CH=CH-CH(OH)-(CH2)6-CH3 |
| 4 | (E)-CH=CH-CH(OH)-(CH2)3-S-C2H5 |
| 5 | (E)-CH=CH-CH(OH)-CH2-CH(C2H5)-CH2-CH3 |
| 6 | (E)-CH=CH-CH(OH)-(CH2)4-cyclopropyl |
| 7 | (E)-CH=CH-CH(OH)-(CH2)4-cyclopentyl |
| 8 | (E)-CH=CH-CH(OH)-(CH2)3-Ph |
| 9 | (E)-CH=CH-CH(OH)-(CH2)3-(3-biphenyl) |
| 10 | (E)-CH=CH-CH(OH)-(CH2)4-Ph |
| 11 | (E)-CH=CH-CH(OH)-(CH2)3-(4-Cl-C6H4) |

TABLE 66-continued (I-E-6)

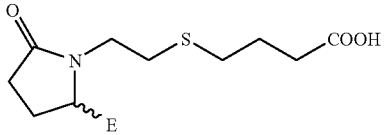

| No. | E |
|---|---|
| 12 | (E)-CH=CH-CH(OH)-(CH2)4-Ph |
| 13 | (E)-CH=CH-CH(OH)-(CH2)4-(3-OCH3-C6H4) |
| 14 | (E)-CH=CH-CH(OH)-(CH2)5-Ph |
| 15 | (E)-CH=CH-CH(OH)-(CH2)2-O-(3-Ph-C6H4) |
| 16 | (E)-CH=CH-CH(OH)-(CH2)2-O-Ph |
| 17 | (E)-CH=CH-CH(OH)-(CH2)3-O-(3,5-Cl2-C6H3) |
| 18 | (E)-CH=CH-CH(OH)-(CH2)3-O-Ph |
| 19 | (E)-CH=CH-CH(OH)-(CH2)3-O-(3-CH3-C6H4) |
| 20 | (E)-CH=CH-CH(OH)-(CH2)3-S-CH2-Ph |
| 21 | (E)-CH=CH-CH(OH)-(CH2)2-C(=O)-NH-Ph |

TABLE 66-continued (I-E-6)

[Structure: pyrrolidinone-N-CH2CH2-S-CH2CH2CH2-COOH with E substituent]

| No. | E |
|-----|---|
| 22 | CH=CH-CH(OH)-CH2CH2CH2CH2-S-C6H4-Cl (4-chlorophenylthio) |
| 23 | CH=CH-CH(OH)-(CH2)4-O-C6H5 (phenoxy) |
| 24 | CH=CH-CH(OH)-CH2CH2CH2-naphthalen-2-yl |
| 25 | CH=CH-CH(OH)-CH2CH2CH2-indol-1-yl |
| 26 | CH=CH-CH(OH)-(CH2)4-benzoxazol-2-yl |

TABLE 67

(I-E-7)

[Structure: pyrrolidinone-N-CH2CH2-(3-carboxyphenyl) with E substituent]

| No. | E |
|-----|---|
| 1 | CH=CH-CH(OH)-CH2CH2CH2CH2-CH3 |
| 2 | CH=CH-CH(OH)-(CH2)5-CH3 |
| 3 | CH=CH-CH(OH)-(CH2)6-CH3 |

TABLE 67-continued (I-E-7)

[Structure: pyrrolidinone-N-CH2CH2-(3-carboxyphenyl) with E substituent]

| No. | E |
|-----|---|
| 4 | CH=CH-CH(OH)-CH2CH2CH2-S-CH2CH2CH3 |
| 5 | CH=CH-CH(OH)-CH2-CH(CH2CH3)(CH2CH3) |
| 6 | CH=CH-CH(OH)-(CH2)4-cyclopropyl |
| 7 | CH=CH-CH(OH)-(CH2)4-cyclopentyl |
| 8 | CH=CH-CH(OH)-CH2CH2CH2-phenyl |
| 9 | CH=CH-CH(OH)-CH2CH2CH2-(3-phenylphenyl) |
| 10 | CH=CH-CH(OH)-(CH2)4-phenyl |
| 11 | CH=CH-CH(OH)-(CH2)4-(4-chlorophenyl) |
| 12 | CH=CH-CH(OH)-(CH2)5-phenyl |
| 13 | CH=CH-CH(OH)-(CH2)4-(3-methoxyphenyl) |

TABLE 67-continued (I-E-7)

| No. | E |
|---|---|
| 14 | 7-phenylhept-1-en-3-ol chain |
| 15 | but-1-en-3-ol-CH₂CH₂-O-(3-biphenyl) |
| 16 | but-1-en-3-ol-(CH₂)₃-O-phenyl |
| 17 | but-1-en-3-ol-(CH₂)₃-O-(3,5-dichlorophenyl) |
| 18 | hex-1-en-3-ol-(CH₂)₃-O-phenyl |
| 19 | hex-1-en-3-ol-(CH₂)₃-O-(3-methylphenyl) |
| 20 | but-1-en-3-ol-(CH₂)₂-S-CH₂-phenyl |
| 21 | hex-1-en-3-ol-CH₂-C(=O)NH-phenyl |
| 22 | but-1-en-3-ol-(CH₂)₃-S-(4-chlorophenyl) |

TABLE 67-continued (I-E-7)

| No. | E |
|---|---|
| 23 | hex-1-en-3-ol-(CH₂)₃-O-phenyl |
| 24 | pent-1-en-3-ol-(CH₂)₂-(2-naphthyl) |
| 25 | pent-1-en-3-ol-(CH₂)₂-N-indolyl |
| 26 | hex-1-en-3-ol-CH₂-(2-benzoxazolyl) |

TABLE 68

(I-E-8)

| No. | E |
|---|---|
| 1 | hept-1-en-3-ol-CH₃ |
| 2 | oct-1-en-3-ol |
| 3 | non-1-en-3-ol |
| 4 | but-1-en-3-ol-(CH₂)₂-S-CH₂CH₃ |

TABLE 68-continued (I-E-8)

| No. | E |
|---|---|
| 5 | (E)-CH=CH-CH(OH)-CH2-CH(CH2CH3)(CH2CH3) variant with propyl groups |
| 6 | (E)-CH=CH-CH(OH)-(CH2)4-cyclopropyl |
| 7 | (E)-CH=CH-CH(OH)-(CH2)4-cyclopentyl |
| 8 | (E)-CH=CH-CH(OH)-(CH2)3-phenyl |
| 9 | (E)-CH=CH-CH(OH)-(CH2)3-(3-biphenyl) |
| 10 | (E)-CH=CH-CH(OH)-(CH2)4-phenyl |
| 11 | (E)-CH=CH-CH(OH)-(CH2)4-(4-chlorophenyl) |
| 12 | (E)-CH=CH-CH(OH)-(CH2)5-phenyl |
| 13 | (E)-CH=CH-CH(OH)-(CH2)5-(3-methoxyphenyl) |
| 14 | (E)-CH=CH-CH(OH)-(CH2)6-phenyl |
| 15 | (E)-CH=CH-CH(OH)-CH2-CH2-O-(3-biphenyl) |
| 16 | (E)-CH=CH-CH(OH)-(CH2)3-O-phenyl |
| 17 | (E)-CH=CH-CH(OH)-(CH2)3-O-(3,5-dichlorophenyl) |
| 18 | (E)-CH=CH-CH(OH)-(CH2)4-O-phenyl |
| 19 | (E)-CH=CH-CH(OH)-(CH2)4-O-(3-methylphenyl) |
| 20 | (E)-CH=CH-CH(OH)-(CH2)3-S-CH2-phenyl |
| 21 | (E)-CH=CH-CH(OH)-(CH2)2-C(=O)-NH-phenyl |
| 22 | (E)-CH=CH-CH(OH)-(CH2)4-S-(4-chlorophenyl) |
| 23 | (E)-CH=CH-CH(OH)-(CH2)5-O-phenyl |
| 24 | (E)-CH=CH-CH(OH)-(CH2)3-(2-naphthyl) |

TABLE 68-continued

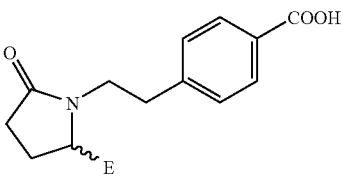
(I-E-8)

| No. | E |
|---|---|
| 25 | 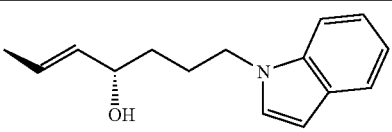 |
| 26 | 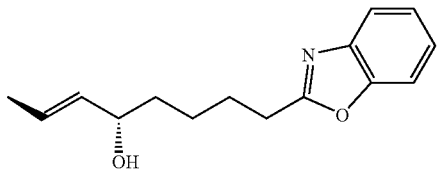 |

Processes for the Preparation of the compound of the present invention:

The compound represented by formula (I) can be prepared by the following method or the method described in Example.

1. Among the compounds represented by formula (I), a compound in which T represents oxygen atom, and X represents —CH$_2$—, i.e., a compound represented by formula (IA):

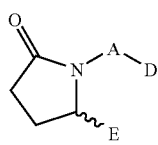
(IA)

(wherein all symbols have the same meanings as described above.) can be prepared by the following method.

The compound represented by formula (IA) can be prepared by reductive amination of the compounds of formula (II):

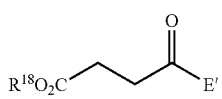
(II)

(wherein R$^{18}$ is C1-10 alkyl and E' has the same meaning as E. With the proviso that, hydroxyl, amino, carboxy or formyl in the group represented by E' may be protected, if necessary.) and a compound represented by formula (III):

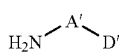
(III)

(wherein A' and D' have the same meanings as A and D, respectively. With the proviso that, hydroxyl, amino, carboxy or formyl in the group represented by A' and D' may be protected, if necessary.), if necessary, followed by removal of the protective group from the resulting product.

The reductive amination is well known. For example, it may be carried out in an organic solvent (e.g., methanol, ethanol, dichloromethane, tetrahydrofuran, dimethoxyethane, diethyl ether) in the presence of reducing agent (e.g., sodium cyanoborohydride, sodium borohydride, sodium triacetoxyborohydride, pyridine borane) at 0 to 100° C.

The removal of the protective group may be carried out by following method.

The reaction for removing the protective group for carboxy, hydroxy, amino or formyl is well known, including, for example, the following:

(1) alkali hydrolysis,
(2) deprotection under acidic condition,
(3) deprotection through hydrogenolysis,
(4) silyl deprotection,
(5) deprotection with metal,
(6) deprotection with organic metal.

These methods are described concretely.

(1) The deprotection through alkali hydrolysis may be effected, for example, in an organic solvent (e.g., methanol, tetrahydrofuran, dioxane) by the use of an alkali metal hydroxide (e.g., sodium hydroxide, potassium hydroxide, lithium hydroxide), an alkaline earth metal hydroxide (e.g., barium hydroxide, calcium hydroxide) or a carbonate (e.g., sodium carbonate, potassium carbonate), or an aqueous solution thereof or their mixture, at 0 to 40° C.

(2) The deprotection under acidic condition may be effected, for example, in an organic solvent (e.g., dichloromethane, chloroform, dioxane, ethyl acetate, anisole) with an organic acid (e.g., acetic acid, trifluoroacetic acid, methanesulfonic acid, p-toluenesulfonic acid) or an inorganic acid (e.g., hydrochloric acid, sulfuric acid) or their mixture (hydrogen bromide/acetic acid), at 0 to 100° C.

(3) The deprotection through hydrogenolysis may be effected, for example, in a solvent (e.g., ether-type (e.g., tetrahydrofuran, dioxane, dimethoxyethane, diethyl ether), alcohol-type (e.g., methanol, ethanol), benzene-type (e.g., benzene, toluene), ketone-type (e.g., acetone, methyl ethyl ketone), nitrile-type (e.g., acetonitrile), amide-type (e.g., dimethylformamide), water, ethyl acetate, acetic acid, or mixed solvent of two or more of these), in the presence of a catalyst (e.g., palladium-carbon, palladium-black, palladium hydroxide, platinum oxide, Raney nickel), in a hydrogen atmosphere under a normal pressure or increased pressure or in the presence of ammonium formate, at 0 to 200° C.

(4) The silyl deprotection may be effected, for example, in a water-miscible organic solvent (e.g., tetrahydrofuran, acetonitrile) by the use of tetrabutylammonium fluoride, at 0 to 40° C.

(5) The deprotection with metal may be effected, for example, in an acidic solvent (acetic acid, buffer having pH 4.2 to 7.2, or mixture of their solution with organic solvent such as tetrahydrofuran) in the presence of zinc powder with or without ultrasonic waves applied thereto, at 0 to 40° C.

(6) The deprotection with metal complex may be effected, for example, in an organic solvent (e.g., dichloromethane, dimethylformamide, tetrahydrofuran, ethyl acetate, acetonitrile, dioxane, ethanol), water or their mixed solvent, in the presence of a trapping reagent (e.g., tributyltin hydride, triethylsilane, dimedone, morpholine, diethylamine, pyrrolidine), an organic acid (e.g., acetic acid, formic acid, 2-ethylhexanoic acid) and/or an organic acid salt (e.g., sodium 2-ethylhexanoate, potassium 2-ethylhexanoate), in the presence or absence of a phosphine-type reagent (e.g., triphenyl phosphine), by the use of a metal complex (tetrakistriphenylphosphine palladium(0), dichlorobis(triphenylphosphine) palladium(II), palladium(II) acetate, chlorotris(triphenylphosphine) rhodium(I)), at 0 to 40° C.

Apart from the above, the deprotection may also be effected, for example, according to the methods described in T. W. Greene, *Protective Groups in Organic Synthesis*, Wiley, New York, 1999.

The intended compounds of the invention may be readily produced through selective use of the deprotecting reaction, which could be readily understood by anyone skilled in the art.

The carboxyl-protective group includes, for example, methyl, ethyl, allyl, t-butyl, trichloroethyl, benzyl (Bn), and phenacyl etc.

The hydroxyl-protective group includes, for example, methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), t-butyldimethylsilyl (TBDMS), t-butyldiphenylsilyl (TBDPS), acetyl (Ac), pivaloyl, benzoyl, benzyl (Bn), p-methoxybenzyl, allyloxycarbonyl (Alloc), and 2,2,2-trichloroethoxycarbonyl (Troc) etc.

The amino-protective group includes, for example, benzyloxycarbonyl, t-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), p-methoxybenzyl, benzyloxymethyl (BOM), and 2-(trimethylsilyl)ethoxymethyl (SEM) etc.

The formyl-protective group is, for example, acetal (e.g., dimethylacetal) etc.

The carboxy, hydroxy, amino or formyl-protective may be any others than those mentioned above, capable of being readily and selectively removed, and are not specifically defined. For example, those described in T. W. Greene, *Protective Groups in Organic Synthesis*, 3rd Ed., Wiley, New York, 1999 may be used.

2. The compounds represented by formula (IA) can be prepared by reductive amination of the compounds of formula (IV):

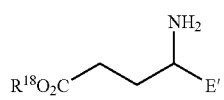

(wherein all symbols have the same meanings as defined above.) and the compounds of formula (V):

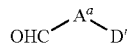

(wherein $A^a$ is $A^{1a}$ or $A^{2a}$, $A^{1a}$ is 1) C1-7 straight-chain alkylene optionally substituted by 1 to 2 C1-4 alkyl(s), 2) C2-7 straight-chain alkenylene optionally substituted by 1 to 2 C1-4 alkyl(s), or 3) C2-7 straight-chain alkynylene optionally substituted by 1 to 2 C1-4 alkyl(s), $A^{2a}$ is -$G^{1a}$-$G^{2a}$-$G^3$-, $G^{1a}$ is 1) C1-3 alkylene optionally substituted by 1 to 2 C1-4 alkyl(s), 2) C2-3 alkenylene optionally substituted by 1 to 2 C1-4 alkyl(s), or 3) C2-3 alkynylene optionally substituted by 1 to 2 C1-4 alkyl(s), $G^{2a}$ has the same meaning as $G^2$. With the proviso that, hydroxyl, amino, carboxy or formyl in the group represented by $G^{2a}$ may be protected, if necessary. Other symbols have the same meanings as defined above.), if necessary, followed by removal of the protective group from the resulting product.

The reductive amination and the removal of the protective group may be carried out by the above method.

3. Among the compounds represented by formula (I), a compound in which T represents oxygen atom, and X represents —O—, i.e., a compound represented by formula (IB):

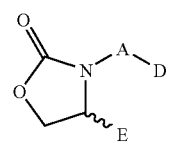

(wherein all symbols have the same meanings as described above.) can be prepared by the following method.

The compounds represented by formula (IB) can be prepared by cyclization of the compounds of formula (VI):

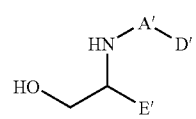

(wherein all symbols have the same meanings as defined above.), if necessary, followed by removal of the protective group from the resulting product.

The cyclization is well known. For example, it may be carried out in an organic solvent (e.g., tetrahydrofuran, dichloromethane, dimethoxyethane, diethyl ether, dimethylformamide) in the presence of a base (e.g., triethylamine, pyridine, potassium carbonate, sodium bicarbonate) with carbonylation agent (e.g., triphosgene, 1,1'-carbonyldiimidazole (CDI), phosgene) at 0 to 50° C.

The removal of the protective group may be carried out by the above method.

4. Among the compounds represented by formula (I), a compound in which T represents oxygen atom, and X represents —S—, i.e., a compound represented by formula (IC):

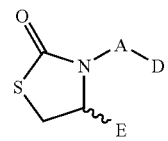

(wherein all symbols have the same meanings as described above.) can be prepared by the following method.

The compounds represented by formula (IC) can be prepared by cyclization of the compounds of formula (VII):

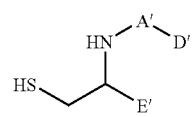

(wherein all symbols have the same meanings as defined above.), if necessary, followed by removal of the protective group from the resulting product.

The cyclization and the removal of the protective group may be carried out by the above method.

5. Among the compounds represented by formula (I), a compound in which T represents sulfur atom, i.e., a compound represented by formula (ID):

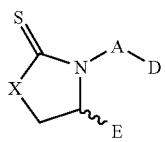

(ID)

(wherein all symbols have the same meanings as described above.) can be prepared by the following method.

The compounds represented by formula (ID) can be prepared by thioamidation of the compounds of formula (VIII):

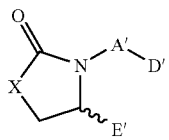

(VIII)

(wherein all symbols have the same meanings as defined above.), if necessary, followed by removal of the protective group from the resulting product.

The thioamidation is well known. For example, it may be carried out in an organic solvent (e.g., toluene, diethyl ether, methylene chloride, chloroform, dioxane, tetrahydrofuran) in the presence of a thyonation agent (e.g., Lawesson's Reagent (2,4-bis(4-methoxyphenyl)-1,3-dithia-2,4-diphosphetane-2,4-disulfide), phosphorus pentoxide) at 0 to 150° C.

The removal of the protective group may be carried out by the above method.

6. Among the compounds represented by formula (I), a compound in which D represents —$CH_2OH$, i.e., a compound represented by formula (IE):

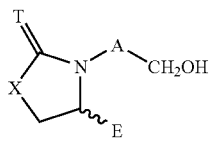

(IE)

(wherein all symbols have the same meanings as described above.) can be prepared by the following method.

The compounds represented by formula (IE) can be prepared by reduction of the compounds of formula (IX):

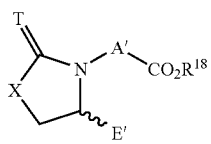

(IX)

(wherein all symbols have the same meanings as defined above.), if necessary, followed by removal of the protective group from the resulting product.

The reduction is well known. For example, it may be carried out in an organic solvent (e.g., tetrahydrofuran, dimethoxyethane, diethyl ether, dimethylformamide, dioxane, methanol, ethanol, isopropanol) or an aqueous solution thereof in the presence of a reducing agent (e.g., sodium borohydride, lithium borohydride) at 0 to 70° C.

The removal of the protective group may be carried out by the above method.

7. Among the compounds represented by formula (I), a compound in which D represents —$CONR^3SO_2R^4$, —$CONR^6R^7$, —$CONR^6SO_2R^8$ or —CO—(NH-amino acid residue-CO)$_m$—OH, i.e., a compound represented by formula (IF):

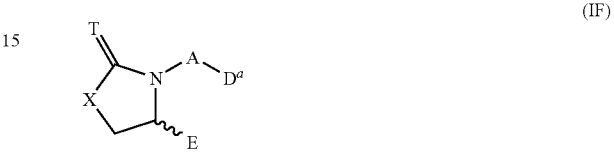

(IF)

(wherein $D^a$ is —$CONR^3SO_2R^4$, —$CONR^6R^7$, —$CONR^6SO_2R^8$ or —CO—(NH-amino acid residue-CO)$_m$—OH and other symbols have the same meanings as described above.) can be prepared by the following method.

The compounds represented by formula (IF) can be prepared by amidation of the compounds of formula (X):

(X)

(wherein all symbols have the same meanings as defined above.) and the compounds of formula (XI-1):

H—$NR^3SO_2R^4$ (XI-1)

(wherein all symbols have the same meanings as defined above.), the compounds of formula (XI-2):

H—$NR^6R^7$ (XI-2)

(wherein all symbols have the same meanings as defined above.), the compounds of formula (XI-3):

H—$NR^6SO_2R^8$ (XI-3)

(wherein all symbols have the same meanings as defined above.), or the compounds of formula (XI-4):

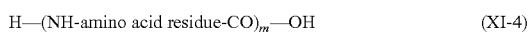

H—(NH-amino acid residue-CO)$_m$—OH (XI-4)

(wherein all symbols have the same meanings as defined above. With the proviso that, amino, hydroxy or carboxy in the compounds represented by formula (XI-4) may be protected, if necessary.), if necessary, followed by removal of the protective group from the resulting product.

The method of amidation is known. For example, it includes the method
(1) via an acyl halide,
(2) via a mixed acid anhydride,
(3) using a condensing agent.

These methods are explained as follows.
(1) The method via an acyl halide may be carried out, for example, by reacting carboxylic acid with an acyl halide (e.g., oxalyl chloride or thionyl chloride etc.) in an organic solvent (e.g., chloroform, dichloromethane, diethyl ether or tetrahydrofuran) or without a solvent at −20° C. to reflux temperature. And then the obtained acyl halide derivative may be reacted with amine in an inert organic solvent (e.g., chloroform, dichloromethane, diethyl ether or tetrahydrofuran) in the presence of a base (e.g., pyridine, triethylamine, dimethylaniline, dimethylaminopyridine or diisopropylethylamine etc.) at 0 to 40° C. As an alternative, the obtained acyl halide derivative may be reacted in an organic solvent (e.g., dioxane, tetrahydrofuran) using an alkaline aqueous solution (e.g., sodium bicarbonate, sodium hydroxide) at 0 to 40° C.

(2) The method via a mixed acid anhydride may be carried out, for example, by reacting carboxylic acid with an acyl halide (e.g., pivaloyl chloride, tosyl chloride or mesyl chloride) or an acid derivative (e.g., ethyl chloroformate or isobutyl chloroformate) in an organic solvent (e.g., chloroform, dichloromethane, diethyl ether, tetrahydrofuran) or without a solvent, in the presence of a base (e.g., pyridine, triethylamine, dimethylaniline, dimethylaminopyridine or diisopropylethylamine) at 0 to 40° C. And then the obtained mixed acid anhydride derivative may be reacted with amine in an organic solvent (e.g., chloroform, methylene chloride, diethyl ether or tetrahydrofuran), at 0 to 40° C.

(3) The method using a condensing agent may be carried out, for example, by reacting carboxylic acid with amine in an organic solvent (e.g., chloroform, dichloromethane, dimethylformamide, diethyl ether or tetrahydrofuran) or without a solvent, in the presence or absence of a base (e.g., pyridine, triethylamine, dimethylaniline or dimethylaminopyridine), using a condensing agent (e.g., 1,3-dicyclohexyl carbodiimide (DCC), 1-ethyl-3-[3-(dimethylamino)propyl]carbodiimide (EDC), 1,1'-carbodiimidazole (CDI), 2-chloro-1-methylpyridinium iodide, or 1-propanephosphonic acid cyclic anhydride (PPA)), in the presence or absence of 1-hydroxybenzothiazole (HOBt), at 0 to 40° C.

The reaction described in (1), (2) and (3) may be carried out under an inert gas (e.g., argon, nitrogen) to avoid water in order to obtain a preferable result.

The removal of the protective group may be carried out by the above method.

8. Among the compounds of the present invention represented by formula (I), a compound in which D represents —O—(CO-amino acid residue-NH)$_m$—H or —OCO—R$^{10}$, i.e., a compound represented by formula (IG):

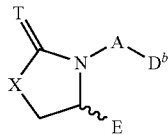

(IG)

(wherein D$^b$ is —O—(CO-amino acid residue-NH)$_m$—H or —OCO—R$^{10}$ and other symbols have the same meanings as described above.) can be prepared by the following method.

The compounds represented by formula (IG) can be prepared by esterifying the compounds of formula (XII):

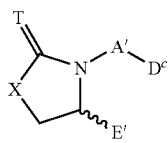

(XII)

(wherein D$^c$ is —OH or —CH$_2$OH and other symbols have the same meanings as described above.) with the compounds of formula (XIII-1):

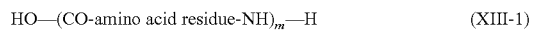

HO—(CO-amino acid residue-NH)$_m$—H           (XIII-1)

(wherein all symbols have the same meanings as defined above. With the proviso that, amino, hydroxy or carboxy in the compounds represented by formula (XIII-1) may be protected, if necessary.) or the compounds of formula (XIII-2):

HO$_2$C—R$^{10}$           (XIII-2)

(wherein R$^{10}$ has the same meaning as defined above.), if necessary, followed by removal of the protective group from the resulting product.

The method of esterification is known. For example, it includes the method
(1) via an acyl halide,
(2) via a mixed acid anhydride,
(3) using a condensing agent.

These methods are explained as follows.

(1) The method via an acyl halide may be carried out, for example, by reacting carboxylic acid with an acid-halogenating agent (e.g., oxalyl chloride or thionyl chloride etc.) in an organic solvent (e.g., chloroform, dichloromethane, diethyl ether or tetrahydrofuran) or without a solvent at −20° C. to reflux temperature. And then the obtained acyl halide derivative may be reacted with alcohol in an inert organic solvent (e.g., chloroform, methylene chloride, diethyl ether or tetrahydrofuran) in the presence of a base (e.g., pyridine, triethylamine, dimethylaniline, dimethylaminopyridine or diisopropylethylamine etc.) at 0 to 40° C. As an alternative, the obtained acyl halide derivative may be reacted in an organic solvent (e.g., dioxane, tetrahydrofuran) using an alkaline aqueous solution (e.g., sodium bicarbonate, sodium hydroxide) at 0 to 40° C.

(2) The method via a mixed acid anhydride may be carried out, for example, by reacting carboxylic acid with an acyl halide (e.g., pivaloyl chloride, tosyl chloride or mesyl chloride) or an acid derivative (ethyl chloroformate or isobutyl chloroformate) in an organic solvent (e.g., chloroform, dichloromethane, diethyl ether, tetrahydrofuran) or without a solvent, in the presence of a base (e.g., pyridine, triethylamine, dimethylaniline, dimethylaminopyridine or diisopropylethylamine) at 0 to 40° C. And then the obtained mixed acid anhydride derivative may be reacted with alcohol in an organic solvent (e.g., chloroform, dichloromethane, diethyl ether or tetrahydrofuran), at 0 to 40° C.

(3) The method using a condensing agent may be carried out, for example, by reacting carboxylic acid with alcohol in an organic solvent (e.g., chloroform, dichloromethane, dimethylformamide, diethyl ether or tetrahydrofuran) or without a solvent, in the presence or absence of a base (e.g., pyridine, triethylamine, dimethylaniline or dimethylaminopyridine), using a condensing agent (e.g., 1,3-dicyclohexyl carbodiimide (DCC), 1-ethyl-3-[3-(dimethylamino)propyl]carbodiimide (EDC), 1,1'-carbodiimidazole (CDI), 2-chloro-1-methylpyridinium iodide, 1-propanephosphonic acid cyclic anhydride (PPA)), in the presence or absence of 1-hydroxybenzothiazole (HOBt), at 0 to 40° C.

The reaction described in (1), (2) and (3) may be carried out under an inert gas (e.g., argon, nitrogen) to avoid water in order to obtain a preferable result.

The removal of the protective group may be carried out by the above method.

9. Among the compound of the present invention represented by formula (I), a compound in which D represents formyl, i.e., a compound represented by formula (IH)

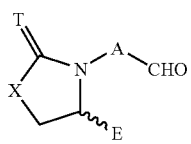

(IH)

(wherein all symbols have the same meanings as described above.) can be prepared by the following method.

The compounds represented by formula (IH) can be prepared by oxidizing the compounds of formula (XIV):

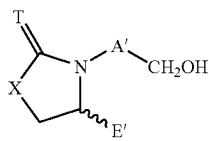

(XIV)

(wherein all symbols have the same meanings as described above.), if necessary, followed by removal of the protective group.

The reaction for oxidation is known, for example, including the following:
(1) Swern oxidation,
(2) oxidation with Dess-Martin reagent,
(3) oxidation with TEMPO reagent.

These methods are described concretely.
(1) The method of Swern oxidation comprises, for example, reacting oxalyl chloride with dimethyl sulfoxide in an organic solvent (e.g., chloroform, dichloromethane) at −78° C., and then reacting the resulting solution with the alcohol compound, and further with a tertiary amine (e.g., triethylamine, N,N-diisopropylethylamine, N-methylmorpholine, N-ethylpiperidine, diazabicyclo[5.4.0]undec-7-ene) at −78 to 20° C.
(2) The method with a Dess-Martin reagent comprises, for example, processing the compound in an organic solvent (e.g., chloroform, dichloromethane, 1,2-dichloroethane, tetrahydrofuran, acetonitrile, t-butyl alcohol) in the presence of a Dess-Martin reagent (1,1,1-triacetoxy-1,1-dihydro-1,2-benzoiodoxol-3-(1H)-one), in the presence or absence of a base (e.g., pyridine) at 0 to 40° C.
(3) The method with a TEMPO reagent comprises, for example, processing the compound in an organic solvent (e.g., chloroform, dichloromethane, tetrahydrofuran, toluene, acetonitrile, ethyl acetate, water) or in a mixed solvent thereof, in the presence of a TEMPO reagent (2,2,6,6-tetramethyl-1-piperidinyloxy, free radical) and a re-oxidizing agent (e.g., aqueous hydrogen peroxide, sodium hypochlorite, 3-chloroperbenzoic acid, iodobenzene diacetate, potassium peroxymonosulfate (Oxon, trade name)), in the presence or absence of a quaternary ammonium salt (e.g., tetrabutylammonium chloride, tetrabutylammonium bromide), in the presence or absence of an inorganic salt (e.g., sodium bromide, potassium bromide), in the presence or absence of an inorganic base (e.g., sodium hydrogencarbonate, sodium acetate), at 20 to 60° C.

The oxidation is not limited to the above, and may be any other capable of readily and selectively oxidizing the alcohol into a ketone. For example, herein employable is any of Johns oxidation, oxidation with PCC (pyridinium chlorochromate), oxidation with sulfur trioxide-pyridine complex, or those described in *Comprehensive Organic Transformations* (Richard C. Larock, VCH Publishers, Inc., (1989), pp. 604-614).

10. Among the compound of the present invention represented by formula (I), a compound in which D represents —$COOR^2$, —$COOR^9$ or —COO—$Z^1$—$Z^2$—$Z^3$—, i.e., a compound represented by formula (IJ):

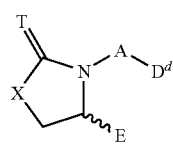

(IJ)

(wherein $D^d$ is —$COOR^2$, —$COOR^9$ or —COO—$Z^1$—$Z^2$—$Z^3$—, and other symbols have the same meanings as described above.) can be prepared by the following method.

The compounds represented by formula (IJ) can be prepared esterifying the compounds of formula (X):

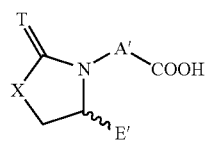

(X)

(wherein all symbols have the same meanings as defined above.) with the compound of formula (XV-1):

$R^{19}$—$R^2$      (XV-1)

(wherein $R^{19}$ is hydroxy or halogen atom, and other symbols have the same meanings as defined above.), the compounds of formula (XV-2):

$R^{19}$—$R^9$      (XV-2)

(wherein all symbols have the same meanings as defined above.) or the compounds of formula (XV-3):

$R^{19}$—$Z^{1a}$—$Z^{2a}$—$Z^{3a}$      (XV-3)

(wherein $Z^{1a}$, $Z^{2a}$ and $Z^{3a}$ are $Z^1$, $Z^2$ and $Z^3$, respectively. With the proviso that, hydroxy, amino, carboxy or formyl in the groups represented by $Z^{1a}$—$Z^{2a}$—$Z^{3a}$ may be protected, if necessary.) if necessary, followed by removal of the protective group.

The esterification with the compound of formulae (XI-1), (XI-2) and (XI-3) in which $R^{17}$ is hydroxyl may be effected in the same manner as above.

The esterification with the compound of formulae (XI-1), (XI-2) and (XI-3) in which $R^{17}$ is halogen may be carried out, for example, in an organic solvent (e.g., dimethylformamide, tetrahydrofuran, dioxane, diethyl ether, dimethylacetamide), in the presence of a base (e.g., potassium carbonate, cesium carbonate, sodium carbonate, potassium hydrogencarbonate, sodium hydrogencarbonate, potassium hydroxide, sodium hydroxide) at 0 to 150° C.

The removal of the protective group may be carried out by the methods described above.

The compounds represented by formulae (II), (III), (IV), (V), (VI), (VIII), (XI-1), (XI-2), (XI-3), (XI-4), (XIII-1), (XIII-2), (XV-1), (XV-2) and (XV-3) are known compounds or can be prepared by known methods.

For example the compounds of formulae (VI) and (VII) can be prepared by the method described in reaction scheme 1.

Reaction scheme 1

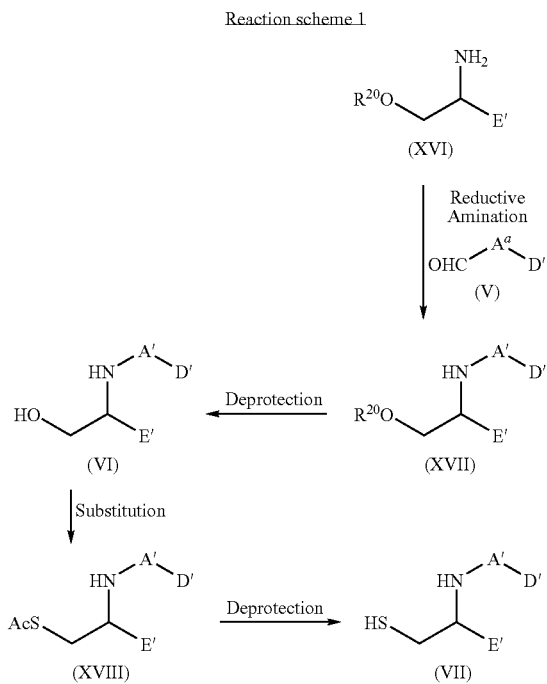

In the reaction scheme 1, $R^{20}$ represents the protecting group of hydroxy, Ac represents an acetyl group, and other symbols have the same meanings as defined above.

In the reaction scheme 1, the compound of formula (XVI) used as the starting material is known compound or can be prepared easily by known methods.

11. Among the compounds represented by formula (I), a compound in which T is oxygen atom, E is $E^2$, $E^2$ is $U^1$—$U^2$—$U^3$, $U^1$ is methylene and $U^2$ is —NH—, i.e., a compound (IK):

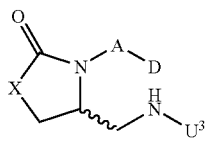

(IK)

(wherein all symbols have the same meanings as defined above.) can be prepared by the following method.

The compounds represented by formula (IK) can be prepared by reductive amination of the compounds of formula (XIX):

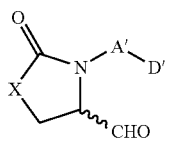

(XIX)

(wherein all symbols have the same meanings as defined above.) and the compounds of formula (XX):

$$H_2N—U^{3'} \qquad (XX)$$

(wherein $U^{3'}$ has the same meaning as $U^3$. With the proviso that, hydroxyl, amino, carboxyl or formyl in the group represented by $U^3$ may be protected, if necessary. Other symbols have the same meanings as defined above.), if necessary, followed by removal of the protecting group.

The reductive amination and the removal of the protective group may be carried out by the methods described above.

12. Among the compounds represented by formula (I), a compound in which T is oxygen atom, A is $A^2$, $A^2$ is $G^1$-$G^2$-$G^3$, $G^1$ is C1-4 alkylene, $G^2$ is —Y—, —Y-ring1- or —Y—C1-4 alkylene-ring1-, Y is —S—, E is $E^2$, $E^2$ is $U^1$—$U^2$—$U^3$, $U^1$ is methylene, and $U^2$—O—, i.e. a compound represented by formula (IL):

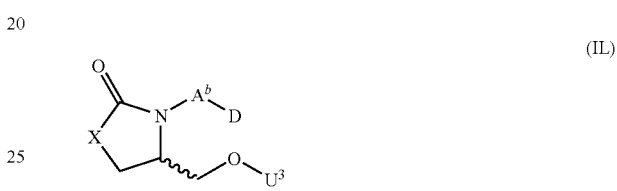

(IL)

(wherein $A^b$ is -$G^{1a}$-$G^{2a}$-$G^3$-, $G^{1a}$ is C1-4 straight-chain alkylene, $G^{2a}$ is —S—, —S-ring1- or —S—C1-4 alkylene-ring1-, and other symbols have the same meanings as defined above) can be prepared by the following method.

The compounds represented formula (IL) can be prepared by reacting the compound of formula (XXI):

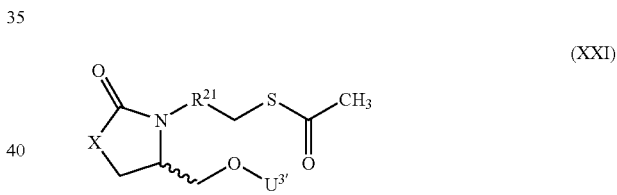

(XXI)

(wherein $R^{21}$ is C1-3 alkylene, and other symbols have the same meanings as defined above.) with the compounds of formula (XXII):

$$R^{22}—R^{23}-G^3-D' \qquad (XXII)$$

(wherein $R^{22}$ is halogen atoms, $R^{23}$ is bond, -ring1- or —C1-4 alkylene-ring1-. With the proviso that, hydroxy, amino, carboxy or formyl in the group represented by $R^{23}$ may be protected, if necessary. Other symbols have the same meanings as defined above.), if necessary, followed by removal of the protecting group.

The reaction is known. For example, it may be carried out in an organic solvent (e.g., ethanol, methanol, tetrahydrofuran, dichloromethane, dimethylformamide) using a base (e.g., sodium hydroxide, potassium hydroxide, sodium carbonate, sodium methylate, diethylamine) at 0 to 40° C.

The removal of the protective group may be carried out by the methods described above.

The compounds represented by formulae (XX) and (XXII) are known compounds or can be prepared by known methods readily.

The compounds of formulae (XIX) and (XXI) can be prepared by the method described in the reaction scheme 2, 3 and 4.

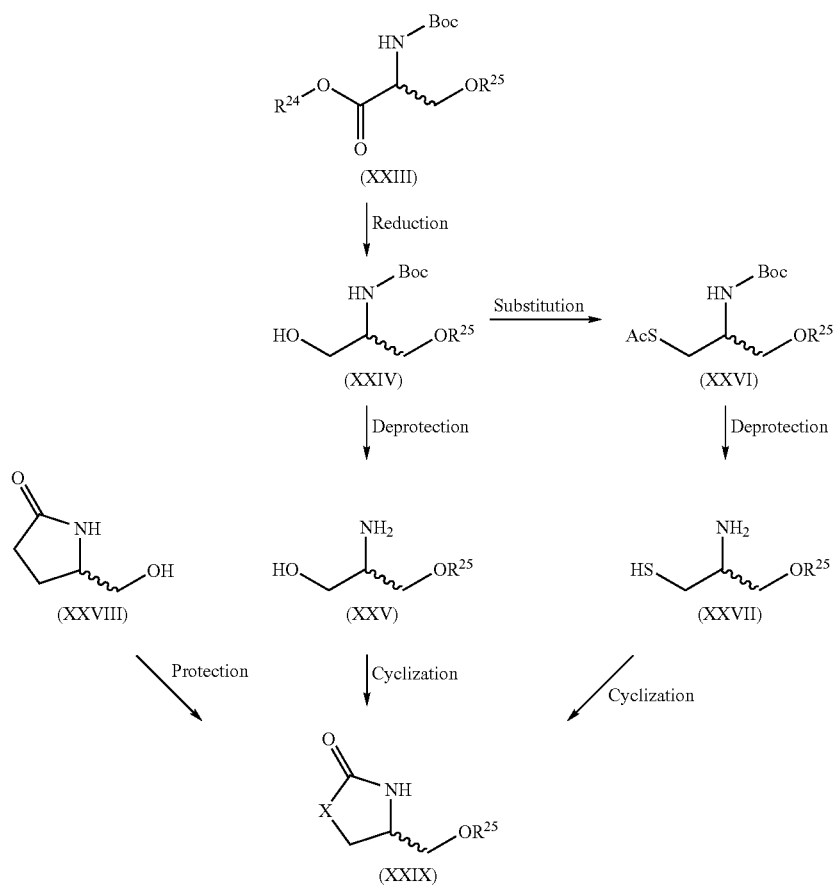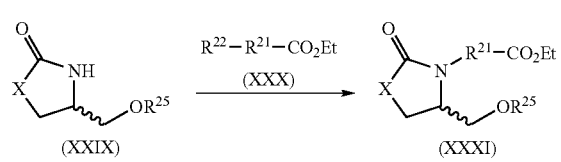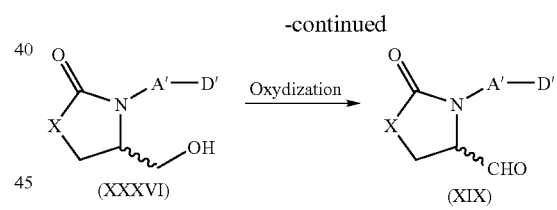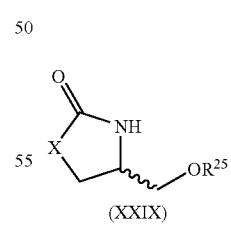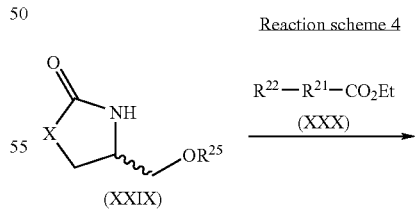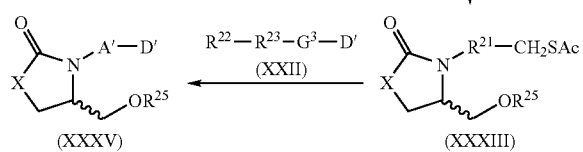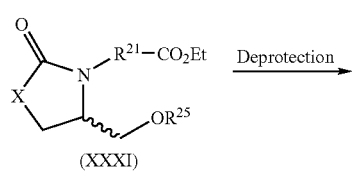

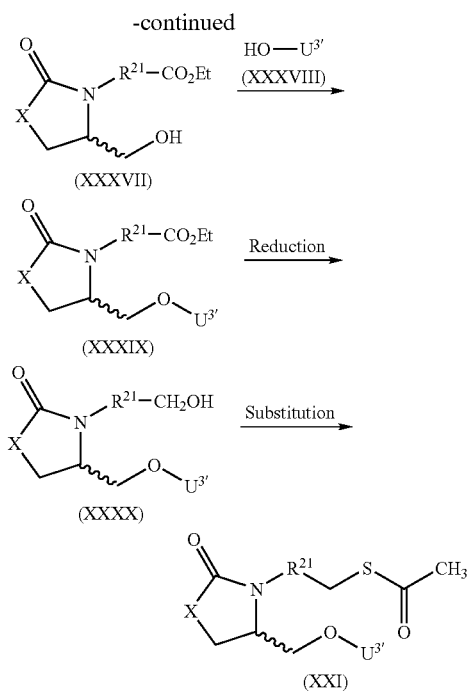

In the reaction scheme 2, 3 and 4, $R^{24}$ represents a hydrogen atom or

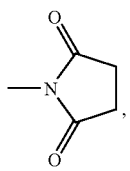

$R^{25}$ is the protecting group of hydroxy, Et is ethyl, Boc is t-butoxycarbonyl, and other symbols have the same meanings as defined above.

In the reaction schemes 2, 3 and 4, the compound of formula (XXIII) used as the starting materials and the compounds of formulae (XXX), (XXXIV) and (XXXVIII) are known compounds or can be prepared easily by known methods.

In each reaction described herein, the reaction product can be purified by general purification techniques such as distillation under ordinary pressure or a reduced pressure, high performance liquid chromatography, thin layer chromatography or column chromatography using silica gel or magnesium silicate, washing and recrystallization. Purification may be carried out in each reaction or after completion of several reactions.

Pharmacological Activity of the Compounds of the Invention:

For example, the pharmacological activities of the compounds of the invention were confirmed in experiments performed in a laboratory using the cells which express prostanoid receptor sub-types.

(i) Experiment for receptor-binding using cells which express prostanoid receptor sub-types According to the method of Sugimoto et al. (*J. Biol. Chem.,* 267, 6463-6466 (1992)), CHO cells which expressed prostanoid receptor sub-types (murine $EP_1$, $EP_2$, $EP_{3\alpha}$, and $EP_4$, respectively) were prepared and used as membrane authentic samples.

A reaction solution (200 μl) containing the prepared membrane fraction (0.5 mg/ml) and $^3H$-$PGE_2$ was incubated at room temperature for 1 hour. The reaction was terminated with ice cold buffer (3 ml), and the reaction mixture was filtered under suction through a glass filter (GF/B), on which the binding $^3H$-$PGE_2$ was trapped, and the binding radioactivity was measured by means of a liquid scintillator.

The Kd value was obtained from the Scatchard plots [*Ann. N.Y. Acad. Sci.,* 51, 660 (1949)]. Non-specific binding was obtained as the binding in the presence of an excess amount (2.5 μM) of unlabelled $PGE_2$. Measurement of the binding inhibition for $^3H$-$PGE_2$ with the compounds of the present invention was performed by adding $^3H$-$PGE_2$ (2.5 nM) and a series of concentrations of the compound of the present invention. In this reaction, the following buffer was used in all cases.

Buffer: 10 mM potassium phosphate (pH 6.0), 1 mM EDTA, 10 mM $MgCl_2$, and 0.1M NaCl.

Dissociation constant Ki (μM) of each compound was calculated from the following equation.

$$Ki = IC_{50}/(1+([\alpha]/Kd))$$

$IC_{50}$ The concentration of the compound of the present invention which inhibits half of the specific binding of $[^3H]PGE_2$
C: The concentration of $[^3H]PGE_2$
Kd: The dissociation constant of $[^3H]PGE_2$ The binding activity (Ki) of the compound prepared in Example 4(1) to the mouse $EP_2$ receptor was 14 nM.

Toxicity:

The toxicity of the compounds of the present invention represented by formula (I) is very low and therefore the compounds may be considered safe for pharmaceutical use.

INDUSTRIAL APPLICABILITY

Application to Pharmaceutical Preparations:

The compounds of the present invention bind to $EP_2$ subtype of PGE receptor specifically and strongly and it is considered that they are related to inhibition of TNF-α production and enhancement of IL-10 production. Therefore it is considered that the compounds which bind to $EP_2$ receptor are useful for prevention and/or treatment of immune diseases (e.g., autoimmune diseases such as amyotrophic lateral sclerosis (ALS), multiple sclerosis, Sjogren's syndrome, rheumatoid arthritis and systemic lupus erythematosus etc., and rejection after organ transplantation), allergic diseases (e.g., asthma, allergic rhinitis, allergic conjunctivitis, atopic dermatitis, food allergy), neuronal cell death, dysmenorrhea, premature birth, abortion, baldness, retinal neuropathy such as glaucoma, erectile dysfunction, arthritis, pulmonary injury, pulmonary fibrosis, pulmonary emphysema, bronchitis, chronic obstructive pulmonary disease, hepatic injury, acute hepatitis, liver cirrhosis, shock, nephritis (acute nephritis, chronic nephritis), renal failure, circulatory diseases (e.g., hypertension, myocardial ischemia, chronic arterial obstruction, vibration disease), systemic inflammatory response syndrome, sepsis, hemophagocytosis syndrome, macrophage activation syndrome, still disease, Kawasaki Disease, burn, systemic granuloma, ulcerative colitis, Crohn disease, hypercytokinemia at dialysis, multiple organ failure, and bone diseases (e.g., fracture, refracture, intractable fracture, nonunion, pseudarthrosis, osteomalacia, Paget's disease of bone, ankylosing spondylitis, bone metastasis, osteoarthritis and destruction of bone/cartilage due to these analogous diseases) etc. It is also considered that the compounds are useful as an agent for accelerating the osteogenesis/cure after bone surgery (e.g., fracture, bone graft, artificial arthrogenesis, spinal fusion, surgery for multiple myeloma, lung cancer, breast cancer, etc., other bone repair) or substitute treatment for bone grafting. It is further considered that the compounds are useful agents for accelerating the regeneration of peridontium in periodontal disease etc.

Among the compounds represented by formula (I) are those which bind to $EP_4$ receptor as well as $EP_2$ receptor. It is considered that the compounds which bind to $EP_4$ receptor are useful for prevention and/or treatment of immune diseases (e.g., autoimmune diseases such as amyotrophic lateral sclerosis (ALS), multiple sclerosis, Sjogren's syndrome, rheumatoid arthritis and systemic lupus erythematosus etc., and rejection after organ transplantation), asthma, neuronal cell death, arthritis, pulmonary injury, pulmonary fibrosis, pulmonary emphysema, bronchitis, chronic obstructive pulmonary disease, hepatic injury, acute hepatitis, nephritis (acute nephritis, chronic nephritis), renal failure, hypertension, myocardial ischemia, systemic inflammatory response syndrome, sepsis, hemophagocytosis syndrome, macrophage activation syndrome, still disease, Kawasaki Disease, burn, systemic granuloma, ulcerative colitis, Crohn disease, hypercytokinemia at dialysis, multiple organ failure and shock etc. $EP_4$ receptor also takes part in mucous membrane protective action and thus is considered useful for prevention and/or treatment of digestive tract ulcer such as gastric ulcer and duodenal ulcer and stomatitis. $EP_4$ receptor further takes part in trichogenous action and hair growing action and is considered useful for prevention and/or treatment of baldness and alopecia etc. Moreover, $EP_4$ receptor takes part in maturation of cervical canal and thus is considered useful as a cervical canal maturing agent.

Furthermore, the compound bound to $EP_4$ receptor has an osteogenesis accelerating action and thus is considered not only useful for prevention and/or treatment of bone diseases in which the amount of bone is decreased, e.g., 1) primary osteoporosis due to, e.g., aging, menopause, overietomy, 2) secondary osteoporosis (e.g., glucocorticoid-induced osteoporosis, hyperhyroidismic osteoporosis, fixed induced osteoporosis, heparin-induced osteoporosis, immunosuppression-induced osteoporosis, osteoporosis due to renal insufficiency, inflammatory osteoporosis, osteoporosis due to Cushing's syndrome, rheumatic osteoporosis), 3) bone diseases such as transfer of cancer to bone, hypercalcemia, Behcet's disease, bone deficiency (e.g., alveolar bone deficiency, mandible deficiency, infantile idiopathic bone deficiency) and osteonecrosis but also useful as a agent for accelerating the osteogenesis/treatment after bone surgery (e.g., fracture, bone graft, artificial arthrogenesis, spinal fusion, other bone repair) or substitute for bone transfer.

Moreover, $EP_4$ acts to induce physiologic sleep and inhibit platelet aggregation and the compound bound to $EP_4$ receptor is considered useful for prevention of somnipathy and thrombosis.

The compound connected both to $EP_2$ receptor and $EP_4$ receptor can be expected to exert an additive or synergistic effect on diseases related to both the receptors.

The compound represented by formula (I) or pharmaceutically acceptable salt thereof may be administered in combination with other pharmaceutical preparations to accomplish the following purposes:
1) To complement for and/or enhance the preventive and/or treatment effect of the compound to be combined;
2) To improve the kinetics/absorption of the compound to be combined and reduce the dose of the compound; and/or
3) To eliminate the side effect of the compound to be combined The compound represented by formula (I) and other pharmaceutical preparations may be administered in the form of formulation having these components incorporated in one preparation or may be administered in separate preparations. In the case where these pharmaceutical preparations are administered in separate preparations, they may be administered simultaneously or at different times. In the latter case, the compound represented by formula (I) may be administered before the other pharmaceutical preparations. Alternatively, the other pharmaceutical preparations may be administered before the compound represented by formula (I). The method for the administration of these pharmaceutical preparations may be the same or different.

The diseases on which the preventive and/or treatment effect of the aforementioned combined preparations works are not specifically limited but may be those for which the preventive and/or treatment effect of the compound represented by formula (I) is complemented and/or enhanced.

Examples of the other pharmaceutical preparations for complementing and/or enhancing the preventive and/or treatment effect of the compound represented by formula (I) on bone diseases include, for example, phosphodiesterases-4 inhibitor, bisphosphonate preparation, vitamin D preparation, calcium adjuvant, estrogen preparation, calcitonin preparation, isoflavone-based preparation, anabolic steroid preparation, vitamin K preparation, cathepsin K inhibitor, prostaglandins, statin, parathyroid hormone, and growth factors etc.

Examples of the other pharmaceutical preparations for complementing and/or enhancing the preventive and/or treatment effect of the compound represented by formula (I) on chronic obstructive lung diseases and/or asthma include, for example, phosphodiesterases-4 inhibitor, steroids, β adrenoreceptor stimulant, leukotriene receptor antagonist, thromboxane synthesis enzyme inhibitor, thromboxane $A_2$ receptor antagonist, mediator release inhibitor, antihistamines, xanthine derivatives, anticholinergic preparation, cytokine inhibitor, prostaglandins, forskolin preparation, elastase inhibitor, metaprotease inhibitor, expectorant, and antibiotic etc.

Examples of the other pharmaceutical preparations for complementing and/or enhancing the preventive and/or treatment effect of the compound represented by formula (I) on dysmenorrhea include, for example, analgesic (nonsteroidal anti-inflammatory drug (NSAID), cyclooxygenase (COX) inhibitor etc.), oral contraceptive, hormone preparation, antispasmodic, β adrenoreceptor stimulant, Vasopressin V1a antagonist, prostaglandin synthetase inhibitor, local anesthetic, calcium channel blocker, potassium channel blocker, leukotriene receptor antagonist, smooth muscle relaxant, vasodilator etc.

Examples of the other pharmaceutical preparations for complementing and/or enhancing the preventive and/or treatment effect of the compound represented by formula (I) on arthritis or rheumatoid arthritis include, for example, metaprotease inhibitor, immunosuppressant, nonsteroidal anti-inflammatory drug (NSAID), steroids, phosphodiesterases-4 inhibitor etc.

Examples of the other pharmaceutical preparations for complementing and/or enhancing the preventive and/or treatment effect of the compound represented by formula (I) on erectile dysfunction include, for example, phosphodiesterases-5 inhibitor etc.

Examples of the other pharmaceutical preparations for complementing and/or enhancing the preventive and/or treatment effect of the compound represented by formula (I) on shock include, for example, elastase inhibitor etc.

Examples of the other pharmaceutical preparations for complementing and/or enhancing the preventive and/or treatment effect of the compound represented by formula (I) on colitis include, for example, nitric oxide synthase inhibitor, poly(ADP-ribose)polymerase, phosphodiesterases-4 inhibitor, elastase inhibitor, interleukin 8 antagonist etc.

Examples of the other pharmaceutical preparations for complementing and/or enhancing the preventive and/or treatment effect of the compound represented by formula (I) on acute nephritis and chronic nephritis include, for example, steroids, phosphodiesterases-4 inhibitor, nonsteroidal anti-inflammatory drug, thromboxane $A_2$ receptor antagonist, leukotriene receptor antagonist, angiotensin 11 antagonist, angiotensin converting enzyme inhibitor, diuretic etc.

Examples of the other pharmaceutical preparations for complementing and/or enhancing the preventive and/or treatment effect of the compound represented by formula (I) on hypertension include, for example, calcium channel blocker, angiotensin II antagonist, angiotensin converting enzyme inhibitor, phosphodiesterases-4 inhibitor, diuretic etc.

Examples of the phosphodiesterases-4 inhibitor include, for example, rolipram, cilomilast (trade name: Ariflo), Bay 19-8004, NIK-616, cilomilast (BY-217), cipamfylline (BGL-61063), atizolam (CP-80633), SCH-351591, YM-976, V-11294A, PD-168787, D-4386, and IC-485 etc.

Examples of the phosphodiesterases-5 inhibitor include, for example, sildenafil etc.

Examples of the bisphonate preparation include, for example, sodium alendronate, disodium chlodronate, disodium pamidronate, disodium ethydronate, ivandronate, disodium incadronate, minodronate, olpadronate, sodium risedronate, tildronate, and zoledronate etc.

Examples of the calcitonin preparation include, for example, calcitonin, and elcatonin etc.

Examples of the prostaglandins (hereinafter abbreviated as "PG") include PG receptor agonist, and PG receptor antagonist.

Examples of PG receptor include PGE receptors ($EP_1$, $EP_2$, $EP_3$, $EP_4$), PGD receptors (DP), PGF receptors (FP), and PGI receptors (IP) etc.

Examples of the steroids for external application include, for example, clobetasol propionate, diflorasone acetate, fluocinonide, mometasone furoate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclomethasone dipropionate, triamcinolone acetonide, flumethasone pivalate, alclometasone dipropionate, clobetasone butyrate, beclomethasone propionate and fludroxycortide etc.

Examples of the steroid preparation for internal use or injection include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methyl prednisolone, methyl prednisolone acetate, methyl prednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, and betamethasone etc.

Examples of the steroid preparation as an inhalant include beclomethasone propionate, fluticasone propionate, budesonide, flunisolide, triamcinolone, ST-126P, ciclesonide, dexamethasone palmitate, mometasone furoate, prasterone sulfate, deflazacort, methyl prednisolone sreptanate, and methylprednisolone sodium succinate etc.

Examples of the β adrenoreceptor stimulant include, for example, fenoterol hydrobromide, salbutamol sulfate, terbutaline sulfate, formoterol fumarate, salmeterol xinafoate, isoproterenol sulfate, orciprenaline sulfate, clorprenaline sulfate, epinephrine, trimetoquinol hydrochloride, hexoprenaline sulfate, procaterol hydrochloride, tulobuterol hydrochloride, tulobuterol, pirbuterol hydrochloride, clenbuterol hydrochloride, mabuterol hydrochloride, ritodrine hydrochloride, bambuterol, dopexamin hydrochloride, meluadrine tartrate, AR-C68397, levosalbutamol, R,R-formoterol, isoxsuprine, metaproterenol, KUR-1246, KUL-7211, AR-C89855, and S-1319 etc.

Examples of the leukotriene receptor antagonist include, for example, pranlukast hydrate, montelukast, zafirlukast, seratrodast, MCC-847, KCA-757, CD-615, YM-158, L-740515, CP-195494, LM-1484, RS-635, A-93178, S-36496, BIIL-284, and ONO-4057 etc.

Examples of the thromboxane synthesis enzyme inhibitor include, for example, ozagrel hydrochloride, and imitrodast sodium etc.

Examples of the thromboxane $A_2$ receptor antagonist include, for example, seratrodast, ramatroban, domitroban calcium dihydrate, and KT-2-962 etc.

Examples of the mediator release inhibitor include, for example, tranilast, sodium cromoglicate, anlexanox, repirinast, ibudilast, tazanolast, and pemirolast potassium.

Examples of the antihistamines include ketotifen fumarate, mequitazine, azelastine hydrochloride, oxatomide, terfenadine, emedastine difumarate, epinastine hydrochloride, astemizole, ebastine, cetirizine hydrochloride, bepotastine, fexofenadine, loratadine, desloratadine, olopatadine hydrochloride, TAK-427, ZCR-2060, NIP-530, mometasone furoate, mizolastine, BP-294, andolast, auranofin, and acribastin etc.

Examples of the xanthine derivatives include, for example, aminophylline, theophylline, doxophylline, cipamphylline, and diprophylline etc.

Examples of the anticholinergic preparation include, for example, ipratropium bromide, oxitropium bromide, flutropium bromide, cimetropium bromide, temiverine, tiotropium bromide and revatropate (UK-112166) etc.

Examples of the cytokine inhibitor include, for example, suplatast tosilate (trade name: IPD) etc.

Examples of the expectorant include, for example, foeniculated ammonia spirit, sodium hydrogen carbonate, bromhexine hydrochloride, carbocisteine, ambroxol hydrochloride, ambroxol hydrochloride sustained release capsule, methylcysteine hydrochloride, acetyl cysteine, ethyl L-cysteine hydrochloride and tyloxapol etc.

Examples of the growth factors include, for example, fibroblast growth factor (FGF), vascular endothelial growth factor (VEGF), hepatocyte growth factor (HGF) and insulin-like growth factor etc.

Examples of the nonsteroid-based antiphlogistic include, for example, sasapyrine, sodium salicylate, aspirin, aspirin dialuminate formulation, diflunisal, indomethacin, suprofen, ufenamate, dimethyl isopropylazulene, bufexamac, felbinac, diclofenac, tolmetin sodium, clinoril, fenbufen, napmetone, proglumetacin, indometacin farnesil, acemetacin, proglumetacin maleate, amfenac sodium, mofezolac, etodolac, ibuprofen, ibuprofen piconol, naproxen, flurbiprofen, flurbiprofen axetil, ketoprofen, fenoprofen calcium, tiaprofen, oxaprozin, pranoprofen, loxoprofen sodium, alminoprofen, zaltoprofen, mefenamic acid, aluminum mefenamate, tolfenamic acid, floctafenine, ketophenylbutazone, Oxyphenbutazone, piroxicam, tenoxicam, ampiroxicam, napageln ointment, epirizole, tiaramide hydrochloride, tinoridine hydrochloride, emorfazone, sulpyrine, migrenin, saridon, sedes G, amipylo N, bisolvon, pyrine system antipyretics, acetaminophen, phenacetin, dimethothiazine mesylate, simetride formulation, antipyrine system antipyretics, bromfenac, fenamate, sulindac, nabumetone and ketorolac etc.

Examples of the COX inhibitor include, for example, celecoxib, rofecoxib and etoricoxib etc.

Examples of the antispasmodic include, for example, scopolamine etc.

Examples of the Vasopressin V1a antagonist include, for example, relcovaptan etc.

Examples of the prostaglandin synthetase inhibitor include, for example, salazosulfapyridine, mesalazine, osalazine, 4-amino salicylic acid, JTE-522, auranofin, carprofen, diphenpyramide, flunoxaprofen, flurbiprofen, indometacin, Ketoprofen, lornoxicam, loxoprofen, meloxicam, oxaprozin, parsalmide, piproxen, piroxicam, piroxicam-β-cyclodextrin, piroxicam cinnamate, tropine indometacinate, zaltoprofen, pranoprofen, touki-syakuyaku-san and syakuyaku-kanzou-tou etc.

Examples of the local anesthetic include, for example, cocaine hydrochloride, procaine hydrochloride, lidocaine, dibucaine hydrochloride, tetracaine hydrochloride, mepivacaine, etidocaine, bupivacaine and 2-chloro butylcaine hydrochloride etc.

Examples of the calcium channel blocker include, for example, nifedipine, benidipine hydrochloride, diltiazem hydrochloride, verapamil hydrochloride, nisoldipine, nitrendipine, bepridil hydrochloride, amlodipine besilate, lomerizine hydrochloride, isradipine, nimodipine, felodipine and nicardipine etc.

Examples of the potassium channel blocker include, for example, dofetilide, E-4031, almokalant, sematilide, ambasilide, azimilide, tedisamil, RP5886, sotalol, piroxicam and ibutilide etc.

Examples of the vasodilator include, for example, nitroglycerin, isosorbide dinitrate and isosorbide mononitrate etc.

Examples of the diuretic include, for example, mannitol, furosemide, acetazolamide, diclofenamide, methazolamide, trichlormethazide, mefruside, spironolactone and aminophylline etc.

The weight proportion of the compound represented by formula (I) and the other pharmaceutical preparations is not specifically limited.

Arbitrary two or more of the other pharmaceutical preparations may be administered in combination.

Examples of the other pharmaceutical preparations for complementing and/or enhancing the preventive and/or treatment effect of the compound represented by formula (I) include not only those which have so far been found but also those which will be found on the basis of the aforementioned mechanism.

In order to use the compound of the present invention represented by formula (I) or the compound represented by formula (I) in combination with the other pharmaceutical preparations, these compounds are normally administered to the entire or local part of human body orally or parenterally.

The doses to be administered are determined depending upon, for example, age, body weight, symptom, the desired therapeutic effect, the route of administration, and the duration of the treatment. In the human adult, the doses per person are generally from 1 ng to 100 mg, by oral administration, up to several times per day, and from 0.1 ng to 10 mg, by parenteral administration, up to several times per day, or continuous administration from 1 to 24 hours per day from vein.

As mentioned above, the doses to be used depend upon various conditions. Therefore, there are cases in which doses lower than or greater than the ranges specified above may be used.

The compound represented by formula (I) of the present invention, or concomitant drug combined the compound represented by formula (I) with other drugs may be administered in the composition of, for example, solid compositions or liquid compositions, each for oral administration, or injections, external use, suppositories, eye drops or inhalat, each for parenteral administration.

Solid compositions for oral administration include compressed tablets, pills, capsules, dispersible powders and granules. Capsules include hard capsules and soft capsules.

In such solid forms, one or more of the active compound(s) may be admixed with vehicles (such as lactose, mannitol, glucose, microcrystalline cellulose, starch), binders (such as hydroxypropyl cellulose, polyvinylpyrrolidone or magnesium metasilicate aluminate), disintegrants (such as cellulose calcium glycolate), lubricants (such as magnesium stearate), stabilizing agents, and solution adjuvants (such as glutamic acid or aspartic acid) and prepared according to methods well known in normal pharmaceutical practice. The solid forms may, if desired, be coated with coating agents (such as sugar, gelatin, hydroxypropyl cellulose or hydroxypropylmethyl cellulose phthalate), or be coated with two or more films. And further, coating may include containment within capsules of absorbable materials such as gelatin.

Liquid forms for oral administration include pharmaceutically acceptable solutions, suspensions and emulsions, syrups and elixirs. In such forms, one or more of the active compound(s) may be dissolved, suspended or emulsified into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent.

In the parenteral administration, formulation of external use include, for example, ointment, gel, cream, poultice, patch, liniment, atomized agent, inhalation, spray, aerosol, eye drops and nasal drops, etc. They includes one or more of the active compound(s) and be prepared by known method or usual method.

Ointment is prepared by known method or usual method. For example, it is prepared by levigation or fusion of one or more of the active compound(s) and substrate. The substrate of ointment is selected from known or usual one. For example, higher fatty acid or higher fatty acid ester (adipic acid, myristic acid, palmitic acid, stearic acid, oleic acid, adipic acid ester, myristic acid ester, palmitic acid ester, stearic acid ester, oleic acid ester, etc.), wax (yellow beeswax, Spermaceti, ceresin, etc.), surfactant (polyoxyethylene alkyl ether phosphoric acid ester, etc.), higher alcohol (cetanol, stearil alcohol, cetostearyl alcohol, etc.), silicon oil (dimethyl polysiloxane, etc.), hydrocarbon (hydrophilic petrolatum, white petrolatum, purified lanolin, light liquid paraffin, etc.), glycol (ethylene glycol, diethylene glycol, propylene glycol, polyethylene glycol, macrogol, etc.), vegetable oil (castor oil, olive oil, sesame oil, turpentine oil, etc.), animal oil (mink oil, egg yolk oil, squalane, squalene, etc.), water, absorption accelerator, skin fit inhibitor, etc. are used as single substance selected from them or mixture which consists of two or more kinds that is selected from them. Moreover, humectant, preservative agent, stabilizer, antioxidative agent, fragrant materials, etc. may be contained.

Gel is prepared by known method or usual method. For example, it is prepared by fusion of one or more of the active compound(s) and substrate. The substrate of gel is selected from known or usual one. For example, lower alcohol (ethanol, isopropylalcohol, etc.), gelling agent (carboxy methyl cellulose, hydroxy ethyl cellulose, hydroxy propyl cellulose, ethyl cellulose, etc.), neutralizing agent, (triethanolamine, diisopropanolamine, etc.), surfactant, (polyethylene glycol monostearate, etc.), gum, water, absorption accelerator, skin fit inhibitor, etc. are used as single substance selected from them or mixture which consists of two or more kinds that is selected from them. Moreover, preservative agent, antioxidative agent, fragrant materials, etc. may be contained.

Cream is prepared by known method or usual method. For example, it is prepared by fusion or emulsification of one or more of the active compound(s) and substrate. The substrate of cream is selected from known or usual one. For example, higher fatty acid ester, lower alcohol, hydrocarbon, polyalcohol (propylene glycol, 1,3-butylene glycol, etc.), higher alcohol (2-hexyldecanol, cetanol, etc.), emulsifying agent (polyoxyethylene alkyl ether, fatty acid ester, etc.), water, absorption accelerator, skin fit inhibitor, etc. are used as single substance selected from them or mixture which consists of two or more kinds that is selected from them. Moreover, preservative agent, antioxidative agent, fragrant materials, etc. may be contained.

Poultice is prepared by known method or usual method. For example, it is prepared by fusion of one or more of the active compound(s) and substrate, and then the kneaded one is laid over support medium. The substrate for poultice is selected from known or usual one. For example, thickening agent (polyacrylic acid, polyvinylpyrolidone, gum acacia, starch, gelatin, methyl cellulose, etc.), bulking agent (kaolin, zinc oxide, talc, calcium, magnesium, etc.), water, solubilizing agent, thickener, skin fit inhibitor, etc. are used as single substance selected from them or mixture which consists of two or more kinds that is selected from them. Moreover, preservative agent, antioxidative agent, fragrant materials, etc. may be contained.

Patch is prepared by known method or usual method. For example, it is prepared by fusion of one or more of the active compound(s) and substrate, and then laid over support medium. The substrate for patch is selected from known or usual one. For example, polymer substrate, fat, higher fatty acid, thickener, skin fit inhibitor, etc. are used as single substance selected from them or mixture which consists of two or more kinds that is selected from them. Moreover, preservative agent, antioxidative agent, fragrant materials, etc. may be contained.

Liniment is prepared by known method or usual method. For example, one or more of the active compound(s) may be dissolved, suspended or emulsified in water, alcohol (ethanol, polyethylene glycol, etc.), higher fatty acid, glycerin, soap, emulsifying agent, suspending agent, etc. as single substance selected from them or mixture which consists of two or more kinds that is selected from them. Moreover, preservative agent, antioxidative agent, fragrant materials, etc. may be contained.

Atomized agent, inhalation and spray may comprise in addition to a diluent, a stabilizer such as sodium bisulfite and an isotonization buffer such as sodium chloride, sodium citrate or citric acid. The preparation process of sprays is described in detail in, for example, U.S. Pat. Nos. 2,868,691 and 3,095,355.

Injections for parenteral administration include sterile aqueous, suspensions, emulsions and solid forms which are dissolved or suspended into solvent(s) for injection immediately before use. In injections, one or more of the active compound(s) may be dissolved, suspended or emulsified into solvent(s). The solvents may include distilled water for injection, physiological salt solution, vegetable oil, propylene glycol, polyethylene glycol, alcohol, e.g., ethanol, or a mixture thereof. Injections may comprise some additives, such as stabilizing agents, solution adjuvants (such as glutamic acid, aspartic acid or Polysolvate 80®), suspending agents, emulsifying agents, soothing agent, buffering agents, preservative.

They may be sterilized at a final step, or may be prepared by an aseptic manipulation. They may also be manufactured in the form of sterile solid forms, for example, freezedried products, which may be dissolved in sterile water or some other sterile diluent(s) for injection immediately before use.

The eye drops for parenteral administration may be in the form of liquid, suspension, emulsion or ointment or may be dissolved in a solvent in use.

These eye drops are prepared by any known method. For example, one or more active materials are dissolved, suspended or emulsified in a solvent. As such a solvent for eye drops there may be used sterilized purified water, physiological saline and other aqueous or nonaqueous solvents (e.g., vegetable oil), singly or in combination. The eye drops may comprise an isotonic agent (e.g., sodium chloride, concentrated glycerin), a buffering agent (e.g., sodium phosphate, sodium acetate), a surface active agent (e.g., Polysolvate 80 (trade name), polyoxyl stearate 40, polyoxyethylene-hardened castor oil), a stabilizer (sodium citrate, sodium edetate), a preservative (e.g., benzalconium chloride, Paraben), etc. properly selectively as necessary. The eye drops are sterilized at the final step or prepared by an aseptic manipulation. Alternatively, an aseptic solid agent such as freeze-dried product which has previously been prepared may be rendered aseptic or dissolved in an aseptic distilled water for injection or other solvent before use.

The dosage of inhalations for parenreral administration include aerosol, powders for inhalation or liquids for inhalation. The liquids for inhalation may be dissolved or suspended in water or the other appropriate solvent as needed.

Such inhalations are prepared in a known method.

For example, a liquid for inhalation is prepared by selecting proper additives from an antiseptic (such as benzalkonium chloride or p-aminobenzonic acid), a coloring agent, a buffering agent (such as sodium phosphate or sodium acetate), an isotonizing agent (such as sodium chloride or concentrated glycerin), thickening agent (such as carboxyvinylpolymer), or an accelerator of absorption, etc., if necessary.

A powder for inhalation is prepared by selecting proper additives from a lubricant agent (such as stearin acid and the salt thereof), a binding agent, (such as starch, dextrin), a diluting agent (such as lactose, cellulose), a coloring agent, an antiseptic (such as benzalkonium chloride or p-aminobenzonic acid), an accelerator of absorption, etc., if necessary.

In case of administration of liquid for inhalation, spray (atomizer, nebulizer) is usually used and in case of administration of powder for inhalation, inhalation administration apparatus for powder agents is usually used.

The other compositions for parenteral administration include suppositories for intrarectal administration and pessaries for vaginal administration which comprise one or more of the active substance(s) and may be prepared by methods known per se.

Local Application:

Referring to the local administration of the invention, the compound of the present invention may be locally administered to site of disease (particularly bone diseases in which the amount of bone is decreased). The form of the compound of present invention is not limited to its administration method. the compound of present invention may be in the form of injection, solid agent such as embedding agent, pellet and powder, and ointment to be administered to intramuscular, subcutaneous or articular site.

The extended-release preparation is not limited to its form so far as the compound of the present invention can be continuously administered to site of disease (particularly bone diseases in which the amount of bone is decreased). The extended-release preparation may be in the form of, e.g., extended-release injection (e.g., microcapsuled preparation, microspheric preparation, nanospheric preparation), embedding preparation (e.g., film-like preparation) or the like.

The microcapsuled preparation, microspheric preparation and nanospheric preparation of the present invention each are a finely divided pharmaceutical composition with an in vivo degradable polymer comprising as active components the compound represented by formula (I) optionally in combination with other pharmaceutical preparations.

Examples of the in vivo degradable polymer of the present invention include aliphatic acid ester polymers and copolymers thereof, polyacrylic acid esters, polyhydroxybutyric acids, polyalkylene oxalates, polyorthoesters, polycarbonates, and polyaminoacids. These compounds may be used singly or in admixture of two or more thereof. Examples of the aliphatic acid ester polymers and copolymers thereof include polylactic acid, polyglycolic acid, polycitric acid, polymalic acid, and lactic acid-glycolic acid copolymer. These compounds may be used singly or in admixture of two or more thereof. Besides these compounds, poly-α-cyanoacrylic acid esters, poly-β-hydroxybutyric acids, polytrimethyleneoxates, polyorthoesters, polyorthocarbonates, polyethylene carbonates, poly-γ-benzyl-L-glutamic acids and poly-L-alanines may be used singly or in admixture of two or more thereof. Among these compounds, preferred are polylactic acids, polyglycolic acids and lactic acid-glycolic acid copolymers, more preferably lactic acid-glycolic acid copolymers.

The average molecular weight of these in vivo degradable polymers to be used in the present invention is preferably from about 2,000 to 800,000, more preferably from about 5,000 to 200,000. For example, the polylactic acid preferably has a weight-average molecular weight of from about 5,000 to 100,000, more preferably from about 6,000 to 50,000. The polylactic acid can be synthesized according to any known preparation method per se. In the lactic acid-glycolic cid copolymer, the composition ratio of the lactic acid to the glycolic acid is preferably from about 100/0 to 50/50 (w/w), particularly from about 90/10 to 50/50. The weight-average molecular weight of the lactic acid-glycolic acid copolymer is preferably from about 5,000 to 100,000, more preferably from about 10,000 to 80,000. The lactic acid-glycolic acid copolymer can be synthesized according to any known preparation method per se.

The term "weight-average molecular weight" as used herein is meant to indicate molecular weight in polystyrene equivalence determined by gel permeation chromatography (GPC).

The aforementioned in vivo degradable polymer may be changed depending on the intensity of pharmacological activity of the compounds represented by formula (I) and the desired medicines to be released so far as the aforementioned aims of the present invention are accomplished. For example, the in vivo degradable polymer may be used in an amount of from about 0.2 to 10,000 times, preferably from about 1 to 1,000 times, more preferably from about 1 to 100 times (by weight) that of the physiologically active material.

Examples of the process for the preparation of microspheric, microcapsuled and nanospheric preparations include submerged drying method (e.g., o/w method, w/o/w method), phase separation method, spray drying method, granulation method by ulractritical fluid, and methods analogous thereto.

The submerged drying method (o/w method) and spray drying method will be further described hereinafter.

(1) In the submerged drying method (o/w method), a solution of an in vivo degradable polymer in an organic solvent is prepared at first. The organic solvent to be used in the preparation of the microspheric, microcapsuled and nanospheric preparations preferably has a boiling point of 120° C. or less. Examples of the organic solvent employable herein include halogenated hydrocarbons (e.g., dichloromethane, chloroform), aliphatic esters (e.g., ethyl acetate), ethers, aromatic hydrocarbons, and ketones (e.g., acetone). These compounds may be used in admixture of two or more at a proper ratio. Among these organic solvents, preferred are dichloromethane and acetonitrile, particularly dichloromethane. The concentration of the in vivo degradable polymer in the organic solution depends on the molecular weight of the in vivo degradable polymer, the kind of the organic solvent, etc. but is normally predetermined to be from about 0.01 to 80% (v/w), preferably from about 0.1 to 70% (v/w), more preferably from about 1 to 60% (v/w).

The compound represented by formula (I) is then added to and dissolved in the solution of the in vivo degradable polymer in an organic solvent thus obtained, optionally in combination with other pharmaceutical preparations. The amount of the compound represented by formula (I) to be added optionally in combination with the other pharmaceutical preparations depends on the kind of the pharmaceutical preparations to be added, the action of the pharmaceutical preparations in osteogenesis, the duration of the action, etc. but is normally from about 0.001% to 90% (w/w), preferably from about 0.01% to 80% (w/w), more preferably from about 0.3 to 30% (w/w) as calculated in terms of concentration in the solution of in vivo degradable polymer in an organic solvent.

Subsequently, the organic solution thus prepared is added to an aqueous phase which is then processed by an agitator, emulsifier or the like to form an o/w emulsion. The volume of the aqueous phase during this procedure is predetermined to be from about 1 to 10,000 times, preferably from about 2 to 5,000 times, particularly from about 5 to 2,000 times that of the oil phase. An emulsifier may be added to the aqueous phase which is an external phase. As such an emulsifier there may be normally used any material capable of forming a stable o/w emulsion. Examples of the emulsifier employable herein include anionic surface active agents, nonionic surface active agents, polyoxyethylene castor oil derivatives, polyvinyl pyrrolidone, polyvinyl alcohol, carboxymethyl cellulose, lecitine, and gelatin. These compounds may be used in proper combination. The concentration of the emulsifier in the external aqueous phase is preferably from about 0.001% to 20% (w/w), more preferably from about 0.01% to 10% (w/w), particularly from about 0.05% to 5% (w/w).

The evaporation of the solvent which is an oil phase can be accomplished by any commonly used method. In some detail, the evaporation of the solvent may be effected at ordinary pressure or gradually falling pressure with stirring by an agitator, magnetic stirrer or the like or may be effected while the pressure is being adjusted using a rotary evaporator. The microspheric preparation thus obtained is then fractionated by centrifugal separation or filtration. The microspheric preparation is washed with a surface active agent solution, alcohol or the like several times to remove the free compound represented by formula (I), optionally in combination with other pharmaceutical preparations, and the emulsifier from the surface thereof, again dispersed in distilled water or a dispersant containing a vehicle (e.g., mannitol, sorbitol, lactose), and then freeze-dried. In the aforementioned o/w method, the microspheric preparation may be prepared by a method involving the dispersion of the compound represented by formula (I) in a solvent of an in vivo degradable polymer in an organic solvent, optionally in combination with other pharmaceutical preparations, i.e., s/o/w method.

(2) In order to prepare the microspheric preparation by the spray drying method, an organic solvent or emulsion having the in vivo degradable polymer and the compound represented by formula (I), optionally in combination with other pharmaceutical preparations, dissolved therein is sprayed into the drying chamber of a spray dryer (spray dryer) through a nozzle so that the organic solvent or water in the atomized droplets is evaporated in an extremely short period of time to prepare a microspheric preparation. Examples of the nozzle employable herein include two liquid nozzle, pressure nozzle, and rotary disc. It is useful to spray an organic solvent or an aqueous solution of an aggregation inhibitor (e.g., mannitol, lactose, gelatin) at the same time with the spray of o/w emulsion as necessary for the purpose of inhibiting the aggregation of microspheres. The microspheric preparation thus obtained is then put under reduced pressure optionally under heating to remove water and solvent therefrom.

Examples of the film-like preparation include film-like material obtained by dissolving the aforementioned in vivo degradable polymer and compound represented by formula (I), optionally in combination with other pharmaceutical preparations, in an organic solvent, and then subjecting the solution to evaporation to dryness and gelled material obtained by dissolving the aforementioned in vivo degradable polymer and compound represented by formula (I), optionally in combination with other pharmaceutical preparations, in a proper solvent, and then adding a granulating agent (e.g., cellulose, polycarbonate) to the solution.

The microsphere, microcapsule and nanosphere of the present invention may be used as they are. Alternatively, a spherical, rod-like, acicular, pelletized, film-like or cream-like pharmaceutical composition may be processed as a starting material to provide preparations in various forms.

Furthermore, this preparation may be used as a parenteral for local administration (e.g., injection, solid agent such as embedding agent, pellet and powder, liquid agent such as suspension, ointment, etc. to be administered to intramuscular, subcutaneous, organic or articular site). For example, in order to make an injection from the microspheric preparation, the microspheric preparation is suspended with a dispersant, a preservative, an isotonic agent, a buffer, a pH adjustor, etc. to make an aqueous suspension as a practical preparation for injection. Alternatively, the microspheric preparation may be dispersed with a vegetable oil optionally in admixture with a phospholipid such as lecitine or with a middle-chain aliphatic acid triglyceride (e.g., Mygliol-812) to make an oil suspension as an injection which can be practically used.

The particle diameter of the microspheric preparation may be arbitrary so far as it suffices the desired dispersibility and passage through syringe if the preparation is used as a suspension for injection. By way of example, the average particle diameter of the microspheric preparation is from about 0.1 to 300 µm, preferably from about 1 to 150 µm, more preferably from about 2 to 100 µm. The pharmaceutical composition of the invention is preferably in the form of suspension as mentioned above. The pharmaceutical composition of the invention is also preferably in particulate form. This is because the pharmaceutical composition gives less excessive pain to patients when administered through a syringe for use in ordinary hypodermic or intramuscular injection. It is particularly preferred that the pharmaceutical composition of the invention be in the form of injection. Examples of the method for rendering the microspheric preparation aseptic include method which is aseptic throughout the entire steps, method involving sterilization by gamma rays, and method involving the addition of preservative. However, the invention is not limited to these methods.

The pharmaceutical composition of the invention can be used for the treatment of bone diseases in which the amount of bone is decreased because the compound represented by formula (I), optionally in combination with other pharmaceutical preparations, can be gradually released normally for 1 week to 3 months, though depending on the kind and added amount of the in vivo degradable polymer. Among these bone disease treatments, the treatment of fracture often requires that the affected part be fixed and covered with a plaster bandage and the administration of pharmaceutical preparations be conducted only once rather than frequently. Accordingly, the pharmaceutical preparations thus administered are required to accelerate treatment continuously. Thus, the pharmaceutical composition of the invention is useful particularly in this treatment.

The dose of the pharmaceutical composition of the present invention depends on the kind, content and form of the compound represented by formula (I), optionally in combination with other pharmaceutical preparations, the duration of release of pharmaceutical preparations, the animal to be administered, etc., but may be the effective amount of the compound represented by formula (I), optionally in combination with other pharmaceutical preparations. When administered to fracture as a microspheric preparation, for example, one time dose for adult (weight: 50 kg) is from about 0.001 mg to 500 mg, preferably from about 0.01 mg to 50 mg as calculated in terms of effective component. The pharmaceutical composition of the invention may be administered once 1 week to 3 months in the aforementioned amount.

BEST MODE FOR CARRYING OUT THE INVENTION

The present invention is explained below in detail based on Reference Examples and Examples, however, the present invention is not limited thereto.

The solvents in the parentheses show the developing or eluting solvents and the ratios of the solvents used are by volume in chromatographic separations or TLC.

The solvents in the parentheses in NMR show the solvents for measurement.

HPLC was carried out in measurement condition F.

THP is tetrahydropyran-2-yl and Boc is t-butoxycalbonyl.

When a compound includes two diastereomers, "more polar" represents a compound having less Rf value, and "less polar" represents a compound having more Rf value.

Name of the compounds in Example 1 to 10 were named according to IUPAC nomenclature system or popular name nomenclature system. Name of the compounds in Example 11 to 22 were named using ACD/Name Pro ver. 6.0 or according to IUPAC nomenclature system or popular name nomenclature system.

Reference Example 1

S-(2,2-diethoxyethyl)ethanethioate

Under an atmosphere of argon, 2-bromoacetaldehyde diethyl acetal (7.29 g) and potassium thioacetate (4.23 g) were mixed in dimethylformamide (20 mL) and the mixture was stirred at 50° C. for 5 hours. After cooling, water was added to the reaction solution, which was extracted by ethyl acetate-hexane mixed solvent. The organic layer was washed with water and brine, dried over anhydrous magnesium sulfate and concentrated to give the title compound (7.10 g) having the following physical data.
TLC: Rf 0.56 (n-hexane:ethyl acetate=9:1);
NMR (CDCl$_3$): δ 4.43 (t, J=5.4 Hz, 1H), 3.67-3.43 (m, 4H), 3.04 (d, J=5.4 Hz, 2H), 2.28 (s, 3H), 1.14 (t, J=7.2 Hz, 3H).

Reference Example 2

2-(2,2-diethoxyethylthio)thiazole-4-carboxylic acid ethyl ester

To a solution of the compound prepared in Reference Example 1 (1.76 g), 2-bromothiazole-4-carboxylic acid ethyl ester (1.80 g) and tributylphosphine (0.19 mL) in ethanol (10 mL) was added potassium carbonate (1.57 g) in ice bath and the mixture was stirred at room temperature overnight. Water was added to the reaction solution, which was extracted with ethyl acetate. The organic layer was washed with water and brine, dried over anhydrous magnesium sulfate and concentrated to give the title compound. The obtained compound was used in next reaction without purification.
TLC: Rf 0.40 (toluene:ethyl acetate=9:1);
NMR (CDCl$_3$): δ 8.02 (s, 1H), 4.77 (t, J=5.4 Hz, 1H), 4.39 (q, J=7.2 Hz, 2H), 3.79-3.54 (m, 4H), 3.47 (d, J=5.4 Hz, 2H), 1.39 (t, J=7.2 Hz, 3H), 1.22 (t, J=7.2 Hz, 6H).

Reference Example 3

2-(formylmethylthio)thiazole-4-carboxylic acid ethyl ester

The compound prepared in Reference Example 2 was dissolved in ethanol (15 mL) and 2N hydrochloric acid (5.7 mL) was added thereto. The mixture was stirred at 60° C. for 3 hours. After cooling, water was added to the reaction solution, which was extracted with ethyl acetate. The organic layer was washed with water and brine, dried over anhydrous magnesium sulfate and concentrated. The obtained residue was purified by column chromatography on silica gel (n-hexane:ethyl acetate=3:1) to give the title compound (714 mg) having the following physical data.
TLC: Rf 0.20 (n-hexane:ethyl acetate=4:1);
NMR (CDCl$_3$): δ 9.72 (t, J=2.1 Hz, 1H), 8.05 (s, 1H), 4.39 (q, J=6.9 Hz, 2H), 4.09 (d, J=2.1 Hz, 2H), 1.39 (t, J=6.9 Hz, 3H).

Reference Example 4

(1S)-1-(1-ethylcyclobutyl)-3-(1-phenyl-1H-tetrazol-5-ylthio)propan-1-ol

To a solution of (1S)-1-(1-ethylcyclobutyl)-propane-1,3-diol (8.90 g) in toluene (110 mL) were added tetrabutylammonium chloride (1.56 g) and a 2N aqueous sodium hydroxide solution (170 mL). At an inner temperature about 25° C., tosyl chloride (11.3 g) was added to the reaction solution, which was stirred at 25° C. for 1 hour. 1-Phenyl-1H-tetrazol-5-thiol (11.0 g) was added to the reaction solution, which was stirred at 60° C. for 1 hour. After cooling, water was added to the reaction solution, which was separated. The water layer was extracted with t-butyl methyl ether. The mixed organic layer was washed with water and brine, dried over anhydrous magnesium sulfate and concentrated to give the title compound (17.9 g) having the following physical data.
TLC: Rf 0.67 (n-hexane:ethyl acetate=1:1).

Reference Example 5

(1S)-1-(1-ethylcyclobutyl)-3-(1-phenyl-1H-tetrazol-5-ylsulfonyl)propan-1-ol

To a solution of the compound prepared in Reference Example 4 (17.9 g) in methanol (225 mL) was added a solution of potassium peroxymonosulfate (OXONE:brand name) (52.0 g) in water (225 mL) at room temperature and the mixture was stirred at 60° C. for 8 hours. After cooling, water was added to the reaction solution, which was extracted with ethyl acetate. The organic layer was washed with water and brine, dried over anhydrous magnesium sulfate and concentrated to give the title compound (19.7 g) having the following physical data. TLC: Rf 0.78 (n-hexane:ethyl acetate=1:1).

Reference Example 6

(1S)-1-(1-ethylcyclobutyl)-3-(1-phenyl-1H-tetrazol-5-ylsulfonyl)-1-(tetrahydropyran-2-yloxy)propane Under an atmosphere of argon, to a solution of the compound prepared in Reference Example 5 (19.7 g) and 2,3-dihydro-2H-pyran (5.68 g) in methylene chloride (100 mL) was added p-toluenesulfonic acid monohydrate (54 mg) in ice bath and the mixture was stirred at 0° C. to 10° C. for 2 hours. Triethylamine (1 mL) was added to the reaction solution, which was concentrated. The obtained residue was purified by column chromatography on silica gel (n-hexane:ethyl acetate=9:1→4:1) to give the title compound (15.3 g) having the following physical data.
TLC: Rf 0.50 and 0.45 (n-hexane:ethyl acetate=4:1);
NMR (CDCl$_3$): δ 7.80-7.50 (m, 5H), 4.65 (m, 0.3H), 4.44 (m, 0.7H), 4.05-3.40 (m, 5H), 2.30-1.35 (m, 16H), 1.00-0.85 (m, 3H).

Reference Example 7

(4R)-4-formyl-4-t-butoxycarbonylaminobutanoic acid ethyl ester

Under an atmosphere of argon, to a mixed solution of (4R)-4-t-butoxycarbonylamino-5-hydroxypentanoic acid ethyl ester (1.62 g) and diisopropylethylamine (6.5 ml) in dimethylsulfoxide-ethyl acetate (1:1, 40 mL) was added sulfur trioxide pyridine complex (2.96 g) in ice bath and the mixture was stirred in ice bath for 1 hour. The reaction solution was poured into ice water and extracted with ethyl acetate. The organic layer was washed with 0.5N hydrochloric acid, water and brine, dried over anhydrous magnesium sulfate and concentrated to give the title compound (1.65 g) having the following physical data.
TLC: Rf 0.25 (n-hexane:ethyl acetate=4:1);
NMR (CDCl$_3$): δ 9.60 (s, 1H), 5.20 (br, 1H), 4.27 (br, 1H), 4.14 (q, J=7.2 Hz, 2H), 2.60-2.20 (m, 3H), 1.91 (m, 1H), 1.45 (s, 9H), 1.26 (t, J=7.2 Hz, 3H).

Reference Example 8

(4R,5E,8S)-4-t-butoxycarbonylamino-8-(1-ethylcyclobutyl)-8-(tetrahydropyran-2-yloxy)oct-5-enoic acid ethyl ester Under an atmosphere of argon, a solution of 0.5M potassium bis(trimethylsilyl)amide in toluene (18.6 ml) was added dropwise to a solution of the compound prepared in Reference Example 6 (4.31 g) in anhydrous 1,2-dimethoxyethane (30 ml) at −78° C. and the mixture was stirred for 1 hour at the same temperature. A solution of the compound prepared in Reference Example 7 (1.65 g) in 1,2-dimethoxyethane (10 ml) was added dropwise to the reaction mixture, which was allowed to return to 0° C. for 2 hours. A saturated aqueous sodium hydrogen carbonate solution was added to the reaction solution, which was extracted with ethyl acetate. The organic layer was washed with water and brine, dried over anhydrous magnesium sulfate and concentrated. The obtained residue was purified by column chromatography on silica gel (n-hexane:ethyl acetate=9:1→4:1) to give the title compound (1.20 g) having the following physical data.
TLC: Rf 0.50 (n-hexane:ethyl acetate=4:1);
NMR (CDCl$_3$): δ 5.85-5.55 (m, 1H), 5.45-5.30 (m, 1H), 4.65-4.55 (m, 1H), 4.20-3.85 (m, 5H), 3.65-3.40 (m, 2H), 2.45-1.40 (m, 20H), 1.43 (s, 9H), 1.30-1.20 (m, 3H), 1.00-0.85 (m, 3H).

Reference Example 9

(4R,5E,8S)-4-amino-8-(1-ethylcyclobutyl)-8-hydroxyoct-5-enoic acid ethyl ester hydrochloride To a solution of the compound prepared in Reference Example 8 (172 mg) in ethanol (2 ml) was added 4N hydrogen chloride dioxane solution (0.5 ml) was the mixture was stirred at room temperature for 8 hours. The reaction solution was concentrated to give the title compound (120 mg).
TLC: Rf 0.20 (chloroform:methanol=9:1).

Example 1

(1E,16α)-17,17-propano-16-hydroxy-5-(4-ethoxycarbonylthiazol-2-yl)-9-oxo-1,2,3,4,20-pentanor-5-thia-8-azaprost-13-ene Under an atmosphere of argon, a solution of the compound prepared in Reference Example 9 (120 mg) and the compound prepared in Reference Example 3 (102 mg) in tetrahydrofuran (2 mL) was stirred at room temperature for 30 minutes. To the solution was added sodium triacetoxyborohydride (116 mg) and the mixture was stirred at room temperature overnight. Water was added to the reaction solution, which was extracted with ethyl acetate. The organic layer was washed with brine, dried over anhydrous magnesium sulfate and concentrated. The obtained residue was purified by column chromatography on silica gel (ethyl acetate) to give the compound of the present invention (93 mg) having the following physical data.
TLC: Rf 0.29 (ethyl acetate);
NMR (CDCl$_3$): δ 8.02 (s, 1H), 5.82 (dt, J=15.3, 6.9 Hz, 1H), 5.39 (dd, J=15.3, 8.7 Hz, 1H), 4.39 (q, J=7.2 Hz, 2H), 4.19 (m, 1H), 3.82 (m, 1H), 3.56-3.35 (m, 4H), 2.50-1.55 (m, 13H), 1.40 (m, 1H), 1.39 (t, J=7.2 Hz, 3H), 1.26 (m, 1H), 0.90 (t, J=7.5 Hz 3H).

Example 1(1) to 1(16)

By the same procedure as described in Example 1, using the compound prepared in Reference Example 3 or a corresponding aldehyde derivative, and the compound prepared in Reference Example 9 or a corresponding amine derivative, the following compounds of the present invention were obtained.

Example 1(1)

(13E)-20-methyl-15-hydroxy-9-oxo-5,17-dithia-8-azaprost-13-enoic acid butyl ester

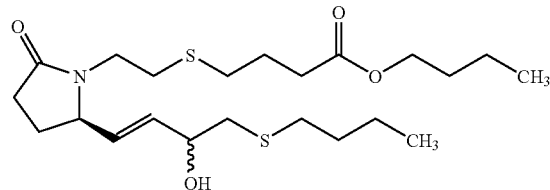

more polar
TLC: Rf 0.40 (ethyl acetate);
NMR (CDCl$_3$): δ 5.73 (dd, J=15.3, 5.1 Hz, 1H), 5.61 (dd, J=15.3, 8.1 Hz, 1H), 4.24 (m, 1H), 4.15 (m, 1H), 4.08 (t, J=7.2 Hz, 2H), 3.68 (m, 1H), 3.11 (m, 1H), 2.80-2.20 (m, 13H), 1.97-1.70 (m, 3H), 1.67-1.32 (m, 8H), 0.94 (t, J=7.5 Hz, 3H), 0.93 (t, J=7.5 Hz, 3H).

The compound is a single isomer although the configuration at 15-position is not determined.

Example 1(2)

(13E,15α)-15-hydroxy-5-(4-ethoxycarbonylthiazol-2-yl)-9-oxo-1,2,3,4-tetranor-5-thia-8-azaprost-13-ene

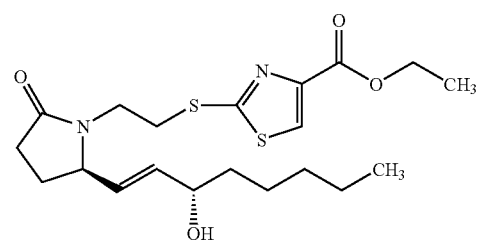

TLC: Rf 0.51 (ethyl acetate);
NMR (CDCl$_3$): δ 8.02 (s, 1H), 5.78 (dd, J=15.3, 5.7 Hz, 1H), 5.54 (dd, J=15.3, 9.0 Hz, 1H), 4.39 (q, J=6.9 Hz, 2H), 4.21 (m, 1H), 4.10 (m, 1H), 3.79 (m, 1H), 3.50-3.38 (m, 3H), 2.50-2.10 (m, 3H), 1.95 (bs, 1H), 1.77 (m, 1H), 1.66-1.20 (m, 11H), 0.87 (t, J=6.9 Hz, 3H).

Example 1(3)

(13E,15α)-20,20-ethano-15-hydroxy-9-oxo-5-thia-8-azaprost-13-enoic acid butyl ester TLC: Rf 0.49 (ethyl acetate);
NMR (CDCl$_3$): δ 5.74 (dd, J=15.9, 6.0 Hz, 1H), 5.52 (dd, J=15.9, 8.4 Hz, 1H), 4.21-4.03 (m, 4H), 3.63 (m, 1H), 3.10

(m, 1H), 2.73-2.20 (m, 9H), 1.98-1.18 (m, 16H), 0.93 (t, J=7.5 Hz, 3H), 0.65 (m, 1H), 0.40 (m, 2H), 0.00 (m, 2H).

Example 1(4)

(13E,16α)-17,17-propano-16-hydroxy-9-oxo-20-nor-8-azaprost-13-enoic acid ethyl ester TLC: Rf 0.42 (ethyl acetate);
NMR (CDCl$_3$): δ 5.77 (dt, J=15.3, 7.2 Hz, 1H), 5.38 (dd, J=15.3, 9.0 Hz, 1H), 4.12 (q, J=7.2 Hz, 2H), 4.03 (m, 1H), 3.62-3.44 (m, 2H), 2.88 (m, 1H), 2.50-1.20 (m, 23H), 2.28 (t, J=7.5 Hz, 2H), 1.25 (t, J=7.2 Hz, 3H), 0.93 (t, J=7.2 Hz, 3H).

Example 1(5)

(13E,16α)-17,17-propano-16-hydroxy-9-oxo-2,7-(1,3-interphenylene)-3,4,5,6,20-pentanor-8-azaprost-13-enoic acid methyl ester

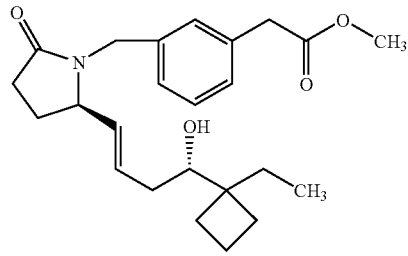

TLC: Rf 0.54 (chloroform:methanol=9:1);
NMR (CDCl$_3$): δ 7.30-7.22 (m, 1H), 7.20-7.10 (m, 3H), 5.70 (dt, J=15.0, 7.2 Hz, 1H), 5.34 (dd, J=15.0, 9.0 Hz, 1H), 4.91 (d, J=15.0 Hz, 1H), 3.92 (d, J=15.0 Hz, 1H), 3.87 (m, 1H), 3.70 (s, 3H), 3.61 (s, 2H), 3.52 (dd, J=9.9, 2.1 Hz, 1H), 2.55-1.35 (m, 14H), 0.93 (t, J=7.2 Hz, 3H).

Example 1(6)

(13E,16α)-17,17-propano-16-hydroxy-9-oxo-1,5-(1,3-interphenylene)-2,3,4,20-tetranor-8-azaprost-13-enoic acid ethyl ester TLC: Rf 0.38 (ethyl acetate);
NMR (CDCl$_3$): δ 7.86 (m, 2H), 7.36 (m, 2H), 5.72 (m, 1H), 5.35 (dd, J=15.3, 8.7 Hz, 1H), 4.37 (q, J=6.9 Hz, 2H), 4.00 (m, 1H), 3.63-3.45 (m, 2H), 2.98 (m, 1H), 2.65 (m, 2H), 2.50-2.07 (m, 4H), 2.05-1.23 (m, 16H), 0.91 (t, J=7.5 Hz, 3H).

Example 1(7)

(13E,16α)-17,17-propano-16-hydroxy-9-oxo-1,5-(2,5-interthienylene)-2,3,4,20-tetranor-8-azaprost-13-enoic acid methyl ester TLC: Rf 0.32 (ethyl acetate);
NMR (CDCl$_3$): δ 7.61 (d, J=3.6 Hz, 1H), 6.80 (d, J=3.6 Hz, 1H), 5.75 (m, 1H), 5.36 (dd, J=15.0, 8.7 Hz, 1H), 4.01 (m, 1H), 3.86 (s, 3H), 3.66 (m, 2H), 3.03 (m, 1H), 2.82 (m, 2H), 2.50-2.15 (m, 4H), 2.10-1.37 (m, 13H), 0.90 (t, J=7.5 Hz, 3H).

Example 1(8)

(13E,16α)-17,17-propano-16-hydroxy-9-oxo-1,6-(1,4-interphenylene)-2,3,4,5,20-pentanor-8-azaprost-13-enoic acid methyl ester TLC: Rf 0.27 (ethyl acetate).

Example 1(9)

(13E)-17,17-propano-5-(4-ethoxycarbonylthiazol-2-yl)-9-oxo-1,2,3,4,19,20-hexanor-5-thia-8-azaprost-13-ene TLC: Rf 0.29 (n-hexane:ethyl acetate=1:2);
NMR (CDCl$_3$): δ 8.02 (s, 1H), 5.68 (dt, J=15.3, 6.6 Hz, 1H), 5.22 (dd, J=15.3, 9.0 Hz, 1H), 4.39 (q, J=7.2 Hz, 2H), 4.13 (m, 1H), 3.83 (m, 1H), 3.49-3.41 (m, 2H), 3.32 (m, 1H), 2.44-2.29 (m, 2H), 2.19 (m, 1H), 2.04-1.48 (m, 8H), 1.43-1.31 (m, 6H), 1.05 (s, 3H).

Example 1(10)

(16α)-17,17-propano-16-hydroxy-5-(4-ethoxycarbonylthiazol-2-yl)-9-oxo-1,2,3,4,20-pentanor-5-thia-8-azaprostane TLC: Rf 0.25 (ethyl acetate);
NMR (CDCl$_3$): δ 8.01 (s, 1H), 4.38 (q, J=7.2 Hz, 2H), 3.89 (m, 1H), 3.72 (m, 1H), 3.56-3.30 (m, 4H), 2.46-2.09 (m, 3H), 2.02-1.20 (m, 16H), 1.39 (t, J=7.2 Hz, 3H), 0.91 (t, J=7.5 Hz, 3H).

Example 1(11)

(13E,16α)-17,17-propano-16-hydroxy-9-oxo-1,5-(1,4-interphenylene)-2,3,4,20-tetranor-8-azaprost-13-enoic acid methyl ester TLC: Rf 0.29 (ethyl acetate);
NMR (CDCl$_3$): δ 7.95 (d, J=8.1 Hz, 2H), 7.25 (d, J=8.1 Hz, 2H), 5.69 (dt, J=15.3, 6.9 Hz, 1H), 5.34 (dd, J=15.3, 8.7 Hz, 1H), 3.97 (m, 1H), 3.90 (s, 3H), 3.72-3.45 (m, 2H), 2.97 (m, 1H), 2.66 (t, J=7.8 Hz, 2H), 2.50-1.55 (m, 15H), 1.50-1.35 (m, 2H), 0.91 (t, J=7.5 Hz, 3H).

Example 1(12)

(13E,16α)-17,17-propano-16-hydroxy-5-(4-ethoxycarbonylthiazol-2-yl)-9-oxo-1,2,3,4,20-pentanor-8-azaprost-13-ene TLC: Rf 0.14 (ethyl acetate);
NMR (CDCl$_3$): δ 8.04 (s, 1H), 5.78 (dt, J=15.3, 6.6 Hz, 1H), 5.38 (dd, J=15.3, 8.7 Hz, 1H), 4.42 (q, J=7.2 Hz, 2H), 4.06 (m, 1H), 3.65-3.50 (m, 2H), 3.10-3.00 (m, 2H), 2.50-1.55 (m, 17H), 1.43 (m, 1H), 1.40 (t, J=7.2 Hz, 3H), 0.92 (t, J=7.2 Hz, 3H).

Example 1(13)

(13E,16α)-17,17-propano-16-hydroxy-5-(4-ethoxycarbonylthiazol-2-yl)-9-oxo-1,2,3,4,20-pentanor-5,8-diazaprost-13-ene TLC: Rf 0.49 (ethyl acetate:methanol=9:1);
NMR (CDCl$_3$): δ 7.37 (s, 1H), 6.07 (br, 1H), 5.81 (dt, J=15.3, 6.6 Hz, 1H), 5.41 (dd, J=15.3, 9.0 Hz, 1H), 4.34 (q, J=6.9 Hz, 2H), 4.07 (m, 1H), 3.66-3.40 (m, 5H), 2.50-1.60 (m, 14H), 1.44 (m, 1H), 1.36 (t, J=6.9 Hz, 3H), 0.92 (t, J=7.5 Hz, 3H).

Example 1(14)

(13E)-5-(4-ethoxycarbonylthiazol-2-yl)-9-oxo-1,2,3,4,20-pentanor-5-thia-8-azaprost-13-ene TLC: Rf 0.30 (hexane:ethyl acetate=1:2);
NMR: δ 8.02 (s, 1H), 5.66 (dt, J=15.3, 6.9 Hz, 1H), 5.21 (dd, J=15.3, 8.7 Hz, 1H), 4.39 (q, J=6.9 Hz, 2H), 4.14 (m, 1H), 3.83 (dt, J=13.5, 6.9 Hz, 1H), 3.48-3.40 (m, 2H), 3.30 (dt, J=13.5, 6.9 Hz, 1H), 2.48-2.10 (m, 4H), 2.08-1.93 (m, 2H), 1.71 (m, 1H), 1.39 (t, J=6.9 Hz, 3H), 1.35-1.16 (m, 5H), 0.86 (t, J=7.2 Hz, 3H).

Example 1(15)

(13E)-17,17-propano-5-(4-ethoxycarbonylthiazol-2-yl)-9-oxo-1,2,3,4,20-pentanor-5-thia-8-azaprost-13-ene TLC: Rf 0.32 (hexane:ethyl acetate=1:2);
NMR (CDCl$_3$): δ 8.02 (s, 1H), 5.69 (dt, J=15.3, 6.6 Hz, 1H), 5.21 (dd, J=15.3, 9.0 Hz, 1H), 4.39 (q, J=7.2 Hz, 2H), 4.12 (m, 1H), 3.84 (dt, J=13.5, 6.9 Hz, 1H), 3.50-3.39 (m, 2H), 3.31 (dt, J=13.5, 6.9 Hz, 1H), 2.48-2.12 (m, 3H), 1.96-1.52 (m, 8H), 1.47-1.32 (m, 8H), 0.74 (t, J=7.2 Hz, 3H).

Example 1(16)

(13E)-14-(3,5-dichlorophenyl)-5-(4-ethoxycarbonylthiazol-2-yl)-9-oxo-1,2,3,4,15,16,17,18,19,20-decanor-5-thia-8-azaprost-13-ene TLC: Rf 0.27 (hexane:ethyl acetate=1:2);
NMR (CDCl$_3$): δ 7.95 (s, 1H), 7.23 (t, J=1.8 Hz, 1H), 7.18 (d, J=1.8 Hz, 2H), 6.50 (d, J=15.9, 1H), 6.04 (dd, J=15.9, 9.0 Hz, 1H), 4.47-4.34 (m, 3H), 3.89 (m, 1H), 3.56-3.28 (m, 3H), 2.55-2.14 (m, 3H), 1.86 (m, 1H), 1.38 (t, J=7.2 Hz, 3H).

Example 2

(13E,16α)-17,17-propano-16-hydroxy-5-(4-carboxythiazol-2-yl)-9-oxo-1,2,3,4,20-pentanor-5-thia-8-azaprost-13-ene

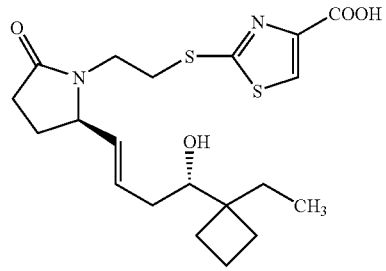

To a solution of the compound prepared in Example 1 (93 mg) in ethanol (2 mL) was added 2N aqueous sodium hydroxide solution (0.5 mL) and the mixture was stirred at room temperature for 2 hours. The reaction solution was neutralized with hydrochloric acid and then extracted with ethyl acetate. The organic layer was washed with brine, dried over anhydrous magnesium sulfate and concentrated. The obtained residue was purified by column chromatography on silica gel (chloroform:methanol:acetic acid=90:10:1) to give the compound of the present invention (78 mg) having the following physical data.
TLC: Rf 0.25 (chloroform:methanol=4:1);
NMR (CDCl$_3$): δ 8.08 (brs, 1H), 5.84 (m, 1H), 5.40 (m, 1H), 4.10 (m, 1H), 4.00-2.50 (br, 2H), 3.78 (m, 1H), 3.59 (m, 1H), 3.49 (m, 1H), 3.32 (m, 2H), 2.50-1.58 (m, 12H), 1.44 (m, 1H), 1.26 (m, 1H), 0.92 (t, J=7.5 Hz, 3H).

Example 2(1) to 2(16)

By the same procedure as described in Example 2, using the compound prepared in Example 1(1) to 1(16) instead of the compound prepared in Example 1, the following compounds of the present invention were obtained.

Example 2(1)

(13E)-20-methyl-15-hydroxy-9-oxo-5,17-dithia-8-azaprost-13-enoic acid

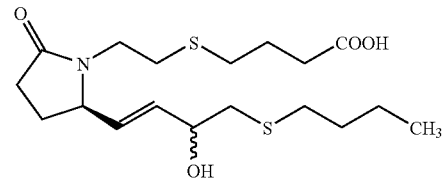

more polar
TLC: Rf 0.37 (chloroform:methanol=9:1);
NMR (CDCl$_3$): δ 5.75 (dd, J=15.6, 4.8 Hz, 1H), 5.63 (dd, J=15.6, 8.1 Hz, 1H), 4.25 (m, 1H), 4.17 (m, 1H), 3.66 (m, 1H), 3.23-2.20 (m, 16H), 1.99-1.70 (m, 3H), 1.58 (m, 2H), 1.40 (m, 2H), 0.93 (t, J=7.2 Hz, 3H).
The compound is a single isomer although the configuration at 15-position is not determined.

Example 2(2)

(15α,13E)-15-hydroxy-5-(4-carboxythiazol-2-yl)-9-oxo-1,2,3,4-tetranor-5-thia-8-azaprost-13-ene TLC: Rf 0.30 (chloroform:methanol=9:1);
NMR (CDCl$_3$): δ 8.10 (s, 1H), 5.80 (dd, J=15.6, 6.0 Hz, 1H), 5.55 (dd, J=15.6, 8.7 Hz, 1H), 4.30-3.77 (m, 5H), 3.60-3.29 (m, 3H), 2.58-2.20 (m, 3H), 1.80 (m, 1H), 1.62-1.21 (m, 8H), 0.88 (t, J=7.5 Hz, 3H).

Example 2(3)

(15α, 13E)-20,20-ethano-15-hydroxy-9-oxo-5-thia-8-azaprost-13-enoic acid

TLC: Rf 0.37 (chloroform:methanol=9:1);
NMR (CDCl$_3$): δ 5.73 (dd, J=15.3, 5.7 Hz, 1H), 5.53 (ddd, J=15.3, 8.1, 1.0 Hz, 1H), 4.18 (m, 2H), 3.63 (m, 1H), 3.30-2.78 (m, 2H), 2.75-2.20 (m, 10H), 1.98-1.67 (m, 3H), 1.62-1.10 (m, 8H), 0.62 (m, 1H), 0.40 (m, 2H), −0.02 (m, 2H).

Example 2(4)

(13E,16α)-17,17-propano-16-hydroxy-9-oxo-20-nor-8-azaprost-13-enoic acid

TLC: Rf 0.38 (chloroform:methanol=9:1);
NMR (CDCl$_3$): δ 5.79 (dt, J=15.3, 6.9 Hz, 1H), 5.38 (dd, J=15.3, 8.7 Hz, 1H), 4.05 (m, 1H), 4.00-3.00 (br, 2H), 3.58

(dd, J=9.9, 2.4 Hz, 1H), 3.52 (m, 1H), 2.87 (m, 1H), 2.50-1.20 (m, 24H), 0.93 (t, J=7.2 Hz, 3H).

Example 2(5)

(13E,16α)-17,17-propano-16-hydroxy-9-oxo-2,7-(1,3-interphenylene)-3,4,5,6,20-pentanor-8-azaprost-13-enoic acid TLC: Rf 0.32 (chloroform:methanol=9:1);
NMR (CDCl$_3$): δ 7.25 (m, 1H), 7.20-7.10 (m, 3H), 5.71 (dt, J=15.3, 7.2 Hz, 1H), 5.32 (dd, J=15.3, 9.0 Hz, 1H), 4.96 (d, J=14.4 Hz, 1H), 4.50-3.00 (br, 2H), 3.86 (d, J=14.4 Hz, 1H), 3.81 (m, 1H), 3.65 (d, J=15.3 Hz, 1H), 3.59 (d, J=15.3 Hz, 1H), 3.56 (dd, J=9.9, 2.1 Hz, 1H), 2.55-1.50 (m, 13H), 1.44 (m, 1H), 0.93 (t, J=7.2 Hz, 3H).

Example 2(6)

(13E,16α)-17,17-propano-16-hydroxy-9-oxo-1,5-(1,3-interphenylene)-2,3,4,20-tetranor-8-azaprost-13-enoic acid TLC: Rf 0.48 (chloroform:methanol=9:1);
NMR (CDCl$_3$): δ 7.93 (m, 2H), 7.45-7.38 (m, 2H), 5.74 (m, 1H), 5.36 (dd, J=15.3, 9.0 Hz, 1H), 4.01 (m, 1H), 3.63-3.51 (m, 2H), 3.00 (m, 1H), 2.67 (t, J=7.0 Hz, 2H), 2.55-2.12 (m, 4H), 2.08-1.58 (m, 12H), 1.41 (m, 1H), 0.91 (t, J=7.8 Hz, 3H).

Example 2(7)

(13E,16α)-17,17-propano-16-hydroxy-9-oxo-1,5-(2,5-interthienylene)-2,3,4,20-tetranor-8-azaprost-13-enoic acid TLC: Rf 0.19 (chloroform:methanol=9:1);
NMR (CDCl$_3$): δ 7.68 (d, J=3.9 Hz, 1H), 6.83 (d, J=3.9 Hz, 1H), 5.77 (m, 1H), 5.65 (bs, 1H), 5.36 (dd, J=15.3, 8.7 Hz, 1H), 4.05 (m, 1H), 3.62-3.50 (m, 2H), 3.03 (m, 1H), 2.86 (t, J=7.0 Hz, 2H), 2.55-2.18 (m, 4H), 2.11-1.58 (m, 12H), 1.41 (m, 1H), 0.92 (t, J=7.2 Hz, 3H).

Example 2(8)

(13E,16α)-17,17-propano-16-hydroxy-9-oxo-1,6-(1,4-interphenylene)-2,3,4,5,20-pentanor-8-azaprost-13-enoic acid TLC: Rf 0.28 (ethyl acetate:acetic acid=100:1);
NMR (CDCl$_3$): δ 8.01 (d, J=8.1 Hz, 2H), 7.29 (d, J=8.1 Hz, 2H), 5.67 (ddd, J=15.3, 8.1, 6.6 Hz, 1H), 5.27 (dd, J=15.3, 9.0 Hz, 1H), 3.88-3.72 (m, 2H), 3.57 (dd, J=9.6, 2.7 Hz, 1H), 3.20 (m, 1H), 3.00-2.80 (m, 2H), 2.50-1.58 (m, 13H), 1.45 (m, 1H), 0.93 (t, J=7.5 Hz, 3H).

Example 2(9)

(13E)-17,17-propano-5-(4-carboxythiazol-2-yl)-9-oxo-1,2,3,4,19,20-hexanor-5-thia-8-azaprost-13-ene TLC: Rf 0.35 (chloroform:methanol:acetic acid=9:1:0.1);
NMR (CDCl$_3$): δ 8.08 (s, 1H), 5.74 (dt, J=15.0, 6.9 Hz, 1H), 5.27 (dd, J=15.0, 8.4 Hz, 1H), 4.06 (m, 1H), 3.82 (m, 1H), 3.49 (m, 1H), 3.40-3.20 (m, 2H), 2.53-2.15 (m, 3H), 2.09-1.53 (m, 9H), 1.50-1.40 (m, 2H), 1.08 (s, 3H).

Example 2(10)

(16α)-17,17-propano-16-hydroxy-5-(4-carboxythiazol-2-yl)-9-oxo-1,2,3,4,20-pentanor-5-thia-8-azaprostane TLC: Rf 0.28 (chloroform:methanol:acetic acid=90:10:1);
NMR (CDCl$_3$): δ 8.07 (s, 1H), 5.00-4.00 (br, 2H), 3.88 (m, 1H), 3.75-3.20 (m, 5H), 2.50-1.20 (m, 18H), 0.91 (t, J=7.2 Hz, 3H).

Example 2(11)

(13E,16α)-17,17-propano-16-hydroxy-9-oxo-1,5-(1,4-interphenylene)-2,3,4,20-tetranor-8-azaprost-13-enoic acid TLC: Rf 0.24 (ethyl acetate:acetic acid=100:1);
NMR (CDCl$_3$): δ 8.00 (d, J=8.1 Hz, 2H), 7.27 (d, J=8.1 Hz, 2H), 7.00-4.00 (br, 2H), 5.71 (dt, J=15.6, 6.9 Hz, 1H), 5.36 (dd, J=15.6, 8.7 Hz, 1H), 4.00 (m, 1H), 3.58 (m, 1H), 3.53 (dd, J=9.9, 2.4 Hz, 1H), 2.98 (m, 1H), 2.67 (t, J=7.5 Hz, 2H), 2.50-1.55 (m, 15H), 1.43 (m, 1H), 0.91 (t, J=7.2 Hz, 3H).

Example 2(12)

(13E,16α)-17,17-propano-16-hydroxy-5-(4-carboxythiazol-2-yl)-9-oxo-1,2,3,4,20-pentanor-8-azaprost-13-ene TLC: Rf 0.47 (chloroform:methanol:acetic acid=80:20:1);
NMR (CDCl$_3$): δ 8.13 (s, 1H), 5.81 (dt, J=15.0, 7.2 Hz, 1H), 5.41 (dd, J=15.0, 8.7 Hz, 1H), 5.50-4.00 (br, 2H), 4.07 (m, 1H), 3.61 (dd, J=9.6, 2.7 Hz, 1H), 3.56 (m, 1H), 3.14 (m, 1H), 3.04 (t, J=7.5 Hz, 2H), 2.50-1.60 (m, 15H), 1.45 (m, 1H), 0.92 (t, J=7.5 Hz, 3H).

Example 2(13)

(13E,16α)-17,17-propano-16-hydroxy-5-(4-carboxythiazol-2-yl)-9-oxo-1,2,3,4,20-pentanor-5,8-diazaprost-13-ene TLC: Rf 0.49 (chloroform:methanol:acetic acid=80:20:1);
NMR (CDCl$_3$): δ 11.78 (br, 1H), 7.31 (s, 1H), 6.03 (dt, J=15.0, 7.2 Hz, 1H), 5.29 (dd, J=15.0, 8.7 Hz, 1H), 4.07 (m, 1H), 3.65-3.30 (m, 5H), 2.50-1.55 (m, 15H), 1.42 (m, 1H), 0.90 (t, J=7.5 Hz, 3H).

Example 2(14)

(13E)-5-(4-carboxythiazol-2-yl)-9-oxo-1,2,3,4,20-pentanor-5-thia-8-azaprost-13-ene TLC: Rf 0.37 (chloroform:methanol:acetic acid=9:1:0.1);
NMR (CDCl$_3$): δ 8.08 (s, 1H), 5.72 (dt, J=15.3, 6.6 Hz, 1H), 5.27 (dd, J=15.3, 9.0 Hz, 1H), 4.05 (m, 1H), 3.80 (m, 1H), 3.51 (m, 1H), 3.40-3.21 (m, 2H), 2.54-2.15 (m, 3H), 2.13-2.00 (m, 2H), 1.75 (m, 1H), 1.45-1.17 (m, 6H), 0.89 (t, J=6.6 Hz, 3H).

Example 2(15)

(13E)-17,17-propano-5-(4-carboxythiazol-2-yl)-9-oxo-1,2,3,4,20-pentanor-5-thia-8-azaprost-13-ene TLC: Rf 0.37 (chloroform:methanol:acetic acid=9:1:0.1);
NMR (CDCl$_3$): δ 8.09 (s, 1H), 5.74 (dt, J=15.3, 6.6 Hz, 1H), 5.28 (dd, J=15.3, 8.7 Hz, 1H), 4.06 (m, 1H), 3.82 (m, 1H), 3.49 (m, 1H), 3.41-3.23 (m, 2H), 2.54-2.16 (m, 3H), 2.04-1.89 (m, 2H), 1.88-1.63 (m, 7H), 1.52-1.40 (m, 4H), 0.77 (t, J=7.2 Hz, 3H).

Example 2(16)

(13E)-14-(3,5-dichlorophenyl)-5-(4-carboxythiazol-2-yl)-9-oxo-1,2,3,4,15,16,17,18,19,20-decanor-5-thia-8-azaprost-13-ene TLC: Rf 0.33 (chloroform:methanol:acetic acid=9:1:0.1);

NMR (CDCl$_3$): δ 8.08 (s, 1H), 7.27 (t, J=1.8 Hz, 1H), 7.24 (d, J=1.8 Hz, 2H), 6.49 (d, J=15.6, 1H), 6.07 (dd, J=15.6, 8.7 Hz, 1H), 4.30 (m, 1H), 3.90 (m, 1H), 3.49 (m, 1H), 3.41-3.30 (m, 2H), 2.62-2.43 (m, 2H), 2.35 (m, 1H), 1.89 (m, 1H).

Reference Example 10

2-(2-aminoethylthio)thiazole-4-carboxylic acid ethyl ester hydrochloride

To a solution of 2-bromothiazole-4-carboxylic acid ethyl ester (3.00 g) in ethanol (15 mL) were added tributylphosphine (25 mg) and cysteamine (1.2 g) and the mixture was stirred at room temperature for 16 hours. Furthermore, cysteamine (1.0 g) was added thereto and the mixture was stirred at 50° C. for 5 hours. After cooling to room temperature, the reaction solution was neutralized with an aqueous saturated sodium hydrogen carbonate solution and extracted with chloroform. The organic layer was washed with brine, dried over anhydrous sodium sulfate and concentrated. The residue was diluted with ethyl acetate (30 mL) and 4N hydrogen chloride-ethyl acetate solution was added thereto. The precipitated solid was collected by filtration to give the title compound (2.28 g) having the following physical data.

TLC: Rf 0.20 (chloroform:methanol=9:1);

NMR (CD$_3$OD): δ 8.33 (s, 1H), 4.37 (q, J=7.2 Hz, 2H), 3.55 (t, J=6.6 Hz, 2H), 3.37 (t, J=6.6 Hz, 2H), 1.38 (t, J=7.2 Hz, 3H).

Reference Example 11

3-(4-t-butylbenzoyl)propanoic acid ethyl ester

To a solution of t-butylbenzene (2.00 g) in 1,2-dichloroethane (30 mL) was added aluminum chloride (2.2 g) in ice bath. Ethyl succinyl chloride (2.3 mL) was added dropwise to the mixture, which was stirred at room temperature for 23 hours. The reaction solution was poured into water and extracted with ethyl acetate. The organic layer was washed with 1N hydrochloric acid, water and brine, dried over anhydrous magnesium sulfate and concentrated. The residue was purified by column chromatography on silica gel (n-hexane:ethyl acetate=9:1→5:1) to give the title compound (629 mg) having the following physical data.

TLC: Rf 0.65 (n-hexane:ethyl acetate=3:1);

NMR (CDCl$_3$): δ 7.92 (d, J=8.7 Hz, 2H), 7.48 (d, J=8.7 Hz, 2H), 4.16 (q, J=7.2 Hz, 2H), 3.29 (t, J=6.6 Hz, 2H), 2.75 (t, J=6.6 Hz, 2H), 1.34 (s, 9H), 1.26 (t, J=7.2 Hz, 3H).

Example 3

2-(2-(2-(4-t-butylphenyl)-5-oxopyrrolidin-1-yl)ethylthio)thiazole-4-carboxylic acid ethyl ester

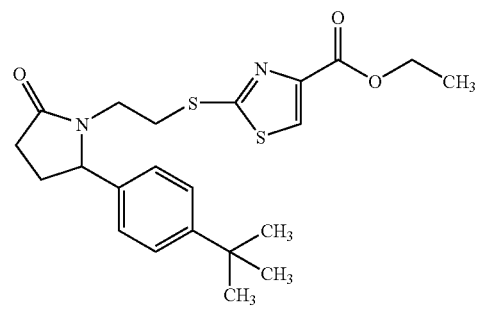

Under an atmosphere of argon, to a solution of the compound prepared in Reference Example 10 (270 mg) in ethanol (5 mL) was added sodium hydrogen carbonate (84 mg) and the mixture was stirred for 10 minutes. And then acetic acid (0.12 mL) and the compound prepared in Reference Example 11 (262 mg) were added thereto and the mixture was stirred at room temperature for 15 minutes. Sodium cyanoborohydride (125 mg) was added to the reaction solution, which was stirred at 70° C. overnight. Water was added to the reaction solution, which was extracted with ethyl acetate. The organic layer was washed with water and brine, dried over anhydrous magnesium sulfate and concentrated. The residue was purified by column chromatography on silica gel (n-hexane:ethyl acetate=1:1→2:3) to give the compound of the present invention (170 mg) having the following physical data.

TLC: Rf 0.28 (hexane:ethyl acetate=1:1);

NMR (CDCl$_3$): δ 7.99 (s, 1H), 7.34 (d, J=8.4 Hz, 2H), 7.12 (d, J=8.4 Hz, 2H), 4.79 (dd, J=7.8, 5.4 Hz, 1H), 4.40 (q, J=7.2 Hz, 2H), 3.93 (dt, J=14.4, 7.2 Hz, 1H), 3.45-3.28 (m, 2H), 3.01 (dt, J=14.4, 6.9 Hz, 1H), 2.64-2.33 (m, 3H), 1.90 (m, 1H), 1.40 (t, J=7.2 Hz, 3H), 1.30 (s, 9H).

Example 3(1) to 3(13)

By the same procedure as described in Example 3, using a corresponding derivative instead of the compound prepared in Reference Example 11, the following compounds of the present invention were obtained.

Example 3(1)

2-(2-(2-(4-n-butylphenyl)-5-oxopyrrolidin-1-yl)ethylthio)thiazole-4-carboxylic acid ethyl ester TLC: Rf 0.64 (chloroform:methanol=9:1);

NMR (CDCl$_3$): δ 8.00 (s, 1H), 7.14 (d, J=8.4 Hz, 2H), 7.10 (d, J=8.4 Hz, 2H), 4.79 (dd, J=7.5, 5.4 Hz, 1H), 4.41 (q, J=7.2 Hz, 2H), 3.93 (dt, J=14.1, 7.2 Hz, 1H), 3.37 (m, 2H), 3.01 (dt, J=14.1, 6.3 Hz, 1H), 2.64-2.35 (m, 5H), 1.90 (m, 1H), 1.55 (m, 2H), 1.40 (t, J=7.2 Hz, 3H), 1.35 (m, 2H), 0.93 (t, J=7.2 Hz, 3H).

Example 3(2)

2-(2-(2-(4-(1-hydroxyhexyl)phenyl)-5-oxopyrrolidin-1-yl)ethylthio)thiazole-4-carboxylic acid ethyl ester TLC: Rf 0.80 (chloroform:methanol:acetic acid=90:10:1);
NMR (CDCl$_3$): δ7.99 (s, 1H), 7.31 (d, J=8.1 Hz, 2H), 7.18 (d, J=8.1 Hz, 2H), 4.82 (m, 1H), 4.65 (m, 1H), 4.40 (q, J=7.2 Hz, 2H), 3.91 (m, 1H), 3.36 (m, 2H), 3.02 (m, 1H), 2.65-2.35 (m, 3H), 2.10-1.55 (m, 6H), 1.40 (t, J=7.2 Hz, 3H), 1.40-1.15 (m, 4H), 0.87 (t, J=6.6 Hz, 3H).

Example 3(3)

2-(2-(2-(4-propoxyphenyl)-5-oxopyrrolidin-1-yl)ethylthio)thiazole-4-carboxylic acid ethyl ester TLC: Rf 0.15 (n-hexane:ethyl acetate=1:1);
NMR (CDCl$_3$): δ 8.00 (s, 1H), 7.11 (d, J=9.0 Hz, 2H), 6.84 (d, J=9.0 Hz, 2H), 4.76 (dd, J=7.8, 5.4 Hz, 1H), 4.40 (q, J=7.2 Hz, 2H), 3.94-3.81 (m, 3H), 3.44-3.28 (m, 2H), 3.01 (dt, J=14.4, 6.9 Hz, 1H), 2.60-2.35 (m, 3H), 1.88 (m, 1H), 1.80 (q, J=7.2 Hz, 2H), 1.40 (t, J=7.2 Hz, 3H), 1.03 (t, J=7.2 Hz, 3H).

Example 3(4)

2-(2-(2-(1,1'-biphenyl-4-yl)-5-oxopyrrolidin-1-yl)ethylthio)thiazole-4-carboxylic acid methyl ester TLC: Rf 0.23 (hexane:ethyl acetate=1:1);
NMR (CDCl$_3$): δ 7.98 (s, 1H), 7.62-7.52 (m, 4H), 7.49-7.32 (m, 3H), 7.31-7.24 (m, 2H), 4.89 (t, J=6.3 Hz, 1H), 4.38 (q, J=7.2 Hz, 2H), 3.98 (dt, J=14.4, 7.2 Hz, 1H), 3.46-3.37 (m, 2H), 3.06 (dt, J=14.4, 6.9 Hz, 1H), 2.64-2.37 (m, 3H), 1.95 (m, 1H), 1.38 (t, J=7.2 Hz, 3H).

Example 3(5)

2-(2-(2-(4-n-hexylphenyl)-5-oxopyrrolidin-1-yl)ethylthio)thiazole-4-carboxylic acid ethyl ester TLC: Rf 0.34 (ethyl acetate:n-hexane=1:1);
NMR (CDCl$_3$): δ 8.00 (s, 1H), 7.21-7.26 (m, 4H), 4.82-4.75 (m, 1H), 4.41 (q, J=6.9 Hz, 2H), 3.98-3.87 (m, 1H), 3.44-3.29 (m, 2H), 3.07-2.95 (m, 1H), 2.63-2.33 (m, 5H), 1.97-1.84 (m, 1H), 1.65-1.51 (m, 2H), 1.46-1.21 (m, 9H), 0.93-0.82 (m, 3H).

Example 3(6)

2-(2-(2-(4-n-propylphenyl)-5-oxopyrrolidin-1-yl)ethylthio)thiazole-4-carboxylic acid ethyl ester TLC: Rf 0.21 (ethyl acetate:n-hexane=1:1);
NMR (CDCl$_3$): δ 8.00 (s, 1H), 7.15-7.09 (m, 4H), 4.79 (dd, J=7.5, 5.7 Hz, 1H), 4.41 (q, J=7.2 Hz, 2H), 3.93 (dt, J=14.1, 7.2 Hz, 1H), 3.42-3.39 (m, 2H), 3.00 (dt, J=14.1, 6.6 Hz, 1H), 2.60-2.35 (m, 5H), 1.96-1.83 (m, 1H), 1.68-1.55 (m, 2H), 1.40 (t, J=7.2 Hz, 3H), 0.93 (t, J=7.2 Hz, 3H).

Example 3(7)

2-(2-(2-phenyl-5-oxopyrrolidin-1-yl)ethylthio)thiazole-4-carboxylic acid ethyl ester TLC: Rf 0.15 (ethyl acetate:n-hexane=1:1);
NMR (CDCl$_3$): δ 8.00 (s, 1H), 7.36-7.27 (m, 3H), 7.24-7.16 (m, 2H), 4.83 (t, J=6.9 Hz, 1H), 4.40 (q, J=6.9 Hz, 2H), 3.95 (dt, J=14.1, 7.2 Hz, 1H), 3.46-3.30 (m, 2H), 3.01 (dt, J=14.1, 6.3 Hz, 1H), 2.64-2.35 (m, 3H), 1.99-1.83 (m, 1H), 1.40 (t, J=6.9 Hz, 3H).

Example 3(8)

2-(2-(2-(4-ethylphenyl)-5-oxopyrrolidin-1-yl)ethylthio)thiazole-4-carboxylic acid ethyl ester TLC: Rf 0.17 (ethyl acetate:n-hexane=1:1);
NMR (CDCl$_3$): δ 8.00 (s, 1H), 7.20-7.07 (m, 4H), 4.79 (dd, J=7.5, 5.4 Hz, 1H), 4.40 (q, J=7.2 Hz, 2H), 3.93 (dt, J=14.1, 6.9 Hz, 1H), 3.37 (dt, J=6.6, 1.8 Hz, 2H), 3.01 (dt, J=14.1, 6.3 Hz, 1H), 2.66-2.37 (m, 5H), 1.96-1.84 (m, 1H), 1.40 (t, J=6.9 Hz, 3H), 1.23 (t, J=7.2 Hz, 3H).

Example 3(9)

2-(2-(2-(4-n-pentylphenyl)-5-oxopyrrolidin-1-yl)ethylthio)thiazole-4-carboxylic acid ethyl ester TLC: Rf 0.31 (ethyl acetate:n-hexane=1:1);
NMR (CDCl$_3$): δ 8.00 (s, 1H), 7.15-7.08 (m, 4H), 4.78 (dd, J=8.1, 5.7 Hz, 1H), 4.41 (q, J=7.2 Hz, 2H), 3.98-3.86 (m, 1H), 3.37 (dt, J=6.6, 2.4 Hz, 2H), 3.06-2.95 (m, 1H), 2.63-2.35 (m, 5H), 1.97-1.86 (m, 1H), 1.40 (t, J=7.2 Hz, 3H), 1.37-1.26 (m, 4H), 0.91-0.85 (m, 3H).

Example 3(10)

2-(2-(2-(4-methylphenyl)-5-oxopyrrolidin-1-yl)ethylthio)thiazole-4-carboxylic acid ethyl ester TLC: Rf 0.33 (ethyl acetate:n-hexane=1:1);
NMR (CDCl$_3$): δ 8.00 (s, 1H), 7.20-7.05 (m, 4H), 4.82-4.75 (m, 1H), 4.40 (q, J=6.9 Hz, 2H), 3.98-3.86 (m, 1H), 3.37 (dt, J=6.3, 2.1 Hz, 2H), 3.06-2.96 (m, 1H), 2.62-2.32 (m, 6H), 1.96-1.83 (m, 1H), 1.40 (t, J=6.9 Hz, 3H).

Example 3(11)

2-(2-(2-(4-n-octylphenyl)-5-oxopyrrolidin-1-yl)ethylthio)thiazole-4-carboxylic acid ethyl ester TLC: Rf 0.25 (ethyl acetate:n-hexane=1:1);
NMR (CDCl$_3$): δ 8.00 (s, 1H), 7.20-7.09 (m, 4H), 4.82-4.76 (m, 1H), 4.41 (q, J=7.2 Hz, 2H), 3.98-3.87 (m, 1H), 3.37 (dt, J=6.3, 2.4 Hz, 2H), 3.06-2.96 (m, 1H), 2.63-2.35 (m, 5H), 1.97-1.84 (m, 1H), 1.65-1.52 (m, 2H), 1.40 (t, J=7.2 Hz, 3H), 1.35-1.23 (m, 10H), 0.92-0.85 (m, 3H).

Example 3(12)

2-(2-(2-(4-n-heptylphenyl)-5-oxopyrrolidin-1-yl)ethylthio)thiazole-4-carboxylic acid ethyl ester TLC: Rf 0.32 (ethyl acetate:n-hexane=1:1);
NMR (CDCl$_3$): δ 8.00 (s, 1H), 7.19-7.05 (m, 4H), 4.82-4.76 (m, 1H), 4.40 (q, J=7.2 Hz, 2H), 3.98-3.87 (m, 1H), 3.37 (dt, J=6.6, 2.1 Hz, 2H), 3.06-2.95 (m, 1H), 2.63-2.34 (m, 5H), 1.98-1.85 (m, 1H), 1.66-1.52 (m, 2H), 1.40 (t, J=7.2 Hz, 3H), 1.37-1.21 (m, 8H), 0.95-0.82 (m, 3H).

Example 3(13)

2-(2-(2-(3-n-hexylphenyl)-5-oxopyrrolidin-1-yl)ethylthio)thiazole-4-carboxylic acid ethyl ester TLC: Rf 0.32 (ethyl acetate:n-hexane=1:1);
NMR (CDCl$_3$): δ 8.00 (s, 1H), 7.24 (t, J=7.8 Hz, 1H), 7.13-7.08 (m, 1H), 7.03-6.97 (m, 2H), 4.82-4.76 (m, 1H), 4.40 (q, J=7.2 Hz, 2H), 3.99-3.89 (m, 1H), 3.38 (dt, J=6.6, 1.2 Hz, 2H), 3.07-2.97 (m, 1H), 2.62-2.36 (m, 5H), 1.97-1.85 (m, 1H), 1.63-1.51 (m, 2H), 1.40 (t, J=7.2 Hz, 3H), 1.37-1.22 (m, 6H), 0.92-0.83 (m, 3H).

Example 4 to 4(13)

By the same procedure as described in Example 2, using the compound prepared in Example 3 to 3(13) instead of the compound prepared in Example 1, the following compounds of the present invention were obtained.

Example 4

2-(2-(2-(4-t-butylphenyl)-5-oxopyrrolidin-1-yl)ethylthio)thiazole-4-carboxylic acid

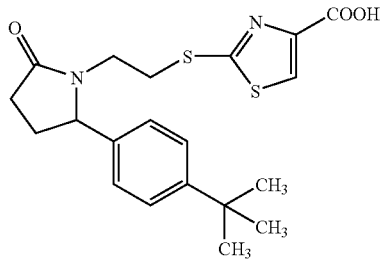

TLC: Rf 0.29 (chloroform:methanol:acetic acid=9:1:0.1);
NMR (CDCl$_3$): δ 8.07 (s, 1H), 7.39 (d, J=8.4 Hz, 2H), 7.14 (d, J=8.4 Hz, 2H), 4.68 (dd, J=7.5, 6.0 Hz, 1H), 3.97 (m, 1H), 3.30-3.10 (m, 3H), 2.69-2.39 (m, 3H), 1.95 (m, 1H), 1.32 (s, 9H).

Example 4(1)

2-(2-(2-(4-n-butylphenyl)-5-oxopyrrolidin-1-yl)ethylthio)thiazole-4-carboxylic acid TLC: Rf 0.25 (chloroform:methanol:acetic acid=200:20:1);
NMR (CDCl$_3$): δ 8.07 (s, 1H), 7.19 (d, J=8.4 Hz, 2H), 7.12 (d, J=8.4 Hz, 2H), 4.67 (dd, J=7.8, 6.0 Hz, 1H), 3.94 (m, 1H), 3.30-3.05 (m, 3H), 2.70-2.40 (m, 5H), 1.95 (m, 1H), 1.60 (m, 2H), 1.36 (m, 2H), 0.93 (t, J=7.5 Hz, 3H).

Example 4(2)

2-(2-(2-(4-(1-hydroxyhexyl)phenyl)-5-oxopyrrolidin-1-yl)ethylthio)thiazole-4-carboxylic acid TLC: Rf 0.51 (chloroform:methanol:acetic acid=90:10:1);
NMR (CDCl$_3$): δ 8.07 (s, 1H), 7.37 (d, J=8.1 Hz, 2H), 7.20 (d, J=8.1 Hz, 2H), 4.77-4.63 (m, 2H), 3.96 (m, 1H), 3.35-3.07 (m, 3H), 2.71-2.40 (m, 3H), 2.02-1.58 (m, 3H), 1.55-1.17 (m, 6H), 0.87 (t, J=6.6 Hz, 3H).

Example 4(3)

2-(2-(2-(4-propoxyphenyl)-5-oxopyrrolidin-1-yl)ethylthio)thiazole-4-carboxylic acid TLC: Rf 0.35 (chloroform:methanol:acetic acid=9:1:0.1);
NMR (CDCl$_3$): δ 8.08 (s, 1H), 7.14 (d, J=8.7 Hz, 2H), 6.89 (d, J=8.7 Hz, 2H), 4.65 (dd, J=7.5, 6.6 Hz, 1H), 3.92 (t, J=6.6 Hz, 2H), 3.89 (m, 1H), 3.32-3.05 (m, 3H), 2.69-2.38 (m, 3H), 1.95 (m, 1H), 1.81 (m, 2H), 1.04 (t, J=7.5 Hz, 3H).

Example 4(4)

2-(2-(2-(1,1'-biphenyl-4-yl)-5-oxopyrrolidin-1-yl)ethylthio)thiazole-4-carboxylic acid TLC: Rf 0.31 (chloroform:methanol:acetic acid=9:1:0.1);
NMR (CDCl$_3$): δ 8.07 (s, 1H), 7.65-7.55 (m, 4H), 7.49-7.41 (m, 2H), 7.40-7.27 (m, 3H), 4.76 (dd, J=7.8, 5.7 Hz, 1H), 4.01 (m, 1H), 3.38-3.11 (m, 3H), 2.76-2.43 (m, 3H), 2.00 (m, 1H).

Example 4(5)

2-(2-(2-(4-n-hexylphenyl)-5-oxopyrrolidin-1-yl)ethylthio)thiazole-4-carboxylic acid TLC: Rf 0.26 (methylene chloride:methanol=5:1);
NMR (CDCl$_3$): δ 8.08 (s, 1H), 7.22-7.10 (m, 4H), 4.72-4.65 (m, 1H), 4.00-3.85 (m, 1H), 3.31-3.08 (m, 3H), 2.71-2.40 (m, 5H), 2.02-1.89 (m, 1H), 1.67-1.54 (m, 2H), 1.43-1.24 (m, 6H), 0.95-0.83 (m, 3H).

Example 4(6)

2-(2-(2-(4-n-propylphenyl)-5-oxopyrrolidin-1-yl)ethylthio)thiazole-4-carboxylic acid TLC: Rf 0.24 (methylene chloride:methanol=5:1);
NMR (CDCl$_3$): δ 8.08 (s, 1H), 7.22-7.11 (m, 4H), 4.72-4.65 (m, 1H), 4.00-3.86 (m, 1H), 3.44-3.09 (m, 3H), 2.70-2.40 (m, 5H), 2.01-1.89 (m, 1H), 1.70-1.57 (m, 2H), 0.94 (t, J=7.2 Hz, 3H).

Example 4(7)

2-(2-(2-phenyl-5-oxopyrrolidin-1-yl)ethylthio)thiazole-4-carboxylic acid

TLC: Rf 0.21 (methylene chloride:methanol=5:1);
NMR (CDCl$_3$): δ 8.08 (s, 1H), 7.42-7.31 (m, 3H), 7.28-7.20 (m, 2H), 4.76-4.70 (m, 1H), 4.02-3.89 (m, 1H), 3.34-3.10 (m, 3H), 2.71-2.42 (m, 3H), 2.02-1.90 (m, 1H).

Example 4(8)

2-(2-(2-(4-ethylphenyl)-5-oxopyrrolidin-1-yl)ethylthio)thiazole-4-carboxylic acid TLC: Rf 0.17 (methylene chloride:methanol=5:1);
NMR (CDCl$_3$): δ 8.07 (s, 1H), 7.22-7.10 (m, 4H), 4.70-4.64 (m, 1H), 4.01-3.88 (m, 1H), 3.29-3.12 (m, 3H), 2.71-2.41 (m, 5H), 2.01-1.89 (m, 1H), 1.25 (t, J=7.5 Hz, 3H).

Example 4(9)

2-(2-(2-(4-n-pentylphenyl)-5-oxopyrrolidin-1-yl)ethylthio)thiazole-4-carboxylic acid TLC: Rf 0.23 (methylene chloride:methanol=5:1);
NMR (CDCl$_3$): δ 8.84 (brs, 1H), 8.08 (s, 1H), 7.22-7.09 (m, 4H), 4.74-4.67 (m, 1H), 3.98-3.87 (m, 1H), 3.35-3.12 (m, 3H), 2.69-2.40 (m, 5H), 2.03-1.88 (m, 1H), 1.66-1.55 (m, 2H), 1.42-1.25 (m, 4H), 0.93-0.85 (m, 3H).

Example 4(10)

2-(2-(2-(4-methylphenyl)-5-oxopyrrolidin-1-yl)ethylthio)thiazole-4-carboxylic acid TLC: Rf 0.17 (dichloroethane:methanol=5:1);

NMR (CDCl₃): δ 8.07 (s, 1H), 7.22-7.09 (m, 4H), 4.70-4.63 (m, 1H), 3.98-3.85 (m, 1H), 3.30-3.03 (m, 3H), 2.69-2.41 (m, 3H), 2.36 (s, 3H), 2.01-1.88 (m, 1H).

Example 4(11)

2-(2-(2-(4-n-octylphenyl)-5-oxopyrrolidin-1-yl)ethylthio)thiazole-4-carboxylic acid TLC: Rf 0.32 (dichloroethane:methanol=5:1);

NMR (CDCl₃): δ 8.08 (s, 1H), 7.22-7.09 (m, 4H), 4.70-4.63 (m, 1H), 4.00-3.89 (m, 1H), 3.31-3.08 (m, 3H), 2.67-2.40 (m, 5H), 2.01-1.90 (m, 1H), 1.68-1.54 (m, 2H), 1.39-1.16 (m, 10H), 0.96-0.82 (m, 3H).

Example 4(12)

2-(2-(2-(4-n-heptylphenyl)-5-oxopyrrolidin-1-yl)ethylthio)thiazole-4-carboxylic acid TLC: Rf 0.16 (dichloroethane:methanol=5:1);

NMR (CDCl₃): δ 9.22 (brs, 1H), 8.09 (s, 1H), 7.23-7.09 (m, 4H), 4.75-4.68 (m, 1H), 4.01-3.86 (m, 1H), 3.36-3.12 (m, 3H), 2.69-2.39 (m, 5H), 2.02-1.89 (m, 1H), 1.67-1.53 (m, 2H), 1.39-1.20 (m, 8H), 0.92-0.83 (m, 3H).

Example 4(13)

2-(2-(2-(3-n-hexylphenyl)-5-oxopyrrolidin-1-yl)ethylthio)thiazole-4-carboxylic acid TLC: Rf 0.32 (dichloroethane:methanol=5:1);

NMR (CDCl₃): δ 8.08 (s, 1H), 7.29 (t, J=8.1 Hz, 1H), 7.18-7.13 (m, 1H), 7.06-7.00 (m, 2H), 4.71-4.65 (m, 1H), 4.01-3.90 (m, 1H), 3.30-3.07 (m, 3H), 2.69-2.41 (m, 5H), 2.02-1.89 (m, 1H), 1.64-1.52 (m, 2H), 1.37-1.22 (m, 6H), 0.91-0.82 (m, 3H).

Example 5(1) to 5(45)

By the same procedure as described in Example 1, using the compound prepared in Reference Example 3 or a corresponding aldehyde derivative, and the compound prepared in Reference Example 9 or a corresponding amine derivative, the following compounds of the present invention were obtained.

Example 5(1)

(13E,16α)-17,17-propano-16-hydroxy-5-(4-methoxycarbonyloxazol-2-yl)-9-oxo-1,2,3,4,20-pentanor-8-azaprost-13-ene

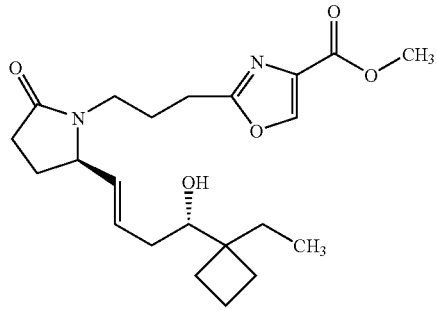

TLC: Rf 0.07 (ethyl acetate);

NMR (CDCl₃): δ 8.14 (s, 1H), 5.78 (dt, J=15.0, 7.5 Hz, 1H), 5.37 (dd, J=15.0, 9.0 Hz, 1H), 4.05 (m, 1H), 3.90 (s, 3H), 3.62-3.49 (m, 2H), 3.05 (m, 1H), 2.80 (t, J=7.5 Hz, 2H), 2.49-2.14 (m, 4H), 2.10-1.52 (m, 11H), 1.44 (m, 1H), 0.91 (t, J=7.5 Hz, 3H).

Example 5(2)

5-(4-ethoxycarbonylthiazol-2-yl)-9-oxo-14,15-(1,4-interphenylene)-1,2,3,4-tetranor-5-thia-8-azaprostane TLC: Rf 0.19 (ethyl acetate:n-hexane=1:1);

NMR (CDCl₃): δ 7.99 (s, 1H), 7.10-7.01 (m, 4H), 4.43-4.34 (m, 3H), 3.44-3.28 (m, 3H), 3.08-2.94 (m, 1H), 2.89-2.41 (m, 8H), 1.84-1.48 (m, 4H), 1.41-1.19 (m, 9H), 0.92-0.81 (m, 3H).

Example 5(3)

(13E)-5-(4-ethoxycarbonylthiazol-2-yl)-9-oxo-1,2,3,4,18,19,20-heptanor-5-thia-8-azaprost-13-ene TLC: Rf 0.29 (hexane:ethyl acetate=1:2);

NMR (CDCl₃): δ 8.03 (s, 1H), 5.65 (dt, J=15.3, 6.6 Hz, 1H), 5.22 (dd, J=15.3, 8.7 Hz, 1H), 4.40 (q, J=7.2 Hz, 2H), 4.14 (m, 1H), 3.83 (dt, J=13.5, 6.9 Hz, 1H), 3.50-3.40 (m, 2H), 3.30 (dt, J=13.5, 6.9 Hz, 1H), 2.46-2.10 (m, 3H), 2.02-1.90 (m, 2H), 1.72 (m, 1H), 1.39 (t, J=7.2 Hz, 3H), 1.38-1.28 (m, 2H), 0.85 (t, J=7.2 Hz, 3H).

Example 5(4)

(13E)-5-(4-ethoxycarbonylthiazol-2-yl)-9-oxo-1,2,3,4,19,20-hexanor-5-thia-8-azaprost-13-ene TLC: Rf 0.30 (hexane:ethyl acetate=1:2);

NMR (CDCl₃): δ 8.02 (s, 1H), 5.65 (dt, J=15.3, 6.6 Hz, 1H), 5.21 (dd, J=15.3, 8.7 Hz, 1H), 4.40 (q, J=7.2 Hz, 2H), 4.14 (m, 1H), 3.83 (dt, J=13.5, 6.9 Hz, 1H), 3.50-3.39 (m, 2H), 3.29 (dt, J=13.5, 6.9 Hz, 1H), 2.46-2.10 (m, 3H), 2.04-1.93 (m, 2H), 1.72 (m, 1H), 1.39 (t, J=7.2 Hz, 3H), 1.36-1.17 (m, 4H), 0.86 (t, J=7.2 Hz, 3H).

Example 5(5)

(2E,13E,16α)-17,17-propano-16-hydroxy-3,6-(1,4-interphenylene)-9-oxo-4,5,20-trinor-8-azaprost-2,13-dienoic acid ethyl ester TLC: Rf 0.30 (ethyl acetate);
NMR (CDCl$_3$): δ 7.65 (d, J=16.0 Hz, 1H), 7.45 (d, J=9.0 Hz, 2H), 7.20 (d, J=9.0 Hz, 2H), 6.40 (d, J=16.0 Hz, 1H), 5.67 (dt, J=15.4, 7.2 Hz, 1H), 5.28 (dd, J=15.4, 8.7 Hz, 1H), 4.25 (q, J=7.2 Hz, 2H), 3.88-3.70 (m, 2H), 3.57 (m, 1H), 3.15 (m, 1H), 2.95-2.70 (m, 2H), 2.50-1.40 (m, 15H), 1.35 (t, J=7.2 Hz, 3H), 0.92 (t, J=7.2 Hz, 3H).

Example 5(6)

(13E,16α)-17,17-propano-16-hydroxy-1,7-(2,5-interthienylene)-9-oxo-2,3,4,5,6,20-hexanor-8-azaprost-13-enoic acid methyl ester TLC: Rf 0.58 (chloroform:methanol=9:1);
NMR (CDCl$_3$): δ 0.93 (t, J=7.2 Hz, 3H), 1.73 (m, 11H), 2.35 (m, 4H), 3.55 (m, 1H), 3.86 (s, 3H), 4.01 (m, 1H), 4.20 (d, J=15.4 Hz, 1H), 4.92 (d, J=15.4 Hz, 1H), 5.37 (dd, J=15.0, 9.0 Hz, 1H), 5.78 (dt, J=15.0, 7.2 Hz, 1H), 6.93 (m, 1H), 7.64 (m, 1H).

Example 5(7)

(13E)-5-(4-ethoxycarbonylthiazol-2-yl)-9-oxo-1,2,3,4-tetranor-5-thia-8-azaprost-13-ene TLC: Rf 0.36 (hexane:ethyl acetate=1:2);
NMR (CDCl$_3$): δ 8.02 (s, 1H), 5.66 (dt, J=15.3, 6.6 Hz, 1H), 5.21 (dd, J=15.3, 8.7 Hz, 1H), 4.40 (q, J=7.2 Hz, 2H), 4.14 (m, 1H), 3.83 (dt, J=13.5, 6.9 Hz, 1H), 3.50-3.40 (m, 2H), 3.29 (dt, J=13.5, 6.9 Hz, 1H), 2.46-2.12 (m, 3H), 2.03-1.91 (m, 2H), 1.72 (m, 1H), 1.39 (t, J=7.2 Hz, 3H), 1.38-1.17 (m, 8H), 0.87 (t, J=7.2 Hz, 3H).

Example 5(8)

(13E)-5-(4-ethoxycarbonylthiazol-2-yl)-9-oxo-20-methyl-1,2,3,4-tetranor-5-thia-8-azaprost-13-ene TLC: Rf 0.37 (hexane:ethyl acetate=1:2);
NMR (CDCl$_3$): δ 8.02 (s, 1H), 5.66 (dt, J=15.0, 6.6 Hz, 1H), 5.21 (dd, J=15.0, 9.0 Hz, 1H), 4.40 (q, J=7.2 Hz, 2H), 4.14 (m, 1H), 3.83 (dt, J=13.8, 6.9 Hz, 1H), 3.50-3.40 (m, 2H), 3.29 (dt, J=13.8, 6.9 Hz, 1H), 2.46-2.12 (m, 3H), 2.03-1.93 (m, 2H), 1.72 (m, 1H), 1.39 (t, J=7.2 Hz, 3H), 1.38-1.16 (m, 10H), 0.88 (t, J=7.2 Hz, 3H).

Example 5(9)

(13E,15α)-15-hydroxy-1,6-(1,4-interphenylene)-9-oxo-2,3,4,5-tetranor-8-azaprost-13-enoic acid methyl ester TLC: Rf 0.18 (ethyl acetate);
NMR (CDCl$_3$): δ 0.89 (m, 3H) 1.49 (m, 9H) 2.12 (m, 1H) 2.35 (m, 2H) 2.87 (m, 2H) 3.12 (m, 1H) 3.79 (m, 2H) 3.91 (s, 3H) 4.11 (m, 1H) 5.38 (dd, J=15.38, 8.52 Hz, 1H) 5.58 (dd, J=15.38, 6.32 Hz, 1H) 7.25 (d, J=7.69 Hz, 2H) 7.96 (d, J=7.97 Hz, 2H).

Example 5(10)

(13E,15α)-15-hydroxy-1,5-(2,5-interthienylene)-9-oxo-2,3,4-trinor-8-azaprost-13-enoic acid methyl ester TLC: Rf 0.26 (ethyl acetate);
NMR (CDCl$_3$): δ 0.89 (t, J=6.59 Hz, 3H) 1.40 (m, 9H) 1.80 (m, 3H) 2.31 (m, 2H) 2.83 (t, J=7.69 Hz, 2H) 2.98 (m, 1H) 3.58 (m, 1H) 3.86 (s, 3H) 4.08 (m, 3H) 5.48 (dd, J=15.38, 8.79 Hz, 1H) 5.68 (dd, J=15.38, 6.32 Hz, 1H) 6.81 (d, J=3.85 Hz, 1H) 7.62 (d, J=3.85 Hz, 1H).

Example 5(11)

(13E,15α)-15-hydroxy-9-oxo-5-thia-8-azaprost-13-enoic acid ethyl ester

TLC: Rf 0.30 (ethyl acetate);
NMR (CDCl$_3$): δ 0.89 (m, 3H) 1.41 (m, 8H) 1.81 (m, 4H) 2.32 (m, 5H) 2.63 (m, 4H) 3.11 (m, 1H) 3.67 (m, 1H) 4.13 (m, 4H) 5.53 (dd, J=15.38, 8.24 Hz, 1H) 5.74 (dd, J=15.38, 5.77 Hz, 1H).

Example 5(12)

(13E)-5-(4-ethoxycarbonylthiazol-2-yl)-9,15-dioxo-1,2,3,4,20-pentanor-5-thia-8-azaprost-13-ene TLC: Rf 0.38 (ethyl acetate);
NMR (CDCl$_3$): δ 8.02 (s, 1H), 6.58 (dd, J=15.6, 7.8 Hz, 1H), 6.24 (d, J=15.6 Hz, 1H), 4.52-4.35 (m, 3H), 3.99-3.88 (m, 1H), 3.53-3.37 (m, 2H), 3.29-3.19 (m, 1H), 2.51 (t, J=7.5 Hz, 2H), 2.47-2.22 (m, 3H), 1.89-1.78 (m, 1H), 1.61-1.50 (m, 2H), 1.42-1.23 (m, 5H), 0.90 (t, J=7.5 Hz, 3H).

Example 5(13)

5-(4-ethoxycarbonylthiazol-2-yl)-9-oxo-1,2,3,4,20-pentanor-5-thia-8-azaprostane

TLC: Rf 0.35 (hexane:ethyl acetate=1:2);
NMR (CDCl$_3$): δ 8.02 (s, 1H), 4.39 (q, J=7.2 Hz, 2H), 3.89 (m, 1H), 3.71 (m, 1H), 3.54-3.31 (m, 3H), 2.46-2.22 (m, 2H), 2.12 (m, 1H), 1.78-1.60 (m, 2H), 1.39 (t, J=7.2 Hz, 3H), 1.38-1.16 (m, 11H), 0.87 (t, J=7.2 Hz, 3H).

Example 5(14)

(13E,15α)-20-ethyl-15-hydroxy-5-(4-butoxycarbonylthiazol-2-yl)-9-oxo-1,2,3,4-tetranor-5-thia-8-azaprost-13-ene TLC: Rf 0.40 (ethyl acetate);
NMR (CDCl$_3$): δ 0.88 (m, 3H) 0.97 (t, J=7.42 Hz, 3H) 1.27 (m, 10H) 1.45 (m, 4H) 1.76 (m, 3H) 1.95 (d, J=4.40 Hz, 1H) 2.30 (m, 3H) 3.41 (m, 3H) 3.76 (m, 1H) 4.08 (m, 1H) 4.22 (m, 1H) 4.33 (m, 2H) 5.55 (m, 1H) 5.79 (m, 1H) 7.99 (d, J=3.02 Hz, 1H).

Example 5(15)

(13E,15α)-20-methyl-15-hydroxy-5-(4-butoxycarbonylthiazol-2-yl)-9-oxo-1,2,3,4-tetranor-5-thia-8-azaprost-13-ene TLC: Rf 0.32 (ethyl acetate);
NMR (CDCl$_3$): δ 7.99 (s, 1H), 5.79 (dd, J=15.3, 5.7 Hz, 1H), 5.54 (ddd, J=15.3, 8.4, 1.2 Hz, 1H), 4.33 (t, J=6.9 Hz, 2H), 4.26-4.16 (m, 1H), 4.14-4.04 (m, 1H), 3.80-3.70 (m, 1H), 3.50-3.30 (m, 4H), 2.45-2.15 (m, 3H), 1.95-1.90 (m, 1H), 1.80-1.65 (m, 3H), 1.50-1.40 (m, 3H), 1.35-1.20 (m, 8H), 0.97 (t, J=7.2 Hz, 3H), 0.90-0.80 (m, 3H).

Example 5(16)

(13E,15α)-20-n-propyl-15-hydroxy-5-(4-butoxycarbonylthiazol-2-yl)-9-oxo-1,2,3,4-tetranor-5-thia-8-azaprost-13-ene TLC: Rf 0.32 (ethyl acetate);
NMR (CDCl$_3$): δ 7.99 (s, 1H), 5.78 (dd, J=15.6, 5.7 Hz, 1H), 5.54 (ddd, J=15.6, 8.4, 1.2 Hz, 1H), 4.33 (t, J=6.9 Hz, 2H), 4.26-4.16 (m, 1H), 4.14-4.04 (m, 1H), 3.80-3.70 (m, 1H), 3.50-3.30 (m, 4H), 2.45-2.15 (m, 3H), 1.95-1.90 (m, 1H), 1.80-1.65 (m, 3H), 1.50-1.40 (m, 3H), 1.35-1.20 (m, 12H), 0.97 (t, J=7.2 Hz, 3H), 0.90-0.80 (m, 3H).

Example 5(17)

(1Z)-5-(4-ethoxycarbonylthiazol-2-yl)-9-oxo-1,2,3,4,20-pentanor-5-thia-8-azaprost-13-ene TLC: Rf 0.28 (hexane:ethyl acetate=1:2);
NMR (CDCl$_3$): δ 8.02 (s, 1H), 5.59 (dt, J=10.5, 7.8 Hz, 1H), 5.22 (dd, J=10.5, 9.9 Hz, 1H), 4.53 (dt, J=9.9, 6.9 Hz, 1H), 4.39 (q, J=7.2 Hz, 2H), 3.77 (dt, J=14.1, 6.3 Hz, 1H), 3.45 (t, J=6.3 Hz, 2H), 3.33 (dt, J=14.1, 6.3 Hz, 1H), 2.45-1.93 (m, 5H), 1.67 (m, 1H), 1.39 (t, J=7.2 Hz, 3H), 1.38-1.16 (m, 6H), 0.87 (t, J=7.2 Hz, 3H).

Example 5(18)

(13Z)-16-oxa-17,17-dimethyl-5-(4-ethoxycarbonylthiazol-2-yl)-9-oxo-1,2,3,4,19,20-hexanor-5-thia-8-azaprost-13-ene TLC: Rf 0.20 (hexane:ethyl acetate=1:2);
NMR (CDCl$_3$): δ 8.02 (s, 1H), 5.76 (dt, J=11.1, 6.3 Hz, 1H), 5.37 (dd, J=11.1, 9.9 Hz, 1H), 4.64 (dt, J=9.9, 6.6 Hz, 1H), 4.39 (q, J=7.2 Hz, 2H), 4.04-3.90 (m, 2H), 3.82 (dt, J=13.5, 6.3 Hz, 1H), 3.54-3.41 (m, 2H), 3.35 (dt, J=13.5, 6.3 Hz, 1H), 2.48-2.13 (m, 3H), 1.71 (m, 1H), 1.39 (t, J=7.2 Hz, 3H), 1.19 (s, 9H).

Example 5(19)

(13E)-16-oxa-17,17-dimethyl-5-(4-ethoxycarbonylthiazol-2-yl)-9-oxo-1,2,3,4,19,20-hexanor-5-thia-8-azaprost-13-ene TLC: Rf 0.20 (hexane:ethyl acetate=1:2);
NMR (CDCl$_3$): δ 8.02 (s, 1H), 5.77 (dt, J=15.3, 5.1 Hz, 1H), 5.50 (dd, J=15.3, 9.0 Hz, 1H), 4.40 (q, J=7.2, Hz, 2H), 4.20 (dt, J=5.1, 8.1 Hz, 1H), 3.90-3.78 (m, 3H), 3.44 (t, J=6.3 Hz, 2H), 3.31 (dt, J=13.2, 6.3 Hz, 1H), 2.48-2.12 (m, 3H), 1.77 (m, 1H), 1.39 (t, J=7.2 Hz, 3H), 1.18 (s, 9H).

Example 5(20)

(13E,15α)-19-phenyl-15-hydroxy-5-(4-butoxycarbonylthiazol-2-yl)-9-oxo-1,2,3,4,20-pentanor-5-thia-8-azaprost-13-ene TLC: Rf 0.27 (ethyl acetate);
NMR (CDCl$_3$): δ 0.96 (t, J=7.14 Hz, 3H) 1.51 (m, 11H) 2.00 (d, J=4.67 Hz, 1H) 2.29 (m, 3H) 2.58 (t, J=7.69 Hz, 2H) 3.37 (m, 3H) 3.76 (m, 1H) 4.14 (m, 2H) 4.31 (t, J=6.59 Hz, 2H) 5.54 (ddd, J=15.38, 8.52, 1.10 Hz, 1H) 5.78 (dd, J=15.66, 5.77 Hz, 1H) 7.21 (m, 5H) 7.98 (s, 1H).

Example 5(21)

(13E,15α)-20-phenyl-15-hydroxy-5-(4-butoxycarbonylthiazol-2-yl)-9-oxo-1,2,3,4-tetranor-5-thia-8-azaprost-13-ene TLC: Rf 0.29 (ethyl acetate);
NMR (CDCl$_3$): δ 0.97 (t, J=7.42 Hz, 3H) 1.52 (m, 13H) 1.97 (d, J=4.67 Hz, 1H) 2.31 (m, 3H) 2.59 (t, J=7.14 Hz, 2H) 3.40 (m, 3H) 3.77 (m, 1H) 4.14 (m, 2H) 4.32 (t, J=6.87 Hz, 2H) 5.54 (ddd, J=15.38, 8.52, 1.10 Hz, 1H) 5.79 (dd, J=15.38, 5.49 Hz, 1H) 7.22 (m, 5H) 7.95 (s, 1H).

Example 5(22)

(13E,15α)-20-benzyl-15-hydroxy-5-(4-butoxycarbonylthiazol-2-yl)-9-oxo-1,2,3,4-tetranor-5-thia-8-azaprost-13-ene TLC: Rf 0.29 (ethyl acetate);
NMR (CDCl$_3$): δ 0.97 (t, J=7.42 Hz, 2H) 1.52 (m, 15H) 1.96 (d, J=4.67 Hz, 1H) 2.31 (m, 3H) 2.59 (t, J=7.42 Hz, 2H) 3.39 (m, 3H) 3.77 (m, 1H) 4.14 (m, 2H) 4.32 (t, J=6.87 Hz, 2H) 5.55 (ddd, J=15.66, 8.79, 1.10 Hz, 1H) 5.78 (dd, J=15.66, 5.77 Hz, 1H) 7.23 (m, 5H) 7.97 (s, 1H).

Example 5(23)

(13E,16α)-17,17-propano-16-hydroxy-1,6-(1,3-interphenylene)-9-oxo-2,3,4,5,20-pentanor-8-azaprost-13-enoic acid methyl ester TLC: Rf 0.29 (ethyl acetate);
NMR (CDCl$_3$): δ 0.92 (t, J=7.4 Hz, 3H), 1.43 (m, 1H), 2.00 (m, 14H), 2.80 (m, 1H), 2.92 (m, 1H), 3.15 (m, 1H), 3.57 (dd, J=9.7, 2.3 Hz, 1H), 3.76 (m, 1H), 3.88 (m, 1H), 3.91 (m, 3H), 5.26 (dd, J=15.2, 8.9 Hz, 1H), 5.79 (dt, J=15.2, 7.2 Hz, 1H), 7.39 (m, 2H), 7.89 (m, 2H).

Example 5(24)

(15α)-15-hydroxy-5-(4-ethoxycarbonylthiazol-2-yl)-9-oxo-1,2,3,4-tetranor-5-thia-8-azaprostane TLC: Rf 0.20 (ethyl acetate);
NMR (CDCl$_3$): δ 0.89 (t, J=6.59 Hz, 3H) 1.48 (m, 15H) 1.97 (m, 1H) 2.14 (m, 1H) 2.36 (m, 2H) 2.53 (d, J=5.22 Hz, 1H) 3.60 (m, 6H) 4.38 (q, J=7.14 Hz, 2H) 7.99 (s, 1H).

Example 5(25)

(15α)-15-hydroxy-1,6-(1,4-interphenylene)-9-oxo-2,3,4,5-tetranor-5-thia-8-azaprostanoic acid methyl ester TLC: Rf 0.20 (ethyl acetate);
NMR (CDCl$_3$): δ 0.90 (t, J=6.59 Hz, 3H) 1.47 (m, 13H) 2.04 (m, 1H) 2.32 (m, 2H) 2.87 (m, 2H) 3.06 (m, 1H) 3.40 (m, 1H) 3.57 (m, 1H) 3.86 (m, 4H) 7.30 (d, J=8.52 Hz, 2H) 7.97 (d, J=8.52 Hz, 2H).

Example 5(26)

(13E)-17,17-dimethyl-5-(4-ethoxycarbonylthiazol-2-yl)-9-oxo-1,2,3,4,19,20-hexanor-5-thia-8-azaprost-13-ene TLC: Rf 0.20 (hexane:ethyl acetate=1:1);
NMR (CDCl$_3$): δ 8.02 (s, 1H), 5.67 (dt, J=15.0, 6.9 Hz, 1H), 5.21 (dd, J=15.0, 8.7 Hz, 1H), 4.39 (q, J=7.2 Hz, 2H), 4.14 (m, 1H), 3.83 (dt, J=13.5, 6.9 Hz, 1H), 3.50-3.37 (m, 2H), 3.30 (dt, J=13.5, 6.9 Hz, 1H), 2.46-2.11 (m, 3H), 2.00-1.89 (m, 3H), 1.71 (m, 1H), 1.39 (t, J=7.2 Hz, 3H), 1.22-1.12 (m, 2H), 0.86 (s, 9H).

Example 5(27)

(13E)-17,17-dimethyl-5-(4-ethoxycarbonylthiazol-2-yl)-9-oxo-1,2,3,4,20-pentanor-5-thia-8-azaprost-13-ene TLC: Rf 0.20 (hexane:ethyl acetate=1:1);
NMR (CDCl$_3$): δ 8.02 (s, 1H), 5.67 (dt, J=15.0, 6.9 Hz, 1H), 5.21 (dd, J=15.0, 8.7 Hz, 1H), 4.39 (q, J=7.2 Hz, 2H), 4.14 (m, 1H), 3.83 (dt, J=13.5, 6.6 Hz, 1H), 3.50-3.38 (m, 2H), 3.30 (dt, J=13.5, 6.6 Hz, 1H), 2.47-2.08 (m, 3H), 1.96-1.84 (m, 3H), 1.72 (m, 1H), 1.39 (t, J=7.2 Hz, 3H), 1.24-1.18 (m, 2H), 0.86-0.71 (m, 9H).

Example 5(28)

(13E,15α)-19-phenyl-15-hydroxy-9-oxo-20-nor-5-thia-8-azaprost-13-enoic acid butyl ester TLC: Rf 0.33 (methylene chloride:methanol=9:1);
NMR (CDCl$_3$): δ 7.32-7.24 (m, 2H), 7.21-7.14 (m, 3H), 5.72 (dd, J=15.3, 6.0 Hz, 1H), 5.50 (ddd, J=15.3, 9.0, 0.6 Hz, 1H), 4.20-4.00 (m, 4H), 3.70-3.60 (m, 1H), 3.10-3.00 (m, 1H), 2.70-2.50 (m, 6H), 2.45-2.15 (m, 5H), 1.95-1.30 (m, 14H), 0.93 (t, J=7.2 Hz, 3H).

Example 5(29)

(13E,15α)-20-phenyl-15-hydroxy-9-oxo-5-thia-8-azaprost-13-enoic acid butyl ester TLC: Rf 0.33 (methylene chloride:methanol=9:1);
NMR (CDCl$_3$): δ 7.30-7.23 (m, 2H), 7.20-7.13 (m, 3H), 5.73 (dd, J=15.3, 5.7 Hz, 1H), 5.51 (ddd, J=15.3, 8.7, 1.2 Hz, 1H), 4.20-4.05 (m, 4H), 3.75-3.60 (m, 1H), 3.15-3.05 (m, 1H), 2.70-2.50 (m, 6H), 2.45-2.15 (m, 5H), 1.95-1.30 (m, 16H), 0.93 (t, J=7.5 Hz, 3H).

Example 5(30)

(13E,15α)-20-benzyl-15-hydroxy-9-oxo-5-thia-8-azaprost-13-enoic acid butyl ester TLC: Rf 0.33 (methylene chloride:methanol=9:1);
NMR (CDCl$_3$): δ 7.30-7.22 (m, 2H), 7.20-7.15 (m, 3H), 5.73 (dd, J=15.3, 5.7 Hz, 1H), 5.52 (ddd, J=15.3, 8.4, 1.2 Hz, 1H), 4.20-4.05 (m, 4H), 3.72-3.60 (m, 1H), 3.15-3.05 (m, 1H), 2.70-2.20 (m, 11H), 1.95-1.20 (m, 18H), 0.93 (t, J=7.5 Hz, 3H).

Example 5(31)

14-oxa-14-phenyl-5-(4-butoxycarbonylthiazol-2-yl)-9-oxo-1,2,3,4,15,16,17,18,19,20-decanor-5-thia-8-azaprostane TLC: Rf 0.45 (ethyl acetate);
NMR (CDCl$_3$): δ 7.97 (s, 1H), 7.25 (dd, J=8.7, 7.5 Hz, 2H), 6.94 (t, J=7.5 Hz, 1H), 6.88 (d, J=8.7 Hz, 2H), 4.37 (dd, J=9.9, 3.6 Hz, 1H), 4.35-4.27 (m, 2H), 4.14 (m, 1H), 4.00 (dd, J=9.9, 3.6 Hz, 1H), 3.64-3.32 (m, 3H), 2.58 (m, 1H), 2.37 (m, 1H), 2.22 (m, 1H), 2.03 (m, 1H), 1.80-1.68 (m, 2H), 1.52-1.37 (m, 2H), 0.97 (t, J=7.2 Hz, 3H).

Example 5(32)

14-oxa-14-(3,5-dichlorophenyl)-5-(4-butoxycarbonylthiazol-2-yl)-9-oxo-1,2,3,4,15,16,17,18,19,20-decanor-5-thia-8-azaprostane TLC: Rf 0.53 (ethyl acetate);
NMR (CDCl$_3$): δ 7.97 (s, 1H), 6.93 (t, J=1.8 Hz, 1H), 6.87 (d, J=1.8 Hz, 2H), 4.69 (dd, J=10.2, 3.0 Hz, 1H), 4.38-4.30 (m, 2H), 4.12 (m, 1H), 4.00 (dd, J=10.2, 3.0 Hz, 1H), 3.84 (m, 1H), 3.61 (m, 1H), 3.47 (m, 1H), 3.26 (m, 1H), 2.57 (m, 1H), 2.39 (m, 1H), 2.23 (m, 1H), 2.06 (m, 1H), 1.80-1.69 (m, 2H), 1.52-1.38 (m, 2H), 0.97 (t, J=7.2 Hz, 3H).

Example 5(33)

(13E,16α)-17,17-propano-16-hydroxy-6-(4-ethoxycarbonylthiazol-2-ylsulfonyl)-9-oxo-1,2,3,4,5,20-hexanor-8-azaprost-13-ene TLC: Rf 0.33 (ethyl acetate);
NMR (CDCl$_3$): δ 0.93 (t, J=7.5 Hz, 3H), 1.42 (m, 1H), 1.42 (t, J=7.2 Hz, 3H), 1.84 (m, 10H), 2.29 (m, 4H), 3.75 (m, 5H), 4.22 (m, 1H), 4.45 (q, J=7.2 Hz, 2H), 5.39 (dd, J=15.1, 9.0 Hz, 1H), 5.93 (dt, J=15.1, 7.2 Hz, 1H), 8.47 (s, 1H).

Example 5(34)

14-oxa-5-(4-butoxycarbonylthiazol-2-yl)-9-oxo-1,2,3,4,19,20-hexanor-5-thia-8-azaprostane TLC: Rf 0.47 (ethyl acetate);
NMR (CDCl$_3$): δ 0.88 (t, J=7.2 Hz, 3H), 0.97 (t, J=7.2 Hz, 3H), 1.23-1.58 (m, 7H), 1.69-1.89 (m, 3H), 2.09 (m, 1H), 2.28 (m, 1H), 2.44 (m, 1H), 3.37-3.60 (m, 6H), 3.63 (dd, J=10.2, 3.6 Hz, 1H), 3.84-3.97 (m, 2H), 4.33 (t, J=6.6 Hz, 2H), 8.00 (s, 1H).

Example 5(35)

17,17-propano-5-(4-ethoxycarbonylthiazol-2-yl)-9,16-dioxo-1,2,3,4,20-pentanor-5-thia-8-azaprostane TLC: Rf 0.41 (ethyl acetate);
NMR (CDCl$_3$): δ 0.74 (t, J=7.5 Hz, 3H), 1.39 (t, J=7.1 Hz, 3H), 1.56 (m, 1H), 1.65-2.00 (m, 9H), 2.10-2.55 (m, 8H), 3.35-3.55 (m, 3H), 3.72 (m, 1H), 3.88 (m, 1H), 4.38 (q, J=7.1 Hz, 2H), 8.01 (s, 1H).

Example 5(36)

(13E)-17-oxa-5-(4-ethoxycarbonylthiazol-2-yl)-9-oxo-1,2,3,4,20-pentanor-5-thia-8-azaprost-13-ene TLC: Rf 0.16 (hexane:ethyl acetate=1:2);
NMR (CDCl$_3$): δ 8.02 (s, 1H), 5.70 (dt, J=15.3, 6.6 Hz, 1H), 5.33 (dd, J=15.3, 8.7 Hz, 1H), 4.40 (q, J=7.2 Hz, 2H), 4.15 (m, 1H), 3.82 (m, 1H), 3.50-3.27 (m, 7H), 2.47-2.12 (m, 5H), 1.73 (m, 1H), 1.39 (t, J=7.2 Hz, 3H), 1.17 (t, J=7.2 Hz, 3H).

Example 5(37)

(13E)-16-oxa-5-(4-ethoxycarbonylthiazol-2-yl)-9-oxo-1,2,3,4,20-pentanor-5-thia-8-azaprost-13-ene TLC: Rf 0.17 (hexane:ethyl acetate=1:2);

NMR (CDCl$_3$): δ 8.02 (s, 1H), 5.79 (dt, J=15.3, 5.1 Hz, 1H), 5.53 (ddt, J=15.3, 8.4, 1.8 Hz, 1H), 4.39 (q, J=7.2 Hz, 2H), 4.24 (m, 1H), 3.92 (dd, J=5.1, 1.8 Hz, 2H), 3.85 (m, 1H), 3.50-3.41 (m, 2H), 3.40-3.24 (m, 3H), 2.49-2.14 (m, 3H), 1.77 (m, 1H), 1.65-1.51 (m, 2H), 1.39 (t, J=7.2 Hz, 3H), 0.90 (t, J=7.2 Hz, 3H).

Example 5(38)

13-(N-(benzylsulfonyl)amino)-5-(4-butoxycarbonylthiazol-2-yl)-9-oxo-1,2,3,4,14,15,16,17,18,19,20-undecanor-5-thia-8-azaprostane TLC: Rf 0.32 (ethyl acetate);

NMR (CDCl$_3$): δ 0.97 (t, J=7.20 Hz, 3H) 1.45 (m, 2H) 1.73 (m, 2H) 1.90 (m, 1H) 2.10 (m, 1H) 2.33 (m, 2H) 3.02 (m, 1H) 3.16 (m, 1H) 3.29 (m, 1H) 3.50 (m, 2H) 3.82 (m, 2H) 4.28 (m, 4H) 5.67 (t, J=6.50 Hz, 1H) 7.30 (m, 3H) 7.42 (m, 2H) 8.01 (s, 1H).

Example 5(39)

(13E)-19-phenyl-5-(4-ethoxycarbonylthiazol-2-yl)-9-oxo-1,2,3,4,20-pentanor-5-thia-8-azaprost-13-ene TLC: Rf 0.41 (hexane:ethyl acetate=1:2);

NMR (CDCl$_3$): δ 8.01 (s, 1H), 5.64 (dt, J=15.6, 6.6 Hz, 1H), 5.20 (dd, J=15.6, 8.7 Hz, 1H), 4.38 (q, J=7.2 Hz, 2H), 4.13 (m, 1H), 3.81 (m, 1H), 3.48-3.38 (m, 2H), 3.27 (m, 1H), 2.58 (t, J=7.5 Hz, 2H), 2.46-2.11 (m, 3H), 2.04-1.93 (m, 2H), 1.69 (m, 1H), 1.64-1.52 (m, 2H), 1.38 (t, J=7.2 Hz, 3H), 1.40-1.22 (m, 4H).

Example 5(40)

5-(4-ethoxycarbonylthiazol-2-yl)-9,13-dioxo-1,2,3,4,20-pentanor-5-thia-8,14-diazaprostane TLC: Rf 0.19 (ethyl acetate);

NMR (CDCl$_3$): δ 8.02 (s, 1H), 7.32 (m, 1H), 4.45-4.34 (m, 3H), 3.88 (m, 1H), 3.48-3.30 (m, 3H), 3.29-3.11 (m, 2H), 2.74 (dt, J=16.2, 7.8 Hz, 1H), 2.39-2.10 (m, 3H), 1.48-1.34 (m, 5H), 1.31-1.10 (m, 4H), 0.81 (t, J=6.9 Hz, 3H).

Example 5(41)

(13E)-16-hydroxy-5-(4-ethoxycarbonylthiazol-2-yl)-9-oxo-1,2,3,4,20-pentanor-5-thia-8-azaprost-13-ene TLC: Rf 0.28 (ethyl acetate);

NMR (CDCl$_3$): δ 0.91 (m, 3H), 1.36 (m, 7H), 1.74 (m, 1H), 2.25 (m, 5H), 3.58 (m, 6H), 4.18 (m, 1H), 4.39 (q, J=7.1 Hz, 2H), 5.37 (m, 1H), 5.80 (m, 1H), 8.01 (m, 1H).

Example 5(42)

13-(N-methyl-N-(benzylsulfonyl)amino)-5-(4-butoxycarbonylthiazol-2-yl)-9-oxo-1,2,3,4,14,15,16,17,18,19,20-undecanor-5-thia-8-azaprostane TLC: Rf 0.55 (ethyl acetate);

NMR (CDCl$_3$): δ 0.96 (t, J=7.28 Hz, 3H) 1.44 (m, 2H) 1.73 (m, 2H) 2.03 (m, 2H) 2.25 (m, 1H) 2.42 (m, 1H) 2.86 (s, 3H) 2.95 (dd, J=13.87, 8.10 Hz, 1H) 3.20 (dd, J=14.01, 4.12 Hz, 1H) 3.29 (m, 1H) 3.42 (m, 2H) 3.82 (m, 2H) 4.30 (m, 4H) 7.38 (m, 5H) 8.01 (s, 1H).

Example 5(43)

14-oxa-14-(pyridin-3-yl)-5-(4-butoxycarbonylthiazol-2-yl)-9-oxo-1,2,3,4,15,16,17,18,19,20-decanor-5-thia-8-azaprostane TLC: Rf 0.47 (ethyl acetate:methanol=9:1);

NMR (CDCl$_3$): δ 0.97 (t, J=7.40 Hz, 3H) 1.46 (m, 2H) 1.74 (m, 2H) 2.07 (m, 1H) 2.32 (m, 2H) 2.60 (m, 1H) 3.34 (m, 1H) 3.49 (m, 1H) 3.61 (m, 1H) 3.89 (m, 1H) 4.13 (m, 2H) 4.32 (m, 2H) 4.59 (dd, J=10.16, 3.30 Hz, 1H) 7.18 (ddd, J=8.40, 4.40, 0.60 Hz, 1H) 7.26 (ddd, J=8.40, 2.90, 1.40 Hz, 1H) 7.97 (s, 1H) 8.22 (dd, J=4.40, 1.40 Hz, 1H) 8.32 (m, 1H).

Example 5(44)

(13E,15α)-19-phenoxy-15-hydroxy-5-(4-butoxycarbonylthiazol-2-yl)-9-oxo-1,2,3,4,20-pentanor-5-thia-8-azaprost-13-ene NMR (CDCl$_3$): δ 7.98 (s, 1H), 7.25 (m, 2H), 6.90 (m, 3H), 5.81 (dd, J=15.0, 5.7 Hz, 1H), 5.58 (dd, J=15.0, 8.4 Hz, 1H), 4.32 (t, J=7.2 Hz, 2H), 4.18 (m, 2H), 3.93 (t, J=7.2 Hz, 2H), 3.67 (m, 1H), 3.42 (m, 3H), 2.31 (m, 3H), 2.12 (d, J=5.1 Hz, 1H), 1.78 (m, 5H), 1.50 (m, 6H), 0.96 (t, J=7.2 Hz, 3H).

Example 5(45)

(13E,15α)-20-phenoxy-15-hydroxy-5-(4-butoxycarbonylthiazol-2-yl)-9-oxo-1,2,3,4-tetranor-5-thia-8-azaprost-13-ene NMR (CDCl$_3$): δ 7.99 (s, 1H), 7.25 (m, 2H), 6.90 (m, 3H), 5.82 (dd, J=15.0, 5.7 Hz, 1H), 5.58 (dd, J=15.0, 8.4 Hz, 1H), 4.32 (t, J=7.2 Hz, 2H), 4.18 (m, 2H), 3.95 (t, J=7.2 Hz, 2H), 3.67 (m, 1H), 3.42 (m, 3H), 2.31 (m, 3H), 2.04 (d, J=5.1 Hz, 1H), 1.78 (m, 5H), 1.50 (m, 8H), 0.96 (t, J=7.2 Hz, 3H).

Example 6(1) to 6(92)

By the same procedure as described in Example 2, using the compound prepared in Example 5(1) to 5(45) or a corresponding ester instead of the compound prepared in Example 1, the following compounds of the present invention were obtained.

Example 6(1)

(13E,16α)-17,17-propano-16-hydroxy-5-(4-carboxy-oxazol-2-yl)-9-oxo-1,2,3,4,20-pentanor-8-azaprost-13-ene

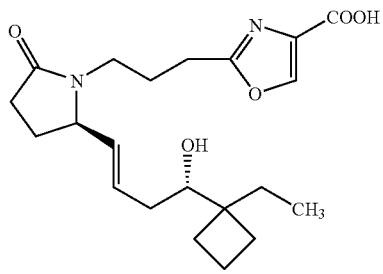

TLC: Rf 0.10 (chloroform:methanol:acetic acid=9:1:0.1);
NMR (CDCl$_3$): δ 8.21 (s, 1H), 5.82 (dt, J=15.3, 7.2 Hz, 1H), 5.42 (dd, J=15.3, 9.0 Hz, 1H), 4.06 (m, 1H), 3.64 (dd, J=9.6, 2.1 Hz, 1H), 3.49 (dt, J=14.1, 7.2 Hz, 1H), 3.16 (ddd, J=14.1, 8.1, 6.0 Hz, 1H), 2.83 (t, J=7.5 Hz, 2H), 2.52-2.16 (m, 4H), 2.15-1.90 (m, 5H), 1.90-1.56 (m, 6H), 1.44 (m, 1H), 0.92 (t, J=7.5 Hz, 3H).

Example 6(2)

5-(4-carboxythiazol-2-yl)-9-oxo-14,15-(1,4-interphenylene)-1,2,3,4-tetranor-5-thia-8-azaprostane TLC: Rf 0.55 (methylene chloride:methanol=5:1);
NMR (CDCl$_3$): δ 8.07 (s, 1H), 7.16-7.01 (m, 4H), 3.98-3.83 (m, 1H), 3.73-3.62 (m, 1H), 3.50-3.19 (m, 4H), 2.71-2.01 (m, 8H), 1.82-1.51 (m, 4H), 1.39-1.18 (m, 6H), 0.93-0.78 (m, 3H).

Example 6(3)

(13E)-5-(4-carboxythiazol-2-yl)-9-oxo-1,2,3,4,18,19,20-heptanor-5-thia-8-azaprost-13-ene TLC: Rf 0.42 (chloroform:methanol:acetic acid=9:1:0.1);
NMR (CDCl$_3$): δ 8.09 (s, 1H), 5.71 (dt, J=15.3, 6.9 Hz, 1H), 5.27 (dd, J=15.3, 8.7 Hz, 1H), 4.07 (m, 1H), 3.82 (ddd, J=15.3, 9.0, 5.7 Hz, 1H), 3.50 (ddd, J=15.3, 9.6, 5.7 Hz, 1H), 3.41-3.22 (m, 2H), 2.55-2.17 (m, 3H), 2.17-1.98 (m, 2H), 1.75 (m, 1H), 1.41 (q, J=7.5 Hz, 2H), 0.90 (t, J=7.5 Hz, 3H).

Example 6(4)

(13E)-5-(4-carboxythiazol-2-yl)-9-oxo-1,2,3,4,19,20-hexanor-5-thia-8-azaprost-13-ene TLC: Rf 0.39 (chloroform:methanol:acetic acid=9:1:0.1);
NMR (CDCl$_3$): δ 8.09 (s, 1H), 5.72 (dt, J=15.3, 6.6 Hz, 1H), 5.27 (dd, J=15.3, 9.0 Hz, 1H), 4.06 (m, 1H), 3.81 (ddd, J=15.3, 9.6, 6.3 Hz, 1H), 3.50 (ddd, J=15.3, 9.6, 5.7 Hz, 1H), 3.42-3.22 (m, 2H), 2.44-2.25 (m, 3H), 2.25-2.01 (m, 2H), 1.75 (m, 1H), 1.44-1.32 (m, 4H), 0.90 (t, J=6.9 Hz, 3H).

Example 6(5)

(13E,16α)-17,17-propano-16-hydroxy-3,6-(1,4-interphenylene)-9-oxo-4,5,20-trinor-3-oxa-8-azaprost-13-enoic acid TLC: Rf 0.30 (chloroform:methanol:acetic acid=90:10:1);
NMR (CDCl$_3$): δ 0.92 (t, J=7.5 Hz, 3H), 1.43 (m, 1H), 1.55-2.50 (m, 13H), 2.65-2.85 (m, 2H), 3.10 (m, 1H), 3.57 (dd, J=9.6, 2.7 Hz, 1H), 3.65-3.80 (m, 2H), 4.00-5.00 (br, 2H), 4.63 (s, 2H), 5.20 (dd, J=15.0, 9.0 Hz, 1H), 5.60 (dt, J=15.0, 7.2 Hz, 1H), 6.85 (d, J=8.2 Hz, 2H), 7.09 (d, J=8.2 Hz, 2H).

Example 6(6)

(2E,13E,16α)-17,17-propano-16-hydroxy-3,6-(1,4-interphenylene)-9-oxo-4,5,20-trinor-8-azaprost-2,13-dienoic acid TLC: Rf 0.48 (chloroform:methanol:acetic acid=90:10:1);
NMR (CDCl$_3$): δ 0.93 (t, J=7.5 Hz, 3H), 1.44 (m, 1H), 1.55-2.50 (m, 13H), 2.75-2.95 (m, 2H), 3.18 (m, 1H), 3.57 (dd, J=9.6, 2.4 Hz, 1H), 3.70-3.90 (m, 2H), 5.29 (dd, J=15.3, 8.7 Hz, 1H), 5.68 (dt, J=15.3, 7.5 Hz, 1H), 6.41 (d, J=15.9 Hz, 1H), 7.23 (d, J=8.2 Hz, 2H), 7.47 (d, J=8.2 Hz, 2H), 7.73 (d, J=15.9 Hz, 1H).

Example 6(7)

(13E,16α)-17,17-propano-16-hydroxy-1,7-(2,5-interthienylene)-9-oxo-2,3,4,5,6,20-hexanor-8-azaprost-13-enoic acid TLC: Rf 0.42 (chloroform:methanol:acetic acid=90:10:1);
NMR (CDCl$_3$): δ 0.93 (t, J=7.5 Hz, 3H), 1.44 (m, 1H), 1.55-2.60 (m, 13H), 3.00-4.50 (br, 2H), 3.57 (dd, J=9.9, 2.1 Hz, 1H), 4.02 (m, 1H), 4.20 (d, J=15.0 Hz, 1H), 4.94 (d, J=15.0 Hz, 1H), 5.37 (dd, J=15.3, 9.3 Hz, 1H), 5.80 (dt, J=15.3, 7.5 Hz, 1H), 6.95 (d, J=3.0 Hz, 1H), 7.68 (d, J=3.0 Hz, 1H).

Example 6(8)

(13E)-5-(4-carboxythiazol-2-yl)-9-oxo-1,2,3,4-tetranor-5-thia-8-azaprost-13-ene

TLC: Rf 0.30 (chloroform:methanol:acetic acid=9:1:0.1);
NMR (CDCl$_3$): δ 8.08 (s, 1H), 5.72 (dt, J=15.0, 6.9 Hz, 1H), 5.26 (dd, J=15.0, 8.7 Hz, 1H), 4.06 (m, 1H), 3.81 (ddd, J=13.5, 9.6, 6.0 Hz, 1H), 3.50 (ddd, J=13.5, 9.6, 5.1 Hz, 1H), 3.40-3.21 (m, 2H), 2.55-2.14 (m, 3H), 2.12-1.99 (m, 2H), 1.75 (m, 1H), 1.45-1.20 (m, 8H), 0.88 (t, J=6.9 Hz, 3H).

Example 6(9) (13E)-5-(4-carboxythiazol-2-yl)-9-oxo-20-methyl-1,2,3,4-tetranor-5-thia-8-azaprost-13-ene TLC: Rf 0.30 (chloroform:methanol:acetic acid=9:1:0.1);
NMR (CDCl$_3$): δ 8.09 (s, 1H), 5.71 (dt, J=15.3, 6.6 Hz, 1H), 5.26 (dd, J=15.3, 8.7 Hz, 1H), 4.06 (m, 1H), 3.81 (ddd, J=13.5, 9.6, 5.7 Hz, 1H), 3.49 (ddd, J=13.5, 9.6, 5.7 Hz, 1H), 3.42-3.20 (m, 2H), 2.54-2.15 (m, 3H), 2.14-1.99 (m, 2H), 1.75 (m, 1H), 1.45-1.17 (m, 10H), 0.88 (t, J=6.9 Hz, 3H).

Example 6(10)

(13E,15α)-15-hydroxy-1,6-(1,4-interphenylene)-9-oxo-2,3,4,5-tetranor-8-azaprost-13-enoic acid TLC: Rf 0.51 (chloroform:methanol:acetic acid=9:1:0.1);
NMR (d6-dmso): δ 7.84 (d, J=8.4 Hz, 2H), 7.28 (d, J=8.4 Hz, 2H), 5.62 (dd, J=15.6, 6.3 Hz, 1H), 5.33 (dd, J=15.6, 8.7 Hz, 1H), 4.71 (d, J=4.8 Hz, 1H), 4.00-3.84 (m, 2H), 3.60 (m, 1H), 2.99 (m, 1H), 2.89-2.66 (m, 2H), 2.30-2.00 (m, 3H), 1.60 (m, 1H), 1.50-1.15 (m, 8H), 0.81 (t, J=6.3 Hz, 3H).

Example 6(11)

(13E,15α)-15-hydroxy-1,5-(2,5-interthienylene)-9-oxo-2,3,4-trinor-8-azaprost-13-enoic acid TLC: Rf 0.44 (chloroform:methanol:acetic acid=9:1:0.1);
NMR (CDCl$_3$): δ 7.69 (d, J=3.9 Hz, 1H), 6.83 (d, J=3.9 Hz, 1H), 5.69 (dd, J=15.3, 6.0 Hz, 1H), 5.49 (ddd, J=15.3, 8.4, 1.0 Hz, 1H), 4.20-3.99 (m, 2H), 3.60 (m, 1H), 3.00 (m, 1H), 2.85 (t, J=7.8 Hz, 2H), 2.52-2.17 (m, 3H), 2.00-1.70 (m, 3H), 1.61-1.20 (m, 8H), 0.89 (t, J=6.3 Hz, 3H).

Example 6(12)

(13E,15α)-15-hydroxy-9-oxo-5-thia-8-azaprost-13-enoic acid

TLC: Rf 0.49 (chloroform:methanol:acetic acid=9:1:0.1);
NMR (CDCl$_3$): δ 5.73 (dd, J=15.3, 5.7 Hz, 1H), 5.53 (ddd, J=15.3, 8.4, 1.2 Hz, 1H), 4.18 (m, 2H), 3.63 (m, 1H), 3.11 (m, 1H), 2.78-2.20 (m, 9H), 2.00-1.70 (m, 3H), 1.62-1.21 (m, 8H), 0.90 (t, J=6.6 Hz, 3H).

Example 6(13)

5-(4-carboxythiazol-2-yl)-9-oxo-1,2,3,4,20-pentanor-5-thia-8-azaprostane

TLC: Rf 0.37 (chloroform:methanol:acetic acid=9:1:0.1);
NMR (CDCl$_3$): δ 8.09 (s, 1H), 3.94 (ddd, J=13.2, 9.3, 5.1 Hz, 1H), 3.65 (m, 1H), 3.54-3.25 (m, 3H), 2.52-2.28 (m, 2H), 2.16 (m, 1H), 1.82-1.62 (m, 2H), 1.46-1.02 (m, 11H), 0.88 (t, J=6.9 Hz, 3H).

Example 6(14)

(13E,15α)-20-ethyl-15-hydroxy-5-(4-carboxythiazol-2-yl)-9-oxo-1,2,3,4-tetranor-5-thia-8-azaprost-13-ene TLC: Rf 0.10 (chloroform:methanol=9:1);
NMR (CDCl$_3$): δ 8.10 (s, 1H), 5.79 (dd, J=15.3, 5.7 Hz, 1H), 5.55 (dd, J=15.3, 8.7 Hz, 1H), 4.21-4.11 (m, 2H), 4.0-3.1 (br), 3.90-3.75 (m, 1H), 3.55-3.30 (m, 3H), 2.56-2.20 (m, 3H), 1.86-1.72 (m, 1H), 1.62-1.42 (m, 2H), 1.42-1.20 (m, 10H), 0.90 (t, J=7.2 Hz, 3H).

Example 6(15)

(13E,15α)-20-methyl-15-hydroxy-5-(4-carboxythiazol-2-yl)-9-oxo-1,2,3,4-tetranor-5-thia-8-azaprost-13-ene TLC: Rf 0.20 (methylene chloride:methanol:acetic acid=90:10:1);
NMR (CDCl$_3$): δ 8.09 (s, 1H), 5.79 (dd, J=15.6, 6.0 Hz, 1H), 5.53 (dd, J=15.6, 9.0 Hz, 1H), 4.20-4.10 (m, 2H), 3.90-3.70 (m, 1H), 3.50-3.30 (m, 3H), 2.50-2.20 (m, 3H), 1.85-1.70 (m, 1H), 1.60-1.40 (m, 2H), 1.40-1.15 (m, 8H), 0.95-0.80 (m, 3H).

Example 6(16)

(13E,15α)-20-n-propyl-15-hydroxy-5-(4-carboxythiazol-2-yl)-9-oxo-1,2,3,4-tetranor-5-thia-8-azaprost-13-ene TLC: Rf 0.23 (methylene chloride:methanol:acetic acid=90:10:1);
NMR (CDCl$_3$): δ 8.09 (s, 1H), 5.79 (dd, J=15.3, 6.0 Hz, 1H), 5.53 (dd, J=15.3, 8.4 Hz, 1H), 4.20-4.10 (m, 2H), 3.90-3.70 (m, 1H), 3.50-3.30 (m, 3H), 2.50-2.20 (m, 3H), 1.85-1.70 (m, 1H), 1.60-1.40 (m, 2H), 1.40-1.15 (m, 12H), 0.90-0.80 (m, 3H).

Example 6(17)

(13Z)-5-(4-carboxythiazol-2-yl)-9-oxo-1,2,3,4,20-pentanor-5-thia-8-azaprost-13-ene TLC: Rf 0.34 (chloroform:methanol:acetic acid=9:1:0.1);
NMR (CDCl$_3$): δ 8.08 (s, 1H), 5.67 (dt, J=10.8, 7.8 Hz, 1H), 5.25 (dd, J=10.8, 9.6 Hz, 1H), 4.49 (dt, J=9.6, 7.2 Hz, 1H), 3.76 (m, 1H), 3.51 (m, 1H), 3.42-3.23 (m, 2H), 2.54-2.32 (m, 2H), 2.22 (m, 1H), 2.17-2.01 (m, 2H), 1.71 (m, 1H), 1.45-1.20 (m, 6H), 0.90 (t, J=6.6 Hz, 3H).

Example 6(18)

(13Z)-16-oxa-17,17-dimethyl-5-(4-carboxythiazol-2-yl)-9-oxo-1,2,3,4,19,20-hexanor-5-thia-8-azaprost-13-ene TLC: Rf 0.30 (chloroform:methanol:acetic acid=9:1:0.1);
NMR (CDCl$_3$): δ 8.08 (s, 1H), 5.84 (dt, J=10.8, 7.2 Hz, 1H), 5.41 (ddt, J=10.8, 9.9, 1.5 Hz, 1H), 4.62 (dt, J=9.9, 7.2 Hz, 1H), 4.07 (ddd, J=11.7, 7.2, 1.5 Hz, 1H), 3.94 (ddd, J=11.7, 7.2, 1.5 Hz, 1H), 3.82 (m, 1H), 3.60-3.38 (m, 2H), 3.24 (m, 1H), 2.56-2.18 (m, 3H), 1.74 (m, 1H), 1.23 (s, 9H).

Example 6(19)

(13E)-16-oxa-17,17-dimethyl-5-(4-carboxythiazol-2-yl)-9-oxo-1,2,3,4,19,20-hexanor-5-thia-8-azaprost-13-ene TLC: Rf 0.28 (chloroform:methanol:acetic acid=9:1:0.1);
NMR (CDCl$_3$): δ 8.08 (s, 1H), 5.83 (dt, J=15.3, 5.1 Hz, 1H), 5.55 (ddt, J=15.3, 9.0, 1.5 Hz, 1H), 4.14 (m, 1H), 3.93 (dd, J=5.1, 1.5 Hz, 2H), 3.83 (dt, J=13.8, 7.8 Hz, 1H), 3.50 (dt, J=13.8, 7.8 Hz, 1H), 3.32 (t, J=7.8 Hz, 2H), 2.55-2.17 (m, 3H), 1.79 (m, 1H), 1.21 (s, 9H).

Example 6(20)

(13E,15α)-19-phenyl-15-hydroxy-5-(4-carboxythiazol-2-yl)-9-oxo-1,2,3,4,20-pentanor-5-thia-8-azaprost-13-ene TLC: Rf 0.34 (chloroform:methanol:acetic acid=9:1:0.1);
NMR (CDCl$_3$): δ 8.09 (s, 1H), 7.36-7.10 (m, 5H), 5.79 (dd, J=15.0, 5.7 Hz, 1H), 5.60-5.15 (m, 1H), 4.22-4.10 (m, 2H), 3.80 (m, 1H), 3.47-3.28 (m, 3H), 2.64-2.18 (m, 5H), 1.82-1.23 (m, 7H).

Example 6(21)

(13E,15α)-20-phenyl-15-hydroxy-5-(4-carboxythiazol-2-yl)-9-oxo-1,2,3,4-tetranor-5-thia-8-azaprost-13-ene TLC: Rf 0.34 (chloroform:methanol:acetic acid=9:1:0.1);
NMR (CDCl$_3$): δ 8.09 (s, 1H), 7.36-7.12 (m, 5H), 5.78 (dd, J=15.3, 5.7 Hz, 1H), 5.54 (dd, J=15.3, 8.7 Hz, 1H), 4.20-4.10 (m, 2H), 3.81 (m, 1H), 3.55-3.27 (m, 3H), 2.65-2.20 (m, 5H), 1.85-1.23 (m, 9H).

Example 6(22)

(13E,15α)-20-benzyl-15-hydroxy-5-(4-carboxythiazol-2-yl)-9-oxo-1,2,3,4-tetranor-5-thia-8-azaprost-13-ene TLC: Rf 0.35 (chloroform:methanol:acetic acid=9:1:0.1);
NMR (CDCl$_3$): δ 8.09 (s, 1H), 7.37-7.12 (m, 5H), 5.78 (dd, J=15.3, 6.0 Hz, 1H), 5.55 (ddd, J=15.3, 8.7, 1.2 Hz, 1H), 4.20-4.08 (m, 2H), 3.81 (m, 1H), 3.55-3.27 (m, 3H), 2.64-2.20 (m, 5H), 1.86-1.21 (m, 11H).

Example 6(23)

(13E,16α)-17,17-propano-16-hydroxy-1,6-(1,3-interphenylene)-9-oxo-2,3,4,5,20-pentanor-8-azaprost-13-enoic acid TLC: Rf 0.41 (ethyl acetate:acetic acid=100:1);
NMR (CDCl$_3$): δ 0.92 (t, J=7.5 Hz, 2H), 1.44 (m, 1H), 1.55-2.50 (m, 13H), 2.75-3.00 (m, 2H), 3.20 (m, 1H), 3.59 (dd, J=9.9, 2.4 Hz, 1H), 3.70-3.90 (m, 2H), 5.28 (dd, J=15.0, 9.0 Hz, 1H), 5.79 (dt, J=15.0, 7.2 Hz, 1H), 7.39 (t, J=7.5 Hz, 1H), 7.46 (m, 1H), 7.92-8.00 (m, 2H).

Example 6(24)

(15α)-15-hydroxy-5-(4-carboxythiazol-2-yl)-9-oxo-1,2,3,4-tetranor-5-thia-8-azaprostane TLC: Rf 0.49 (chloroform:methanol:acetic acid=9:1:0.1);
NMR (CDCl$_3$): δ 8.08 (s, 1H), 3.95-3.23 (m, 6H), 2.55-2.06 (m, 3H), 1.94 (m, 1H), 1.78-1.60 (m, 2H), 1.59-1.00 (m, 10H), 0.89 (t, J=6.6 Hz, 3H).

Example 6(25)

(15α)-15-hydroxy-1,6-(1,4-interphenylene)-9-oxo-2,3,4,5-tetranor-5-thia-8-azaprostanoic acid TLC: Rf 0.21 (chloroform:methanol=9:1);
NMR (CDCl$_3$-CD$_3$OD): δ 7.97 (d, J=8.1 Hz, 2H), 7.30 (d, J=8.1 Hz, 2H), 3.82 (m, 1H), 3.60-3.30 (m, 3H), 3.20 (m, 1H), 3.01-2.80 (m, 2H), 2.45-2.21 (m, 2H), 2.08 (m, 1H), 1.80-1.20 (m, 13H), 0.89 (t, J=6.6 Hz, 3H).

Example 6(26)

(13E)-17,17-dimethyl-5-(4-carboxythiazol-2-yl)-9-oxo-1,2,3,4,19,20-hexanor-5-thia-8-azaprost-13-ene TLC: Rf 0.34 (chloroform:methanol:acetic acid=9:1:0.1);
NMR (CDCl$_3$): δ 8.08 (s, 1H), 5.73 (dt, J=15.3, 6.6 Hz, 1H), 5.27 (dd, J=15.3, 9.0 Hz, 1H), 4.05 (m, 1H), 3.83 (ddd, J=13.5, 9.0, 6.3 Hz, 1H), 3.49 (ddd, J=13.5, 9.6, 6.0 Hz, 1H), 3.39-3.21 (m, 2H), 2.54-2.15 (m, 3H), 2.09-1.97 (m, 2H), 1.75 (m, 1H), 1.30-1.20 (m, 2H), 0.89 (s, 9H).

Example 6(27)

(13E)-17,17-dimethyl-5-(4-carboxythiazol-2-yl)-9-oxo-1,2,3,4,20-pentanor-5-thia-8-azaprost-13-ene TLC: Rf 0.35 (chloroform:methanol:acetic acid=9:1:0.1);
NMR (CDCl$_3$): δ 8.09 (s, 1H), 5.72 (dt, J=15.0, 6.9 Hz, 1H), 5.26 (dd, J=15.0, 8.7 Hz, 1H), 4.05 (m, 1H), 3.82 (ddd, J=13.5, 9.0, 6.9 Hz, 1H), 3.49 (ddd, J=13.5, 9.9, 6.0 Hz, 1H), 3.40-3.24 (m, 2H), 2.54-2.15 (m, 3H), 2.10-1.93 (m, 2H), 1.75 (m, 1H), 1.29-1.16 (m, 4H), 0.98-0.75 (m, 9H).

Example 6(28)

(13E,15α)-19-phenyl-15-hydroxy-9-oxo-20-nor-5-thia-8-azaprost-13-enoic acid

TLC: Rf 0.24 (methylene chloride:methanol=9:1);
NMR (CDCl$_3$): δ 7.30-7.23 (m, 2H), 7.21-7.14 (m, 3H), 5.71 (dd, J=15.3, 5.7 Hz, 1H), 5.50 (dd, J=15.3, 8.4 Hz, 1H), 4.20-4.06 (m, 2H), 3.72-3.58 (m, 1H), 3.14-3.00 (m, 1H), 2.70-2.16 (m, 11H), 1.96-1.82 (m, 2H), 1.80-1.20 (m, 7H).

Example 6(29)

(13E,15α)-20-phenyl-15-hydroxy-9-oxo-5-thia-8-azaprost-13-enoic acid

TLC: Rf 0.24 (methylene chloride:methanol=9:1);
NMR (CDCl$_3$): δ 7.30-7.23 (m, 2H), 7.21-7.14 (m, 3H), 5.72 (dd, J=15.3, 5.7 Hz, 1H), 5.51 (dd, J=15.3, 8.1 Hz, 1H), 4.20-4.06 (m, 2H), 3.72-3.58 (m, 1H), 3.16-3.04 (m, 1H), 2.72-2.16 (m, 11H), 1.96-1.82 (m, 2H), 1.80-1.24 (m, 9H).

Example 6(30)

(13E,15α)-20-benzyl-15-hydroxy-9-oxo-5-thia-8-azaprost-13-enoic acid

TLC: Rf 0.24 (methylene chloride:methanol=9:1);
NMR (CDCl$_3$): δ 7.30-7.23 (m, 2H), 7.21-7.14 (m, 3H), 5.73 (dd, J=15.3, 5.4 Hz, 1H), 5.51 (ddd, J=15.3, 8.1, 0.9 Hz, 1H), 4.20-4.06 (m, 2H), 3.72-3.60 (m, 1H), 3.16-3.04 (m, 1H), 2.72-2.16 (m, 11H), 1.96-1.84 (m, 2H), 1.80-1.20 (m, 11H).

Example 6(31)

14-oxa-14-phenyl-5-(4-carboxythiazol-2-yl)-9-oxo-1,2,3,4,15,16,17,18,19,20-decanor-5-thia-8-azaprostane TLC: Rf 0.35 (chloroform:methanol:acetic acid=9:1:0.1);
NMR (CDCl$_3$): δ 8.08 (s, 1H), 7.29 (dd, J=8.4, 7.5 Hz, 2H), 6.98 (t, J=7.5 Hz, 1H), 6.88 (d, J=8.4 Hz, 2H), 4.20 (dd, J=9.9, 3.6 Hz, 1H), 4.09 (m, 1H), 3.99 (dd, J=9.9, 5.4 Hz, 1H), 3.91 (m, 1H), 3.75 (m, 1H), 3.51 (m, 1H), 3.29 (m, 1H), 2.60 (m, 1H), 2.43 (m, 1H), 2.25 (m, 1H), 1.96 (m, 1H).

Example 6(32)

14-oxa-14-(3,5-dichlorophenyl)-5-(4-carboxythiazol-2-yl)-9-oxo-1,2,3,4,15,16,17,18,19,20-decanor-5-thia-8-azaprostane TLC: Rf 0.41 (chloroform:methanol:acetic acid=9:1:0.1);
NMR (CDCl$_3$): δ 8.11 (s, 1H), 6.98 (t, J=1.8 Hz, 1H), 6.82 (d, J=1.8 Hz, 2H), 4.31 (dd, J=9.9, 3.0 Hz, 1H), 4.08 (m, 1H), 3.98 (dd, J=9.9, 3.0 Hz, 1H), 3.90 (m, 1H), 3.68 (m, 1H), 3.48 (m, 1H), 3.28 (m, 1H), 2.59 (m, 1H), 2.43 (m, 1H), 2.25 (m, 1H), 1.97 (m, 1H).

Example 6(33)

(13E,16α)-17,17-propano-16-hydroxy-6-(4-carboxythiazol-2-ylsulfonyl)-9-oxo-1,2,3,4,5,20-hexanor-8-azaprost-13-ene TLC: Rf 0.14 (chloroform:methanol:acetic acid=90:10:1);
NMR (CDCl$_3$): δ 0.93 (t, J=7.5 Hz, 3H), 1.44 (m, 1H), 1.55-2.20 (m, 10H), 2.20-2.55 (m, 4H), 3.60-4.00 (m, 5H), 4.00-4.40 (m, 2H), 5.41 (dd, J=15.3, 9.0 Hz, 1H), 5.96 (dt, J=15.3, 7.2 Hz, 1H), 8.54 (s, 1H).

Example 6(34)

14-oxa-5-(4-carboxythiazol-2-yl)-9-oxo-1,2,3,4,19,20-hexanor-5-thia-8-azaprostane TLC: Rf 0.25 (chloroform:methanol:acetic acid=9:1:0.1);
NMR (CDCl$_3$): δ 8.08 (s, 1H), 3.96-3.69 (m, 3H), 3.58-3.38 (m, 5H), 3.29 (m, 1H), 2.56-2.29 (m, 2H), 2.12 (m, 1H), 1.75 (m, 1H), 1.60-1.48 (m, 2H), 1.42-1.24 (m, 2H), 0.91 (t, J=7.2 Hz, 3H).

Example 6(35)

17,17-propano-5-(4-carboxythiazol-2-yl)-9,16-dioxo-1,2,3,4,20-pentanor-5-thia-8-azaprostane TLC: Rf 0.43 (chloroform:methanol:acetic acid=90:10:1);
NMR (CDCl$_3$): δ 0.75 (t, J=7.5 Hz, 3H), 1.30-2.00 (m, 11H), 2.10-2.55 (m, 7H), 3.25-3.55 (m, 3H), 3.67 (m, 1H), 3.95 (m, 1H), 8.09 (s, 1H).

Example 6(36)

(13E)-17-oxa-5-(4-carboxythiazol-2-yl)-9-oxo-1,2,3,4,20-pentanor-5-thia-8-azaprost-13-ene TLC: Rf 0.34 (chloroform:methanol:acetic acid=9:1:0.1);
NMR (CDCl$_3$): δ 8.08 (s, 1H), 5.77 (dt, J=15.3, 6.9 Hz, 1H), 5.37 (dd, J=15.3, 8.7 Hz, 1H), 4.07 (m, 1H), 3.76 (m, 1H), 3.63-3.42 (m, 5H), 3.38-3.28 (m, 2H), 2.55-2.17 (m, 5H), 1.76 (m, 1H), 1.20 (t, J=7.2 Hz, 3H).

Example 6(37)

(13E)-16-oxa-5-(4-carboxythiazol-2-yl)-9-oxo-1,2,3,4,20-pentanor-5-thia-8-azaprost-13-ene TLC: Rf 0.36 (chloroform:methanol:acetic acid=9:1:0.1);
NMR (CDCl$_3$): δ 8.09 (s, 1H), 5.83 (dt, J=15.3, 5.4 Hz, 1H), 5.57 (ddt, J=15.3, 8.7, 1.2 Hz, 1H), 4.15 (m, 1H), 3.98 (dd, J=5.4, 1.2 Hz, 2H), 3.85 (m, 1H), 3.55-3.26 (m, 5H), 2.55-2.17 (m, 3H), 1.79 (m, 1H), 1.68-1.53 (m, 2H), 0.92 (t, J=7.2 Hz, 3H).

Example 6(38)

13-(N-(phenylsulfonyl)amino)-5-(4-carboxythiazol-2-yl)-9-oxo-1,2,3,4,14,15,16,17,18,19,20-undecanor-5-thia-8-azaprostane TLC: Rf 0.22 (chloroform:methanol=9:1);
NMR (CDCl$_3$): δ 2.00-2.25 (m, 2H), 2.38 (m, 1H), 2.60 (m, 1H), 3.00-3.42 (m, 5H), 3.90-4.02 (m, 2H), 6.19 (t, J=6.6 Hz, 1H), 7.45-7.60 (m, 3H), 7.86 (m, 2H), 8.09 (s, 1H).

Example 6(39)

1-(N-(benzylsulfonyl)amino)-5-(4-carboxythiazol-2-yl)-9-oxo-1,2,3,4,14,15,16,17,18,19,20-undecanor-5-thia-8-azaprostane TLC: Rf 0.27 (chloroform:methanol=9:1);
NMR (CDCl$_3$): δ 1.90-2.18 (m, 2H), 2.31 (m, 1H), 2.51 (m, 1H), 2.95-3.40 (m, 5H), 3.76 (m, 1H), 3.91 (m, 1H), 4.31 (s, 2H), 5.72 (t, J=6.6 Hz, 1H), 7.30-7.40 (m, 3H), 7.40-7.45 (m, 2H), 8.12 (s, 1H).

Example 6(40)

(13E)-19-phenyl-5-(4-carboxythiazol-2-yl)-9-oxo-1,2,3,4,20-pentanor-5-thia-8-azaprost-13-ene TLC: Rf 0.43 (chloroform:methanol:acetic acid=9:1:0.1);
NMR (CDCl$_3$): δ 8.08 (s, 1H), 7.36-7.23 (m, 2H), 7.22-7.14 (m, 3H), 5.69 (dt, J=15.0, 6.6 Hz, 1H), 5.25 (dd, J=15.0, 8.7 Hz, 1H), 4.04 (m, 1H), 3.80 (m, 1H), 3.48 (m, 1H), 3.38-3.18 (m, 2H), 2.61 (t, J=7.5 Hz, 2H), 2.53-2.29 (m, 2H), 2.21 (m, 1H), 2.13-1.98 (m, 2H), 1.73 (m, 1H), 1.68-1.54 (m, 2H), 1.48-1.34 (m, 4H).

Example 6(41)

5-(4-carboxythiazol-2-yl)-9,13-dioxo-1,2,3,4,20-pentanor-5-thia-8,14-diazaprostane TLC: Rf 0.17 (chloroform:methanol:acetic acid=9:1:0.1);
NMR (CDCl$_3$): δ 8.11 (s, 1H), 7.16 (t, J=5.4 Hz, 1H), 4.41 (dd, J=8.4, 3.6 Hz, 1H), 3.90 (m, 1H), 3.53-3.23 (m, 5H), 2.72 (m, 1H), 2.47-2.03 (m, 3H), 1.52-1.35 (m, 2H), 1.34-1.10 (m, 4H), 0.82 (t, J=6.9 Hz, 3H).

Example 6(42)

(13E)-16-hydroxy-5-(4-carboxythiazol-2-yl)-9-oxo-1,2,3,4,20-pentanor-5-thia-8-azaprost-13-ene TLC: Rf 0.28 (chloroform:methanol:acetic acid=90:10:1);
NMR (CDCl$_3$): δ 0.92 (t, J=6.30 Hz, 3H) 1.41 (m, 4H) 1.74 (m, 1H) 2.30 (m, 5H) 3.52 (m, 5H) 4.10 (m, 1H) 4.52 (br. s., 2H) 5.37 (m, 1H) 5.82 (m, 1H) 8.07 (s, 1H).

Example 6(43)

13-(N-methyl-N-(benzylsulfonyl)amino)-5-(4-carboxythiazol-2-yl)-9-oxo-1,2,3,4,14,15,16,17,18,19,20-undecanor-5-thia-8-azaprostane TLC: Rf 0.33 (chloroform:methanol:acetic acid=90:10:1);
NMR (CDCl$_3$): δ 1.89 (m, 1H) 2.06 (m, 1H) 2.29 (m, 1H) 2.44 (m, 1H) 2.76 (dd, J=14.30, 7.80 Hz, 1H) 2.85 (s, 3H) 3.02 (dd, J=14.30, 4.40 Hz, 1H) 3.20 (m, 1H) 3.34 (m, 2H) 3.72 (m, 1H) 3.90 (m, 1H) 4.30 (s, 2H) 7.39 (s, 5H) 8.10 (s, 1H).

Example 6(44)

14-oxa-14-(pyridin-3-yl)-5-(4-carboxythiazol-2-yl)-9-oxo-1,2,3,4,15,16,17,18,19,20-decanor-5-thia-8-azaprostane TLC: Rf 0.32 (chloroform:methanol:acetic acid=90:10:1);
NMR (CDCl$_3$): δ 2.09 (m, 1H) 2.26 (m, 1H) 2.43 (ddd, J=16.80, 9.90, 5.70 Hz, 1H) 2.62 (ddd, J=16.80, 10.00, 6.90 Hz, 1H) 3.23 (m, 1H) 3.47 (m, 1H) 3.68 (m, 1H) 3.84 (m, 1H) 4.17 (m, 2H) 4.88 (m, 1H) 6.64 (br. s., 1H) 7.31 (m, 2H) 8.03 (s, 1H) 8.22 (m, 1H) 8.58 (m, 1H).

Example 6(45)

14-oxa-14-(2,5-dichlorophenyl)-5-(4-carboxythiazol-2-yl)-9-oxo-1,2,3,4,15,16,17,18,19,20-decanor-5-thia-8-azaprostane TLC: Rf 0.44 (chloroform:methanol:acetic acid=90:10:1);
NMR (CDCl$_3$): δ 1.94 (m, 1H) 2.29 (m, 1H) 2.45 (m, 1H) 2.68 (m, 1H) 3.28 (m, 1H) 3.55 (m, 1H) 3.81 (m, 1H) 3.99 (m, 2H) 4.15 (m, 1H) 4.30 (dd, J=9.89, 2.47 Hz, 1H) 6.93 (m, 2H) 7.29 (d, J=9.60 Hz, 1H) 8.08 (s, 1H).

Example 6(46)

14-oxa-14-(2,4,5-trichlorophenyl)-5-(4-carboxythiazol-2-yl)-9-oxo-1,2,3,4,15,16,17,18,19,20-decanor-5-thia-8-azaprostane TLC: Rf 0.44 (chloroform:methanol:acetic acid=90:10:1);
NMR (CDCl$_3$): δ 1.96 (m, 1H) 2.37 (m, 2H) 2.69 (m, 1H) 3.27 (m, 1H) 3.53 (m, 1H) 3.77 (m, 1H) 3.97 (m, 2H) 4.13 (m, 1H) 4.37 (dd, J=9.89, 2.47 Hz, 1H) 7.07 (s, 1H) 7.46 (s, 1H) 8.09 (s, 1H).

Example 6(47)

14-oxa-14-(3,4-dichlorophenyl)-5-(4-carboxythiazol-2-yl)-9-oxo-1,2,3,4,15,16,17,18,19,20-decanor-5-thia-8-azaprostane TLC: Rf 0.40 (chloroform:methanol:acetic acid=90:10:1);
NMR (CDCl$_3$): δ 1.97 (m, 1H) 2.26 (m, 1H) 2.43 (m, 1H) 2.59 (m, 1H) 3.28 (m, 1H) 3.48 (m, 1H) 3.70 (m, 1H) 3.94 (m, 2H) 4.08 (m, 1H) 4.25 (m, 1H) 6.76 (dd, J=8.80, 2.70 Hz, 1H) 7.02 (d, J=2.70 Hz, 1H) 7.33 (d, J=8.80 Hz, 1H) 8.10 (s, 1H).

Example 6(48)

14-oxa-14-(2,3,4,5,6-pentafluorophenyl)-5-(4-carboxythiazol-2-yl)-9-oxo-1,2,3,4,15,16,17,18,19,20-decanor-5-thia-8-azaprostane TLC: Rf 0.38 (chloroform:methanol:acetic acid=90:10:1);
NMR (CDCl$_3$): δ 2.01 (m, 1H) 2.28 (m, 1H) 2.43 (m, 1H) 2.59 (m, 1H) 3.39 (m, 1H) 3.52 (m, 1H) 3.70 (m, 1H) 4.10 (m, 3H) 4.38 (dd, J=9.90, 3.00 Hz, 1H) 8.10 (s, 1H).

Example 6(49)

14-oxa-14-(3,4-difluorophenyl)-5-(4-carboxythiazol-2-yl)-9-oxo-1,2,3,4,15,16,17,18,19,20-decanor-5-thia-8-azaprostane TLC: Rf 0.36 (chloroform:methanol:acetic acid=90:10:1);
NMR (CDCl$_3$): δ 1.97 (m, 1H) 2.26 (m, 1H) 2.43 (m, 1H) 2.59 (m, 1H) 3.29 (m, 1H) 3.48 (m, 1H) 3.71 (m, 1H) 3.94 (m, 2H) 4.07 (m, 1H) 4.18 (m, 1H) 6.59 (m, 1H) 6.73 (m, 1H) 7.07 (m, 1H) 8.10 (s, 1H).

Example 6(50)

14-oxa-14-(2-nitro-3-methylphenyl)-5-(4-carboxythiazol-2-yl)-9-oxo-1,2,3,4,15,16,17,18,19,20-decanor-5-thia-8-azaprostane TLC: Rf 0.33 (chloroform:methanol:acetic acid=90:10:1);
NMR (CDCl$_3$): δ 1.84 (m, 1H) 2.32 (m, 1H) 2.32 (s, 2H) 2.48 (m, 2H) 3.27 (m, 1H) 3.45 (m, 1H) 3.69 (m, 1H) 3.96 (m, 1H) 4.10 (m, 2H) 4.23 (m, 1H) 6.87 (d, J=8.10 Hz, 1H) 6.92 (d, J=8.10 Hz, 1H) 7.32 (t, J=8.10 Hz, 1H) 8.07 (s, 1H).

Example 6(51)

14-oxa-14-(3-chloro-4-formylphenyl)-5-(4-carboxythiazol-2-yl)-9-oxo-1,2,3,4,15,16,17,18,19,20-decanor-5-thia-8-azaprostane TLC: Rf 0.56 (chloroform:methanol:acetic acid=90:10:1);
NMR (CDCl$_3$): δ 2.00 (m, 1H) 2.29 (m, 1H) 2.45 (m, 1H) 2.61 (m, 1H) 3.29 (m, 1H) 3.48 (m, 1H) 3.69 (m, 1H) 3.94 (m, 1H) 4.12 (m, 2H) 4.40 (m, 1H) 6.91 (m, 1H) 6.98 (d, J=2.20 Hz, 1H) 7.90 (d, J=8.79 Hz, 1H) 8.10 (s, 1H) 10.32 (s, 1H).

Example 6(52)

14-oxa-14-(4-nitro-3-methylphenyl)-5-(4-carboxythiazol-2-yl)-9-oxo-1,2,3,4,15,16,17,18,19,20-decanor-5-thia-8-azaprostane TLC: Rf 0.51 (chloroform:methanol:acetic acid=90:10:1);
NMR (CDCl$_3$): δ 2.00 (m, 1H) 2.29 (m, 1H) 2.45 (m, 1H) 2.62 (m, 1H) 2.62 (s, 3H) 3.29 (m, 1H) 3.48 (m, 1H) 3.70 (m, 1H) 3.94 (m, 1H) 4.11 (m, 2H) 4.36 (m, 1H) 6.81 (m, 2H) 8.07 (m, 1H) 8.10 (s, 1H).

Example 6(53)

14-oxa-14-(3-nitro-2-methylphenyl)-5-(4-carboxythiazol-2-yl)-9-oxo-1,2,3,4,15,16,17,18,19,20-decanor-5-thia-8-azaprostane TLC: Rf 0.47 (chloroform:methanol:acetic acid=90:10:1);
NMR (CDCl$_3$): δ 2.02 (m, 1H) 2.33 (m, 1H) 2.33 (s, 3H) 2.47 (m, 1H) 2.62 (m, 1H) 3.29 (m, 1H) 3.50 (m, 1H) 3.72 (m, 1H) 3.96 (m, 1H) 4.14 (m, 2H) 4.29 (dd, J=9.60, 3.00 Hz, 1H) 7.07 (d, J=8.20 Hz, 1H) 7.27 (t, J=8.20 Hz, 1H) 7.44 (m, 1H) 8.09 (s, 1H).

Example 6(54)

14-oxa-14-(4-chloro-3-methylphenyl)-5-(4-carboxythiazol-2-yl)-9-oxo-1,2,3,4,15,16,17,18,19,20-decanor-5-thia-8-azaprostane TLC: Rf 0.51 (chloroform:methanol:acetic acid=90:10:1);
NMR (CDCl$_3$): δ 1.95 (m, 1H) 2.33 (m, 2H) 2.33 (s, 3H) 2.59 (m, 1H) 3.27 (m, 1H) 3.49 (m, 1H) 3.74 (m, 1H) 3.92 (m, 2H) 4.06 (m, 1H) 4.16 (dd, J=9.60, 3.00 Hz, 1H) 6.66 (dd, J=8.80, 2.70 Hz, 1H) 6.76 (d, J=2.70 Hz, 1H) 7.23 (d, J=8.80 Hz, 1H) 8.09 (s, 1H).

Example 6(55)

14-oxa-14-(3-nitro-4-methylphenyl)-5-(4-carboxythiazol-2-yl)-9-oxo-1,2,3,4,15,16,17,18,19,20-decanor-5-thia-8-azaprostane TLC: Rf 0.56 (chloroform:methanol:acetic acid=90:10:1);
NMR (CDCl$_3$): δ 2.02 (m, 1H) 2.35 (m, 2H) 2.51 (s, 3H) 2.63 (m, 1H) 3.29 (m, 1H) 3.49 (m, 1H) 3.70 (m, 1H) 3.93 (m, 1H) 4.10 (m, 2H) 4.41 (dd, J=10.03, 2.88 Hz, 1H) 5.66 (br. s., 1H) 7.06 (dd, J=8.38, 2.61 Hz, 1H) 7.24 (d, J=8.52 Hz, 1H) 7.54 (d, J=2.75 Hz, 1H) 8.10 (s, 1H).

Example 6(56)

14-oxa-14-(3-bromophenyl)-5-(4-carboxythiazol-2-yl)-9-oxo-1,2,3,4,15,16,17,18,19,20-decanor-5-thia-8-azaprostane TLC: Rf 0.46 (chloroform:methanol:acetic acid=9:1:0.1); NMR (CDCl$_3$): δ 1.96 (m, 1H) 2.25 (m, 1H) 2.43 (m, 1H) 2.60 (m, 1H) 3.28 (ddd, J=13.40, 10.16, 5.36 Hz, 1H) 3.49 (ddd, J=13.40, 10.16, 5.22 Hz, 1H) 3.72 (m, 1H) 4.01 (m, 3H) 4.22 (dd, J=9.89, 3.02 Hz, 1H) 6.82 (td, J=4.60, 2.34 Hz, 1H) 7.10 (m, 3H) 8.09 (s, 1H).

Example 6(57)

14-oxa-14-(2,3-dimethylphenyl)-5-(4-carboxythiazol-2-yl)-9-oxo-1,2,3,4,15,16,17,18,19,20-decanor-5-thia-8-azaprostane TLC: Rf 0.48 (chloroform:methanol:acetic acid=9:1:0.1); NMR (CDCl$_3$): δ 1.97 (m, 1H) 2.11 (s, 3H) 2.27 (s, 3H) 2.27 (m, 1H) 2.45 (m, 1H) 2.63 (m, 1H) 3.26 (ddd, J=13.40, 10.16, 5.49 Hz, 1H) 3.52 (ddd, J=13.40, 10.16, 5.22 Hz, 1H) 3.88 (m, 3H) 4.17 (m, 2H) 6.68 (d, J=8.52 Hz, 1H) 6.81 (d, J=7.69 Hz, 1H) 7.05 (t, J=7.97 Hz, 1H) 8.08 (s, 1H).

Example 6(58)

14-oxa-14-(4-chloro-2,6-dimethylphenyl)-5-(4-carboxythiazol-2-yl)-9-oxo-1,2,3,4,15,16,17,18,19,20-decanor-5-thia-8-azaprostane TLC: Rf 0.47 (chloroform:methanol:acetic acid=9:1:0.1); NMR (CDCl$_3$): δ 1.94 (m, 1H) 2.34 (m, 2H) 2.34 (s, 6H) 2.59 (m, 1H) 3.27 (ddd, J=13.32, 10.03, 5.22 Hz, 1H) 3.49 (m, 1H) 3.74 (m, 1H) 3.91 (m, 2H) 4.12 (m, 2H) 6.62 (s, 2H) 8.08 (s, 1H).

Example 6(59)

14-oxa-14-(naphthalen-2-yl)-5-(4-carboxythiazol-2-yl)-9-oxo-1,2,3,4,15,16,17,18,19,20-decanor-5-thia-8-azaprostane TLC: Rf 0.44 (chloroform:methanol:acetic acid=9:1:0.1); NMR (CDCl$_3$): δ 2.01 (m, 1H) 2.28 (m, 1H) 2.45 (m, 1H) 2.64 (m, 1H) 3.29 (m, 1H) 3.52 (m, 1H) 3.80 (m, 1H) 3.94 (m, 1H) 4.12 (m, 2H) 4.32 (m, 1H) 7.12 (m, 2H) 7.36 (td, J=7.49, 1.24 Hz, 1H) 7.46 (td, J=7.55, 1.37 Hz, 1H) 7.75 (m, 3H) 8.06 (s, 1H).

Example 6(60)

14-oxa-14-(2-fluoro-3-trifluoromethylphenyl)-5-(4-carboxythiazol-2-yl)-9-oxo-1,2,3,4,15,16,17,18,19,20-decanor-5-thia-8-azaprostane TLC: Rf 0.35 (chloroform:methanol:acetic acid=9:1:0.1); NMR (CDCl$_3$): δ 1.95 (m, 1H) 2.28 (m, 1H) 2.44 (m, 1H) 2.61 (m, 1H) 3.35 (ddd, J=13.40, 10.10, 5.40 Hz, 1H) 3.52 (ddd, J=13.40, 10.10, 5.40 Hz, 1H) 3.72 (m, 1H) 4.09 (m, 3H) 4.33 (dd, J=9.48, 2.88 Hz, 1H) 7.17 (m, 3H) 8.09 (s, 1H).

Example 6(61)

14-oxa-14-(3,5-dimethylphenyl)-5-(4-carboxythiazol-2-yl)-9-oxo-1,2,3,4,15,16,17,18,19,20-decanor-5-thia-8-azaprostane TLC: Rf 0.45 (chloroform:methanol:acetic acid=90:10:1); NMR (CDCl$_3$): δ 1.93 (m, 1H) 2.23 (m, 1H) 2.28 (s, 6H) 2.42 (m, 1H) 2.59 (m, 1H) 3.27 (m, 1H) 3.51 (m, 1H) 3.95 (m, 5H) 6.50 (s, 2H) 6.64 (s, 1H) 8.08 (s, 1H).

Example 6(62)

14-oxa-14-(3,4,5-trimethylphenyl)-5-(4-carboxythiazol-2-yl)-9-oxo-1,2,3,4,15,16,17,18,19,20-decanor-5-thia-8-azaprostane TLC: Rf 0.43 (chloroform:methanol:acetic acid=90:10:1); NMR (CDCl$_3$): δ 1.92 (m, 1H) 2.10 (s, 3H) 2.20 (m, 1H) 2.25 (s, 6H) 2.42 (m, 1H) 2.58 (m, 1H) 3.26 (m, 1H) 3.51 (m, 1H) 3.96 (m, 5H) 6.55 (s, 2H) 8.07 (s, 1H).

Example 6(63)

14-oxa-14-(5,6,7,8-tetrahydronaphthalen-1-yl)-5-(4-carboxythiazol-2-yl)-9-oxo-1,2,3,4,15,16,17,18,19,20-decanor-5-thia-8-azaprostane TLC: Rf 0.42 (chloroform:methanol:acetic acid=90:10:1); NMR (CDCl$_3$): δ 1.76 (m, 4H) 1.97 (m, 1H) 2.27 (m, 1H) 2.58 (m, 6H) 3.23 (m, 1H) 3.51 (m, 1H) 3.96 (m, 5H) 6.61 (d, J=8.24 Hz, 1H) 6.74 (d, J=7.42 Hz, 1H) 7.06 (t, J=7.97 Hz, 1H) 8.07 (s, 1H).

Example 6(64)

14-oxa-14-(4-acetyl-3-methylphenyl)-5-(4-carboxythiazol-2-yl)-9-oxo-1,2,3,4,15,16,17,18,19,20-decanor-5-thia-8-azaprostane TLC: Rf 0.42 (chloroform:methanol:acetic acid=90:10:1); NMR (CDCl$_3$): δ 1.97 (m, 1H) 2.45 (m, 3H) 2.55 (s, 6H) 3.27 (m, 1H) 3.49 (m, 1H) 3.74 (m, 1H) 3.93 (m, 1H) 4.08 (m, 2H) 4.24 (m, 1H) 6.74 (m, 2H) 7.74 (d, J=9.34 Hz, 1H) 8.08 (s, 1H).

Example 6(65)

14-oxa-14-(naphthalen-1-yl)-5-(4-carboxythiazol-2-yl)-9-oxo-1,2,3,4,15,16,17,18,19,20-decanor-5-thia-8-azaprostane TLC: Rf 0.43 (chloroform:methanol:acetic acid=90:10:1); NMR (CDCl$_3$): δ 2.07 (m, 1H) 2.35 (m, 1H) 2.51 (m, 1H) 2.70 (m, 1H) 3.26 (m, 1H) 3.55 (m, 1H) 3.92 (m, 2H) 4.23 (m, 2H) 4.36 (m, 1H) 6.82 (m, 1H) 7.37 (m, 1H) 7.50 (m, 3H) 7.82 (m, 1H) 8.03 (s, 1H) 8.09 (m, 1H).

Example 6(66)

14-oxa-14-(2-chloro-3-trifluoromethylphenyl)-5-(4-carboxythiazol-2-yl)-9-oxo-1,2,3,4,15,16,17,18,19,20-decanor-5-thia-8-azaprostane TLC: Rf 0.42 (chloroform:methanol:acetic acid=90:10:1); NMR (CDCl$_3$): δ 1.96 (m, 1H) 2.38 (m, 2H) 2.69 (m, 1H) 3.31 (m, 1H) 3.55 (m, 1H) 3.81 (m, 1H) 4.11 (m, 3H) 4.33 (m, 1H) 7.14 (m, 1H) 7.34 (m, 2H) 8.08 (s, 1H).

Example 6(67)

14-oxa-14-(3-methylphenyl)-5-(4-carboxythiazol-2-yl)-9-oxo-1,2,3,4,15,16,17,18,19,20-decanor-5-thia-8-azaprostane TLC: Rf 0.49 (chloroform:methanol:acetic acid=90:10:1);

NMR (CDCl$_3$): δ 1.95 (m, 1H) 2.25 (s, 1H) 2.33 (s, 3H) 2.43 (m, 1H) 2.60 (m, 1H) 3.15 (br. s., 1H) 3.28 (m, 1H) 3.51 (m, 1H) 3.76 (m, 1H) 3.94 (m, 2H) 4.12 (m, 2H) 6.68 (m, 2H) 6.81 (m, 1H) 7.17 (t, J=7.69 Hz, 1H) 8.08 (s, 1H).

Example 6(68)

14-oxa-14-(4-methylphenyl)-5-(4-carboxythiazol-2-yl)-9-oxo-1,2,3,4,15,16,17,18,19,20-decanor-5-thia-8-azaprostane TLC: Rf 0.47 (chloroform:methanol:acetic acid=90:10:1);
NMR (CDCl$_3$): δ 1.94 (m, 1H) 2.23 (m, 1H) 2.29 (s, 3H) 2.42 (ddd, J=16.80, 10.00, 6.00 Hz, 1H) 2.59 (ddd, J=16.80, 10.00, 6.90 Hz, 1H) 3.28 (ddd, J=13.20, 10.20, 5.40 Hz, 1H) 3.50 (ddd, J=13.20, 10.20, 5.40 Hz, 1H) 3.77 (ddd, J=13.20, 10.20, 5.40 Hz, 1H) 3.93 (m, 2H) 4.10 (m, 2H) 6.77 (d, J=8.80 Hz, 2H) 7.09 (d, J=8.80 Hz, 2H) 8.08 (s, 1H).

Example 6(69)

14-oxa-14-(2,3,5-trichlorophenyl)-5-(4-carboxythiazol-2-yl)-9-oxo-1,2,3,4,15,16,17,18,19,20-decanor-5-thia-8-azaprostane TLC: Rf 0.55 (chloroform:methanol:acetic acid=90:10:1);
NMR (CDCl$_3$): δ 1.95 (m, 1H) 2.30 (m, 1H) 2.45 (m, 1H) 2.68 (m, 1H) 3.26 (m, 1H) 3.54 (m, 1H) 3.78 (m, 1H) 3.99 (m, 2H) 4.15 (m, 1H) 4.32 (m, 1H) 6.88 (d, J=2.20 Hz, 1H) 7.14 (dd, J=2.20, 0.55 Hz, 1H) 8.08 (s, 1H).

Example 6(70)

14-oxa-14-(3-chloro-4-fluorophenyl)-5-(4-carboxythiazol-2-yl)-9-oxo-1,2,3,4,15,16,17,18,19,20-decanor-5-thia-8-azaprostane TLC: Rf 0.52 (chloroform:methanol:acetic acid=90:10:1);
NMR (CDCl$_3$): δ 1.96 (m, 1H) 2.25 (m, 1H) 2.43 (m, 1H) 2.59 (m, 1H) 3.28 (m, 1H) 3.48 (m, 1H) 3.70 (m, 1H) 3.93 (m, 2H) 4.07 (m, 1H) 4.21 (m, 1H) 6.75 (dt, J=9.00, 3.00 Hz, 1H) 6.94 (dd, J=5.70, 3.00 Hz, 1H) 7.05 (t, J=9.00 Hz, 1H) 8.09 (s, 1H).

Example 6(71)

14-oxa-14-(2,3-dichlorophenyl)-5-(4-carboxythiazol-2-yl)-9-oxo-1,2,3,4,15,16,17,18,19,20-decanor-5-thia-8-azaprostane TLC: Rf 0.41 (chloroform:methanol:acetic acid=90:10:1);
NMR (CDCl$_3$): δ 1.93 (m, 1H) 2.29 (m, 1H) 2.45 (m, 1H) 2.67 (m, 1H) 3.29 (m, 1H) 3.56 (m, 1H) 3.81 (m, 1H) 4.12 (m, 4H) 6.84 (dd, J=7.42, 1.92 Hz, 1H) 7.14 (m, 2H) 8.07 (s, 1H).

Example 6(72)

14-oxa-14-(3-nitrophenyl)-5-(4-carboxythiazol-2-yl)-9-oxo-1,2,3,4,15,16,17,18,19,20-decanor-5-thia-8-azaprostane TLC: Rf 0.45 (chloroform:methanol:acetic acid=90:10:1);
NMR (CDCl$_3$): δ 2.04 (m, 1H) 2.29 (m, 1H) 2.45 (m, 1H) 2.63 (m, 1H) 3.30 (m, 1H) 3.49 (m, 1H) 3.69 (m, 1H) 3.95 (m, 1H) 4.13 (m, 2H) 4.45 (m, 1H) 7.23 (m, 1H) 7.44 (t, J=8.24 Hz, 1H) 7.76 (t, J=2.34 Hz, 1H) 7.85 (m, 1H) 8.09 (s, 1H).

Example 6(73)

14-oxa-14-(3-trifluoromethylphenyl)-5-(4-carboxythiazol-2-yl)-9-oxo-1,2,3,4,15,16,17,18,19,20-decanor-5-thia-8-azaprostane TLC: Rf 0.43 (chloroform:methanol:acetic acid=90:10:1);
NMR (CDCl$_3$): δ 1.98 (m, 1H) 2.27 (m, 1H) 2.44 (m, 1H) 2.61 (m, 1H) 3.29 (m, 1H) 3.49 (m, 1H) 3.71 (m, 1H) 4.02 (m, 3H) 4.30 (dd, J=9.75, 2.88 Hz, 1H) 7.07 (m, 1H) 7.13 (br. s., 1H) 7.25 (m, 1H) 7.41 (t, J=7.97 Hz, 1H) 8.09 (s, 1H).

Example 6(74)

14-oxa-14-(3-trifluoromethoxyphenyl)-5-(4-carboxythiazol-2-yl)-9-oxo-1,2,3,4,15,16,17,18,19,20-decanor-5-thia-8-azaprostane TLC: Rf 0.43 (chloroform:methanol:acetic acid=90:10:1);
NMR (CDCl$_3$): δ 1.98 (m, 1H) 2.26 (m, 1H) 2.43 (m, 1H) 2.60 (m, 1H) 3.29 (m, 1H) 3.49 (m, 1H) 3.71 (m, 1H) 4.02 (m, 3H) 4.24 (dd, J=9.89, 3.02 Hz, 1H) 6.75 (br. s., 1H) 6.84 (m, 2H) 7.30 (t, J=8.24 Hz, 1H) 8.09 (s, 1H).

Example 6(75)

14-oxa-14-(2-chloro-4-methoxyphenyl)-5-(4-carboxythiazol-2-yl)-9-oxo-1,2,3,4,15,16,17,18,19,20-decanor-5-thia-8-azaprostane TLC: Rf 0.43 (chloroform:methanol:acetic acid=90:10:1);
NMR (CDCl$_3$): δ 1.92 (m, 1H) 2.26 (m, 1H) 2.43 (m, 1H) 2.65 (m, 1H) 3.31 (m, 1H) 3.56 (m, 1H) 3.76 (s, 3H) 3.80 (m, 2H) 4.06 (m, 3H) 6.75 (dd, J=9.00, 2.70 Hz, 1H) 6.85 (d, J=9.00 Hz, 1H) 6.96 (d, J=2.70 Hz, 1H) 8.07 (s, 1H).

Example 6(76)

14-oxa-14-(4-chloro-3-ethylphenyl)-5-(4-carboxythiazol-2-yl)-9-oxo-1,2,3,4,15,16,17,18,19,20-decanor-5-thia-8-azaprostane TLC: Rf 0.50 (chloroform:methanol:acetic acid=90:10:1);
NMR (CDCl$_3$): δ 1.21 (t, J=7.50 Hz, 3H) 1.95 (m, 1H) 2.25 (m, 1H) 2.43 (m, 1H) 2.59 (m, 1H) 2.70 (q, J=7.50 Hz, 2H) 3.27 (m, 1H) 3.49 (m, 1H) 3.73 (m, 1H) 4.03 (m, 4H) 6.66 (dd, J=8.70, 3.00 Hz, 1H) 6.76 (d, J=3.00 Hz, 1H) 7.23 (d, J=8.70 Hz, 1H) 8.08 (s, 1H).

Example 6(77)

14-oxa-14-(4-methylindan-7-yl)-5-(4-carboxythiazol-2-yl)-9-oxo-1,2,3,4,15,16,17,18,19,20-decanor-5-thia-8-azaprostane TLC: Rf 0.52 (chloroform:methanol:acetic acid=90:10:1);
NMR (CDCl$_3$): δ 1.91 (m, 1H) 2.10 (m, 2H) 2.20 (s, 3H) 2.24 (m, 1H) 2.42 (m, 1H) 2.60 (m, 1H) 2.84 (m, 4H) 3.25 (m, 1H) 3.52 (m, 1H) 3.96 (m, 5H) 6.55 (d, J=8.20 Hz, 1H) 6.92 (d, J=8.20 Hz, 1H) 8.07 (s, 1H).

Example 6(78)

14-oxa-14-(4-fluoro-3-methylphenyl)-5-(4-carboxythiazol-2-yl)-9-oxo-1,2,3,4,15,16,17,18,19,20-decanor-5-thia-8-azaprostane TLC: Rf 0.50 (chloroform:methanol:acetic acid=90:10:1); NMR (CDCl$_3$): δ 1.94 (m, 1H) 2.24 (d, J=1.90 Hz, 3H) 2.25 (m, J=1.92 Hz, 1H) 2.42 (m, 1H) 2.59 (m, 1H) 3.27 (m, 1H) 3.49 (m, 1H) 3.75 (m, 1H) 4.01 (m, 4H) 6.66 (m, 2H) 6.91 (t, J=9.00 Hz, 1H) 8.08 (s, 1H).

Example 6(79)

14-oxa-14-(2,3,4-trichlorophenyl)-5-(4-carboxythiazol-2-yl)-9-oxo-1,2,3,4,15,16,17,18,19,20-decanor-5-thia-8-azaprostane TLC: Rf 0.41 (chloroform:methanol:acetic acid=9:1:0.1); NMR (CDCl$_3$): δ 1.94 (m, 1H) 2.36 (m, 2H) 2.67 (m, 1H) 3.28 (ddd, J=13.20, 10.40, 5.22 Hz, 1H) 3.54 (ddd, J=13.20, 10.40, 4.94 Hz, 1H) 3.80 (m, 1H) 4.06 (m, 3H) 4.28 (dd, J=9.75, 2.61 Hz, 1H) 6.83 (d, J=9.07 Hz, 1H) 7.34 (d, J=9.07 Hz, 1H) 8.08 (s, 1H).

Example 6(80)

14-oxa-14-(2-chloro-4-fluorophenyl)-5-(4-carboxythiazol-2-yl)-9-oxo-1,2,3,4,15,16,17,18,19,20-decanor-5-thia-8-azaprostane TLC: Rf 0.33 (chloroform:methanol:acetic acid=9:1:0.1); NMR (CDCl$_3$): δ 1.94 (m, 1H) 2.28 (m, 1H) 2.45 (m, 1H) 2.66 (m, 1H) 3.31 (ddd, J=13.20, 10.40, 5.22 Hz, 1H) 3.55 (ddd, J=13.20, 10.40, 4.94 Hz, 1H) 3.80 (m, 1H) 4.01 (m, 2H) 4.13 (m, 1H) 4.23 (dd, J=9.60, 1.80 Hz, 1H) 6.91 (m, 2H) 7.15 (dd, J=7.97, 3.02 Hz, 1H) 8.08 (s, 1H).

Example 6(81)

14-oxa-14-(4-chloro-3-nitrophenyl)-5-(4-carboxythiazol-2-yl)-9-oxo-1,2,3,4,15,16,17,18,19,20-decanor-5-thia-8-azaprostane TLC: Rf 0.37 (chloroform:methanol:acetic acid=9:1:0.1); NMR (CDCl$_3$): δ 2.03 (m, 1H) 2.29 (m, 1H) 2.45 (m, 1H) 2.62 (m, 1H) 3.27 (ddd, J=13.50, 10.10, 5.36 Hz, 1H) 3.47 (ddd, J=13.50, 10.10, 5.49 Hz, 1H) 3.68 (m, 1H) 3.89 (m, 1H) 4.10 (m, 2H) 4.51 (dd, J=9.89, 2.75 Hz, 1H) 7.09 (dd, J=9.00, 2.90 Hz, 1H) 7.43 (d, J=9.00 Hz, 1H) 7.49 (d, J=2.90 Hz, 1H) 8.11 (s, 1H).

Example 6(82)

14-oxa-14-(2,4-dichlorophenyl)-5-(4-carboxythiazol-2-yl)-9-oxo-1,2,3,4,15,16,17,18,19,20-decanor-5-thia-8-azaprostane TLC: Rf 0.34 (chloroform:methanol:acetic acid=9:1:0.1); NMR (CDCl$_3$): δ 1.93 (m, 1H) 2.29 (m, 1H) 2.45 (m, 1H) 2.66 (m, 1H) 3.29 (ddd, J=13.32, 10.40, 5.22 Hz, 1H) 3.55 (ddd, J=13.32, 10.40, 5.22 Hz, 1H) 3.80 (m, 1H) 4.00 (m, 2H) 4.14 (m, 1H) 4.25 (dd, J=9.60, 1.80 Hz, 1H) 6.86 (d, J=8.79 Hz, 1H) 7.20 (dd, J=8.79, 2.47 Hz, 1H) 7.38 (d, J=2.47 Hz, 1H) 8.08 (s, 1H).

Example 6(83)

14-oxa-14-(4-chloro-3-trifluoromethylphenyl)-5-(4-carboxythiazol-2-yl)-9-oxo-1,2,3,4,15,16,17,18,19,20-decanor-5-thia-8-azaprostane TLC: Rf 0.34 (chloroform:methanol:acetic acid=9:1:0.1); NMR (CDCl$_3$): δ 2.00 (m, 1H) 2.27 (m, 1H) 2.44 (m, 1H) 2.62 (m, 1H) 3.29 (m, 1H) 3.48 (m, 1H) 3.69 (m, 1H) 4.01 (m, 3H) 4.33 (dd, J=9.75, 2.88 Hz, 1H) 7.01 (dd, J=8.80, 2.90 Hz, 1H) 7.21 (d, J=2.90 Hz, 1H) 7.40 (d, J=8.80 Hz, 1H) 8.10 (s, 1H).

Example 6(84)

14-oxa-14-(2,4-dimethylphenyl)-5-(4-carboxythiazol-2-yl)-9-oxo-1,2,3,4,15,16,17,18,19,20-decanor-5-thia-8-azaprostane TLC: Rf 0.34 (chloroform:methanol:acetic acid=9:1:0.1); NMR (CDCl$_3$): δ 1.95 (m, 1H) 2.16 (s, 3H) 2.26 (s, 3H) 2.26 (m, 1H) 2.43 (m, 1H) 2.61 (m, 1H) 3.25 (ddd, J=13.30, 10.30, 5.22 Hz, 1H) 3.51 (ddd, J=13.30, 10.30, 5.22 Hz, 1H) 3.79 (m, 1H) 3.95 (m, 2H) 4.12 (m, 2H) 6.68 (d, J=8.24 Hz, 1H) 6.95 (m, 2H) 8.07 (s, 1H).

Example 6(85)

14-oxa-14-(3-ethylphenyl)-5-(4-carboxythiazol-2-yl)-9-oxo-1,2,3,4,15,16,17,18,19,20-decanor-5-thia-8-azaprostane TLC: Rf 0.34 (chloroform:methanol:acetic acid=9:1:0.1); NMR (CDCl$_3$): δ 1.23 (t, J=7.69 Hz, 3H) 1.94 (m, 1H) 2.24 (m, 1H) 2.42 (m, 1H) 2.61 (m, 3H) 3.27 (ddd, J=13.30, 10.40, 5.49 Hz, 1H) 3.51 (ddd, J=13.30, 10.40, 5.22 Hz, 1H) 3.78 (m, 1H) 3.94 (m, 2H) 4.07 (m, 1H) 4.16 (dd, J=9.60, 3.00 Hz, 1H) 6.70 (m, 2H) 6.84 (d, J=7.97 Hz, 1H) 7.21 (t, J=7.69 Hz, 1H) 8.08 (s, 1H).

Example 6(86)

14-oxa-14-(3-methyl-4-methylthiophenyl)-5-(4-carboxythiazol-2-yl)-9-oxo-1,2,3,4,15,16,17,18,19,20-decanor-5-thia-8-azaprostane TLC: Rf 0.36 (chloroform:methanol:acetic acid=9:1:0.1); NMR (CDCl$_3$): δ 1.93 (m, 1H) 2.38 (m, J=14.28 Hz, 2H) 2.36 (s, 3H) 2.40 (s, 3H) 2.60 (m, 1H) 3.26 (ddd, J=13.30, 10.40, 5.22 Hz, 1H) 3.50 (ddd, J=13.30, 10.40, 5.36 Hz, 1H) 3.75 (m, 1H) 4.04 (m, 4H) 6.72 (m, 2H) 7.17 (d, J=7.97 Hz, 1H) 8.08 (s, 1H).

Example 6(87)

14-oxa-14-(4-chloro-3,5-dimethylphenyl)-5-(4-carboxythiazol-2-yl)-9-oxo-1,2,3,4,15,16,17,18,19,20-decanor-5-thia-8-azaprostane TLC: Rf 0.36 (chloroform:methanol:acetic acid=9:1:0.1); NMR (CDCl$_3$): δ 1.93 (m, 1H) 2.34 (m, 2H) 2.34 (s, 6H) 2.59 (m, 1H) 3.25 (ddd, J=13.30, 10.50, 5.49 Hz, 1H) 3.49 (ddd, J=13.30, 10.50, 5.22 Hz, 1H) 3.76 (m, 1H) 3.91 (m, 2H) 4.09 (m, 2H) 6.61 (s, 2H) 8.08 (s, 1H).

Example 6(88)

14-oxa-14-(2,3,5-trifluorophenyl)-5-(4-carboxythiazol-2-yl)-9-oxo-1,2,3,4,15,16,17,18,19,20-decanor-5-thia-8-azaprostane TLC: Rf 0.32 (chloroform:methanol:acetic acid=9:1:0.1);
NMR (CDCl$_3$): δ 1.95 (m, 1H) 2.28 (m, 1H) 2.44 (m, 1H) 2.62 (m, 1H) 3.31 (m, 1H) 3.51 (m, 1H) 3.72 (m, 1H) 4.05 (m, 3H) 4.32 (dd, J=9.75, 2.88 Hz, 1H) 6.55 (m, 2H) 8.09 (s, 1H).

Example 6(89)

14-oxa-14-(4-fluoro-3-trifluoromethylphenyl)-5-(4-carboxythiazol-2-yl)-9-oxo-1,2,3,4,15,16,17,18,19,20-decanor-5-thia-8-azaprostane TLC: Rf 0.36 (chloroform:methanol:acetic acid=9:1:0.1);
NMR (CDCl$_3$): δ 1.98 (m, 1H) 2.27 (m, 1H) 2.44 (m, 1H) 2.60 (m, 1H) 3.29 (ddd, J=13.30, 10.20, 5.08 Hz, 1H) 3.48 (ddd, J=13.30, 10.20, 4.94 Hz, 1H) 3.70 (m, 1H) 4.01 (m, 3H) 4.27 (dd, J=9.61, 3.02 Hz, 1H) 7.08 (m, 3H) 8.09 (s, 1H).

Example 6(90)

14-oxa-14-(4-chloro-3-fluorophenyl)-5-(4-carboxythiazol-2-yl)-9-oxo-1,2,3,4,15,16,17,18,19,20-decanor-5-thia-8-azaprostane TLC: Rf 0.41 (chloroform:methanol:acetic acid=9:1:0.1);
NMR (CDCl$_3$): δ 1.96 (m, 1H) 2.26 (m, 1H) 2.43 (m, 1H) 2.59 (m, 1H) 3.27 (ddd, J=13.32, 10.30, 5.22 Hz, 1H) 3.48 (ddd, J=13.32, 10.30, 5.40 Hz, 1H) 3.71 (m, 1H) 3.93 (m, 2H) 4.08 (m, 1H) 4.21 (dd, J=9.75, 3.16 Hz, 1H) 6.64 (m, 1H) 6.72 (dd, J=10.44, 2.75 Hz, 1H) 7.28 (t, J=8.65 Hz, 1H) 8.09 (s, 1H).

Example 6(91)

(13E,15α)-19-phenoxy-15-hydroxy-5-(4-carboxythiazol-2-yl)-9-oxo-1,2,3,4,20-pentanor-5-thia-8-azaprost-13-ene TLC: Rf 0.22 (chloroform:methanol=9:1);
NMR (CDCl$_3$): δ 1.63 (m, 7H) 2.35 (m, 3H) 3.39 (m, 3H) 3.78 (m, 1H) 3.94 (t, J=6.18 Hz, 2H) 4.18 (m, 2H) 5.09 (m, 2H) 5.56 (dd, J=15.38, 8.52 Hz, 1H) 5.81 (dd, J=15.38, 5.77 Hz, 1H) 6.89 (m, 3H) 7.26 (m, 2H) 8.07 (s, 1H).

Example 6(92)

(13E,15α)-20-phenoxy-15-hydroxy-5-(4-carboxythiazol-2-yl)-9-oxo-1,2,3,4-tetranor-5-thia-8-azaprost-13-ene TLC: Rf 0.22 (chloroform:methanol=9:1);
NMR (CDCl$_3$): δ 1.47 (m, 6H) 1.76 (m, 3H) 2.35 (m, 3H) 3.38 (m, 3H) 3.79 (m, 1H) 3.94 (t, J=6.32 Hz, 2H) 4.16 (m, 2H) 4.76 (m, 2H) 5.55 (ddd, J=15.31, 8.58, 0.82 Hz, 1H) 5.80 (dd, J=15.38, 5.77 Hz, 1H) 6.91 (m, 3H) 7.27 (m, 2H) 8.08 (s, 1H).

Example 7(1) and (2)

By the same procedure as described in Example 3, using a corresponding derivative instead of the compound prepared in Reference Example 11, the following compounds of the present invention were obtained.

Example 7(1)

2-(2-(2-(4-(2-hydroxymethylphenyl)phenyl)-5-oxopyrrolidin-1-yl)ethylthio)thiazole-4-carboxylic acid ethyl ester

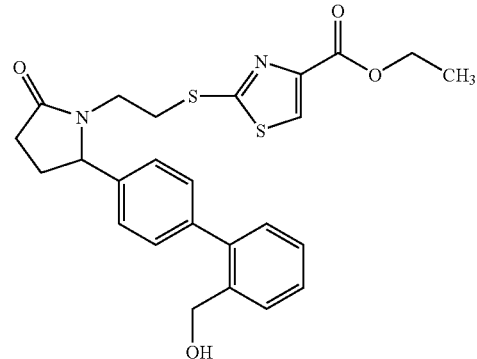

TLC: Rf 0.11 (ethyl acetate:n-hexane=3:1);
NMR (CDCl$_3$): δ 8.02 (s, 1H), 7.59-7.55 (m, 1H), 7.44-7.32 (m, 4H), 7.30-7.23 (m, 3H), 4.93-4.86 (m, 1H), 4.58 (d, J=5.4 Hz, 2H), 4.38 (q, J=7.2 Hz, 2H), 3.99-3.87 (m, 1H), 3.51-3.30 (m, 2H), 3.16-3.05 (m, 1H), 2.68-2.45 (m, 3H), 2.03-1.89 (m, 1H), 1.81 (t, J=5.4 Hz, 1H), 1.38 (t, J=7.2 Hz, 3H).

Example 7(2)

2-(2-(2-(4-(2-propoxyethyl)phenyl)-5-oxopyrrolidin-1-yl)ethylthio)thiazole-4-carboxylic acid ethyl ester TLC: Rf 0.13 (hexane:ethyl acetate=1:1);
NMR (CDCl$_3$): δ 8.00 (s, 1H), 7.19 (d, J=8.4 Hz, 2H), 7.12 (d, J=8.4 Hz, 2H), 4.79 (m, 1H), 4.40 (q, J=7.2 Hz, 2H), 3.93 (m, 1H), 3.61 (t, J=7.2 Hz, 2H), 3.44-3.32 (m, 4H), 3.01 (m, 1H), 2.87 (t, J=7.2 Hz, 2H), 2.64-2.34 (m, 3H), 1.88 (m, 1H), 1.68-1.48 (m, 2H), 1.40 (t, J=7.2 Hz, 3H), 0.89 (t, J=7.2 Hz, 3H).

Example 8(1) and (2)

By the same procedure as described in Example 2, using the compound prepared in Example 7(1) or 7(2) instead of the compound prepared in Example 1, the following compounds of the present invention were obtained.

Example 8(1)

2-(2-(2-(4-(2-hydroxymethylphenyl)phenyl)-5-oxopyrrolidin-1-yl)ethylthio)thiazole-4-carboxylic acid

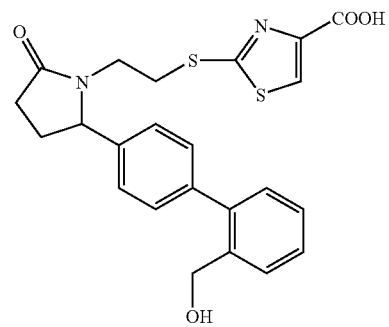

TLC: Rf 0.16 (methylene chloride:methanol=5:1);

NMR (CDCl$_3$): δ 8.08 (s, 1H), 7.58-7.53 (m, 1H), 7.45-7.32 (m, 4H), 7.29-7.22 (m, 3H), 4.83-4.76 (m, 1H), 4.61 (s, 2H), 4.05-3.96 (m, 1H), 3.37-3.21 (m, 3H), 2.70-2.44 (m, 3H), 2.07-1.94 (m, 1H).

Example 8(2)

2-(2-(2-(4-(2-propoxyethyl)phenyl)-5-oxopyrrolidin-1-yl)ethylthio)thiazole-4-carboxylic acid TLC: Rf 0.27 (chloroform:methanol:acetic acid=9:1:0.1);

NMR (CDCl$_3$): δ8.06 (s, 1H), 7.25 (d, J=8.1 Hz, 2H), 7.13 (d, J=8.1 Hz, 2H), 4.67 (m, 1H), 3.94 (m, 1H), 3.67 (t, J=6.9 Hz, 2H), 3.43 (t, J=6.9 Hz, 2H), 3.35-3.04 (m, 3H), 2.90 (t, J=6.9 Hz, 2H), 2.70-2.36 (m, 3H), 1.94 (m, 1H), 1.69-1.50 (m, 2H), 0.90 (t, J=7.2 Hz, 3H).

Example 9

(13E,15α)-15-hydroxy-5-(4-(2-(2-ethyl-2-methylbutanoyloxy)ethoxycarbonyl)thiazol-2-yl)-9-oxo-1,2,3,4-tetranor-5-thia-8-azaprost-13-ene

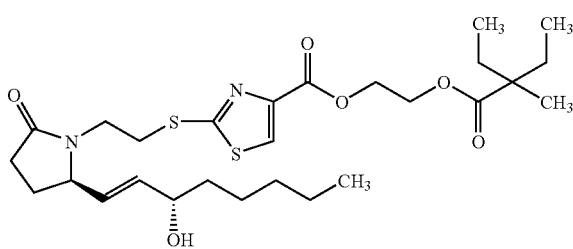

The compound prepared in Example 2(2) (312 mg), 2-(2-ethyl-2-methylbutanoyloxy)ethanol (700 mg) and triethylamine (0.33 mL) was dissolved into ethyl acetate (8 mL) and then the mixture was stirred for 5 minutes. 1-Methanesulfonyloxybenzotriazole (341 mg) was added to the reaction solution, which was stirred at room temperature for 3 hours. Water was added to the reaction solution, which was extracted with ethyl acetate. The extract was washed with water, an aqueous saturated sodium hydrogen carbonate solution and brine sequentially, dried over anhydrous sodium sulfate and concentrated. The residue was purified by column chromatography on silica gel (hexane:ethyl acetate=1:3→ethyl acetate) to give the compound of the present invention (316 mg) having the following physical data.

TLC: Rf 0.30 (ethyl acetate);

NMR (CDCl$_3$): δ 8.00 (s, 1H), 5.79 (d, J=15.6, 5.7 Hz, 1H), 5.54 (ddd, J=15.6, 8.4, 1.0 Hz, 1H), 4.55 (m, 2H), 4.40 (m, 2H), 4.20 (m, 1H), 4.10 (m, 1H), 3.79 (m, 1H), 3.53-3.31 (m, 3H), 2.50-2.19 (m, 3H), 2.09 (d, J=4.7 Hz, 1H), 1.83-1.61 (m, 3H), 1.58-1.20 (m, 10H), 1.10 (s, 3H), 0.95-0.78 (m, 9H).

Example 9(1) to Example 9(4)

By the same procedure as described in Example 9, using a corresponding carboxylic acid derivative instead of the compound prepared in Example 2(2), the following compounds of the present invention were obtained.

Example 9(1)

(13E,15α)-15-hydroxy-1,6-(1,4-interphenylene)-9-oxo-2,3,4,5-tetranor-8-azaprost-13-enoic acid 2-(2-ethyl-2-methylbutanoyloxy)ethyl ester

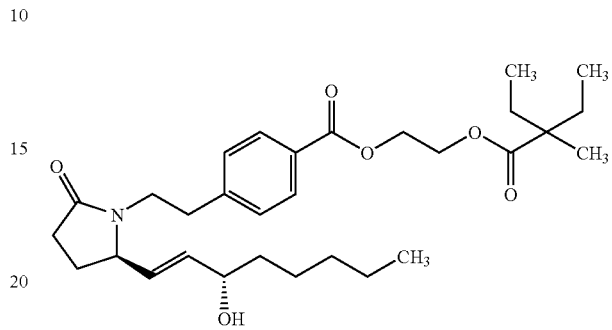

TLC: Rf 0.28 (ethyl acetate);

NMR (CDCl$_3$): δ 7.92 (d, J=8.1 Hz, 2H), 7.25 (d, J=8.1 Hz, 2H), 5.59 (dd, J=15.6, 6.3 Hz, 1H), 5.39 (dd, J=15.6, 8.7 Hz, 1H), 4.55 (m, 2H), 4.41 (m, 2H), 4.12 (m, 1H), 3.80 (m, 2H), 3.11 (m, 1H), 3.00-2.80 (m, 2H), 2.44-2.25 (m, 2H), 2.16 (m, 1H), 1.79-1.23 (m, 14H), 1.10 (s, 3H), 0.95-0.78 (m, 9H).

Example 9(2)

(13E,15α)-15-hydroxy-1,5-(2,5-interthienylene)-9-oxo-2,3,4-trinor-8-azaprost-13-enoic acid 2-(2-ethyl-2-methylbutanoyloxy)ethyl ester TLC: Rf 0.26 (ethyl acetate);

NMR (CDCl$_3$): δ 7.62 (d, J=3.3 Hz, 1H), 6.81 (d, J=3.3 Hz, 1H), 5.68 (dd, J=15.6, 6.3 Hz, 1H), 5.48 (dd, J=15.6, 8.7 Hz, 1H), 4.47 (m, 2H), 4.38 (m, 2H), 4.18-4.00 (m, 2H), 3.60 (m, 1H), 2.99 (m, 1H), 2.83 (t, J=7.8 Hz, 2H), 2.50-2.16 (m, 3H), 1.97-1.23 (m, 16H), 1.10 (s, 3H), 0.98-0.80 (m, 9H).

Example 9(3)

(13E,15α)-15-hydroxy-9-oxo-5-thia-8-azaprost-13-enoic acid 2-(2-ethyl-2-methylbutanoyloxy)ethyl ester TLC: Rf 0.26 (ethyl acetate);

NMR (CDCl$_3$): δ 5.73 (dd, J=15.3, 5.7 Hz, 1H), 5.52 (dd, J=15.3, 9.0 Hz, 1H), 4.28 (s, 4H), 4.15 (m, 2H), 3.66 (m, 1H), 3.09 (m, 1H), 2.77-2.50 (m, 4H), 2.49-2.20 (m, 5H), 1.96-1.82 (m, 2H), 1.80-1.22 (m, 14H), 1.10 (s, 3H), 0.94-0.80 (m, 9H).

Example 9(4)

(15α)-15-hydroxy-5-(4-(2-(2-ethyl-2-methylbutanoyloxy)ethoxycarbonyl)thiazol-2-yl)-9-oxo-1,2,3,4-tetranor-5-thia-8-azaprostane TLC: Rf 0.45 (ethyl acetate);

NMR (CDCl$_3$): δ 0.85 (m, 9H) 1.10 (s, 3H) 1.51 (m, 16H) 1.98 (m, 1H) 2.13 (m, 1H) 2.39 (m, 3H) 3.59 (m, 6H) 4.39 (m, 2H) 4.52 (m, 2H) 7.97 (s, 1H).

Example 10

14-oxa-14-(3,5-dichlorophenyl)-5-(4-hydroxymethylthiazol-2-yl)-9-oxo-1,2,3,4,15,16,17,18,19,20-decanor-5-thia-8-azaprostane

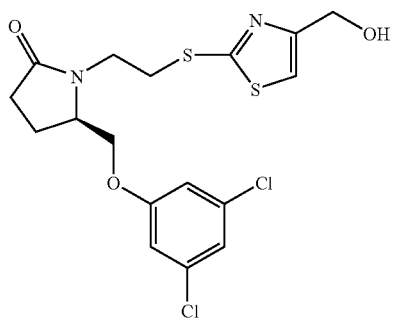

To a solution of the compound prepared in Example 5(32) (125 mg) in tetrahydrofuran (3 mL) was added sodium borohydride (40 mg) and the mixture was stirred at room temperature for 1 day. The reaction mixture was poured into water and extracted with ethyl acetate. The organic layer was washed with water and brine, dried over anhydrous magnesium sulfate and concentrated. The obtained residue was purified by column chromatography on silica gel (n-hexane:ethyl acetate=1:4) to give the compound of the present invention (68.9 mg) having the following physical data.

TLC: Rf 0.34 (ethyl acetate);

NMR (CDCl$_3$): δ 1.93 (m, 1H) 2.22 (m, 1H) 2.38 (m, 1H) 2.53 (m, 2H) 3.34 (m, 1H) 3.51 (m, 2H) 3.93 (m, 2H) 4.11 (m, 2H) 4.68 (br. s., 2H) 6.77 (d, J=1.70 Hz, 2H) 6.99 (t, J=1.70 Hz, 1H) 7.05 (s, 1H).

Example 11

(2R)-2-(3,5-dichlorophenoxymethyl)-1-(2-(4-methoxymethyl-1,3-thiazol-2-ylthio)ethyl)pyrrolidin-5-one

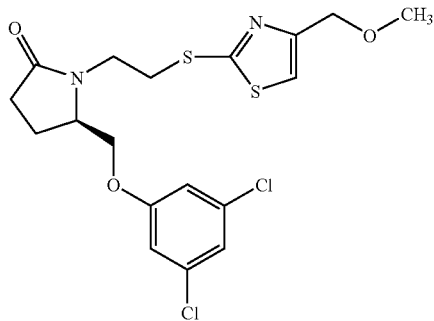

Under an atmosphere of argon, to a solution of the compound prepared in Example 10 (112 mg) in tetrahydrofuran (1 mL) was added sodium hydride (13 mg) and the mixture was stirred at room temperature for 30 minutes. Methyl iodide (0.1 mL) was added to the reaction solution, which was stirred for 1 hour. Water was added to the reaction mixture, which was extracted with ethyl acetate. The organic layer was washed with water and brine, dried over anhydrous magnesium sulfate and concentrated. The obtained residue was purified by column chromatography on silica gel (n-hexane:ethyl acetate=1:4→ethyl acetate) to give the compound of the present invention (98.2 mg) having the following physical data.

TLC: Rf 0.44 (ethyl acetate);

NMR (CDCl$_3$): δ 1.96 (m, 1H) 2.22 (m, 1H) 2.38 (ddd, J=16.90, 9.80, 5.13 Hz, 1H) 2.54 (ddd, J=16.90, 9.80, 7.30 Hz, 1H) 3.42 (s, 3H) 3.42 (m, 3H) 3.87 (ddd, J=13.55, 7.78, 6.04 Hz, 1H) 3.97 (dd, J=9.60, 4.00 Hz, 1H) 4.10 (ddd, J=11.63, 7.78, 3.30 Hz, 1H) 4.18 (dd, J=9.60, 3.90 Hz, 1H) 4.48 (m, 2H) 6.78 (d, J=1.65 Hz, 2H) 6.98 (t, J=1.65 Hz, 1H) 7.09 (s, 1H).

Example 12

2-(2-((2R)-2-(3,5-dichlorophenoxymethyl)-5-oxopyrrolidin-1-yl)ethylthio)-1,3-thiazole-4-carboxamide

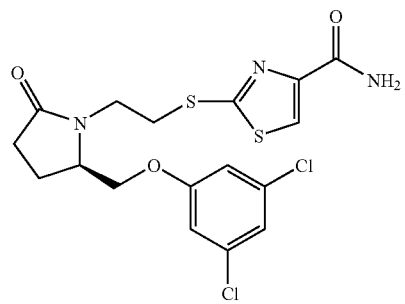

To a solution of the compound prepared in Example 6(32) (300 mg) in toluene (4.0 mL) were added oxalyl chloride (0.07 mL) and dimethylformamide (one drop) and the mixture was stirred at room temperature and 40 minutes. The reaction mixture was concentrated and dissolved into anhydrous tetrahydrofuran (2.0 mL). To ammonia water (1.0 mL) was added the above tetrahydrofuran solution at 0° C. and the mixture was stirred for 30 minutes. The reaction mixture was concentrated and extracted with dichloromethane. The organic layer was dried over anhydrous magnesium sulfate and concentrated. The obtained residue was purified by column chromatography on silica gel (ethyl acetate) to give the compound of the present invention (280 mg) having the following physical data.

TLC: Rf 0.55 (ethyl acetate);

NMR (CDCl$_3$): δ 8.02 (s, 1H), 7.99 (s, 1H), 7.01 (t, J=1.5 Hz, 1H), 6.78 (d, J=1.5 Hz, 2H), 5.65 (s, 1H), 4.17-3.91 (m, 4H), 3.63 (m, 1H), 3.50 (m, 1H), 3.31 (m, 1H), 2.53 (m, 1H), 2.40 (m, 1H), 2.22 (m, 1H), 1.92 (m, 1H).

Example 12(1) to 12(4)

By the same procedure as described in Example 12, using a corresponding amine derivative, amide derivative or sulfonamide derivative instead of ammonia water, the following compounds of the present invention were obtained.

Example 12(1)

2-(2-((2R)-2-(3,5-dichlorophenoxymethyl)-5-oxopyrrolidin-1-yl)ethylthio)-N,N-dimethyl-1,3-thiazole-4-carboxamide

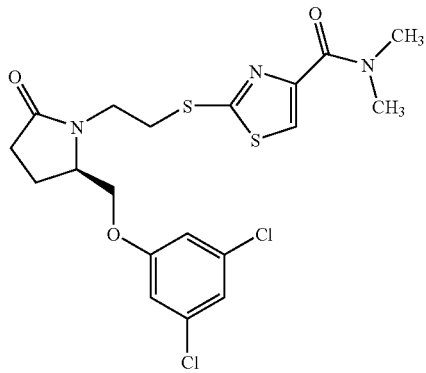

TLC: Rf 0.23 (ethyl acetate);
NMR (CDCl$_3$): δ 1.94 (m, 1H) 2.23 (m, 1H) 2.38 (ddd, J=16.93, 9.80, 5.00 Hz, 1H) 2.53 (ddd, J=16.93, 9.70, 7.23 Hz, 1H) 3.10 (s, 3H) 3.22 (s, 3H) 3.47 (m, 3H) 3.92 (m, 2H) 4.06 (m, 1H) 4.14 (dd, J=9.60, 3.90 Hz, 1H) 6.77 (d, J=1.74 Hz, 2H) 6.99 (t, J=1.74 Hz, 1H) 7.68 (s, 1H).

Example 12(2)

(2R)-2-(3,5-dichlorophenoxymethyl)-1-(2-(4-(4-methylpiperazin-1-ylcarbonyl)-1,3-thiazol-2-ylthio)ethyl)pyrrolidin-5-one TLC: Rf 0.55 (methylene chloride:methanol=9:1);
NMR (CDCl$_3$): δ 1.93 (m, 1H) 2.23 (m, 1H) 2.31 (s, 3H) 2.46 (m, 6H) 3.47 (m, 3H) 3.80 (m, 4H) 3.95 (m, 2H) 4.08 (m, 2H) 6.76 (d, J=1.74 Hz, 2H) 6.99 (t, J=1.74 Hz, 1H) 7.71 (s, 1H).

Example 12(3)

2-(2-((2R)-2-(3,5-dichlorophenoxymethyl)-5-oxopyrrolidin-1-yl)ethylthio)-N-methylsulfonyl-1,3-thiazole-4-carboxamide TLC: Rf 0.47 (methylene chloride:methanol=9:1);
NMR (DMSO-D6): δ 8.00 (s, 1H), 7.15 (d, J=1.8 Hz, 2H), 7.11 (t, J=1.8 Hz, 1H), 4.59 (m, 1H), 4.16-4.00 (m, 2H), 3.70 (m, 1H), 3.50-3.20 (m, 2H), 2.97 (s, 3H), 2.60-2.25 (m, 2H), 2.25-2.00 (m, 2H), 1.85 (m, 1H).

Example 12(4)

N-benzoyl-2-(2-((2R)-2-(3,5-dichlorophenoxymethyl)-5-oxopyrrolidin-1-yl)ethylthio)-1,3-thiazole-4-carboxamide TLC: Rf 0.20 (hexane:ethyl acetate=1:2);
NMR (CDCl$_3$): δ 8.21 (s, 1H), 8.00-7.92 (m, 2H), 7.61 (m, 1H), 7.55-7.46 (m, 2H), 6.99 (t, J=1.5 Hz, 1H), 6.71 (d, J=1.5 Hz, 2H), 4.10-3.88 (m, 4H), 3.72-3.54 (m, 2H), 3.42 (m, 1H), 2.44 (m, 1H), 2.35-2.06 (m, 2H), 1.86 (m, 1H).

Example 13(1) to 13(8)

By the same procedure as described in Example 1, using the compound prepared in Reference Example 3 or a corresponding aldehyde derivative, and the compound prepared in Reference Example 9 or a corresponding amine derivative, the following compounds of the present invention were obtained.

Example 13(1)

2-(2-((2R)-2-(2-naphthyloxymethyl)-5-oxopyrrolidin-1-yl)ethylthio)-1,3-thiazole-4-carboxylic acid butyl ester

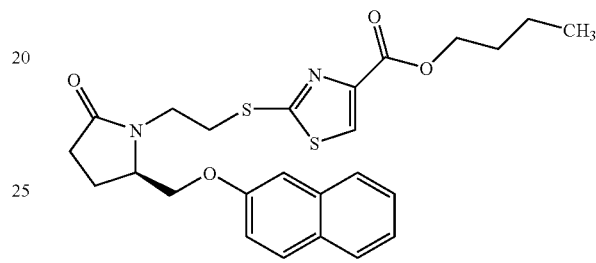

TLC: Rf 0.22 (hexane:ethyl acetate=1:1);
NMR (CDCl$_3$): δ 0.96 (t, J=7.30 Hz, 3H) 1.44 (m, 2H) 1.74 (m, 2H) 2.10 (m, 1H) 2.26 (m, 1H) 2.41 (m, 1H) 2.63 (m, 1H) 3.39 (m, 1H) 3.51 (m, 1H) 3.64 (m, 1H) 3.94 (m, 1H) 4.13 (dd, J=9.60, 3.60 Hz, 1H) 4.21 (m, 1H) 4.33 (m, 2H) 4.57 (dd, J=9.60, 3.00 Hz, 1H) 7.10 (m, 1H) 7.19 (m, 1H) 7.33 (m, 1H) 7.42 (m, 1H) 7.71 (m, 3H) 7.94 (s, 1H).

Example 13(2)

2-(2-((2R)-2-(3-ethylphenoxymethyl)-5-oxopyrrolidin-1-yl)ethylthio)-1,3-thiazole-4-carboxylic acid butyl ester TLC: Rf 0.28 (hexane:ethyl acetate=1:1);
NMR (CDCl$_3$): δ 0.97 (t, J=7.30 Hz, 3H) 1.20 (t, J=7.70 Hz, 3H) 1.45 (m, 2H) 1.73 (m, 2H) 2.03 (m, 1H) 2.21 (m, 1H) 2.37 (m, 1H) 2.59 (m, 3H) 3.48 (m, 3H) 3.95 (m, 2H) 4.14 (m, 1H) 4.35 (m, 3H) 6.73 (m, 3H) 7.15 (m, 1H) 7.98 (s, 1H).

Example 13(3)

2-(2-((2R)-5-oxo-2-(3-trifluoromethylphenoxymethyl)pyrrolidin-1-yl)ethylthio)-1,3-thiazole-4-carboxylic acid butyl ester TLC: Rf 0.63 (ethyl acetate);
NMR (CDCl$_3$): δ 0.97 (t, J=7.32 Hz, 3H) 1.45 (m, 2H) 1.74 (m, 2H) 2.10 (m, 1H) 2.25 (m, 1H) 2.40 (ddd, J=16.84, 9.98, 5.22 Hz, 1H) 2.61 (ddd, J=16.84, 9.98, 7.14 Hz, 1H) 3.32 (ddd, J=13.46, 9.25, 5.68 Hz, 1H) 3.48 (ddd, J=13.46, 9.25, 5.18 Hz, 1H) 3.62 (ddd, J=13.90, 9.00, 5.50 Hz, 1H) 3.88 (ddd, J=13.90, 9.00, 5.50 Hz, 1H) 4.06 (dd, J=10.34, 3.02 Hz, 1H) 4.17 (m, 1H) 4.32 (t, J=6.68 Hz, 2H) 4.68 (dd, J=10.34, 3.02 Hz, 1H) 7.09 (m, 1H) 7.20 (m, 2H) 7.35 (m, 1H) 7.96 (s, 1H).

Example 13(4)

2-(2-((2R)-5-oxo-2-(3-trifluoromethoxyphenoxymethyl)pyrrolidin-1-yl)ethylthio)-1,3-thiazole-4-carboxylic acid butyl ester TLC: Rf 0.64 (ethyl acetate);
NMR (CDCl$_3$): δ 0.97 (t, J=7.32 Hz, 3H) 1.45 (m, 2H) 1.74 (m, 2H) 2.07 (m, 1H) 2.24 (m, 1H) 2.39 (ddd, J=16.90, 10.00, 5.20 Hz, 1H) 2.59 (ddd, J=16.90, 10.20, 7.15 Hz, 1H) 3.33 (ddd, J=13.40, 9.00, 5.80 Hz, 1H) 3.49 (ddd, J=13.40, 9.20, 5.20 Hz, 1H) 3.60 (ddd, J=13.70, 9.00, 5.20 Hz, 1H) 3.89 (ddd, J=13.70, 9.20, 5.80 Hz, 1H) 4.02 (dd, J=10.25, 3.48 Hz, 1H) 4.15 (m, 1H) 4.32 (t, J=6.68 Hz, 2H) 4.57 (dd, J=10.25, 3.11 Hz, 1H) 6.82 (m, 3H) 7.24 (m, 1H) 7.97 (s, 1H).

Example 13(5)

(3-((2R)-2-(3,5-dichlorophenoxymethyl)-5-oxopyrrolidin-1-ylmethyl)phenoxy)acetic acid ethyl ester TLC: Rf 0.25 (hexane:ethyl acetate=1:1);
NMR (CDCl$_3$): δ 1.30 (t, J=7.14 Hz, 3H) 1.96 (m, 1H) 2.21 (m, 1H) 2.46 (m, 1H) 2.63 (m, 1H) 3.87 (m, 3H) 4.21 (d, J=15.11 Hz, 1H) 4.27 (q, J=7.14 Hz, 2H) 4.56 (s, 2H) 4.83 (d, J=15.11 Hz, 1H) 6.68 (d, J=1.65 Hz, 2H) 6.76 (m, 1H) 6.81 (m, 1H) 6.88 (m, 1H) 6.97 (t, J=1.65 Hz, 1H) 7.20 (t, J=7.80 Hz, 1H).

Example 13(6)

(2E)-3-(3-((2R)-2-(3,5-dichlorophenoxymethyl)-5-oxopyrrolidin-1-ylmethyl)phenyl)-2-propenoic acid methyl ester TLC: Rf 0.25 (hexane:ethyl acetate=1:1);
NMR (CDCl$_3$): δ 1.97 (m, 1H) 2.23 (m, 1H) 2.48 (m, 1H) 2.66 (m, 1H) 3.81 (s, 3H) 3.88 (m, 3H) 4.40 (d, J=15.11 Hz, 1H) 4.74 (d, J=15.11 Hz, 1H) 6.38 (d, J=16.21 Hz, 1H) 6.62 (d, J=1.79 Hz, 2H) 6.95 (t, J=1.79 Hz, 1H) 7.30 (m, 2H) 7.38 (m, 2H) 7.59 (d, J=16.21 Hz, 1H).

Example 13(7)

3-(3-((2R)-2-(3,5-dichlorophenoxymethyl)-5-oxopyrrolidin-1-ylmethyl)phenyl)propanoic acid methyl ester TLC: Rf 0.22 (hexane:ethyl acetate=1:1);
NMR (CDCl$_3$): δ 1.96 (m, 1H) 2.21 (m, 1H) 2.56 (m, 4H) 2.88 (t, J=7.69 Hz, 2H) 3.66 (s, 3H) 3.86 (m, 3H) 4.25 (d, J=15.11 Hz, 1H) 4.80 (d, J=15.11 Hz, 1H) 6.66 (d, J=1.65 Hz, 2H) 6.97 (t, J=1.65 Hz, 1H) 7.08 (m, 3H) 7.20 (t, J=7.83 Hz, 1H).

Example 13(8)

2-(2-((2R)-5-oxo-2-(pyridin-2-yloxymethyl)pyrrolidin-1-yl)ethylthio)-1,3-thiazole-4-carboxylic acid ethyl ester TLC: Rf 0.50 (ethyl acetate);
NMR (CDCl$_3$): δ 1.38 (t, J=7.00 Hz, 3H) 1.98 (m, 1H) 2.21 (m, 1H) 2.34 (m, 1H) 2.52 (m, 1H) 3.50 (m, 3H) 3.97 (m, 1H) 4.16 (m, 1H) 4.38 (m, 3H) 4.53 (dd, J=12.00, 4.00 Hz, 1H) 6.69 (m, 1H) 6.88 (m, 1H) 7.56 (m, 1H) 8.01 (s, 1H) 8.10 (m, 1H).

Example 14(1) to 14(52)

By the same procedure as described in Example 2, using the compound prepared in Example 13(1) to 13(8) or a corresponding ester instead of the compound prepared in Example 1, the following compounds of the present invention were obtained.

Example 14(1)

(15α,13E)-15-hydroxy-9-oxo-17-phenyl-18,19,20-trinor-5-thia-8-azaprost-13-enoic acid

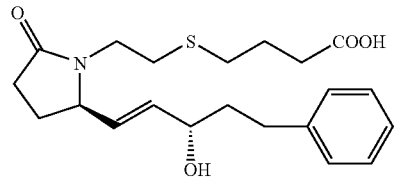

TLC: Rf 0.44 (chloroform:methanol=9:1);
NMR (CDCl$_3$): δ 7.37-7.15 (m, 5H), 5.78 (dd, J=15.3, 5.4 Hz, 1H), 5.60 (ddd, J=15.3, 8.4, 1.2 Hz, 1H), 4.25-4.10 (m, 2H), 3.64 (m, 1H), 3.12 (m, 1H), 2.82-2.10 (m, 12H), 2.00-1.70 (m, 5H).

Example 14(2)

(15α,13E)-15-hydroxy-9-oxo-18-phenyl-19,20-dinor-5-thia-8-azaprost-13-enoic acid TLC: Rf 0.43 (chloroform:methanol=9:1);
NMR (CDCl$_3$): δ 7.37-7.15 (m, 5H), 5.72 (dd, J=15.3, 5.7 Hz, 1H), 5.50 (dd, J=15.3, 8.4 Hz, 1H), 4.65-4.08 (m, 4H), 3.63 (m, 1H), 3.10 (m, 1H), 2.72-2.19 (m, 11H), 1.99-1.50 (m, 7H).

Example 14(3)

2-(2-((2R)-5-oxo-2-(5-oxo-5,6,7,8-tetrahydronaphthalen-1-yloxymethyl)pyrrolidin-1-yl)ethylthio)-1,3-thiazole-4-carboxylic acid

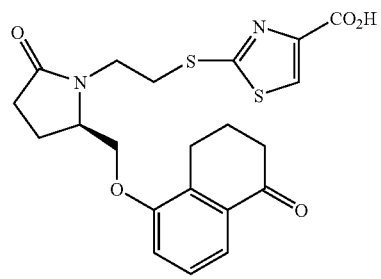

TLC: Rf 0.59 (chloroform:methanol:acetic acid=90:10:1);
NMR (CDCl$_3$): δ 2.07 (m, 3H) 2.31 (m, 1H) 2.47 (m, 1H) 2.64 (m, 3H) 2.83 (m, 2H) 3.28 (m, 1H) 3.51 (m, 1H) 3.73 (m, 1H) 4.04 (m, 3H) 4.26 (dd, J=10.00, 3.00 Hz, 1H) 7.02 (m, 1H) 7.27 (m, 1H) 7.70 (m, 1H) 8.09 (s, 1H).

Example 14(4)

2-(2-((2R)-2-(3,5-difluorophenoxymethyl)-5-oxopyrrolidin-1-yl)ethylthio)-1,3-thiazole-4-carboxylic acid TLC: Rf 0.52 (chloroform:methanol:acetic acid=90:10:1);
NMR (CDCl$_3$): δ 1.95 (m, 1H) 2.23 (m, 1H) 2.41 (ddd, J=17.10, 9.90, 5.50 Hz, 1H) 2.58 (ddd, J=17.10, 10.10, 7.10 Hz, 1H) 3.26 (ddd, J=13.50, 10.00, 5.40 Hz, 1H) 3.48 (dd, J=13.50, 10.00, 5.40 Hz, 1H) 3.65 (ddd, J=13.50, 10.00, 5.40 Hz, 1H) 3.90 (m, 1H) 3.95 (dd, J=9.90, 4.70 Hz, 1H) 4.08 (m, 1H) 4.23 (dd, J=9.90, 3.00 Hz, 1H) 6.43 (m, 3H) 8.08 (s, 1H).

Example 14(5)

2-(2-((2R)-2-(4-methoxy-2-nitrophenoxymethyl)-5-oxopyrrolidin-1-yl)ethylthio)-1,3-thiazole-4-carboxylic acid TLC: Rf 0.43 (chloroform:methanol:acetic acid=90:10:1);
NMR (CDCl$_3$): δ 1.91 (m, 1H) 2.28 (m, 1H) 2.43 (ddd, J=17.00, 10.20, 6.60 Hz, 1H) 2.60 (ddd, J=17.00, 10.20, 6.60 Hz, 1H) 3.34 (ddd, J=13.20, 10.20, 5.20 Hz, 1H) 3.51 (d dd, J=13.20, 10.20, 5.20 Hz, 1H) 3.76 (m, 1H) 3.82 (s, 3H) 4.09 (m, 3H) 4.25 (m, 1H) 7.04 (d, J=9.00 Hz, 1H) 7.11 (dd, J=9.00, 3.00 Hz, 1H) 7.41 (d, J=3.00 Hz, 1H) 8.07 (s, 1H).

Example 14(6)

2-(2-((2R)-2-(4-acetyl-3-fluorophenoxymethyl)-5-oxopyrrolidin-1-yl)ethylthio)-1,3-thiazole-4-carboxylic acid TLC: Rf 0.50 (chloroform:methanol:acetic acid=90:10:1);
NMR (CDCl$_3$): δ 1.99 (m, 1H) 2.28 (m, 1H) 2.44 (m, 1H) 2.59 (d, J=4.90 Hz, 3H) 2.59 (m, 1H) 3.28 (ddd, J=13.50, 10.40, 5.40 Hz, 1H) 3.48 (ddd, J=13.50, 10.40, 5.40 Hz, 1H) 3.70 (m, 1H) 3.94 (ddd, J=13.50, 10.40, 5.40 Hz, 1H) 4.10 (m, 2H) 4.33 (dd, J=9.60, 3.00 Hz, 1H) 6.65 (dd, J=12.50, 2.50 Hz, 1H) 6.76 (dd, J=8.65, 2.50 Hz, 1H) 7.89 (t, J=8.65 Hz, 1H) 8.10 (s, 1H).

Example 14(7)

2-(2-((2R)-2-(3-ethynylphenoxymethyl)-5-oxopyrrolidin-1-yl)ethylthio)-1,3-thiazole-4-carboxylic acid TLC: Rf 0.48 (chloroform:methanol:acetic acid=90:10:1);
NMR (CDCl$_3$): δ 1.95 (m, 1H) 2.25 (m, 1H) 2.42 (m, 1H) 2.59 (m, 1H) 3.08 (s, 1H) 3.27 (ddd, J=13.50, 10.20, 5.00 Hz, 1H) 3.49 (ddd, J=13.50, 10.20, 5.00 Hz, 1H) 3.74 (m, 1H) 4.18 (dd, J=10.00, 3.00 Hz, 1H) 6.88 (m, 1H) 7.00 (m, 1H) 7.13 (m, 1H) 7.24 (m, 1H) 8.08 (s, 1H).

Example 14(8)

2-(2-((2R)-2-(4-formyl-3-methoxyphenoxymethyl)-5-oxopyrrolidin-1-yl)ethylthio)-1,3-thiazole-4-carboxylic acid TLC: Rf 0.48 (chloroform:methanol:acetic acid=90:10:1);
NMR (CDCl$_3$): δ 2.02 (m, 1H) 2.29 (m, 1H) 2.45 (ddd, J=17.00, 10.00, 7.00 Hz, 1H) 2.63 (ddd, J=17.00, 10.00, 7.00 Hz, 1H) 3.29 (ddd, J=13.40, 10.20, 5.20 Hz, 1H) 3.49 (d dd, J=13.40, 10.20, 5.20 Hz, 1H) 3.71 (m, 1H) 3.90 (s, 3H) 3.94 (m, 1H) 4.11 (m, 2H) 4.38 (m, 1H) 6.44 (d, J=2.20 Hz, 1H) 6.56 (m, 1H) 7.81 (d, J=8.50 Hz, 1H) 8.10 (s, 1H) 10.29 (s, 1H).

Example 14(9)

2-(2-((2R)-2-(2-chloro-3,5-difluorophenoxymethyl)-5-oxopyrrolidin-1-yl)ethylthio)-1,3-thiazole-4-carboxylic acid TLC: Rf 0.54 (chloroform:methanol:acetic acid=90:10:1);
NMR (CDCl$_3$): δ 1.96 (m, 1H) 2.38 (m, 2H) 2.69 (m, 1H) 3.29 (m, 1H) 3.55 (m, 1H) 3.78 (m, 1H) 4.00 (m, 2H) 4.17 (m, 1H) 4.33 (dd, J=10.20, 2.80 Hz, 1H) 6.58 (m, 2H) 8.09 (s, 1H).

Example 14(10)

(15α,13E)-15-hydroxy-5-(4-carboxythiazol-2-yl)-9-oxo-18-phenoxy-1,2,3,4,19,20-hexanor-5-thia-8-azaprost-13-ene TLC: Rf 0.59 (chloroform:methanol=4:1);
NMR (CDCl$_3$): δ 8.07 (s, 1H), 7.31-7.25 (m, 2H), 6.97-6.87 (m, 3H), 5.82 (dd, J=15.0, 5.1 Hz, 1H), 5.59 (dd, J=15.0, 8.4 Hz, 1H), 4.30-4.24 (m, 1H), 4.18-4.12 (m, 1H), 4.00 (t, J=5.7 Hz, 2H), 3.86-3.74 (m, 1H), 3.56-3.27 (m, 5H), 2.53-2.18 (m, 3H), 2.10-1.76 (m, 5H).

Example 14(11)

(15α,13E)-15-hydroxy-5-(4-carboxythiazol-2-yl)-9-oxo-17-phenoxy-1,2,3,4,18,19,20-heptanor-5-thia-8-azaprost-13-ene TLC: Rf 0.38 (chloroform:methanol:acetic acid=9:1:0.1);
NMR (CDCl$_3$): δ 8.08 (s, 1H), 7.31-7.26 (m, 2H), 6.98-6.88 (m, 3H), 5.86 (dd, J=15.3, 5.7 Hz, 1H), 5.64 (dd, J=15.3, 8.4 Hz, 1H), 4.53-4.48 (m, 1H), 4.19-4.07 (m, 3H), 3.81-3.74 (m, 1H), 3.50-3.30 (m, 3H), 2.46-2.19 (m, 3H), 2.04-1.99 (m, 1H), 1.79-1.73 (m, 1H), 1.30-1.24 (m, 1H), 0.93-0.83 (m, 1H).

Example 14(12)

2-(2-((2R)-2-(3,5-dichlorophenylthiomethyl)-5-oxopyrrolidin-1-yl)ethylthio)-1,3-thiazole-4-carboxylic acid TLC: Rf 0.56 (chloroform:methanol:acetic acid=90:10:1);
NMR (CDCl$_3$): δ 1.94 (m, 1H) 2.32 (m, 2H) 2.54 (ddd, J=18.30, 10.50, 6.00 Hz, 1H) 3.17 (dd, J=12.90, 6.90 Hz, 1H) 3.40 (m, 4H) 3.96 (m, 2H) 7.18 (t, J=1.80 Hz, 1H) 7.21 (d, J=1.80 Hz, 2H) 8.11 (s, 1H).

Example 14(13)

(15α,13E)-15-hydroxy-5-(4-carboxythiazol-2-yl)-9-oxo-18-(naphthalen-2-yl)-1,2,3,4,19,20-hexanor-5-thia-8-azaprost-13-ene

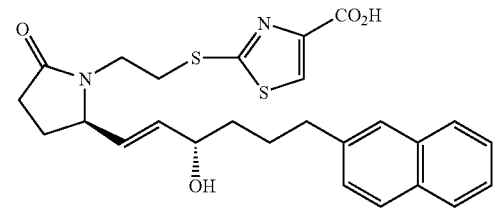

TLC: Rf 0.26 (chloroform:methanol:acetic acid=9:1:0.1);
NMR (CDCl₃): δ 8.03 (s, 1H), 7.81-7.74 (m, 4H), 7.58 (s, 1H), 7.47-7.39 (m, 2H), 7.31-7.28 (m, 1H), 5.76 (dd, J=15.3, 5.4 Hz, 1H), 5.52 (dd, J=15.3, 8.1 Hz, 1H), 4.22-4.07 (m, 4H), 3.79-3.72 (m, 1H), 3.45-3.25 (m, 3H), 2.79 (t, J=7.2 Hz, 2H), 2.44-2.18 (m, 3H), 1.84-1.55 (m, 5H).

Example 14(14)

(15α,13E)-15-hydroxy-5-(4-carboxythiazol-2-yl)-9-oxo-19-(naphthalen-2-yl)-1,2,3,4,20-pentanor-5-thia-8-azaprost-13-ene TLC: Rf 0.22 (chloroform:methanol:acetic acid=9:1:0.1);
NMR (CDCl₃): δ 8.07 (s, 1H), 7.81-7.74 (m, 3H), 7.59 (s, 1H), 7.47-7.39 (m, 2H), 7.33-7.28 (m, 1H), 5.74 (dd, J=15.3, 6.0 Hz, 1H), 5.49 (dd, J=15.9, 9.0 Hz, 1H), 4.16-4.07 (m, 4H), 3.79-3.72 (m, 1H), 3.45-3.25 (m, 5H), 2.79-2.74 (m, 2H), 2.44-2.18 (m, 3H), 1.84-1.55 (m, 5H).

Example 14(15)

(15α,13E, 18E)-15-hydroxy-5-(4-carboxythiazol-2-yl)-9-oxo-19-naphthalen-2-yl-1,2,3,4,19,20-hexanor-5-thia-8-azaprost-13,18-diene TLC: Rf 0.22 (chloroform:methanol:acetic acid=9:1:0.1);
NMR (CDCl₃): δ 8.06 (s, 1H), 7.78-7.74 (m, 3H), 7.65 (s, 1H), 7.55 (dd, J=8.7, 2.8 Hz, 1H), 7.46-7.39 (m, 2H), 6.55 (d, J=15.3 Hz, 1H), 6.36-6.27 (m, 1H), 5.84 (dd, J=15.3, 5.4 Hz, 1H), 5.59 (dd, J=15.0, 9.6 Hz, 1H), 4.30-4.12 (m, 2H), 3.86-3.71 (m, 4H), 3.47-3.32 (m, 3H), 2.47-2.18 (m, 4H), 1.79-1.69 (m, 3H).

Example 14(16)

2-(2-((2R)-2-benzyloxymethyl-5-oxopyrrolidin-1-yl)ethylthio)-1,3-thiazole-4-carboxylic acid TLC: Rf 0.36 (methylene chloride:methanol=9:1);
NMR (CDCl₃): δ 8.06 (s, 1H), 7.40-7.24 (m, 5H), 4.53 (s, 2H), 3.85-3.82 (m, 2H), 3.75-3.56 (m, 2H), 3.52-3.34 (m, 2H), 3.24 (m, 1H), 2.57-2.25 (m, 2H), 2.12 (m, 1H), 1.78 (m, 1H).

Example 14(17)

2-(2-((2R)-2-(3-dimethylaminophenoxymethyl)-5-oxopyrrolidin-1-yl)ethylthio)-1,3-thiazole-4-carboxylic acid TLC: Rf 0.44 (chloroform:methanol:acetic acid=90:10:1);
NMR (CDCl₃): δ 1.95 (m, 1H) 2.24 (m, 1H) 2.42 (ddd, J=17.00, 10.20, 5.70 Hz, 1H) 2.60 (ddd, J=17.00, 10.20, 6.60 Hz, 1H) 2.94 (s, 6H) 3.28 (ddd, J=13.20, 10.40, 5.20 Hz, 1H) 3.52 (ddd, J=13.20, 10.40, 5.20 Hz, 1H) 3.92 (m, 4H) 4.18 (dd, J=9.90, 3.00 Hz, 1H) 4.79 (br. s., 1H) 6.26 (m, 2H) 6.41 (m, 1H) 7.14 (t, J=8.40 Hz, 1H) 8.07 (s, 1H).

Example 14(18)

3-((2R)-2-(3,5-dichlorophenoxymethyl)-5-oxopyrrolidin-1-ylmethyl)phenoxyacetic acid TLC: Rf 0.31 (chloroform:methanol:acetic acid=90:10:1);
NMR (CDCl₃): δ 1.97 (m, 1H) 2.23 (m, 1H) 2.52 (m, 1H) 2.68 (m, 1H) 3.88 (m, 3H) 4.26 (d, J=15.11 Hz, 1H) 4.59 (s, 2H) 4.78 (d, J=15.11 Hz, 1H) 6.67 (d, J=1.65 Hz, 2H) 6.82 (m, 3H) 6.96 (t, J=1.65 Hz, 1H) 7.19 (t, J=7.83 Hz, 1H).

Example 14(19)

(2E)-3-(3-((2R)-2-(3,5-dichlorophenoxymethyl)-5-oxopyrrolidin-1-ylmethyl)phenyl)-2-propenoic acid TLC: Rf 0.46 (chloroform:methanol:acetic acid=90:10:1);
NMR (CDCl₃): δ 1.98 (m, 1H) 2.25 (m, 1H) 2.52 (m, 1H) 2.69 (m, 1H) 3.86 (m, 3H) 4.41 (d, J=15.38 Hz, 1H) 4.76 (d, J=15.38 Hz, 1H) 6.42 (d, J=16.21 Hz, 1H) 6.63 (d, J=1.79 Hz, 2H) 6.96 (t, J=1.79 Hz, 1H) 7.31 (m, 2H) 7.42 (m, 2H) 7.69 (d, J=16.21 Hz, 1H).

Example 14(20)

3-(3-((2R)-2-(3,5-dichlorophenoxymethyl)-5-oxopyrrolidin-1-ylmethyl)phenyl)propanoic acid TLC: Rf 0.64 (ethyl acetate:methanol=9:1);
NMR (CDCl₃): δ 1.97 (m, 1H) 2.22 (m, 1H) 2.48 (m, 1H) 2.65 (m, 3H) 2.89 (t, J=7.51 Hz, 2H) 3.87 (m, 3H) 4.26 (d, J=15.01 Hz, 1H) 4.79 (d, J=15.01 Hz, 1H) 6.66 (d, J=1.83 Hz, 2H) 6.97 (t, J=1.83 Hz, 1H) 7.09 (m, 3H) 7.20 (m, 1H).

Example 14(21)

5-(3-((2R)-2-(3,5-dichlorophenoxymethyl)-5-oxopyrrolidin-1-yl)propyl)thiophene-2-carboxylic acid TLC: Rf 0.23 (methylene chloride:methanol=15:1);
NMR (CDCl₃): δ 7.69 (d, J=3.6 Hz, 1H), 7.00 (t, J=1.8 Hz, 1H), 6.82 (d, J=3.6 Hz, 1H), 6.75 (d, J=1.8 Hz, 2H), 4.06-3.86 (m, 2H), 3.69 (m, 1H), 3.17 (m, 1H), 2.88 (t, J=7.5 Hz, 2H), 2.54 (m, 1H), 2.41 (m, 1H), 2.21 (m, 1H), 2.10-1.78 (m, 4H).

Example 14(22)

4-(2-((2R)-2-(3,5-dichlorophenoxymethyl)-5-oxopyrrolidin-1-yl)ethyl)benzoic acid TLC: Rf 0.34 (methylene chloride:methanol=15:1);
NMR (CDCl₃): δ 8.02 (d, J=8.4 Hz, 2H), 7.30 (d, J=8.4 Hz, 2H), 7.00 (t, J=2.1 Hz, 1H), 6.74 (d, J=2.1 Hz, 2H), 3.98-3.72 (m, 4H), 3.37 (m, 1H), 3.02 (m, 1H), 2.92 (m, 1H), 2.52 (m, 1H), 2.39 (m, 1H), 2.16 (m, 1H), 1.86 (m, 1H).

Example 14(23)

2-(2-((2R)-5-oxo-2-(pyridin-2-yloxymethyl)pyrrolidin-1-yl)ethylthio)-1,3-thiazole-4-carboxylic acid TLC: Rf 0.24 (methylene chloride:methanol:acetic acid=90:10:0.3);
NMR (CDCl₃): δ 2.03 (m, 1H) 2.24 (m, 1H) 2.41 (m, 1H) 2.58 (m, 1H) 3.28 (m, 1H) 3.41 (m, 1H) 3.75 (m, 2H) 4.05 (m, 1H) 4.28 (dd, J=11.50, 4.40 Hz, 1H) 4.75 (m, 1H) 6.75 (d, J=8.20 Hz, 1H) 6.92 (m, 1H) 7.61 (m, 1H) 8.08 (s, 1H) 8.10 (m, 1H).

Example 14(24)

2-(2-((2R)-5-oxo-2-(quinolin-5-yloxymethyl)pyrrolidin-1-yl)ethylthio)-1,3-thiazole-4-carboxylic acid TLC: Rf 0.16 (chloroform:methanol=9:1);
NMR (DMSO-D6): δ 8.68 (dd, J=4.2, 1.2 Hz, 1H), 8.35 (d, J=8.4 Hz, 1H), 7.79 (s, 1H), 7.69-7.53 (m, 2H), 7.50 (dd, J=8.4, 4.2 Hz, 1H), 7.17 (d, J=6.9 Hz, 1H), 4.51 (m, 1H), 4.30-4.12 (m, 2H), 3.80 (m, 1H), 3.50-3.10 (m, 3H), 2.55-2.38 (m, 1H), 2.35-2.05 (m, 2H), 1.98 (m, 1H).

Example 14(25)

2-(2-((2R)-5-oxo-2-(quinolin-6-yloxymethyl)pyrrolidin-1-yl)ethylthio)-1,3-thiazole-4-carboxylic acid TLC: Rf 0.16 (chloroform:methanol=9:1);
NMR (DMSO-D6): δ 8.71 (dd, J=4.5, 1.5 Hz, 1H), 8.24 (d, J=8.4 Hz, 1H), 7.88 (d, J=9.0 Hz, 1H), 7.79 (s, 1H), 7.55 (m, 1H), 7.43 (dd, J=8.4, 4.5 Hz, 1H), 7.37 (dd, J=9.0, 3.0 Hz, 1H), 4.54 (brs, 1H), 4.18-4.06 (m, 2H), 3.75 (m, 1H), 3.50-3.10 (m, 3H), 2.60-2.30 (m, 1H), 2.30-2.02 (m, 2H), 1.93 (m, 1H).

Example 14(26)

2-(2-((2R)-5-oxo-2-(quinolin-8-yloxymethyl)pyrrolidin-1-yl)ethylthio)-1,3-thiazole-4-carboxylic acid TLC: Rf 0.08 (chloroform:methanol=9:1);
NMR (DMSO-D6): δ 8.84 (dd, J=4.5, 2.1 Hz, 1H), 8.31 (s, 1H), 8.27 (d, J=6.9 Hz, 1H), 7.56-7.44 (m, 3H), 7.23 (dd, J=6.6, 2.1 Hz, 1H), 4.49 (d, J=8.1 Hz, 1H), 4.27-4.13 (m, 2H), 3.86 (m, 1H), 3.65-3.20 (m, 3H), 2.62 (m, 1H), 2.30-2.05 (m, 2H), 1.95 (m, 1H).

Example 14(27)

2-(2-((2R)-5-oxo-2-(2-phenylethoxymethyl)pyrrolidin-1-yl)ethylthio)-1,3-thiazole-4-carboxylic acid TLC: Rf 0.23 (chloroform:methanol=9:1);
NMR (CDCl$_3$): δ 8.08 (s, 1H), 7.33-7.24 (m, 2H), 7.23-7.14 (m, 3H), 3.86-3.51 (m, 4H), 3.69 (t, J=6.6 Hz, 2H), 3.44 (dd, J=9.9, 5.7 Hz, 1H), 3.29 (m, 1H), 3.16 (m, 1H), 2.86 (t, J=6.6 Hz, 2H), 2.52-2.24 (m, 2H), 2.11 (m, 1H), 1.71 (m, 1H).

Example 14(28)

2-(2-((2R)-5-oxo-2-(2-phenylpropoxymethyl)pyrrolidin-1-yl)ethylthio)-1,3-thiazole-4-carboxylic acid TLC: Rf 0.23 (chloroform:methanol=9:1);
NMR (CDCl$_3$): δ 8.08 (s, 1H), 7.33-7.24 (m, 2H), 7.23-7.13 (m, 3H), 3.91-3.79 (m, 2H), 3.72 (m, 1H), 3.59-3.38 (m, 5H), 3.31 (m, 1H), 2.70-2.61 (m, 2H), 2.56-2.28 (m, 2H), 2.13 (m, 1H), 1.96-1.70 (m, 3H).

Example 14(29)

(15α,13E)-15-hydroxy-9-oxo-3,7-(1,3-interphenylene)-3-thia-20-ethyl-4,5,6-trinor-8-azaprost-13-enoic acid TLC: Rf 0.28 (chloroform:methanol=6:1);
NMR (CDCl$_3$): δ 0.88 (m, 3H) 1.26 (m, 10H) 1.53 (m, 2H) 1.76 (m, 1H) 2.20 (m, 1H) 2.44 (m, 2H) 3.59 (s, 2H) 3.90 (m, 1H) 3.97 (d, J=14.65 Hz, 1H) 4.14 (m, 1H) 4.78 (d, J=14.65 Hz, 1H) 5.43 (ddd, J=15.60, 8.56, 1.19 Hz, 1H) 5.65 (dd, J=15.60, 5.40 Hz, 1H) 7.07 (d, J=8.06 Hz, 1H) 7.23 (m, 2H) 7.32 (m, 1H).

Example 14(30)

2-(2-((2R)-5-oxo-2-(pyridin-4-yloxymethyl)pyrrolidin-1-yl)ethylthio)-1,3-thiazole-4-carboxylic acid TLC: Rf 0.32 (methylene chloride:methanol:water=80:20:1);
NMR (DMSO-D6): δ 1.86 (m, 1H) 2.30 (m, 3H) 3.36 (m, 3H) 3.77 (m, 1H) 4.11 (m, 2H) 4.37 (m, 1H) 6.96 (d, J=6.00 Hz, 2H) 8.36 (m, 3H) 13.09 (br. s., 1H).

Example 14(31)

(15α,13E)-15-hydroxy-5-(4-carboxythiazol-2-yl)-9-oxo-17-phenyl-1,2,3,4,18,19,20-heptanor-5-thia-8-azaprost-13-ene TLC: Rf 0.47 (methylene chloride:methanol=5:1);
NMR (CDCl$_3$): δ 1.83 (m, 3H) 2.34 (m, 4H) 2.67 (m, 2H) 3.33 (m, 2H) 3.46 (m, 1H) 3.83 (m, 1H) 4.15 (m, 2H) 5.58 (ddd, J=15.33, 8.65, 1.28 Hz, 1H) 5.81 (dd, J=15.30, 5.40 Hz, 1H) 7.25 (m, 5H) 8.07 (s, 1H).

Example 14(32)

2-(2-((2R)-5-oxo-2-(2-trifluoromethoxyphenoxymethyl)pyrrolidin-1-yl)ethylthio)-1,3-thiazole-4-carboxylic acid TLC: Rf 0.38 (chloroform:methanol:acetic acid=90:10:1);
NMR (CDCl$_3$): δ 1.94 (m, 1H) 2.28 (m, 1H) 2.44 (m, 1H) 2.61 (m, 1H) 3.32 (m, 1H) 3.50 (m, 1H) 3.75 (m, 1H) 4.01 (m, 2H) 4.14 (m, 1H) 4.25 (dd, J=9.90, 3.00 Hz, 1H) 7.00 (m, 2H) 7.26 (m, 2H) 8.08 (s, 1H).

Example 14(33)

2-(2-((2R)-5-oxo-2-(4-trifluoromethoxyphenoxymethyl)pyrrolidin-1-yl)ethylthio)-1,3-thiazole-4-carboxylic acid TLC: Rf 0.43 (chloroform:methanol:acetic acid=90:10:1);
NMR (CDCl$_3$): δ 1.97 (m, 1H) 2.27 (m, 1H) 2.44 (m, 1H) 2.60 (m, 1H) 3.29 (m, 1H) 3.49 (m, 1H) 3.73 (m, 1H) 3.96 (m, 2H) 4.09 (m, 1H) 4.18 (dd, J=9.90, 3.30 Hz, 1H) 6.88 (d, J=9.10 Hz, 2H) 7.16 (d, J=9.10 Hz, 2H) 8.09 (s, 1H).

Example 14(34)

2-(2-((2R)-2-(3-(t-butyl)phenoxymethyl)-5-oxopyrrolidin-1-yl)ethylthio)-1,3-thiazole-4-carboxylic acid TLC: Rf 0.48 (chloroform:methanol:acetic acid=90:10:1);
NMR (CDCl$_3$): δ 1.31 (s, 9H) 1.97 (m, 1H) 2.25 (m, 1H) 2.43 (m, 1H) 2.61 (m, 1H) 3.29 (m, 1H) 3.52 (m, 1H) 3.78 (m, 1H) 3.96 (m, 2H) 4.08 (m, 1H) 4.18 (dd, J=9.30, 3.00 Hz, 1H) 6.69 (dd, J=7.70, 2.40 Hz, 1H) 6.90 (m, 1H) 7.04 (m, 1H) 7.22 (d, J=7.70 Hz, 1H) 8.08 (s, 1H).

Example 14(35)

2-(2-((2R)-2-(4-chlorophenoxymethyl)-5-oxopyrrolidin-1-yl)ethylthio)-1,3-thiazole-4-carboxylic acid TLC: Rf 0.43 (chloroform:methanol:acetic acid=90:10:1);
NMR (CDCl$_3$): δ 1.97 (m, 1H) 2.25 (m, 1H) 2.43 (m, 1H) 2.60 (m, 1H) 3.29 (m, 1H) 3.49 (m, 1H) 3.71 (m, 1H) 3.94 (m, 2H) 4.08 (m, 1H) 4.20 (dd, J=9.90, 3.00 Hz, 1H) 6.82 (d, J=9.10 Hz, 2H) 7.24 (d, J=9.10 Hz, 2H) 8.09 (s, 1H).

Example 14(36)

2-(2-((2R)-2-(2-chloro-5-methylphenoxymethyl)-5-oxopyrrolidin-1-yl)ethylthio)-1,3-thiazole-4-carboxylic acid TLC: Rf 0.40 (chloroform:methanol:acetic acid=90:10:1);
NMR (CDCl$_3$): δ 1.91 (m, 1H) 2.29 (m, 1H) 2.33 (s, 3H) 2.45 (m, 1H) 2.66 (m, 1H) 3.30 (m, 1H) 3.58 (m, 1H) 3.86 (m, 1H) 4.02 (m, 2H) 4.18 (m, 2H) 6.74 (m, 2H) 7.24 (d, J=8.10 Hz, 1H) 8.07 (s, 1H).

Example 14(37)

2-(2-((2R)-2-(3-chloro-5-methoxyphenoxymethyl)-5-oxopyrrolidin-1-yl)ethylthio)-1,3-thiazole-4-carboxylic acid TLC: Rf 0.43 (chloroform:methanol:acetic acid=90:10:1);
NMR (CDCl$_3$): δ 1.95 (m, 1H) 2.25 (m, 1H) 2.43 (m, 1H) 2.59 (m, 1H) 3.27 (m, 1H) 3.49 (m, 1H) 3.72 (m, 1H) 3.77 (s, 3H) 3.92 (m, 2H) 4.06 (m, 1H) 4.18 (dd, J=9.90, 3.00 Hz, 1H) 6.32 (t, J=2.00 Hz, 1H) 6.50 (t, J=2.00 Hz, 1H) 6.54 (t, J=2.00 Hz, 1H) 8.09 (s, 1H).

Example 14(38)

2-(2-((2R)-2-(2-acetyl-4-chloro-5-methylphenoxymethyl)-5-oxopyrrolidin-1-yl)ethylthio)-1,3-thiazole-4-carboxylic acid TLC: Rf 0.48 (chloroform:methanol:acetic acid=90:10:1);
NMR (CDCl$_3$): δ 2.02 (m, 1H) 2.38 (s, 3H) 2.43 (m, 3H) 2.54 (s, 3H) 3.32 (m, 1H) 3.48 (m, 1H) 3.69 (m, 1H) 3.99 (m, 1H) 4.15 (m, 2H) 4.27 (m, 2H) 6.86 (s, 1H) 7.68 (s, 1H) 8.08 (s, 1H).

Example 14(39)

2-(2-((2R)-2-(3-methoxyphenoxymethyl)-5-oxopyrrolidin-1-yl)ethylthio)-1,3-thiazole-4-carboxylic acid TLC: Rf 0.14 (methylene chloride:methanol=9:1);
NMR (CDCl$_3$): δ 1.93 (m, 1H) 2.22 (m, 1H) 2.42 (m, 1H) 2.58 (m, 1H) 3.27 (m, 1H) 3.48 (m, 1H) 3.75 (m, 4H) 3.96 (m, 2H) 4.13 (m, 2H) 6.48 (m, 3H) 7.17 (t, J=8.24 Hz, 1H) 8.06 (s, 1H).

Example 14(40)

2-(2-((2R)-2-(3-ethoxyphenoxymethyl)-5-oxopyrrolidin-1-yl)ethylthio)-1,3-thiazole-4-carboxylic acid TLC: Rf 0.13 (methylene chloride:methanol=9:1);
NMR (CDCl$_3$): δ 1.34 (t, J=7.14 Hz, 3H) 1.88 (m, 1H) 2.19 (d, J=6.96 Hz, 1H) 2.36 (m, 1H) 2.50 (dd, J=10.07, 6.77 Hz, 1H) 3.21 (m, 1H) 3.44 (m, 1H) 3.92 (m, 7H) 6.38 (m, 2H) 6.47 (dd, J=8.06, 2.20 Hz, 1H) 7.11 (t, J=8.24 Hz, 1H) 8.02 (s, 1H).

Example 14(41)

2-(2-((2R)-2-(3-difluoromethoxyphenoxymethyl)-5-oxopyrrolidin-1-yl)ethylthio)-1,3-thiazole-4-carboxylic acid TLC: Rf 0.08 (methylene chloride:methanol=9:1);
NMR (CDCl$_3$): δ 2.03 (m, 1H) 2.24 (m, 1H) 2.42 (s, 1H) 2.58 (s, 1H) 3.26 (m, 1H) 3.48 (m, 1H) 3.71 (m, 1H) 4.07 (m, 4H) 6.60 (m, 4H) 7.25 (m, 1H) 8.07 (s, 1H).

Example 14(42)

2-(2-((2R)-5-oxo-2-(3-(1,1,2,2-tetrafluoroethoxy)phenoxymethyl)pyrrolidin-1-yl)ethylthio)-1,3-thiazole-4-carboxylic acid TLC: Rf 0.11 (methylene chloride:methanol=9:1);
NMR (CDCl$_3$): δ 2.00 (m, 1H) 2.42 (m, 3H) 3.28 (m, 1H) 3.48 (m, 1H) 3.71 (s, 1H) 4.00 (m, 3H) 4.22 (dd, J=9.79, 3.02 Hz, 1H) 5.89 (m, 1H) 6.81 (m, 3H) 7.27 (m, 1H) 8.08 (s, 1H).

Example 14(43)

(15α,13E)-15-hydroxy-5-(4-carboxythiazol-2-yl)-9-oxo-17-(3,4-dichlorophenyl)-1,2,3,4,18,19,20-heptanor-5-thia-8-azaprost-13-ene TLC: Rf 0.38 (chloroform:methanol:acetic acid=50:10:1);
NMR (CD$_3$OD): δ 1.74 (m, 3H), 2.29 (m, 3H), 2.64 (m, 2H), 3.36 (m, 3H), 3.78 (m, 1H), 4.03 (m, 1H), 4.28 (m, 1H), 5.52 (m, 1H), 5.80 (m, 1H), 7.10 (dd, J=8.06, 2.20 Hz, 1H), 7.34 (d, J=2.20 Hz, 1H), 7.39 (d, J=8.06 Hz, 1H), 8.06 (s, 1H).

Example 14(44)

2-(2-((2R)-2-(3-aminophenoxymethyl)-5-oxopyrrolidin-1-yl)ethylthio)-1,3-thiazole-4-carboxylic acid TLC: Rf 0.16 (methylene chloride:methanol:acetic acid=18:2:1);
NMR (CDCl$_3$): δ 1.90 (m, 1H) 2.16 (m, 1H) 2.35 (m, 1H) 2.51 (m, 1H) 3.20 (m, 1H) 3.44 (m, 1H) 3.89 (m, 7H) 6.23 (m, 3H) 6.99 (t, J=8.06 Hz, 1H) 7.99 (s, 1H).

Example 14(45)

2-(2-((2R)-2-(3-methylaminophenoxymethyl)-5-oxopyrrolidin-1-yl)ethylthio)-1,3-thiazole-4-carboxylic acid TLC: Rf 0.09 (methylene chloride:methanol:acetic acid=9:1:0.1);
NMR (CDCl$_3$): δ 1.93 (m, 1H) 2.23 (m, 1H) 2.41 (m, 1H) 2.57 (m, 1H) 2.82 (s, 3H) 3.25 (m, 1H) 3.50 (m, 1H) 3.96 (m, 6H) 6.14 (t, J=2.29 Hz, 1H) 6.25 (m, 2H) 7.08 (t, J=8.06 Hz, 1H) 8.06 (s, 1H).

Example 14(46)

2-(2-((2R)-2-(3-amino-2-methylphenoxymethyl)-5-oxopyrrolidin-1-yl)ethylthio)-1,3-thiazole-4-carboxylic acid TLC: Rf 0.15 (methylene chloride:methanol:acetic acid=9:1:0.1);
NMR (CDCl$_3$): δ 1.98 (m, 4H) 2.27 (m, 1H) 2.44 (m, 1H) 2.60 (m, 1H) 3.23 (m, 1H) 3.51 (m, 1H) 4.00 (m, 7H) 6.28 (d, J=8.06 Hz, 1H) 6.38 (d, J=8.06 Hz, 1H) 6.96 (t, J=7.87 Hz, 1H) 8.06 (s, 1H).

Example 14(47)

2-(2-((2R)-2-(3-amino-4-methylphenoxymethyl)-5-oxopyrrolidin-1-yl)ethylthio)-1,3-thiazole-4-carboxylic acid TLC: Rf 0.20 (methylene chloride:methanol:acetic acid=9:1:0.1);
NMR (CDCl$_3$): δ 1.92 (m, 1H) 2.09 (s, 3H) 2.22 (m, 1H) 2.40 (m, 1H) 2.55 (m, 1H) 3.24 (m, 1H) 3.49 (m, 1H) 3.97 (m, 7H) 6.22 (m, 2H) 6.93 (d, J=7.87 Hz, 1H) 8.06 (s, 1H).

Example 14(48)

(15α,13E)-15-hydroxy-5-(4-carboxythiazol-2-yl)-9-oxo-17-(naphthalen-2-yl)-1,2,3,4,18,19,20-heptanor-5-thia-8-azaprost-13-ene TLC: Rf 0.39 (chloroform:methanol:acetic acid=50:10:1);
NMR (CD$_3$OD): δ 2.02 (m, 7H), 2.82 (m, 2H), 3.21 (m, 2H), 3.72 (m, 1H), 4.13 (m, 2H), 5.47 (m, 1H), 5.78 (m, 1H), 7.36 (m, 4H), 7.60 (m, 1H), 7.78 (m, 3H).

Example 14(49)

2-(2-((2R)-2-(3-aminomethylphenoxymethyl)-5-oxopyrrolidin-1-yl)ethylthio)-1,3-thiazole-4-carboxylic acid TLC: Rf 0.02 (methylene chloride:methanol=9:1);
NMR (DMSO-D6): δ 1.93 (m, 1H) 2.36 (m, 3H) 3.34 (m, 7H) 3.97 (s, 2H) 4.13 (d, J=2.93 Hz, 1H) 4.60 (dd, J=10.44, 3.48 Hz, 1H) 6.84 (dd, J=8.24, 2.38 Hz, 1H) 6.92 (d, J=7.32 Hz, 1H) 7.21 (m, 1H) 7.60 (s, 1H) 7.72 (s, 1H).

Example 14(50)

2-(2-((2R)-2-(3-dimethylaminomethylphenoxymethyl)-5-oxopyrrolidin-1-yl)ethylthio)-1,3-thiazole-4-carboxylic acid TLC: Rf 0.17 (methylene chloride:methanol=9:1);
NMR (CDCl$_3$): δ 2.04 (m, 1H) 2.33 (m, 3H) 2.67 (s, 6H) 3.07 (m, 1H) 3.68 (m, 5H) 4.09 (m, 1H) 4.29 (m, 2H) 6.75 (d, J=7.32 Hz, 1H) 6.88 (dd, J=7.87, 2.01 Hz, 1H) 7.18 (m, 1H) 7.53 (s, 1H) 7.81 (s, 1H).

Example 14(51)

2-(2-((2R)-2-(3,5-dichlorobenzyloxymethyl)-5-oxopyrrolidin-1-yl)ethylthio)-1,3-thiazole-4-carboxylic acid TLC: Rf 0.09 (methylene chloride:methanol=9:1);
NMR (DMSO-D6): δ 1.74 (m, 1H) 1.97 (m, 1H) 2.20 (m, 2H) 3.43 (m, 4H) 3.75 (m, 3H) 4.53 (s, 2H) 7.34 (s, 2H) 7.50 (s, 1H) 7.88 (s, 1H).

Example 14(52)

2-(2-((2S)-2-(2-(3,5-dichlorophenyl)ethyl)-5-oxopyrrolidin-1-yl)ethylthio)-1,3-thiazole-4-carboxylic acid TLC: Rf 0.44 (methylene chloride:methanol:acetic acid=9:1:0.1);
NMR (CDCl$_3$): δ 1.68 (m, 2H) 2.29 (m, 6H) 3.32 (m, 3H) 3.63 (m, 1H) 3.90 (m, 1H) 7.01 (d, J=2.20 Hz, 2H) 7.16 (t, J=2.01 Hz, 1H) 8.03 (s, 1H).

Reference Example 12

(5R)-5-(t-butoxydimethylsilyloxymethyl)pyrrolidin-2-one

Under an atmosphere of argon, to a solution of (5R)-5-hydroxymethylpyrrolidin-2-one (15.0 g) in dimethylformamide (130 mL) were added imidazole (10.6 g) and t-butyldimethylsilyl chloride (20.5 g) and the mixture was stirred at room temperature for 3 hours. The reaction solution was poured into ice and extracted with ethyl acetate. The organic layer was washed with water and brine, dried over anhydrous magnesium sulfate and concentrated to give the title compound (33.0 g) having the following physical data.
TLC: Rf 0.71 (methylene chloride:methanol=9:1);
NMR (CDCl$_3$): δ 0.06 (s, 6H) 0.89 (s, 9H) 1.73 (m, 1H) 2.17 (m, 1H) 2.35 (m, 2H) 3.44 (dd, J=10.20, 7.80 Hz, 1H) 3.63 (dd, J=10.20, 3.90 Hz, 1H) 3.76 (m, 1H) 5.76 (br. s., 1H).

Reference Example 13

((2R)-2-(t-butoxydimethylsilyloxymethyl)-5-oxopyrrolidin-1-yl)acetic acid ethyl ester Under an atmosphere of argon, to a solution of the compound prepared in Reference Example 12 (33.0 g) in anhydrous tetrahydrofuran (300 mL) was added potassium t-butoxide (16.0 g) in ice bath and the mixture was stirred for 10 minutes. Bromoethyl acetate (15.9 mL) was added dropwise to the reaction solution, which was stirred at room temperature overnight. An aqueous saturated ammonium chloride solution was added to the reaction solution, which was extracted with ethyl acetate. The obtained organic layer was washed with brine, dried over anhydrous magnesium sulfate and concentrated to give the title compound (41.0 g) having the following physical data.
TLC: Rf 0.73 (ethyl acetate).

Reference Example 14

(5R)-1-(2-hydroxyethyl)-5-(t-butoxydimethylsilyloxymethyl)pyrrolidin-2-one

Under an atmosphere of argon, to a solution of the compound prepared in Reference Example 13 (41.0 g) in tetrahydrofuran-ethanol (9:1, 300 mL) was added sodium borohydride (14.7 g) and the mixture was stirred at room temperature for 6 hours. The reaction solution was poured into ice—an aqueous saturated ammonium chloride solution and extracted with ethyl acetate. The obtained organic layer was washed with water and brine, dried over anhydrous magnesium sulfate and concentrated to give the title compound (36.7 g) having the following physical data.
TLC: Rf 0.29 (ethyl acetate).

Reference Example 15

((2R)-2-(t-butoxydimethylsilyloxymethyl)-5-oxopyrrolidin-1-yl)ethyl methanesulfonate Under an atmosphere of argon, methanesulfonyl chloride (11.1 mL) was added dropwise to a solution of the compound prepared in Reference Example 14 (36.7 g) and triethylamine (27.1 mL) in methylene chloride (250 mL) in ice bath and the mixture was stirred for 1 hour. Water was added to the reaction solution, which was extracted with methylene chloride. The obtained organic layer was washed with hydrochloric acid, water and brine, dried over anhydrous magnesium sulfate and concentrated to give the title compound (45.6 g) having the following physical data.

TLC: Rf 0.53 (ethyl acetate).

Reference Example 16

S-((2R)-2-(t-butoxydimethylsilyloxymethyl)-5-oxopyrrolidin-1-yl)ethyl ethanethioate Under an atmosphere of argon, to a solution of the compound prepared in Reference Example 15 (45.6 g) in dimethylformamide (130 mL) was added potassium thiosulfate (14.8 g) and the mixture was stirred at room temperature overnight. Water was added to the reaction solution, which was extracted with ethyl acetate. The obtained organic layer was washed with water and brine, dried over anhydrous magnesium sulfate and concentrated to give the title compound (39.9 g) having the following physical data.

TLC: Rf 0.26 (n-hexane:ethyl acetate=1:1).

Reference Example 17

2-(2-((2R)-2-(t-butoxydimethylsilyloxymethyl)-5-oxopyrrolidin-1-yl)ethylthio-1,3-thiazole-4-carboxylic acid ethyl ester Under an atmosphere of argon, to a solution of the compound prepared in Reference Example 16 (39.9 g), 2-bromo-1,3-thiazole-4-carboxylic acid ethyl ester (30.7 g) and tributylphosphine (2.63 g) in ethanol (260 mL) was added potassium carbonate (26.9 g) in ice bath and the mixture was stirred at room temperature overnight. Water was added to the reaction solution, which was extracted with ethyl acetate. The obtained organic layer was washed with water and brine, dried over anhydrous magnesium sulfate and concentrated to give the title compound (57.0 g).

TLC: Rf 0.26 (n-hexane:ethyl acetate=1:1).

Reference Example 18

2-(2-((2R)-2-(t-butoxydimethylsilyloxymethyl)-5-oxopyrrolidin-1-yl)ethylthio-1,3-thiazole-4-carboxylic acid butyl ester To a solution of the compound prepared in Reference Example 17 (57.0 g) in butanol (260 mL) was added potassium carbonate (17.9 g) and the mixture was stirred at 80° C. for 4 hours. After cooling, the reaction solution was filtrated and concentrated. The obtained residue was dissolved into ethyl acetate. The solution was washed water and brine, dried over anhydrous magnesium sulfate and concentrated to give the title compound (64.1 g) having the following physical data. TLC: Rf 0.39 (n-hexane:ethyl acetate=1:1).

Reference Example 19

2-(2-((2R)-2-hydroxymethyl-5-oxopyrrolidin-1-yl)ethylthio-1,3-thiazole-4-carboxylic acid butyl ester To a solution of the compound prepared in Reference Example 18 (64.1 g) in tetrahydrofuran (130 mL) was added a solution of tetrabutylammonium fluoride (1.0 mol/L) in tetrahydrofuran (130 mL) and the mixture was stirred at room temperature overnight. Water was added to the reaction solution, which was extracted with ethyl acetate. The organic layer was washed with water and brine, dried over anhydrous magnesium sulfate and concentrated. The obtained residue was purified by column chromatography on silica gel (ethyl acetate-hexane) to give the title compound (24.0 g) having the following physical data.

TLC: Rf 0.19 (ethyl acetate);
NMR (CDCl₃): δ 0.97 (t, J=7.30 Hz, 3H) 1.45 (m, 2H) 1.74 (m, 2H) 1.90 (m, 1H) 2.13 (m, 1H) 2.40 (m, 2H) 3.32 (t, J=5.50 Hz, 1H) 3.43 (m, 1H) 3.56 (m, 1H) 3.80 (m, 5H) 4.33 (t, J=6.70 Hz, 2H) 7.99 (s, 1H).

Reference Example 20

2-(2-((2R)-2-formyl-5-oxopyrrolidin-1-yl)ethylthio-1,3-thiazole-4-carboxylic acid butyl ester Under an atmosphere of argon, to a solution of the compound prepared in Reference Example 19 (205 mg) and triethylamine (0.48 mL) in ethyl acetate (4 mL) were added dimethylsulfoxide (2 mL) and sulfur trioxide pyridine complex (273 mg) at 10° C. and the mixture was stirred at 10 to 20° C. for 2 hours. Water was added to the reaction solution, which was extracted with ethyl acetate. The obtained organic layer was washed with hydrochloric acid, water and brine, dried over anhydrous magnesium sulfate and concentrated to give the title compound (219 mg) having the following physical data.

TLC: Rf 0.26 (ethyl acetate);
NMR (CDCl₃): δ 0.98 (t, J=7.60 Hz, 3H) 1.58 (m, 5H) 2.25 (m, 3H) 3.43 (m, 2H) 4.03 (m, 2H) 4.32 (t, J=6.70 Hz, 2H) 4.64 (m, 1H) 8.00 (s, 1H) 9.69 (d, J=1.10 Hz, 1H).

Example 15

2-(2-((2R)-2-heptylaminomethyl-5-oxopyrrolidin-1-yl)ethylthio)-1,3-thiazole-4-carboxylic acid butyl ester

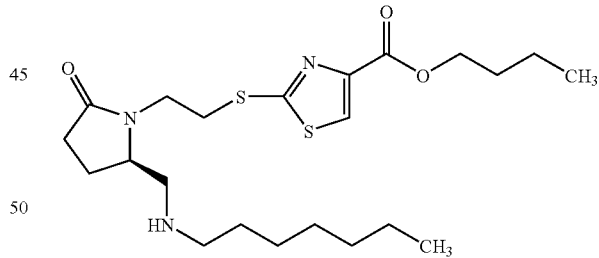

Under an atmosphere of argon, to a solution of the compound prepared in Reference Example 20 (120 mg) in methylene chloride (3 mL) was added n-heptylamine (98 μL) and the mixture was stirred at room temperature for 1 hour. Sodium triacetoxyborohydride (140 mg) was added to the reaction solution, which was stirred at room temperature for 2 hours. An aqueous saturated sodium bicarbonate solution was added to the reaction mixture, which was extracted with methylene chloride. The extract was washed with brine, dried over anhydrous magnesium sulfate and concentrated. The obtained residue was purified by column chromatography on silica gel (ethyl acetate→ethyl acetate:methanol=9:1) to give the compound of the present invention (119 mg) having the following physical data.

TLC: Rf 0.14 (ethyl acetate:methanol=9:1);

NMR (CDCl$_3$): δ 0.88 (t, J=6.90 Hz, 3H) 0.97 (t, J=7.40 Hz, 3H) 1.26 (m, 8H) 1.43 (m, 4H) 1.74 (m, 2H) 1.89 (m, 1H) 2.12 (m, 1H) 2.30 (ddd, J=16.90, 9.90, 5.60 Hz, 1H) 2.45 (ddd, J=17.20, 10.00, 7.20 Hz, 1H) 2.57 (m, 2H) 2.78 (m, 2H) 3.47 (m, 3H) 3.87 (m, 2H) 4.33 (t, J=6.77 Hz, 2H) 8.00 (s, 1H).

Example 15(1) to 15(10)

By the same procedure as described in Example 15, using a corresponding amine derivative instead of n-heptylamine, the following compounds of the present invention were obtained.

Example 15(1)

2-(2-((2R)-2-(3,5-dichlorophenylaminomethyl)-5-oxopyrrolidin-1-yl)ethylthio)-1,3-thiazole-4-carboxylic acid butyl ester

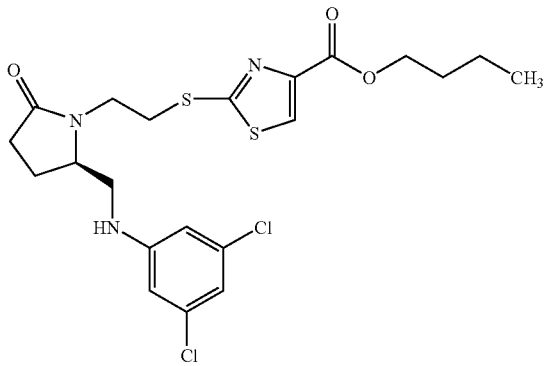

TLC: Rf 0.63 (ethyl acetate);

NMR (CDCl$_3$): δ 0.96 (t, J=7.28 Hz, 3H) 1.43 (m, 2H) 1.72 (m, 2H) 1.88 (m, 1H) 2.36 (m, 3H) 3.32 (m, 3H) 3.55 (m, 2H) 3.94 (m, 1H) 4.10 (m, 1H) 4.31 (t, J=6.46 Hz, 2H) 4.73 (m, 1H) 6.45 (d, J=1.79 Hz, 2H) 6.64 (t, J=1.79 Hz, 1H) 8.01 (s, 1H).

Example 15(2)

2-(2-((2R)-5-oxo-2-(piperidin-1-ylmethyl)pyrrolidin-1-yl)ethylthio)-1,3-thiazole-4-carboxylic acid butyl ester TLC: Rf 0.29 (chloroform:methanol:acetic acid=90:10:1);

NMR (CDCl$_3$): δ 0.97 (t, J=7.50 Hz, 2H) 1.44 (m, 8H) 1.72 (m, 3H) 2.07 (m, 1H) 2.26 (m, 4H) 2.41 (m, 4H) 3.50 (t, J=6.59 Hz, 2H) 3.67 (m, 1H) 3.92 (m, 2H) 4.33 (t, J=6.77 Hz, 2H) 8.01 (s, 1H).

Example 15(3)

2-(2-((2R)-2-(morpholin-4-ylmethyl)-5-oxopyrrolidin-1-yl)ethylthio)-1,3-thiazole-4-carboxylic acid butyl ester TLC: Rf 0.51 (chloroform:methanol:acetic acid=90:10:1);

NMR (CDCl$_3$): δ 0.97 (t, J=7.41 Hz, 3H) 1.45 (m, 2H) 1.74 (m, 3H) 2.10 (m, 1H) 2.32 (m, 5H) 2.51 (m, 3H) 3.51 (t, J=7.05 Hz, 2H) 3.65 (m, 5H) 3.96 (m, 2H) 4.33 (t, J=6.77 Hz, 2H) 8.00 (s, 1H).

Example 15(4)

2-(2-((2R)-2-(4-methylpiperazin-1-ylmethyl)-5-oxopyrrolidin-1-yl)ethylthio)-1,3-thiazole-4-carboxylic acid butyl ester TLC: Rf 0.27 (chloroform:methanol:acetic acid=90:10:1);

NMR (CDCl$_3$): δ 0.97 (t, J=7.41 Hz, 3H) 1.45 (m, 2H) 1.73 (m, 3H) 2.08 (m, 1H) 2.25 (s, 3H) 2.45 (m, 12H) 3.51 (t, J=6.68 Hz, 2H) 3.66 (m, 1H) 3.93 (m, 2H) 4.33 (t, J=6.77 Hz, 2H) 8.01 (s, 1H).

Example 15(5)

2-(2-((2R)-2-(4-(t-butoxycarbonyl)piperazin-1-ylmethyl)-5-oxopyrrolidin-1-yl)ethylthio)-1,3-thiazole-4-carboxylic acid butyl ester TLC: Rf 0.37 (ethyl acetate);

NMR (CDCl$_3$): δ 0.97 (t, J=7.50 Hz, 3H) 1.45 (m, 2H) 1.45 (s, 9H) 1.74 (m, 3H) 2.11 (m, 1H) 2.40 (m, 8H) 3.35 (t, J=4.94 Hz, 4H) 3.50 (t, J=6.87 Hz, 2H) 3.63 (m, 1H) 3.95 (m, 2H) 4.33 (t, J=6.77 Hz, 2H) 8.01 (s, 1H).

Example 15(6)

2-(2-((2R)-2-(4-benzylpiperazin-1-ylmethyl)-5-oxopyrrolidin-1-yl)ethylthio)-1,3-thiazole-4-carboxylic acid butyl ester TLC: Rf 0.08 (ethyl acetate);

NMR (CDCl$_3$): δ 0.96 (t, J=7.41 Hz, 3H) 1.44 (m, 2H) 1.71 (m, 3H) 2.09 (m, 1H) 2.40 (m, 12H) 3.45 (s, 2H) 3.50 (t, J=6.77 Hz, 2H) 3.67 (m, 1H) 3.91 (m, 2H) 4.30 (t, J=6.77 Hz, 2H) 7.28 (m, 5H) 8.00 (s, 1H).

Example 15(7)

2-(2-((2R)-2-(cyclohexylaminomethyl)-5-oxopyrrolidin-1-yl)ethylthio)-1,3-thiazole-4-carboxylic acid butyl ester TLC: Rf 0.44 (chloroform:methanol:acetic acid=90:10:1);

NMR (CDCl$_3$): δ 0.99 (m, 5H) 1.21 (m, 4H) 1.49 (m, 4H) 1.81 (m, 5H) 2.13 (m, 1H) 2.38 (m, 3H) 2.79 (d, J=5.13 Hz, 2H) 3.47 (m, 3H) 3.87 (m, 2H) 4.33 (t, J=6.59 Hz, 2H) 8.00 (s, 1H).

Example 15(8)

2-(2-((2R)-2-benzylaminomethyl-5-oxopyrrolidin-1-yl)ethylthio)-1,3-thiazole-4-carboxylic acid butyl ester TLC: Rf 0.36 (ethyl acetate:methanol=9:1);

NMR (CDCl$_3$): δ 0.96 (t, J=7.30 Hz, 3H) 1.44 (m, 2H) 1.72 (m, 2H) 1.96 (m, 1H) 2.22 (m, 2H) 2.46 (m, 1H) 2.90 (m, 2H) 3.43 (m, 3H) 3.90 (m, 4H) 4.29 (t, J=6.70 Hz, 2H) 7.29 (m, 5H) 7.97 (s, 1H).

Example 15(9)

2-(2-((2R)-2-(N-cyclohexyl-N-methylaminomethyl)-5-oxopyrrolidin-1-yl)ethylthio)-1,3-thiazole-4-carboxylic acid butyl ester TLC: Rf 0.59 (ethyl acetate:methanol=4:1);
NMR (CDCl$_3$): δ 0.97 (t, J=7.51 Hz, 3H) 1.15 (m, 5H) 1.45 (m, 2H) 1.72 (m, 8H) 2.06 (m, 1H) 2.20 (s, 3H) 2.28 (m, 2H) 2.41 (m, 2H) 2.53 (dd, J=12.90, 6.30 Hz, 1H) 3.49 (t, J=6.68 Hz, 2H) 3.63 (dt, J=13.73, 6.68 Hz, 1H) 3.80 (m, 1H) 3.95 (dt, J=13.73, 6.68 Hz, 1H) 4.33 (t, J=6.77 Hz, 2H) 8.01 (s, 1H).

Example 15(10)

2-(2-((2R)-2-(N-benzyl-N-cyclohexylaminomethyl)-5-oxopyrrolidin-1-yl)ethylthio)-1,3-thiazole-4-carboxylic acid butyl ester TLC: Rf 0.76 (ethyl acetate);
NMR (CDCl$_3$): δ 0.97 (t, J=7.32 Hz, 3H) 1.17 (m, 5H) 1.45 (m, 2H) 1.78 (m, 8H) 1.96 (m, 1H) 2.21 (m, 2H) 2.40 (m, 2H) 2.69 (dd, J=13.18, 5.13 Hz, 1H) 3.45 (m, 5H) 3.64 (d, J=13.80 Hz, 1H) 3.85 (m, 1H) 4.31 (t, J=6.68 Hz, 2H) 7.24 (m, 5H) 7.97 (s, 1H).

Example 16(1) to 16(61)

By the same procedure as described in Example 2, using the compound prepared in Example 15, 15(1) to 15(10) or a corresponding ester instead of the compound prepared in Example 1, the following compounds of the present invention were obtained.

Example 16(1)

2-(2-((2R)-2-heptylaminomethyl-5-oxopyrrolidin-1-yl)ethylthio)-1,3-thiazole-4-carboxylic acid

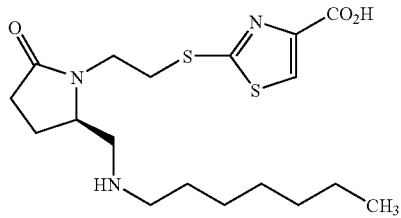

TLC: Rf 0.33 (methylene chloride:methanol=9:1);
NMR (CDCl$_3$): δ 0.85 (t, J=6.90 Hz, 3H) 1.25 (m, 8H) 1.79 (m, 3H) 2.32 (m, 3H) 2.52 (m, 1H) 2.91 (dd, J=11.81, 9.34 Hz, 1H) 3.09 (dd, J=9.34, 7.32 Hz, 2H) 3.32 (m, 2H) 3.58 (m, 1H) 3.74 (m, 2H) 4.39 (m, 1H) 7.88 (s, 1H).

Example 16(2)

2-(2-((2R)-2-(3,5-dichlorophenylaminomethyl)-5-oxopyrrolidin-1-yl)ethylthio)-1,3-thiazole-4-carboxylic acid TLC: Rf 0.40 (chloroform:methanol:acetic acid=90:10:1);
NMR (CDCl$_3$): δ 1.88 (m, 1H) 2.21 (m, 1H) 2.45 (m, 2H) 3.42 (m, 5H) 3.61 (br. s., 2H) 4.00 (m, 2H) 6.47 (d, J=1.80 Hz, 2H) 6.67 (t, J=1.80 Hz, 1H) 8.10 (s, 1H).

Example 16(3)

2-(2-((2R)-2-(N-acetyl-N-(3,5-dichlorophenyl)aminomethyl)-5-oxopyrrolidin-1-yl)ethylthio)-1,3-thiazole-4-carboxylic acid TLC: Rf 0.31 (chloroform:methanol:acetic acid=90:10:1);
NMR (CDCl$_3$): δ 1.71 (m, 1H) 1.96 (s, 3H) 2.15 (m, 1H) 2.39 (m, 2H) 3.44 (m, 4H) 3.95 (m, 2H) 4.28 (m, 1H) 7.13 (d, J=1.65 Hz, 2H) 7.40 (t, J=1.65 Hz, 1H) 8.10 (s, 1H).

Example 16(4)

2-(2-((2R)-5-oxo-2-(piperidin-1-ylmethyl)pyrrolidin-1-yl)ethylthio)-1,3-thiazole-4-carboxylic acid TLC: Rf 0.20 (chloroform:methanol:water=40:10:1);
NMR (CDCl$_3$): δ 1.51 (m, 2H) 1.82 (m, 5H) 2.34 (m, 3H) 2.65 (dd, J=13.18, 6.77 Hz, 1H) 2.84 (m, 3H) 3.08 (dd, J=13.18, 4.03 Hz, 1H) 3.47 (m, 4H) 3.90 (m, 1H) 4.27 (m, 1H) 7.98 (s, 1H).

Example 16(5)

2-(2-((2R)-2-(morpholin-4-ylmethyl)-5-oxopyrrolidin-1-yl)ethylthio)-1,3-thiazole-4-carboxylic acid TLC: Rf 0.28 (chloroform:methanol:water=40:10:1);
NMR (CDCl$_3$): δ 1.78 (m, 1H) 2.16 (m, 1H) 2.51 (m, 8H) 3.44 (m, 2H) 3.70 (m, 5H) 3.95 (m, 2H) 8.08 (s, 1H).

Example 16(6)

2-(2-((2R)-2-(4-methylpiperazin-1-ylmethyl)-5-oxopyrrolidin-1-yl)ethylthio)-1,3-thiazole-4-carboxylic acid TLC: Rf 0.07 (chloroform:methanol:water=40:10:1);
NMR (CDCl$_3$): δ 1.59 (m, 1H) 2.05 (m, 1H) 2.23 (m, 1H) 2.39 (m, 2H) 2.68 (s, 3H) 2.68 (m, 2H) 3.06 (m, 7H) 3.46 (m, 1H) 3.62 (m, 2H) 3.97 (m, 2H) 7.89 (s, 1H).

Example 16(7)

2-(2-((2R)-2-(4-(t-butoxycarbonyl)piperazin-1-ylmethyl)-5-oxopyrrolidin-1-yl)ethylthio)-1,3-thiazole-4-carboxylic acid TLC: Rf 0.42 (chloroform:methanol:water=40:10:1);
NMR (CDCl$_3$): δ 1.47 (s, 9H) 1.83 (m, 1H) 2.18 (m, 1H) 2.53 (m, 8H) 3.43 (m, 6H) 3.70 (m, 1H) 3.95 (m, 2H) 8.08 (s, 1H).

Example 16(8)

2-(2-((2R)-2-(4-benzylpiperazin-1-ylmethyl)-5-oxopyrrolidin-1-yl)ethylthio)-1,3-thiazole-4-carboxylic acid TLC: Rf 0.35 (chloroform:methanol:water=40:10:1);
NMR (CDCl$_3$): δ 1.69 (m, 1H) 2.09 (m, 1H) 2.35 (m, 3H) 2.91 (m, 9H) 3.48 (m, 3H) 3.83 (m, 2H) 4.00 (d, J=13.18 Hz, 1H) 4.13 (d, J=13.18 Hz, 1H) 7.40 (m, 5H) 8.07 (s, 1H).

Example 16(9)

2-(2-((2R)-2-cyclohexylaminomethyl-5-oxopyrrolidin-1-yl)ethylthio)-1,3-thiazole-4-carboxylic acid TLC: Rf 0.36 (chloroform:methanol:water=40:10:1);
NMR (CDCl$_3$): δ 1.21 (m, 3H) 1.59 (m, 3H) 1.83 (m, 2H) 2.37 (m, 6H) 2.81 (m, 1H) 3.26 (m, 3H) 3.57 (m, 1H) 3.77 (m, 2H) 4.44 (m, 1H) 7.88 (s, 1H).

Example 16(10)

2-(2-((2R)-2-benzylaminomethyl-5-oxopyrrolidin-1-yl)ethylthio)-1,3-thiazole-4-carboxylic acid TLC: Rf 0.70 (methylene chloride:methanol:water=80:20:1);
NMR (DMSO-D6): δ 1.81 (m, 1H) 2.07 (m, 2H) 2.28 (m, 1H) 2.76 (m, 1H) 2.88 (m, 1H) 3.34 (m, 3H) 3.51 (br. s., 2H) 3.81 (m, 4H) 7.32 (m, 5H) 8.26 (s, 1H).

Example 16(11)

2-(2-((2R)-2-(N-cyclohexyl-N-methylaminomethyl)-5-oxopyrrolidin-1-yl)ethylthio)-1,3-thiazole-4-carboxylic acid TLC: Rf 0.13 (methylene chloride:methanol:water=40:10:1);
NMR (CDCl$_3$): δ 1.09 (m, 1H) 1.30 (m, 4H) 1.68 (m, 1H) 1.92 (m, 5H) 2.36 (m, 3H) 2.63 (s, 3H) 2.77 (dd, J=12.90, 8.33 Hz, 1H) 2.93 (m, 1H) 3.03 (dd, J=12.90, 3.00 Hz, 1H) 3.42 (m, 3H) 3.95 (m, 1H) 4.37 (m, 1H) 7.96 (s, 1H).

Example 16(12)

2-(2-((2R)-2-(N-benzyl-N-cyclohexylaminomethyl)-5-oxopyrrolidin-1-yl)ethylthio)-1,3-thiazole-4-carboxylic acid TLC: Rf 0.29 (ethyl acetate:methanol=4:1);
NMR (CDCl$_3$): δ 1.19 (m, 5H) 1.63 (m, 1H) 1.80 (m, 5H) 1.99 (m, 1H) 2.26 (m, 2H) 2.49 (m, J=13.27, 7.23 Hz, 2H) 2.72 (dd, J=13.36, 5.49 Hz, 1H) 3.16 (m, 2H) 3.47 (m, 2H) 3.61 (d, J=13.20 Hz, 1H) 3.69 (d, J=13.20 Hz, 1H) 3.94 (m, 1H) 7.28 (m, 5H) 8.05 (s, 1H).

Example 16(13)

2-(2-((2R)-2-hexylaminomethyl-5-oxopyrrolidin-1-yl)ethylthio)-1,3-thiazole-4-carboxylic acid TLC: Rf 0.32 (methylene chloride:methanol=9:1);
NMR (CDCl$_3$): δ 0.84 (t, J=6.90 Hz, 3H) 1.29 (m, 6H) 1.79 (m, 3H) 2.32 (m, 3H) 2.51 (m, 1H) 2.93 (dd, J=11.90, 8.88 Hz, 1H) 3.09 (dd, J=8.88, 7.60 Hz, 2H) 3.32 (m, 2H) 3.58 (m, 1H) 3.74 (m, 2H) 4.39 (m, 1H) 7.89 (s, 1H).

Example 16(14)

2-(2-((2R)-5-oxo-2-(4-phenylpiperidin-1-ylmethyl)pyrrolidin-1-yl)ethylthio)-1,3-thiazole-4-carboxylic acid TLC: Rf 0.30 (methylene chloride:methanol=9:1);
NMR (CDCl$_3$): δ 1.94 (m, 5H) 2.25 (m, 2H) 2.55 (m, 5H) 3.01 (m, 1H) 3.36 (m, 4H) 3.63 (m, 1H) 3.92 (m, 1H) 4.19 (m, 1H) 7.19 (m, 3H) 7.28 (m, 2H) 8.01 (s, 1H).

Example 16(15)

2-(2-((2R)-2-(4-benzylpiperidin-1-ylmethyl)-5-oxopyrrolidin-1-yl)ethylthio)-1,3-thiazole-4-carboxylic acid TLC: Rf 0.32 (methylene chloride:methanol=9:1);
NMR (CDCl$_3$): δ 1.64 (m, 5H) 1.90 (m, 1H) 2.32 (m, 5H) 2.53 (d, J=4.94 Hz, 2H) 2.66 (dd, J=13.09, 7.14 Hz, 1H) 3.11 (dd, J=13.09, 4.67 Hz, 1H) 3.44 (m, 5H) 3.89 (dt, J=14.01, 7.09 Hz, 1H) 4.25 (m, 1H) 7.10 (m, 2H) 7.24 (m, 3H) 8.00 (s, 1H).

Example 16(16)

2-(2-((2R)-5-oxo-2-(3-phenylpropylaminomethyl)pyrrolidin-1-yl)ethylthio)-1,3-thiazole-4-carboxylic acid TLC: Rf 0.35 (methylene chloride:methanol=9:1);
NMR (CDCl$_3$): δ 2.16 (m, 6H) 2.45 (m, 1H) 2.56 (t, J=7.69 Hz, 2H) 2.93 (dd, J=12.36, 8.33 Hz, 1H) 3.04 (dd, J=9.06, 7.05 Hz, 2H) 3.22 (m, 1H) 3.34 (m, 1H) 3.58 (m, 3H) 4.28 (m, 1H) 7.04 (m, 2H) 7.19 (m, 3H) 7.89 (s, 1H).

Example 16(17)

2-(2-((2R)-2-((naphthalen-2-ylmethyl)aminomethyl)-5-oxopyrrolidin-1-yl)ethylthio)-1,3-thiazole-4-carboxylic acid TLC: Rf 0.28 (methylene chloride:methanol=9:1);
NMR (CDCl$_3$): δ 7.98 (s, 1H), 7.77-7.63 (m, 4H), 7.52 (dd, J=8.7, 1.8 Hz, 1H), 7.8-7.37 (m, 2H), 4.34 (d, J=133.2 Hz, 1H), 4.26 (m, 1H), 4.10 (d, J=13.2 Hz, 1H), 3.66-3.32 (m, 3H), 3.13 (m, 2H), 2.80 (m, 1H), 2.42-1.98 (m, 4H).

Example 16(18)

2-(2-((2R)-2-(3,5-dimethylpiperidin-1-ylmethyl)-5-oxopyrrolidin-1-yl)ethylthio)-1,3-thiazole-4-carboxylic acid TLC: Rf 0.19 (methylene chloride:methanol=9:1);
NMR (CDCl$_3$): δ 7.99 (s, 1H), 4.26 (m, 1H), 3.88 (m, 1H), 3.57 (m, 1H), 3.85-3.65 (m, 2H), 3.55-3.02 (m, 3H), 2.84 (m, 2H), 2.58 (dd, J=12.9 Hz, 6.9 Hz, 1H), 2.50-2.15 (m, 3H), 2.10-1.70 (m, 4H), 0.90 (d, J=6.3 Hz, 3H), 0.88 (d, J=7.5 Hz, 3H), 0.61 (q, J=11.9 Hz, 1H).

Example 16(19)

2-(2-((2R)-5-oxo-2-(2-phenylethylamino)methyl)pyrrolidin-1-yl)ethylthio)-1,3-thiazole-4-carboxylic acid TLC: Rf 0.25 (methylene chloride:methanol=9:1);
NMR (CDCl$_3$): δ 7.91 (s, 1H), 7.21-7.13 (m, 3H), 7.09-7.01 (m, 2H), 4.35 (m, 1H), 3.76-3.47 (m, 3H), 3.44-3.04 (m, 6H), 2.94 (dd, J=12.0, 8.7 Hz, 1H), 2.50 (m, 1H), 2.39-2.18 (m, 3H).

Example 16(20)

2-(2-((2R)-5-oxo-2-(1,2,3,4-tetrahydronaphthalen-1-ylaminomethyl)pyrrolidin-1-yl)ethylthio)-1,3-thiazole-4-carboxylic acid TLC: Rf 0.37 (methylene chloride:methanol=9:1);
NMR (CDCl$_3$): δ 7.96 and 7.69 (each m, 1H), 7.91 and 7.87 (each s, 1H), 7.36-7.21 (m, 1H), 7.19-7.00 (m, 1H), 7.19-7.00 and 6.89 (each m, 1H), 5.05 and 4.43 (each m, 1H), 4.72-4.55

(m, 1H), 3.86-3.66 (m, 1H), 3.64-3.43 (m, 1H), 3.38-3.10 (m, 3H), 2.90-2.62 (m, 3H), 2.58-1.85 (m, 8H).

Example 16(21)

2-(2-((2R)-2-(1,2,3,4-tetrahydroisoquinolin-2-ylmethyl)-5-oxopyrrolidin-1-yl)ethylthio)-1,3-thiazole-4-carboxylic acid TLC: Rf 0.24 (methylene chloride:methanol=9:1);
NMR (CDCl$_3$): δ 8.00 (s, 1H), 7.24-7.07 (m, 3H), 7.03 (m, 1H), 4.15 (m, 1H), 3.94 (m, 1H), 3.91 (d, J=12.0 Hz, 1H), 3.83 (d, J=12.0 Hz, 1H), 3.65 (m, 1H), 3.45-3.34 (m, 2H), 3.20-2.85 (m, 5H), 2.70 (dd, J=12.9, 6.0 Hz, 1H), 2.54-2.10 (m, 3H), 1.88 (m, 1H).

Example 16(22)

2-(2-((2R)-2-(2-(3,5-dichlorophenoxy)ethylaminomethyl)-5-oxopyrrolidin-1-yl)ethylthio)-1,3-thiazole-4-carboxylic acid trifluoroacetic acid TLC: Rf 0.22 (chloroform:methanol:acetic acid=40:10:1);
NMR (CD$_3$OD): δ 2.02 (m, 1H) 2.39 (m, 3H) 3.30 (m, 1H) 3.58 (m, 6H) 3.84 (m, 1H) 4.25 (m, 1H) 4.37 (m, 2H) 6.93 (d, J=1.74 Hz, 2H) 7.04 (t, J=1.74 Hz, 1H) 8.23 (s, 1H).

Example 16(23)

2-(2-((2R)-5-oxo-2-(3-trifluoromethoxyphenylaminomethyl)pyrrolidin-1-yl)ethylthio)-1,3-thiazole-4-carboxylic acid TLC: Rf 0.33 (methylene chloride:methanol:acetic acid=9:1:0.3);
NMR (CDCl$_3$): δ 1.86 (m, 1H) 2.14 (m, 1H) 2.40 (m, 2H) 3.37 (m, 5H) 3.96 (m, 2H) 6.37 (s, 1H) 6.47 (m, 2H) 7.08 (m, 1H) 8.04 (s, 1H).

Example 16(24)

2-(2-((2R)-2-(((1S,2R,5S)-6,6-dimethylbicyclo[3.1.1]hept-2-yl)methylaminomethyl)-5-oxopyrrolidin-1-yl)ethylthio)-1,3-thiazole-4-carboxylic acid

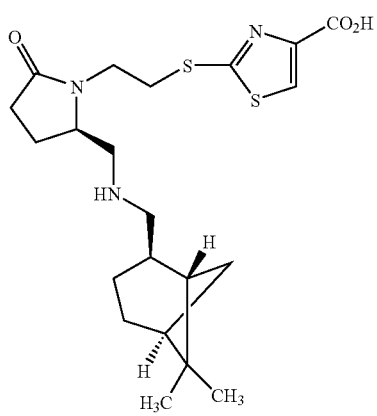

TLC: Rf 0.52 (methylene chloride:methanol:water=40:10:1);
NMR (CDCl$_3$): δ 0.90 (m, 1H) 0.97 (s, 3H) 1.17 (s, 3H) 1.43 (m, 1H) 1.97 (m, 6H) 2.32 (m, 4H) 2.52 (m, 2H) 2.96 (m, 2H) 3.29 (m, 3H) 3.53 (m, 2H) 3.80 (m, 1H) 4.49 (m, 1H) 7.83 (s, 1H).

Example 16(25)

2-(2-((2R)-2-(3-methylcyclohexylaminomethyl)-5-oxopyrrolidin-1-yl)ethylthio)-1,3-thiazole-4-carboxylic acid more polar TLC: Rf 0.43 (methylene chloride:methanol:water=40:10:1);
NMR (CDCl$_3$): δ 0.98 (m, 3H) 1.65 (m, 7H) 2.11 (m, 2H) 2.30 (m, 3H) 2.48 (m, 1H) 2.84 (m, 1H) 3.54 (m, 6H) 4.39 (m, 1H) 7.83 (m, 1H).

Example 16(26)

2-(2-((2R)-2-(3-methylcyclohexylaminomethyl)-5-oxopyrrolidin-1-yl)ethylthio)-1,3-thiazole-4-carboxylic acid less polar TLC: Rf 0.45 (methylene chloride:methanol:water=40:10:1);
NMR (CDCl$_3$): δ 0.89 (m, 4H) 1.34 (m, 4H) 1.68 (m, 1H) 1.84 (m, 1H) 2.22 (m, 5H) 2.48 (m, 1H) 2.81 (m, 1H) 3.25 (m, 3H) 3.58 (m, 1H) 3.74 (m, 2H) 4.41 (m, 1H) 7.83 (m, 1H).

Example 16(27)

2-(2-((2R)-2-(4-methylcyclohexylaminomethyl)-5-oxopyrrolidin-1-yl)ethylthio)-1,3-thiazole-4-carboxylic acid more polar TLC: Rf 0.45 (methylene chloride:methanol:water=40:10:1);
NMR (CDCl$_3$): δ 0.93 (d, J=6.96 Hz, 3H) 1.55 (m, 4H) 1.87 (m, 5H) 2.31 (m, 3H) 2.48 (m, 1H) 2.88 (m, 1H) 3.18 (m, 1H) 3.31 (m, 2H) 3.57 (m, 1H) 3.74 (m, 2H) 4.44 (m, 1H) 7.86 (s, 1H).

Example 16(28)

2-(2-((2R)-2-(4-methylcyclohexylaminomethyl)-5-oxopyrrolidin-1-yl)ethylthio)-1,3-thiazole-4-carboxylic acid less polar TLC: Rf 0.46 (methylene chloride:methanol:water=40:10:1);
NMR (CDCl$_3$): δ 0.90 (d, J=6.60 Hz, 3H) 1.00 (m, 2H) 1.37 (m, 1H) 1.60 (m, 2H) 1.80 (m, 2H) 2.24 (m, 5H) 2.49 (m, 1H) 2.80 (m, 1H) 3.19 (m, 1H) 3.30 (m, 2H) 3.57 (m, 1H) 3.74 (m, 2H) 4.41 (m, 1H) 7.82 (s, 1H).

Example 16(29)

2-(2-((2R)-2-cyclohexylmethylaminomethyl-5-oxopyrrolidin-1-yl)ethylthio)-1,3-thiazole-4-carboxylic acid TLC: Rf 0.41 (methylene chloride:methanol:water=40:10:1);
NMR (CDCl$_3$): δ 1.07 (m, 5H) 1.76 (m, 6H) 2.41 (m, 4H) 2.95 (m, 3H) 3.29 (m, 2H) 3.52 (m, 1H) 3.64 (m, 1H) 3.81 (m, 1H) 4.50 (m, 1H) 7.85 (s, 1H).

Example 16(30)

2-(2-((2R)-2-(indan-1-ylaminomethyl)-5-oxopyrrolidin-1-yl)ethylthio)-1,3-thiazole-4-carboxylic acid TLC: Rf 0.47 (methylene chloride:methanol:water=40:10:1);
NMR (CD$_3$OD): δ 1.90 (m, 1H) 2.40 (m, 5H) 3.33 (m, 8H) 3.87 (m, 1H) 4.48 (m, 1H) 7.27 (m, 3H) 7.54 (d, J=7.2 Hz, 0.4H) 7.67 (d, J=7.2 Hz, 0.6H) 7.89 (s, 0.6H) 7.97 (s, 0.4H).

Example 16(31)

2-(2-((2R)-5-oxo-2-((tetrahydrofuran-2-ylmethyl)aminomethyl)pyrrolidin-1-yl)ethylthio)-1,3-thiazole-4-carboxylic acid TLC: Rf 0.19 (methylene chloride:methanol:water=40:10:1);
NMR (CDCl$_3$): δ 1.50 (m, 1H) 1.87 (m, 2H) 2.06 (m, 1H) 2.38 (m, 4H) 2.97 (m, 2H) 3.36 (m, 4H) 3.57 (m, 1H) 3.81 (m, 3H) 4.35 (m, 2H) 7.84 (m, 1H).

Example 16(32)

2-(2-((2R)-2-(2-methylbenzylaminomethyl)-5-oxopyrrolidin-1-yl)ethylthio)-1,3-thiazole-4-carboxylic acid TLC: Rf 0.43 (methylene chloride:methanol:water=40:10:1);
NMR (CDCl$_3$): δ 2.08 (m, 1H) 2.31 (m, 3H) 2.35 (s, 3H) 2.76 (m, 1H) 3.21 (m, 2H) 3.50 (m, 2H) 3.70 (m, 1H) 4.00 (d, J=13.60 Hz, 1H) 4.21 (d, J=13.60 Hz, 1H) 4.38 (m, 1H) 7.14 (m, 3H) 7.47 (d, J=7.30 Hz, 1H) 7.91 (s, 1H).

Example 16(33)

2-(2-((2R)-2-(2-(1-cyclohexen-1-yl)ethylaminomethyl)-5-oxopyrrolidin-1-yl)ethylthio)-1,3-thiazole-4-carboxylic acid TLC: Rf 0.49 (methylene chloride:methanol:water=40:10:1);
NMR (CDCl$_3$): δ 1.53 (m, 4H) 1.88 (m, 4H) 2.41 (m, 6H) 2.93 (m, 1H) 3.19 (m, 2H) 3.34 (m, 2H) 3.58 (m, 1H) 3.73 (m, 2H) 4.38 (m, 1H) 5.41 (m, 1H) 7.86 (s, 1H).

Example 16(34)

2-(2-((2R)-5-oxo-2-((2R)-2-phenylpropylaminomethyl)pyrrolidin-1-yl)ethylthio)-1,3-thiazole-4-carboxylic acid TLC: Rf 0.43 (methylene chloride:methanol:water=40:10:1);
NMR (CDCl$_3$): δ 1.34 (d, J=7.00 Hz, 3H) 2.24 (m, 4H) 2.59 (m, 1H) 3.18 (m, 6H) 3.60 (m, 2H) 4.30 (m, 1H) 7.13 (m, 2H) 7.22 (m, 3H) 7.90 (s, 1H).

Example 16(35)

2-(2-((2R)-2-(2-(ethylthio)ethylaminomethyl)-5-oxopyrrolidin-1-yl)ethylthio)-1,3-thiazole-4-carboxylic acid TLC: Rf 0.32 (methylene chloride:methanol:water=40:10:1);
NMR (CDCl$_3$): δ 1.18 (t, J=7.40 Hz, 3H) 2.30 (m, 3H) 2.50 (q, J=7.40 Hz, 2H) 2.52 (m, 1H) 2.91 (m, 2H) 3.07 (dd, J=12.30, 7.70 Hz, 1H) 3.28 (m, 3H) 3.41 (m, 1H) 3.68 (m, 3H) 4.28 (m, 1H) 7.92 (s, 1H).

Example 16(36)

2-(2-((2R)-2-(2-(2-fluorophenyl)ethylaminomethyl)-5-oxopyrrolidin-1-yl)ethylthio)-1,3-thiazole-4-carboxylic acid TLC: Rf 0.43 (methylene chloride:methanol:water=40:10:1);
NMR (CDCl$_3$): δ 2.31 (m, 3H) 2.53 (m, 1H) 2.99 (m, 1H) 3.15 (m, 2H) 3.26 (m, 1H) 3.38 (m, 3H) 3.66 (m, 3H) 4.33 (m, 1H) 6.94 (m, 2H) 7.06 (m, 1H) 7.16 (m, 1H) 7.89 (s, 1H).

Example 16(37)

2-(2-((2R)-2-cyclooctylaminomethyl-5-oxopyrrolidin-1-yl)ethylthio)-1,3-thiazole-4-carboxylic acid TLC: Rf 0.49 (methylene chloride:methanol:water=40:10:1);
NMR (CDCl$_3$): δ 1.51 (m, 8H) 1.79 (m, 4H) 2.14 (m, 2H) 2.31 (m, 2H) 2.48 (m, 1H) 2.78 (m, 1H) 3.30 (m, 2H) 3.52 (m, 3H) 3.74 (m, 2H) 4.41 (m, 1H) 7.82 (s, 1H).

Example 16(38)

2-(2-((2R)-2-(2,3-dimethylphenylaminomethyl)-5-oxopyrrolidin-1-yl)ethylthio)-1,3-thiazole-4-carboxylic acid TLC: Rf 0.59 (methylene chloride:methanol:acetic acid=9:1:0.2);
NMR (CDCl$_3$): δ 1.97 (m, 4H) 2.19 (m, 4H) 2.44 (m, 2H) 3.35 (m, 4H) 3.57 (m, 1H) 3.98 (m, 2H) 6.47 (d, J=8.42 Hz, 1H) 6.61 (d, J=7.32 Hz, 1H) 6.99 (t, J=7.87 Hz, 1H) 8.04 (s, 1H).

Example 16(39)

2-(2-((2R)-2-(3,4-dimethylphenylaminomethyl)-5-oxopyrrolidin-1-yl)ethylthio)-1,3-thiazole-4-carboxylic acid TLC: Rf 0.54 (methylene chloride:methanol:acetic acid=9:1:0.2);
NMR (CDCl$_3$): δ 1.87 (m, 1H) 2.12 (m, 7H) 2.38 (m, 2H) 3.37 (m, 5H) 3.93 (m, 2H) 6.34 (m, 2H) 6.88 (d, J=8.06 Hz, 1H) 8.02 (s, 1H).

Example 16(40)

2-(2-((2R)-5-oxo-2-(5,6,7,8-tetrahydronaphthalen-1-ylaminomethyl)pyrrolidin-1-yl)ethylthio)-1,3-thiazole-4-carboxylic acid TLC: Rf 0.57 (chloroform:methanol:acetic acid=9:1:0.2);
NMR (CDCl$_3$): δ 1.88 (m, 3H) 2.35 (m, 5H) 2.73 (t, J=6.04 Hz, 2H) 3.38 (m, 4H) 3.59 (m, 1H) 4.02 (dd, J=8.42, 4.76 Hz, 2H) 4.02 (m, 2H) 6.44 (d, J=8.06 Hz, 1H) 6.56 (d, J=6.96 Hz, 1H) 7.02 (d, J=7.69 Hz, 1H) 8.07 (s, 1H).

Example 16(41)

2-(2-((2R)-2-(3-chloro-4-fluorophenylaminomethyl)-5-oxopyrrolidin-1-yl)ethylthio)-1,3-thiazole-4-carboxylic acid TLC: Rf 0.47 (chloroform:methanol:acetic acid=9:1:0.2);
NMR (CDCl$_3$): δ 1.86 (m, 1H) 2.15 (m, 1H) 2.39 (m, 2H) 3.34 (m, 5H) 3.95 (m, 2H) 6.38 (m, 1H) 6.55 (dd, J=5.86, 2.93 Hz, 1H) 6.88 (t, J=8.79 Hz, 1H) 8.04 (s, 1H).

Example 16(42)

2-(2-((2R)-2-(3-chloro-4-methylphenylaminomethyl)-5-oxopyrrolidin-1-yl)ethylthio)-1,3-thiazole-4-carboxylic acid TLC: Rf 0.53 (chloroform:methanol:acetic acid=9:1:0.2);
NMR (CDCl$_3$): δ 1.85 (m, 1H) 2.13 (m, 4H) 2.38 (m, 2H) 3.36 (m, 5H) 3.94 (m, 2H) 6.36 (dd, J=8.24, 2.38 Hz, 1H) 6.55 (d, J=2.56 Hz, 1H) 6.93 (d, J=8.42 Hz, 1H) 8.03 (s, 1H).

Example 16(43)

2-(2-((2R)-2-(3,5-dimethylphenylaminomethyl)-5-oxopyrrolidin-1-yl)ethylthio)-1,3-thiazole-4-carboxylic acid TLC: Rf 0.54 (chloroform:methanol:acetic acid=9:1:0.2);
NMR (CDCl$_3$): δ 1.89 (m, 1H) 2.11 (m, 7H) 2.37 (m, 2H) 3.30 (m, 4H) 3.50 (m, 1H) 3.93 (m, 2H) 6.19 (s, 2H) 6.35 (s, 1H) 8.02 (s, 1H).

Example 16(44)

2-(2-((2R)-2-(3-bromophenylaminomethyl)-5-oxopyrrolidin-1-yl)ethylthio)-1,3-thiazole-4-carboxylic acid TLC: Rf 0.57 (methylene chloride:methanol:acetic acid=80:20:1);
NMR (CDCl$_3$): δ 1.92 (m, 1H) 2.21 (m, 1H) 2.46 (m, 2H) 3.43 (m, 5H) 4.01 (m, 2H) 6.54 (m, 1H) 6.77 (t, J=2.00 Hz, 1H) 6.86 (m, 1H) 7.02 (t, J=8.10 Hz, 1H) 8.11 (s, 1H).

Example 16(45)

2-(2-((2R)-2-(3,4-dichlorophenylaminomethyl)-5-oxopyrrolidin-1-yl)ethylthio)-1,3-thiazole-4-carboxylic acid TLC: Rf 0.59 (methylene chloride:methanol:acetic acid=80:20:1);
NMR (CDCl$_3$): δ 1.91 (m, 1H) 2.21 (m, 1H) 2.46 (m, 2H) 3.43 (m, 5H) 4.02 (m, 2H) 6.47 (dd, J=8.80, 2.80 Hz, 1H) 6.70 (d, J=2.80 Hz, 1H) 7.19 (d, J=8.80 Hz, 1H) 8.12 (s, 1H).

Example 16(46)

2-(2-((2R)-5-oxo-2-(3-trifluoromethylphenylaminomethyl)pyrrolidin-1-yl)ethylthio)-1,3-thiazole-4-carboxylic acid TLC: Rf 0.59 (methylene chloride:methanol:acetic acid=80:20:1);
NMR (CDCl$_3$): δ 1.94 (m, 1H) 2.20 (m, 1H) 2.48 (m, 2H) 3.46 (m, 5H) 4.05 (m, 2H) 6.79 (m, 2H) 6.97 (m, 1H) 7.26 (m, 1H) 8.11 (s, 1H).

Example 16(47)

2-(2-((2R)-2-(4-fluoro-3-trifluoromethylphenylaminomethyl)-5-oxopyrrolidin-1-yl)ethylthio)-1,3-thiazole-4-carboxylic acid TLC: Rf 0.57 (methylene chloride:methanol:acetic acid=80:20:1);
NMR (CDCl$_3$): δ 1.94 (m, 1H) 2.24 (m, 1H) 2.48 (m, 2H) 3.45 (m, 5H) 4.04 (m, 2H) 6.76 (m, 2H) 7.01 (t, J=9.30 Hz, 1H) 8.11 (s, 1H).

Example 16(48)

2-(2-((2R)-2-(4-chloro-3-trifluoromethylphenylaminomethyl)-5-oxopyrrolidin-1-yl)ethylthio)-1,3-thiazole-4-carboxylic acid TLC: Rf 0.57 (methylene chloride:methanol:acetic acid=80:20:1);
NMR (CDCl$_3$): δ 1.92 (m, 1H) 2.24 (m, 1H) 2.47 (m, 2H) 3.45 (m, 5H) 4.03 (m, 2H) 6.69 (dd, J=8.60, 2.60 Hz, 1H) 6.89 (d, J=2.60 Hz, 1H) 7.25 (m, 1H) 8.11 (s, 1H).

Example 16(49)

2-(2-((2R)-5-oxo-2-(3,4,5-trichlorophenylaminomethyl)pyrrolidin-1-yl)ethylthio)-1,3-thiazole-4-carboxylic acid TLC: Rf 0.57 (methylene chloride:methanol:acetic acid=80:20:1);
NMR (CDCl$_3$): δ 1.90 (m, 1H) 2.23 (m, 1H) 2.47 (m, 2H) 3.45 (m, 5H) 4.01 (m, 2H) 6.64 (m, 2H) 8.12 (m, 1H).

Example 16(50)

2-(2-((2R)-2-(3-bromo-4-methylphenylaminomethyl)-5-oxopyrrolidin-1-yl)ethylthio)-1,3-thiazole-4-carboxylic acid TLC: Rf 0.57 (methylene chloride:methanol:acetic acid=80:20:1);
NMR (CDCl$_3$): δ 1.93 (m, 1H) 2.19 (m, 1H) 2.27 (s, 3H) 2.46 (m, 2H) 3.43 (m, 5H) 4.01 (m, 2H) 6.50 (dd, J=8.40, 2.40 Hz, 1H) 6.84 (d, J=2.40 Hz, 1H) 7.01 (d, J=8.40 Hz, 1H) 8.10 (s, 1H).

Example 16(51)

2-(2-((2R)-2-(1-methylhexylaminomethyl)-5-oxopyrrolidin-1-yl)ethylthio)-1,3-thiazole-4-carboxylic acid TLC: Rf 0.50 (methylene chloride:methanol:water=40:10:1);

NMR (CDCl₃): δ 0.85 (m, 3H) 1.31 (m, 9H) 1.56 (m, 1H) 1.92 (m, 1H) 2.32 (m, 3H) 2.49 (m, 1H) 2.76 (m, 1H) 3.31 (m, 3H) 3.56 (m, 3H) 3.80 (m, 1H) 4.46 (m, 1H) 7.81 (m, 1H).

Example 16(52)

2-(2-((2R)-2-(2-ethylhexylaminomethyl)-5-oxopyrrolidin-1-yl)ethylthio)-1,3-thiazole-4-carboxylic acid TLC: Rf 0.51 (methylene chloride:methanol:water=40:10:1);
NMR (CDCl₃): δ 0.80 (m, 6H) 1.27 (m, 9H) 1.76 (m, 1H) 2.34 (m, 3H) 2.51 (m, 1H) 2.99 (m, 3H) 3.28 (m, 2H) 3.57 (m, 2H) 3.80 (m, 1H) 4.54 (m, 1H) 7.89 (s, 1H).

Example 16(53)

2-(2-((2R)-2-octylaminoethyl-5-oxopyrrolidin-1-yl)ethylthio)-1,3-thiazole-4-carboxylic acid TLC: Rf 0.52 (methylene chloride:methanol:water=40:10:1);
NMR (CDCl₃): δ 0.85 (t, J=6.90 Hz, 3H) 1.27 (m, 10H) 1.79 (m, 2H) 2.33 (m, 3H) 2.51 (m, 1H) 2.88 (m, 1H) 3.09 (m, 2H) 3.31 (m, 2H) 3.68 (m, 3H) 4.41 (m, 1H) 7.82 (s, 1H).

Example 16(54)

2-(2-((2R)-2-nonylaminomethyl-5-oxopyrrolidin-1-yl)ethylthio)-1,3-thiazole-4-carboxylic acid TLC: Rf 0.52 (methylene chloride:methanol:water=40:10:1);
NMR (CDCl₃): δ 0.86 (t, J=6.90 Hz, 3H) 1.25 (m, 12H) 1.79 (m, 2H) 2.32 (m, 3H) 2.51 (m, 1H) 2.90 (m, 1H) 3.08 (m, 2H) 3.31 (m, 2H) 3.66 (m, 3H) 4.40 (m, 1H) 7.85 (s, 1H).

Example 16(55)

2-(2-((2R)-2-((1S)-1-cyclohexylethylaminomethyl)-5-oxopyrrolidin-1-yl)ethylthio)-1,3-thiazole-4-carboxylic acid TLC: Rf 0.46 (methylene chloride:methanol:water=40:10:1);
NMR (CDCl₃): δ 1.08 (m, 5H) 1.35 (d, J=6.80 Hz, 3H) 1.72 (m, 6H) 2.31 (m, 3H) 2.48 (m, 1H) 2.80 (m, 1H) 3.29 (m, 3H) 3.52 (m, 1H) 3.65 (m, 1H) 3.82 (m, 1H) 4.53 (m, 1H) 7.83 (s, 1H).

Example 16(56)

2-(2-((2R)-2-(adamantan-1-ylmethyl)amino)methyl)-5-oxopyrrolidin-1-yl)ethylthio)-1,3-thiazole-4-carboxylic acid TLC: Rf 0.49 (methylene chloride:methanol:water=40:10:1);
NMR (CDCl₃): δ 1.58 (m, 12H) 1.86 (m, 3H) 2.35 (m, 3H) 2.53 (m, 1H) 2.72 (s, 2H) 3.23 (m, 3H) 3.58 (m, 2H) 3.83 (m, 1H) 4.66 (m, 1H) 7.94 (s, 1H).

Example 16(57)

2-(2-((2R)-2-(3-chloro-2-methylphenylaminomethyl)-5-oxopyrrolidin-1-yl)ethylthio)-1,3-thiazole-4-carboxylic acid TLC: Rf 0.64 (methylene chloride:methanol:acetic acid=80:20:1);
NMR (CDCl₃): δ 1.97 (m, 1H) 2.18 (s, 3H) 2.21 (m, 1H) 2.48 (m, 2H) 3.39 (m, 4H) 3.59 (m, 1H) 4.04 (m, 2H) 6.51 (d, J=8.00 Hz, 1H) 6.82 (d, J=8.00 Hz, 1H) 7.03 (t, J=8.00 Hz, 1H) 8.09 (s, 1H).

Example 16(58)

2-(2-((2R)-2-(2,4-dichlorophenylaminomethyl)-5-oxopyrrolidin-1-yl)ethylthio)-1,3-thiazole-4-carboxylic acid TLC: Rf 0.66 (methylene chloride:methanol:acetic acid=80:20:1);
NMR (CDCl₃): δ 1.94 (m, 1H) 2.25 (m, 1H) 2.49 (m, 2H) 3.40 (m, 4H) 3.58 (m, 1H) 4.01 (m, 2H) 6.59 (d, J=8.60 Hz, 1H) 7.11 (dd, J=8.60, 2.40 Hz, 1H) 7.27 (m, 1H) 8.10 (s, 1H).

Example 16(59)

2-(2-((2R)-2-(5-chloro-2-methoxyphenylaminomethyl)-5-oxopyrrolidin-1-yl)ethylthio)-1,3-thiazole-4-carboxylic acid TLC: Rf 0.68 (methylene chloride:methanol:acetic acid=80:20:1);
NMR (CDCl₃): δ 1.94 (m, 1H) 2.23 (m, 1H) 2.48 (m, 2H) 3.37 (m, 4H) 3.57 (m, 1H) 3.81 (s, 3H) 4.01 (m, 2H) 6.54 (m, 1H) 6.65 (m, 2H) 8.08 (s, 1H).

Example 16(60)

2-(2-((2R)-2-(4-bromo-3-methylphenylaminomethyl)-5-oxopyrrolidin-1-yl)ethylthio)-1,3-thiazole-4-carboxylic acid TLC: Rf 0.64 (methylene chloride:methanol:acetic acid=80:20:1);
NMR (CDCl₃): δ 1.92 (m, 1H) 2.22 (m, 1H) 2.30 (s, 3H) 2.46 (m, 2H) 3.42 (m, 5H) 4.01 (m, 2H) 6.33 (dd, J=8.40, 2.50 Hz, 1H) 6.50 (d, J=2.50 Hz, 1H) 7.28 (m, 1H) 8.10 (s, 1H).

Example 16(61)

2-(2-((2R)-5-oxo-2-(3-trifluoromethylthiophenylaminomethyl)pyrrolidin-1-yl)ethylthio)-1,3-thiazole-4-carboxylic acid TLC: Rf 0.64 (methylene chloride:methanol:acetic acid=80:20:1);
NMR (CDCl₃): δ 1.94 (m, 1H) 2.23 (m, 1H) 2.48 (m, 2H) 3.45 (m, 5H) 4.03 (m, 2H) 6.71 (m, 1H) 6.87 (m, 1H) 7.00 (m, 1H) 7.20 (t, J=7.80 Hz, 1H) 8.11 (s, 1H).

Example 17(1) to (345)

By the same procedure as described in Example 15→Example 16, using a corresponding amine derivative instead of n-heptylamine, the following compounds of the present invention were obtained. With the proviso that, the following compounds was extracted by reverse extraction process or ion-exchange resin.

Example 17(1)

2-(2-((2R)-2-((naphthalen-1-ylmethyl)aminomethyl)-5-oxopyrrolidin-1-yl)ethylthio)-1,3-thiazole-4-carboxylic acid HPLC retention time: 3.08 minutes;
MASS data (ESI, Pos. 20 V): 442 (M+H)+.

Example 17(2)

2-(2-((2R)-2-(2-(morpholin-4-yl)ethylaminomethyl)-5-oxopyrrolidin-1-yl)ethylthio)-1,3-thiazole-4-carboxylic acid HPLC retention time: 2.70 minutes;
MASS data (ESI, Pos. 20 V): 415 (M+H)+.

Example 17(3)

2-(2-((2R)-2-(N,N-bis(3-methylbutyl)aminomethyl)-5-oxopyrrolidin-1-yl)ethylthio)-1,3-thiazole-4-carboxylic acid HPLC retention time: 3.18 minutes;
MASS data (ESI, Pos. 20 V): 442 (M+H)+.

Example 17(4)

2-(2-((2R)-2-(azocan-1-ylmethyl)-5-oxopyrrolidin-1-yl)ethylthio)-1,3-thiazole-4-carboxylic acid HPLC retention time: 2.90 minutes;
MASS data (ESI, Pos. 20 V): 398 (M+H)+.

Example 17(5)

2-(2-((2R)-2-(N-(2-diethylaminoethyl)-N-ethylaminomethyl)-5-oxopyrrolidin-1-yl)ethylthio)-1,3-thiazole-4-carboxylic acid HPLC retention time: 2.78 minutes;
MASS data (ESI, Pos. 20 V): 429 (M+H)+.

Example 17(6)

2-(2-((2R)-5-oxo-2-(piperidin-1-ylmethyl)pyrrolidin-1-yl)ethylthio)-1,3-thiazole-4-carboxylic acid HPLC retention time: 2.79 minutes;
MASS data (ESI, Pos. 20 V): 370 (M+H)+.

Example 17(7)

2-(2-((2R)-2-(cyclobutylaminomethyl)-5-oxopyrrolidin-1-yl)ethylthio)-1,3-thiazole-4-carboxylic acid HPLC retention time: 2.80 minutes;
MASS data (ESI, Pos. 20 V): 356 (M+H)+.

Example 17(8)

2-(2-((2R)-2-((1S,2R,5S)-6,6-dimethylbicyclo[3.1.1]hept-2-ylmethylaminomethyl)-5-oxopyrrolidin-1-yl)ethylthio)-1,3-thiazole-4-carboxylic acid HPLC retention time: 3.18 minutes;
MASS data (ESI, Pos. 20 V): 438 (M+H)+.

Example 17(9)

2-(2-((2R)-2-cyclopentylaminomethyl-5-oxopyrrolidin-1-yl)ethylthio)-1,3-thiazole-4-carboxylic acid HPLC retention time: 2.85 minutes;
MASS data (ESI, Pos. 20 V): 370 (M+H)+.

Example 17(10)

2-(2-((2R)-2-(2-methylcyclohexylaminomethyl)-5-oxopyrrolidin-1-yl)ethylthio)-1,3-thiazole-4-carboxylic acid HPLC retention time: 2.96 minutes;
MASS data (ESI, Pos. 20 V): 398 (M+H)+.

Example 17(11)

2-(2-((2R)-2-(3-methylcyclohexylaminomethyl)-5-oxopyrrolidin-1-yl)ethylthio)-1,3-thiazole-4-carboxylic acid HPLC retention time: 3.00 minutes;
MASS data (ESI, Pos. 20 V): 398 (M+H)+.

Example 17(12)

2-(2-((2R)-2-(4-methylcyclohexylaminomethyl)-5-oxopyrrolidin-1-yl)ethylthio)-1,3-thiazole-4-carboxylic acid HPLC retention time: 3.00 minutes;
MASS data (ESI, Pos. 20 V): 398 (M+H)+.

Example 17(13)

2-(2-((2R)-2-cyclohexylmethylaminomethyl-5-oxopyrrolidin-1-yl)ethylthio)-1,3-thiazole-4-carboxylic acid HPLC retention time: 3.03 minutes;
MASS data (ESI, Pos. 20 V): 398 (M+H)+.

Example 17(14)

2-(2-((2R)-2-(2-(1-methylpyrrolidin-2-yl)ethylaminomethyl)-5-oxopyrrolidin-1-yl)ethylthio)-1,3-thiazole-4-carboxylic acid HPLC retention time: 2.69 minutes;
MASS data (ESI, Pos. 20 V): 413 (M+H)+.

Example 17(15)

2-(2-((2R)-2-(1-ethylpyrrolidin-2-ylmethylaminomethyl)-5-oxopyrrolidin-1-yl)ethylthio)-1,3-thiazole-4-carboxylic acid HPLC retention time: 2.70 minutes;
MASS data (ESI, Pos. 20 V): 413 (M+H)$^+$.

Example 17(16)

2-(2-((2R)-2-(furan-2-ylmethylaminomethyl)-5-oxopyrrolidin-1-yl)ethylthio)-1,3-thiazole-4-carboxylic acid HPLC retention time: 2.85 minutes;
MASS data (ESI, Pos. 20 V): 382 (M+H)$^+$.

Example 17(17)

2-(2-((2R)-2-(indan-1-ylaminomethyl)-5-oxopyrrolidin-1-yl)ethylthio)-1,3-thiazole-4-carboxylic acid HPLC retention time: 2.98 minutes;
MASS data (ESI, Pos. 20 V): 418 (M+H)$^+$.

Example 17(18)

2-(2-((2R)-2-(N-(2-propenyl)-N-cyclohexylaminomethyl)-5-oxopyrrolidin-1-yl)ethylthio)-1,3-thiazole-4-carboxylic acid HPLC retention time: 2.97 minutes;
MASS data (ESI, Pos. 20 V): 424 (M+H)$^+$.

Example 17(19)

2-(2-((2R)-2-cycloheptylaminomethyl-5-oxopyrrolidin-1-yl)ethylthio)-1,3-thiazole-4-carboxylic acid HPLC retention time: 2.98 minutes;
MASS data (ESI, Pos. 20 V): 398 (M+H)$^+$.

Example 17(20)

2-(2-((2R)-5-oxo-2-(1,2,3,4-tetrahydro-β-carbolin-2-ylmethyl)pyrrolidin-1-yl)ethylthio)-1,3-thiazole-4-carboxylic acid HPLC retention time: 3.04 minutes;
MASS data (ESI, Pos. 20 V): 457 (M+H)$^+$.

Example 17(21)

2-(2-((2R)-5-oxo-2-(pyrrolidin-1-ylmethyl)pyrrolidin-1-yl)ethylthio)-1,3-thiazole-4-carboxylic acid HPLC retention time: 2.74 minutes;
MASS data (ESI, Pos. 20 V): 356 (M+H)$^+$.

Example 17(22)

2-(2-((2R)-5-oxo-2-(tetrahydrofuran-2-ylmethylaminomethyl)pyrrolidin-1-yl)ethylthio)-1,3-thiazole-4-carboxylic acid HPLC retention time: 2.81 minutes;
MASS data (ESI, Pos. 20 V): 386 (M+H)$^+$.

Example 17(23)

2-(2-((2R)-2-(2-(indol-3-yl)-1-methylethylaminomethyl)-5-oxopyrrolidin-1-yl)ethylthio)-1,3-thiazole-4-carboxylic acid HPLC retention time: 3.06 minutes;
MASS data (ESI, Pos. 20 V): 459 (M+H)$^+$.

Example 17(24)

2-(2-((2R)-2-(N-(2-(indol-3-yl)ethyl)-N-methylaminomethyl)-5-oxopyrrolidin-1-yl)ethylthio)-1,3-thiazole-4-carboxylic acid HPLC retention time: 3.05 minutes;
MASS data (ESI, Pos. 20 V): 459 (M+H)$^+$.

Example 17(25)

2-(2-((2R)-5-oxo-2-(4-phenylpiperazin-1-ylmethyl)pyrrolidin-1-yl)ethylthio)-1,3-thiazole-4-carboxylic acid HPLC retention time: 3.02 minutes;
MASS data (ESI, Pos. 20 V): 447 (M+H)$^+$.

Example 17(26)

2-(2-((2R)-2-(4-hydroxy-4-phenylpiperidin-1-ylmethyl)-5-oxopyrrolidin-1-yl)ethylthio)-1,3-thiazole-4-carboxylic acid HPLC retention time: 2.95 minutes;
MASS data (ESI, Pos. 20 V): 462 (M+H)$^+$.

Example 17(27)

2-(2-((2R)-5-oxo-2-(pyridin-2-ylmethylaminomethyl)pyrrolidin-1-yl)ethylthio)-1,3-thiazole-4-carboxylic acid HPLC retention time: 2.83 minutes;
MASS data (ESI, Pos. 20 V): 393 (M+H)$^+$.

Example 17(28)

2-(2-((2R)-5-oxo-2-(2-(pyridin-2-yl)ethylaminomethyl)pyrrolidin-1-yl)ethylthio)-1,3-thiazole-4-carboxylic acid HPLC retention time: 2.71 minutes;
MASS data (ESI, Pos. 20 V): 407 (M+H)$^+$.

Example 17(29)

2-(2-((2R)-5-oxo-2-(pyridin-3-ylmethylaminomethyl)pyrrolidin-1-yl)ethylthio)-1,3-thiazole-4-carboxylic acid HPLC retention time: 2.66 minutes;
MASS data (ESI, Pos. 20 V): 393 (M+H)$^+$.

Example 17(30)

2-(2-((2R)-5-oxo-2-(pyridin-4-ylmethylaminomethyl)pyrrolidin-1-yl)ethylthio)-1,3-thiazole-4-carboxylic acid HPLC retention time: 2.65 minutes;
MASS data (ESI, Pos. 20 V): 393 (M+H)$^+$.

Example 17(31)

2-(2-((2R)-2-(1-ethoxycarbonylpiperidin-4-ylaminomethyl)-5-oxopyrrolidin-1-yl)ethylthio)-1,3-thiazole-4-carboxylic acid HPLC retention time: 2.93 minutes;
MASS data (ESI, Pos. 20 V): 457 (M+H)$^+$.

Example 17(32)

2-(2-((2R)-5-oxo-2-(2-(piperidin-1-yl)ethylaminomethyl)pyrrolidin-1-yl)ethylthio)-1,3-thiazole-4-carboxylic acid HPLC retention time: 2.73 minutes;
MASS data (ESI, Pos. 20 V): 413 (M+H)$^+$.

Example 17(33)

2-(2-((2R)-2-(perhydroquinolin-1-ylmethyl)-5-oxopyrrolidin-1-yl)ethylthio)-1,3-thiazole-4-carboxylic acid HPLC retention time: 2.97 minutes;
MASS data (ESI, Pos. 20 V): 424 (M+H)$^+$.

Example 17(34)

2-(2-((2R)-2-(t-butylaminomethyl)-5-oxopyrrolidin-1-yl)ethylthio)-1,3-thiazole-4-carboxylic acid HPLC retention time: 2.80 minutes;
MASS data (ESI, Pos. 20 V): 358 (M+H)$^+$.

Example 17(35)

2-(2-((2R)-5-oxo-2-(1-phenylethylaminomethyl)pyrrolidin-1-yl)ethylthio)-1,3-thiazole-4-carboxylic acid HPLC retention time: 2.98 minutes;
MASS data (ESI, Pos. 20 V): 406 (M+H)$^+$.

Example 17(36)

2-(2-((2R)-2-(1,2-dimethylpropylaminomethyl)-5-oxopyrrolidin-1-yl)ethylthio)-1,3-thiazole-4-carboxylic acid HPLC retention time: 2.88 minutes;
MASS data (ESI, Pos. 20 V): 372 (M+H)$^+$.

Example 17(37)

2-(2-((2R)-2-(2-methoxy-1-methylethylaminomethyl)-5-oxopyrrolidin-1-yl)ethylthio)-1,3-thiazole-4-carboxylic acid HPLC retention time: 2.80 minutes;
MASS data (ESI, Pos. 20 V): 374 (M+H)$^+$.

Example 17(38)

2-(2-((2R)-2-(1,3-dimethylbutylaminomethyl)-5-oxopyrrolidin-1-yl)ethylthio)-1,3-thiazole-4-carboxylic acid HPLC retention time: 2.98 minutes;
MASS data (ESI, Pos. 20 V): 386 (M+H)$^+$.

Example 17(39)

2-(2-((2R)-2-(1-methylpropylaminomethyl)-5-oxopyrrolidin-1-yl)ethylthio)-1,3-thiazole-4-carboxylic acid HPLC retention time: 2.83 minutes;
MASS data (ESI, Pos. 20 V): 358 (M+H)$^+$.

Example 17(40)

2-(2-((2R)-2-(1-ethylpropylaminomethyl)-5-oxopyrrolidin-1-yl)ethylthio)-1,3-thiazole-4-carboxylic acid HPLC retention time: 2.88 minutes;
MASS data (ESI, Pos. 20 V): 372 (M+H)$^+$.

Example 17(41)

2-(2-((2R)-2-(1-methylbutylaminomethyl)-5-oxopyrrolidin-1-yl)ethylthio)-1,3-thiazole-4-carboxylic acid HPLC retention time: 2.93 minutes;
MASS data (ESI, Pos. 20 V): 372 (M+H)$^+$.

Example 17(42)

2-(2-((2R)-2-(2-methoxybenzylaminomethyl)-5-oxopyrrolidin-1-yl)ethylthio)-1,3-thiazole-4-carboxylic acid HPLC retention time: 2.97 minutes;
MASS data (ESI, Pos. 20 V): 422 (M+H)$^+$.

Example 17(43)

2-(2-((2R)-2-(2-methylbenzylaminomethyl)-5-oxopyrrolidin-1-yl)ethylthio)-1,3-thiazole-4-carboxylic acid HPLC retention time: 2.99 minutes;
MASS data (ESI, Pos. 20 V): 406 (M+H)$^+$.

Example 17(44)

2-(2-((2R)-2-(3-methoxybenzylaminomethyl)-5-oxopyrrolidin-1-yl)ethylthio)-1,3-thiazole-4-carboxylic acid HPLC retention time: 2.97 minutes;
MASS data (ESI, Pos. 20 V): 422 (M+H)$^+$.

Example 17(45)

2-(2-((2R)-2-(4-chlorobenzylaminomethyl)-5-oxopyrrolidin-1-yl)ethylthio)-1,3-thiazole-4-carboxylic acid HPLC retention time: 3.04 minutes;
MASS data (ESI, Pos. 20 V): 426 (M+H)$^+$.

Example 17(46)

2-(2-((2R)-2-(4-methoxybenzylaminomethyl)-5-oxopyrrolidin-1-yl)ethylthio)-1,3-thiazole-4-carboxylic acid HPLC retention time: 2.96 minutes;
MASS data (ESI, Pos. 20 V): 422 (M+H)$^+$.

Example 17(47)

2-(2-((2R)-2-(4-methylbenzylaminomethyl)-5-oxopyrrolidin-1-yl)ethylthio)-1,3-thiazole-4-carboxylic acid HPLC retention time: 3.00 minutes;
MASS data (ESI, Pos. 20 V): 406 (M+H)$^+$.

Example 17(48)

2-(2-((2R)-2-(2,2-dimethylpropylaminomethyl)-5-oxopyrrolidin-1-yl)ethylthio)-1,3-thiazole-4-carboxylic acid HPLC retention time: 2.91 minutes;
MASS data (ESI, Pos. 20 V): 372 (M+H)$^+$.

Example 17(49)

2-(2-((2R)-2-(2-methylpropylaminomethyl)-5-oxopyrrolidin-1-yl)ethylthio)-1,3-thiazole-4-carboxylic acid HPLC retention time: 2.83 minutes;
MASS data (ESI, Pos. 20 V): 358 (M+H)$^+$.

Example 17(50)

2-(2-((2R)-2-(2-fluoroethylaminomethyl)-5-oxopyrrolidin-1-yl)ethylthio)-1,3-thiazole-4-carboxylic acid HPLC retention time: 2.70 minutes;
MASS data (ESI, Pos. 20 V): 348 (M+H)$^+$.

Example 17(51)

2-(2-((2R)-2-(2-phenylaminoethylaminomethyl)-5-oxopyrrolidin-1-yl)ethylthio)-1,3-thiazole-4-carboxylic acid HPLC retention time: 3.01 minutes;
MASS data (ESI, Pos. 20 V): 421 (M+H)$^+$.

Example 17(52)

2-(2-((2R)-2-(N-(2-diethylaminoethyl)-N-methylaminomethyl)-5-oxopyrrolidin-1-yl)ethylthio)-1,3-thiazole-4-carboxylic acid HPLC retention time: 2.73 minutes;
MASS data (ESI, Pos. 20 V): 415 (M+H)$^+$.

Example 17(53)

2-(2-((2R)-2-(2-methoxyethylaminomethyl)-5-oxopyrrolidin-1-yl)ethylthio)-1,3-thiazole-4-carboxylic acid HPLC retention time: 2.77 minutes;
MASS data (ESI, Pos. 20 V): 360 (M+H)$^+$.

Example 17(54)

2-(2-((2R)-2-(2-(4-methylphenyl)ethylaminomethyl)-5-oxopyrrolidin-1-yl)ethylthio)-1,3-thiazole-4-carboxylic acid HPLC retention time: 3.09 minutes;
MASS data (ESI, Pos. 20 V): 420 (M+H)$^+$.

Example 17(55)

2-(2-((2R)-2-(4-phenylbutylaminomethyl)-5-oxopyrrolidin-1-yl)ethylthio)-1,3-thiazole-4-carboxylic acid HPLC retention time: 3.16 minutes;
MASS data (ESI, Pos. 20 V): 434 (M+H)$^+$.

Example 17(56)

2-(2-((2R)-2-(pentylaminomethyl)-5-oxopyrrolidin-1-yl)ethylthio)-1,3-thiazole-4-carboxylic acid HPLC retention time: 2.97 minutes;
MASS data (ESI, Pos. 20 V): 372 (M+H)$^+$.

Example 17(57)

2-(2-((2R)-2-(N-benzyl-N-methylaminomethyl)-5-oxopyrrolidin-1-yl)ethylthio)-1,3-thiazole-4-carboxylic acid HPLC retention time: 2.94 minutes;
MASS data (ESI, Pos. 20 V): 406 (M+H)$^+$.

Example 17(58)

2-(2-((2R)-2-(N-methyl-N-(2-phenylethyl)aminomethyl)-5-oxopyrrolidin-1-yl)ethylthio)-1,3-thiazole-4-carboxylic acid HPLC retention time: 3.02 minutes;
MASS data (ESI, Pos. 20 V): 420 (M+H)$^+$.

Example 17(59)

2-(2-((2R)-2-(N-benzyl-N-isopropylaminomethyl)-5-oxopyrrolidin-1-yl)ethylthio)-1,3-thiazole-4-carboxylic acid HPLC retention time: 2.96 minutes;
MASS data (ESI, Pos. 20 V): 434 (M+H)$^+$.

Example 17(60)

2-(2-((2R)-2-(N,N-bis(2-methylpropyl)aminomethyl)-5-oxopyrrolidin-1-yl)ethylthio)-1,3-thiazole-4-carboxylic acid HPLC retention time: 2.97 minutes;
MASS data (ESI, Pos. 20 V): 414 (M+H)$^+$.

Example 17(61)

2-(2-((2R)-2-(N-benzyl-N-ethylaminomethyl)-5-oxopyrrolidin-1-yl)ethylthio)-1,3-thiazole-4-carboxylic acid HPLC retention time: 2.96 minutes;
MASS data (ESI, Pos. 20 V): 420 (M+H)$^+$.

Example 17(62)

2-(2-((2R)-2-(N,N-diethylaminomethyl)-5-oxopyrrolidin-1-yl)ethylthio)-1,3-thiazole-4-carboxylic acid HPLC retention time: 2.76 minutes;
MASS data (ESI, Pos. 20 V): 358 (M+H)$^+$.

Example 17(63)

2-(2-((2R)-2-(N-methyl-N-propylaminomethyl)-5-oxopyrrolidin-1-yl)ethylthio)-1,3-thiazole-4-carboxylic acid HPLC retention time: 2.81 minutes;
MASS data (ESI, Pos. 20 V): 358 (M+H)$^+$.

Example 17(64)

2-(2-((2R)-2-(N,N-dipropylaminomethyl)-5-oxopyrrolidin-1-yl)ethylthio)-1,3-thiazole-4-carboxylic acid HPLC retention time: 2.88 minutes;
MASS data (ESI, Pos. 20 V): 386 (M+H)$^+$.

Example 17(65)

2-(2-((2R)-2-(N-benzyl-N-butylaminomethyl)-5-oxopyrrolidin-1-yl)ethylthio)-1,3-thiazole-4-carboxylic acid HPLC retention time: 3.08 minutes;
MASS data (ESI, Pos. 20 V): 448 (M+H)$^+$.

Example 17(66)

2-(2-((2R)-2-butylaminomethyl-5-oxopyrrolidin-1-yl)ethylthio)-1,3-thiazole-4-carboxylic acid HPLC retention time: 2.88 minutes;
MASS data (ESI, Pos. 20 V): 358 (M+H)$^+$.

Example 17(67)

2-(2-((2R)-2-(2-(1-cyclohexen-1-yl)ethylaminomethyl)-5-oxopyrrolidin-1-yl)ethylthio)-1,3-thiazole-4-carboxylic acid HPLC retention time: 3.09 minutes;
MASS data (ESI, Pos. 20 V): 410 (M+H)$^+$.

Example 17(68)

2-(2-((2R)-2-(cyclopropylmethylaminomethyl)-5-oxopyrrolidin-1-yl)ethylthio)-1,3-thiazole-4-carboxylic acid HPLC retention time: 2.82 minutes;
MASS data (ESI, Pos. 20 V): 356 (M+H)$^+$.

Example 17(69)

2-(2-((2R)-2-(4-t-butylcyclohexylaminomethyl)-5-oxopyrrolidin-1-yl)ethylthio)-1,3-thiazole-4-carboxylic acid HPLC retention time: 3.23 minutes;
MASS data (ESI, Pos. 20 V): 440 (M+H)$^+$.

Example 17(70)

2-(2-((2R)-2-(1-propylbutylaminomethyl)-5-oxopyrrolidin-1-yl)ethylthio)-1,3-thiazole-4-carboxylic acid HPLC retention time: 3.06 minutes;
MASS data (ESI, Pos. 20 V): 400 (M+H)$^+$.

Example 17(71)

2-(2-((2R)-2-(N-methyl-N-(2-methylpropyl)aminomethyl)-5-oxopyrrolidin-1-yl)ethylthio)-1,3-thiazole-4-carboxylic acid HPLC retention time: 2.85 minutes;
MASS data (ESI, Pos. 20 V): 372 (M+H)$^+$.

Example 17(72)

2-(2-((2R)-2-(N-ethyl-N-propylaminomethyl)-5-oxopyrrolidin-1-yl)ethylthio)-1,3-thiazole-4-carboxylic acid HPLC retention time: 2.81 minutes;
MASS data (ESI, Pos. 20 V): 372 (M+H)$^+$.

Example 17(73)

2-(2-((2R)-2-(N-ethyl-N-(pyridin-4-ylmethyl)aminomethyl)-5-oxopyrrolidin-1-yl)ethylthio)-1,3-thiazole-4-carboxylic acid HPLC retention time: 2.78 minutes;
MASS data (ESI, Pos. 20 V): 421 (M+H)$^+$.

Example 17(74)

2-(2-((2R)-2-(2-(N-ethyl-N-(3-methylphenyl))ethylaminomethyl)-5-oxopyrrolidin-1-yl)ethylthio)-1,3-thiazole-4-carboxylic acid HPLC retention time: 3.09 minutes;
MASS data (ESI, Pos. 20 V): 463 (M+H)$^+$.

Example 17(75)

2-(2-((2R)-2-(2-(pyridin-4-yl)ethylaminomethyl)-5-oxopyrrolidin-1-yl)ethylthio)-1,3-thiazole-4-carboxylic acid HPLC retention time: 2.66 minutes;
MASS data (ESI, Pos. 20 V): 407 (M+H)$^+$.

Example 17(76)

2-(2-((2R)-2-(4-t-butylbenzylaminomethyl)-5-oxopyrrolidin-1-yl)ethylthio)-1,3-thiazole-4-carboxylic acid HPLC retention time: 3.21 minutes;
MASS data (ESI, Pos. 20 V): 448 (M+H)$^+$.

Example 17(77)

2-(2-((2R)-2-(3-methylthiopropylaminomethyl)-5-oxopyrrolidin-1-yl)ethylthio)-1,3-thiazole-4-carboxylic acid HPLC retention time: 2.88 minutes;
MASS data (ESI, Pos. 20 V): 390 (M+H)$^+$.

Example 17(78)

2-(2-((2R)-2-(N-methyl-N-isopropylaminomethyl)-5-oxopyrrolidin-1-yl)ethylthio)-1,3-thiazole-4-carboxylic acid HPLC retention time: 2.76 minutes;
MASS data (ESI, Pos. 20 V): 358 (M+H)$^+$.

Example 17(79)

2-(2-((2R)-2-isopropylaminomethyl-5-oxopyrrolidin-1-yl)ethylthio)-1,3-thiazole-4-carboxylic acid HPLC retention time: 2.76 minutes;
MASS data (ESI, Pos. 20 V): 344 (M+H)$^+$.

Example 17(80)

2-(2-((2R)-2-(2-(thiophene-2-yl)ethylaminomethyl)-5-oxopyrrolidin-1-yl)ethylthio)-1,3-thiazole-4-carboxylic acid HPLC retention time: 2.96 minutes;
MASS data (ESI, Pos. 20 V): 412 (M+H)$^+$.

Example 17(81)

2-(2-((2R)-2-(2-t-butylthioethylaminomethyl)-5-oxopyrrolidin-1-yl)ethylthio)-1,3-thiazole-4-carboxylic acid HPLC retention time: 3.02 minutes;
MASS data (ESI, Pos. 20 V): 418 (M+H)$^+$.

Example 17(82)

2-(2-((2R)-2-(1-benzylpyrrolidin-3-ylaminomethyl)-5-oxopyrrolidin-1-yl)ethylthio)-1,3-thiazole-4-carboxylic acid HPLC retention time: 2.86 minutes;
MASS data (ESI, Pos. 20 V): 461 (M+H)$^+$.

Example 17(83)

2-(2-((2R)-2-(N-(2-propenyl)-N-cyclopentylaminomethyl)-5-oxopyrrolidin-1-yl)ethylthio)-1,3-thiazole-4-carboxylic acid HPLC retention time: 2.89 minutes;
MASS data (ESI, Pos. 20 V): 410 (M+H)$^+$.

Example 17(84)

2-(2-((2R)-2-(5-methylfuran-2-ylmethylaminomethyl)-5-oxopyrrolidin-1-yl)ethylthio)-1,3-thiazole-4-carboxylic acid HPLC retention time: 2.93 minutes;
MASS data (ESI, Pos. 20 V): 396 (M+H)$^+$.

Example 17(85)

2-(2-((2R)-2-(2-(pyridin-3-yl)ethylaminomethyl)-5-oxopyrrolidin-1-yl)ethylthio)-1,3-thiazole-4-carboxylic acid HPLC retention time: 2.67 minutes;
MASS data (ESI, Pos. 20 V): 407 (M+H)$^+$.

Example 17(86)

2-(2-((2R)-2-((2R)-2-phenylpropylaminomethyl)-5-oxopyrrolidin-1-yl)ethylthio)-1,3-thiazole-4-carboxylic acid HPLC retention time: 3.02 minutes;
MASS data (ESI, Pos. 20 V): 420 (M+H)$^+$.

Example 17(87)

2-(2-((2R)-2-(pyrazol-3-ylaminomethyl)-5-oxopyrrolidin-1-yl)ethylthio)-1,3-thiazole-4-carboxylic acid HPLC retention time: 2.81 minutes;
MASS data (ESI, Pos. 20 V): 368 (M+H)$^+$.

Example 17(88)

2-(2-((2R)-2-(1,2,3,6-tetrahydropyridin-1-ylmethyl)-5-oxopyrrolidin-1-yl)ethylthio)-1,3-thiazole-4-carboxylic acid HPLC retention time: 2.76 minutes;
MASS data (ESI, Pos. 20 V): 368 (M+H)$^+$.

Example 17(89)

2-(2-((2R)-2-(2-fluorobenzylaminomethyl)-5-oxopyrrolidin-1-yl)ethylthio)-1,3-thiazole-4-carboxylic acid HPLC retention time: 2.93 minutes;
MASS data (ESI, Pos. 20 V): 410 (M+H)$^+$.

Example 17(90)

2-(2-((2R)-2-(3-fluorobenzylaminomethyl)-5-oxopyrrolidin-1-yl)ethylthio)-1,3-thiazole-4-carboxylic acid HPLC retention time: 2.96 minutes;
MASS data (ESI, Pos. 20 V): 410 (M+H)$^+$.

Example 17(91)

2-(2-((2R)-2-(2-phenylpropylaminomethyl)-5-oxopyrrolidin-1-yl)ethylthio)-1,3-thiazole-4-carboxylic acid HPLC retention time: 3.03 minutes;
MASS data (ESI, Pos. 20 V): 420 (M+H)$^+$.

Example 17(92)

2-(2-((2R)-2-(2,5-difluorobenzylaminomethyl)-5-oxopyrrolidin-1-yl)ethylthio)-1,3-thiazole-4-carboxylic acid HPLC retention time: 2.96 minutes;
MASS data (ESI, Pos. 20 V): 428 (M+H)$^+$.

Example 17(93)

2-(2-((2R)-2-(1-ethylpyrazol-5-ylaminomethyl)-5-oxopyrrolidin-1-yl)ethylthio)-1,3-thiazole-4-carboxylic acid HPLC retention time: 2.80 minutes;
MASS data (ESI, Pos. 20 V): 396 (M+H)$^+$.

Example 17(94)

2-(2-((2R)-2-(2-ethylthioethylaminomethyl)-5-oxopyrrolidin-1-yl)ethylthio)-1,3-thiazole-4-carboxylic acid HPLC retention time: 2.90 minutes;
MASS data (ESI, Pos. 20 V): 390 (M+H)$^+$.

Example 17(95)

2-(2-((2R)-2-(N-(3-dimethylaminopropyl)-N-methylaminomethyl)-5-oxopyrrolidin-1-yl)ethylthio)-1,3-thiazole-4-carboxylic acid HPLC retention time: 2.63 minutes;
MASS data (ESI, Pos. 20 V): 401 (M+H)$^+$.

Example 17(96)

2-(2-((2R)-2-(2-(2-fluorophenyl)ethylaminomethyl)-5-oxopyrrolidin-1-yl)ethylthio)-1,3-thiazole-4-carboxylic acid HPLC retention time: 3.02 minutes;
MASS data (ESI, Pos. 20 V): 424 (M+H)$^+$.

Example 17(97)

2-(2-((2R)-2-cyclooctylaminomethyl-5-oxopyrrolidin-1-yl)ethylthio)-1,3-thiazole-4-carboxylic acid HPLC retention time: 3.06 minutes;
MASS data (ESI, Pos. 20 V): 412 (M+H)$^+$.

Example 17(98)

2-(2-((2R)-2-(3-pyrrolin-1-ylmethyl)-5-oxopyrrolidin-1-yl)ethylthio)-1,3-thiazole-4-carboxylic acid HPLC retention time: 2.73 minutes;
MASS data (ESI, Pos. 20 V): 354 (M+H)$^+$.

Example 17(99)

2-(2-((2R)-2-(2-methylpiperidin-1-ylmethyl)-5-oxopyrrolidin-1-yl)ethylthio)-1,3-thiazole-4-carboxylic acid HPLC retention time: 2.79 minutes;
MASS data (ESI, Pos. 20 V): 384 (M+H)$^+$.

Example 17(100)

2-(2-((2R)-2-(3-methylpiperidin-1-ylmethyl)-5-oxopyrrolidin-1-yl)ethylthio)-1,3-thiazole-4-carboxylic acid HPLC retention time: 2.86 minutes;
MASS data (ESI, Pos. 20 V): 384 (M+H)$^+$.

Example 17(101)

2-(2-((2R)-2-(4-methylpiperidin-1-ylmethyl)-5-oxopyrrolidin-1-yl)ethylthio)-1,3-thiazole-4-carboxylic acid HPLC retention time: 2.86 minutes;
MASS data (ESI, Pos. 20 V): 384 (M+H)$^+$.

Example 17(102)

2-(2-((2R)-2-(3-(morpholin-4-yl)propylaminomethyl)-5-oxopyrrolidin-1-yl)ethylthio)-1,3-thiazole-4-carboxylic acid HPLC retention time: 2.67 minutes;
MASS data (ESI, Pos. 20 V): 429 (M+H)$^+$.

Example 17(103)

2-(2-((2R)-2-(azepan-1-ylmethyl)-5-oxopyrrolidin-1-yl)ethylthio)-1,3-thiazole-4-carboxylic acid HPLC retention time: 2.84 minutes;
MASS data (ESI, Pos. 20 V): 384 (M+H)$^+$.

Example 17(104)

2-(2-((2R)-2-(1,1,3,3-tetramethylbutylaminomethyl)-5-oxopyrrolidin-1-yl)ethylthio)-1,3-thiazole-4-carboxylic acid HPLC retention time: 3.06 minutes;
MASS data (ESI, Pos. 20 V): 414 (M+H)$^+$.

Example 17(105)

2-(2-((2R)-2-(1,1-dimethylpropylaminomethyl)-5-oxopyrrolidin-1-yl)ethylthio)-1,3-thiazole-4-carboxylic acid HPLC retention time: 2.85 minutes;
MASS data (ESI, Pos. 20 V): 372 (M+H)$^+$.

Example 17(106)

2-(2-((2R)-2-(1-methyl-3-phenylpropylaminomethyl)-5-oxopyrrolidin-1-yl)ethylthio)-1,3-thiazole-4-carboxylic acid HPLC retention time: 3.10 minutes;
MASS data (ESI, Pos. 20 V): 434 (M+H)$^+$.

Example 17(107)

2-(2-((2R)-2-(1,5-dimethylhexylaminomethyl)-5-oxopyrrolidin-1-yl)ethylthio)-1,3-thiazole-4-carboxylic acid HPLC retention time: 3.18 minutes;
MASS data (ESI, Pos. 20 V): 414 (M+H)$^+$.

Example 17(108)

2-(2-((2R)-2-(1-methylhexylaminomethyl)-5-oxopyrrolidin-1-yl)ethylthio)-1,3-thiazole-4-carboxylic acid HPLC retention time: 3.09 minutes;
MASS data (ESI, Pos. 20 V): 400 (M+H)$^+$.

Example 17(109)

2-(2-((2R)-2-(1-methylheptylaminomethyl)-5-oxopyrrolidin-1-yl)ethylthio)-1,3-thiazole-4-carboxylic acid HPLC retention time: 3.20 minutes;
MASS data (ESI, Pos. 20 V): 414 (M+H)$^+$.

Example 17(110)

2-(2-((2R)-2-(2-chlorobenzylaminomethyl)-5-oxopyrrolidin-1-yl)ethylthio)-1,3-thiazole-4-carboxylic acid HPLC retention time: 2.96 minutes;
MASS data (ESI, Pos. 20 V): 426 (M+H)$^+$.

Example 17(111)

2-(2-((2R)-2-(4-fluorobenzylaminomethyl)-5-oxopyrrolidin-1-yl)ethylthio)-1,3-thiazole-4-carboxylic acid HPLC retention time: 2.98 minutes;
MASS data (ESI, Pos. 20 V): 410 (M+H)$^+$.

Example 17(112)

2-(2-((2R)-2-(2-ethylhexylaminomethyl)-5-oxopyrrolidin-1-yl)ethylthio)-1,3-thiazole-4-carboxylic acid HPLC retention time: 3.18 minutes;
MASS data (ESI, Pos. 20 V): 414 (M+H)$^+$.

Example 17(113)

2-(2-((2R)-2-(2-dimethylaminoethylaminomethyl)-5-oxopyrrolidin-1-yl)ethylthio)-1,3-thiazole-4-carboxylic acid HPLC retention time: 2.65 minutes;
MASS data (ESI, Pos. 20 V): 373 (M+H)$^+$.

Example 17(114)

2-(2-((2R)-2-(2-propynylaminomethyl)-5-oxopyrrolidin-1-yl)ethylthio)-1,3-thiazole-4-carboxylic acid HPLC retention time: 2.74 minutes;
MASS data (ESI, Pos. 20 V): 340 (M+H)$^+$.

Example 17(115)

2-(2-((2R)-2-(2-propenylaminomethyl)-5-oxopyrrolidin-1-yl)ethylthio)-1,3-thiazole-4-carboxylic acid HPLC retention time: 2.76 minutes;
MASS data (ESI, Pos. 20 V): 342 (M+H)$^+$.

Example 17(116)

2-(2-((2R)-2-(3-methylbutylaminomethyl)-5-oxopyrrolidin-1-yl)ethylthio)-1,3-thiazole-4-carboxylic acid HPLC retention time: 2.95 minutes;
MASS data (ESI, Pos. 20 V): 372 (M+H)$^+$.

Example 17(117)

2-(2-((2R)-2-(3-dimethylaminopropylaminomethyl)-5-oxopyrrolidin-1-yl)ethylthio)-1,3-thiazole-4-carboxylic acid HPLC retention time: 2.64 minutes;
MASS data (ESI, Pos. 20 V): 387 (M+H)$^+$.

Example 17(118)

2-(2-((2R)-2-(3-ethoxypropylaminomethyl)-5-oxopyrrolidin-1-yl)ethylthio)-1,3-thiazole-4-carboxylic acid HPLC retention time: 2.86 minutes;
MASS data (ESI, Pos. 20 V): 388 (M+H)$^+$.

Example 17(119)

2-(2-((2R)-2-octylaminomethyl-5-oxopyrrolidin-1-yl)ethylthio)-1,3-thiazole-4-carboxylic acid HPLC retention time: 3.25 minutes;
MASS data (ESI, Pos. 20 V): 414 (M+H)$^+$.

Example 17(120)

2-(2-((2R)-2-nonylaminomethyl-5-oxopyrrolidin-1-yl)ethylthio)-1,3-thiazole-4-carboxylic acid HPLC retention time: 3.34 minutes;
MASS data (ESI, Pos. 20 V): 428 (M+H)$^+$.

Example 17(121)

2-(2-((2R)-2-(2,6-difluorobenzylaminomethyl)-5-oxopyrrolidin-1-yl)ethylthio)-1,3-thiazole-4-carboxylic acid HPLC retention time: 2.93 minutes;
MASS data (ESI, Pos. 20 V): 428 (M+H)$^+$.

Example 17(122)

2-(2-((2R)-2-(3-methoxypropylaminomethyl)-5-oxopyrrolidin-1-yl)ethylthio)-1,3-thiazole-4-carboxylic acid HPLC retention time: 2.81 minutes;
MASS data (ESI, Pos. 20 V): 374 (M+H)$^+$.

Example 17(123)

2-(2-((2R)-2-(3-butoxypropylaminomethyl)-5-oxopyrrolidin-1-yl)ethylthio)-1,3-thiazole-4-carboxylic acid HPLC retention time: 3.05 minutes;
MASS data (ESI, Pos. 20 V): 416 (M+H)$^+$.

Example 17(124)

2-(2-((2R)-2-(N,N-bis(2-methoxyethyl)aminomethyl)-5-oxopyrrolidin-1-yl)ethylthio)-1,3-thiazole-4-carboxylic acid HPLC retention time: 2.83 minutes;
MASS data (ESI, Pos. 20 V): 418 (M+H)$^+$.

Example 17(125)

2-(2-((2R)-2-(3-chlorobenzylaminomethyl)-5-oxopyrrolidin-1-yl)ethylthio)-1,3-thiazole-4-carboxylic acid HPLC retention time: 3.03 minutes;
MASS data (ESI, Pos. 20 V): 426 (M+H)$^+$.

Example 17(126)

2-(2-((2R)-2-(3-dimethylamino-2,2-dimethylpropylaminomethyl)-5-oxopyrrolidin-1-yl)ethylthio)-1,3-thiazole-4-carboxylic acid HPLC retention time: 2.69 minutes;
MASS data (ESI, Pos. 20 V): 415 (M+H)$^+$.

Example 17(127)

2-(2-((2R)-2-(4-methyl-1,4-diazepan-1-ylmethyl)-5-oxopyrrolidin-1-yl)ethylthio)-1,3-thiazole-4-carboxylic acid HPLC retention time: 2.66 minutes;
MASS data (ESI, Pos. 20 V): 399 (M+H)$^+$.

Example 17(128)

2-(2-((2R)-2-(4-ethylpiperazin-1-ylmethyl)-5-oxopyrrolidin-1-yl)ethylthio)-1,3-thiazole-4-carboxylic acid HPLC retention time: 2.75 minutes;
MASS data (ESI, Pos. 20 V): 399 (M+H)$^+$.

Example 17(129)

2-(2-((2R)-2-((1S)-1-cyclohexylethylaminomethyl)-5-oxopyrrolidin-1-yl)ethylthio)-1,3-thiazole-4-carboxylic acid HPLC retention time: 3.06 minutes;
MASS data (ESI, Pos. 20 V): 412 (M+H)$^+$.

Example 17(130)

2-(2-((2R)-2-(5-methylpyrazol-3-ylaminomethyl)-5-oxopyrrolidin-1-yl)ethylthio)-1,3-thiazole-4-carboxylic acid HPLC retention time: 2.85 minutes;
MASS data (ESI, Pos. 20 V): 382 (M+H)$^+$.

Example 17(131)

2-(2-((2R)-2-((1R)-1-(4-methylphenyl)ethylaminomethyl)-5-oxopyrrolidin-1-yl)ethylthio)-1,3-thiazole-4-carboxylic acid HPLC retention time: 3.04 minutes;
MASS data (ESI, Pos. 20 V): 420 (M+H)$^+$.

Example 17(132)

2-(2-((2R)-2-(1-ethynylcyclohexylaminomethyl)-5-oxopyrrolidin-1-yl)ethylthio)-1,3-thiazole-4-carboxylic acid HPLC retention time: 2.96 minutes;
MASS data (ESI, Pos. 20 V): 408 (M+H)$^+$.

Example 17(133)

2-(2-((2R)-2-(2,6-dimethylmorpholin-4-ylmethyl)-5-oxopyrrolidin-1-yl)ethylthio)-1,3-thiazole-4-carboxylic acid HPLC retention time: 2.81 minutes;
MASS data (ESI, Pos. 20 V): 400 (M+H)$^+$.

Example 17(134)

2-(2-((2R)-2-(N-methyl-N-(2-(pyridin-2-yl)ethyl)aminomethyl)-5-oxopyrrolidin-1-yl)ethylthio)-1,3-thiazole-4-carboxylic acid HPLC retention time: 2.73 minutes;
MASS data (ESI, Pos. 20 V): 421 (M+H)$^+$.

Example 17(135)

2-(2-((2R)-2-(N-methyl-N-(1-methylpiperidin-4-yl)aminomethyl)-5-oxopyrrolidin-1-yl)ethylthio)-1,3-thiazole-4-carboxylic acid HPLC retention time: 2.61 minutes;
MASS data (ESI, Pos. 20 V): 413 (M+H)$^+$.

Example 17(136)

2-(2-((2R)-2-(1,1-diethyl-2-propynylaminomethyl)-5-oxopyrrolidin-1-yl)ethylthio)-1,3-thiazole-4-carboxylic acid HPLC retention time: 2.91 minutes;
MASS data (ESI, Pos. 20 V): 396 (M+H)$^+$.

Example 17(137)

2-(2-((2R)-2-(N-ethyl-N-methylaminomethyl)-5-oxopyrrolidin-1-yl)ethylthio)-1,3-thiazole-4-carboxylic acid HPLC retention time: 2.71 minutes;
MASS data (ESI, Pos. 20 V): 344 (M+H)$^+$.

Example 17(138)

2-(2-((2R)-2-(N-ethyl-N-(2-methyl-2-propenyl)aminomethyl)-5-oxopyrrolidin-1-yl)ethylthio)-1,3-thiazole-4-carboxylic acid HPLC retention time: 2.78 minutes;
MASS data (ESI, Pos. 20 V): 384 (M+H)$^+$.

Example 17(139)

2-(2-((2R)-2-(1-(4-fluorophenyl)ethylaminomethyl)-5-oxopyrrolidin-1-yl)ethylthio)-1,3-thiazole-4-carboxylic acid HPLC retention time: 3.01 minutes;
MASS data (ESI, Pos. 20 V): 424 (M+H)$^+$.

Example 17(140)

2-(2-((2R)-2-((1R,2R,4S)-bicyclo[2.2.1]hept-2-ylaminomethyl)-5-oxopyrrolidin-1-yl)ethylthio)-1,3-thiazole-4-carboxylic acid HPLC retention time: 2.95 minutes;
MASS data (ESI, Pos. 20 V): 396 (M+H)$^+$.

Example 17(141)

2-(2-((2R)-2-((2S)-2-methoxymethylpyrrolidin-1-ylaminomethyl)-5-oxopyrrolidin-1-yl)ethylthio)-1,3-thiazole-4-carboxylic acid HPLC retention time: 2.83 minutes;
MASS data (ESI, Pos. 20 V): 400 (M+H)$^+$.

Example 17(142)

2-(2-((2R)-2-(1,2,4-triazol-4-ylaminomethyl)-5-oxopyrrolidin-1-yl)ethylthio)-1,3-thiazole-4-carboxylic acid HPLC retention time: 2.79 minutes;
MASS data (ESI, Pos. 20 V): 369 (M+H)$^+$.

Example 17(143)

2-(2-((2R)-2-(1-methylbenzimidazol-2-ylaminomethyl)-5-oxopyrrolidin-1-yl)ethylthio)-1,3-thiazole-4-carboxylic acid HPLC retention time: 2.93 minutes;
MASS data (ESI, Pos. 20 V): 432 (M+H)$^+$.

Example 17(144)

2-(2-((2R)-5-oxo-2-(5-phenylpyrazol-3-ylaminomethyl)pyrrolidin-1-yl)ethylthio)-1,3-thiazole-4-carboxylic acid HPLC retention time: 3.03 minutes;
MASS data (ESI, Pos. 20 V): 444 (M+H)$^+$.

Example 17(145)

2-(2-((2R)-5-oxo-2-(thiophene-2-ylmethylaminomethyl)pyrrolidin-1-yl)ethylthio)-1,3-thiazole-4-carboxylic acid HPLC retention time: 2.89 minutes;
MASS data (ESI, Pos. 20 V): 398 (M+H)$^+$.

Example 17(146)

2-(2-((2R)-2-(2-(4-aminosulfonylphenyl)ethylaminomethyl)-5-oxopyrrolidin-1-yl)ethylthio)-1,3-thiazole-4-carboxylic acid HPLC retention time: 2.85 minutes;
MASS data (ESI, Pos. 20 V): 485 (M+H)$^+$.

Example 17(147)

2-(2-((2R)-2-(adamantan-1-ylmethyl)amino)methyl)-5-oxopyrrolidin-1-yl)ethylthio)-1,3-thiazole-4-carboxylic acid HPLC retention time: 3.18 minutes;
MASS data (ESI, Pos. 20 V): 450 (M+H)$^+$.

Example 17(148)

2-(2-((2R)-2-(4-aminosulfonylbenzylaminomethyl)-5-oxopyrrolidin-1-yl)ethylthio)-1,3-thiazole-4-carboxylic acid HPLC retention time: 2.83 minutes;
MASS data (ESI, Pos. 20 V): 471 (M+H)$^+$.

Example 17(149)

2-(2-((2R)-2-(6,7-dimethoxy-1,2,3,4-tetrahydroisoquinolin-2-ylmethyl)-5-oxopyrrolidin-1-yl)ethylthio)-1,3-thiazole-4-carboxylic acid HPLC retention time: 2.93 minutes;
MASS data (ESI, Pos. 20 V): 478 (M+H)$^+$.

Example 17(150)

2-(2-((2R)-2-(6,7-hydroxy-1-methyl-1,2,3,4-tetrahydroisoquinolin-2-ylmethyl)-5-oxopyrrolidin-1-yl)ethylthio)-1,3-thiazole-4-carboxylic acid HPLC retention time: 2.81 minutes;
MASS data (ESI, Pos. 20 V): 464 (M+H)$^+$.

Example 17(151)

2-(2-((2R)-2-(2-(3,4-dihydroxyphenyl)ethylaminomethyl)-5-oxopyrrolidin-1-yl)ethylthio)-1,3-thiazole-4-carboxylic acid HPLC retention time: 2.83 minutes;
MASS data (ESI, Pos. 20 V): 438 (M+H)$^+$.

Example 17(152)

2-(2-((2R)-5-oxo-2-(2,2,2-trifluoroethylaminomethyl)pyrrolidin-1-yl)ethylthio)-1,3-thiazole-4-carboxylic acid HPLC retention time: 2.89 minutes;
MASS data (ESI, Pos. 20 V): 384 (M+H)$^+$.

Example 17(153)

2-(2-((2R)-2-(3-methylbenzylaminomethyl)-5-oxopyrrolidin-1-yl)ethylthio)-1,3-thiazole-4-carboxylic acid HPLC retention time: 3.01 minutes;
MASS data (ESI, Pos. 20 V): 406 (M+H)$^+$.

Example 17(154)

2-(2-((2R)-2-(1,4'-bipiperidin-1'-ylmethyl)-5-oxopyrrolidin-1-yl)ethylthio)-1,3-thiazole-4-carboxylic acid HPLC retention time: 2.73 minutes;
MASS data (ESI, Pos. 20 V): 453 (M+H)$^+$.

Example 17(155)

2-(2-((2R)-2-(4-(1,3-benzodioxol-5-ylmethyl)piperazin-1-ylmethyl)-5-oxopyrrolidin-1-yl)ethylthio)-1,3-thiazole-4-carboxylic acid HPLC retention time: 2.96 minutes;
MASS data (ESI, Pos. 20 V): 505 (M+H)$^+$.

Example 17(156)

2-(2-((2R)-5-oxo-2-(4-(3-trifluoromethylphenyl)piperazin-1-ylmethyl)pyrrolidin-1-yl)ethylthio)-1,3-thiazole-4-carboxylic acid HPLC retention time: 3.22 minutes;
MASS data (ESI, Pos. 20 V): 515 (M+H)+.

Example 17(157)

2-(2-((2R)-2-(4-(4-methoxyphenyl)piperazin-1-ylmethyl)-5-oxopyrrolidin-1-yl)ethylthio)-1,3-thiazole-4-carboxylic acid HPLC retention time: 3.01 minutes;
MASS data (ESI, Pos. 20 V): 477 (M+H)+.

Example 17(158)

2-(2-((2R)-5-oxo-2-(4-(4-trifluoromethylphenyl)piperazin-1-ylmethyl)pyrrolidin-1-yl)ethylthio)-1,3-thiazole-4-carboxylic acid HPLC retention time: 3.23 minutes;
MASS data (ESI, Pos. 20 V): 515 (M+H)+.

Example 17(159)

2-(2-((2R)-2-(N-methyl-N-(4-(pyridin-3-yl)butyl)aminomethyl)-5-oxopyrrolidin-1-yl)ethylthio)-1,3-thiazole-4-carboxylic acid HPLC retention time: 2.75 minutes;
MASS data (ESI, Pos. 20 V): 449 (M+H)+.

Example 17(160)

2-(2-((2R)-2-(N-methyl-N-(2-(pyridin-4-yl)ethyl)aminomethyl)-5-oxopyrrolidin-1-yl)ethylthio)-1,3-thiazole-4-carboxylic acid HPLC retention time: 2.68 minutes;
MASS data (ESI, Pos. 20 V): 421 (M+H)+.

Example 17(161)

2-(2-((2R)-2-(N-methyl-N-(pyridin-3-ylmethyl)aminomethyl)-5-oxopyrrolidin-1-yl)ethylthio)-1,3-thiazole-4-carboxylic acid HPLC retention time: 2.73 minutes;
MASS data (ESI, Pos. 20 V): 407 (M+H)+.

Example 17(162)

2-(2-((2R)-2-(N-methyl-N-(6-methylpyridin-2-ylmethyl)aminomethyl)-5-oxopyrrolidin-1-yl)ethylthio)-1,3-thiazole-4-carboxylic acid HPLC retention time: 2.91 minutes;
MASS data (ESI, Pos. 20 V): 421 (M+H)+.

Example 17(163)

2-(2-((2R)-2-(4-cyclohexylpiperazin-1-ylmethyl)-5-oxopyrrolidin-1-yl)ethylthio)-1,3-thiazole-4-carboxylic acid HPLC retention time: 2.91 minutes;
MASS data (ESI, Pos. 20 V): 453 (M+H)+.

Example 17(164)

2-(2-((2R)-2-(4-(3-methoxyphenyl)piperazin-1-ylmethyl)-5-oxopyrrolidin-1-yl)ethylthio)-1,3-thiazole-4-carboxylic acid HPLC retention time: 3.05 minutes;
MASS data (ESI, Pos. 20 V): 477 (M+H)+.

Example 17(165)

2-(2-((2R)-2-(4-(2-methoxyphenyl)piperazin-1-ylmethyl)-5-oxopyrrolidin-1-yl)ethylthio)-1,3-thiazole-4-carboxylic acid HPLC retention time: 3.02 minutes;
MASS data (ESI, Pos. 20 V): 477 (M+H)+.

Example 17(166)

2-(2-((2R)-2-(4-(2,4-dimethoxyphenyl)piperazin-1-ylmethyl)-5-oxopyrrolidin-1-yl)ethylthio)-1,3-thiazole-4-carboxylic acid HPLC retention time: 3.04 minutes;
MASS data (ESI, Pos. 20 V): 507 (M+H)+.

Example 17(167)

2-(2-((2R)-2-(4-(2,4-dimethylphenyl)piperazin-1-ylmethyl)-5-oxopyrrolidin-1-yl)ethylthio)-1,3-thiazole-4-carboxylic acid HPLC retention time: 3.21 minutes;
MASS data (ESI, Pos. 20 V): 475 (M+H)+.

Example 17(168)

2-(2-((2R)-5-oxo-2-(4-((2E)-3-phenyl-2-propenyl)piperazin-1-ylmethyl)pyrrolidin-1-yl)ethylthio)-1,3-thiazole-4-carboxylic acid HPLC retention time: 3.07 minutes;
MASS data (ESI, Pos. 20 V): 487 (M+H)+.

Example 17(169)

2-(2-((2R)-5-oxo-2-(4-(2-oxo-2-pyrrolidin-1-ylethyl)piperazin-1-ylmethyl)pyrrolidin-1-yl)ethylthio)-1,3-thiazole-4-carboxylic acid HPLC retention time: 2.84 minutes;
MASS data (ESI, Pos. 20 V): 482 (M+H)+.

Example 17(170)

2-(2-((2R)-2-(4-ethoxycarbonylpiperazin-1-ylmethyl)-5-oxopyrrolidin-1-yl)ethylthio)-1,3-thiazole-4-carboxylic acid HPLC retention time: 2.89 minutes;
MASS data (ESI, Pos. 20 V): 443 (M+H)$^+$.

Example 17(171)

2-(2-((2R)-5-oxo-2-(4-oxo-1-phenyl-1,3,8-triazaspiro[4.5]decan-8-ylmethyl)pyrrolidin-1-yl)ethylthio)-1,3-thiazole-4-carboxylic acid HPLC retention time: 3.01 minutes;
MASS data (ESI, Pos. 20 V): 516 (M+H)$^+$.

Example 17(172)

2-(2-((2R)-5-oxo-2-(4-(5-trifluoromethylpyridin-2-yl)-1,4-diazepan-1-ylmethyl)pyrrolidin-1-yl)ethylthio)-1,3-thiazole-4-carboxylic acid HPLC retention time: 3.15 minutes;
MASS data (ESI, Pos. 20 V): 530 (M+H)$^+$.

Example 17(173)

2-(2-((2R)-2-(N-(2-(3,4-dimethoxyphenyl)ethyl)-N-methylaminomethyl)-5-oxopyrrolidin-1-yl)ethylthio)-1,3-thiazole-4-carboxylic acid HPLC retention time: 2.98 minutes;
MASS data (ESI, Pos. 20 V): 480 (M+H)$^+$.

Example 17(174)

2-(2-((2R)-2-(N-benzyl-N-(2-cyanoethyl)aminomethyl)-5-oxopyrrolidin-1-yl)ethylthio)-1,3-thiazole-4-carboxylic acid HPLC retention time: 3.18 minutes;
MASS data (ESI, Pos. 20 V): 445 (M+H)$^+$.

Example 17(175)

2-(2-((2R)-2-(N-benzyl-N-(2-dimethylaminoethyl)aminomethyl)-5-oxopyrrolidin-1-yl)ethylthio)-1,3-thiazole-4-carboxylic acid HPLC retention time: 3.03 minutes;
MASS data (ESI, Pos. 20 V): 463 (M+H)$^+$.

Example 17(176)

2-(2-((2R)-2-(N-(furan-2-ylmethyl)-N-methylaminomethyl)-5-oxopyrrolidin-1-yl)ethylthio)-1,3-thiazole-4-carboxylic acid HPLC retention time: 2.88 minutes;
MASS data (ESI, Pos. 20 V): 396 (M+H)$^+$.

Example 17(177)

2-(2-((2R)-2-(N-ethyl-N-(4-hydroxybutyl)aminomethyl)-5-oxopyrrolidin-1-yl)ethylthio)-1,3-thiazole-4-carboxylic acid HPLC retention time: 2.77 minutes;
MASS data (ESI, Pos. 20 V): 402 (M+H)$^+$.

Example 17(178)

2-(2-((2R)-2-(N,N-bis(2-ethoxyethyl)aminomethyl)-5-oxopyrrolidin-1-yl)ethylthio)-1,3-thiazole-4-carboxylic acid HPLC retention time: 3.00 minutes;
MASS data (ESI, Pos. 20 V): 446 (M+H)$^+$.

Example 17(179)

2-(2-((2R)-2-(N-(2-cyanoethyl)-N-ethylaminomethyl)-5-oxopyrrolidin-1-yl)ethylthio)-1,3-thiazole-4-carboxylic acid HPLC retention time: 2.79 minutes;
MASS data (ESI, Pos. 20 V): 383 (M+H)$^+$.

Example 17(180)

2-(2-((2R)-2-(N-(2-methoxyethyl)-N-methylaminomethyl)-5-oxopyrrolidin-1-yl)ethylthio)-1,3-thiazole-4-carboxylic acid HPLC retention time: 2.80 minutes;
MASS data (ESI, Pos. 20 V): 374 (M+H)$^+$.

Example 17(181)

2-(2-((2R)-2-(6-methoxy-1,2,3,4-tetrahydro-β-carbolin-2-ylmethyl)-5-oxopyrrolidin-1-yl)ethylthio)-1,3-thiazole-4-carboxylic acid HPLC retention time: 3.03 minutes;
MASS data (ESI, Pos. 20 V): 487 (M+H)$^+$.

Example 17(182)

2-(2-((2R)-2-(3,4-dihydropyrido[4,3-b]-1,6-naphthylidin-2-ylmethyl)-5-oxopyrrolidin-1-yl)ethylthio)-1,3-thiazole-4-carboxylic acid HPLC retention time: 2.74 minutes;
MASS data (ESI, Pos. 20 V): 470 (M+H)$^+$.

Example 17(183)

2-(2-((2R)-2-phenylaminomethyl-5-oxopyrrolidin-1-yl)ethylthio)-1,3-thiazole-4-carboxylic acid HPLC retention time: 3.20 minutes;
MASS data (ESI, Pos. 20 V): 378 (M+H)$^+$.

Example 17(184)

2-(2-((2R)-2-(2-methoxyphenylaminomethyl)-5-oxopyrrolidin-1-yl)ethylthio)-1,3-thiazole-4-carboxylic acid HPLC retention time: 3.18 minutes;
MASS data (ESI, Pos. 20 V): 408 (M+H)$^+$.

Example 17(185)

2-(2-((2R)-2-(2-methylphenylaminomethyl)-5-oxopyrrolidin-1-yl)ethylthio)-1,3-thiazole-4-carboxylic acid HPLC retention time: 3.35 minutes;
MASS data (ESI, Pos. 20 V): 392 (M+H)$^+$.

Example 17(186)

2-(2-((2R)-2-(2,3-dimethylphenylaminomethyl)-5-oxopyrrolidin-1-yl)ethylthio)-1,3-thiazole-4-carboxylic acid HPLC retention time: 3.34 minutes;
MASS data (ESI, Pos. 20 V): 406 (M+H)$^+$.

Example 17(187)

2-(2-((2R)-2-(2,4-dimethylphenylaminomethyl)-5-oxopyrrolidin-1-yl)ethylthio)-1,3-thiazole-4-carboxylic acid HPLC retention time: 3.33 minutes;
MASS data (ESI, Pos. 20 V): 406 (M+H)$^+$.

Example 17(188)

2-(2-((2R)-2-(2,5-dimethylphenylaminomethyl)-5-oxopyrrolidin-1-yl)ethylthio)-1,3-thiazole-4-carboxylic acid HPLC retention time: 3.43 minutes;
MASS data (ESI, Pos. 20 V): 406 (M+H)$^+$.

Example 17(189)

2-(2-((2R)-2-(2,6-dimethylphenylaminomethyl)-5-oxopyrrolidin-1-yl)ethylthio)-1,3-thiazole-4-carboxylic acid HPLC retention time: 3.13 minutes;
MASS data (ESI, Pos. 20 V): 406 (M+H)$^+$.

Example 17(190)

2-(2-((2R)-2-(3-methoxyphenylaminomethyl)-5-oxopyrrolidin-1-yl)ethylthio)-1,3-thiazole-4-carboxylic acid HPLC retention time: 3.26 minutes;
MASS data (ESI, Pos. 20 V): 408 (M+H)$^+$.

Example 17(191)

2-(2-((2R)-2-(3-methylphenylaminomethyl)-5-oxopyrrolidin-1-yl)ethylthio)-1,3-thiazole-4-carboxylic acid HPLC retention time: 3.26 minutes;
MASS data (ESI, Pos. 20 V): 392 (M+H)$^+$.

Example 17(192)

2-(2-((2R)-2-(3,4-dimethylphenylaminomethyl)-5-oxopyrrolidin-1-yl)ethylthio)-1,3-thiazole-4-carboxylic acid HPLC retention time: 3.19 minutes;
MASS data (ESI, Pos. 20 V): 406 (M+H)$^+$.

Example 17(193)

2-(2-((2R)-2-(4-chlorophenylaminomethyl)-5-oxopyrrolidin-1-yl)ethylthio)-1,3-thiazole-4-carboxylic acid HPLC retention time: 3.46 minutes;
MASS data (ESI, Pos. 20 V): 412 (M+H)$^+$.

Example 17(194)

2-(2-((2R)-2-(4-diethylaminophenylaminomethyl)-5-oxopyrrolidin-1-yl)ethylthio)-1,3-thiazole-4-carboxylic acid HPLC retention time: 2.93 minutes;
MASS data (ESI, Pos. 20 V): 449 (M+H)$^+$.

Example 17(195)

2-(2-((2R)-2-(4-methylthiophenylaminomethyl)-5-oxopyrrolidin-1-yl)ethylthio)-1,3-thiazole-4-carboxylic acid HPLC retention time: 3.38 minutes;
MASS data (ESI, Pos. 20 V): 424 (M+H)$^+$.

Example 17(196)

2-(2-((2R)-2-(4-t-butylphenylaminomethyl)-5-oxopyrrolidin-1-yl)ethylthio)-1,3-thiazole-4-carboxylic acid HPLC retention time: 3.51 minutes;
MASS data (ESI, Pos. 20 V): 434 (M+H)$^+$.

Example 17(197)

2-(2-((2R)-2-(4-isopropylphenylaminomethyl)-5-oxopyrrolidin-1-yl)ethylthio)-1,3-thiazole-4-carboxylic acid HPLC retention time: 3.40 minutes;
MASS data (ESI, Pos. 20 V): 420 (M+H)$^+$.

Example 17(198)

2-(2-((2R)-2-(4-methylphenylaminomethyl)-5-oxopyrrolidin-1-yl)ethylthio)-1,3-thiazole-4-carboxylic acid HPLC retention time: 3.16 minutes;
MASS data (ESI, Pos. 20 V): 392 (M+H)$^+$.

Example 17(199)

2-(2-((2R)-2-(2,4-dimethoxyphenylaminomethyl)-5-oxopyrrolidin-1-yl)ethylthio)-1,3-thiazole-4-carboxylic acid HPLC retention time: 2.98 minutes;
MASS data (ESI, Pos. 20 V): 438 (M+H)$^+$.

Example 17(200)

2-(2-((2R)-2-(3,4-dimethoxyphenylaminomethyl)-5-oxopyrrolidin-1-yl)ethylthio)-1,3-thiazole-4-carboxylic acid HPLC retention time: 2.98 minutes;
MASS data (ESI, Pos. 20 V): 438 (M+H)$^+$.

Example 17(201)

2-(2-((2R)-2-(4-isopropoxyphenylaminomethyl)-5-oxopyrrolidin-1-yl)ethylthio)-1,3-thiazole-4-carboxylic acid HPLC retention time: 3.16 minutes;
MASS data (ESI, Pos. 20 V): 436 (M+H)$^+$.

Example 17(202)

2-(2-((2R)-2-(2-t-butylphenylaminomethyl)-5-oxopyrrolidin-1-yl)ethylthio)-1,3-thiazole-4-carboxylic acid HPLC retention time: 3.71 minutes;
MASS data (ESI, Pos. 20 V): 434 (M+H)$^+$.

Example 17(203)

2-(2-((2R)-2-(2-fluoro-5-methylphenylaminomethyl)-5-oxopyrrolidin-1-yl)ethylthio)-1,3-thiazole-4-carboxylic acid HPLC retention time: 3.46 minutes;
MASS data (ESI, Pos. 20 V): 410 (M+H)$^+$.

Example 17(204)

2-(2-((2R)-2-(2-chloro-6-methylphenylaminomethyl)-5-oxopyrrolidin-1-yl)ethylthio)-1,3-thiazole-4-carboxylic acid HPLC retention time: 3.48 minutes;
MASS data (ESI, Pos. 20 V): 426 (M+H)$^+$.

Example 17(205)

2-(2-((2R)-2-(4-methoxy-2-methylphenylaminomethyl)-5-oxopyrrolidin-1-yl)ethylthio)-1,3-thiazole-4-carboxylic acid HPLC retention time: 3.09 minutes;
MASS data (ESI, Pos. 20 V): 422 (M+H)$^+$.

Example 17(206)

2-(2-((2R)-2-(3,5-difluorophenylaminomethyl)-5-oxopyrrolidin-1-yl)ethylthio)-1,3-thiazole-4-carboxylic acid HPLC retention time: 3.46 minutes;
MASS data (ESI, Pos. 20 V): 414 (M+H)$^+$.

Example 17(207)

2-(2-((2R)-2-(3-ethoxyphenylaminomethyl)-5-oxopyrrolidin-1-yl)ethylthio)-1,3-thiazole-4-carboxylic acid HPLC retention time: 3.36 minutes;
MASS data (ESI, Pos. 20 V): 422 (M+H)$^+$.

Example 17(208)

2-(2-((2R)-2-(3-(1-hydroxyethyl)phenylaminomethyl)-5-oxopyrrolidin-1-yl)ethylthio)-1,3-thiazole-4-carboxylic acid HPLC retention time: 3.05 minutes;
MASS data (ESI, Pos. 20 V): 422, 404 (M+H)$^+$.

Example 17(209)

2-(2-((2R)-2-(3-hydroxymethylphenylaminomethyl)-5-oxopyrrolidin-1-yl)ethylthio)-1,3-thiazole-4-carboxylic acid HPLC retention time: 3.00 minutes;
MASS data (ESI, Pos. 20 V): 408 (M+H)$^+$.

Example 17(210)

2-(2-((2R)-2-(4-fluoro-2-methylphenylaminomethyl)-5-oxopyrrolidin-1-yl)ethylthio)-1,3-thiazole-4-carboxylic acid HPLC retention time: 3.41 minutes;
MASS data (ESI, Pos. 20 V): 410 (M+H)$^+$.

Example 17(211)

2-(2-((2R)-2-(4-cyanomethylphenylaminomethyl)-5-oxopyrrolidin-1-yl)ethylthio)-1,3-thiazole-4-carboxylic acid HPLC retention time: 3.21 minutes;
MASS data (ESI, Pos. 20 V): 417 (M+H)$^+$.

Example 17(212)

2-(2-((2R)-2-(3-hydroxymethyl-2-methylphenylaminomethyl)-5-oxopyrrolidin-1-yl)ethylthio)-1,3-thiazole-4-carboxylic acid HPLC retention time: 3.05 minutes;
MASS data (ESI, Pos. 20 V): 422 (M+H)$^+$.

Example 17(213)

2-(2-((2R)-2-(5-methoxy-2-methylphenylaminomethyl)-5-oxopyrrolidin-1-yl)ethylthio)-1,3-thiazole-4-carboxylic acid HPLC retention time: 3.37 minutes;
MASS data (ESI, Pos. 20 V): 422 (M+H)$^+$.

Example 17(214)

2-(2-((2R)-2-(2-methoxy-6-methylphenylaminomethyl)-5-oxopyrrolidin-1-yl)ethylthio)-1,3-thiazole-4-carboxylic acid HPLC retention time: 3.00 minutes;
MASS data (ESI, Pos. 20 V): 422 (M+H)$^+$.

Example 17(215)

2-(2-((2R)-2-(2-cyanomethylphenylaminomethyl)-5-oxopyrrolidin-1-yl)ethylthio)-1,3-thiazole-4-carboxylic acid HPLC retention time: 3.33 minutes;
MASS data (ESI, Pos. 20 V): 417 (M+H)$^+$.

Example 17(216)

2-(2-((2R)-5-oxo-2-(5,6,7,8-tetrahydronaphthalen-1-ylaminomethyl)pyrrolidin-1-yl)ethylthio)-1,3-thiazole-4-carboxylic acid HPLC retention time: 3.58 minutes;
MASS data (ESI, Pos. 20 V): 432 (M+H)$^+$.

Example 17(217)

2-(2-((2R)-2-(indan-5-ylaminomethyl)-5-oxopyrrolidin-1-yl)ethylthio)-1,3-thiazole-4-carboxylic acid HPLC retention time: 3.23 minutes;
MASS data (ESI, Pos. 20 V): 418 (M+H)$^+$.

Example 17(218)

2-(2-((2R)-2-(1,3-benzodioxol-5-ylaminomethyl)-5-oxopyrrolidin-1-yl)ethylthio)-1,3-thiazole-4-carboxylic acid HPLC retention time: 3.07 minutes;
MASS data (ESI, Pos. 20 V): 422 (M+H)$^+$.

Example 17(219)

2-(2-((2R)-5-oxo-2-(quinolin-5-ylaminomethyl)pyrrolidin-1-yl)ethylthio)-1,3-thiazole-4-carboxylic acid HPLC retention time: 2.91 minutes;
MASS data (ESI, Pos. 20 V): 429 (M+H)$^+$.

Example 17(220)

2-(2-((2R)-5-oxo-2-(quinolin-6-ylaminomethyl)pyrrolidin-1-yl)ethylthio)-1,3-thiazole-4-carboxylic acid HPLC retention time: 2.89 minutes;
MASS data (ESI, Pos. 20 V): 429 (M+H)$^+$.

Example 17(221)

2-(2-((2R)-5-oxo-2-(quinolin-8-ylaminomethyl)pyrrolidin-1-yl)ethylthio)-1,3-thiazole-4-carboxylic acid HPLC retention time: 3.08 minutes;
MASS data (ESI, Pos. 20 V): 429 (M+H)$^+$.

Example 17(222)

2-(2-((2R)-2-(2-cyanophenylaminomethyl)-5-oxopyrrolidin-1-yl)ethylthio)-1,3-thiazole-4-carboxylic acid HPLC retention time: 3.31 minutes;
MASS data (ESI, Pos. 20 V): 403 (M+H)$^+$.

Example 17(223)

2-(2-((2R)-2-(2-fluorophenylaminomethyl)-5-oxopyrrolidin-1-yl)ethylthio)-1,3-thiazole-4-carboxylic acid HPLC retention time: 3.37 minutes;
MASS data (ESI, Pos. 20 V): 396 (M+H)$^+$.

Example 17(224)

2-(2-((2R)-2-(2,4-difluorophenylaminomethyl)-5-oxopyrrolidin-1-yl)ethylthio)-1,3-thiazole-4-carboxylic acid HPLC retention time: 3.41 minutes;
MASS data (ESI, Pos. 20 V): 414 (M+H)$^+$.

Example 17(225)

2-(2-((2R)-5-oxo-2-(2,4,5-trifluorophenylaminomethyl)pyrrolidin-1-yl)ethylthio)-1,3-thiazole-4-carboxylic acid HPLC retention time: 3.44 minutes;
MASS data (ESI, Pos. 20 V): 432 (M+H)$^+$.

Example 17(226)

2-(2-((2R)-5-oxo-2-(2,4,6-trifluorophenylaminomethyl)pyrrolidin-1-yl)ethylthio)-1,3-thiazole-4-carboxylic acid HPLC retention time: 3.43 minutes;
MASS data (ESI, Pos. 20 V): 432 (M+H)+.

Example 17(227)

2-(2-((2R)-2-(2,5-difluorophenylaminomethyl)-5-oxopyrrolidin-1-yl)ethylthio)-1,3-thiazole-4-carboxylic acid HPLC retention time: 3.41 minutes;
MASS data (ESI, Pos. 20 V): 414 (M+H)+.

Example 17(228)

2-(2-((2R)-2-(2,6-difluorophenylaminomethyl)-5-oxopyrrolidin-1-yl)ethylthio)-1,3-thiazole-4-carboxylic acid HPLC retention time: 3.38 minutes;
MASS data (ESI, Pos. 20 V): 414 (M+H)+.

Example 17(229)

2-(2-((2R)-2-(2-chlorophenylaminomethyl)-5-oxopyrrolidin-1-yl)ethylthio)-1,3-thiazole-4-carboxylic acid HPLC retention time: 3.46 minutes;
MASS data (ESI, Pos. 20 V): 412 (M+H)+.

Example 17(230)

2-(2-((2R)-2-(2-ethoxyphenylaminomethyl)-5-oxopyrrolidin-1-yl)ethylthio)-1,3-thiazole-4-carboxylic acid HPLC retention time: 3.28 minutes;
MASS data (ESI, Pos. 20 V): 422 (M+H)+.

Example 17(231)

2-(2-((2R)-2-(2-methylthiophenylaminomethyl)-5-oxopyrrolidin-1-yl)ethylthio)-1,3-thiazole-4-carboxylic acid HPLC retention time: 3.50 minutes;
MASS data (ESI, Pos. 20 V): 424 (M+H)+.

Example 17(232)

2-(2-((2R)-2-(2-isopropylphenylaminomethyl)-5-oxopyrrolidin-1-yl)ethylthio)-1,3-thiazole-4-carboxylic acid HPLC retention time: 3.55 minutes;
MASS data (ESI, Pos. 20 V): 420 (M+H)+.

Example 17(233)

2-(2-((2R)-2-(2,4,6-trimethylphenylaminomethyl)-5-oxopyrrolidin-1-yl)ethylthio)-1,3-thiazole-4-carboxylic acid HPLC retention time: 3.15 minutes;
MASS data (ESI, Pos. 20 V): 420 (M+H)+.

Example 17(234)

2-(2-((2R)-2-(2-isopropyl-6-methylphenylaminomethyl)-5-oxopyrrolidin-1-yl)ethylthio)-1,3-thiazole-4-carboxylic acid HPLC retention time: 3.35 minutes;
MASS data (ESI, Pos. 20 V): 434 (M+H)+.

Example 17(235)

2-(2-((2R)-2-(2-ethylphenylaminomethyl)-5-oxopyrrolidin-1-yl)ethylthio)-1,3-thiazole-4-carboxylic acid HPLC retention time: 3.48 minutes;
MASS data (ESI, Pos. 20 V): 406 (M+H)+.

Example 17(236)

2-(2-((2R)-2-(2-ethyl-6-methylphenylaminomethyl)-5-oxopyrrolidin-1-yl)ethylthio)-1,3-thiazole-4-carboxylic acid HPLC retention time: 3.27 minutes;
MASS data (ESI, Pos. 20 V): 420 (M+H)+.

Example 17(237)

2-(2-((2R)-2-(2,6-diethylphenylaminomethyl)-5-oxopyrrolidin-1-yl)ethylthio)-1,3-thiazole-4-carboxylic acid HPLC retention time: 3.40 minutes;
MASS data (ESI, Pos. 20 V): 434 (M+H)+.

Example 17(238)

2-(2-((2R)-2-(3-cyanophenylaminomethyl)-5-oxopyrrolidin-1-yl)ethylthio)-1,3-thiazole-4-carboxylic acid HPLC retention time: 3.31 minutes;
MASS data (ESI, Pos. 20 V): 403 (M+H)+.

Example 17(239)

2-(2-((2R)-2-(3-fluorophenylaminomethyl)-5-oxopyrrolidin-1-yl)ethylthio)-1,3-thiazole-4-carboxylic acid HPLC retention time: 3.38 minutes;
MASS data (ESI, Pos. 20 V): 396 (M+H)+.

Example 17(240)

2-(2-((2R)-2-(3,4-difluorophenylaminomethyl)-5-oxopyrrolidin-1-yl)ethylthio)-1,3-thiazole-4-carboxylic acid HPLC retention time: 3.43 minutes;
MASS data (ESI, Pos. 20 V): 414 (M+H)$^+$.

Example 17(241)

2-(2-((2R)-2-(5-fluoro-2-methylphenylaminomethyl)-5-oxopyrrolidin-1-yl)ethylthio)-1,3-thiazole-4-carboxylic acid HPLC retention time: 3.48 minutes;
MASS data (ESI, Pos. 20 V): 410 (M+H)$^+$.

Example 17(242)

2-(2-((2R)-2-(3-chlorophenylaminomethyl)-5-oxopyrrolidin-1-yl)ethylthio)-1,3-thiazole-4-carboxylic acid HPLC retention time: 3.48 minutes;
MASS data (ESI, Pos. 20 V): 412 (M+H)$^+$.

Example 17(243)

2-(2-((2R)-2-(3-chloro-2-methylphenylaminomethyl)-5-oxopyrrolidin-1-yl)ethylthio)-1,3-thiazole-4-carboxylic acid HPLC retention time: 3.57 minutes;
MASS data (ESI, Pos. 20 V): 426 (M+H)$^+$.

Example 17(244)

2-(2-((2R)-2-(3-chloro-4-fluorophenylaminomethyl)-5-oxopyrrolidin-1-yl)ethylthio)-1,3-thiazole-4-carboxylic acid HPLC retention time: 3.50 minutes;
MASS data (ESI, Pos. 20 V): 430 (M+H)$^+$.

Example 17(245)

2-(2-((2R)-2-(3-chloro-4-methylphenylaminomethyl)-5-oxopyrrolidin-1-yl)ethylthio)-1,3-thiazole-4-carboxylic acid HPLC retention time: 3.56 minutes;
MASS data (ESI, Pos. 20 V): 426 (M+H)$^+$.

Example 17(246)

2-(2-((2R)-2-(3,5-dimethylphenylaminomethyl)-5-oxopyrrolidin-1-yl)ethylthio)-1,3-thiazole-4-carboxylic acid HPLC retention time: 3.32 minutes;
MASS data (ESI, Pos. 20 V): 406 (M+H)$^+$.

Example 17(247)

2-(2-((2R)-2-(2-methoxy-5-methylphenylaminomethyl)-5-oxopyrrolidin-1-yl)ethylthio)-1,3-thiazole-4-carboxylic acid HPLC retention time: 3.25 minutes;
MASS data (ESI, Pos. 20 V): 422 (M+H)$^+$.

Example 17(248)

2-(2-((2R)-2-(3-ethylphenylaminomethyl)-5-oxopyrrolidin-1-yl)ethylthio)-1,3-thiazole-4-carboxylic acid HPLC retention time: 3.38 minutes;
MASS data (ESI, Pos. 20 V): 406 (M+H)$^+$.

Example 17(249)

2-(2-((2R)-2-(4-fluorophenylaminomethyl)-5-oxopyrrolidin-1-yl)ethylthio)-1,3-thiazole-4-carboxylic acid HPLC retention time: 3.26 minutes;
MASS data (ESI, Pos. 20 V): 396 (M+H)$^+$.

Example 17(250)

2-(2-((2R)-2-(4-chloro-2-methylphenylaminomethyl)-5-oxopyrrolidin-1-yl)ethylthio)-1,3-thiazole-4-carboxylic acid HPLC retention time: 3.57 minutes;
MASS data (ESI, Pos. 20 V): 426 (M+H)$^+$.

Example 17(251)

2-(2-((2R)-2-(4-nitrophenylaminomethyl)-5-oxopyrrolidin-1-yl)ethylthio)-1,3-thiazole-4-carboxylic acid HPLC retention time: 3.29 minutes;
MASS data (ESI, Pos. 20 V): 423 (M+H)$^+$.

Example 17(252)

2-(2-((2R)-2-(4-ethoxyphenylaminomethyl)-5-oxopyrrolidin-1-yl)ethylthio)-1,3-thiazole-4-carboxylic acid HPLC retention time: 3.09 minutes;
MASS data (ESI, Pos. 20 V): 422 (M+H)$^+$.

Example 17(253)

2-(2-((2R)-2-(4-ethylphenylaminomethyl)-5-oxopyrrolidin-1-yl)ethylthio)-1,3-thiazole-4-carboxylic acid HPLC retention time: 3.31 minutes;
MASS data (ESI, Pos. 20 V): 406 (M+H)$^+$.

Example 17(254)

2-(2-((2R)-2-(4-(2-hydroxyethyl)phenylaminomethyl)-5-oxopyrrolidin-1-yl)ethylthio)-1,3-thiazole-4-carboxylic acid HPLC retention time: 2.95 minutes;
MASS data (ESI, Pos. 20 V): 422 (M+H)$^+$.

Example 17(255)

2-(2-((2R)-5-oxo-2-(4-propylphenylaminomethyl)pyrrolidin-1-yl)ethylthio)-1,3-thiazole-4-carboxylic acid HPLC retention time: 3.44 minutes;
MASS data (ESI, Pos. 20 V): 420 (M+H)$^+$.

Example 17(256)

2-(2-((2R)-2-(4-butylphenylaminomethyl)-5-oxopyrrolidin-1-yl)ethylthio)-1,3-thiazole-4-carboxylic acid HPLC retention time: 3.56 minutes;
MASS data (ESI, Pos. 20 V): 434 (M+H)$^+$.

Example 17(257)

2-(2-((2R)-5-oxo-2-(2-propylphenylaminomethyl)pyrrolidin-1-yl)ethylthio)-1,3-thiazole-4-carboxylic acid HPLC retention time: 3.61 minutes;
MASS data (ESI, Pos. 20 V): 420 (M+H)$^+$.

Example 17(258)

2-(2-((2R)-2-(4-(1-methylpropyl)phenylaminomethyl)-5-oxopyrrolidin-1-yl)ethylthio)-1,3-thiazole-4-carboxylic acid HPLC retention time: 3.53 minutes;
MASS data (ESI, Pos. 20 V): 434 (M+H)$^+$.

Example 17(259)

2-(2-((2R)-2-(4-chloro-2-fluorophenylaminomethyl)-5-oxopyrrolidin-1-yl)ethylthio)-1,3-thiazole-4-carboxylic acid HPLC retention time: 3.52 minutes;
MASS data (ESI, Pos. 20 V): 430 (M+H)$^+$.

Example 17(260)

2-(2-((2R)-5-oxo-2-(2,3,4-trifluorophenylaminomethyl)pyrrolidin-1-yl)ethylthio)-1,3-thiazole-4-carboxylic acid HPLC retention time: 3.48 minutes;
MASS data (ESI, Pos. 20 V): 432 (M+H)$^+$.

Example 17(261)

2-(2-((2R)-2-(2-butylphenylaminomethyl)-5-oxopyrrolidin-1-yl)ethylthio)-1,3-thiazole-4-carboxylic acid HPLC retention time: 3.72 minutes;
MASS data (ESI, Pos. 20 V): 434 (M+H)$^+$.

Example 17(262)

2-(2-((2R)-2-(2-chloro-4-methylphenylaminomethyl)-5-oxopyrrolidin-1-yl)ethylthio)-1,3-thiazole-4-carboxylic acid HPLC retention time: 3.57 minutes;
MASS data (ESI, Pos. 20 V): 426 (M+H)$^+$.

Example 17(263)

2-(2-((2R)-2-(2-isopropenylphenylaminomethyl)-5-oxopyrrolidin-1-yl)ethylthio)-1,3-thiazole-4-carboxylic acid HPLC retention time: 3.56 minutes;
MASS data (ESI, Pos. 20 V): 418 (M+H)$^+$.

Example 17(264)

2-(2-((2R)-2-(3-fluoro-4-methylphenylaminomethyl)-5-oxopyrrolidin-1-yl)ethylthio)-1,3-thiazole-4-carboxylic acid HPLC retention time: 3.46 minutes;
MASS data (ESI, Pos. 20 V): 410 (M+H)$^+$.

Example 17(265)

2-(2-((2R)-2-(3-methylthiophenylaminomethyl)-5-oxopyrrolidin-1-yl)ethylthio)-1,3-thiazole-4-carboxylic acid HPLC retention time: 3.43 minutes;
MASS data (ESI, Pos. 20 V): 424 (M+H)$^+$.

Example 17(266)

2-(2-((2R)-2-(2-(1-methylpropyl)phenylaminomethyl)-5-oxopyrrolidin-1-yl)ethylthio)-1,3-thiazole-4-carboxylic acid HPLC retention time: 3.66 minutes;
MASS data (ESI, Pos. 20 V): 434 (M+H)$^+$.

Example 17(267)

2-(2-((2R)-2-(3-fluoro-2-methylphenylaminomethyl)-5-oxopyrrolidin-1-yl)ethylthio)-1,3-thiazole-4-carboxylic acid HPLC retention time: 3.47 minutes;
MASS data (ESI, Pos. 20 V): 410 (M+H)$^+$.

Example 17(268)

2-(2-((2R)-2-(2-fluoro-4-methylphenylaminomethyl)-5-oxopyrrolidin-1-yl)ethylthio)-1,3-thiazole-4-carboxylic acid HPLC retention time: 3.47 minutes;
MASS data (ESI, Pos. 20 V): 410 (M+H)$^+$.

Example 17(269)

2-(2-((2R)-2-(1H-indazol-6-ylaminomethyl)-5-oxopyrrolidin-1-yl)ethylthio)-1,3-thiazole-4-carboxylic acid HPLC retention time: 2.96 minutes;
MASS data (ESI, Pos. 20 V): 418 (M+H)$^+$.

Example 17(270)

2-(2-((2R)-2-(1,4-benzodioxan-6-ylaminomethyl)-5-oxopyrrolidin-1-yl)ethylthio)-1,3-thiazole-4-carboxylic acid HPLC retention time: 3.05 minutes;
MASS data (ESI, Pos. 20 V): 436 (M+H)$^+$.

Example 17(271)

2-(2-((2R)-2-(4-methyl-2-oxo-2H-chromen-7-ylaminomethyl)-5-oxopyrrolidin-1-yl)ethylthio)-1,3-thiazole-4-carboxylic acid HPLC retention time: 3.22 minutes;
MASS data (ESI, Pos. 20 V): 460 (M+H)$^+$.

Example 17(272)

2-(2-((2R)-2-(2-bromophenylaminomethyl)-5-oxopyrrolidin-1-yl)ethylthio)-1,3-thiazole-4-carboxylic acid HPLC retention time: 3.49 minutes;
MASS data (ESI, Pos. 20 V): 458 (M+H)$^+$.

Example 17(273)

2-(2-((2R)-2-(2-bromo-4-methylphenylaminomethyl)-5-oxopyrrolidin-1-yl)ethylthio)-1,3-thiazole-4-carboxylic acid HPLC retention time: 3.56 minutes;
MASS data (ESI, Pos. 20 V): 472 (M+H)$^+$.

Example 17(274)

2-(2-((2R)-2-(2,3-dichlorophenylaminomethyl)-5-oxopyrrolidin-1-yl)ethylthio)-1,3-thiazole-4-carboxylic acid HPLC retention time: 3.54 minutes;
MASS data (ESI, Pos. 20 V): 446 (M+H)$^+$.

Example 17(275)

2-(2-((2R)-2-(2,4-dichlorophenylaminomethyl)-5-oxopyrrolidin-1-yl)ethylthio)-1,3-thiazole-4-carboxylic acid HPLC retention time: 3.59 minutes;
MASS data (ESI, Pos. 20 V): 446 (M+H)$^+$.

Example 17(276)

2-(2-((2R)-2-(2,5-dichlorophenylaminomethyl)-5-oxopyrrolidin-1-yl)ethylthio)-1,3-thiazole-4-carboxylic acid HPLC retention time: 3.56 minutes;
MASS data (ESI, Pos. 20 V): 446 (M+H)$^+$.

Example 17(277)

2-(2-((2R)-2-(2-chloro-5-trifluoromethylphenylaminomethyl)-5-oxopyrrolidin-1-yl)ethylthio)-1,3-thiazole-4-carboxylic acid HPLC retention time: 3.63 minutes;
MASS data (ESI, Pos. 20 V): 480 (M+H)$^+$.

Example 17(278)

2-(2-((2R)-5-oxo-2-(2-trifluoromethylphenylaminomethyl)pyrrolidin-1-yl)ethylthio)-1,3-thiazole-4-carboxylic acid HPLC retention time: 3.51 minutes;
MASS data (ESI, Pos. 20 V): 446 (M+H)$^+$.

Example 17(279)

2-(2-((2R)-2-(3-bromophenylaminomethyl)-5-oxopyrrolidin-1-yl)ethylthio)-1,3-thiazole-4-carboxylic acid HPLC retention time: 3.47 minutes;
MASS data (ESI, Pos. 20 V): 458 (M+H)$^+$.

Example 17(280)

2-(2-((2R)-2-(3,4-dichlorophenylaminomethyl)-5-oxopyrrolidin-1-yl)ethylthio)-1,3-thiazole-4-carboxylic acid HPLC retention time: 3.58 minutes;
MASS data (ESI, Pos. 20 V): 446 (M+H)$^+$.

Example 17(281)

2-(2-((2R)-2-(3,5-dichlorophenylaminomethyl)-5-oxopyrrolidin-1-yl)ethylthio)-1,3-thiazole-4-carboxylic acid HPLC retention time: 3.63 minutes;
MASS data (ESI, Pos. 20 V): 446 (M+H)$^+$.

Example 17(282)

2-(2-((2R)-2-(5-chloro-2-methoxyphenylaminomethyl)-5-oxopyrrolidin-1-yl)ethylthio)-1,3-thiazole-4-carboxylic acid HPLC retention time: 3.47 minutes;
MASS data (ESI, Pos. 20 V): 442 (M+H)$^+$.

Example 17(283)

2-(2-((2R)-5-oxo-2-(3-trifluoromethylphenylaminomethyl)pyrrolidin-1-yl)ethylthio)-1,3-thiazole-4-carboxylic acid HPLC retention time: 3.54 minutes;
MASS data (ESI, Pos. 20 V): 446 (M+H)$^+$.

Example 17(284)

2-(2-((2R)-2-(4-cyanophenylaminomethyl)-5-oxopyrrolidin-1-yl)ethylthio)-1,3-thiazole-4-carboxylic acid HPLC retention time: 3.23 minutes;
MASS data (ESI, Pos. 20 V): 403 (M+H)$^+$.

Example 17(285)

2-(2-((2R)-2-(4-bromophenylaminomethyl)-5-oxopyrrolidin-1-yl)ethylthio)-1,3-thiazole-4-carboxylic acid HPLC retention time: 3.48 minutes;
MASS data (ESI, Pos. 20 V): 458 (M+H)$^+$.

Example 17(286)

2-(2-((2R)-2-(4-bromo-2-methylphenylaminomethyl)-5-oxopyrrolidin-1-yl)ethylthio)-1,3-thiazole-4-carboxylic acid HPLC retention time: 3.58 minutes;
MASS data (ESI, Pos. 20 V): 472 (M+H)$^+$.

Example 17(287)

2-(2-((2R)-2-(4-bromo-3-methylphenylaminomethyl)-5-oxopyrrolidin-1-yl)ethylthio)-1,3-thiazole-4-carboxylic acid HPLC retention time: 3.56 minutes;
MASS data (ESI, Pos. 20 V): 472 (M+H)$^+$.

Example 17(288)

2-(2-((2R)-2-(4-fluoro-3-trifluoromethylphenylaminomethyl)-5-oxopyrrolidin-1-yl)ethylthio)-1,3-thiazole-4-carboxylic acid HPLC retention time: 3.56 minutes;
MASS data (ESI, Pos. 20 V): 464 (M+H)$^+$.

Example 17(289)

2-(2-((2R)-2-(4-chloro-3-trifluoromethylphenylaminomethyl)-5-oxopyrrolidin-1-yl)ethylthio)-1,3-thiazole-4-carboxylic acid HPLC retention time: 3.64 minutes;
MASS data (ESI, Pos. 20 V): 480 (M+H)$^+$.

Example 17(290)

2-(2-((2R)-2-(4-methoxyphenylaminomethyl)-5-oxopyrrolidin-1-yl)ethylthio)-1,3-thiazole-4-carboxylic acid HPLC retention time: 2.96 minutes;
MASS data (ESI, Pos. 20 V): 408 (M+H)$^+$.

Example 17(291)

2-(2-((2R)-2-(4-butoxyphenylaminomethyl)-5-oxopyrrolidin-1-yl)ethylthio)-1,3-thiazole-4-carboxylic acid HPLC retention time: 3.29 minutes;
MASS data (ESI, Pos. 20 V): 450 (M+H)$^+$.

Example 17(292)

2-(2-((2R)-5-oxo-2-(4-pentylphenylaminomethyl)pyrrolidin-1-yl)ethylthio)-1,3-thiazole-4-carboxylic acid HPLC retention time: 3.66 minutes;
MASS data (ESI, Pos. 20 V): 448 (M+H)$^+$.

Example 17(293)

2-(2-((2R)-2-(4-hexylphenylaminomethyl)-5-oxopyrrolidin-1-yl)ethylthio)-1,3-thiazole-4-carboxylic acid HPLC retention time: 3.79 minutes;
MASS data (ESI, Pos. 20 V): 462 (M+H)$^+$.

Example 17(294)

2-(2-((2R)-2-(4-heptylphenylaminomethyl)-5-oxopyrrolidin-1-yl)ethylthio)-1,3-thiazole-4-carboxylic acid HPLC retention time: 3.92 minutes;
MASS data (ESI, Pos. 20 V): 476 (M+H)$^+$.

Example 17(295)

2-(2-((2R)-2-(3-aminocarbonylphenylaminomethyl)-5-oxopyrrolidin-1-yl)ethylthio)-1,3-thiazole-4-carboxylic acid HPLC retention time: 2.98 minutes;
MASS data (ESI, Pos. 20 V): 421 (M+H)$^+$.

Example 17(296)

2-(2-((2R)-2-(2,5-dimethoxyphenylaminomethyl)-5-oxopyrrolidin-1-yl)ethylthio)-1,3-thiazole-4-carboxylic acid HPLC retention time: 3.25 minutes;
MASS data (ESI, Pos. 20 V): 438 (M+H)$^+$.

Example 17(297)

2-(2-((2R)-5-oxo-2-(3,4,5-trimethoxyphenylaminomethyl)pyrrolidin-1-yl)ethylthio)-1,3-thiazole-4-carboxylic acid HPLC retention time: 3.11 minutes;
MASS data (ESI, Pos. 20 V): 468 (M+H)$^+$.

Example 17(298)

2-(2-((2R)-2-(2,6-diisopropylphenylaminomethyl)-5-oxopyrrolidin-1-yl)ethylthio)-1,3-thiazole-4-carboxylic acid HPLC retention time: 3.55 minutes;
MASS data (ESI, Pos. 20 V): 462 (M+H)$^+$.

Example 17(299)

2-(2-((2R)-2-(4-bromo-2-fluorophenylaminomethyl)-5-oxopyrrolidin-1-yl)ethylthio)-1,3-thiazole-4-carboxylic acid HPLC retention time: 3.52 minutes;
MASS data (ESI, Pos. 20 V): 476 (M+H)$^+$.

Example 17(300)

2-(2-((2R)-2-(2-chloro-5-methoxyphenylaminomethyl)-5-oxopyrrolidin-1-yl)ethylthio)-1,3-thiazole-4-carboxylic acid HPLC retention time: 3.44 minutes;
MASS data (ESI, Pos. 20 V): 442 (M+H)$^+$.

Example 17(301)

2-(2-((2R)-2-(2,5-diethoxyphenylaminomethyl)-5-oxopyrrolidin-1-yl)ethylthio)-1,3-thiazole-4-carboxylic acid HPLC retention time: 3.46 minutes;
MASS data (ESI, Pos. 20 V): 466 (M+H)$^+$.

Example 17(302)

2-(2-((2R)-2-(2-methylquinolin-8-ylaminomethyl)-5-oxopyrrolidin-1-yl)ethylthio)-1,3-thiazole-4-carboxylic acid HPLC retention time: 2.98 minutes;
MASS data (ESI, Pos. 20 V): 443 (M+H)$^+$.

Example 17(303)

2-(2-((2R)-2-(2-(1-methylpropyl)-6-ethylphenylaminomethyl)-5-oxopyrrolidin-1-yl)ethylthio)-1,3-thiazole-4-carboxylic acid HPLC retention time: 3.59 minutes;
MASS data (ESI, Pos. 20 V): 462 (M+H)$^+$.

Example 17(304)

2-(2-((2R)-2-(5-chloro-2,4-dimethoxyphenylaminomethyl)-5-oxopyrrolidin-1-yl)ethylthio)-1,3-thiazole-4-carboxylic acid HPLC retention time: 3.26 minutes;
MASS data (ESI, Pos. 20 V): 472 (M+H)$^+$.

Example 17(305)

2-(2-((2R)-2-(5-chloro-2-methylphenylaminomethyl)-5-oxopyrrolidin-1-yl)ethylthio)-1,3-thiazole-4-carboxylic acid HPLC retention time: 3.54 minutes;
MASS data (ESI, Pos. 20 V): 426 (M+H)$^+$.

Example 17(306)

2-(2-((2R)-2-(1H-indazol-5-ylaminomethyl)-5-oxopyrrolidin-1-yl)ethylthio)-1,3-thiazole-4-carboxylic acid HPLC retention time: 2.85 minutes;
MASS data (ESI, Pos. 20 V): 418 (M+H)$^+$.

Example 17(307)

2-(2-((2R)-5-oxo-2-(4-trifluoromethoxyphenylaminomethyl)pyrrolidin-1-yl)ethylthio)-1,3-thiazole-4-carboxylic acid HPLC retention time: 3.59 minutes;
MASS data (ESI, Pos. 20 V): 462 (M+H)$^+$.

Example 17(308)

2-(2-((2R)-2-(4-cyano-3-trifluoromethylphenylaminomethyl)-5-oxopyrrolidin-1-yl)ethylthio)-1,3-thiazole-4-carboxylic acid HPLC retention time: 3.42 minutes;
MASS data (ESI, Pos. 20 V): 471 (M+H)$^+$.

Example 17(309)

2-(2-((2R)-2-(2-bromo-4-fluorophenylaminomethyl)-5-oxopyrrolidin-1-yl)ethylthio)-1,3-thiazole-4-carboxylic acid HPLC retention time: 3.51 minutes;
MASS data (ESI, Pos. 20 V): 476 (M+H)$^+$.

Example 17(310)

2-(2-((2R)-2-(2-chloro-4-fluorophenylaminomethyl)-5-oxopyrrolidin-1-yl)ethylthio)-1,3-thiazole-4-carboxylic acid HPLC retention time: 3.47 minutes;
MASS data (ESI, Pos. 20 V): 430 (M+H)$^+$.

Example 17(311)

2-(2-((2R)-5-oxo-2-(2,3,4-trichlorophenylaminomethyl)pyrrolidin-1-yl)ethylthio)-1,3-thiazole-4-carboxylic acid HPLC retention time: 3.68 minutes;
MASS data (ESI, Pos. 20 V): 482 (M+H)$^+$.

Example 17(312)

2-(2-((2R)-2-(5-isopropyl-2-methylphenylaminomethyl)-5-oxopyrrolidin-1-yl)ethylthio)-1,3-thiazole-4-carboxylic acid HPLC retention time: 3.62 minutes;
MASS data (ESI, Pos. 20 V): 434 (M+H)$^+$.

Example 17(313)

2-(2-((2R)-2-(2-methylquinolin-6-ylaminomethyl)-5-oxopyrrolidin-1-yl)ethylthio)-1,3-thiazole-4-carboxylic acid HPLC retention time: 2.91 minutes;
MASS data (ESI, Pos. 20 V): 443 (M+H)$^+$.

Example 17(314)

2-(2-((2R)-2-(3-isopropoxyphenylaminomethyl)-5-oxopyrrolidin-1-yl)ethylthio)-1,3-thiazole-4-carboxylic acid HPLC retention time: 3.41 minutes;
MASS data (ESI, Pos. 20 V): 436 (M+H)$^+$.

Example 17(315)

2-(2-((2R)-5-oxo-2-(4-trifluoromethylphenylaminomethyl)pyrrolidin-1-yl)ethylthio)-1,3-thiazole-4-carboxylic acid HPLC retention time: 3.55 minutes;
MASS data (ESI, Pos. 20 V): 446 (M+H)$^+$.

Example 17(316)

2-(2-((2R)-2-(3-methylaminocarbonylphenylaminomethyl)-5-oxopyrrolidin-1-yl)ethylthio)-1,3-thiazole-4-carboxylic acid HPLC retention time: 3.01 minutes;
MASS data (ESI, Pos. 20 V): 435 (M+H)$^+$.

Example 17(317)

2-(2-((2R)-2-(3-chloro-2,6-diethylphenylaminomethyl)-5-oxopyrrolidin-1-yl)ethylthio)-1,3-thiazole-4-carboxylic acid HPLC retention time: 3.81 minutes;
MASS data (ESI, Pos. 20 V): 468 (M+H)$^+$.

Example 17(318)

2-(2-((2R)-2-(3-isopropylphenylaminomethyl)-5-oxopyrrolidin-1-yl)ethylthio)-1,3-thiazole-4-carboxylic acid HPLC retention time: 3.46 minutes;
MASS data (ESI, Pos. 20 V): 420 (M+H)$^+$.

Example 17(319)

2-(2-((2R)-2-(2,3-dimethoxyphenylaminomethyl)-5-oxopyrrolidin-1-yl)ethylthio)-1,3-thiazole-4-carboxylic acid HPLC retention time: 3.26 minutes;
MASS data (ESI, Pos. 20 V): 438 (M+H)$^+$.

Example 17(320)

2-(2-((2R)-2-(3-methoxy-5-trifluoromethylphenylaminomethyl)-5-oxopyrrolidin-1-yl)ethylthio)-1,3-thiazole-4-carboxylic acid HPLC retention time: 3.56 minutes;
MASS data (ESI, Pos. 20 V): 476 (M+H)$^+$.

Example 17(321)

2-(2-((2R)-2-(4-(morpholin-4-yl)phenylaminomethyl)-5-oxopyrrolidin-1-yl)ethylthio)-1,3-thiazole-4-carboxylic acid HPLC retention time: 2.87 minutes;
MASS data (ESI, Pos. 20 V): 463 (M+H)$^+$.

Example 17(322)

2-(2-((2R)-2-(2-fluoro-5-trifluoromethylphenylaminomethyl)-5-oxopyrrolidin-1-yl)ethylthio)-1,3-thiazole-4-carboxylic acid HPLC retention time: 3.56 minutes;
MASS data (ESI, Pos. 20 V): 464 (M+H)$^+$.

Example 17(323)

2-(2-((2R)-2-(2-chloro-5-methylphenylaminomethyl)-5-oxopyrrolidin-1-yl)ethylthio)-1,3-thiazole-4-carboxylic acid HPLC retention time: 3.54 minutes;
MASS data (ESI, Pos. 20 V): 426 (M+H)$^+$.

Example 17(324)

2-(2-((2R)-5-oxo-2-(3,4,5-trichlorophenylaminomethyl)pyrrolidin-1-yl)ethylthio)-1,3-thiazole-4-carboxylic acid HPLC retention time: 3.71 minutes;
MASS data (ESI, Pos. 20 V): 482 (M+H)$^+$.

Example 17(325)

2-(2-((2R)-2-(3-chloro-4-methoxyphenylaminomethyl)-5-oxopyrrolidin-1-yl)ethylthio)-1,3-thiazole-4-carboxylic acid HPLC retention time: 3.30 minutes;
MASS data (ESI, Pos. 20 V): 442 (M+H)$^+$.

Example 17(326)

2-(2-((2R)-2-(4-chloro-2-methoxy-5-methylphenylaminomethyl)-5-oxopyrrolidin-1-yl)ethylthio)-1,3-thiazole-4-carboxylic acid HPLC retention time: 3.55 minutes;
MASS data (ESI, Pos. 20 V): 456 (M+H)$^+$.

Example 17(327)

2-(2-((2R)-5-oxo-2-(4-pentyloxyphenylaminomethyl)pyrrolidin-1-yl)ethylthio)-1,3-thiazole-4-carboxylic acid HPLC retention time: 3.40 minutes;
MASS data (ESI, Pos. 20 V): 464 (M+H)$^+$.

Example 17(328)

2-(2-((2R)-2-(4-hexyloxyphenylaminomethyl)-5-oxopyrrolidin-1-yl)ethylthio)-1,3-thiazole-4-carboxylic acid HPLC retention time: 3.52 minutes;
MASS data (ESI, Pos. 20 V): 478 (M+H)$^+$.

Example 17(329)

2-(2-((2R)-2-(2,3-difluorophenylaminomethyl)-5-oxopyrrolidin-1-yl)ethylthio)-1,3-thiazole-4-carboxylic acid HPLC retention time: 3.40 minutes;
MASS data (ESI, Pos. 20 V): 414 (M+H)$^+$.

Example 17(330)

2-(2-((2R)-5-oxo-2-(2,3,4,5-tetrafluorophenylaminomethyl)pyrrolidin-1-yl)ethylthio)-1,3-thiazole-4-carboxylic acid HPLC retention time: 3.50 minutes;
MASS data (ESI, Pos. 20 V): 450 (M+H)$^+$.

Example 17(331)

2-(2-((2R)-2-(5-t-butyl-2-methoxyphenylaminomethyl)-5-oxopyrrolidin-1-yl)ethylthio)-1,3-thiazole-4-carboxylic acid HPLC retention time: 3.49 minutes;
MASS data (ESI, Pos. 20 V): 464 (M+H)$^+$.

Example 17(332)

2-(2-((2R)-2-(3-chloro-4-cyanophenylaminomethyl)-5-oxopyrrolidin-1-yl)ethylthio)-1,3-thiazole-4-carboxylic acid HPLC retention time: 3.35 minutes;
MASS data (ESI, Pos. 20 V): 437 (M+H)$^+$.

Example 17(333)

2-(2-((2R)-5-oxo-2-(2-trifluoromethoxyphenylaminomethyl)pyrrolidin-1-yl)ethylthio)-1,3-thiazole-4-carboxylic acid HPLC retention time: 3.57 minutes;
MASS data (ESI, Pos. 20 V): 462 (M+H)$^+$.

Example 17(334)

2-(2-((2R)-5-oxo-2-(4-trifluoromethylthiophenylaminomethyl)pyrrolidin-1-yl)ethylthio)-1,3-thiazole-4-carboxylic acid HPLC retention time: 3.70 minutes;
MASS data (ESI, Pos. 20 V): 478 (M+H)$^+$.

Example 17(335)

2-(2-((2R)-5-oxo-2-(3-trifluoromethoxyphenylaminomethyl)pyrrolidin-1-yl)ethylthio)-1,3-thiazole-4-carboxylic acid HPLC retention time: 3.59 minutes;
MASS data (ESI, Pos. 20 V): 462 (M+H)$^+$.

Example 17(336)

2-(2-((2R)-2-(2-methoxy-5-trifluoromethylphenylaminomethyl)-5-oxopyrrolidin-1-yl)ethylthio)-1,3-thiazole-4-carboxylic acid HPLC retention time: 3.56 minutes;
MASS data (ESI, Pos. 20 V): 476 (M+H)$^+$.

Example 17(337)

2-(2-((2R)-2-(2-chloro-4,6-dimethylphenylaminomethyl)-5-oxopyrrolidin-1-yl)ethylthio)-1,3-thiazole-4-carboxylic acid HPLC retention time: 3.56 minutes;
MASS data (ESI, Pos. 20 V): 440 (M+H)$^+$.

Example 17(338)

2-(2-((2R)-2-(2-chloro-4-fluoro-5-methylphenylaminomethyl)-5-oxopyrrolidin-1-yl)ethylthio)-1,3-thiazole-4-carboxylic acid HPLC retention time: 3.58 minutes;
MASS data (ESI, Pos. 20 V): 444 (M+H)$^+$.

Example 17(339)

2-(2-((2R)-2-(2-cyano-4,5-dimethoxyphenylaminomethyl)-5-oxopyrrolidin-1-yl)ethylthio)-1,3-thiazole-4-carboxylic acid HPLC retention time: 3.20 minutes;
MASS data (ESI, Pos. 20 V): 463 (M+H)$^+$.

Example 17(340)

2-(2-((2R)-2-(2-fluoro-3-trifluoromethylphenylaminomethyl)-5-oxopyrrolidin-1-yl)ethylthio)-1,3-thiazole-4-carboxylic acid HPLC retention time: 3.57 minutes;
MASS data (ESI, Pos. 20 V): 464 (M+H)$^+$.

Example 17(341)

2-(2-((2R)-2-(3-fluoro-4-methoxyphenylaminomethyl)-5-oxopyrrolidin-1-yl)ethylthio)-1,3-thiazole-4-carboxylic acid HPLC retention time: 3.23 minutes;
MASS data (ESI, Pos. 20 V): 426 (M+H)$^+$.

Example 17(342)

2-(2-((2R)-2-(4-difluoromethoxyphenylaminomethyl)-5-oxopyrrolidin-1-yl)ethylthio)-1,3-thiazole-4-carboxylic acid HPLC retention time: 3.39 minutes;
MASS data (ESI, Pos. 20 V): 444 (M+H)$^+$.

Example 17(343)

2-(2-((2R)-2-(3-bromo-4-methylphenylaminomethyl)-5-oxopyrrolidin-1-yl)ethylthio)-1,3-thiazole-4-carboxylic acid HPLC retention time: 3.56 minutes;
MASS data (ESI, Pos. 20 V): 472 (M+H)$^+$.

Example 17(344)

2-(2-((2R)-2-(2-difluoromethoxyphenylaminomethyl)-5-oxopyrrolidin-1-yl)ethylthio)-1,3-thiazole-4-carboxylic acid HPLC retention time: 3.44 minutes;
MASS data (ESI, Pos. 20 V): 444 (M+H)$^+$.

Example 17(345)

2-(2-((2R)-5-oxo-2-(3-trifluoromethylthiophenylaminomethyl)pyrrolidin-1-yl)ethylthio)-1,3-thiazole-4-carboxylic acid HPLC retention time: 3.66 minutes;
MASS data (ESI, Pos. 20 V): 478 (M+H)$^+$.

Reference Example 21 t-butyl (1R)-2-benzyloxy-1-hydroxymethylethylcarbamate

Under an atmosphere of argon, to a solution of 2,5-dioxopyrrolidin-1-yl O-benzyl-N-t-butoxycarbonyl-L-serinate (4.41 g) in tetrahydrofuran (30 mL) was added sodium borohydride (644 mg) in ice bath and the mixture was stirred at room temperature overnight. Water was added to the reaction solution, which was extracted with ethyl acetate. The organic layer was washed with an aqueous saturated ammonium chloride solution and brine, dried over anhydrous magnesium sulfate and concentrated to give the title compound (3.30 g) having the following physical data.

TLC: Rf 0.42 (n-hexane:ethyl acetate=1:1);
NMR (CDCl$_3$): δ 1.45 (s, 9H) 2.61 (br. s., 1H) 3.72 (m, 5H) 4.53 (s, 2H) 5.17 (br. s., 1H) 7.34 (m, 5H).

Reference Example 22

(2R)-2-amino-3-benzyloxypropanol hydrochloride

To a solution of the compound prepared in Reference Example 21 (3.30 g) in toluene (20 mL) was added 4N hydrogen chloride dioxane solution (4 mL) and the mixture was stirred at room temperature for 2 hours and at 60° C. for 1 hour. After cooling, hexane was added to the reaction mixture, which was filtrated. The obtained residue was dried to give the title compound (2.18 g) having the following physical data.

TLC: Rf 0.21 (chloroform:methanol=9:1);
NMR (CDCl$_3$): δ 2.31 (br. s., 4H) 3.69 (m, 5H) 4.55 (s, 2H) 7.31 (m, 5H).

Reference Example 23

(4R)-4-benzyloxymethyl-2-oxo-1,3-oxazolidine

Under an atmosphere of argon, to a solution of the compound prepared in Reference Example 22 (2.15 g) in tetrahydrofuran (20 mL) were 1,1'-carbonyldiimidazole (1.77 g) and triethylamine (2.75 mL) in ice bath and the mixture was stirred at room temperature overnight. To the reaction solution was added 1,1'-carbonyldiimidazole (1.77 g) and the mixture was stirred at 60° C. for 3 hours. After cooling, hydrochloric acid was added to the reaction solution. The reaction mixture was extracted with ethyl acetate. The obtained organic layer was washed with water and brine, dried over anhydrous magnesium sulfate and concentrated to give the title compound (2.00 g) having the following physical data.

TLC: Rf 0.68 (ethyl acetate);

NMR (CDCl$_3$): δ 3.47 (d, J=6.20 Hz, 2H) 4.03 (m, 1H) 4.11 (dd, J=8.40, 5.10 Hz, 1H) 4.45 (t, J=8.40 Hz, 1H) 4.54 (s, 2H) 5.62 (br. s., 1H) 7.32 (m, 5H).

Reference Example 24

(4R)-4-benzyloxymethyl-2-oxo-1,3-oxazolidin-1-ylacetic acid ethyl ester

Under an atmosphere of argon, to a solution of the compound prepared in Reference Example 23 (2.00 g) and bromoethyl acetate (2.42 g) in tetrahydrofuran (20 mL) was added potassium t-butoxide (1.29 g) and the mixture was stirred at room temperature overnight. Water was added to the reaction solution, which was extracted with ethyl acetate. The organic layer was washed with water and brine, dried over anhydrous magnesium sulfate and concentrated. The obtained residue was purified by column chromatography on silica gel (n-hexane:ethyl acetate=1:1) to give the title compound (1.18 g) having the following physical data.

TLC: Rf 0.42 (n-hexane:ethyl acetate=1:1);

NMR (CDCl$_3$): δ 1.24 (t, J=7.10 Hz, 3H) 3.52 (dd, J=9.60, 4.00 Hz, 1H) 3.60 (dd, J=9.60, 6.60 Hz, 1H) 3.97 (d, J=18.00 Hz, 1H) 4.01 (dd, J=8.70, 6.30 Hz, 1H) 4.15 (m, 3H) 4.22 (d, J=18.00 Hz, 1H) 4.44 (t, J=8.70 Hz, 1H) 4.47 (d, J=12.00 Hz, 1H) 4.53 (d, J=12.00 Hz, 1H) 7.33 (m, 5H).

Reference Example 25

(4R)-4-hydroxymethyl-2-oxo-1,3-oxazolidin-1-ylacetic acid ethyl ester

Under an atmosphere of argon, to a solution of the compound prepared in Reference Example 24 (1.17 g) in ethanol (20 mL) was added palladium hydroxide on carbon (200 mg). Under an atmosphere of hydrogen, the mixture was stirred overnight. The reaction mixture was filtrated and concentrated to give the title compound (810 mg) having the following physical data.

TLC: Rf 0.42 (ethyl acetate);

NMR (CDCl$_3$): δ 1.32 (t, J=7.10 Hz, 3H) 3.63 (m, 3H) 3.74 (d, J=18.00 Hz, 1H) 3.86 (m, 1H) 4.26 (m, 2H) 4.39 (d, J=18.00 Hz, 1H) 4.42 (d, J=8.00 Hz, 1H)

Reference Example 26

(4R)-4-(3,5-dichlorophenoxymethyl)-2-oxo-1,3-oxazalidin-1-ylacetic acid ethyl ester Under an atmosphere of argon, diethyl azodicarboxylate (40% solution in toluene) (0.54 mL) was added dropwise to a solution of the compound prepared in Reference Example 25 (203 mg), 3,5-dichlorophenol (196 mg) and triphenylphosphine (314 mg) in tetrahydrofuran (5 mL) and the mixture was stirred at room temperature for 4 hours. Triphenylphosphine (157 mg) and diethyl azodicarboxylate (40% solution in toluene) (0.27 mL) was added to the reaction solution, which was stirred at room temperature for 4 hours. The reaction solution was concentrated and the obtained residue was purified by column chromatography on silica gel (methylene chloride:ethyl acetate=100:3) to give the title compound (271 mg) having the following physical data.

TLC: Rf 0.45 (methylene chloride:ethyl acetate=4:1);

NMR (CDCl$_3$): δ 1.26 (t, J=7.14 Hz, 3H) 4.14 (m, 7H) 4.37 (m, 1H) 4.57 (t, J=8.93 Hz, 1H) 6.78 (d, J=1.65 Hz, 2H) 7.02 (t, J=1.65 Hz, 1H).

Example 18

(4R)-4-(3,5-dichlorophenoxymethyl)-1-(2-hydroxyethyl)-2-oxo-1,3-oxazolidine

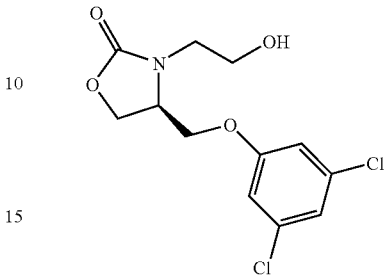

Under an atmosphere of argon, to a solution of the compound prepared in Reference Example 26 (270 mg) in tetrahydrofuran (5 mL) was added sodium borohydride (88 mg) and the mixture was stirred at room temperature overnight. Water was added to the reaction mixture, which was extracted with ethyl acetate. The organic layer was washed with water and brine, dried over anhydrous magnesium sulfate and concentrated. The obtained residue was purified by column chromatography on silica gel (ethyl acetate) to give the title compound (138 mg) having the following physical data.

TLC: Rf 0.21 (methylene chloride:ethyl acetate=1:1);

NMR (CDCl$_3$): δ 3.41 (m, 1H) 3.59 (m, 1H) 3.86 (m, 2H) 4.10 (m, 2H) 4.28 (m, 2H) 4.51 (t, J=8.10 Hz, 1H) 6.82 (d, J=1.80 Hz, 2H) 7.02 (t, J=1.80 Hz, 1H).

Reference Example 27

(2-((4R)-4-(3,5-dichlorophenoxymethyl)-2-oxo-1,3-oxazolidin-1-yl)ethyl methanesulfonate methanesulfonyl chloride (0.051 mL) was added dropwise to the compound prepared in Example 18 (135 mg) and triethylamine (0.12 mL) in methylene chloride (2 mL) in ice bath and the mixture was stirred for 1 hour. Hydrochloric acid was added to the reaction solution, which was extracted with ethyl acetate. The organic layer was washed with water and brine, dried over anhydrous magnesium sulfate and concentrated to give the title compound (193 mg) having the following physical data.

TLC: Rf 0.53 (methylene chloride:ethyl acetate=1:1);

NMR (CDCl$_3$): δ 3.03 (s, 3H) 3.58 (m, 1H) 3.81 (m, 1H) 4.09 (m, 2H) 4.23 (dd, J=8.50, 4.80 Hz, 1H) 4.38 (m, 3H) 4.53 (t, J=8.50 Hz, 1H) 6.83 (d, J=1.80 Hz, 2H) 7.03 (t, J=1.80 Hz, 1H).

Reference Example 28

S-((4R)-4-(3,5-dichlorophenoxymethyl)-2-oxo-1,3-oxazolidin-1-yl)ethyl ethanethioate Under an atmosphere of argon, a solution of the compound prepared in Reference Example 27 (193 mg) and potassium thioacetate (75 mg) in dimethylformamide (2 mL) was stirred at 60° C. for 2 hours. Water was added to the reaction solution, which was extracted with ethyl acetate. The organic layer was washed with water and brine, dried over anhydrous magnesium sulfate and concentrated to give the title compound (165 mg) having the following physical data.

TLC: Rf 0.65 (methylene chloride:ethyl acetate=1:2);

NMR (CDCl$_3$): δ 2.34 (s, 3H) 3.07 (m, 2H) 3.37 (m, 1H) 3.60 (m, 1H) 4.17 (m, 4H) 4.46 (m, 1H) 6.85 (d, J=1.80 Hz, 2H) 7.02 (t, J=1.80 Hz, 1H).

Example 19

2-(2-((4S)-4-(3,5-dichlorophenoxymethyl)-2-oxo-1,3-oxazolidin-3-yl)ethylthio)-1,3-thiazole-4-carboxylic acid ethyl ester

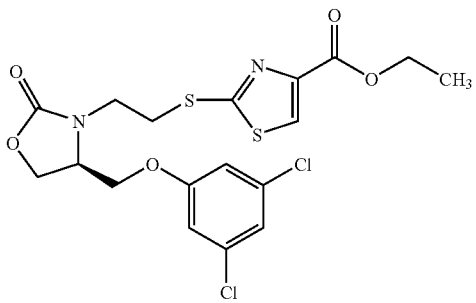

Under an atmosphere of argon, a solution of the compound prepared Reference Example 28 (165 mg) and ethyl 2-bromothiazole-4-carboxylate (114 mg) in ethanol was deaerated and potassium carbonate (91 mg) was added thereto. The mixture was stirred at room temperature overnight. Water was added to the reaction solution, which was extracted with ethyl acetate. The organic layer was washed with water and brine, dried over anhydrous magnesium sulfate and concentrated. The obtained residue was purified by column chromatography on silica gel (n-hexane:ethyl acetate=1:1) to give the compound of the present invention (144 mg) having the following physical data.

TLC: Rf 0.43 (toluene:ethyl acetate=1:1);

NMR (CDCl$_3$): δ 1.39 (t, J=7.10 Hz, 3H) 3.33 (ddd, J=13.80, 9.30, 6.00 Hz, 1H) 3.49 (ddd, J=13.80, 9.30, 5.10 Hz, 1H) 3.65 (ddd, J=14.30, 9.30, 5.10 Hz, 1H) 3.81 (ddd, J=14.30, 9.30, 6.00 Hz, 1H) 4.07 (dd, J=10.50, 3.00 Hz, 1H) 4.40 (m, 5H) 4.69 (dd, J=10.50, 3.00 Hz, 1H) 6.90 (d, J=1.80 Hz, 2H) 6.96 (t, J=1.80 Hz, 1H) 8.00 (s, 1H).

Example 20(1) and 20(2)

By the same procedure as described in Example 2, using the compound prepared in Example 19 or a corresponding ester instead of the compound prepared in Example 1, the following compounds of the present invention were obtained.

Example 20(1)

2-(2-((4S)-4-(3,5-dichlorophenoxymethyl)-2-oxo-1,3-oxazolidin-3-yl)ethylthio)-1,3-thiazole-4-carboxylic acid

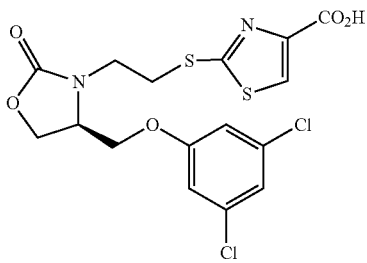

TLC: Rf 0.58 (chloroform:methanol:acetic acid=90:10:1);

NMR (CDCl$_3$): δ 3.37 (ddd, J=13.50, 9.30, 6.00 Hz, 1H) 3.53 (ddd, J=13.50, 9.30, 6.00 Hz, 1H) 3.69 (ddd, J=14.10, 9.30, 5.20 Hz, 1H) 3.83 (ddd, J=14.10, 9.30, 6.00 Hz, 1H) 4.06 (m, 1H) 4.36 (m, 4H) 6.84 (d, J=1.80 Hz, 2H) 6.98 (t, J=1.80 Hz, 1H) 8.14 (s, 1H).

Example 20(2)

2-(2-((4S)-2-oxo-4-((3-(trifluoromethoxy)phenoxy)methyl)-1,3-oxazolidin-3-yl)ethylthio)-1,3-thiazole-4-carboxylic acid TLC: Rf 0.26 (chloroform:methanol:acetic acid=90:10:1);

NMR (CDCl$_3$): δ 3.39 (m, J=14.20, 9.00, 5.90 Hz, 1H) 3.54 (ddd, J=14.20, 9.00, 5.30 Hz, 1H) 3.71 (ddd, J=14.20, 9.00, 5.30 Hz, 1H) 3.85 (ddd, J=14.20, 9.00, 5.90 Hz, 1H) 4.08 (m, 1H) 4.31 (m, 3H) 4.47 (t, J=7.90 Hz, 1H) 6.78 (s, 1H) 6.86 (m, 2H) 7.31 (d, J=8.10 Hz, 1H) 8.13 (s, 1H).

Example 21

2-(2-((2R)-2-(3,5-dichlorophenoxymethyl)-5-thioxopyrrolidin-1-yl)ethylthio)-1,3-thiazole-4-carboxylic acid ethyl ester

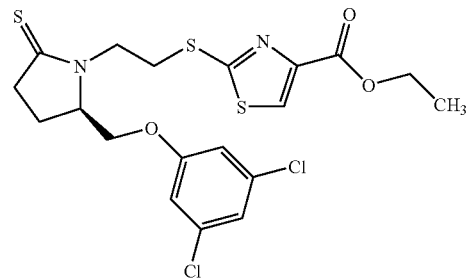

To a solution of the compound prepared in Example 5(32) (190 mg) in toluene (3 mL) was added Lawesson's Reagent (97 mg) and the mixture was stirred at 50° C. for 1 hour. After cooling to room temperature, the reaction solution was purified by column chromatography on silica gel (hexane:ethyl acetate=4:1) to give the compound of the present invention having the following physical data.

TLC: Rf 0.35 (hexane:ethyl acetate=4:1);

NMR (CDCl$_3$): δ 1.34 (t, J=7.14 Hz, 3H) 2.17 (m, 2H) 2.97 (m, 1H) 3.21 (m, 2H) 3.64 (m, 1H) 4.03 (m, 2H) 4.19 (m, 1H) 4.36 (m, 3H) 4.92 (dd, J=10.71, 2.75 Hz, 1H) 6.86 (m, 3H) 7.94 (s, 1H).

Example 21(1) and 21(2)

By the same procedure as described in Example 21, using a corresponding ester instead of the compound prepared in Example 5(32), the following compounds of the present invention were obtained.

Example 21(1)

2-(2-((4S)-4-(3,5-dichlorophenoxymethyl)-2-thioxo-1,3-oxazolidin-3-yl)ethylthio)-1,3-thiazol-4-carboxylic acid methyl ester

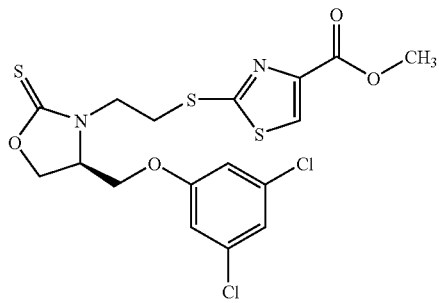

TLC: Rf 0.47 (hexane:ethyl acetate=1:1);
NMR (CDCl$_3$): δ 3.36 (ddd, J=13.50, 9.90, 5.10 Hz, 1H) 3.65 (ddd, J=13.50, 10.20, 5.10 Hz, 1H) 3.93 (s, 3H) 3.97 (m, 1H) 4.14 (m, 2H) 4.63 (m, 3H) 4.92 (m, 1H) 6.93 (d, J=1.80 Hz, 2H) 6.97 (t, J=1.80 Hz, 1H) 8.02 (s, 1H).

Example 21(2)

2-(2-((4S)-2-thioxo-4-(3-trifluoromethoxyphenoxymethyl)-1,3-oxazolidin-3-yl)ethylthio)-1,3-thiazol-4-carboxylic acid methyl ester TLC: Rf 0.43 (hexane:ethyl acetate=1:1);
NMR (CDCl$_3$): δ 3.41 (ddd, J=13.70, 9.70, 5.30 Hz, 1H) 3.65 (ddd, J=13.70, 9.80, 5.40 Hz, 1H) 3.89 (s, 3H) 3.96 (ddd, J=13.80, 9.60, 5.50 Hz, 1H) 4.17 (m, 2H) 4.64 (m, 3H) 4.82 (m, 1H) 6.86 (m, 3H) 7.26 (m, 1H) 8.01 (s, 1H).

Example 22(1) to 22(3)

By the same procedure as described in Example 2, using the compound prepared in 21, 21(1) or 21(2) instead of the compound prepared in Example 1, the following compounds of the present invention were obtained.

Example 22(1)

2-(2-((2R)-2-(3,5-dichlorophenoxymethyl)-5-thioxopyrrolidin-1-yl)ethylthio)-1,3-thiazole-4-carboxylic acid

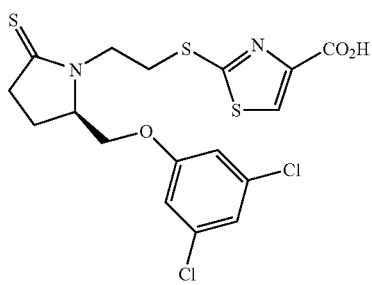

TLC: Rf 0.26 (chloroform:methanol=9:1);
NMR (CDCl$_3$): δ 8.17 (s, 1H), 6.96 (t, J=2.1 Hz, 1H), 6.86 (d, J=2.1 Hz, 2H), 4.66 (dd, J=10.2, 3.0 Hz, 1H), 4.44-4.24 (m, 2H), 4.16-3.95 (m, 2H), 3.73 (m, 1H), 3.39 (m, 1H), 3.17 (m, 1H), 3.04 (m, 1H), 2.26 (m, 1H), 2.06 (m, 1H).

Example 22(2)

2-(2-((4S)-4-(3,5-dichlorophenoxymethyl)-2-thioxo-1,3-oxazolidin-3-yl)ethylthio)-1,3-thiazole-4-carboxylic acid TLC: Rf 0.57 (methylene chloride:methanol:acetic acid=90:10:1);
NMR (CDCl$_3$): δ 3.43 (m, 1H) 3.70 (m, 1H) 3.96 (m, 1H) 4.08 (m, 1H) 4.19 (m, 1H) 4.57 (m, 4H) 6.87 (d, J=1.80 Hz, 2H) 6.98 (t, J=1.80 Hz, 1H) 8.16 (s, 1H).

Example 22(3)

2-(2-((4S)-2-thioxo-4-(3-trifluoromethoxyphenoxymethyl)-1,3-oxazolidin-3-yl)ethylthio)-1,3-thiazole-4-carboxylic acid TLC: Rf 0.54 (methylene chloride:methanol:acetic acid=90:10:1);
NMR (CDCl$_3$): δ 3.46 (m, 1H) 3.70 (m, 1H) 3.97 (m, 1H) 4.10 (m, 1H) 4.22 (m, 1H) 4.58 (m, 4H) 6.84 (m, 3H) 7.28 (t, J=8.20 Hz, 1H) 8.16 (s, 1H).

Formulation Example 1

The following components were admixed in a conventional method, punched out to give 100 tablets each containing 0.5 mg of active ingredient.

| | |
|---|---|
| 2-(2-(2-(4-n-butylphenyl)-5-oxopyrrolidin-1-yl)ethylthio)thiazole-4-carboxylic acid α-cyclodextrin | 250 mg (content 50 mg) |
| calcium carboxymethylcellulose | 200 mg |
| magnesium stearate | 100 mg |
| microcrystalline cellulose | 9.2 g |

Formulation Example 2

After mixing the following components by a conventional method, the resulting solution was sterilized by a conventional method and 1 ml portions thereof were filled in vials, respectively, and freeze-dried by a conventional method to obtain 100 vials of injection containing each 0.2 mg of the active ingredient.

| | |
|---|---|
| 2-(2-(2-(4-n-butylphenyl)-5-oxopyrrolidin-1-yl)ethylthio)thiazole-4-carboxylic acid α-cyclodextrin | 100 mg (content 20 mg) |
| Mannitol | 5 g |
| Distilled water | 100 ml |

The invention claimed is:

1. An 8-azaprostaglandin derivative compound represented by formula (I):

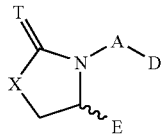

wherein T is (1) an oxygen atom;
X is (1) —CH$_2$—;
A is A$^2$;
A$^2$ is -G$^1$-G$^2$-G$^3$-;
G$^1$ is C1-4 straight-chain alkylene optionally substituted by 1 to 2 C1-4 alkyl(s);
G$^2$ is —Y-ring1-;
Y is (1) —S—, (2) —SO—, or (3) —SO$_2$—;
G$^3$ is a bond;
D is D$^1$;
D$^1$ is (1) —COOH, or (2) —COOR$^2$;
R$^2$ is (1) C1-10 alkyl, (2) phenyl, (3) C1-10 alkyl substituted by phenyl or (4) biphenyl;
E is E$^1$ or E$^2$;
E$^1$ is

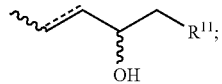

R$^{11}$ is (1) C1-10 alkyl, (2) C1-10 alkylthio, (3) C1-10 alkyl substituted by C3-8 cycloalkyl, (4) C1-10 alkyl substituted by ring2 or (5) C1-10 alkyl substituted by —W$^1$—W$^2$-ring2;
W$^1$ is (1) —O—, (2) —S—, (3) —SO—, (4) —SO$_2$—, (5) —NR$^{11-1}$—, (6) carbonyl, (7) —NR$^{11-1}$SO$_2$—, (8) carbonylamino or (9) aminocarbonyl;
R$^{11-1}$ is (1) a hydrogen atom, (2) C1-10 alkyl or (3) C2-10 acyl;
W$^2$ is (1) a bond or (2) C1-8 alkyl optionally substituted by C1-4 alkyl, halogen or hydroxy;
E$^2$ is (1) U$^1$—U$^2$—U$^3$ or (2) ring4;
U$^1$ is (1) C1-4 alkylene, (2) C2-4 alkenylene, or (3) C2-4 alkynylene;
U$^2$ is (1) a bond, (2) —CH$_2$—, (3) —CHOH—, or (9) carbonyl;
U$^3$ is (1) C1-8 alkyl optionally substituted by 1 to 3 substituent(s) selected from C1-10 alkyl, halogen, hydroxy, alkoxy, alkylthio and NR$^{13}$R$^{14}$, (2) C2-8 alkenyl optionally substituted by 1 to 3 substituent(s) selected from C1-10 alkyl, halogen, hydroxyl, alkoxy, alkylthio and —NR$^{13}$R$^{14}$, (3) C2-8 alkynyl optionally substituted by 1 to 3 substituent(s) selected from C1-10 alkyl, halogen, hydroxy, alkoxy, alkylthio and —NR$^{13}$R$^{14}$, (4) C1-8 alkyl substituted by ring4 or (5) ring4;
R$^{13}$ and R$^{14}$ are, each independently, (1) a hydrogen atom or (2) C1-10 alkyl;
ring1, ring2, ring3 or ring4 may be substituted by 1 to 5R;
R is (1) C1-10 alkyl, (2) C2-10 alkenyl, (3) C2-10 alkynyl, (4) C1-10 alkoxy, (5) C1-10 alkylthio, (6) halogen, (7) hydroxy, (8) nitro, (9) —NR$^{15}$R$^{16}$, (10) C1-10 alkyl substituted by C1-10 alkoxy, (11) C1-10 alkyl substituted by 1 to 3 halogen atom(s), (12) C1-10 alkyl substituted by C1-10 alkoxy substituted by 1 to 3 halogen atom(s), (13) C1-10 alkyl substituted by —NR$^{15}$R$^{16}$, (14) ring5, (15) —O-ring5, (16) C1-10 alkyl substituted by ring5, (17) C2-10 alkenyl substituted by ring5, (18) C2-10 alkynyl substituted by ring5, (19) C1-10 alkoxy substituted by ring5, (20) C1-10 alkyl substituted by —O-ring5, (21) COOR$^{17}$, (22) C1-10 alkoxy substituted by 1 to 4 halogen atom(s), (23) formyl, (24) C1-10 alkyl substituted by hydroxy or (25) C2-10 acyl;
R$^{15}$, R$^{16}$ and R$^{17}$ are, each independently, (1) a hydrogen atom or (2) C1-10 alkyl;
ring5 may be substituted by 1 to 3 substituent(s) selected from following (1)-(9):
(1) C1-10 alkyl, (2) C2-10 alkenyl, (3) C2-10 alkynyl, (4) C1-10 alkoxy, (5) C1-10 alkyl substituted by C1-10 alkoxy, (6) halogen atom, (7) hydroxy, (8) C1-10 alkyl substituted by 1 to 3 halogen atom(s), (9) C1-10 alkyl substituted by C1-10 alkoxy substituted by 1 to 3 halogen atom(s);
ring1, ring2, ring3, ring4 and ring5 are, each independently,
(1) C3-15 mono-, bi- or tri-carbocyclic aryl which may be partially or fully saturated or (2) 3- to 15-membered mono-, bi- or tri-heterocyclic aryl which may be partially or fully saturated and contains a hetero atom(s) selected from 1 to 4 nitrogen, 1 to 2 oxygen and/or 1 to 2 sulfur atom(s); and
wherein
1) when E is E$^2$, E$^2$ is U$^1$—U$^2$—U$^3$, and U$^1$ is C2 alkylene or C2 alkenylene, U$^2$ is not —CHOH—,
2) when U$^3$ is C1-8 alkyl substituted by at least one hydroxy, U$^1$—U$^2$ is not C2 alkylene or C2 alkenylene, or
a pharmaceutically acceptable salt thereof.

2. The 8-azaprostaglandin derivative compound according to claim 1, which is represented by formula (I-A1-a):

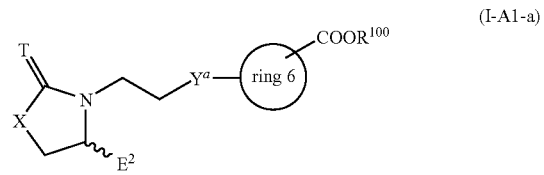

wherein Y$^a$ is —S— or —SO$_2$—, ring6 is C5 or 6 monocarbocyclic aryl, or 5- or 6-membered mono-heterocyclic aryl which may be partially or fully saturated and contains a hetero atom(s) selected from 1 to 4 nitrogen, 1 to 2 oxygen, and/or 1 to 2 sulfur atom(s); R$^{100}$ is a hydrogen atom or C1-4 alkyl; and other symbols have the same meanings as described in claim 1, or a pharmaceutically acceptable salt thereof.

3. The 8-azaprostaglandin derivative compound according to claim 1 or 2, which is represented by formula (I-A1-a3):

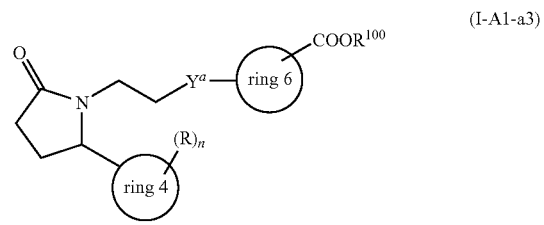

wherein all symbols have the same meanings as described in claims 1 and 2, or a pharmaceutically acceptable salt thereof.

4. The 8-azaprostaglandin derivative compound according to claim 1 or 2, which is represented by formula (I-A1-a4):

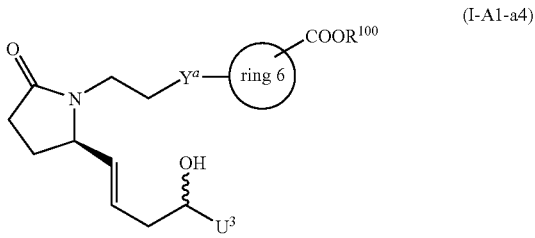

(I-A1-a4)

wherein all symbols have the same meanings as described in claims 1 and 2, or a pharmaceutically acceptable salt thereof.

5. The 8-azaprostaglandin derivative compound according to claim 4, wherein the compound represented by formula (I-A1-a4) is:

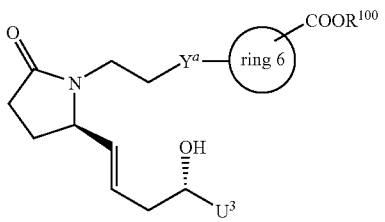

wherein all symbols have the same meanings as described in claims 1 and 2, or a pharmaceutically acceptable salt thereof.

6. The 8-azaprostaglandin derivative compound according to claim 1, which is represented by formula (I-E1):

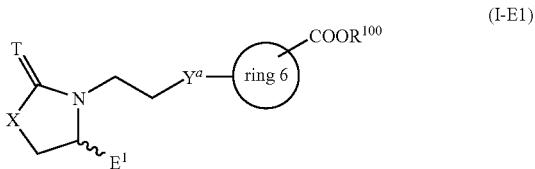

(I-E1)

wherein $Y^a$ is —S— or —$SO_2$—, ring6 is C5 or 6 monocarbocyclic aryl, or 5- or 6-membered mono-heterocyclic aryl which may be partially or fully saturated and contains a hetero atom(s) selected from 1 to 4 nitrogen, 1 to 2 oxygen, and/or 1 to 2 sulfur atom(s); $R^{100}$ is a hydrogen atom or C1-4 alkyl; and other symbols have the same meanings as described in claim 1, or a pharmaceutically acceptable salt.

7. The 8-azaprostaglandin derivative compound according to claim 1, which is selected from the group consisting of
 (13E,16α)-17,17-propano-16-hydroxy-5-(4-ethoxycarbonylthiazol-2-yl)-9-oxo-1,2,3,4,20-pentanor-5-thia-8-azaprost-13-ene;
 (15α,13E)-15-hydroxy-5-(4-carboxythiazol-2-yl)-9-oxo-1,2,3,4-tetranor-5-thia-8-azaprost-13-ene;
 (16α)-17,17-propano-16-hydroxy-5-(4-carboxythiazol-2-yl)-9-oxo-1,2,3,4,20-pentanor-5-thia-8-azaprostane;
 (13E)-17,17-propano-5-(4-carboxythiazol-2-yl)-9-oxo-1,2,3,4,20-pentanor-5-thia-8-azaprost-13-ene;
 (13E,15α)-20-phenyl-15-hydroxy-5-(4-carboxythiazol-2-yl)-9-oxo-1,2,3,4-tetranor-5-thia-8-azaprost-13-ene;
 (13E,15α)-20-benzyl-15-hydroxy-5-(4-carboxythiazol-2-yl)-9-oxo-1,2,3,4-tetranor-5-thia-8-azaprost-13-ene;
 (15α)-15-hydroxy-5-(4-carboxythiazol-2-yl)-9-oxo-1,2,3,4-tetranor-5-thia-8-azaprostane;
 (13E)-17,17-dimethyl-5-(4-carboxythiazol-2-yl)-9-oxo-1,2,3,4,19,20-hexanor-5-thia-8-azaprost-13-ene;
 (13E)-17,17-dimethyl-5-(4-carboxythiazol-2-yl)-9-oxo-1,2,3,4,20-pentanor-5-thia-8-azaprost-13-ene;
 (13E,16α)-17,17-propano-16-hydroxy-6-(4-carboxythiazol-2-ylsulfonyl)-9-oxo-1,2,3,4,5,20-hexanor-8-azaprost-13-ene;
 17,17-propano-5-(4-carboxythiazol-2-yl)-9,16-dioxo-1,2,3,4,20-pentanor-5-thia-8-azaprostane;
 (13E)-16-hydroxy-5-(4-carboxythiazol-2-yl)-9-oxo-1,2,3,4,20-pentanor-5-thia-8-azaprost-13-ene; and
 (13E,15α)-20-phenoxy-15-hydroxy-5-(4-carboxythiazol-2-yl)-9-oxo-1,2,3,4-tetranor-5-thia-8-azaprost-13-ene,
or a pharmaceutically acceptable salt thereof.

8. A pharmaceutical composition, which comprises the 8-azaprostaglandin derivative compound according to claim 1, or a pharmaceutically acceptable salt thereof and a pharmaceutically acceptable carrier.

* * * * *